(12) United States Patent
Burke et al.

(10) Patent No.: US 11,229,708 B2
(45) Date of Patent: Jan. 25, 2022

(54) CONJUGATES OF QUATERNIZED TUBULYSIN COMPOUNDS

(71) Applicant: SEATTLE GENETICS, INC., Bothell, WA (US)

(72) Inventors: Patrick J. Burke, Seattle, WA (US); Joel Courter, Lynnwood, WA (US)

(73) Assignee: SEAGEN INC., Bothell, WA (US)

( * ) Notice: Subject to any disclaimer, the term of this patent is extended or adjusted under 35 U.S.C. 154(b) by 0 days.

(21) Appl. No.: 15/781,244

(22) PCT Filed: Dec. 2, 2016

(86) PCT No.: PCT/US2016/064834
§ 371 (c)(1),
(2) Date: Jun. 4, 2018

(87) PCT Pub. No.: WO2017/096311
PCT Pub. Date: Jun. 8, 2017

(65) Prior Publication Data
US 2019/0015517 A1    Jan. 17, 2019

Related U.S. Application Data

(60) Provisional application No. 62/263,578, filed on Dec. 4, 2015, provisional application No. 62/263,587, filed (Continued)

(51) Int. Cl.
*A61K 47/55* (2017.01)
*A61K 47/68* (2017.01)
(Continued)

(52) U.S. Cl.
CPC .......... *A61K 47/551* (2017.08); *A61K 9/0019* (2013.01); *A61K 9/08* (2013.01);
(Continued)

(58) Field of Classification Search
None
See application file for complete search history.

(56) References Cited

U.S. PATENT DOCUMENTS 4,816,397 A   3/1989 Boss
4,816,567 A   3/1989 Cabilly
(Continued)

FOREIGN PATENT DOCUMENTS

CN   101663044 A   3/2010
CN   104379602 A   2/2015
(Continued)

OTHER PUBLICATIONS

Ahrens et al., "A Cleavable Cytolysin-Neuropeptide Y Bioconjugate Enables Specific Drug Delivery and Demonstrates Intracellular Mode of Action," J. of Controlled Release, 209, pp. 170-178, (2015).
(Continued)

*Primary Examiner* — Karl J Puttlitz
(74) *Attorney, Agent, or Firm* — Morrison & Foerster LLP

(57) ABSTRACT

Compounds and compositions are disclosed in which a quaternized drug unit is linked to a targeting ligand unit from which a tertiary amine-containing drug is released at the targeted site of action. Methods for treating diseases characterized by the targeted abnormal cells, such as cancer or an autoimmune disease using the compounds and compositions of the invention are also disclosed.

28 Claims, 10 Drawing Sheets

Related U.S. Application Data on Dec. 4, 2015, provisional application No. 62/309,448, filed on Mar. 16, 2016, provisional application No. 62/309,462, filed on Mar. 17, 2016.

(51) Int. Cl.

| | | |
|---|---|---|
| *C07K 5/02* | (2006.01) | |
| *A61K 47/65* | (2017.01) | |
| *A61K 47/64* | (2017.01) | |
| *A61P 35/02* | (2006.01) | |
| *A61K 9/00* | (2006.01) | |
| *A61K 9/08* | (2006.01) | |
| *A61K 31/454* | (2006.01) | |
| *A61K 38/05* | (2006.01) | |
| *A61K 38/06* | (2006.01) | |
| *A61K 38/00* | (2006.01) | |

(52) U.S. Cl.
CPC ............ *A61K 31/454* (2013.01); *A61K 38/05* (2013.01); *A61K 38/06* (2013.01); *A61K 47/64* (2017.08); *A61K 47/65* (2017.08); *A61K 47/6811* (2017.08); *A61K 47/6817* (2017.08); *A61K 47/6849* (2017.08); *A61K 47/6883* (2017.08); *A61K 47/6889* (2017.08); *A61P 35/02* (2018.01); *C07K 5/021* (2013.01); *A61K 38/00* (2013.01)

(56) References Cited

U.S. PATENT DOCUMENTS

| | | |
|---|---|---|
| 5,225,539 A | 7/1993 | Writer |
| 5,492,841 A | 2/1996 | Craig |
| 5,585,089 A | 12/1996 | Queen et al. |
| 5,605,976 A | 2/1997 | Martinez et al. |
| 5,672,662 A | 9/1997 | Harris |
| 5,681,567 A | 10/1997 | Martinez et al. |
| 5,756,593 A | 5/1998 | Martinez et al. |
| 5,757,078 A | 5/1998 | Matsuda |
| 5,851,527 A | 12/1998 | Hansen |
| 5,919,455 A | 7/1999 | Greenwald et al. |
| 5,935,995 A | 8/1999 | Bosslet et al. |
| 5,965,119 A | 10/1999 | Greenwald et al. |
| 6,077,499 A | 6/2000 | Griffiths et al. |
| 6,077,939 A | 6/2000 | Wei |
| 6,113,906 A | 9/2000 | Greenwald et al. |
| 6,124,431 A | 9/2000 | Sakakibara et al. |
| 6,153,655 A | 11/2000 | Martinez et al. |
| 6,214,330 B1 | 4/2001 | Greenwald et al. |
| 6,214,345 B1 | 4/2001 | Firestone et al. |
| 6,261,537 B1 | 7/2001 | Klaveness et al. |
| 6,303,569 B1 | 10/2001 | Greenwald et al. |
| 6,323,322 B1 | 11/2001 | Filpula et al. |
| 6,331,289 B1 | 12/2001 | Klaveness et al. |
| 6,361,774 B1 | 3/2002 | Griffiths et al. |
| 6,395,266 B1 | 5/2002 | Martinez et al. |
| 6,556,506 B2 | 5/2003 | Greenwald et al. |
| 6,569,834 B1 | 5/2003 | Petit et al. |
| 6,602,498 B2 | 8/2003 | Shen |
| 6,624,142 B2 | 9/2003 | Greenwald et al. |
| 6,638,499 B2 | 10/2003 | Martinez et al. |
| 6,643,575 B2 | 11/2003 | Ishida et al. |
| 6,680,047 B2 | 1/2004 | Klaveness et al. |
| 6,743,896 B2 | 6/2004 | Filpula et al. |
| 6,743,908 B2 | 6/2004 | Filpula et al. |
| 6,777,387 B2 | 8/2004 | Greenwald et al. |
| 6,824,782 B2 | 11/2004 | Whitlow et al. |
| 6,872,393 B2 | 3/2005 | Whitlow et al. |
| 7,011,812 B1 | 3/2006 | Griffiths et al. |
| 7,026,440 B2 | 4/2006 | Bentley et al. |
| 7,091,186 B2 | 8/2006 | Senter et al. |
| 7,150,872 B2 | 12/2006 | Whitlow et al. |
| 7,273,845 B2 | 9/2007 | Zhao et al. |
| 7,300,644 B2 | 11/2007 | Griffiths et al. |
| 7,332,164 B2 | 2/2008 | Greenwald et al. |
| 7,374,762 B2 | 5/2008 | Amphlett et al. |
| 7,375,078 B2 | 5/2008 | Feng |
| 7,462,687 B2 | 12/2008 | Greenwald et al. |
| 7,494,649 B2 | 2/2009 | Amphlett et al. |
| 7,498,298 B2 | 3/2009 | Doronina |
| 7,501,120 B2 | 3/2009 | Amphlett et al. |
| 7,514,066 B2 | 4/2009 | Griffiths et al. |
| 7,514,080 B2 | 4/2009 | Amphlett et al. |
| 7,553,816 B2 | 6/2009 | Senter et al. |
| 7,595,304 B2 | 9/2009 | Zhao et al. |
| 7,632,504 B2 | 12/2009 | Whitlow et al. |
| 7,659,241 B2 | 2/2010 | Senter |
| 7,754,681 B2 | 7/2010 | Feng |
| 7,754,885 B2 | 7/2010 | Hoefle et al. |
| 7,767,205 B2 | 8/2010 | Mao et al. |
| 7,776,814 B2 | 8/2010 | Domling et al. |
| 7,785,618 B2 | 8/2010 | Elmaleh et al. |
| 7,816,377 B2 | 10/2010 | Domling et al. |
| 7,872,072 B2 | 1/2011 | Bentley et al. |
| 7,884,869 B2 | 2/2011 | Shurboff et al. |
| 7,888,536 B2 | 2/2011 | Davis et al. |
| 7,931,890 B2 | 4/2011 | Griffiths et al. |
| 7,947,839 B2 | 5/2011 | Gazzard et al. |
| 7,968,687 B2 | 6/2011 | Medonagh |
| 7,989,434 B2 | 8/2011 | Feng |
| 7,989,598 B2 | 8/2011 | Steeves et al. |
| 7,994,135 B2 | 8/2011 | Doronina et al. |
| 8,012,485 B2 | 9/2011 | Amphlett et al. |
| 8,012,488 B2 | 9/2011 | Sakanoue et al. |
| 8,039,273 B2 | 10/2011 | Jeffrey |
| 8,088,387 B2 | 1/2012 | Steeves et al. |
| 8,163,888 B2 | 4/2012 | Steeves et al. |
| 8,168,605 B2 | 5/2012 | Zhao et al. |
| 8,198,417 B2 | 6/2012 | Steeves et al. |
| 8,257,706 B2 | 9/2012 | Medonagh |
| 8,268,317 B2 | 9/2012 | Govindan et al. |
| 8,273,833 B2 | 9/2012 | Bentley et al. |
| 8,343,928 B2 | 1/2013 | Doronina |
| 8,367,065 B2 | 2/2013 | Zhao et al. |
| 8,394,922 B2 | 3/2013 | Cheng et al. |
| 8,440,816 B2 | 5/2013 | Bentley et al. |
| 8,455,622 B2 | 6/2013 | Mcdonagh et al. |
| 8,563,509 B2 | 10/2013 | Chari et al. |
| 8,568,728 B2 | 10/2013 | Jeffrey |
| 8,580,820 B2 | 11/2013 | Zanda et al. |
| 8,609,092 B2 | 12/2013 | Torgov et al. |
| 8,772,244 B2 | 7/2014 | Richter |
| 8,980,824 B2 | 3/2015 | Cong et al. |
| 8,980,833 B2 | 3/2015 | Richter |
| 9,061,074 B2 | 6/2015 | Carter et al. |
| 9,109,008 B2 | 8/2015 | Cong et al. |
| 9,138,484 B2 | 9/2015 | Leamon et al. |
| 9,144,615 B2 | 9/2015 | Yurkovetskiy et al. |
| 9,163,060 B2 | 10/2015 | Richter |
| 9,192,682 B2 | 11/2015 | Leamon et al. |
| 9,242,013 B2 | 1/2016 | Howard et al. |
| 9,254,339 B2 | 2/2016 | Yurkovetskiy et al. |
| 9,273,091 B2 | 3/2016 | Vlahov et al. |
| 9,295,731 B2 | 3/2016 | Nguyen |
| 9,427,479 B2 | 8/2016 | Gingipalli et al. |
| 9,610,360 B2 | 4/2017 | Davis et al. |
| 9,629,918 B2 | 4/2017 | Low et al. |
| 2002/0102215 A1 | 8/2002 | Klaveness |
| 2003/0083263 A1 | 5/2003 | Doronina |
| 2004/0001820 A1 | 1/2004 | Hahn et al. |
| 2004/0009166 A1 | 1/2004 | Filpula et al. |
| 2004/0053976 A1 | 3/2004 | Martinez et al. |
| 2004/0141922 A1 | 7/2004 | Klaveness et al. |
| 2005/0002865 A1 | 1/2005 | Klaveness et al. |
| 2005/0009751 A1 | 1/2005 | Senter |
| 2005/0042680 A1 | 2/2005 | Filpula et al. |
| 2005/0238649 A1 | 10/2005 | Doronina |
| 2005/0239713 A1 | 10/2005 | Domling et al. |
| 2005/0249740 A1 | 11/2005 | Domling et al. |
| 2006/0128754 A1 | 6/2006 | Hoefle et al. |
| 2006/0130160 A1 | 6/2006 | Dumas Milne Edwards et al. |
| 2007/0134243 A1 | 6/2007 | Gazzard et al. |
| 2008/0176958 A1 | 7/2008 | Davis |

(56) References Cited

U.S. PATENT DOCUMENTS

| | | |
|---|---|---|
| 2008/0279922 A1 | 11/2008 | Zalipsky et al. |
| 2009/0018086 A1 | 1/2009 | Doronina |
| 2009/0111756 A1 | 4/2009 | Doronina |
| 2009/0202573 A1 | 8/2009 | Zhao et al. |
| 2009/0203706 A1 | 8/2009 | Zhao et al. |
| 2009/0221471 A1 | 9/2009 | Greenwald et al. |
| 2009/0274713 A1 | 11/2009 | Chari |
| 2010/0047841 A1 | 2/2010 | Wipf et al. |
| 2010/0062008 A1 | 3/2010 | Senter et al. |
| 2010/0092496 A1 | 4/2010 | Boyd |
| 2010/0145036 A1 | 6/2010 | Sufi et al. |
| 2010/0158909 A1 | 6/2010 | McDonagh et al. |
| 2010/0203007 A1 | 8/2010 | Li et al. |
| 2010/0203066 A1 | 8/2010 | Zhao et al. |
| 2010/0260786 A1 | 10/2010 | Doronina et al. |
| 2010/0273843 A1 | 10/2010 | Feng |
| 2010/0278842 A1 | 11/2010 | Mao et al. |
| 2011/0014151 A1 | 1/2011 | Nilsson et al. |
| 2011/0020343 A1 | 1/2011 | Senter |
| 2011/0206658 A1 | 8/2011 | Crowley et al. |
| 2011/0243880 A1 | 10/2011 | Yurkovetskiy et al. |
| 2011/0245295 A1 | 10/2011 | Chai et al. |
| 2011/0263650 A1 | 10/2011 | Ellman et al. |
| 2011/0268751 A1 | 11/2011 | Sievers et al. |
| 2011/0281856 A1 | 11/2011 | Chari et al. |
| 2011/0300162 A1 | 12/2011 | Amphlett et al. |
| 2012/0129779 A1 | 5/2012 | Richter |
| 2012/0226025 A1 | 9/2012 | Chari et al. |
| 2012/0252738 A1 | 10/2012 | Richter |
| 2012/0252739 A1 | 10/2012 | Richter |
| 2013/0101546 A1 | 4/2013 | Yurkovetskiy et al. |
| 2013/0217638 A1 | 8/2013 | Wessjohann et al. |
| 2013/0224228 A1 | 8/2013 | Jackson et al. |
| 2013/0225789 A1 | 8/2013 | Sun et al. |
| 2013/0259860 A1 | 10/2013 | Smith |
| 2013/0295639 A1 | 11/2013 | Bentley et al. |
| 2013/0309223 A1 | 11/2013 | Sutherland |
| 2013/0309256 A1 | 11/2013 | Lyon et al. |
| 2014/0050746 A1 | 2/2014 | Senter et al. |
| 2014/0080175 A1 | 3/2014 | Vlahov et al. |
| 2014/0086942 A1 | 3/2014 | Carter et al. |
| 2014/0127197 A1 | 5/2014 | Ebens |
| 2014/0249315 A1 | 9/2014 | Vlahov et al. |
| 2014/0356375 A1 | 12/2014 | Brown et al. |
| 2014/0356376 A1 | 12/2014 | Brown et al. |
| 2014/0363454 A1 | 12/2014 | Jackson et al. |
| 2015/0191430 A1 | 7/2015 | Kolb et al. |
| 2015/0250896 A1 | 9/2015 | Zhao |
| 2015/0284416 A1 | 10/2015 | Zhao |
| 2015/0290152 A1 | 10/2015 | Kelner |
| 2015/0352224 A1 | 12/2015 | Naito et al. |
| 2015/0366982 A1 | 12/2015 | Bodyak et al. |
| 2015/0366985 A1 | 12/2015 | Brown et al. |
| 2016/0051695 A1 | 2/2016 | Lin et al. |
| 2016/0067341 A1 | 3/2016 | Low et al. |
| 2016/0074529 A1 | 3/2016 | Brown et al. |
| 2016/0130299 A1 | 5/2016 | Perez et al. |
| 2016/0130358 A1 | 5/2016 | Bhakta et al. |
| 2016/0303247 A1 | 10/2016 | Jackson et al. |
| 2016/0303251 A1 | 10/2016 | Vlahov et al. |
| 2017/0007716 A1 | 1/2017 | Kontermann et al. |
| 2017/0021033 A1 | 1/2017 | Geierstanger et al. |
| 2017/0029490 A1 | 2/2017 | Winters et al. |
| 2017/0043033 A1 | 2/2017 | Strop et al. |
| 2017/0247412 A1 | 8/2017 | Burke |

FOREIGN PATENT DOCUMENTS

| | | | |
|---|---|---|---|
| DE | 10200403227 A1 | 1/2006 | |
| EP | 0171496 A2 | 2/1986 | |
| EP | 0173494 A2 | 3/1986 | |
| EP | 0184187 A2 | 6/1986 | |
| EP | 0401384 A1 | 12/1990 | |
| EP | 2461830 B1 | 6/2012 | |
| JP | 2011-037846 A | 2/2011 | |
| JP | 2011-500835 A | 6/2011 | |
| JP | 2014-240387 A | 12/2014 | |
| WO | 198601533 A1 | 3/1986 | |
| WO | 198702671 A1 | 5/1987 | |
| WO | 199012874 A2 | 11/1990 | |
| WO | 199012874 A3 | 1/1991 | |
| WO | WO1998/013375 A1 | 4/1998 | |
| WO | 2002083172 A2 | 11/2002 | |
| WO | 2002083172 A3 | 2/2003 | |
| WO | WO2003/026577 A2 | 4/2003 | |
| WO | WO2004/005269 A1 | 1/2004 | |
| WO | WO2004/005326 A2 | 1/2004 | |
| WO | WO2004/005327 A1 | 1/2004 | |
| WO | WO2004/010957 A2 | 2/2004 | |
| WO | WO2004/046170 A2 | 6/2004 | |
| WO | WO2004/046170 A3 | 6/2004 | |
| WO | WO2004/085386 A2 | 10/2004 | |
| WO | WO2005/081711 A2 | 9/2005 | |
| WO | WO2007/011968 A2 | 1/2007 | |
| WO | WO2008/034124 A2 | 3/2008 | |
| WO | WO2008/056346 A2 | 5/2008 | |
| WO | 2008104000 A2 | 8/2008 | |
| WO | WO2008/101202 A1 | 8/2008 | |
| WO | WO2008/106080 A2 | 9/2008 | |
| WO | WO2008/112873 A2 | 9/2008 | |
| WO | 2008104000 A3 | 11/2008 | |
| WO | WO2008/138561 A1 | 11/2008 | |
| WO | WO2009/012958 A2 | 1/2009 | |
| WO | WO2009/055562 A1 | 4/2009 | |
| WO | WO2009/134279 A1 | 11/2009 | |
| WO | WO2010/034724 A1 | 4/2010 | |
| WO | WO2010/048018 A1 | 4/2010 | |
| WO | WO2010/126551 A1 | 11/2010 | |
| WO | WO2011/017249 A1 | 2/2011 | |
| WO | WO2011/057805 A1 | 5/2011 | |
| WO | WO2011/057806 A1 | 5/2011 | |
| WO | WO2011/069116 A1 | 6/2011 | |
| WO | WO2011/130599 A1 | 10/2011 | |
| WO | WO2011/130616 A1 | 10/2011 | |
| WO | WO2012/010287 A1 | 1/2012 | |
| WO | WO2012/019123 A1 | 2/2012 | |
| WO | WO2012/113847 A1 | 8/2012 | |
| WO | WO2012/171020 A1 | 12/2012 | |
| WO | WO2013/053873 A1 | 4/2013 | |
| WO | WO2013/055990 A1 | 4/2013 | |
| WO | WO2013/055993 A1 | 4/2013 | |
| WO | WO2013/085925 A1 | 6/2013 | |
| WO | 2013123152 A2 | 8/2013 | |
| WO | WO2013/126797 A1 | 8/2013 | |
| WO | 2013134743 A1 | 9/2013 | |
| WO | WO2013/130776 A1 | 9/2013 | |
| WO | WO2013/149185 A1 | 10/2013 | |
| WO | 2013173392 | 11/2013 | |
| WO | WO2013/170272 A2 | 11/2013 | |
| WO | WO2013/173337 A2 | 11/2013 | |
| WO | WO2013/173391 A1 | 11/2013 | |
| WO | WO2013/173392 A1 | 11/2013 | |
| WO | WO2013/173393 A1 | 11/2013 | |
| WO | WO2013173337 A2 | 11/2013 | |
| WO | WO2014/009774 A1 | 1/2014 | |
| WO | WO2014/040752 A1 | 3/2014 | |
| WO | WO-2014040752 A1 * | 3/2014 | ............ A61K 47/64 |
| WO | WO2014/062697 A2 | 4/2014 | |
| WO | WO2014/064423 A1 | 5/2014 | |
| WO | WO2014/078484 A1 | 5/2014 | |
| WO | WO2014/085575 A1 | 6/2014 | |
| WO | WO2014/093394 A1 | 6/2014 | |
| WO | WO2014/093640 A1 | 6/2014 | |
| WO | WO2014/126836 A1 | 8/2014 | |
| WO | WO2014/134543 A1 | 9/2014 | |
| WO | WO2014/160360 A1 | 10/2014 | |
| WO | WO2014/172478 A1 | 10/2014 | |
| WO | 2013123152 A3 | 11/2014 | |
| WO | WO2014/193722 A1 | 12/2014 | |
| WO | WO2014/194247 A1 | 12/2014 | |
| WO | WO2014/197849 A2 | 12/2014 | |
| WO | WO2014/197849 A3 | 12/2014 | |
| WO | WO2014/197854 A1 | 12/2014 | |
| WO | WO2014/197871 A2 | 12/2014 | |

(56) References Cited

FOREIGN PATENT DOCUMENTS

| | | | |
|---|---|---|---|
| WO | WO2015/057585 A1 | 4/2015 | |
| WO | WO2015/057699 A2 | 4/2015 | |
| WO | WO-2015057699 A2 * | 4/2015 | ......... A61K 47/6817 |
| WO | WO2015/106599 A1 | 7/2015 | |
| WO | WO2015/113760 A1 | 8/2015 | |
| WO | WO2015/118031 A1 | 8/2015 | |
| WO | 2015151078 A2 | 10/2015 | |
| WO | WO2015/157594 A1 | 10/2015 | |
| WO | WO2015/157595 A1 | 10/2015 | |
| WO | WO2016/040684 A1 | 3/2016 | |
| WO | WO2016/040856 A2 | 3/2016 | |
| WO | WO2016/046574 A1 | 3/2016 | |
| WO | WO2016/049313 A1 | 3/2016 | |
| WO | WO2016/077260 A1 | 5/2016 | |
| WO | WO2016/089879 A1 | 6/2016 | |
| WO | WO2016/090038 A1 | 6/2016 | |
| WO | WO2016/090040 A1 | 6/2016 | |
| WO | WO2016/090050 A1 | 6/2016 | |
| WO | WO2016/140957 A1 | 9/2016 | |
| WO | WO2016/168471 A1 | 10/2016 | |
| WO | WO2017/008169 A1 | 1/2017 | |
| WO | WO2017/011803 A1 | 1/2017 | |
| WO | WO2017/030859 A1 | 2/2017 | |
| WO | WO2017/031209 A1 | 2/2017 | |
| WO | WO2017/053619 A1 | 3/2017 | |
| WO | WO2017/096311 A1 | 6/2017 | |

OTHER PUBLICATIONS

Allen, "Ligand-Targeted Therapeutics in Anticancer Therapy," Nature Reviews, 2:750-765, 2002.
Alley et al., "Contribution of Linker Stability to the Activities of Anticancer Immunoconjugates," Bioconjugate Chem. 19:759-765, 2008.
Balasubramanian et al., "Total Synthesis and Biological Evaluation of Tubulysin U, Tubulysin V, and Their Analogues," J. Med. Chem., 52, pp. 238-240, (2009).
Balasubramanian et al., "Tubulysin Analogs Incorporating Desmethyl and Dimethyl Tubuphenylalanine Derivatives," Bioorg. & Med. Chem. Lett., 18, pp. 2996-2999, (2008).
Baldwin et al., "Tunable Degradation of Maleimide—Thiol Adducts in Reducing Environments," Bioconjugate Chem. 22:1946-1953, 2011.
Burke, et al., "Development of Novel Quaternary Ammonium linkers for Antibody-Drug Conjugates", Molecular Cancer Therapy, 15(5), pp. 938-945, May 2016.
Burkhart et al., "Syntheses and Evaluation of Simplified Pretubulysin Analogues," Eur. J. Org. Chem., pp. 3050-3059, (2011).
Chai et al., "Discovery of 23 Natural Tubulysins from Angiococcus disciformis an d48 and Cystobacter SBCb004," Chemistry & Biology, 17, pp. 296-309, (Mar. 26, 2010).
Chandrasekhar et al., "Toward Tubulysin: Gram-Scale Synthesis of Tubuvaline-Tubuphenylalanine Fragment," J. Org. Chem., 74, pp. 9531-9534, (2009).
Chen et al, "Design, Synthesis, and Pharmacological Evaluation of Haloperidol Derivatives as Novel Potent Calcium Channel Blockers with Vasodilator Activity," PLoS One vol. 6, No. 11, pp. 1-9 (2011).
Chen et al., Glucuronides in Anti-Cancer Therapy, Curr. Med. Chem. 3:139-150, 2003.
Cohen et al., "Development of Novel ADCs: Conjugation of Tubulysin Analogues to Trastuzumab Monitored by Dual Radiolabeling," Cancer Res., 74(20), pp. 5700-5710, (Oct. 15, 2014).
de Graff et al., "Beta-Glucuronidase-Mediated Drug Release," Current Pharmaceutical Design 8:1391-1403, 2002.
Desbene et al., "Application of the ADEPT Strategy to the MDR Resistance in Cancer Chemotherapy," Anti-Cancer Drug Design, 14, pp. 93-106, (1999).
Domling et al., "Total Synthesis of Tubulysin U and V," Angew. Chem. Int. Ed., 45, pp. 7235-7239, (2006).

Doronina, et al., "Development of potent monoclonal antibody auristatin conjugates for cancer therapy", Nature Biotechnology, vol. 21, No. 7, pp. 778-784, Jul. 2003.
Floyd III et al., Author Manuscript "Chemotherapeutic Evaluation of a Novel Synthetic Tubulysin Analogue-Dendrimer Conjugate in C26 Tumor Bearing Mice," ChemMedChem., 6(1), pp. 49-53, (Jan. 3, 2011).
Friestad et al., "Stereoselective Mn-Mediated Coupling of Functionalized Iodides and Hydrazones: A Synthetic Entry to the Tubulysin Y-Amino Acids," Org. Letters, 6(19), pp. 3249-3252, (2004).
G.M. Dubowchik, M.A. Walker, Pharmacology & Therapeutics 83:67-123, 1999.
Gamage et al., "Dicationic Bis(9-methylphenazine-1-carboxamides): Relationships between Biological Activity and Linker Chain Structure for a Series of Potent Topoisomerase Targeted Anticancer Drugs," J. Med. Chem., 44, pp. 1407-1415, (2001).
Gamage et al., "Phenazine-1-carboxamides: Structure—cytotoxicity relationships for H-substituents and changes in the H-bonding pattern of the cationic side chain," Bioorganic & Medicinal Chemistry, 14, pp. 1168-1168, (2006).
Greenwald, et al., "Effective drug delivery by PEGylated drug conjugates", Advanced Drug Delivery Reviews, 55, pp. 217-250, (2003).
Hamel et al., "Antimitotic Peptides and Depsipeptides," Curr. Med. Chem., 2, pp. 19-53, (2002).
Hermann et al., "Pretubulysin: From Hypothetical Biosynthetic Intermediate to Potential Lead in Tumor Therapy," PLOS One, 7(5), 12 pages, (May 2012).
Hoffman et al., "A Straightforward Approach Towards Cyclic Photoactivatable Tubulysin Derivatives," Angew. Chem. Int. Ed., 53, pp. 11356-11360, (2014).
Hofle et al., "Semisynthesis and Degradation of the Tubulin Inhibitors Epothilon and Tubulysin," Pure Appl. Chem., 75, pp. 167-178, (2003).
Huang et al., "Drug-targeting strategies in cancer therapy," Current Opinion in Genetics & Development 11:104-110, 2001.
Jeffrey et al, "Development and Properties of Beta-Glucuronide Linkers for Monoclonal Antibody-Drug Conjugates," American Chemical Society, 2006.
Jeffrey et al., "Development and Properties of Beta-Glucuronide Linkers for Monoclonal antibody-Drug Conjugates," Bioconjugate Chem. 17:831-840, 2006.
Jeffrey et al., "Expanded Utility of the Beta-Glucuronide Linker: ADCs That Deliver Henolic Cytotoxic Agents," ACS Medicinal Chemistry Letters, 1:277-280, 2010.
Kametani et al., "Studies on the Syntheses of Analgesics. XLVI. An Abnormal Hofmann Degradation of N-(4-Hydroxybenzyl)-3-benzazocinium Halides (Studies on the Syntheses of Heterocyclic Compounds. DCLXVII)," Chem. Pharm. Bull., 24(6), pp. 1246-1253, (1976).
King et al., "Monoclonal Antibody Conjugates of Doxorubicin Prepared with Branched Peptide Linkers: Inhibition of Aggregation by Methoxytriethyleneglycol Chains," J. Med. Chem. 45:4336-4343, 2002.
Kirschke, "Lysosomal Cysteine Peptidases and Malignant Tumours," Cellular Peptidases in Immune Functions and Diseases, edited by Ansorge and Langner plenum Press, New York, 1997.
Kularatne et al., "Synthesis and Biological Analysis of Prostate-Specific Membrane Antigen-Targeted Anticancer Prodrugs," J. Med. Chem., 53, pp. 7767-7777, (2010).
Lamidi et al., "The Tubulysin Analogue KEMTUB10 Induces Apoptosis in Breast Cancer Cells Via p53, Bim and Bcl-2," J. Cancer Res. Clin. Oncol., 141(9), pp. 1575-1583, (Sep. 2015).
Leamon et al., "Folate Targeting Enables Durable and Specific Antitumor Responses from a Therapeutically Null Tubulysin B Analogue," Cancer Res., 68(23), pp. 9839-9844, (Dec. 1, 2008).
Lehar et al., "Novel antibody-antibiotic conjugate eliminates intracellular S. aureus," Nature, 16057, pp. 1-19, (2015).
Lyon et al., "Self-hydrolyzing maleimides improve the stability and pharmacological properties of antibody-drug conjugates," Nature Biotechnology, Jan. 7, 2014.

(56) References Cited

OTHER PUBLICATIONS

Miller et al., "Potent antigen-specific anti-tumor activity obserbed with antibody-drug conjugates (ADCs) made using a new class of DNA-crosslinking agents," Poster, Nov. 2009.
Molineaux, "Pegylation: engineering improved pharmaceuticals for enhanced therapy," Cancer Treatment Reviews 28(Suppl. A):13-16, 2002.
Murray et al., "Chemistry and Biology of Tubulysins: Antimitotic Tetrapeptides with Activity Against Drug Resistant Cancers," Nat. Prod. Rep., 32, pp. 654-662, (2015).
Neri et al., "Efforts Toward the Total Synthesis of Tubulysins: New Hopes for a More Effective Targeted Drug Delivery to Tumors," ChemMedChem, 1, pp. 175-180, (2006).
Pando et al., "First Total Synthesis of Tubulysin B," Org. Lett., 11(24), pp. 5567-5569, (2009).
Pando et al., "The Multiple Multicomponent Approach to Natural Product Mimics: Tubugis, N-Substituted Anticancer Peptides with Picomolar Activity," J. Am. Chem. Soc., 133, pp. 7692-7695, (2011).
Papot et al., "Design of Selectively Activated Anticancer Prodrugs: Elimination and Cyclization Strategies," Curr. Med. Chem. Anti-Cancer Agents 2:155-185, 2002.
Park et al., "Synthesis of a Cyclic Analogue of Tuv N-Methyl Tubulysin," Synlett, 26, pp. 1063-1068, (2015).
Park et al., "Synthesis of Stereochemically Diverse Cyclic Analogs of Tubulysins," Bioorg. & Med. Chem., 23, pp. 6827-6843, (2015).
Patterson et al., "Design, Synthesis, and Biological Properties of Highly Potent Tubulysin D Analogues," Chem. Eur. J., 13(34), pp. 9534-9541, (2007).
Patterson et al., "Expedient Synthesis of N-Methyl Tubulysin Analogues with High Cytotoxicity," J. Org. Chem., 73, pp. 4362-4369, (2008).
Peltier et al., "The Total Synthesis of Tubulysin D," J. Am. Chem. Soc., 128, pp. 16018-16019, (2006).
Raghavan et al., "Cytotoxic Simplified Tubulysin Analogues," J. Med. Chem., 51, pp. 1530-1533, (2008).
Rath et al., "Anti-Angiogenic Effects of the Tubulysin Precursor Pretubulysin and of Simplified Pretubulysin Derivatives," British Journal of Pharmacology, 197, pp. 1048-1061, (2012).
Reddy et al., "In Vivo Structural Activity and Optimization Studies of Folate—Tubulysin Conjugates," Molecular Pharmaceutics, 6(5), pp. 1518-1525, (2009).
Sanderson et al., "In Vivo Drug-Linker Stability of an Anti-CD30 Dipeptide-Linked Auristatin Immunoconjugate," Clin. Cancer Res. 11:843-852, 2005.
Sani et al., "Total Synthesis of Tubulysins U and V," Angew. Chem. Int. Ed., 46, pp. 3526-3529, (2007).
Sasse et al., "Success in Tubulysin D Synthesis," Nature Chemical Biology, 3(2), pp. 87-89, (Feb. 2007).
Sasse et al., "Tubulysins, New Cytostatic Peptides from Myxobacteria Acting on Microtubuli Production, Isolation, Physico-Chemical and Biological Properties," J. of Antibiotics, 53(9), pp. 879-885, (Sep. 2000).
Scarpi et al., "A Short and Efficient Route to Enantiopure 3,5-Diarylpyrrolizidines," J. Org. Chem., 64, pp. 1727-1732, (1999).
Schluep et al., "Polymeric Tubulysin-Peptide Nanoparticles with Potent Antitumor Activity," Clin. Cancer Res., 15(1), pp. 181-189, (Jan. 1, 2009).
Schluep et al., Supplementary Data, Clin. Cancer Res., 15(1), 6 pages, (2009).
Shankar et al., "Synthesis and Cytotoxicity Evaluation of Diastereoisomers and N-Terminal Analogues of Tubulysin-U," Tetrahedron Letters, 54, pp. 6137-6141, (2013).
Shankar et al., "Total Synthesis and Cytotoxicity Evaluation of an Oxazole Analogue of Tubulysin U," Synlett, 12, pp. 1673-1676, (2011).
Shibue et al., "Synthesis and Biological Evaluation of Tubulysin D Analogs Related to Stereoisomers of Tubuvaline," Bioorg. & Med. Chem. Lett., 21, pp. 431-434, (2011).

Shibue et al., "Total Syntheses of Tubulysins," Chem. Eur. J., 16, pp. 11678-11688, (2010).
Sperker et al., "The Role of Beta-Glucuronidase in Drug Disposition and Drug Targeting in Humans," Clin. Pharmocokinet, 33(1):18-31, 1997.
Spicer et al, "Bis(phenazine-1-carboxamides): Structure-Activity Relationships for a New Class of Dual Topoisomerase I/II-Directed Anticancer Drugs," J. Chem. Chem., 43, pp. 1350-1358, (2000).
Ullrich et al., "Pretubulysin, A Potent and Chemically Accessible Tubulysin Precursor from Angiococcus disciformis," Angew. Chem. Int. Ed., 48, pp. 4422-4425, (2009).
Ullrich et al., "Synthesis and Biological Evaluation of Pretubulysin and Derivatives," Eur. J. Org. Chem., 36, 25 pages, (2009).
Vlahov et al., "Acid Mediated Formation of an N-acyliminium Ion from Tubulysins: A New Methodology for the Synthesis of Natural Tubulysins and Their Analogs," Bioorg. & Med. Chem. Lett., 21, pp. 6778-6781, (2011).
Vlahov et al., "Design and Regioselective Synthesis of a New Generation of Targeted Chemotherapeutics. Part II: Folic Acid Conjugates of Tubulysins and Their Hydrazides," Bioorg. & Med. Chem. Lett., 18, pp. 4558-4561, (2008).
Wang et al., "6-Substituted Pyrrolo[2,3-d]pyrimidine Thienoyl Regioisomers as Targeted Antifolates for Folate Receptor A and the Proton-Coupled Folate Transporter in Human Tumors," J. Med. Chem., 58(17), pp. 6938-6959, (Sep. 10, 2015).
Wang et al., "Structure-Activity and High-Content Imaging Analyses of Novel Tubulysins," Chem. Biol. Drug Des., 70, pp. 75-86, (2007).
Wayua et al., "Selective Tumor Targeting of Desacetyl Vinblastine Hydrazide and Tubulysin B via Conjugation to a Cholecystokinin 2 Receptor (CCK2R) Ligand," Mol. Pharm., 12(7), pp. 2477-2483, (Jul. 6, 2015).
Wipf et al., "Synthesis of the Tubuvaline-Tubuphenylalanine (Tuv-Tup) Fragment of Tubulysin," Org. Lett., 6(22), pp. 4057-4060, (2004).
Wipf et al., "Total Synthesis of N14-Desacetoxytubulysin H," Org. Lett., 9(8), pp. 1605-1607, (2007).
Xiangming et al., "Recent Advances in the Synthesis of Tubulysins," Mini-Reviews in Medicinal Chemistry, 13(11), pp. 1572-1578, (2013).
Yang et al., "Design, Synthesis, and Biological Activities of Triazole Tubulysin V Analogue," Tetrahedron Letters, 54, pp. 2986-2988, (2013).
Yang et al., "Total Synthesis of Tubulysin U and Its C-4 Epimer," Chem. Asian J., 8, pp. 1213-1222, (2013).
Harlow, E. et al. (1988). Antibodies: A Laboratory Manual, p. 676.
International Preliminary Report on Patentability, dated Jun. 5, 2018, for PCT Application No. PCT/US2016/064834, filed Dec. 2, 2016, 5 pages.
International Preliminary Report on Patentability, dated Mar. 23, 2017, for PCT Application No. PCT/US2015/49494, filed Sep. 10, 2015, 11 pages.
International Search Report and Written Opinion, dated Dec. 11, 2015, for PCT Application No. PCT/US2015/49494, filed Sep. 10, 2015, 19 pages.
International Search Report and Written Opinion, dated Feb. 3, 2017, for PCT Application No. PCT/US2016/064834, filed Dec. 2, 2016, 11 pages.
Schmidt, F. et al. (Jun. 2001, e-pub, May 10, 2001). "Cancer Chemotherapy: A Paclitaxel Prodrug for ADEPT (Antibody-Directed Enzyme Prodrug Therapy," Eur. J. Org, Chem. pp. 2129-2134.
Turk, V. et al. (2012, e-pub. Oct. 12, 2011). "Cysteine Cathepsins: From Structure, Function, and Regulations to New Frontiers," Biochimica et Biophysica Acta 1824:68-88.
Vlahov, I.R. et al. (Jun. 6, 2012). "Engineering Folate-Drug Conjugates to Target Cancer: From Chemistry to Clinic". Bioconjugate Chemistry 23:1357-1369.
Lyon. R.P. et al. (Jul. 2015. e-pub. Jun. 15, 2015). "Reducing Hydrophobicity of Homogeneous Antibody-Drug Conjugates Improves Pharmacokinetics and Therapeutic Index," Nature Biotechnology 33(7):733-736.

(56) References Cited

OTHER PUBLICATIONS

Behrens, C.R. et al. (2014, e-pub. Sep. 27, 2013). "Methods For Site-Specific Drug Conjugation To Antibodies," mAB 6(1):46-53.
Beidler, C.B. et al. (Dec. 1, 1988). "Cloning and High Level Expression Of A Chimeric Antibody With Specificity For Human Carcinoembryonic Antigen," J. Immunol. 141 (11):4053-4060.
Better, M. et al. (May 20, 1988). "*Escherichia coli* Secretion of An Active Chimerica Antibody Fragment," Science 240:1041-1043.
Blencowe, C.A. etal, (2011). "Self-immoiative Linkers in Polymeric Delivery Systems," Polymer Chem 2:773-790.
Doronina, S.O. et al. (Jan. 2006). "Enhanced Activity Of Monomethylauristatin F Through Monoclonal Antibody Delivery: Effects Of Linker Technology On Efficacy And Toxicity," Bioconjug. Chem. 17(1):114-124,.
Fridkin, M. et al. (1974). "Peptide Synthesis" Ann. Rev Biochem. 43:419-443.
Gaertner, H.F. et al. (Mar. 11, 1994). "Chemo-Enzymic Backbone Engineering of Proteins," J. Biol. Chem. 269 (10)7224-7230.
Gamage, S.A. et al. (2002, e-pub. Jan. 8, 2002). "Structure-Activity Relationships For Pyrido-, Imidazo-, Pyrazaio-, Pyrazino-, and Pyrrolophenazinecarboxamidies As Topoisomerase-Targeted Anticancer Agents," J. Med. Chem. 45(3)740-743.
Goodson, R.J. et al. (Apr. 1990). Site-Directed Pegylation of Recombinatnt Interleukin-2 At Its Glycosylation Site, Bio/technology 8:343-346.
Greenwald, R.B. et al. (1999, e-pub. Aug. 13, 1999), "Drug Delivery Systems Employing 1,4- Or 1,6-Elimination: Poly(Ethylene Glycol) Prodrugs Of Amine-Containlng Compounds," J, Med. Chem. 42:3657-3667.
Han, et al. (2004). "Recent Development Of Peptide Coupling Agents In Organic Synthesis," Tet. 60:2447-2476.
Hay, M.P. et al., (Aug. 2, 1999). "A 2-nitroimidazole Carbamate Prodrug of 5-amino-1-(chloromethyl)-3-[(5,6,7-trimethoxyindol-2-yl)carbonyl]-1,2-dihydro-3H-benz[e]indole (amino-seco-CBI-TMl) for Use With ADEPT and GDEPT," Bioorganic & Medicinal Chemistry Letters 9(15):22 37-2242.
Horwell, D.C. (Apr. 1995). "The 'Peptoid' Approach To The Design Of Non-Peptide, Small Molecule Agonists and Antagonists Of Neuropeptides," Trends Biotechnol. 13(4):132-134.
International Union of Pure and Appiied Chemistry (Nov. 5, 1960). "Definitive Rules for Nomenclature of Organic Chemistry," J. Am. Chem. Soc. 82:5545-5473, 30 pages.
Jones, P.T. et al. (May 29, 1986). "Replacing the Complementarity-Determining Regions in a Human Antibody With Those From a Mouse," Nature 321:522-525.
Kabat, E.A. et al. (1991). Sequences of Proteins of Immunological Interest, Fifth Edition, National Institute of Health, Bethesda, Md., 10 pages.
Kabat, E.A. et al. (Sep. 1980). "Origins of Antibody Complementarity and Specificity-Hypervariable Regions and the Minigene Hypothesis," J Immunology 125(3)1961-969.
Kondratyuk, T.P. et al. (Feb. 16, 2012). "Novel Marine Phenazines As Potential Cancer Chemopreventive and Anti-inflammatory Agents," Marine Drugs 10(2):451-464.
Kozbor, D. et al. (1983). "The Production of Monoclonal Antibodies From Human Lymphocytes," Immunology Today 4(3):72-79.
Laguzza, B.C. et al. (Mar. 1989). "New Antitumor Monoclonal Antibody-Vinca Conjugates LY203725 and Related Compounds: Design, Preparation, and Respresentative in Vivo Activity," J. Med. Chem. 32(3)1548-555.
Liu, A.Y. et al. (May 1987). "Chimeric Mouse-Human IgG1 Antibody That Can Mediate Lysis of Cancer Cells," Proc. Natl. Acad. Sci. USA 84:3439-3443.
Liu, A.Y. et al. (Nov. 15, 1987). "Production of a Mouse-Human Chimeric Monoclonal Antibody to CD20 With Potent Fc-Dependent Biologic Activity," J. Immunol. 139(10):3521-3526,.
Malik, F. et al. (Sep. 1992). "Polyethylene glycol (PEG)-Modified Granulocyte-Macrophage Colony-Stimulating Factor (GM-CSF) With Conserved Biological Activity," Exp. Hematol. 20(8):1028-1035.

Mekapati S.B. et al. (2001). "QSAR of Anticancer Compounds: Bis(11-ox0-11H-indeno[1,2-b]quinoline-6-carboxamides), Bis(phenazine-l-carboxamides), and Bis(naphthalimides)," Bioorg. Med. Chem. 9(11):2757-2762.
Moorthy et al. (2014). "Fused Aryl-Phenazines—Scaffold For The Development Of 15 Bioactive Molecules," Curr. Drug Targets 15(7):681-688.
Morrison, S.L. (Sep. 1985). "Transfectomas Provide Novel Chimeric Antibodies," Science 229 (4719):1202-1207.
Nishimura, Y. et al. (Feb. 15, 1987). "Recombinant Human-Mouse Chimeric Monoclonal Antibody Specific For Common Acute Lymphocytic Leukemia Antigen," Cancer. Res. 47(4)1999-1005.
Ol V.T. et al. (1986). "Chimeric Antibodies," Bio Techniques 4:214-219.
Olsson, L. et al, (1983), "[1] Human-Human Monoclonal Antibody-Producing Hlybrldomas: Technical Aspects," Meth Enzymol. 92:3-16.
Paleva, I.K. et al. (2013). "Interactions Of The Multidrug Resistance Modulators Tariquidar and Elacridar and Their Analogues With P-Glycoprotein," Chem. Med. Chem. 8:1701-1713,.
Rose, K. et al. (May-Jun. 1991). "Preparation Of Well-Defined Protein Conjugates Using Enzyme-Assisted Reverse Proteolysis," Bioconjugate Chem. 2(3):1 54-159.
Schmidt, M.M. et al., (Oct. 2009). "A Modeling Analysis of the Effects of Molecular Size and Binding Affinity on Tumor Targeting," Mol. Cancer Ther. 8(10):2861-2871.
Schmitt et al. (1998)."Synthesis Of Dolastatin 15 Mimetic Peptoids," Bioorg. Med. Chem. Lett. 8(4):385-383.
Schwartz, A. et al. (1990). "Enzymatic C-Terminal Biotinylation Of Proteins," Methods Enzymol. 184:160-162.
Shankar, S.P. et al. (2013). "Synthesis And Structure-Activity Relationship Studies Of Novel Tubulysin U Analogs-Effect On Cytotoxicity Of Structural Variations In The Tubuvaline Fragment," Org. Biomol, Chem. 11:2273-2287.
Shaw, D.R. et al. (Dec. 7, 1988). "Mouse/Human Chimeric Antibodies To A Tumor-Associated Antigen: Biologic Activily Of The Four Human IgG Subclasses," J. Natl. Cancer Inst. 80(19):1553-1559.
Simon, R.J. et al. (Oct. 1992). "Peptoids: A Modular Approach to Drug Discovery," Proc. Nat'l. Acad. Sci. USA 89 (20):9367-9371.
Sun, L.K. et al. (Jan. 1987). "Chimeric Antibody With Human Constant Regions and Mouse Variable Regions Directed Against Carcinoma-Associated Antigen 17-1A," Proc, Natl. Acad. Sci. USA 84(1):214-218.
Teng, N.N.H. et al. (Dec. 1983). "Construction and Testing of Mouse-Human Heteromyelomas For Human Monoclonal Antibody Production," Proc. Natl. Acad. Sci, USA, 80:7308-7312.
Verhoeyan. M. et al. (Mar. 25, 1988). "Reshaping Human Antibodies: Grafting an Antilysozyme Activity," Science 239:1534-1536.
Veronese, F.M. (2001). "Peptide and Protein PEGylation A Review Of Problems and Solutions," Biomaterials 22:405-417.
Veronese, F.M. et al. (Apr. 1985). "Surface Modification Of Proteins: Activation Of Monomethoxy-Polyethylene Glycols By Phenylchloroformates and Modification Of Ribonuclease and Superoxide Dismutase," Appl. Biochem. Bioechnol 11(2):141-152.
Vicker, N. et al. (2002, e-pub. Jan. 8, 2002)."Novel Angular Benzophenazines: Dual Topoisomerase I and Topoisomerase II Inhibitors As Potential Anticancer Agents," J. Med. Chem. 45(3);721-739,.
Wood, C.R. et al. (Apr. 10, 1985). "The Synthesis and in vivo Assembly of Functional Antibodies in Yeast," Nature 314(6010):446-449.
Xia et al. (2012). "Drug Efflux and Multidrug Resistance in Acute Leukemia: Therapeutic Impact and Novel Approaches To Mediation," Mol. Pharmacol. 82(6):1008-1021.
Yang, P. et al. (2005, e-pub. Aug. 22, 2005). "Novel Synthetic Isoquinolino[ 5,4-ab]Phenazines: Inhibition Toward Topoisomerase I, Antitumor and DNA Photo-Cleaving Activities," Bioorg. Med. Chem. 13(21):5909-5914.
Zhuo, S.-T. et al. (2013). "Synthesis and Biological Evaluation Of Benzo[a]Phenazine Derivatives As A Dual Inhibitor Of Topoisomerase I and II," Org. Biomol. Chem. 11(24):3989-4005.

(56) References Cited

OTHER PUBLICATIONS

Zinzi, L. et al. (Jan. 2014). "Small and Innovative Molecules As New Strategy To Revert MDR," Front. Oncol. 4 (2):1-12.
Staben, L.R. et al. (Dec. 2016, e-pub. Oct. 17, 2016). "Targeted Drug Delivery Through the Traceless Release of Tertiary and Heteroaryl Amines From Antibody-Drug Conjugates," Nature Chemistry 8:1112-1119.

* cited by examiner

CONJUGATES OF QUATERNIZED TUBULYSIN COMPOUNDS

CROSS REFERENCE TO RELATED APPLICATIONS

This application is a U.S. national stage filing under 35 USC § 371 of International Application No. PCT/US2016/064834, filed Dec. 2, 2016, which application claims benefit of priority to U.S. Appl. Ser. No. 62/263,578, filed Dec. 4, 2015, U.S. Appl. Ser. No. 62/263,587, filed Dec. 4, 2015, U.S. Appl. Ser. No. 62/309,448, filed Mar. 16, 2016, and U.S. Appl. Ser. No. 62/309,462, filed Mar. 17, 2016, all of which are incorporated by reference herein in their entireties.

BACKGROUND OF THE INVENTION

The invention relates to ligand-drug conjugates (LDCs) for targeted delivery of tubulysin compounds to abnormal cells associated with a given disease state or to the vicinity of such cells. The targeting ligand of such an LDC selectively exposes abnormal cells, in contrast to normal cells distant from the abnormal cells, to the tubulysin compound. That selective exposure is accomplished by concentrating the compound at the desired site of action as a result binding of the targeting ligand of the LDC on, or in the vicinity of, the abnormal cells. As a result, exposure of distant normal cells to the tubulysin compound is reduced, thus reducing undesired side effects due to the cytotoxicity of the tubulysin compound while reducing the contribution of abnormal cells to the disease state as a result of that cytotoxicity.

In general, the design of an LDC involves consideration of a variety of factors including the requirement that the drug has a site for attachment to a linker moiety that joins the drug to the targeting ligand and is capable of releasing the drug at the target site. In one approach, tubulysin compounds have previously been incorporated into LDCs through covalent attachment of a linker moiety to the C-terminal component of a tubulysin compound, which usually is tubuphenylalanine (Tup) or tubutyrosine (Tut), either through its carboxylic acid moiety that has been transformed to a hydrazide functional group or through the C-terminal component's phenyl moiety through an amino substituent introduced into that moiety. In another approach, attachment of a linker moiety is to the N-terminal component, which in naturally-occurring tubulysins is D-N-methylpipecolic acid (D-Mep), after removal of its methyl substituent. In both approaches a modified tubulysin compound is released with a significant loss of cytotoxicity in comparison to the parent compound, which reduces its effectiveness as a therapeutic compound.

Because of the difficulty in incorporating a tubulysin compound into a LDC that will conditionally release that compound in unaltered form so as to retain its cytotoxic activity, there is a need in the art for such conjugates that use the tertiary amine nitrogen of a tubulysin's N-terminal component as the site of conjugation in order for release of fully active tubulysin compound at the targeted site of action. There is also a need to mask the hydrophobicity of a hydrophobic tubulysin compound within a LDC to allow for increased loading of the compound to the LDC's targeting Ligand Unit so as to increase the amount of tubulysin compound delivered to the desired site of action while diminishing aggregation resulting in elimination of the LDC and to rectify the loss of the acetate moiety in the tubuvaline (Tuv) component in vivo. Either event alone or in combination diminishes the efficacy of the administered LDC.

SUMMARY OF THE INVENTION

Principle embodiments of the invention are Ligand Drug Conjugate (LDC) compositions, wherein a LDC composition is represented by the structure of Formula 1A

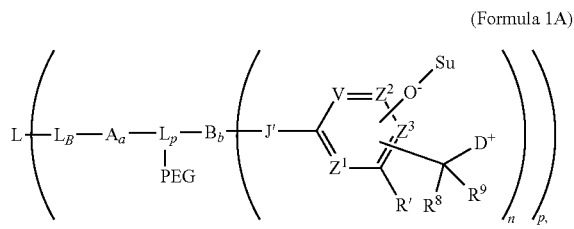

(Formula 1A)

wherein L is a Ligand Unit (L); $L_B$ is a Ligand Covalent Binding Unit; $L_P$ is a Parallel Connector Unit; PEG is a Polyethylene Glycol Unit; subscript a is 0 or 1; subscript b is 0 or 1; A is a first optional Stretcher Unit so that subscript a is 0 when A is absent or A is present so that subscript a is 1 and is optionally comprised of two, three or four independently selected subunits ($A_1$, $A_2$, $A_3$, $A_4$); B is an Branching Unit or a second optional Stretcher Unit ($A_O$) so that subscript b is 0 when B is absent or B is present so that subscript b is 1 and is optionally comprised of two, three or four subunits independently of A; subscript n is 1, 2, 3 or 4, provided that subscript b is 1 and B is a Branching when subscript n is 2, 3 or 4 and subscript b is 0 or 1 so that B is $A_O$ when subscript b is 1 and subscript n is 1; Su is a carbohydrate moiety; —O'— represents an oxygen atom of an O-glycosidic bond cleavable by a glycosidase; -J'- represents a heteroatom, optionally substituted when nitrogen; V, $Z^1$, $Z^2$ and $Z^3$ are =N— or =C($R^{24}$)—, wherein $R^{24}$ is hydrogen, or alkyl, alkenyl or alkynyl, optionally substituted, or halogen, —$NO_2$, —CN or other electron withdrawing group, or —$OCH_3$ or other an electron donating group, —O'-Su, or —C($R^8$)($R^9$)-$D^+$, wherein at least two of V, $Z^1$, $Z^2$ and $Z^3$ are =C($R^{24}$)—, provided, one any only one $R^{24}$ is —C($R^8$)($R^9$)-$D^+$ so that —C($R^8$)($R^9$)-$D^+$ is bonded to one of V, $Z^1$, $Z^2$, $Z^3$ when that variable group is =C($R^{24}$)— and one and only one other $R^{24}$ is —O'-Su so that —O'-Su is bonded to another one of V, $Z^1$, $Z^2$, $Z^3$ when that variable group is =C($R^{24}$)—, and the —O'-Su and —C($R^8$)($R^9$)-$D^+$ substituents are ortho or para to each other; $R^8$ and $R^9$ independently are hydrogen, alkyl, alkenyl or alkynyl, optionally substituted, or aryl or heteroaryl, optionally substituted; R' is hydrogen or is halogen, —$NO_2$, —CN or other electron withdrawing group; $D^+$ is a quaternized tubulysin Drug Unit; subscript p is a number ranging from 1 to 24; and wherein said glycosidase cleavage initiates release of a tubulysin therapeutic compound (D) from a Ligand Drug Conjugate compound of the composition.

In some aspects, the Ligand Unit is that of an antibody, thereby defining an antibody drug conjugate (ADC) having an antibody Ligand Unit, and the targeted moiety to which the antibody Ligand Unit is capable of binding is an cell-surface antigen of targeted abnormal cells that is capable of cellular internalization of bound ADC.

Other principle embodiments of the invention provide for Drug Linker compounds having the structure of Formula IA:

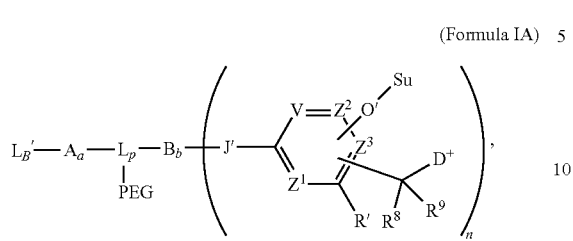

(Formula IA)

wherein $L_B'$ is a Ligand Covalent Binding Unit precursor and the remaining variable groups are as defined for Formula 1A.

In other principle embodiments the invention provide for Ligand Drug Conjugate compositions and Drug Linker compounds having the structures of Formula 1B and Formula IB, respectively:

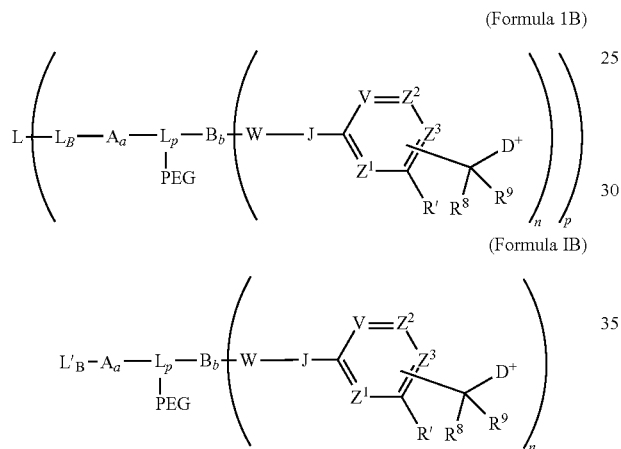

(Formula 1B)

(Formula IB)

wherein V, $Z^1$, $Z^2$ and $Z^3$ are =N— or =C($R^{24}$)—, wherein $R^{24}$ is hydrogen or alkyl, alkenyl or alkynyl, optionally substituted, or halogen, —$NO_2$, —CN or other electron withdrawing group, or —$OCH_3$ or other an electron donating group, or —C($R^8$)($R^9$)-$D^+$, wherein at least one of V, $Z^1$, and $Z^3$ is =C($R^{24}$)—, provided that one any only one $R^{24}$ is —C($R^8$)($R^9$)-$D^+$ so that —C($R^8$)($R^9$)-$D^+$ is bonded to one of V, $Z^1$, and $Z^3$ when that variable group is =C($R^{24}$)—, J represents a heteroatom, optionally substituted when nitrogen; R' is hydrogen or —$OCH_3$ or other electron donating group, W is a peptide comprised of an amino acid sequence covalently attached to J through an amide bond wherein that amide bond is cleavable by a protease and the other variable groups are as defined for Formula 1A and Formula IB; and wherein said protease cleavage initiates release of a tubulysin therapeutic compound (D) from a Ligand Drug Conjugate compound of the composition.

In some aspects, the invention provides for LDC conjugate compositions prepared from contacting a Formula IA compound or Formula IB compound with a targeting moiety having a reactive sulfhydryl, amino or aldehyde moiety under suitable conditions to effect condensation of the reactive moiety with the $L_B'$ moiety of the Formula I compound, wherein $L_B'$ is converted to $L_B$ covalently bonded to a Ligand Unit that corresponds to or incorporates the targeting agent as a result of said contact.

In some aspects, $L_B'$ has the structure of one of:

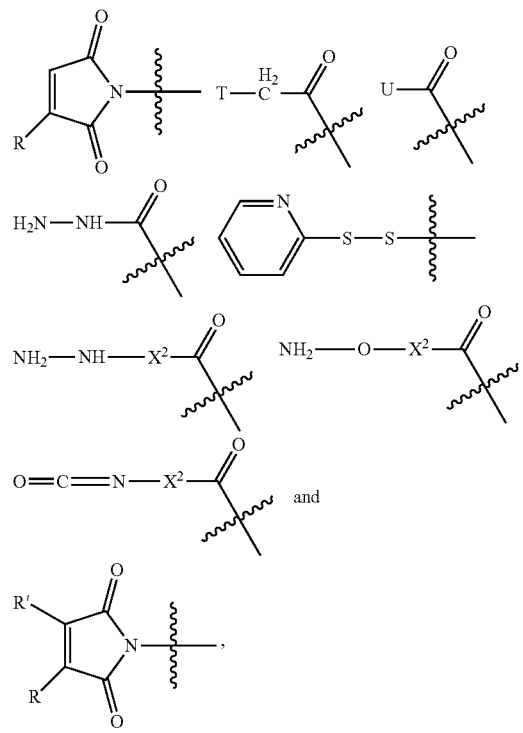

and wherein R is hydrogen or $C_1$-$C_6$ optionally substituted alkyl; R' is hydrogen or halogen or R and R' are independently selected halogen; T is —Cl, —Br, —I, —O-mesyl or —O— tosyl or other sulfonate leaving group; U is —F, —Cl, —Br, —I, —O—N-succinimide, —O-(4-nitrophenyl), —O-pentafluorophenyl, —O-tetrafluorophenyl or —O—C(=O)—$OR^{57}$; $X^2$ is $C_{1-10}$ alkylene, $C_3$-$C_8$-carbocycle, —O—($C_1$-$C_6$ alkyl), -arylene-, $C_1$-$C_{10}$ alkylene-arylene, -arylene-$C_1$-$C_{10}$ alkylene, —$C_1$-$C_{10}$ alkylene-($C_3$-$C_6$-carbocycle)-, —($C_3$-$C_8$ carbocycle)-$C_1$-$C_{10}$ alkylene-, $C_3$-$C_8$-heterocycle, —$C_1$-$C_{10}$ alkylene-($C_3$-$C_8$ heterocyclo)-, —($C_3$-$C_8$-heterocyclo)-$C_1$-$C_{10}$ alkylene, —($CH_2CH_2O)_u$, or —$CH_2CH_2O)_u$—$CH_2$—, wherein u is an integer ranging from 1 to 10 and $R^{57}$ is $C_1$-$C_6$ alkyl or aryl.

DETAILED DESCRIPTION OF THE INVENTION

Definitions

Figure 1:
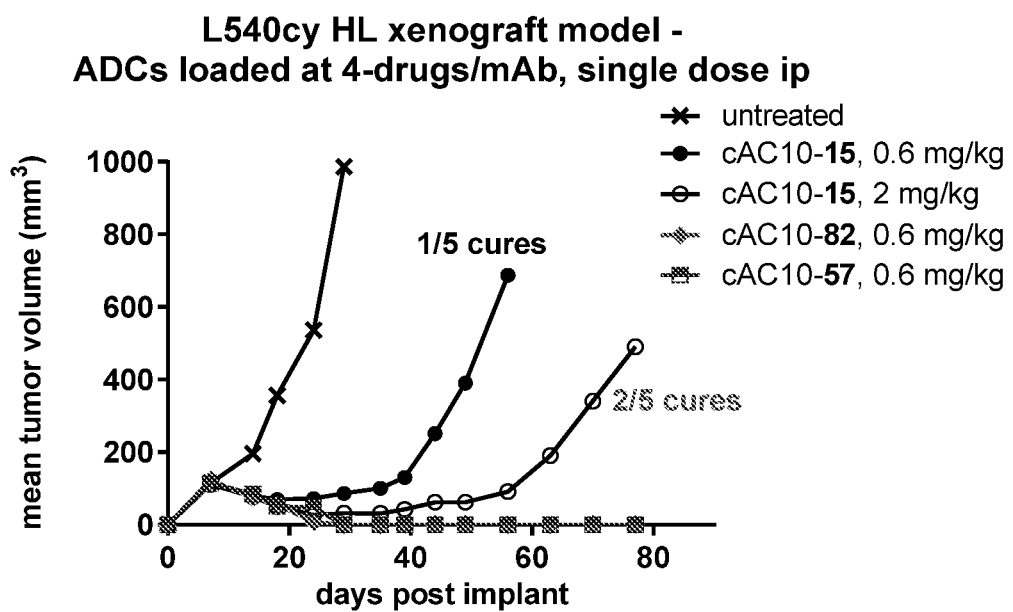
FIG. 1. Mean tumor volume ($mm^3$) versus time (days) post-implant subsequent to treatment of $CD30^+$ L540cy Hodgkin lymphoma xenograft with DAR 4 quaternary amine-linked tubulysin antibody-drug conjugates having quaternized Tubulysin M Drug Units linked via a val-ala dipeptide (cAC10-15) protease-cleavable unit in comparison to conjugation via a β-glucuronidase-cleavable glucuronide unit (cAC10-82), and comparison of antibody-drug conjugates having quaternized Tubulysin M (cAC10-82) and tubulysin ethyl ether (cAC10-57) Drug Units both linked through β-glucuronide-cleavable glucuronide linkers, all of have non-PEGylated Linker Units.

As used herein and unless otherwise stated or implied by context, terms that are used herein have the meanings defined below. Unless otherwise contraindicated or implied, e.g., by including mutually exclusive elements or options, in these definitions and throughout this specification, the terms "a" and "an" mean one or more and the term "or" means and/or where permitted by context. Thus, as used in the specification and the appended claims, the singular forms "a," "an" and "the" include plural referents unless the context clearly dictates otherwise.

At various locations in the present disclosure, e.g., in any disclosed embodiments or in the claims, reference is made to compounds, compositions, or methods that "comprise" one or more specified components, elements or steps. Invention embodiments also specifically include those compounds, compositions, compositions or methods that are or that consist of or that consist essentially of those specified components, elements or steps. The term "comprised of" is used interchangeably with the term "comprising" and are stated as equivalent terms. For example, disclosed compositions, devices, articles of manufacture or methods that "comprise" a component or step are open and they include or read on those compositions or methods plus an additional component(s) or step(s). However, those terms do not encompass unrecited elements that would destroy the functionality of the disclosed compositions, devices, articles of manufacture or methods for its intended purpose. Similarly, disclosed compositions, devices, articles of manufacture or methods that "consist of" a component or step are closed and they would not include or read on those compositions or methods having appreciable amounts of an additional component(s) or an additional step(s). Furthermore, use of the term "including", as well as other forms, such as "include", "includes," and "included", is not limiting. Finally, the term "consisting essentially of" admits for the inclusion of unrecited elements that have no material effect on the functionality of the disclosed compositions, devices, articles of manufacture or methods for its intended purpose and is further defined herein. The section headings used herein are for organizational purposes only and are not to be construed as limiting the subject matter described therein. Unless otherwise indicated, conventional methods of mass spectroscopy, NMR, HPLC, protein chemistry, biochemistry, recombinant DNA techniques and pharmacology are employed.

"About" as used herein when used in connection with a numeric value or range of values provided to describe a particular property of a compound or composition indicate that the value or range of values may deviate to an extent deemed reasonable to one of ordinary skill in the art while still describing the particular property. Reasonable deviations include those that are within the accuracy or precision of the instrument(s) used in measuring, determining or deriving the particular property. Specifically, the term "about" when used in this context, indicate that the numeric value or range of values may vary by 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1% or 0.01% of the recited value or range of values, typically by 10% to 0.5%, more typically by 5% to 1%, while still describing the particular property.

"Essentially retains", "essentially retaining and like terms as used herein refers to a property, characteristic or activity of a compound or composition or moiety thereof that has not detectably changed or is within experimental error of determination of that same activity, characteristic or property of another compound or composition or moiety from which it was derived.

"Negligibly" or "negligible" as used herein is an amount of an impurity below the level of quantification by HPLC analysis and if present represents from about 0.5% to about 0.1 w/w % of the composition that it contaminates. Depending on context those terms may also mean that no statistically significant difference is observed between measured values or outcomes or within experimental error of the instrumentation used to obtain those values. Negligible differences in values of a parameter determined experimentally do not imply that an impurity characterized by that parameter is present in negligible amount.

"Substantially retains" as used herein refers to a measured value of a physical property of a compound or composition or moiety thereof that is statistically different of the determination of that same physical property of another compound or composition or moiety from which it was derived, but which such difference does not translate it a statistically significant difference in biological activity in a suitable biological test system for evaluating that activity (i.e., biological activity is essentially retained) or which has no biological consequence. Thus the phrase "substantially retains" is made in reference to the effect that a physical property of a compound or composition has on a biological activity that is explicitly associated with that property.

"Predominately containing", "predominately having" and like terms refers to the major component of a mixture. When the mixture is of two components, then the major component represents more than 50% by weight of the mixture. With a mixture of three or more components the predominant component is the one present in greatest amount in the mixture and may or may not represent a majority of the mass of the mixture.

The term "electron-withdrawing group" as the term is used herein refers to a functional group or electronegative atom that draws electron density away from an atom to which it is bonded either inductively and/or through resonance, whichever is more dominant (i.e., a functional group or atom may be electron donating through resonance but may overall be electron withdrawing inductively), and tends to stabilize anions or electron rich moieties. The electron withdrawing effect is typically transmitted inductively, albeit in attenuated form, to other atoms attached to the bonded atom that has been made electron deficient by the electron withdrawing group (EWG) thus affecting the electrophilicity of a more remote reactive center. Exemplary electron withdrawing groups include, but are not limited to, —C(=O), —CN, —NO$_2$, —CX$_3$, —X, —C(=O)OR', —C(=O)NH$_2$, —C(=O)N(R')R$^{op}$, —C(=O)R', —C(=O)X, —S(=O)$_2$R$^{op}$, —S(=O)$_2$OR', —SO$_3$H$_2$, —S(=O)$_2$NH$_2$, —S(=O)$_2$N(R')R$^{op}$, —PO$_3$H$_2$, —P(=O)(OR')(OR$^P$)$_2$, —NO, —NH$_2$, —NH(R')(R$^{op}$), —N(R$^{op}$)$_3{}^+$, and salts thereof, wherein X is —F, —Br, —Cl, or —I, and R$^{op}$ is, at each occurrence, independently selected from a group previously described for optional substituents and is sometimes selected from the group consisting of C$_1$-C$_6$ alkyl and phenyl and R' is selected from a group previously described for optional substituents and is sometimes a C$_1$-C$_6$ alkyl. Exemplary EWGs can also include aryl groups (e.g., phenyl) depending on substitution and certain heteroaryl groups (e.g., pyridine). Thus, the term "electron withdrawing group" also includes aryls or heteroaryls that are further substituted with electron withdrawing groups. Typically, electron withdrawing groups are —C(=O), —CN, —NO$_2$, —CX$_3$, and —X, wherein X is halogen. Depending on their substituents, an unsaturated alkyl moiety may also be an electron withdrawing group.

The term "electron donating group" refers to a functional group or electropositive atom that increases electron density of an atom to which it is bonded either inductively and/or through resonance, whichever is more dominant (i.e., a functional group or atom may be electron withdrawing inductively but may overall be electron donating through resonance), and tends to stabilize cations or electron poor systems. The electron donating effect is typically transmitted through resonance to other atoms attached to the bonded atom that has been made electron rich by the electron donating group (EDG) thus affecting the nucleophilicity of a more remote reactive center. Exemplary electron donating groups include, but are not limited to, —OH, —OR', —NH$_2$, —NHR' and N(R')$_2$, wherein each R' is an independently selected alkyl, typically C$_1$-C$_6$ alkyl. Depending on their substituents, an aryl, heteroaryl or unsaturated alkyl moiety may also be an electron donating group.

"Moiety" as used herein means a specified segment, fragment or functional group of a molecule or compound. Chemical moieties are sometimes indicated as chemical entities that are embedded in or appended (i.e., a substituent or variable group) to a molecule, compound or chemical formula.

For any substituent group or moiety described herein by a given range of carbon atoms, the designated range means that any individual number of carbon atoms is described. Thus, reference to, e.g., "optionally substituted C$_1$-C$_4$ alkyl", "optionally substituted alkenyl C$_2$-C$_6$ alkenyl", "optionally substituted C$_3$-C$_8$ heterocycle" specifically means that a 1, 2, 3 or 4 carbon optionally substituted alkyl moiety as defined herein is present, or a 2, 3, 4, 5 or 6 carbon alkenyl, a 3, 4, 5, 6, 7 or 8 membered heterocycle or a 3, 4, 5, 6, 7 or 8 carbon optionally substituted alkenyl moiety as defined herein is present. All such numerical designations are expressly intended to disclose all of the individual carbon atom groups; and thus "optionally substituted C$_1$-C$_4$ alkyl" includes, methyl, ethyl, 3 carbon alkyls, and 4 carbon alkyls, including all of their positional isomers, whether substituted or unsubstituted. Thus, when an alkyl moiety is substituted, the numerical designations refer to an unsubstituted base moiety and are not intended to include carbon atoms that may be present in the substituents of that base moiety. For esters, carbonates, carbamates and ureas as defined herein that are identified by a given range of carbon atoms, the designated range includes the carbonyl carbon of the respective functional group. Thus, an C$_1$ ester refers to a formate ester, a C$_2$ ester refers to an acetate ester and an unsubstituted C$_1$ urea refers to NH$_2$(C=O)NH$_2$.

The organic substituents, moieties and groups described herein, and for other any other moieties described herein, usually will exclude unstable moieties except where such unstable moieties are transient species that one can use to make a compound with sufficient chemical stability for the one or more of the uses described herein. Substituents, moieties or groups by operation of the definitions provided herein that results in those having a pentavalent carbon are specifically excluded.

"Alkyl" as used herein by itself or as part of another term refers to methyl or a collection of carbon atoms, wherein one or more of the carbon atoms is saturated (i.e., is comprised of one or more $sp^3$ carbons) that are covalently linked together in normal, secondary, tertiary or cyclic arrangements, i.e., in a linear, branched, cyclic arrangement or some combination thereof. When the contiguous saturated carbon atoms are in a cyclic arrangement such alkyl moieties are sometimes referred to as cycloalkyl as defined herein. Saturated alkyl substituents contain saturated carbon atoms (i.e., $sp^3$ carbons) and no aromatic, $sp^2$ or sp carbon atoms (i.e., is not substituted with unsaturated, aromatic and heteroaromatic moieties). Unsaturated alkyl substituents are alkyl moieties or groups that contain moieties as described herein for alkenyl, alkynyl, aryl and heteroaryl moieties.

Thus, unless otherwise indicated, the term "alkyl" will indicate a saturated non-cyclic hydrocarbon radical, optionally substituted with one or more cycloalkyl or unsaturated, aromatic or heteroaromatic moieties or some combination thereof, wherein the saturated hydrocarbon radical has the indicated number of covalently linked saturated carbon atoms (e.g., "$C_1$-$C_6$ alkyl" or "$C_1$-$C_6$ alkyl" means an alkyl moiety or group containing 1, 2, 3, 4, 5 or 6 contiguous non-cyclic saturated carbon atoms and "$C_1$-$C_8$ alkyl" refers to an alkyl moiety or group having 1, 2, 3, 4, 5, 6, 7 or 8 contiguous saturated non-cyclic carbon atoms). The number of saturated carbon atoms in an alkyl moiety or group can vary and typically is 1-50, 1-30 or 1-20, and more typically is 1-8 or 1-6. Typically, alkyl will refer to a saturated $C_1$-$C_8$ alkyl moiety, or more typically is a $C_1$-$C_6$ or $C_1$-$C_4$ alkyl moiety with the latter sometimes referred to as lower alkyl. When the number of carbon atoms is not indicated, the alkyl moiety or group has from 1 to 8 carbon atoms.

When referring to an alkyl moiety or group as an alkyl substituent, that alkyl substituent to a Markush structure or another organic moiety with which it is associated is that chain of contiguous saturated carbon atoms covalently attached to the structure or moiety through a $sp^3$ carbon of the alkyl substituent. An alkyl substituent, as used herein, therefore contains at least one saturated moiety and may also contain or be optionally substituted with cycloalkyl, unsaturated alkyl, aromatic or heteroaromatic moieties or groups. Thus, an alkyl substituent may additionally comprise one, two, three or more independently selected double bonds, triple bonds or cycloalkyl, aromatic or heteroaromatic moieties or some combination thereof, typically one double bond, one triple bond or is substituted with one cycloalkyl, aromatic or heteroaromatic moiety. When an alkyl substituent, moiety or group is specified, species include those derived from removing a hydrogen atom from a parent alkane (i.e., is monovalent) and may include methyl, ethyl, 1-propyl (n-propyl), 2-propyl (iso-propyl, —CH(CH$_3$)$_2$), 1-butyl (n-butyl), 2-methyl-1-propyl (iso-butyl, —CH$_2$CH (CH$_3$)$_2$), 2-butyl (sec-butyl, —CH(CH$_3$)CH$_2$CH$_3$), 2-methyl-2-propyl (t-butyl, —C(CH$_3$)$_3$), amyl, isoamyl, sec-amyl and other linear, cyclic and branch chain alkyl moieties.

"Alkylene," as used herein by itself of as part of another term, refers to a saturated, branched, cyclic or straight chain hydrocarbon diradical, substituted or unsubstituted, wherein one or more of the carbon atoms is unsaturated (i.e., is comprised of one or more $sp^3$ carbons), of the stated number of carbon atoms, typically 1-10 carbon atoms, and having two radical centers (i.e., is divalent) derived by the removal of two hydrogen atoms from the same or two different saturated (i.e., $sp^3$) carbon atoms of a parent alkane. Alkylene moieties further include alkyl radicals as described herein in which a hydrogen atom has been removed from a saturated moiety or the radical carbon of an alkyl radical to form a diradical. Typically, alkylene moieties include, but are not limited to, divalent moieties derived from removing a hydrogen atom from saturated carbon atom of a parent alkyl moiety and are exemplified by methylene (—CH$_2$—), 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), and like diradicals. Typically, an alkylene is a branched or straight chain hydrocarbon typically containing only $sp^3$ carbons (i.e., is fully saturated notwithstanding the radical carbon atoms).

"Cycloalkyl" as used herein is a radical of a monocyclic, bicyclic or tricyclic ring system, wherein each of the atoms forming the ring system (i.e., skeletal atoms) is a carbon atom and wherein one or more of these carbon atoms in each ring of the cyclic ring system is saturated (i.e., is comprised of one or more $sp^3$ carbons). Thus, a cycloalkyl is a cyclic arrangement of saturated carbons but may also contain unsaturated carbon atom(s) and therefore its carbocyclic ring may be saturated or partially unsaturated or may be fused with an aromatic ring, wherein the points of fusion to a cycloalkyl and aromatic ring are to adjacent unsaturated carbons of the cycloalkyl moiety, group or substituent and adjacent aromatic carbons of the aromatic ring.

Unless otherwise specified, a cycloalkyl moiety, group or substituent can be substituted with moieties described for alkyl, alkenyl, alkynyl, aryl, arylalkyl, alkylaryl and the like or can be substituted with another cycloalkyl moieties. Cycloalkyl moieties, groups or substituents include cyclopropyl, cyclopentyl, cyclohexyl, adamantly or other cyclic moieties having only carbon atoms. Cycloalkyls further include cyclobutyl, cyclopentenyl, cyclohexenyl, cycloheptyl and cyclooctyl. Depending on its structure, a cycloalkyl substituent can be a monoradical as described above for cycloalkyl moieties or groups or a diradical (i.e., a cycloalkylene, or alternatively, carbocyclo) such as, but not limited to, cyclopropan-1,1-diyl, cyclobutan-1,1-diyl, cyclopentan-1,1-diyl, cyclohexan-1,1-diyl, cyclohexan-1,4-diyl, cycloheptan-1,1-diyl, and the like).

When cycloalkyl is used as a Markush group (i.e., a substituent) the cycloalkyl is attached to a Markush formula or another organic moiety with which it is associated through a carbon that is involved in the carbocyclic ring system of the cycloalkyl group provided that carbon is not an aromatic carbon of a fused ring system. When an unsaturated carbon of an alkene moiety comprising the cycloalkyl substituent is attached to a Markush formula with which it is associated that cycloalkyl is sometimes referred to as a cycloalkenyl substituent. The number of carbon atoms in a cycloalkyl substituent is defined by the total number of skeletal atoms of the ring system. That number can vary and typically ranges from 3 to 50, 1-30 or 1-20, and more typically 3-8 or 3-6 unless otherwise specified, e.g., $C_{3-8}$ cycloalkyl means an cycloalkyl substituent, moiety or group containing 3, 4, 5, 6, 7 or 8 carbocyclic carbon atoms and $C_{3-6}$ cycloalkyl means an cycloalkyl substituent, moiety or group containing 3, 4, 5 or 6 carbocyclic carbon atoms. Therefore cycloalkyl substituents, moieties or groups usually have 3, 4, 5, 6, 7, 8 carbon atoms in its carbocyclic ring system and may contain exo or endo-cyclic double bonds or endo-cyclic triple bonds or a combination of both wherein the endo-cyclic double or triple bonds, or the combination of both, do not form a cyclic conjugated system of 4n+2 electrons. A bicyclic ring system may share one (i.e., is a spiro ring system) or two carbon atoms and a tricyclic ring system may share a total of 2, 3 or 4 carbon atoms, typically 2 or 3.

"Alkenyl" as used herein means a substituent, moiety or group that comprises one or more double bond moieties (e.g., a —CH═CH— functional group) or 1, 2, 3, 4, 5 or 6 or more, typically 1, 2 or 3 of such moieties and can be substituted with an aryl moiety or group such as benzene, or linked normal, secondary, tertiary or cyclic carbon atoms, i.e., linear, branched, cyclic or any combination thereof unless the alkenyl substituent, moiety or group is a vinyl moiety (e.g., a —CH═CH$_2$ functional group). An alkenyl moiety, group or substituent having multiple double bonds may have the double bonds arranged contiguously (i.e., a 1,3 butadienyl moiety) or non-contiguously with one or more intervening saturated carbon atoms or a combination thereof, provided that a cyclic, contiguous arrangement of double bonds do not form a cyclic conjugated system of 4n+2 electrons (i.e., is not aromatic).

When an alkenyl moiety, group or substituent is specified, species include, by way of example and not limitation, any of the alkyl or cycloalkyl, groups moieties or substituents described herein that has an one or more endo double bonds and monovalent moieties derived from removal of a hydrogen atom from a sp$^2$ carbon of a parent alkene compound. Such monovalent moieties typically include vinyl (—CH═CH$_2$), allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, and other linear, cyclic and branched chained, all carbon-containing moieties containing at least one double bond. When alkenyl is used as a Markush group (i.e., is a substituent) the alkenyl is attached to a Markush formula or another organic moiety with which it is associated through a double-bonded carbon (i.e., an sp$^2$ carbon) of the alkenyl moiety or group. The number of carbon atoms in an alkenyl substituent is defined by the number of sp$^2$ carbon atoms of the alkene functional group that defines it as an alkenyl substituent and the total number of contiguous saturated carbon atoms appended to each of these sp$^2$ carbons. That number can vary and unless otherwise specified ranges from 1 to 50, e.g., typically 1-30 or 1-20, more typically 1-8 or 1-6, when the double bond functional group is exo in a Markush structure, or can vary and ranges from 2 to 50, typically 2-30 or 2-20, more typically 2 to 8 or 2-6, when the double bond functional group is endo to the Markush structure. For example, C$_{2-8}$ alkenyl or C2-8 alkenyl means an alkenyl moiety containing 2, 3, 4, 5, 6, 7 or 8 carbon atoms in which at least two are sp$^2$ carbons in conjugation with each other and C$_{2-6}$ alkenyl or C2-6 alkenyl means an alkenyl moiety containing 2, 3, 4, 5 or 6 carbon atoms in which at least two are sp$^2$ carbons that are in conjugation with each other. Typically, an alkenyl substituent is a C$_2$-C$_6$ or C$_2$-C$_4$ alkenyl moiety having two sp$^2$ carbons that are in conjugation with each other.

"Alkenylene" as used herein by itself of as part of another term, refers to a substituent, moiety or group that comprises one or more double bond moieties, as previously described for alkenyl, of the stated number of carbon atoms, typically 1-10 carbon atoms when the double bond functional group is exo to a larger moiety or 2-10, when the double bond functional group is endo in the alkenylene moiety, and has two radical centers derived by the removal of two hydrogen atoms from the same or two different sp$^2$ carbon atoms of a double bond moiety in a parent alkene. Alkenylene moieties further include alkenyl radicals as described herein in which a hydrogen atom has been removed from the same or different sp$^2$ carbon atom of a double bond moiety of an alkenyl radical to form a diradical, or from a sp$^2$ carbon from a different double bonded moiety to provide another radical carbon. Typically, alkenylene moieties include diradicals having the structure of —C═C— or —C═C—X$^1$—C═C— wherein X$^1$ is absent or is an alkylene as defined herein.

"Aryl" as used here means an organic moiety, substituent or group defined by an aromatic ring system or a fused ring system with no ring heteroatoms comprising 1, 2, 3 or 4 to 6 rings, typically 1 to 3 rings, wherein the rings are composed of only carbon atoms that participate in a cyclically conjugated system of 4n+2 electrons (Hückel rule), typically 6, 10 or 14 electrons some of which may additionally participate in exocyclic conjugation with a heteroatom (cross-conjugated, e.g., quinone). Aryl substituents, moieties or groups are typically formed by six, eight, ten or more aromatic carbon atoms. Aryl substituents, moieties or groups are optionally substituted. Exemplary aryls include C$_6$-C$_{10}$ aryls such as phenyl and naphthalenyl and phenanthryl. As aromaticity in a neutral aryl moiety requires an even number or elections it will be understood that a given range for that moiety will not encompass species with an odd number of aromatic carbons. When aryl is used as a Markush group (i.e., a substituent) the aryl is attached to a Markush formula or another organic moiety with which it is associated through an aromatic carbon of the aryl group. Depending on the structure, an aryl group can be a monoradical (i.e., monovalent) or a diradical (i.e., an arylene group as described herein, which is divalent).

"Arylene," or "heteroarylene" as used herein by itself or as part of another term, is an aryl or heteroaryl moiety, group or substituent as defined herein that forms two covalent bonds (i.e., it is divalent) within a larger moiety, which can be in the ortho, meta, or para configurations or an aromatic diradical moiety. Exemplary arylenes include, but are not limited to, phenyl-1,2-ene, phenyl-1,3-ene, and phenyl-1,4-ene as shown in the following structures:

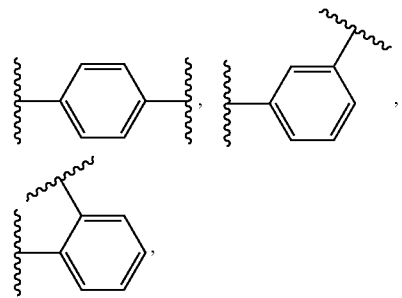

"Arylalkyl" as used herein means a substituent, moiety or group where an aryl moiety is bonded to an alkyl moiety, i.e., -alkyl-aryl, where alkyl and aryl groups are as described above, e.g., —CH$_2$—C$_6$H$_5$, —CH$_2$CH(CH$_3$)—C$_6$H$_5$ or —CH(CH$_2$CH$_2$CH$_3$)—CH$_2$—C$_6$H$_5$. When arylalkyl is used as a Markush group (i.e., a substituent) the alkyl moiety of the arylalkyl is attached to a Markush formula with which it is associated through a sp$^3$ carbon of the alkyl moiety.

"Alkylaryl" as used herein means a substituent, moiety or group where an alkyl moiety is bonded to an aryl moiety, i.e., -aryl-alkyl, where aryl and alkyl groups are as described above, e.g., —$C_6H_4$—$CH_3$ or —$C_6H_4$—$CH_2CH(CH_3)$. When alkylaryl is used as a Markush group (i.e., a substituent) the aryl moiety of the alkylaryl is attached to a Markush formula with which it is associated through an aromatic carbon of the aryl moiety.

"Optionally substituted alkyl", "optionally substituted alkenyl", "optionally substituted alkynyl", "optionally substituted alkylaryl", "optionally substituted arylalkyl", "optionally substituted heterocycle", "optionally substituted aryl", "optionally substituted heteroaryl", "optionally substituted alkylheteroaryl", "optionally substituted heteroarylalkyl" and like terms refer to an alkyl, alkenyl, alkynyl, alkylaryl, arylalkyl heterocycle, aryl, heteroaryl, alkylheteroaryl, heteroarylalkyl, or other substituent, moiety or group as defined or disclosed herein wherein hydrogen atom(s) of that substituent, moiety or group has been optionally replaced with different moiety(ies) or group(s) or wherein an alicyclic carbon chain that comprise one of those substituents, moiety or group is interrupted by replacing carbon atom(s) of that chain with different moiety(ies) or group(s).

Optional substituent(s) replacing hydrogen(s) in any one of the foregoing substituents, moieties or groups include those independently selected from the group consisting of halogen, —CN, —$NH_2$, —OH, —$N(CH_3)_2$, alkyl, fluoroalkyl, heteroalkyl, cycloalkyl, heterocycloalkyl, aryl, heteroaryl, alkoxy, aryloxy, alkylthio, arylthio, alkylsulfoxide, arylsulfoxide, alkylsulfone, and arylsulfone or those selected from the group consisting of halogen, —CN, —$NH_2$, —OH, —$NH(CH_3)$, —$N(CH_3)_2$, —C(=O)OH (i.e., $CO_2H$), —C(=O)O-alkyl (i.e., $CO_2$-alkyl), —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, —S-alkyl and —S(=O)$_2$alkyl.

Typically, optional substituent(s) replacing hydrogen(s) in any one of the foregoing substituents, moieties or groups are independently selected from the group consisting of alkyl, cycloalkyl, aryl, heteroaryl, heteroalicyclic, hydroxyl, alkoxy, aryloxy, cyano, halogen, nitro, haloalkyl, fluoroalkyl, fluoroalkoxy, and amino, including mono-, di- and tri-substituted amino groups, and the protected derivatives thereof, or is selected from the group consisting of halogen, —CN, —$NH_2$, —OH, —NH(CH$_3$), —N(CH$_3$)$_2$, —CH$_3$, —CH$_2$CH$_3$, —CF$_3$, —OCH$_3$, and —OCF$_3$. Typically, any one of the foregoing substituents, moieties or groups that is optionally substituted by replacing one or more its hydrogens has its hydrogen(s) replaced with one or two of the preceding optional substituents, or more typically with one of the preceding optional substituents. An optional substituent on a saturated aliphatic carbon atom within an acyclic or cyclic ring system further includes oxo (=O). For a phenyl or a 6-membered heteroaryl moiety, the arrangement of any two substituents present on the aromatic or heteroaromatic ring can be ortho (o), meta (m), or para (p).

Typically, an optional substituent replacing carbon in an acyclic carbon chain is selected from the group consisting of —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$, —OC(=O)NH—, and —NHC(=O)O—.

Typically, any one of the foregoing substituents, moieties or groups that is optionally substituted by replacing one or more alicyclic carbon atoms has the carbon atom(s) replaced with one or two of the preceding optional substituents, or more typically with one of the preceding optional substituents.

It will be understood that an optional substituent of an alkyl or alkylene substituent, moeity or group excludes alkyl and that an optional substituent of an alkene or alkenylene substituent, moeity or group excludes alkenyl as such substitutions provide moieties falling within the definition of the base moieties so substituted and an optional substituent of an alkyl or alkylene further exclude alkylene or alkenylene as such substitution provide moieties falling with the definition of unsaturated alkyl and unsaturated alkylene, respectively.

"Heterocycle" as used herein means a carbocycle in which one or more, but not all of the skeletal carbon atoms within the carbocyclic ring system are independently replaced by a heteroatom, optionally substituted where permitted, including N, O, S, Se, B, Si, P, wherein two or more heteroatoms may be adjacent to each other or separated by one or more carbon atoms within the same ring system, typically by 1-3 atoms. Those heteroatoms typically include N, O or S. A heterocycle typically contains a total of one to ten heteroatoms in the heterocyclic ring system provided that not all of the skeletal atoms of any one ring in the heterocyclic ring system are heteroatoms, wherein each heteroatom in the ring(s), optionally substituted where permitted, is independently selected from the group consisting of O, S and N, with the proviso that any one ring does not contain two adjacent O or S atoms. When non-aromatic, heterocycles have at least 3 atoms in their ring system, and when aromatic, heterocycles have at least 5 atoms in their ring system. Exemplary heterocycles are provided by Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82:5545-5473 particularly 5566-5573).

When heterocycle is used as a Markush group (i.e., a substituent) the heterocycle is attached to a Markush formula or larger moiety with which it is associated through a carbon or a heteroatom of the heterocycle, where such attachment does not result in an unstable or disallowed formal oxidation state of that carbon or heteroatom. Thus, heterocycles in that context are monovalent moieties sometimes referred to as heterocyclyls that include heteroaryls, which have a heteroaromatic ring system, or a heterocycloalkyl, in which the ring system is non-aromatic, either of which may be fused with a carbocyclic, aryl or heteroaryl moiety and includes phenyl- (i.e., benzo) fused heterocycloalkyl and heteroaryl moieties, provided that when a heteroaryl moiety is fused to a heterocycloalkyl or carbocyclic moiety (i.e., when the heterocyclic portion of the fused ring system is monovalent) the resulting fused ring system is classified as a heteroaryl and when a heterocycloalkyl moiety is fused to a carbocyclic moiety (i.e., when the carbocyclic portion of the fused ring system is monovalent) the resulting fused ring system is classified as a heterocycloalkyl.

Typically, a heterocycloalkyl is a cycloalkyl group, moiety or substituent wherein 1, 2 or 3 carbons of the cycloalkyl chain is replaced with a heteroatom selected from the group consisting of nitrogen, oxygen and sulfur and is a $C_3$-$C_{10}$ heterocycloalkyl, more typically a $C_5$-$C_{10}$ heterocycloalkyl in which the subscript indicates the total number of skeletal atoms (inclusive of its carbon atoms and heteroatoms) of the ring system of the heterocycloalkyl. Non-limiting heterocycloalkyls may contain 0-2 N atoms, 0-2 O atoms or 0-1 S atoms or some combination thereof provided at least one of said heteroatoms is present in the cyclic ring system and may be substituted with one or two oxo (=O) moieties, as in pyrrolidin-2-one. More typically, heterocycloalkyls include pyrrolidinyl, piperidinyl, morpholinyl and piperazinyl.

Heteroaryls typically contain a total one to four heteroatoms in the ring(s) of the heteroaryl ring system, provided that not all of the skeletal atoms of any one ring system in the heteroaryl are heteroatoms, optionally substituted where permitted, and have 0-3 N atoms, 1-3 N atoms or 0-3 N atoms with 0-1 O atoms or 0-1 S atoms, provided that at least one heteroatom is present. A heteroaryl may be monocyclic, bicyclic or polycyclic. Monocyclic heteroaryls include $C_5$-$C_{24}$ heteroaryls, typically $C_5$-$C_{12}$ or $C_5$-$C_6$ heteroaryls, in which the subscript indicates the total number of skeletal atoms (inclusive of its carbon atoms and heteroatoms) of the aromatic ring system of the heteroaryl. More typically a heteroaryl is an aryl moiety wherein one 1, 2 or 3 of the carbon atoms of the aromatic ring(s) of a parent aryl moiety are replaced by a heteroatom, optionally substituted where permitted, including N, O and S, provided that not all of the skeletal atoms of any one aromatic ring system in the aryl moiety are replaced by heteroatoms and more typically are replaced by oxygen (—O—), sulfur (—S—) nitrogen (=N—) or —NR— wherein R is —H, a protecting group or alkyl, aryl or is nitrogen substituted with another organic moiety in a manner which retains the cyclic conjugated system, wherein the nitrogen, sulfur or oxygen heteroatom participates in the conjugated system either through pi-bonding with an adjacent atom in the ring system or through a lone pair of electrons on the heteroatom.

In other aspects, a heteroaryl is monocyclic and typically is one having 5-membered or 6-membered heteroaromatic ring system. A 5-membered heteroaryl is a monocyclic $C_5$-heteroaryl containing 1 to 4 carbon atoms and the requisite number of heteroatoms within its heteroaromatic ring system. A 6-membered heteroaryl is a monocyclic $C_6$ heteroaryl containing 1 to 5 carbon atoms and the requisite number of heteroatoms within its heteroaromatic ring system. Heteroaryls that are 5-membered have four, three, two or one aromatic heteroatom(s), and heteroaryls that are 6-membered include heteroaryls having four, three, two or one aromatic heteroatom(s). $C_5$-heteroaryls are monovalent moieties derived from removing a hydrogen atom from an aromatic carbon or an electron from an aromatic heteroatom, where permitted, from a parent heterocycle compound including pyrrole, furan, thiophene, oxazole, isoxazole, thiazole, isothiazole, imidazole, pyrazole, triazole and tetrazole. $C_6$ heteroaryls, which are 6-membered, are exemplified by monovalent moieties derived from removing a hydrogen atom from an aromatic carbon or an electron from an aromatic heteroatom, where permitted, from the following parent heterocycle compounds: pyridine, pyridazine, pyrimidine, and triazine.

A "5-membered nitrogen-containing heteroaryl", 5-membered nitrogen heteroaryl and like terms refer to a 5-membered heteroaromatic moiety containing at least one nitrogen atom it its aromatic ring system and is a monocyclic heteroaryl or is fused to an aryl or another heteroaryl ring system and may contain one or more other independently selected heteroatoms such as N, O or S. Exemplary 5-membered nitrogen heteroaryls include thiazole, imidazole, oxazole, and triazole and is typically thiazole or oxazole, more typically thiazole.

"Heteroarylalkyl" as used herein means a substituent, moiety or group where a heteroaryl moiety is bonded to an alkyl moiety, i.e., -alkyl-heteroaryl, where alkyl and heteroaryl groups are as described above. When heteroarylalkyl is used as a Markush group (i.e., a substituent) the alkyl moiety of the heteroarylalkyl is attached to a Markush formula with which it is associated through a $sp^3$ carbon of the alkyl moiety.

"Alkylheteroaryl" as used herein means a substituent, moiety or group where a heteroaryl moiety is bonded to an alkyl moiety, i.e., -heteroaryl-alkyl, where heteroaryl and alkyl groups are as described above. When heteroarylalkyl is used as a Markush group (i.e., a substituent) the heteroaryl moiety of the heteroarylalkyl is attached to a Markush formula with which it is associated through a $sp^2$ carbon or heteroatom of the alkyl moiety.

"O-linked moiety", "O-linked substituent" and like terms as used herein refers to a group or substituent that is attached to a moiety directly through an oxygen atom of the group or substituent. An O-linked group may be monovalent including groups such as —OH, acetoxy (i.e., —OC(=O)CH$_3$), acyloxy (i.e., —OC(=O)R$^a$, wherein R$^a$ is —H, optionally substituted alkyl, optionally substituted cycloalkyl, optionally substituted alkenyl, optionally substituted alkynyl, optionally substituted aryl, optionally substituted heteroaryl or optionally substituted heterocycle), and further include monovalent groups such as alkyloxy, optionally substituted, wherein the alkyl moiety is saturated or unsaturated, and other ethers including aryloxy (Aryl-O—), phenoxy (Ph-O—), heteroaryloxy (Heteroaryl-O—), optionally substituted and silyloxy, (i.e., R$_3$SiO—, wherein each R independently is alkyl or aryl, optionally substituted), and —OR$^{PR}$, wherein R$^{PR}$ is a protecting group as previously defined, or an O-linked group may be divalent, i.e., =O or —X—(CH$_2$)$_n$—Y—, wherein X and Y independently are S and O and n is 2 to 3, to form a spiro ring system with the carbon to which X and Y are attached. Typically, a O-linked substituent is a monovalent moiety selected from the group consisting of —OH, —OC(=O)CH$_3$, —OC(=O)R$^a$, $C_1$-$C_6$ saturated alkyl ether and $C_3$-$C_6$ unsaturated ether, wherein R$^a$ is $C_1$-$C_6$ saturated alkyl or $C_3$-$C_6$ unsaturated alkyl or $C_2$-$C_6$ alkenyl or is selected from that group excluding —OH. Other exemplary O-linked substituent are provided by definitions for carbamate, ether and carbonate as disclosed herein "Halogen" or "halo" as used herein means fluorine, chlorine, bromine or iodine and is typically —F or —Cl.

"Protecting group" as used here means a moiety that prevents or reduces the ability of the atom or functional group to which it is linked from participating in unwanted reactions. Typical protecting groups for atoms or functional groups are given in Greene (1999), "Protective groups in organic synthesis, 3$^{rd}$ ed.", Wiley Interscience. Protecting groups for heteroatoms such as oxygen, sulfur and nitrogen are sometime used to minimize or avoid unwanted their reactions with electrophilic compounds. Other times the protecting group is used to reduce or eliminate the nucleophilicity and/or basicity of the unprotected heteroatom. Non-limiting examples of protected oxygen are given by —OR$^{PR}$, wherein R$^{PR}$ is a protecting group for hydroxyl, wherein hydroxyl is typically protected as an ester (e.g., acetate, propionate or benzoate). Other protecting groups for hydroxyl avoid interfering with the nucleophilicity of organometallic reagents or other highly basic reagents, where hydroxyl is typically protected as an ether, including alkyl or heterocycloalkyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —NHR$^{PR}$ or —N(R$^{PR}$)$_2$—, wherein least one of R$^{PR}$ is a nitrogen atom protecting group or both R$^{PR}$ together comprise a protecting group.

A protecting group is a suitable protecting when it is capable of preventing or avoiding unwanted side-reactions or premature loss of the protecting group under reaction conditions required to effect desired chemical transformation elsewhere in the molecule and during purification of the newly formed molecule when desired, and can be removed under conditions that do not adversely affect the structure or stereochemical integrity of that newly formed molecule. By way of example and not limitation, a suitable protecting group may include those previously described for protecting functional groups. In some aspects a suitable protecting group is typically a protecting group used in peptide coupling reactions. For example, a suitable protecting group for nitrogen is an acid-labile carbamate protecting group such as BOC.

"Ester" as used herein means a substituent, moiety or group that contains a —C(=O)—O— structure (i.e., ester functional group) wherein the carbon atom of the structure is not directly connected to another heteroatom and is directly connected to —H or another carbon atom of an organic moiety, and the monovalent oxygen atom is attached to the same organic moiety to provide a lactone or a different organic moiety. Typically, esters comprise or consist of organic moieties containing 1-50 carbon atoms, typically 1-20 carbon atoms or more typically 1-8 carbon atoms and 0 to 10 independently selected heteroatoms (e.g., O, S, N, P, Si, but usually O, S and N), typically 0-2 where the organic moieties are bonded through the —C(O)—O— structure (i.e., through the ester functional group). When an ester is a substituent or variable group of a Markush structure that substituent is bonded to the structure through the monovalent oxygen atom of the ester functional group. In those instances the organic moiety attached to the carbonyl carbon of the ester functional group comprises any one of the organic groups described herein, e.g., $C_1$-$C_{20}$ alkyl moieties, $C_2$-$C_{20}$ alkenyl moieties, $C_2$-$C_{20}$ alkynyl moieties, $C_6$-$C_{24}$ aryl moieties, $C_5$-$C_{24}$ heterocycles or substituted derivatives of any of these, e.g., comprising 1, 2, 3, 4 or more substituents, where each substituent is independently chosen. Exemplary esters include, by way of example and not limitation, acetate, propionate, isopropionate, isobutyrate, butyrate, valerate, isovalerate, caproate, isocaproate, hexanoate, heptanoate, octanoate, phenylacetate esters or benzoate esters or have the structure of —OC(=O)R$^a$ wherein R$^a$ is as defined for acyloxy O-linked substituent and is typically selected from the group consisting of methyl, ethyl, propyl, isopropyl, 3-methyl-prop-1-yl, 3,3-dimethyl-prop-1-yl and vinyl. Ester substituents as disclosed herein are exemplary monovalent 0-linked substituents.

"Ether" as used herein means an organic moiety, group or substituent that comprises 1, 2, 3, 4 or more —O— (i.e., oxy) moieties that are not bonded to carbonyl moiety(ies), usually 1 or 2, wherein no two —O— moieties are immediately adjacent (i.e., directly attached) to each other. Typically, an ether structure is comprised or consists of the formula —O-organic moiety wherein organic moiety is as described for an organic moiety bonded to an ester functional group. More typically, an ether moiety, group or substituent has the formula of —O-organic moiety wherein the organic moiety is as described herein for an optionally substituted alkyl group. When ether is used as a Markush group (i.e., an ether substituent) the oxygen of the ether functional group is attached to a Markush formula with which it is associated. When ether is a used as substituent in a Markush group it is sometimes designated as an "alkoxy" group, which is an exemplary O-linked substituent. Alkoxy includes $C_1$-$C_4$ ether substituents such as, by way of example and not limitation, methoxy, ethoxy, propoxy, isopropoxy, butoxy and allyloxy.

"Amide" or "carboxamide" as used here means an moiety that contains a R—C(=O)N(R)— or —C(=O)N(R)$_2$ structure (i.e., amide or carboxamide or functional group, respectively) with no other heteroatom directly attached to the carbonyl carbon of the structure and where R, independently selected, is hydrogen, a protecting group or an organic moiety as described herein for an organic moiety bonded to an ester functional group and is typically an optionally substituted alkyl group. Typically, hydrogen or an organic moiety, independently selected from R, is bonded to the carboxamide or amide functional group, wherein that organic moiety is also as described herein for an organic moiety bonded to an ester functional group. When bonded to an organic moiety the resulting structure is represented by R—C(=O)N(R)-organic moiety or organic moiety-C(=O)N(R)$_2$. When an amide is recited as a variable for a Markush structure, the amide nitrogen is bonded to that structure. For carboxamide substituents the carbonyl carbon of the amide functional group is bonded to the Markush structure. Amides and carboxamides are typically prepared by condensing an acid halide, such an acid chloride with a molecule containing a primary or secondary amine. Alternatively, amide coupling reactions well-known in the art of peptide synthesis, which oftentimes proceed through an activated ester of a carboxylic acid-containing molecule, are used. Exemplary preparations of amide bonds through peptide coupling methods is provided in Benoiton (2006) Chemistry of peptide synthesis CRC Press, Bodansky "Peptide synthesis: A practical textbook" (1988) Springer-Verlag; Frinkin, M. et al. "Peptide Synthesis" *Ann. Rev. Biochem.* (1974) 43: 419-443. Reagents used in the preparation of activated carboxylic acids is provided in Han, et al. "Recent development of peptide coupling agents in organic synthesis" *Tet.* (2004) 60: 2447-2476.

"Carbonate" as used here means a substituent, moiety or group that contains a —O—C(=O)—O— structure (i.e., carbonate functional group). Typically, carbonate groups as used here comprise or consist of an organic moiety, wherein the organic moiety is as described herein for an organic moiety bonded to an ester functional group, bonded through the —O—C(=O)—O— structure, e.g., organic moiety-O—C(=O)—O—. When carbonate is used as a Markush group (i.e., a substituent) one of the singly bonded oxygen atoms of the carbonate functional group is attached to a Markush formula with which it is associated and the other is bonded to a carbon atom of an organic moiety as previously described for an organic moiety bonded to an ester functional group. In such instances carbonate is an exemplary O-linked substituent.

"Carbamate" or "urethane" as used here means a substituent, moiety or group that contains a carbamate functional represented by —O—C(=O)N(R$^a$)— or —O—C(=O)N(R$^a$)$_2$, and include —O—C(=O)NH(optionally substituted alkyl) or —O—C(=O)N(optionally substituted alkyl)$_2$, which are exemplary carbamate substituents, wherein R$^a$ and optionally substituted alkyl are independently selected wherein R$^a$, independently selected, is hydrogen, a protecting group or an organic moiety, wherein the organic moiety is as described herein for an organic moiety bonded to an ester functional group and is typically an optionally substituted alkyl. Typically, carbamate groups as used herein comprise or consist of an organic moiety, independently selected from $R^a$, wherein the organic moiety is as described herein for an organic moiety bonded to an ester functional group, bonded through the —O—C(=O)—N($R^a$)— structure, wherein the resulting group has the formula of organic moiety-O—C(=O)—N($R^a$)— or —O—C(=O)—N($R^a$)-organic moiety. When carbamate is used as a Markush group (i.e., a substituent), the singly bonded oxygen (O-linked) or nitrogen (N-linked) of the carbamate functional group is attached to a Markush formula with which it is associated. The linkage of the carbamate substituent is either explicitly stated (N- or O-linked) or implicit in the context to which this substituent is referred. O-linked carbamates described herein are exemplary monovalent O-linked substituents.

"Antibody" as used herein is used in the broadest sense and specifically covers intact monoclonal antibodies, polyclonal antibodies, monospecific antibodies, multispecific antibodies (e.g., bispecific antibodies), and antibody fragments that exhibit the desired biological activity provided that the antibody fragment have the requisite number of attachment sites for a drug-linker. The native form of an antibody is a tetramer and consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs." The constant regions may be recognized by and interact with the immune system (see, e.g., Janeway et al., 2001, *Immunol. Biology*, 5th Ed., Garland Publishing, New York). An antibody can be of any type (e.g., IgG, IgE, IgM, IgD, and IgA), class (e.g., IgG1, IgG2, IgG3, IgG4, IgA1 and IgA2) or subclass. The antibody can be derived from any suitable species. In some embodiments, the antibody is of human or murine origin. An antibody can be, for example, human, humanized or chimeric. An antibody or antibody fragment thereof, is an exemplary targeting agent that corresponds to or is incorporated into an LDC of the present invention as an antibody Ligand Unit.

In some aspects an antibody selectively and specifically binds to an epitope on hyper-proliferating cells or hyper-stimulated mammalian cells (i.e., abnormal cells), wherein the epitope is preferentially displayed by or is more characteristic the abnormal cells in contrast to normal cells, or is preferentially displayed by or is more characteristic of normal cells in the vicinity of abnormal cells in contrast to normal cells not localized to the abnormal cells. In those aspects the mammalian cells are typically human cells. Other aspects of antibodies incorporated into Ligand Units are described by embodiments for Ligand-Drug Conjugates "Monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

"Cytotoxic activity" as used herein refers to a cell-killing effect of a drug, Ligand-Drug Conjugate, or an intracellular metabolite of a Ligand-Drug Conjugate. Cytotoxic activity may be expressed as the $IC_{50}$ value, which is the concentration (molar or mass) per unit volume at which half the cells survive.

"Cytostatic activity" as used herein refers to an anti-proliferative effect of a drug, Ligand-Drug Conjugate, or an intracellular metabolite of a Ligand-Drug Conjugate that is not dependent on cell killing but whose effect is due to inhibition of cell division of hyper-proliferating cells, hyper-stimulated immune cells or other abnormal or unwanted cells.

The terms "specific binding" and "specifically binds" mean that an antibody or antibody Ligand Unit in an LDC as the targeting moiety is capable of binding, in a selective or highly selective manner, with its corresponding target antigen and not with a multitude of other antigens. Typically, the antibody or antibody derivative binds with an affinity of at least about $1\times10^{-7}$ M, and preferably $10^{-8}$ M to $10^{-9}$ M, $10^{-10}$ M, $10^{-11}$ M, or $10^{-12}$ M and binds to the predetermined antigen with an affinity that is at least two-fold greater than its affinity for binding to a non-specific antigen (e.g., BSA, casein) other than for a closely-related antigen.

"Ligand-Drug Conjugate" or "LDC" as the term is used herein refers to a construct comprised of a Ligand Unit from a targeting agent and a quaternized tertiary amine-containing Drug Unit ($D^+$) corresponding in structure to a tertiary-amine containing drug that are bonded to each other through a Linker Unit, wherein the LDC selectively binds to a targeted moiety through its targeting Ligand Unit. In some instances, the term LDC is a plurality (i.e., composition) of individual LDC compounds differing primarily by the number of $D^+$ units bonded to each Ligand Unit and/or the location on the Ligand Unit at which the $D^+$ units are bound. In other instances the term LDC applies to an individual member or compound of the composition.

"Targeting agent" as the term is used herein is a moiety corresponding to or incorporated as a Ligand Unit in a Ligand Drug Conjugate so that the Ligand Unit is the targeting moeity of the Conjugate that is capable of binding selectively to a targeted moiety typically present on, within, or in the vicinity of hyper-proliferating cells, hyper-stimulated immune cells or other abnormal or unwanted cells in comparison to other moieties present on, within, or in the vicinity of normal cells where these abnormal or unwanted cells are typically not present. Sometimes a targeted moiety is present on, within, or in the vicinity of abnormal in greater abundance in comparison to normal cells or the environment of normal cells where abnormal cells are typically not present. In some instances the targeting agent is an antibody that specifically binds to an accessible antigen characteristic of an abnormal cell or is an accessible antigen that is particular to the surrounding environment in which these cells are found. In other instances the targeting agent is a ligand that specifically binds to an accessible receptor characteristic of, or in greater abundance on, abnormal cells or other unwanted cells, or is an accessible receptor that is particular to cells of the surrounding environment in which abnormal cells are found. Typically a targeting agent is an antibody as defined herein that binds selectively to a targeted moiety of an abnormal or unwanted mammalian cell, more typically a targeted moiety of an abnormal or unwanted a human cell.

"Target cells" or "targeted cells" as the term is used herein are the intended cells (i.e., abnormal or other unwanted cells) to which an LDC is designed to interact in order to inhibit the proliferation or other unwanted activity of the intended cells. In some instances the targeted cells are hyper-proliferating cells or hyper-activated immune cells, which are exemplary abnormal cells. Typically those abnormal cells are mammalian cells and more typically are human cells. In other instances the targeted cells are within the vicinity of abnormal or unwanted cells so that action of the LDC on the nearby cells has an intended effect on the abnormal or unwanted cells. For example, the nearby cells may be epithelial cells that are characteristic of the abnormal vasculature of a tumor. Targeting of those vascular cells by an LDC will either have a cytotoxic or cytostatic effect on these cells by inhibiting nutrient delivery to the abnormal cells of the tumor or indirectly have a cytotoxic or cytostatic effect on the abnormal cells, and/or have a direct a cytotoxic or cytostatic effect on the abnormal cells by releasing $D^+$ as a tubulysin drug compound (D) in the vicinity of these cells.

"Targeted moiety" as the term is used herein is a moiety preferentially recognized by a targeting agent or Ligand Unit of a Ligand-Drug Conjugate corresponding to or incorporating that targeting agent (i.e., is selectively bound by the Ligand Unit) and is present on, within or in the vicinity of targeted cells. Sometimes the targeted moiety is an antigen accessible to selective binding by an antibody, which is an exemplary targeting agent that corresponds to or is incorporated in a LDC as an antibody Ligand Unit. In those instances, such an antigen is a cell-surface protein present on abnormal cells or other unwanted cells, or is present on cells that are particular to the surrounding environment in which the abnormal or unwanted cells are found, such as vascular cells that are characteristic of the environment of hyper-proliferating cells in a tumor. More typically, the antigen is a cell-surface protein of an abnormal cell or other unwanted cell that is capable of internalization upon binding with its cognate targeting agent or moiety. In other instances the targeting agent is a ligand for an extracellularly accessible cell membrane receptor that may be internalized upon binding of the targeting moiety or is capable of passive or facilitative transport of the LDC targeting the cell-surface receptor so that the receptor is the targeted moiety. In some aspects, the targeted moiety is present on abnormal mammalian cells or on mammalian cells characteristic of the environment of such abnormal cells.

"Antibody-drug conjugate" or "ADC" as the term is used herein refers to a Ligand Drug Conjugate wherein the targeting agent corresponding to or is incorporated into its Ligand Unit is an antibody, thereby defining an antibody Ligand Unit, wherein the antibody Ligand Unit is covalently attached to a quaternized drug unit ($D^+$), typically through an intervening Linker Unit. Oftentimes the term refers to a collection (i.e., population or plurality) of conjugate compound having the same antibody Ligand Unit, quaternized Drug unit, and Linker Unit, but having variable loading and/or distribution of the linker-drug moieties for each antibody (as, for example, when the number of quaternized Drug Units ($D^+$) of any two ADC compounds in a plurality of such compounds is the same but the location of their sites of attachment to the targeting moiety differ). In those instances an ADC is described by the averaged drug loading of the Conjugate compounds. An ADC obtained from the methods described herein have the general structure of Ab-$L_B$-$L_O$-$D^+$ wherein -$L_B$-$L_O$- defines the Linker Unit in which $L_B$ is a ligand covalent binding moiety or Ligand Covalent Binding Unit sometimes referred to as a primary linker ($L_R$), so named because that moiety or unit is required to be present in a Linker Unit of an ADC, and $L_O$ is a secondary linker susceptible to enzymatic (e.g., protease or glycosidase) or non-enzymatic (e.g., reductive or hydrolytic) cleavage. In some instances that cleavage is enhanced in the environment of abnormal cells or occurs subsequent to intracellular internalization of the ADC subsequent to binding of the ADC's targeting antibody Ligand Unit to its cognate antigen; $D^+$ is a quaternized Drug Unit and is typically is derived from quaternization of a tertiary amine-containing drug (D), or corresponds to the quaternized from of D wherein $D^+$ is released as the tertiary amine-containing drug as a result of that enzymatic or non-enzymatic action on $L_O$.

The average number of quaternized Drug Units per antibody Ligand Unit, or fragment thereof, in an ADC composition (i.e., an averaged number for a population of ADC conjugate compounds that differ primarily by the number of conjugated quaternized Drug Units on the antibody Ligand Unit in each of the ADC compounds that are present in that population and/or by their location) when the Linker Units are not branched is designated as p or when the linkers are branched, p is the average number of drug-linker moieties attached to the antibody Ligand Unit. In either context p is a number ranging from about 2 to about 24 or about 2 to about 20 and is typically about 2, about 4, or about 8. In other contexts p represents the number of quaternized Drug Units when the Linker Units are not branched, or the number of quaternized drug linker moieties when the Linker Units are branched, that are covalently bonded to a single antibody Ligand Unit of an ADC within a population of antibody-drug conjugate compounds in which the compounds of that population may primarily differ by the number and/or location of the conjugated quaternized Drug Units or quaternized drug linker moieties in each of the ADC compounds. In that context p is designated as p' and is an integer ranging from 1 to 24 or from 1 to 20, typically from 1 to 12 or 1 to 10, and more typically from 1 to 8.

The average number of quaternized Drugs Units per Ligand Unit in a preparation from a conjugation reaction may be characterized by conventional means such as mass spectroscopy, ELISA assay, HIC and/or HPLC. The quantitative distribution of conjugate compounds in terms of p' may also be determined. In some instances, separation, purification, and characterization of homogeneous Ligand-Drug Conjugate compounds in which p' is a certain value from a Ligand-Drug Conjugate composition from those with other drug loadings may be achieved by means such as reverse phase HPLC or electrophoresis.

"Antigen" is an entity that is capable of selective binding to an unconjugated antibody or a fragment thereof or to an ADC comprising an antibody Ligand Unit corresponding to or incorporating that antibody or fragment thereof. In some aspects, the antigen is an extracellularly-accessible cell-surface protein, glycoprotein, or carbohydrate preferentially displayed by abnormal or other unwanted cells in comparison to normal cells. In some instances the unwanted cells having the antigen are hyper-proliferating cells in a mammal. In other instances, the unwanted cells having the antigen are hyper-activated immune cells in a mammal. In other aspects, the specifically bound antigen is present in the particular environment of hyper-proliferating cells or hyper-activated immune cells in a mammal in contrast to the environment typically experienced by normal cells in the absence of such abnormal cells. In still other aspects the cell-surface antigen is capable of internalization upon selective binding of an ADC compound and is associated with cells that are particular to the environment in which hyper-proliferating or hyper-stimulated immune cells are found in the absence of such abnormal cells. An antigen is an exemplary targeted moiety of an LDC wherein its targeting Ligand Unit corresponds to or incorporates an antibody to a targeted antigen and is capable of preferentially recognizing that antigen through selective binding.

Antigens associated with hyper-proliferating cells that are cell-surface accessible to an ADC include by way of example and not limitation CD19, CD70, CD30, CD33, NTB-A, αvβ6, and CD123.

"Ligand Unit" is a moiety comprising a Ligand Drug Conjugate that is capable of binding selectively to its cognate targeted moiety and is sometimes referred to as the targeting moeity of a LDC. A Ligand Unit includes without limitation those of targeting agents such as receptor ligands, antibodies to cell-surface antigens and transporter substrates. Sometimes, the receptor, antigen or transporter to be bound by a LDC is present in greater abundance on abnormal cells in contrast to normal cells. Other times the receptor, antigen or transporter to be bound by an LDC is present in greater abundance on normal cells that are peculiar to the environment of abnormal cells in contrast to normal cells of the periphery. Various aspects of Ligand Units are further described by the of the embodiments of the invention.

"Ligand covalent binding moiety" or "Ligand Covalent Binding Unit" is a moiety or component of a Linker Unit (LU) in an LDC that is covalently attached to the Ligand Unit that targets the abnormal or unwanted cells or their environment and to the remainder of the Linker Unit and is derived from reaction of the corresponding $L_B'$ moiety or component in a Linker Unit precursor with a targeting agent. For example, when $L_B'$ is comprised of a maleimide moiety, reaction of that moiety with a reactive sulfhydryl group of a targeting agent converts $L_B'$ to $L_B$, which is comprised of a thio substituted succinimide moiety, bound to a Ligand Unit, which corresponds to or incorporates the targeting agent. In another example, when $L_B'$ is comprised of an activated carboxylic acid functional group, reaction of that functional group with an epsilon amino group of a lysine in a targeting agent converts the functional group to an amide, wherein that amide comprises the $L_B$ moiety covalently attached to a Ligand Unit that corresponds to or incorporates that targeting agent. Other $L_B$ moieties or units and their conversion from $L_B'$-containing moieties or units are described in the embodiments of the invention. In some instances a targeting agent is derivatized with a bi-functional molecule to provide an intermediate that is condensed with a ligand covalent binding precursor ($L_B'$) moiety or unit. As a result of that condensation the $L_B$ moiety or unit so formed has atoms attributable to the bi-functional molecule and $L_B'$.

"Ligand covalent binding moiety precursor" or "Ligand Covalent Binding Unit precursor" is a moiety or component of a Linker Unit, or substructure thereof used in the preparation of a Linker Unit, that is capable of covalent binding to a targeting agent during the preparation of an LDC whereupon the ligand binding ($L_B'$) moiety or unit precursor is converted to a ligand covalent binding ($L_B$) moiety or unit covalently attached to a Ligand Unit corresponding to or incorporating the targeting agent. In some aspects a $L_B'$ moiety typically has a functional group capable of reacting with a nucleophile or electrophile native to an antibody or fragment thereof or is introduced into an antibody by chemical transformation or genetic engineering. In some aspect the nucleophile is an N-terminal amino group of a peptide comprising an antibody or the epsilon amino group of a lysine residue of an antibody. In other aspects the nucleophile is a sulfhydryl group of a cysteine residue of an antibody introduced by genetic engineering or from chemical reduction of an interchain disulfide of an antibody. In some aspects the electrophile is an aldehyde introduced by selective oxidation of an antibody's carbohydrate moiety or is a ketone from an unnatural amino acid introduced into an antibody using a genetically engineered tRNA/tRNA synthetase pair. Those and other methods are reviewed by Behrens and Liu "Methods for site-specific drug conjugation to antibodies" *mAB* (2014) 6(1): 46-53.

"Linker Unit" as the term is used herein refers to an organic moiety in a Ligand Drug Conjugate (LDC) intervening between and covalently attached to a quaternized drug unit ($D^+$) and Ligand Unit or to an organic moiety of a Drug Linker compound intervening between and covalently attached to a quaternized drug unit ($D^+$) and a ligand covalent binding precursor ($L_B'$) moiety or unit. Typically, a Linker Unit (LU) of a LDC or Drug Linker compound is comprised of a ligand covalent binding ($L_B$) moiety or unit or a ligand covalent binding precursor ($L_B'$) moiety or unit, respectively, and a secondary linker ($L_O$) as described herein. In some aspects the ligand covalent binding precursor or unit contains a maleimide ($M^1$) moiety. Attachment of the targeting agent through $M^1$ resulting in covalent attachment of the corresponding Ligand Unit to a Linker Unit occurs through a cysteine sulfhydryl group of the targeting agent by Michael addition of the sulfhydryl group sulfur atom to the maleimide ring system of $M^1$. As a result of that addition a succinimide ($M^2$) moiety having a sulfur substituted succinimide ring system is obtained. Subsequent hydrolysis of that ring system, either spontaneously or under controlled conditions, as when that system is part of a self-stabilizing linker ($L_{SS}$) moiety, results in a succinic acid-amide ($M^3$) moiety, which is an exemplary self-stabilized ($L_S$) moiety, as further described herein. Also covalently bonded to $L_B$ or $L_B'$, which are primary linker ($L_R$ moieties), is a secondary linker ($L_O$) moiety, which further intervenes between the Ligand Unit and quaternized Drug Unit ($D^+$) in an LDC or between $L_B'$ and $D^+$ in a Drug Linker compound, wherein covalently bonding to $L_R$ is through intermediacy of an ether, ester, carbonate, urea, disulfide, amide or carbamate functional group, more typically through an ether, amide or carbamate functional group.

"Parallel Connector Unit" as used herein refers to a branched Linker Unit component that connects a PEG Unit in parallel orientation to a quaternized Drug Unit ($D^+$). As used herein, the phrase "parallel orientation", "parallel placement", "parallel connection" and like terms refers to a configuration wherein the parallel-placed or parallel-oriented or parallel-connected components are attached to a parallel connecter unit ($L^P$) in such a manner that each component has one end tethered to $L_P$ and one free end. Typically $L_P$ connects a quaternized Drug Unit ($D^+$) through one or more Linker Unit components, such as $A_O$-W—Y—, - or $A_O$-Y(W')— wherein $A_O$ is optionally present, and a PEG Unit so that the quaternized Drug and PEG Units are in a parallel orientation such that the hydrophobicity of the quaternized Drug Unit is masked to an effective extent by the PEG Unit. Only those PEG Units required for masking hydrophobicity for a given LU-$D^+$ moiety (i.e. quaternized drug linker moiety) need be in parallel orientation to its quaternized Drug Unit, which does not necessarily require all of the quaternized Drug Units and polyethylene glycol (PEG) units connected to $L^P$ be in parallel orientations to one another. Thus, one PEG Unit may effectively mask the hydrophobicity or 1, 2, 3, 4 or more quaternized Drug Units, typically 1 to 4 $D^+$ and more typically 1 or 2 $D^+$.

The term "parallel" is used herein to denote branching of two components of a Ligand-Drug Conjugate (LDC) or Drug Linker compound from a $L^P$ that comprises the LDC or Drug Linker compound and is not being used to denote that the two components are side-by-side in space or have the same distance between them throughout some or their entire lengths. A LDC or Drug Linker compound having a PEG Unit that is in a parallel orientation in relation to a quaternized Drug Unit of the LDC or Drug Linker compound refers to a LDC or Drug Linker compound comprising a PEG Unit having one its termini connected to a component of a Linker Unit (i.e., a Parallel Connector Unit) and one or more free untethered terminus (or termini). The free untethered terminus of the PEG Unit when attached to $L^P$ can take the form, for example, of an unreacted functional group, e.g., alkoxy, carboxylic acid, alkylenecarboxylic acid, alcohol, or other functional group. In instances where a parallel-oriented PEG component is itself branched and thus has multiple ends, it still has only one tethered end to $L^P$. The parallel orientation of the PEG Unit in relationship to $D^+$ also acts to minimize the number of atoms between the Ligand Unit and the Drug Unit as the atoms of the PEG Unit are not interposed between $D^+$ and the Ligand Unit.

An exemplary graphical representation of a LDC having a PEG Unit that is in a parallel (i.e., branched) orientation in relation to the quaternized Drug Unit is as follows:

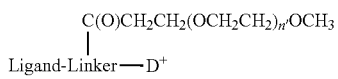

wherein subscript n' ranges from 1 to 24.

"Primary linker" as used is a ligand covalent binding ($L_B$) moiety or unit, or a ligand covalent binding ($L_B'$) precursor moiety or unit, and is present as a component of a Linker Unit of a LDC, or as a component of a $L_B'$-containing moiety such as $L_B'$-$L_O$- or $L_B'$-$L_O$-$D^+$ in a Drug Linker compound. A $L_B'$ primary linker is comprised of a reactive functional group capable of reacting with an electrophilic or nucleophilic functional group of a targeting agent. As a result of that reaction, the targeting agent becomes covalently bonded as a Ligand Unit to $L_B$ of a primary linker through a functional group derived from the reactive functional group of $L_B'$.

"Secondary linker" moiety as used herein refers to an organic moiety in a Linker Unit wherein the secondary linker ($L_O$) is covalently attached to a $L_B$ or $L_B'$ moiety (i.e., a primary linker unit) through intermediacy of a functional group between the $L_B$ or $L_B'$ moiety and the remainder of the Linker Unit to which a quaternized Drug Unit may be covalently attached. In a LDC, the secondary linker is also covalently attached to a quaternized Drug Unit ($D^+$) through the benzylic position of a PAB or PAB-type self-immolating moiety that comprises a self-immolative Spacer unit. In addition to such a Spacer unit (Y), secondary linkers are comprised of a Cleavable (W or W'), wherein W, Y and $D^+$ or W', Y and $D^+$ are arranged either in a linear or orthogonal relationship, respectively, and is further comprised of a -$L^P$(PEG)- moiety and first optional Stretcher unit (A), and/or a Branching Unit, in which the latter may be replaced with a second optional Stretcher Unit ($A_O$) when LU is attached to only one quaternized drug unit ($D^+$). When present, A interconnects $L_B'$, or $L_B$ derived therefrom, with the remainder of the secondary linker through -$L^P$(PEG)-, or through $A_O$, or B, when either is present, or interconnects $D^+$ and -$L^P$(PEG)- through —W—Y— or —Y(W')— when B and $A_O$ are absent.

In an LDC, $L_O$ is comprised of a self-immolative Spacer unit (Y), which contains a self-immolating moiety, and is covalently attached to a Cleavable Unit (W or W') such that cleavage of W or W' under conditions more likely experienced by abnormal cells results in self-destruction of the self-immolating moiety with concomitant release of $D^+$ as a drug compound (D). Alternatively, that cleavage may be affected within the vicinity of those abnormal cells, in comparison to normal cells in their normal environment. Typically, that self-destruction occurs through a 1,6-elimination in an self-immolative moiety as described herein. In those instances a self-immolative moiety of a self-immolative Spacer Unit is attached to a tertiary amine-containing drug through quaternization of that drug's tertiary amine nitrogen.

A secondary linker ($L_O$) when bonded to $D^+$ in a Linker Unit attached to only one $D^+$ is typically represented by the structure of (1) or (2):

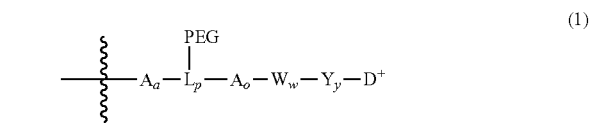

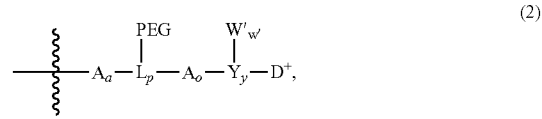

wherein the variable groups are as defined herein. In some aspects of the invention Y in structure (1) is comprised or consists of a self-immolative moiety (SI) as described herein substituted with W and $D^+$. In other aspects of the invention Y in structure (2) is comprised or consists of a self-immolating moiety as described herein substituted with $D^+$ through a quaternary amine nitrogen of a tubulysin compound and is further substituted with W' and Ligand-$L_B$-$A_a$-$L^P$(PEG)-$A_O$- or $L_B'$-$A_a$-$L^P$(PEG)-$A_O$- in a Ligand Drug Conjugate or Drug Linker compound, respectively, wherein $A_O$ is optionally present (i.e., $A_O$ is bonded to a self-immolative moiety of Y when $A_O$ is present) or is further substituted by $L_B$-$A_a$-$L_P$(PEG)- or $L_B'$-$A_a$-$L_P$(PEG)- in a Ligand Drug Conjugate or Drug Linker compound, respectively, when $A_O$ is absent.

Typically, secondary linkers with structure (1) are represented by

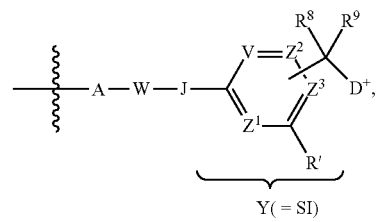

and secondary linkers with structure (2) are represented by

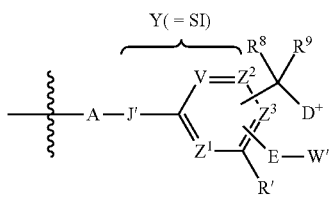

wherein Y is a self-immolative PAB or PAB-type moeity and E, J/J', V, $Z^1$, $Z^2$, $Z^3$, R', $R^8$ and $R^9$ are as defined in embodiments for PAB or PAB-type self-immolative moieties.

"Maleimide moiety" as used herein is a ligand covalent binding precursor moiety having a maleimide ring system. A maleimide moiety ($M^1$) as $L_B$' is capable of participating in Michael addition (i.e., 1,4-conjugate addition) of thiol functional group of a targeting agent to provide a thio-substituted succinimide ($M^2$) moiety, as described herein, which becomes a component in a Linker Unit in an LDC. An $M^1$ moiety is attached to the remainder of the Linker Unit of a Drug Linker compound through its imide nitrogen prior to its conversion to a thio-substituted succinimide moiety. Other than the imide nitrogen, an $M^1$ moiety is typically un-substituted, but may be asymmetrically substituted at the cyclic double bond of its maleimide ring system. Such substitution typically results in regiochemically preferred addition of a sulfhydryl group sulfur atom to the less hindered or more electronically deficient double bond carbon (dependent on the more dominant contribution) of the maleimide ring system. When present in a self-stabilizing linker ($L_{SS}$) moiety of a LDC, controlled hydrolysis of the succinimide ring system of the thio-substituted succinimide moiety $M^2$ derived from such a substituted $M^1$ moiety is expected to or may provide regiochemical isomers of succinic acid-amide ($M^3$) moieties as $L_B$ in a self-stabilized linker ($L_S$) moiety whose relative amount are due to differences in reactivity of the two carbonyl carbons of $M^2$ attributable to the substituent(s) that were present in the $M^1$ precursor.

"Succinimide moiety" as used herein is an organic moiety of a Linker Unit of an Ligand Drug Conjugate and results from Michael addition of a thiol functional group of a targeting agent to the maleimide ring system of a maleimide moiety ($M^1$) as $L_B$', wherein $M^1$ is typically that of a Drug Linker compound. In some aspects, the Ligand Drug Conjugate is an Antibody Drug Conjugate and the thiol functional group is from a cysteine residue of an antibody or fragment thereof. A succinimide ($M^2$) moiety as $L_B$ is therefore comprised of a thio-substituted succinimide ring system and has its imide nitrogen substituted with the remainder of the Linker Unit and is optionally substituted with substituent(s) that were present on the $M^1$ precursor. Typically, when A is present (i.e., subscript a of $A_a$ is 1) the imide nitrogen is covalently attached to the Stretcher Unit (A) or subunit thereof (i.e., $A_1$) as described herein. Sometimes $M^2$-A (or $M^2$-$A_1$) provides for a self-stabilizing linker ($L_{SS}$) moiety as described herein.

"Succinic acid-amide moiety" as used herein refers to succinic acid having an amide substituent that results from the thio-substituted succinimide ring system of a succinimide moiety $M^2$ as $L_B$ having undergone breakage of one of its carbonyl-nitrogen bonds by hydrolysis. In a ADC hydrolysis resulting in a succinic acid-amide ($M^3$) moiety provides a Linker Unit less likely to suffer premature loss of its antibody Ligand Unit having that $M^3$ moiety through elimination of the antibody-thio substituent. When present in a self-stabilizing linker ($L_{SS}$) moiety, controlled hydrolysis of the succinimide ring system of the thio-substituted succinimide moiety $M^2$ derived from a substituted $M^1$ moiety as $L_B$' is expected to provide regiochemical isomers of $M^3$ moieties (individually referred to as $M^{3A}$ and $M^{3B}$) that are due to differences in reactivity of the two carbonyl carbons of $M^2$ attributable to the substituent(s) that were present in the $M^1$ precursor and the thio-substituent of Ligand Unit, which is from or corresponds to the antibody targeting agent.

"Self-stabilizing linker" as used herein is an $L_B$-containing moiety of Linker Unit of an LDC, or precursor thereof (i.e., a $L_B$'-containing moiety) that under controlled conditions is capable of undergoing a chemical transformation to a self-stabilized linker ($L_S$), such that an LDC initially comprised of a self-stabilizing ($L_{SS}$) becomes more resistant to premature loss of its targeting Ligand Unit. Usually, a $L_{SS}$ moiety in addition to a $L_B$ or $L_B$' moiety is comprised of a first Stretcher Unit (A) to which $L_{SS}$ and -$L^P$(PEG)- are covalently attached. However, sometimes no intervening A is present and $L_{SS}$ is covalently attached directly to -$L^P$ (PEG)-. In some aspects, a $L_{SS}$ prior to its incorporation into an LDC contains a maleimide ($M^1$) moiety as its $L_B$' moiety (through which a targeting agent is to be attached as a Ligand Unit) and a first Stretcher Unit (A) or subunit thereof (i.e., $A_1$) and is represented by the formula of $M^1$-A- or $M^1$-$A_1$-. After incorporation into an LDC (i.e., after attachment of the targeting moiety as a Ligand Unit through Michael addition to the maleimide moiety) the $M^1$-A- (or $M^1$-$A_1$-) moiety of an $L_{SS}$ is converted to its corresponding thio-substituted succinimide moiety $M^2$-A- (or $M_2$-$A_1$-). Usually, $L_{SS}$ is also comprised of a Basic unit (BU) as described herein and is typically a substituent of a Stretcher Unit bound to $M^2$ or its $M^1$ precursor. In those aspects, BU assists in the hydrolysis of the succinimide moiety of $M^2$ to its corresponding ring-opened form $M^3$ [i.e., $M^2$-A(BU)— or $M^2$-$A_1$(BU)— is converted to $M^3$-A(BU) or $M^3$-$A_1$(BU)].

"Self-stabilized linker" is an organic moiety derived from an $L_{SS}$ moiety, both of which are $L_B$-containing moieties, of an LDC that has undergone hydrolysis, typically under controlled conditions, to provide a new $L_B$-containing moiety that is less likely to reverse the condensation reaction of a targeting agent with a $L_B$'-containing moiety that provided the original $L_B$-containing moiety. Usually, a self-stabilized linker ($L_S$) is comprised of a Stretcher Unit or subunit thereof covalently attached to a moiety obtained from conversion of a succinimide moiety ($M^2$) by hydrolysis of its succinimide ring system. In those instances, the $M^2$ precursor to that moeity has a thio-substituted succinimide ring system resulting from Michael addition of a thiol functional group of a targeting agent to the maleimide ring system of $M^1$, so that the $M^2$-derived moiety ($M^3$) has reduced reactivity for elimination of its thio-substituent in comparison to the corresponding substituent in $M^2$. In those aspects, the $M^2$-derived moiety has the structure of a succinic acid-amide ($M^3$) moiety corresponding to $M^2$ wherein $M^2$ has undergone hydrolysis of one of its carbonyl-nitrogen bonds of its succinimide ring system. That hydrolysis may occur spontaneously or more typically is catalyzed by the basic functional group of BU. For that purpose BU is covalently attached to a Stretcher Unit bound to $M^2$ such that BU is in appropriate proximity as a result of that attachment to assist in the rupture of the carbonyl-nitrogen. The product of that hydrolysis therefore has a carboxylic acid functional group and an amide functional group substituted at its amide nitrogen atom, wherein that nitrogen atom corresponds to the imide nitrogen atom in the $M^2$-containing $L_{SS}$ precursor, by the structure of the aforementioned Stretcher Unit. Typically, that basic functional group is an amino group whose effectiveness for increasing the rate of hydrolysis for the conversion of $M^2$ to $M^3$ is controlled by pH. Thus, a self-stabilized linker ($L_S$) typically has the structure of $M^3$ covalently bond to a Stretcher Unit or subunit thereof that in turn is covalently bonded to the remainder of the secondary linker $L_O(L_O')$ in a linear arrangement and has a Basic Unit covalently to the Stretcher Unit (A) in orthogonal arrangement relative to A and $L_O'$. Ls with $M^3$, A, BU and $L_O$ arranged in the manner so indicated is represented by the formula of $M^3$-A(BU)-$L_{O'}$- or $M^3$-$A_1$(BU)-$L_{O'}$-.

After hydrolysis, the resulting self-stabilized linker ($L_S$) will typically have the structure of $M^3$ covalently bond to the BU-substituted Stretcher Unit (e.g., $M^3$-A(Bu)- or $M^3A_1$ (BU)—). That first Stretcher Unit in turn is covalently bonded to the remainder of $L_O$ in a linear arrangement with the Basic Unit orthogonally arranged with respect to $M^3$ and the other $L_O$ component units. Exemplary structures of $L_{SS}$ and Ls moieties with $M^2$ or $M^3$, A(BU) [or $A_1$(BU)] and $L_O'$-, wherein $L_O'$- represents the remainder of $L_O$-, arranged in the manner indicated is shown by way of example but not limitation by:

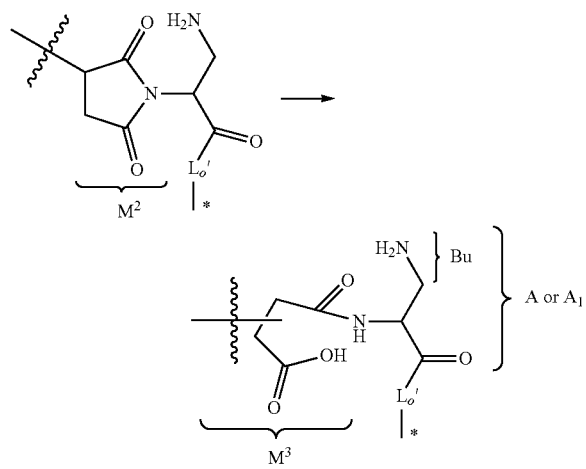

wherein the shown —$CH(CH_2NH_2)C(=O)$— moiety is the structure of the first Stretcher Unit (A), or subunit thereof, covalently bonded to the imide or amide nitrogen of $M^2$ or $M^3$, respectively, wherein the —$CH_2NH_2$ moiety is the BU substituent of that Stretcher Unit. The remainder of the $L_{SS}$ and Ls structures represents the succinimide moiety $M^2$ and succinic acid-amide moiety $M^3$ from succinimide ring hydrolysis of $M^2$, respectively, wherein $M^2$ and $M^3$ are substituted at its imide and corresponding amide nitrogen, respectively, with a $sp^3$-carbon of the Stretcher Unit. The wavy line indicates the point of covalent attachment to a Ligand Unit resulting from Michael addition of a thiol functional group of a targeting agent to the maleimide ring system of $M^1$ and the asterisk indicates the point of covalent attachment to $D^+$. Since the succinimide ring system of $M^2$ is asymmetrically substituted due to its thio substitution by the Ligand Unit, regiochemical isomers of succinic acid-amide ($M^3$) moieties may be obtained that differ in position of the Ligand Unit relative to the liberated carboxylic acid group resulting from $M^2$ hydrolysis. In the above structures, the carbonyl functional group of the shown Stretcher Unit exemplifies a hydrolysis enhancer (HE) as defined herein that is incorporated into the structure of such a unit.

$M^3$-A(BU)— represents exemplary structures of a self-stabilized linker ($L_S$), since these structures are less likely to eliminate the thio substituent of the targeting Ligand Unit, and thus cause loss of the targeting moiety from its Ligand Drug Conjugate, in comparison to the corresponding $M^2$-A (BU)— structure of an $L_{SS}$ moiety. Without being bound by theory, that increased stability is believed to result from the greater conformational flexibility in $M^3$ in comparison to $M^2$, which no longer constrains the thio substituent in a conformation favorable for E2 elimination.

"Basic Unit" as used herein is an organic moiety within a self-stabilizing linker ($L_{SS}$), as described herein, that can be carried forward into a corresponding Ls by effecting hydrolysis of the succinimide ring system within a $M^2$ moiety comprising $L_{SS}$ (i.e., catalyzes water addition of a water molecule to one of the succinimide carbonyl-nitrogen bonds) and can be initiated or enhanced under controlled conditions tolerable by the targeting Ligand Unit attached to $L_{SS}$. For that purpose, the basic functional group of the Basic Unit (BU) and its relative position in $L_{SS}$ with respect to its $M^2$ component in some aspects is selected for its ability to hydrogen bond to a carbonyl group of $M^2$, which effectively increases its electrophilicity and hence its susceptibility to water attack. In another aspect, those selections are made so that a water molecule, whose nucleophilicity is increased by hydrogen bonding to the basic functional group of BU, is directed to an $M^2$ carbonyl group. In a third aspect, those selections are made so the basic nitrogen on protonation increases the electrophilicity of the succinimide carbonyls by inductive electron withdrawing. In a final aspect, some combination of those mechanisms contributes to catalysis for hydrolysis of $L_{SS}$ to $L_S$.

For increasing the electrophilicity of an $M^2$ carbonyl by hydrogen bonding, BU is required to have a primary or secondary amine as its basic functional group whereas increasing water nucleophilicity or carbonyl electrophilicity in the manner described above may be done with a primary, secondary or tertiary amine as the basic functional group. In order that a basic amine be in the required proximity to assist in the hydrolysis of a succinimide moiety $M^2$ to its corresponding ring opened carboxylic acid amide $M^3$ by any one of those mechanisms, the amine-bearing carbon chain of BU is typically attached to a Stretcher Unit of $L_{SS}$ at the alpha carbon of that moiety relative to the point of attachment of A (or $A_1$) to the succinimide nitrogen of $M^2$ (and hence to the maleimide nitrogen of its corresponding precursor $M^1$-A or $M^1$-$A_1$ structure). In some aspects, that alpha carbon has the (S) stereochemical configuration or the configuration corresponding to that of the alpha carbon of L-amino acids.

"Hydrolysis Enhancer Unit" as used herein is electron withdrawing group or moiety and is an optional substituent of a Stretcher Unit comprising an $L_{SS}$ moiety. When present, a Hydrolysis Enhancer Unit (HE) is usually incorporated into a Stretcher Unit that is bonded to the imide nitrogen of an $M^2$ moiety so that its electron withdrawing effects increases the electrophilicity of the succinimide carbonyl groups in that moiety. When the Stretcher Unit also has a BU substituent, the effect of HE on the carbonyl groups coupled with the effect of BU, which is dependent on the basicity of the BU basic functional group and the distance of that functional group in relation to those carbonyl, are balanced so that premature hydrolysis of $M^1$ or of $M^2$ to $M^3$ does not occur to an appreciable extent that would require an excessive excess of a Drug Linker compound for the preparation of an LDC from an $L_{SS}$ precursor having the structure of $M^1$-A(BU)—, but allows for hydrolysis (i.e., conversion of an LDC-containing -$M^2$-A(BU)— moiety to its corresponding -M³-A(BU)— moiety) under controlled conditions (as when pH is purposely increased) that are tolerable by the attached targeting Ligand Unit. Typically, the HE Unit is a carbonyl or carbonyl-containing functional group located distal to the end of the Stretcher Unit that is bonded to $M^2$, or $M^3$ derived therefrom, so that HE is covalently attached to that stretcher unit and to the remainder of the secondary linker. Carbonyl-containing functional groups other than ketone (i.e. HE is —C(=O)—) include esters, carbamates, carbonates and ureas. When HE is a carbonyl-containing functional group other than ketone the carbonyl moiety of that functional group is typically bonded to A. In some aspects, the HE Unit may be sufficiently distant within a Stretcher Unit from the imide nitrogen to which the stretcher unit is covalently bonded so that no discernable effect on hydrolytic sensitivity of the succinimide carbonyl-nitrogen bonds of an $M^2$-containing moiety is observable.

"Stretcher Unit" as the term is used herein refers to an organic moiety in a secondary linker that physically separates the targeting moiety from other intervening components of a Linker unit that are distal to the stretcher unit, such as a cleavable unit and/or a spacer unit. A first Stretcher Unit (A) and/or second Stretcher Unit ($A_O$) may be required when a $L_B$ and/or a -$L^P$(PEG)- moiety provides insufficient steric relief to allow for efficient processing of the Linker Unit at W or W' for release of $D^+$ as a tubulysin drug and/or is sometime included for synthetic ease in constructing a Linker Unit of the present invention. A first or second Stretcher unit can comprise one or multiple stretcher sub-units as described herein. Prior to incorporation into an LDC, A has functional groups capable of covalently binding $L_B'$ to -$L^P$(PEG)-, and $A_O$ has functional groups capable of covalently binding -$L^P$(PEG)- and a Cleavable unit (W) together in certain linker constructs (as with A, W and Y in a linear arrangement, i.e., -A-Y—W—) or $A_O$ has functional groups capable of covalently binding -$L^P$(PEG)- and a Spacer unit (Y) together in other linker constructs (as with W' orthogonal to A and Y, i.e., -A-Y(W')—). In some aspects of the invention, the secondary linker is attached to a $L_B$ or $L_B'$ moiety through a subunit of a first Stretcher Unit while another of its subunits is covalently bonded to -$L_P$(PEG)-.

A first Stretcher unit (A), when present in an LDC or Drug Linker compound, are typically in Linker Units having the formula of -A-$L^P$(PEG)-W—Y—, -A-$L^P$(PEG)-$A_O$-W—Y—, A-$L^P$(PEG)-Y(W')— or A-$L^P$(PEG)-$A_O$-Y(W')— in which A is attached to a Ligand Covalent Binding Unit or a Ligand Covalent Binding Unit precursor. A first or second Stretcher Unit may comprise or consist of two, three or more subunits. Typically, A is one distinct unit or has 2 to 4 additional distinct subunits referred to as $A_2$, $A_3$ and $A_4$. In those $A_a$ is -$A_1$-$A_2$-. -$A_1$-$A_2$-$A_3$-, and -$A_1$-$A_2$-$A_3$-$A_4$-, collectively described as -$A_1$-$A_{2-4}$-. Typically, a first Stretcher Unit or a subunit thereof has one to six contiguous carbon atoms that are between a Ligand Covalent Binding Unit or a Ligand Covalent Binding Unit precursor and a functional group that covalently attaches A to -$L^P$(PEG)- or to another subunit of A. In some aspects that functional group may also serve as a hydrolysis enhancing (HE) unit.

"Branching Unit" as used herein refers to an tri-functional organic moiety that is an optional component of a Linker Unit (LU). A Branching Unit (B) is present when more than one quaternary tubulysin Drug Unit ($D^+$), typically 2, 3 or 4, are attached to a Linker Unit (LU) of a Ligand Drug Conjugate or Drug Linker compound. In a Ligand Drug Conjugate of Formula 1A, 1B, 1C or 1D or a Drug Linker compound of Formula IA, IB or 1D, the presence of a Branching Unit is indicated when subscript b of $B_b$ is 1, and occurs when subscript n greater than 1 in either one of these structural formulae. A Branching Unit is trifunctional in order to be incorporated into a secondary linker unit ($L_O$). In aspects where n is 1 in either of those structural formulae, a Branching Unit is either not present, as indicated when subscript b is 0 or subscript b is 1 and B is replaced by second optional Stretcher Unit designated as $A_O$. A Drug Linker compound or Ligand Drug Conjugate having a Branching Unit due to multiple $D^+$ units per LU have Linker Units comprised of moieties such as -$A_a$-$L^P$(PEG)-B—W—Y— or -$A_a$-$L^P$(PEG)-B—Y(W')—.

In some aspects a natural or un-natural amino acid or other amine-containing acid compound having a functionalized side chain serves as a Branching unit. In some aspects B is a lysine, glutamic acid or aspartic acid moiety in the L- or D-configuration in which the epsilon-amino, gamma-carboxylic acid or beta-carboxylic acid functional group, respectively, interconnects B to the remainder of LU.

"Cleavable Unit" as defined provides for a reactive site in which reactivity to that site is greater within or surrounding a hyper-proliferating cell or a hyper-stimulated immune cell (i.e., an abnormal cell) in comparison to a normal cell such that action upon that site results in preferential exposure to the abnormal cell to tubulysin drug (D). That exposure results from eventual release of a quaternized tubulysin Drug Unit ($D^+$) as D from an LDC having that Cleavable Unit. In some aspects of the invention, a Cleavable Unit, W or W' is comprised of a reactive site cleavable by an enzyme (i.e., W or W' is comprised of an enzyme substrate) whose activity or abundance is greater within or surrounding the hyper-proliferating, immune-stimulating or other abnormal or unwanted cell. In other aspects, a Cleavable Unit is comprised of a reactive site cleavable by other mechanisms (i.e., non-enzymatic) more likely operable in the environment within or surrounding abnormal cells of the target site in comparison to the environment of normal cells in which abnormal cells are typically not present. In still other aspects of the invention, the reactive site is more likely operated upon subsequent to cellular internalization of the LDC into an abnormal cell. That internalization more likely occurs in those cells in comparison to normal cells due to greater presentation of the targeted moiety that is recognized by the targeting Ligand Unit of the LDC on the cellular membrane of the abnormal or unwanted cells. Therefore, the targeted cells will more likely be exposed intracellularly to an active drug moiety when liberated from its LDC. The Cleavable Unit can comprise one or multiple sites susceptible to cleavage under those conditions of the targeted site, but typically has only one such site.

In some aspects of the invention, the Cleavable Unit is a substrate for a regulatory protease, hydrolase or glycosidase located intracellularly in the targeted cells (i.e., the reactive site of W or W' is a peptide bond or glycoside bond, respectively, cleavable by the regulatory protease, hydrolase or glycosidase). In those aspects the peptide or glycoside bond is capable of selective cleavage by the regulatory protease, hydrolase or glycosidase in comparison to serum proteases, hydrolases, or glycosidases. Those regulatory proteases, hydrolases or glycosidases may be more specific to the targeted abnormal or other unwanted cells in comparison to normal cells, or W or W' is capable of selective cleavage by a protease, hydrolase or glycosidase excreted in greater amounts by the targeted abnormal or other unwanted cells in comparison to normal cells or by targeted normal cells that are peculiar to the environment of the abnormal cells in comparison to normal cells in the periphery. Alternatively, W provides for a functional group that when incorporated into an LDC is susceptible to the acidic environment of lysozymes when the LDC is preferentially internalized into an abnormal cell, or to the greater reductive environment in or around these cells in comparison to the environment of normal cells where abnormal cells usually are not present such that release of $D^+$ as a tubulysin drug preferentially exposes the abnormal cells to that drug in comparison to normal cells distant from the site of the abnormal cells.

The Cleavable unit (W or W'), in a Drug Linker compound or after its incorporation into an LDC, provides for a cleavable bond (i.e., a reactive site) that in some aspects upon action by an enzyme present within a hyper-proliferating cell or hyper-activated immune cells releases a tertiary amine-containing drug from $D^+$. In other aspects, the releasing enzyme is characteristic of the immediate environment of those abnormal or unwanted cells. In still other aspects non-enzymatic action on W due to conditions more likely experienced by hyper-proliferating cells in comparison to normal cells will release free tubulysin drug from $D^+$. Typically, W or W' provides for a cleavable bond that is more likely acted upon intracellularly in a hyper-proliferating cell or hyper-activated immune cell due to preferential entry into such cells in comparison to normal cells. Typically, W or W' in an LDC or Drug Linker compound is covalently attached to a Spacer Unit (Y) having a self-immolating moiety such that enzymatic action on W or W' triggers self-destruction of that moiety within —Y-$D^+$ of —W—Y-$D^+$ or —Y(W')-$D^+$, respectively, to release $D^+$ as D.

Functional groups that provide for cleavable bonds include, by way of example and not limitation, (a) sulfhydryl groups that form a disulfide bond, which are more susceptible to the greater reductive conditions of abnormal cells in comparison to normal cells or excess glutathione produced under hypoxic conditions experienced by such cells, (b) aldehyde, ketone, or hydrazine groups that form a Schiff base or hydrazone functional groups, which are more susceptible to the acidic conditions of lysozymes upon selective internalization of an LDC having a Linker Unit with that cleavable bond into an abnormal cell in comparison to its internalization into normal cells, (c) carboxylic or amino groups that form an amide bond, as in peptide bonds, that are more susceptible to enzymatic cleavage by proteases produced or excreted preferentially by abnormal cells in comparison to normal cells, or preferentially excreted by normal cells that are peculiar to the environment of abnormal cells in comparison to normal cells in the periphery, or by a regulatory protease within a targeted cell, (d) amino or hydroxyl groups that form certain urea or carbamate groups or carboxylic or hydroxy groups that form ester or carbonate groups that are more susceptible to enzymatic cleavage by hydrolases or esterases that are produced or excreted preferentially by abnormal cells in comparison to normal cells or are excreted preferentially be normal cells peculiar to the environment of abnormal cells in comparison to normal cells in the periphery.

Still other functional groups that provide for cleavable bonds are found in sugars or carbohydrates having a glycosidic linkage that are substrates for glycosides which sometimes may be produced preferentially by abnormal cells in comparison to normal cells. Alternatively, the protease, hydrolase or glycosidase enzyme required for processing of the Linker Unit to release $D^+$ as an active tubulysin drug need not be produced preferentially by abnormal cells in comparison to normal cells provided the processing enzyme is not excreted by normal cells to an extent that would cause undesired side effects from premature release of free drug. In other instances the required protease, hydrolase or glycosidase enzyme may be excreted but to avoid undesired premature release of drug, it is preferred that the processing enzyme be excreted in the vicinity of abnormal cells and remain localized to that environment, whether produced by abnormal cells or nearby normal cells in response to the abnormal environment caused by the abnormal cells. In that respect W or W' is selected to be preferentially acted upon by a protease, hydrolase or glycosidase in or within the environment of abnormal cells in contrast to freely circulating enzymes. In those instances, a LDC is less likely to release the tubulysin drug in the vicinity of normal cells distant from the desired site of action nor would it be internalized into normal cells that do produce but not excrete the selected enzyme since such cells are less likely to display a targeted moiety required for entry by the LDC through selective binding by its targeting Ligand Unit.

In some aspects, W is a Peptide Cleavable Unit comprised of an amino acid or is comprised or consists of one or more sequences of amino acids that provide a substrate for a protease present within abnormal cells or localized to the environment of these abnormal cells. Thus, W may be comprised or consist of a dipeptide, tripeptide, tetrapeptide, pentapeptide, hexapeptide, heptapeptide, octapeptide, nonapeptide, decapeptide, undecapeptide or dodecapeptide moiety incorporated into a Linker Unit through an amide bond to a self-immolative Y wherein that peptide moiety is a recognition sequence for that protease. In some aspects W is a single natural L-amino acid, such as L-glutamate.

In some aspects, W' of a Glucuronide Unit of formula —Y(W')— is comprised or consists of a carbohydrate moiety attached to a self-immolative moiety of Y by a glycosidic bond that is cleavable by a glycosidase preferentially produced by abnormal cells, or is found in such cells to which an LDC, which is comprised of that self-immolative and carbohydrate moieties, has selective entry due to the presence of the targeted moiety on the abnormal cells.

"Spacer Unit" as used herein is an organic moiety in a secondary linker ($L_O$) within a Linker Unit that is covalently bonded to $D^+$ and a second optional Stretcher Unit ($A_O$) or a Branching Unit (B), if either is present, or to -$L^P$(PEG)- if $A_O$ And B are absent and/or to a cleavable unit (W or W') depending on the configuration of the Cleavable Unit to the Spacer Unit relative to each other. Typically, in one configuration, a quaternized drug unit ($D^+$) and W' are both covalently bonded to Y which in turn is also bonded to $A_O$ or B, when either is present, or to $L^P$(PEG) when both are absent so that W' is orthogonal to the remainder of $L_O$, whereas in another configuration W, Y, $D^+$ are arranged in a linear configuration with $D^+$ bonded to Y. In either arrangement, Y may also serve to separate the cleavage site of W or W' from $D^+$ to avoid steric interactions from that unit that would interfere with cleavage of W/W' whenever that cleavage is preformed through enzymatic action.

Typically, a Spacer Unit (Y) having a self-immolating moiety as defined herein has that moiety covalently bonded to a cleavage unit (W/W') so that in vivo processing of the Cleavable Unit activates self-destruction of Y thus a tubulysin drug from $D^+$. In some aspects the self-immolative moiety of Y is bonded to W through a amide (or anilide) functional group with Y also covalently bonded to the quaternary amine nitrogen of $D^+$ so that spontaneous self-destruction of the self-immolative moeity occurs upon enzymatic action on that functional group to result in release of free tubulysin drug from $D^+$. In other aspects the self-immolative moeity of Y is attached to W' through a glycosidic bond so that cleavage of that bond releases free tubulysin drug from $D^+$.

"Self-immolating moiety" as used herein refers to a bifunctional moiety within a spacer unit (Y) having an organic moiety that intervenes between the first and second functional group moieties and covalently incorporates these moieties into a normally stable tripartite molecule unless activated. On activation when the covalent bond to the first functional group moiety is cleaved, the second functional group moiety spontaneously separates from the tripartite molecule by self-destruction of the remainder of the self-immolative moiety. That self-destruction on activation releases free tubulysin drug (D). In some aspects that self-destruction occurs after cellular internalization of an LDC comprising $D^+$ and a Linker Unit having a self-immolating Spacer Unit. The intervening organic moiety in between the functional group moieties of a self-immolating moiety is sometimes an arylene or heteroarylene moiety capable of undergoing fragmentation to form a quinone methide or related structure by 1,4 or 1,6-elimination with concomitant release of free tubulysin drug. Such self-immolative moieties are exemplified by optionally substituted p-aminobenzyl alcohol (PAB) moieties, ortho or para-aminobenzylacetals, or aromatic compounds that are electronically similar to the PAB group (i.e., PAB-type) such as 2-aminoimidazol-5-methanol derivatives (see, e.g., Hay et al., 1999, *Bioorg. Med. Chem. Lett.* 9:2237) and other heteroaryls as described herein.

In one aspect, an aromatic carbon of an arylene or heteroarylene group of a PAB or PAB-type self-immolative moiety when incorporated into a Linker Unit is substituted with an electron-donating (EDG) heteroatom attached to the cleavage site of W through a first functional group comprising the heteroatom wherein that heteroatom is functionalized so that its electron-donating capacity is attenuated (i.e., the EDG is masked by incorporation of the self-immolative moeity of Y into a Linker unit). The other substituent that provides the second functional group is a benzylic carbon that is also attached to another aromatic carbon atom of the central arylene or heteroarylene group and has a quaternary amine substituent, in which the quaternary amine corresponds to or incorporates a tubulysin drug, is bonded through the benzylic carbon, wherein the aromatic carbon bearing the attenuated electron-donating heteroatom is adjacent to (i.e., 1,2-relationship), or two additional positions removed (i.e., 1,4-relationship) from that benzylic carbon atom. The EDG is chosen so that processing of the cleavage site of W restores the electron-donating capacity of the masked EDG thus triggering a 1,4- or 1,6-elimination to expel the tubulysin drug from the benzylic quaternary amine substituent.

Exemplary $-L_O-D^+$ moieties having PAB or PAB-related self-immolative moieties containing a central arylene or heteroarylene with the requisite 1,2- or 1,4-substitution patterns that allow for 1,4- or 1,6-fragmentation to release D from a quaternized Drug Unit are represented by:

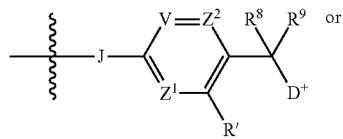 or

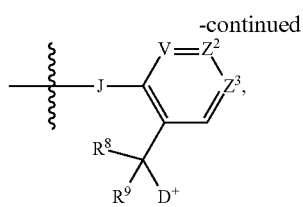

wherein $D^+$ in $-C(R^8)(R^9)-D^+$ is covalently attached to the aforementioned benzylic carbon through a quaternary amine nitrogen that corresponding to the tertiary amine nitrogen of a tubulysin drug (D) to be released from $D^+$, and J is the heteroatom, which is bonded to W through the aforementioned attenuating functional group comprising J and is optionally substituted if nitrogen (i.e., J is optionally substituted $-NH$), wherein J is $-O-$, $-N(R^{33})-$, or $-S-$, and $R^8$, $R^9$, $R^{33}$, R', V, $Z^1$, $Z^2$, $Z^3$ are defined in embodiments of self-immolative Spacer Units containing PAB or PAB-type moieties. Those variables are selected so that reactivity of J when released from processing of W at the targeted site is appropriately balanced with the reactivity of the tertiary amine of the tubulysin drug eliminated from the self-immolative moeity of Y and the stability of the quinone-methide type intermediate resulting from that elimination for effective release of $D^+$ as D.

In some aspects for a $-L_O-D^+$ moiety of structure (2), the Spacer Unit of $L_O$ having a PAB or PAB-type self-immolative moiety bound to $D^+$ has the structure of:

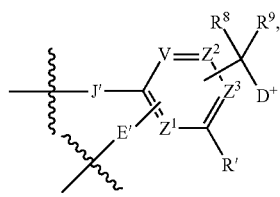

wherein the wavy line to J' indicates stable covalent bonding (i.e., not processed at the targeted site) to Ligand-$L_B$-A-$L^P$(PEG)-$A_O$- in a Ligand Drug Conjugate, or $L_B$'-A-$L^P$(PEG)-$A_O$- in a Drug Linker compound when a is 1 and $A_O$ is optionally present, or to Ligand-$L_B$-$A_a$-$L^P$(PEG)-B— or $L_B$'-$A_a$-$L^P$(PEG)-B—, wherein a is 0 or 1 and wherein J' is $-O-$, $-N(R^{33})-$, or $-S-$ bonded directly to $A_O$, B or a subunit thereof, or to Ligand-$L_B$-$L^P$(PEG)-, or $L_B$'-$L^P$(PEG)- when none of A, B and $A_O$ is present, through a functional group comprising J', and wherein R', $R^8$, $R^9$, V, $Z^1$, $Z^2$ and $Z^3$ are as defined in Formula 1A or Formula IA and E', independently selected from J', is an electron donating group from W' such as $-O-$, $-N(R^{33})-$, or $-S-$, wherein $R^{33}$ is $-H$, optionally substituted alkyl or optionally substituted aralkyl and the electron donating ability of E' is attenuated by its bonding to the carbohydrate moiety of W', wherein the W'-E' bond provides for a cleavage site for a glycosidase, and E' and the benzylic carbon of the $-C(R^8)(R^9)-D^+$ moiety are bonded to the aforementioned central arylene or heteroarylene at positions defined by V, $Z^1$, $Z^2$ or $Z^3$, such that E' and the $-C(R^8)(R^9)-D^+$ moiety are in a 1,2 or 1,4 relationship so as to permit the 1,4- or 1,6-fragmentation that results in release of $D^+$ as a tubulysin drug.

In some aspects for a $-L_O-D^+$ moiety of structure (1), the Spacer Unit of $L_O$ having a PAB or PAB-type self-immolative moiety bound to $D^+$ has the structure of:

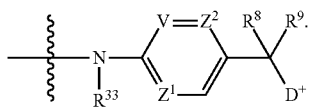

wherein R', $R^8$, $R^9$, V, $Z^1$ and $Z^2$ are as defined in Formula 1D or Formula ID, $R^{33}$ is —H, optionally substituted alkyl or optionally substituted aralkyl and the waving line adjacent to the optionally substituted nitrogen heteroatom indicates the site of covalent bonding to W to the remainder of $L_O$ wherein W is bonded to Ligand-$L_B$-A-$L^P$(PEG)-$A_O$-, in a Ligand Drug Conjugate or to $L_B$'-A-$L^P$(PEG)-$A_O$- in a Drug Linker compound when subscript a is 1 and $A_O$ is optionally present, or to Ligand-$L_B$-$A_a$-$L^P$(PEG)-B— or $L_B$'-$A_a$-$L^P$(PEG)-B— wherein subscript a is 0 or 1, or to Ligand-$L_B$-$L^P$(PEG)-, or $L_B$'-$L^P$(PEG)- when none of A, B and $A_O$ is present, wherein selective protease action at that covalent bond initiates self-immolation of the Spacer Unit to release $D^+$ as D.

In some aspects for a -$L_O$-$D^+$ moiety of structure (2), the Spacer Unit of $L_O$ having a PAB or PAB-type self-immolative moiety bound to $D^+$ has the structure of

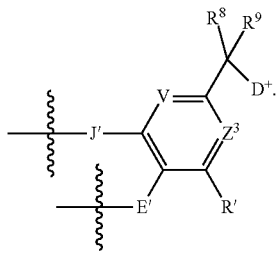

wherein E', J', R', $R^8$, $R^9$, V, and $Z^3$ are as defined in Formula 1A or Formula IA. Other structures and their variable group definitions incorporating an self-immolative moiety in a secondary linker-$D^+$ moiety of structure (2) are provided by the embodiments.

The arylene or heteroarylene of an self immolative moiety of Y may be further substituted to affect the kinetics of the 1,2- or 1,4-elimination in order to modulate the release of $D^+$ as D or to improve the physiochemical properties of the Ligand Drug Conjugate (e.g., reduce hydrophobicity) into which it is incorporated. For example, other than hydrogen R' can be an electron withdrawing group such as chloro, fluoro, or —$NO_2$, as when E' is an oxygen atom of a glycosidic bond to the carbohydrate moiety of W'.

Other exemplary and non-limiting examples of self-immolative structures that can be modified to accommodate benzylic quaternary amine substituents are provided by Blencowe et al. "Self-immolative linkers in polymeric delivery systems" Polym. Chem. (2011) 2: 773-790; Greenwald et al. "Drug delivery systems employing 1,4- or 1,6-elimination: poly(ethylene glycol) prodrugs of amine-containing compounds" J. Med. Chem. (1999) 42: 3657-3667; and in U.S. Pat. Nos. 7,091,186; 7,754,681; 7,553,816; and 7,989,434, all of which are incorporated by reference herein in their entireties with the structures and variable groups provided therein specifically incorporated by reference.

"Cytotoxic drug" as used herein refers to compound or a metabolite derived from an LDC that exerts an anti-survival effect on hyper-proliferating cells, hyper-activated immune cells or other abnormal or unwanted cells. In some aspects the cytotoxic drug acts directly upon those cells or indirectly by acting upon the abnormal vasculature that supports the survival and/or growth of the hyper-proliferating or other abnormal or unwanted cells, or the cytotoxic drug acts within sites of infiltrating hyper-activated immune cells. Typically, the abnormal or unwanted cells acted upon by the cytotoxic drug are mammalian cells, more typically human cells. Cytotoxic activity of a cytotoxic drug may be expressed as an $IC_{50}$ value, which is the effective concentration, typically molar amount per unit volume, at which half the cancer cells in an in vitro cell model system survive exposure to the cytotoxic agent. Thus, an $IC_{50}$ value is model-dependent. Typically, a cytotoxic agent incorporated into an LDC will have an $IC_{50}$ value in an in vitro cell model comprised of hyper-proliferating cells of between 100 nM to 0.1 pM or more typically about 10 nM to 1 pM. A highly toxic cytotoxic drug typically has an $IC_{50}$ value in such models of about 100 pM or lower. Although multiple drug resistant inhibitors that reverse resistance to cytotoxic drugs are not cytotoxic in their own right they are sometimes included as cytotoxic drugs. In some instances, a cytotoxic drug for use in the present invention is a cytotoxic tubulysin compound containing a tertiary amine nitrogen that can be quaternized for incorporation as $D^+$ into a structure representing Ligand Drug Conjugate composition. In other instances a cytotoxic tubulysin drug compound having a tertiary amine results when $D^+$ is released as D from a Ligand Drug Conjugate compound in a composition of the present invention.

"Cytostatic drug" as used herein refers to compound or a metabolite derived from an LDC that exerts an inhibitory effect on the growth and proliferation of hyper-proliferating cells, hyper-activated immune cells or other abnormal or unwanted cells. In some aspects the cytostatic drug acts directly upon those cells or indirectly by acting upon the abnormal vasculature that supports the survival and/or growth of the hyper-proliferating or other abnormal or unwanted cells, or the cytotoxic drug acts within sites of infiltrating hyper-activated immune cells. Typically, the abnormal or unwanted cells acted upon by the cytotoxic drug are mammalian cells, more typically human cells. Although multiple drug resistant inhibitors that reverse resistance to cytostatic drugs are not cytostatic in their own right they are sometimes included as cytostatic drugs. In some instances, a cytostatic drug for use in the present invention is a cytostatic tubulysin compound containing a tertiary amine nitrogen that can be quaternized for incorporation as $D^+$ into a structure representing Ligand Drug Conjugate composition. In other instances a tubulysin compound that is cytostatic and having a tertiary amine nitrogen results when $D^+$ is released as D from a Ligand Drug Conjugate compound in a composition of the present invention.

"Hematological malignancy" as the term is used herein refers to a blood cell tumor that originates from cells of lymphoid or myeloid origin and is synonymous with the term "liquid tumor". Hematological malignancies may be categorized as indolent, moderately aggressive or highly aggressive.

"Lymphoma" as used herein is hematological malignancy that usually develops from hyper-proliferating cells of lymphoid origin. Lymphomas are sometimes classified into two major types: Hodgkin lymphoma (HL) and non-Hodgkin lymphoma (NHL). Lymphomas may also be classified according to the normal cell type that most resemble the cancer cells in accordance with phenotypic, molecular or cytogenic markers. Lymphoma subtypes under that classification include without limitation mature B-cell neoplasms, mature T cell and natural killer (NK) cell neoplasms, Hodgkin lymphoma and immunodeficiency-associated lymphoproliferative disorders. Lymphoma subtypes include precursor T-cell lymphoblastic lymphoma (sometimes referred to as a lymphoblastic leukemia since the T-cell lymphoblasts are produced in the bone marrow), follicular lymphoma, diffuse large B cell lymphoma, mantle cell lymphoma, B-cell chronic lymphocytic lymphoma (sometimes referred to as a leukemia due to peripheral blood involvement), MALT lymphoma, Burkitt's lymphoma, mycosis fungoides and its more aggressive variant Sezary's disease, peripheral T-cell lymphomas not otherwise specified, nodular sclerosis of Hodgkin lymphoma, and mixed-cellularity subtype of Hodgkin lymphoma.

"Leukemia" as the term is used herein is a hematological malignancy that usually develops from hyper-proliferating cells of myeloid origin, and include without limitation, acute lymphoblastic leukemia (ALL), acute myelogenous leukemia (AML), chronic lymphocytic leukemia (CLL), chronic myelogenous leukemia (CML) and acute monocytic leukemia (AMoL). Other leukemias include hairy cell leukemia (HCL), T-cell lymphatic leukemia (T-PLL), large granular lymphocytic leukemia and adult T-cell leukemia.

"Quaternized Drug Unit" or quaternized tubulysin Drug Unit as used herein is an incorporated tertiary amine-containing tubulysin compound (D) or corresponds to such a compound in which the tertiary amine nitrogen is present in the compound structure as quaternary amine salt and exhibits cytotoxic, cytostatic, immunosuppressive or anti-inflammatory property, typically against mammalian cells, when released from a Ligand Drug Conjugate compound. In some aspects, a quaternized tubulysin Drug Unit ($D^+$) is obtained by condensing the tertiary amine nitrogen of the C-terminal component of a tubulysin compound with a secondary linker $L_O$ precursor having a suitable leaving group. In some aspects the tertiary amine-containing tubulysin compound is converted to its quaternized form upon its incorporation into a $L_B$ or $L_B'$-containing moiety. In other aspects the C-terminal component is first quaternized with the remainder of the tubulysin then appended to complete the $D^+$ Unit. Therefore, structures such as L-$L_B$-$L_O$-$D^+$ and $L_B'$-$L_O$-$D^+$ imply no particular method in which $D^+$ was formed and does not require that a reactant used in its formation be a tertiary-amine containing drug, but only require $D^+$ to incorporate or correspond to the structure of the tertiary-amine containing intended to be released from a Ligand Drug Conjugate compound. The class of tertiary-amine containing drugs released from an LDC of the present invention encompasses tubulysin compounds as described herein having cytotoxic or cytostatic effects on abnormal or other unwanted cells.

"Hyper-proliferating cells" as used herein refers to cells that are characterized by unwanted cellular proliferation or an abnormally high rate or persistent state of cell division that is unrelated or uncoordinated with that of the surrounding normal tissues. Typically, the hyper-proliferating cells are mammalian cells. In some aspects the hyper-proliferating cells are hyper-stimulated immune cells as defined herein whose persistent state of cell division occurs after the cessation of the stimulus that may have initially evoked the change in their cell division. In other aspects the hyper-proliferating cells are transformed normal cells or cancer cells and their uncontrolled and progressive state of cell proliferation may result in a tumor that is benign, potentially malignant (premalignant) or frankly malignant. Hyperproliferation conditions resulting from transformed normal cells or cancer cells include but are not limited to those characterized as a precancer, hyperplasia, dysplasia, adenoma, sarcoma, blastoma, carcinoma, lymphoma, leukemia or papilloma. Precancers are usually defined as lesions that exhibit histological changes which are associated with an increased risk of cancer development and sometimes have some, but not all, of the molecular and phenotypic properties that characterize the cancer. Hormone associated or hormone sensitive precancers include, prostatic intraepithelial neoplasia (PIN), particularly high-grade PIN (HGPIN), atypical small acinar proliferation (ASAP), cervical dysplasia and ductal carcinoma in situ. Hyperplasias generally refers to the proliferation of cells within an organ or tissue beyond that which is ordinarily seen that may result in the gross enlargement of an organ or in the formation of a benign tumor or growth. Hyperplasias include, but are not limited to endometrial hyperplasia (endometriosis), benign prostatic hyperplasia and ductal hyperplasia.

"Normal cells" as used herein refers to cells undergoing coordinated cell division related to maintenance of cellular integrity of normal tissue or replenishment of circulating lymphatic or blood cells that is required by regulated cellular turnover, or tissue repair necessitated by injury, or to a regulated immune or inflammatory response resulting from pathogen exposure or other cellular insult, where the provoked cell division or immune response terminates on completion of the necessary maintenance, replenishment or pathogen clearance. Normal cells include normally proliferating cells, normal quiescent cells and normally activated immune cells.

"Normal quiescent cells" are noncancerous cells in their resting $G_o$ state and have not been stimulated by stress or a mitogen or are immune cells that are normally inactive or have not been activated by pro-inflammatory cytokine exposure.

"Hyper-stimulated immune cells" as the term is used herein refers to cells involved in innate or adaptive immunity characterized by an abnormally persistent proliferation or inappropriate state of stimulation that occurs after the cessation of the stimulus that may have initially evoked the change in proliferation or stimulation or that occurs in the absence of any external insult. Oftentimes, the persistent proliferation or inappropriate state of stimulation results in a chronic state of inflammation characteristic of a disease state or condition. In some instance the stimulus that may have initially evoked the change in proliferation or stimulation is not attributable to an external insult but is internally derived as in an autoimmune disease. In some aspects a hyper-stimulated immune cells is a pro-inflammatory immune cell that has been hyper-activated through chronic pro-inflammatory cytokine exposure.

In some aspects of the invention an LDC binds to an antigen preferentially displayed by pro-inflammatory immune cells that are abnormally proliferating or are inappropriately activated. Those immune cells include classically activated macrophages or Type 1 T helper (Th1) cells, which produce interferon-gamma (INF-$\gamma$), interleukin-2 (IL-2), interleukin-10 (IL-10), and tumor necrosis factor-beta (TNF-$\beta$), which are cytokines that are involved in macrophage and $CD8^+$ T cell activation.

"Glycosidase" as used herein refers to a protein capable of enzymatic cleavage of a glycosidic bond. Typically, the glycosidic bond to be cleaved is present in a Cleavable unit (W') of an LDC. Sometimes the glycosidase acting upon an LDC is present intracellularly in hyper-proliferating cells, hyper-activated immune cells or other abnormal or unwanted cells to which the LDC has preferential access in comparison to normal cells, which is attributable to the targeting capability of the ligand-binding component (i.e., the Ligand Unit). Sometimes the glycoside is more specific to the abnormal or unwanted cells or is preferentially excreted by abnormal or unwanted cells in comparison to normal cells or is present in greater amount in the vicinity of abnormal or unwanted in comparison to serum amounts. Oftentimes the glycosidic bond in W' acted upon by a glycosidase attaches the anomeric carbon of a carbohydrate moiety (Su) to a phenolic oxygen of a self-immolating (SI) moiety that comprises a self-immolative Spacer Unit (Y) such that glycosidic cleavage of that bond triggers 1,4- or 1,6-elimination of an tertiary amine-containing tubulysin drug from the quaternary amine moiety bonded to the benzylic position of SI.

In some aspects, Drug Linker compounds or Ligand Drug Conjugates are comprised of moieties such as -$A_a$-$L_P$(PEG)-$B_b$—Y(W')-$D^+$ or -$A_a$-$L_P$(PEG)-$A_O$-Y(W')-$D^+$, in which the subscripts a and b are independently 0 or 1, wherein the —Y(W')— moiety is typically a Su-O'— moiety bonded to a self-immolative moiety of Y as defined herein with $A_O$ or -$L_P$(PEG)-, W' and $D^+$ attached to the self-immolative moiety in a manner that permits self-immolative release of free tertiary amine containing tubulysin compound upon action by a glycosidase. Such —Y(W')— moieties are sometimes referred to as a Glucuronide Unit in which Su is a carbohydrate moiety, which is not limited to that of a glucuronic acid.

Typically, a Su-O'— moiety (where —O'— represents the oxygen of the glycosidic bond and Su is a carbohydrate moiety) bonded to a self-immolative moiety of Y is represented by the structure described for self-immolating moieties wherein E' bonded to the central arylene or heteroarylene of the self-immolative moeity is oxygen and wherein that heteroatom is substituted with a carbohydrate moiety through its anomeric carbon atom. More typically Su-O'—Y-$D^+$ has the structure of:

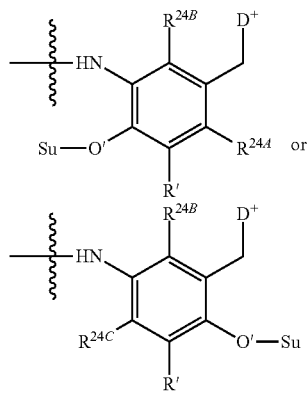

wherein $R^{24A}$, $R^{24B}$ and $R^{24C}$, is as defined for $R^{24}$ in the summary of the invention and is selected so that the electron donating ability of the phenolic —OH released from the glycosidic bond, the sensitivity to selective cleavage by a desired glycosidase of the glycosidic bond to the carbohydrate moiety Su, and the stability of the quinone methide intermediate upon fragmentation is balanced with the leaving ability of the tertiary amine-containing tubulysin drug so that efficient release of D from $D^+$ through 1,4- or 1,6-elimination occurs. Those Su-O'—Y— structures having a PAB or PAB-type moiety for self-immolation are representative Glucuronide Units. When the glycosidic bond is to the carbohydrate moeity of glucuronic acid, the glycosidase capable of enzymatic cleavage of that glycosidic bond is a glucuronidase.

"Carbohydrate moiety" as used herein refers to a monosaccharide having the empirical formula of $C_m(H_2O)_n$, wherein n is equal to m, containing an aldehyde moiety in its hemiacetal form or a derivative thereof in which a —$CH_2OH$ moiety within that formula has been oxidized to a carboxylic acid (e.g., glucuronic acid from oxidation of the $CH_2OH$ group in glucose). Typically, a carbohydrate moiety (Su) is a cyclic hexose, such as a pyranose, or a cyclic pentose, such as a furanose. Usually, the pyranose is a glucuronide or hexose in the β-D conformation. In some instances, the pyranose is a β-D-glucuronide moiety (i.e., β-D-glucuronic acid linked to the self-immolative moiety of Y via a glycosidic bond that is cleavable by β-glucuronidase). Oftentimes, the carbohydrate moiety is unsubstituted (e.g., is a naturally occurring cyclic hexose or cyclic pentose). Other times, the carbohydrate moiety can be a cyclic hexose or cyclic pentose in which a hydroxyl group has been removed or replaced with halogen, or lower alkyl or alkylated by lower alkyl.

"Protease" as defined herein refers to a protein capable of enzymatic cleavage of a carbonyl-nitrogen bond such as an amide bond typically found in a peptide. Proteases are classified into major six classes: serine proteases, threonine proteases, cysteine proteases, glutamic acid proteases, aspartic acid proteases and metalloproteases so named for the catalytic residue in the active site that is primarily responsible for cleaving the carbonyl-nitrogen bond of its substrate. Proteases are characterized by various specificities, which are dependent of identities of the residues at the N-terminal and/or C-terminal side of the carbonyl-nitrogen bond and various distributions.

When W is comprised of amide or other carbonyl-nitrogen containing functional group cleavable by a protease that cleavage site is oftentimes limited to those recognized by proteases that are found in hyper-proliferating cells or hyper-stimulated immune cells or within cells particular to the environment in which hyper-proliferating cells or hyper-stimulated immune cells are present. In those instances, the protease is not necessarily required to be preferentially present or found in greater abundance in the cells targeted by the LDC since an LDC will have poorer access to those cells that do not preferential display the targeted moiety. Other times, the protease is preferentially excreted by abnormal cells or by normal cells peculiar to the environment in which those abnormal cells are found in comparison to the environment normal cells distant from the site of the abnormal cells. Thus, in those instances where the protease is excreted, the protease is necessarily required to be preferentially present or found in greater abundance in the vicinity of cells targeted by the LDC in comparison to that of normal cells not in the vicinity of the abnormal cells.

When incorporated into an LDC, a peptide comprising W will present a recognition sequence to a protease that cleaves a carbonyl-nitrogen bond in W to initiate fragmentation of the Linker Unit so as to cause release of an tertiary amine-containing drug from $D^+$. Sometimes, the recognition sequence is selectively recognized by an intracellular protease present in abnormal cells to which the LDC has preferred access in comparison to normal cells due to targeting of the abnormal cells, or is preferentially produced by abnormal cells in comparison to normal cells, for the purpose of appropriately delivering the drug to the desired site of action. Usually the peptide is resistant to circulating proteases in order to minimize premature expulsion of the tubulysin drug compound and thus minimize unwanted systemic exposure to that compound. Typically, the peptide will have one or more unnatural or non-classical amino acids in its sequence in order to have that resistance. Oftentimes, the amide bond that is specifically cleaved by a protease produced by an abnormal cell is an anilide wherein the nitrogen of that anilide is a nascent electron-donating heteroatom (i.e., J) of an self-immolative moiety having the previously defined structures. Thus, protease action on such a peptide sequence in W results in release of $D^+$ as D from the Linker Unit through a 1,4- or 1,6-elimination proceeding through the central arylene or heteroarylene moiety of the self-immolative moeity.

Regulatory proteases are typically located intracellularly and are required for the regulation of cellular activities that sometimes becomes aberrant or dysregulated in abnormal or other unwanted cells. In some instances, when W is directed to a protease having preferential distribution intracellularly, that protease is a regulatory protease involved in cellular maintenance or proliferation. In some instances, those proteases include cathepsins. Cathepsins include the serine proteases, Cathepsin A, Cathepsin G, aspartic acid proteases Cathepsin D, Cathepsin E and the cysteine proteases, Cathepsin B, Cathepsin C, Cathepsin F, Cathepsin H, Cathepsin K, Cathepsin L1, Cathepsin L2, Cathepsin O, Cathepsin S, Cathepsin W and Cathepsin Z.

Tubulysin compounds have the structure of $D_G$ or $D_H$:

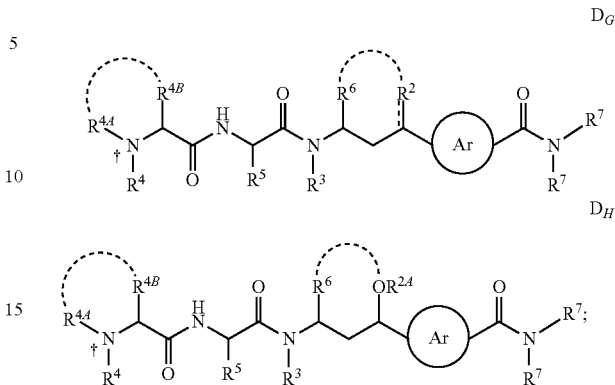

wherein the straight dashed line indicates an optional double bond, the curved dash line indicates optional cyclization, the circled Ar indicates an arylene or heteroarylene that is 1,3-substituted within the tubulysin carbon skeleton and is optionally substituted elsewhere, wherein the arylene or heteroarylene and other variable groups are as defined in the embodiments of the invention.

Naturally-occurring tubulysin compounds have the structure of $D_{G-6}$.

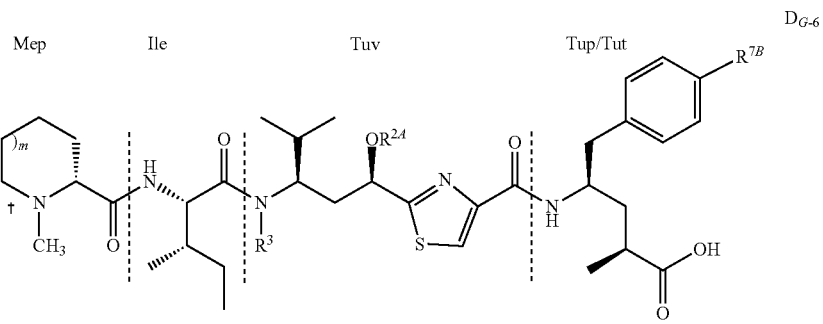

In other instances, when W is directed to a protease that is preferentially distributed extracellularly in the vicinity of hyper-proliferating or hyper-stimulated immune cells due to preferential excretion by such cells or by neighboring cells whose excretion is peculiar to the environment of hyper-proliferating or hyper-stimulated immune cells, that protease is usually a metalloprotease. Typically, those proteases are involved in tissue remodeling, which aids in the invasiveness of hyper-proliferating cells or result from undesired accumulation of hyper-activated immune cells that results in further recruit of such cells.

"Tubulysin drug" or "tubulysin compound" as used is a peptide-based tubulin disrupting agent having cytotoxic activity, cytostatic or anti-inflammatory activity and is comprised of one natural or un-natural amino acid component and three other un-natural amino acid components wherein one of those components is characterized by a central 5-membered or 6-membered heteroarylene moiety and another component provides for a tertiary amine for incorporation into a quaternized drug unit.

and are conveniently divided into four amino acid subunits, as indicated by the dashed vertical lines, named N-methyl-pipecolinic acid (Mep), isoleucine (Ile), tubuvaline (Tuv), and either tubuphenylalanine (Tup, when $R^{7A}$ is hydrogen) or tubutyrosine (Tut, when $R^{7A}$ is —OH). There are about a dozen naturally occurring tubulysins presently known named Tubulysin A-I, Tubulysin U, Tubulysin V and Tubulysin Z, whose structures are indicated by variable groups for structure $D_{G-6}$ defined in in embodiments of tubulysin-based quaternized drug units.

Pretubulysins have the structure $D_G$ or $D_H$, wherein $R^3$ is —$CH_3$ and $R^2$ is hydrogen, and desmethyl tubulysins have the structure of $D_G$, $D_{G-1}$, $D_{G-6}$, $D_H$ or $D_{H-1}$ in which $R^3$ is hydrogen and other tubulysin structures given by the embodiments of tubulysin-based quaternized drug units, wherein $R^3$ is hydrogen, and wherein the other variable groups as described for tubulysins. Pretubulysins and desmethyl tubulysins are optionally included in the definition of tubulysins.

In structures $D_G$, $D_{G-1}$, $D_{G-6}$, $D_H$, $D_{H-1}$ and other tubulysin structures described herein in embodiments of tubulysin-based quaternized Drug Units, the indicated (t) nitrogen atom is the site of quaternization when such structures correspond to or are incorporated into an LDC or precursor thereof as a quaternized tubulysin Drug Unit. When incorporated into an LDC or precursor thereof that nitrogen is quaternized by covalent binding to $L_O$ or to $L_O$ of an $L_B$ or $L_B'$-containing moiety comprised of $L_O$. Typically, that quaternized moiety of $D^+$ results from covalent attachment of the nitrogen atom of the tertiary amine moiety to the benzylic carbon of a PAB or PAB-type moiety in a self-immolative Spacer Unit Y unit of $L_O$. Structures of other exemplary tertiary amine-containing tubulysins and pretubulysins and manner of their incorporation into an LDC as $D^+$ are provided in embodiments of tubulysin-based quaternized drug units.

Exemplary methods of preparing tubulysin drugs and their structure-activity relationships are provided by Shankar et al. "Synthesis and structure-activity relationship studies of novel tubulysin U analogs-effect on cytotoxicity of structural variations in the tubuvaline fragment" *Org. Biomol. Chem.* (2013) 11: 2273-2287; Xiangming et al. "Recent advances in the synthesis of tubulysins" *Mini-Rev. Med. Chem.* (2013) 13: 1572-8; Shankar et al. "Synthesis and cytotoxic evaluation of diastereomers and N-terminal analogs of Tubulysin-U" *Tet. Lett.* (2013) 54: 6137-6141; Shankar et al. "Total synthesis and cytotoxicity evaluation of an oxazole analogue of Tubulysin U" *Synlett* (2011) 2011(12): 1673-6; Raghavan et al. *J. Med. Chem.* (2008) 51: 1530-3; Balasubramanian, R. et al. "Tubulysin analogs incorporating desmethyl and dimethyl tubuphenylalanine derivatives" *Bioorg. Med. Chem. Lett.* (2008) 18: 2996-9; and Raghavan et al. "Cytotoxic simplified tubulysin analogues" *J. Med. Chem.* (2008) 51: 1530-3.

"Intracellularly cleaved", "intracellular cleavage" and like terms used herein refer to a metabolic process or reaction inside a cell on an LDC or the like, whereby the covalent attachment, e.g., the linker, between the quaternary amine of the quaternized tubulysin compound and the antibody is broken, resulting in the free tertiary amine-containing drug, or other metabolite of the conjugate dissociated from the targeting moiety inside the cell. The cleaved moieties of the LDC are thus intracellular metabolites.

"Bioavailability" as used herein refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

"Subject" as used herein refers to a human, non-human primate or mammal having a hyper-proliferation, inflammatory or immune disorder or prone to such disorder that would benefit from administering an effective amount of an LDC. Non-limiting examples of a subject include human, rat, mouse, guinea pig, monkey, pig, goat, cow, horse, dog, cat, bird and fowl. Typically, the subject is a human, non-human primate, rat, mouse or dog.

The term "inhibit" or "inhibition of" means to reduce by a measurable amount, or to prevent entirely. Inhibition of proliferation of hyper-proliferating cells to an ADC is typically determined relative to untreated cells (sham treated with vehicle) in a suitable test system as in cell culture (in vitro) or in a xenograft model (in vivo). Typically an LDC comprised of a targeting moiety to an antigen that is not present on the hyper-proliferating cells or activated immune-stimulating cells of interest is used as a negative control.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit growth and/or kill existing cancer cells, it may be cytostatic and/or cytotoxic. For cancer therapy, efficacy can, for example, be measured by assessing the time to disease progression (TTP) and/or determining the response rate (RR).

In the case of immune disorders resulting from hyper-stimulated immune cells, a therapeutically effective amount of the drug may reduce the number of hyper-stimulated immune cells, the extent of their stimulation and/or infiltration into otherwise normal tissue and/or relieve to some extent one or more of the symptoms associated with a dysregulated immune system due to hyper-stimulated immune cells. For immune disorders due to hyper-stimulated immune cells, efficacy can, for example be measured by assessing one or more inflammatory surrogates, including one or more cytokines levels such as those for IL-1β, TNFα, INFγ and MCP-1, or numbers of classically activated macrophages.

In some aspects of the invention the Ligand-Drug Conjugate associates with an antigen on the surface of a targeted cell (i.e., a hyper-proliferating cell or a hyper-stimulated immune cell), and the ligand drug conjugate is then taken up inside a target cell through receptor-mediated endocytosis. Once inside the cell, one or more cleavage units within the Linker unit are cleaved, resulting in release of the tertiary amine-containing drug. The released tertiary amine-containing tubulysin drug is then free to migrate in the cytosol and induce cytotoxic or cytostatic activities or in the case of hyper-stimulated immune cells may alternatively inhibit pro-inflammatory signal transduction. In another aspect of the invention, the quaternized Drug Unit is cleaved from the Ligand-Drug Conjugate outside the target cell but within the vicinity of the target cell so that the released tertiary amine-containing tubulysin compound subsequently penetrates the cell rather than being released at distal sites.

"Carrier" as the term is used herein refers to a diluent, adjuvant or excipient, with which a compound is administered. Such pharmaceutical carriers can be liquids, such as water and oils, including those of petroleum, animal, vegetable or synthetic origin, such as peanut oil, soybean oil, mineral oil, sesame oil. The carriers can be saline, gum acacia, gelatin, starch paste, talc, keratin, colloidal silica, urea. In addition, auxiliary, stabilizing, thickening, lubricating and coloring agents can be used. In one embodiment, when administered to a patient, the compound or compositions and pharmaceutically acceptable carriers are sterile. Water is an exemplary carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. The present compositions, if desired, can also contain minor amounts of wetting or emulsifying agents, or pH buffering agents.

"Treat", "treatment," and like terms, unless otherwise indicated by context, refer to therapeutic treatment and prophylactic measures to prevent relapse, wherein the object is to inhibit or slow down (lessen) an undesired physiological change or disorder, such as the development or spread of cancer or tissue damage from chronic inflammation. Typically, beneficial or desired clinical results of such therapeutic treatments include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival or quality of like as compared to expected survival or quality of life if not receiving treatment. Those in need of treatment include those already having the condition or disorder as well as those prone to have the condition or disorder.

In the context of cancer or a disease state related to chronic inflammation, the term "treating" includes any or all of inhibiting growth of tumor cells, cancer cells, or of a tumor; inhibiting replication of tumor cells or cancer cells, inhibiting dissemination of tumor cells or cancer cell, lessening of overall tumor burden or decreasing the number of cancerous cells, inhibiting replication or stimulation of pro-inflammatory immune cells, inhibiting or decreasing the chronic inflammatory state of a dysregulated immune system or decreasing the frequency and/or intensity of flares experienced by subjects having an autoimmune condition or disease or ameliorating one or more symptoms associated with cancer or a hyper-immune stimulated disease or condition.

"Pharmaceutically acceptable salt" as used herein, refers to pharmaceutically acceptable organic or inorganic salts of a compound. The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterions. Typically, a quaternized tubulysin Drug Unit is in pharmaceutically acceptable salt form.

Typically, a pharmaceutically acceptable salt is selected from those described in P. H. Stahl and C. G. Wermuth, editors, *Handbook of Pharmaceutical Salts: Properties, Selection and Use*, Weinheim/Zürich:Wiley-VCH/VHCA, 2002. Salt selection is dependent on properties the drug product must exhibit, including adequate aqueous solubility at various pH values, depending upon the intended route(s) of administration, crystallinity with flow characteristics and low hygroscopicity (i.e., water absorption versus relative humidity) suitable for handling and required shelf life by determining chemical and solid-state stability under accelerated conditions (i.e., for determining degradation or solid-state changes when stored at 40° C. and 75% relative humidity).

"Loading", "drug loading", "payload loading" or like terms represent or refer to the average number of payloads ("payload" and "payloads" are used interchangeable herein with "drug" and "drugs") in an population of LDCs (i.e., a composition of LDC differing in number of attached $D^+$ units having either the same or different attachment locations, but otherwise essentially identical in structure). Drug loading may range from 1 to 24 drugs per targeting moiety. That is sometimes referred to as the DAR, or drug to targeting moiety ratio. Compositions of LDCs described herein typically have DAR's of from 1-24 or 1-20, and in some aspects from 1-8, from 2-8, from 2-6, from 2-5 and from 2-4. Typical DAR values are about 2, about 4, about 6 and about 8. The average number of drugs per antibody, or DAR value, may be characterized by conventional means such as UV/visible spectroscopy, mass spectrometry, ELISA assay, and HPLC. A quantitative DAR value may also be determined. In some instances, separation, purification, and characterization of homogeneous LDCs having a particular DAR value may be achieved by means such as reverse phase HPLC or electrophoresis. DAR may be limited by the number of attachment sites on the targeting moiety.

For example, when the targeting moiety is an antibody and the attachment site is a cysteine thiol, an antibody may have only one or several sufficiently reactive thiol groups that react with a $L_B'$-containing moiety. Sometimes, the cysteine thiol is a thiol group derived from of a cysteine residue that participated in an interchain disulfide bond. Other times, the cysteine thiol is a thiol group of a cysteine residue that did not participate in an interchain disulfide bond, but was introduced through genetic engineering. Typically, less than the theoretical maximum of $D^+$ moieties is conjugated to an antibody during a conjugation reaction. For example, an antibody may contain many lysine residues that do not react with a $L_B'$-containing moiety, since only the most reactive lysine groups may react with that moiety.

I. Embodiments

Provided herein are Ligand-drug conjugates (LDCs) capable of preferential delivery of a tertiary amine-containing tubulysin compound to hyperproliferating cells or hyper-activated immune cells or to the vicinity of such abnormal cells in comparison to normal cells or the environment of normal cells where the abnormal cells are typically not present and are thus useful for treating diseases and conditions characterized by these abnormal cells.

1.1 General

A LDC has three major components: (1) a Ligand Unit corresponding to or incorporating a targeting agent that selectively binds to a targeted moiety present on, within or in the vicinity of abnormal cells or other unwanted cells in comparison to other moieties present on, within, or in the vicinity of normal cells where these abnormal or unwanted cells are typically not present, or is present on, within, or in the vicinity of abnormal or other unwanted cells in greater abundance in comparison to normal cells or the environment of normal cells where abnormal or unwanted cells are typically not present, (2) a quaternized tubulysin Drug Unit ($D^+$) incorporating or corresponding to the structure of a tertiary amine-containing tubulysin compound by quaternization of the tertiary amine nitrogen atom and (3) a Linker Unit that connects $D^+$ to the Ligand Unit and is capable of conditionally releasing free tertiary amine-containing tubulysin drug within or in the vicinity of abnormal or unwanted cells that are targeted by the Ligand Unit.

A tubulysin compound to be used in the present invention is one that primarily or selectively exerts its effect (e.g., cytotoxic, cytostatic effect) on mammalian cells as compared to prokaryotic cells. In some aspects the targeted moiety is an epitope of an extracellular displayed membrane protein that is preferentially found on abnormal or unwanted cells in comparison to normal cells. Specificity towards the abnormal or unwanted cells (i.e., the targeted cells) results from the Ligand Unit (L) of the LDC into which D is incorporated. In addition to L and $D^+$, an LDC that targets abnormal or unwanted cells has a Linker Unit that covalently interconnects a quaternized tubulysin Drug Unit with the Ligand Unit. In some aspects the Ligand Unit is from an antibody, which is an exemplary targeting agent, which recognizes abnormal mammalian cells.

In some aspects the targeted moiety recognized by the Ligand Unit is an epitope of an extracellular displayed membrane protein that is preferentially found on abnormal or unwanted cells in comparison to normal cells. In some of those aspects, and as a further requirement, the membrane protein targeted by the Ligand Unit must have sufficient copy number and be internalized upon binding of the LDC in order to intracellularly deliver an effective amount of the cytotoxic, cytostatic, immune-suppressive or anti-inflammatory tubulysin compound preferentially to the abnormal cells.

A tertiary-amine containing tubulysin compound typically exhibits adverse peripheral effects when administered in unconjugated form. Therefore, that compound needs to be selectively delivered by its LDC so that the Linker Unit of an LDC is not merely a passive structure that serves as a bridge between a targeting Ligand Unit and $D^+$ from which the tubulysin compound is released, but must be carefully engineered to have stability from the site of administration of the LDC until its delivery to the targeted site and then must efficiently release an active tubulysin compound. To accomplish that task, a targeting agent is reacted with a $L_B$'-containing moiety to form a $L_B$-containing moiety within a Ligand Drug Conjugate. When the $L_B$-containing moiety is so formed, the resulting Ligand Drug Conjugate is typically comprised of the targeting moiety (in the form of a Ligand Unit), a Ligand Covalent Binding Unit ($L_B$), also referred to as a primary linker ($L_R$), a quaternized tubulysin compound ($D^+$) and a secondary linker ($L_O$) intervening between $L_B$ and $D^+$.

1.1 Primary Linker ($L_R$)

A primary linker ($L_R$) is a Ligand Covalent Binding Unit ($L_B$) or a Ligand Covalent Binding Unit precursor ($L_B$') and typically is present as a component of a Linker Unit of a LDC or of a $L_B$'-containing moiety such as $L_B$'-$L_O$ in a Drug Linker compound having the formula $L_B$'-$L_O$-$D^+$. The primary linker of a $L_B$'-containing moiety is comprised of a functional group capable of reacting with an electrophilic or nucleophilic functional group of a targeting agent. As a result of that reaction, the targeting agent becomes covalently bonded as a Ligand Unit to a primary linker through $L_B$, wherein the primary linker is now $L_B$ having a functional group derived from $L_B$'.

In some embodiments $L_B$' in a $L_B$'-containing moiety has the structure of one of 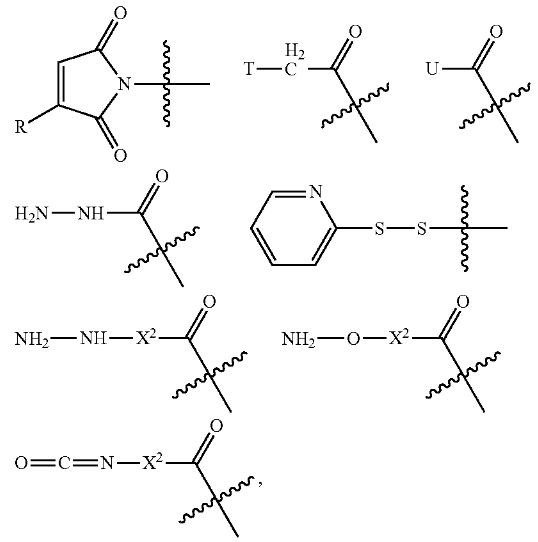 wherein R is hydrogen or $C_1$-$C_6$ optionally substituted alkyl; T is —Cl, —Br, —I, —O-mesyl, —O-tosyl or other sulfonate leaving group; U is —F, —Cl, —Br, —I, —O—N-succinimide, —O-(4-nitrophenyl), —O-pentafluorophenyl, tetrafluorophenyl or —O—C(═O)—$OR^{57}$;_$X^2$ is $C_{1-10}$ alkylene, $C_3$-$C_8$-carbocycle, —O—($C_1$-$C_6$ alkyl), -arylene-, $C_1$-$C_{10}$ alkylene-arylene, -arylene-$C_1$-$C_{10}$ alkylene, —$C_1$-$C_{10}$ alkylene-($C_3$-$C_6$-carbocycle)-, —($C_3$-$C_8$ carbocycle)-$C_1$-$C_{10}$ alkylene-, $C_3$-$C_8$-heterocycle, —$C_1$-$C_{10}$ alkylene-($C_3$-$C_8$ heterocyclo)-, —$C_3$-$C_8$-heterocyclo)-$C_1$-$C_{10}$ alkylene, —$(CH_2CH_2O)_u$, or —$CH_2CH_2O)_u$—$CH_2$—, wherein u is an integer ranging from 1 to 10 and $R^{57}$ is $C_1$-$C_6$ alkyl or aryl; and wherein the wavy line indicates covalent binding to a subunit of $L_O$.

On interaction with an electrophile or nucleophile of a targeting agent $L_B$ is converted to Ligand-$L_B$- moiety as exemplified below where one such interaction has taken place:

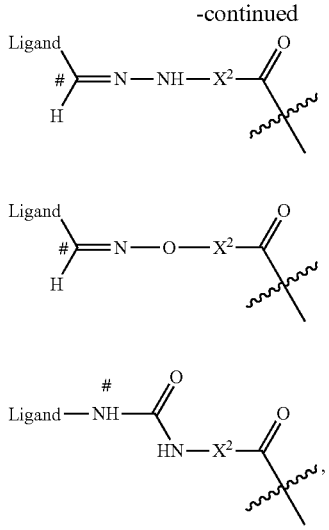

wherein the indicated (#) atom is derived from the reactive moiety of the ligand and $X^2$ is as defined.

1.2 Secondary Linkers ($L_O$)

Secondary linkers in a LDC or a $L_B'$-containing precursor thereof, is an organic moiety situated between the primary linker ($L_R$) and the quaternized drug unit ($D^+$) that provides for processing of a Cleavable Unit (W or W') within the LDC's Linker Unit subsequent to selective binding of the LDC's targeting moiety to its cognate target moiety present on, within or in the vicinity of hyper-proliferating cells, hyper-activated immune cells or other abnormal or unwanted cells targeted by the LDC. In some embodiments W provides a substrate for a protease that is present within hyper-proliferating cells or hyper-activated immune cells. Preferred are those cleavage units that are not recognized by proteases excreted by normal cells that are not typically in the presence of hyper-proliferating cells or hyper-activated immune cells or are substrates for proteases having systemic circulation in order to minimize non-targeted drug release or systemic exposure to the tertiary amine-containing drug due its premature released from its LDC. More preferred are those proteases that are regulatory proteases or proteases found in lysosomes, which are cellular compartments to which an LDC is delivered upon internalization of a membrane-surface receptor to which the LDC has specifically bound. Regulatory and lysosomal proteases are exemplary intracellular proteases.

In one embodiment W within a secondary linker is comprised or consists of a dipeptide moiety having the structure of;

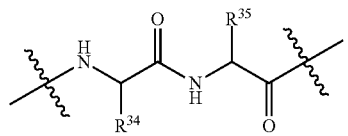

wherein $R^{29}$ is benzyl, methyl, isopropyl, isobutyl, sec-butyl, —CH(OH)CH$_3$ or has the structure of

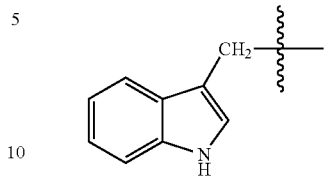

and $R^{30}$ is methyl, —(CH$_2$)$_4$—NH$_2$, —(CH$_2$)$_3$NH(C=O)NH$_2$, —(CH$_2$)$_3$NH(C=NH)NH$_2$, or, —(CH$_2$)$_2$CO$_2$H, wherein the dipeptide moiety provides for a recognition site for a regulatory or lysosomal protease.

In preferred embodiments the dipeptide is valine-alanine (val-ala). In another preferred embodiment, W is comprised or consists of the dipeptide valine-citrulline (val-cit). In another preferred embodiment W is comprised or consists of the dipeptide threonine-glutamic acid (thr-glu). In other embodiments W is a single naturally-occurring L-amino acid, preferably L-glutamate or L-lysine. In some of those embodiments the dipeptide moiety or L-amino acid is covalently attached to a self-immolative moeity (SI) of Y through an amide bond formed between the alanine or citrulline carboxylic acid functional group or the alpha carboxylic acid functional group of glutamate and an aryl or heteroaryl amino group of SI. Thus, in those embodiments SI is comprised of an arylamine or heteroarylamine moiety and the aforementioned carboxylic acid functional group of a dipeptide moiety forms an anilide bond with the amino nitrogen that arylamine moiety.

In another embodiment, W' within a secondary linker is comprised of a glycoside-bonded carbohydrate moiety having a recognition site for an intracellularly located glycosidase. In those embodiments W' is a carbohydrate moiety bonded to E' through a glycosidic bond wherein W'-E' provides the recognition site for cleavage of W' from E', and wherein E' is an optionally substituted heteroatom, of which a self-immolative Space Unit to which W' is attached within a Glucuronide Unit of formula —Y(W')— is comprised. In those embodiments W'-E'- typically has the structure of

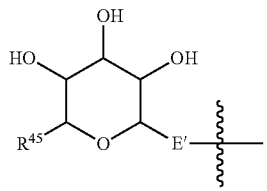

wherein $R^{45}$ is —CH$_2$OH or —CO$_2$H and E' is a heteroatom moiety such as —O—, —S— or —NH— bonded to the carbohydrate moiety and to a self-immolative moiety of Y (as indicated by the wavy line) wherein the bond to the carbohydrate moiety provides for a recognition site for a glycosidase. Preferably that site is recognized by a lysosome glycosidase. In some embodiments the glycosidase is a glucuronidase as when $R^{45}$ is —CO$_2$H.

A Secondary Linker Unit ($L_O$) in addition to W or W' are also comprised of a spacer (Y) unit and a -$L_P$(PEG)- moiety and may be additionally comprised of second stretcher ($A_O$) or a Branching Unit (B) arranged with respect to W/W' in a linear relationship represented by $L_O$-$D^+$ structures of (1a) and (1b), or an orthogonal relationship represented by $L_O$-$D^+$ structures of (2a) and (2b), respectively

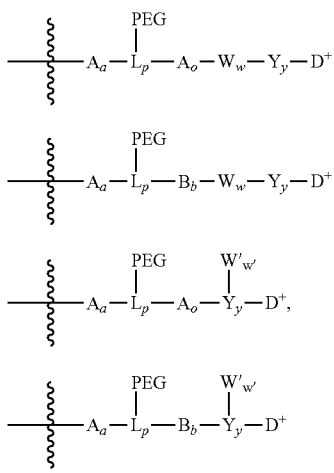

(1a)
(1b)
(2a)
(2b)

wherein $A_a$ is a first optional Stretcher unit, $A_O$ is a second optional Stretcher Unit; $W_w$ and $W'_{w'}$ are Cleavable units; and Y, is a Spacer unit, wherein subscripts a and b are independently 0 or 1, subscript w or w' is 1 and subscript y is 1. When subscript a is 1 the wavy line before $A_a$ indicates covalent bonding of that $L_O$ subunit to $L_B$' or $L_B$(resulting from $L_B$' after its incorporation into an LDC). When subscript a is 0 that wavy line indicates covalent binding of $L_B$' or $L_B$ to the -$L_P$(PEG)- moiety in structure (1a), (1b) (2a) or (2b).

In preferred embodiments subscript a is 1. In other preferred embodiments -$L_O$-$D^+$ has the structure of (2a) or 2(b), more preferably when $A_O$ is present or subscript b is 0. In particularly preferred embodiments -$L_O$-$D^+$ has the structure of (2a), wherein $A_O$ is present and subscript a is 1 so that A is also present.

Structures of some exemplary $A/A_O$, W and Y moieties in $L_O$ and their substituents are described in WO 2004/010957, WO 2007/038658, U.S. Pat. Nos. 6,214,345, 7,498,298, 7,968,687 and 8,163,888, and US Pat. Publ. Nos. 2009-0111756, 2009-0018086 and 2009-0274713 which are incorporated by reference herein.

In some embodiments $A_O$, A, or subunits thereof have the structure of

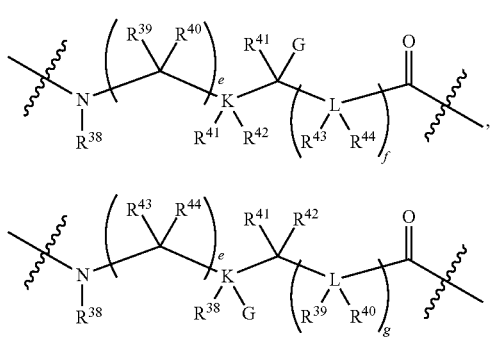

(3)

(4)

wherein the wavy lines indicated covalent attachment within the remainder of $L_O$, and wherein for $A_O$ the wavy line to the carbonyl moiety in either structure within (1a) represents the point of attachment to the amino terminus of a dipeptide moiety or a naturally-occurring L-amino acid comprising W when Y is arranged linearly with respect to Y and $D^+$ or within (2b) represents the point of attachment to a self-immolating moiety of Y described herein to which W' is bonded to Y and is arranged orthogonal with respect to Y and $D^+$, and wherein the wavy line to the amino moiety of either structure represents within (1a) or (2a) the point of attachment to a carbonyl-containing functional group of $L_P$ in -$L_P$(PEG);

wherein K and L independently are C, N, O or S, provided that when K or L is O or S, $R^{41}$ and $R^{42}$ to K or $R^{43}$ and $R^{44}$ to L are absent, and when K or L are N, one of $R^{41}$, $R^{42}$ to K or one of $R^{42}$, $R^{43}$ to L are absent, and provided that no two adjacent L are independently selected as N, O, or S;

wherein subscripts e and f are independently selected integers that range from 0 to 12, and subscript g is an integer ranging from 1 to 12:

wherein G is hydrogen, optionally substituted $C_1$-$C_6$ alkyl, —OH, —$OR^{PR}$, —$CO_2H$, $CO_2R^{PR}$, wherein $R^{PR}$ is a suitable protecting, —$N(R^{PR})(R^{PR})$, wherein $R^{PR}$ are independently a protecting group or $R^{PR}$ together form a suitable protecting group, or —$N(R^{45})(R^{46})$, wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl;

wherein $R^{38}$ is hydrogen or optionally substituted $C_1$-$C_6$ alkyl; $R^{39}$-$R^{44}$ independently are hydrogen, optionally substituted $C_1$-$C_6$ alkyl, optionally substituted aryl, or optionally substituted heteroaryl, or both $R^{39}$, $R^{40}$ together with the carbon to which they are attached comprise a $C_3$-$C_6$ cycloalkyl, or $R^{41}$, $R^{42}$ together with K to which they are attached when K is C, or $R^{43}$, $R^{44}$ together with L to which they are attached when L is C comprise a $C_3$-$C_6$ cycloalkyl, or $R^{40}$ and $R^{41}$, or $R^{40}$ and $R^{43}$, or $R^{41}$ and $R^{43}$ to together with the carbon or heteroatom to which they are attached and the atoms intervening between those carbon and/or heteroatoms comprise a 5- or 6-membered cycloalkyl or heterocycloalkyl, provided that when K is O or S, $R^{41}$ and $R^{42}$ are absent, when K is N, one of $R^{41}$, $R^{42}$ is absent, when L is O or S, $R^{43}$ and $R^{44}$ are absent, and when L is N, one of $R^{43}$, $R^{44}$ is absent.

In some embodiments $R^{38}$ is hydrogen. In other embodiments —$K(R^{41})(R^{42})$ is —$(CH_2)$—. In other embodiments when subscript e is not 0, $R^{39}$ and $R^{40}$ are hydrogen in each occurrence. In other embodiments when subscript f is not 0, -$L(R^{43})(R^{44})$— is —$CH_2$— in each occurrence.

In preferred embodiments G is —$CO_2H$. In other preferred embodiments K and/or L are C. In other preferred embodiments subscript e or f is 0. In still other preferred embodiments e+f is an integer ranging from 1 to 4.

In some embodiments $A_O$, A, or a subunit thereof has the structure of —NH—$C_1$-$C_{10}$ alkylene-C(=O)—, —NH—$C_1$-$C_{10}$ alkylene-NH—C(=O)—$C_1$-$C_{10}$ alkylene-C(=O)—, —NH—$C_1$-$C_{10}$ alkylene-C(=O)—NH—$C_1$-$C_{10}$ alkylene (C=O)—, —NH—$(CH_2CH_2O)_s$—$CH_2(C=O)$—, —NH—$(C_3$-$C_8$ carbocyclo)(C=O)—, —NH-(arylene-)—C(=O)—, and —NH—$(C_3$-$C_8$ heterocyclo-)C(=O).

In other embodiments $A_O$, A, or a subunit thereof has the structure of

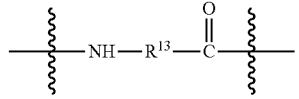

wherein $R^{13}$ is —$C_1$-$C_{10}$ alkylene-, —$C_3$-$C_8$carbocyclo-, -arylene-, —$C_1$-$C_{30}$heteroalkylene-, —$C_3$-$C_8$heterocyclo-, —$C_1$-$C_{10}$ alkylene-arylene-, -arylene-$C_1$-$C_{10}$alkylene-, —$C_1$-$C_{10}$ alkylene-($C_3$-$C_8$carbocyclo)-, —($C_3$-$C_8$ carbocyclo)-$C_1$-$C_{10}$ alkylene-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O)_{1-10}$(—$CH_2)_{1-3}$—, or —($CH_2CH_2NH)_{1-10}$(—$CH_2)_{1-3}$—. In some embodiments, $R^{13}$ is —$C_1$-$C_{10}$ alkylene- or —$C_1$-$C_{30}$heteroalkylene-. In some embodiments, $R^{13}$ is —$C_1$-$C_{10}$ alkylene-, —($CH_2CH_2O)_{1-10}$(—$CH_2)_{1-3}$—, or —($CH_2CH_2NH)_{1-10}$(—$CH_2)_{1-3}$—. In some embodiments, $R^{13}$ is —$C_1$-$C_{10}$ alkylene-polyethylene glycol, or polyethyleneimine.

In more preferred embodiments $A_O$, $A$, or a subunit thereof corresponds in structure to or is a residue of an alpha-amino acid-, a beta-amino acid moiety, or other amine-containing acid. Other embodiments of A as a single unit and subunits $A_{1-4}$ of A are described in embodiments for Linker Units having the formula of $L_R$-$L_O$.

In some embodiments, Spacer Units are capable of undergoing a 1,4- or 1,6-elimination reaction subsequent to enzymatic processing of W covalently bonded to Y (i.e., Y is comprised of a self-immolative Spacer Unit). In some embodiments Y-D⁺ arranged linearly with W in $L_O$ has the structure of:

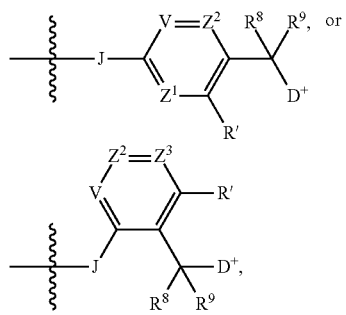

wherein V, $Z^1$, $Z^2$ and $Z^3$ independently are —C($R^{24}$)= or —N=; U is —O—, —S— or —N($R^{25}$)—; $R^{24}$ independently are hydrogen, halogen, —$NO_2$, —CN, —$OR^{25}$, —$SR^{26}$, —N($R^{27}$)($R^{28}$), optionally substituted $C_1$-$C_6$ alkyl, or —C($R^{29}$)=C($R^{30}$)—$R^{31}$, wherein $R^{25}$ is hydrogen, optionally substituted $C_1$-$C_6$ alkyl, optionally substituted aryl or optionally substituted heteroaryl, $R^{26}$ is optionally substituted $C_1$-$C_6$ alkyl, optionally substituted aryl or optionally substituted heteroaryl, $R^{27}$ and $R^{28}$ independently are hydrogen, optionally substituted $C_1$-$C_6$ alkyl, optionally substituted aryl or optionally substituted heteroaryl or both $R^{27}$ and $R^{28}$ together with the nitrogen to which they are attached comprises a 5- or 6-membered heterocycle, $R^{29}$ and $R^{30}$ independently are hydrogen, or optionally substituted $C_1$-$C_6$ alkyl, and $R^{31}$ is hydrogen, optionally substituted $C_1$-$C_6$ alkyl, optionally substituted aryl, optionally substituted heteroaryl, —C(=O)$OR^{32}$ or —C(=O)N$R^{32}$, wherein $R^{32}$ is hydrogen, optionally substituted $C_1$-$C_6$ alkyl, optionally substituted aryl, or optionally substituted heteroaryl, $R^8$ and $R^9$ independently are hydrogen or optionally substituted $C_1$-$C_6$ alkyl; and R' is hydrogen or is halogen, —$NO_2$, —CN or other electron withdrawing group or is an electron donating group, provided that no more than two of $R^{24}$ are other than hydrogen; wherein J is —O—, S—, or —N($R^{33}$)—, wherein $R^{33}$ is hydrogen or methyl;

wherein the wavy line to J represents covalent bonding of J comprising a functional group of W that inhibits the electron donating ability of J sufficiently to stabilizes the (hetero)arylene moiety of SI to 1,4- or 1,6-elimination and wherein enzymatic processing of W results in dis-inhibition of that ability to trigger the elimination so as to release $D^+$ bonded to Y as a tertiary amine-containing tubulysin drug (e.g., when J is bonded to the carbonyl moiety of a carbonyl-containing functional group of W);

In other embodiments W' and Y are arranged orthogonally in $L_O$(i.e., is —Y(W')— within the Linker Unit) wherein SI of Y is bonded to a glycoside-bonded carbohydrate moiety having a recognition site for a glycosidase wherein the orthogonal arrangement involving SI of Y is typically represented by the structure of

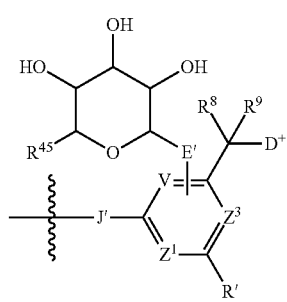

wherein E' is bonded to one of V, $Z^1$, $Z^3$, provided that the other V, $Z^1$, $Z^2$ (i.e., not bonded to E') is defined by =C($R^{24}$)— or =N—. In preferred embodiments the orthogonal arrangement involving SI of Y is represented by the structure of

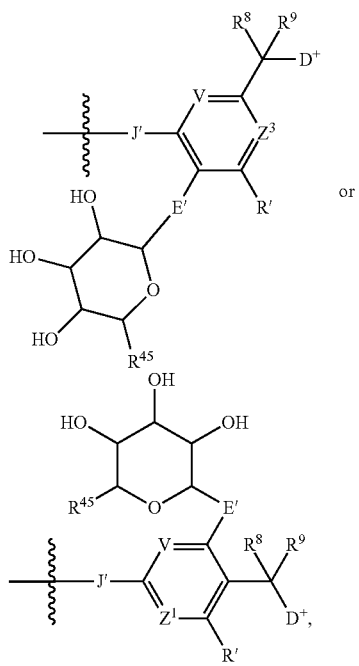

wherein V, $Z^1$ and $Z^3$ independently are —C($R^{24}$)= or —N=; $R^{24}$ independently are hydrogen, halogen, —$NO_2$, —CN, —$OR^{25}$, —$SR^{26}$, —N($R^{27}$)($R^{28}$), —C($R^{29}$)=C ($R^{30}$)—$R^{31}$ or optionally substituted $C_1$-$C_6$;

wherein $R^{25}$ is hydrogen, optionally substituted $C_1$-$C_6$ alkyl, optionally substituted aryl or optionally substituted heteroaryl; $R^{26}$ is optionally substituted $C_1$-$C_6$ alkyl, optionally substituted aryl or optionally substituted heteroaryl, and $R^{27}$ and $R^{28}$ independently are hydrogen, optionally substituted $C_1$-$C_6$ alkyl, optionally substituted aryl or optionally substituted heteroaryl or both $R^{27}$ and $R^{28}$ together with the nitrogen to which they are attached comprise or define a 5- or 6-membered heterocycle, $R^{29}$ and $R^{30}$ independently are hydrogen, or optionally substituted $C_1$-$C_6$ alkyl, and $R^{31}$ is hydrogen, optionally substituted $C_1$-$C_6$ alkyl, optionally substituted aryl, optionally substituted heteroaryl, —CN, —C(=O)OR$^{32}$ or —C(=O)NR$^{32}$; wherein $R^{32}$ is hydrogen, optionally substituted $C_1$-$C_6$ alkyl, optionally substituted aryl, or optionally substituted heteroaryl;

$R^8$ and $R^9$ independently are hydrogen or optionally substituted $C_1$-$C_6$ alkyl; R' is hydrogen or is halogen, —NO$_2$, —CN or other electron withdrawing group, or is an electron withdrawing group; $R^{45}$ is —CH$_2$OH, —CO$_2$H; E' is —O— or —NH—; J' is —NH—; and D$^+$ is as defined in embodiments described for quaternized drug units.

In more preferred embodiments the orthogonal arrangement involving SI of Y has the structure of:

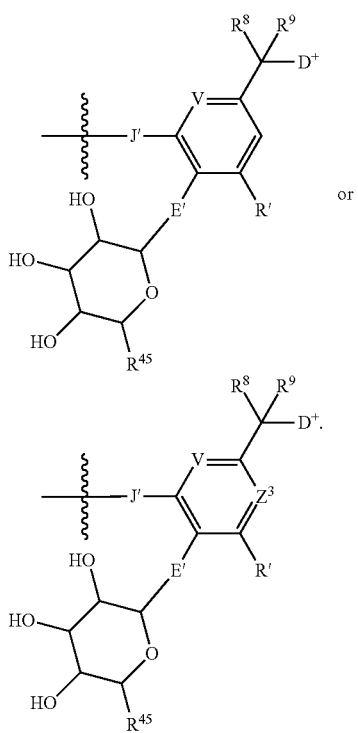

In preferred embodiments -E'- is —O— or —NH— and V or $Z^3$ is =C($R^{24}$), wherein $R^{24}$ is hydrogen or an electron withdrawing group. In other preferred embodiments $R^8$ and $R^9$ are hydrogen and V, $Z^1$ or $Z^2$ is =CH—. In other preferred embodiments -J'- is —NH, V, $Z^1$ or $Z^2$ is =CH— and R' is hydrogen or an electron withdrawing group, preferably —Cl, —F or —NO$_2$.

1.3 $L_R$-$L_O$ as Linker Units

The quaternary drug unit (D$^+$) attached to any of the above self-immolative moieties disclosed herein represents any quaternized tubulysin compound in which the tertiary amine of the C-terminal component of a tubulysin compound is quaternized (i.e., D$^+$ is a quaternized tertiary amine-containing tubulysin compound) in which the quaternized nitrogen is attached to the benzylic position of an SI moiety in a self-immolative Spacer Unit.

In some embodiments, -$L_B$-$L_O$-D$^+$ or $L_B$'-$L_O$-D$^+$ has the structure of:

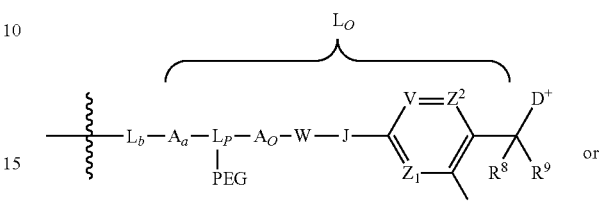

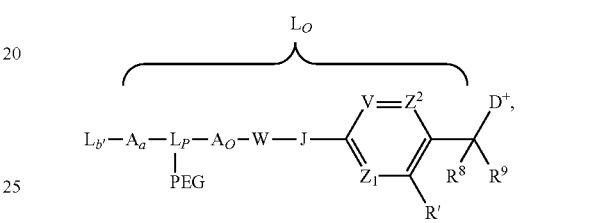

wherein V, $Z^1$ and $Z^2$ are independently =N— or =C($R^{24}$)—, wherein $R^{24}$, independently selected, is hydrogen, optionally substituted alkyl or an electron donating group, and $R^8$ and $R^9$ independently are hydrogen or optionally substituted alkyl and J is —O— or —N($R^{33}$), wherein $R^{33}$ is hydrogen or lower alkyl.

In preferred embodiments where A, W and Y are in a linear configuration, -$L_B$-$L_O$-D$^+$ or $L_B$'-$L_O$-D$^+$ has the structure of:

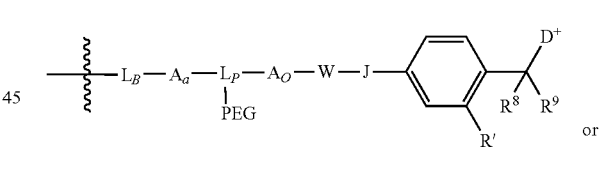

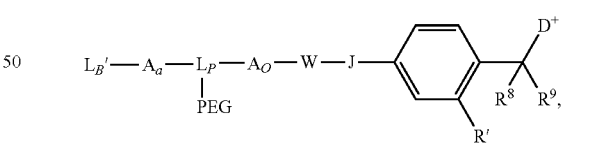

In more preferred embodiments where A, W and Y are in a linear configuration, a Ligand Drug Conjugate or a Drug Linker compound of formula $L_R$-$L_O$-D$^+$ has the structure of:

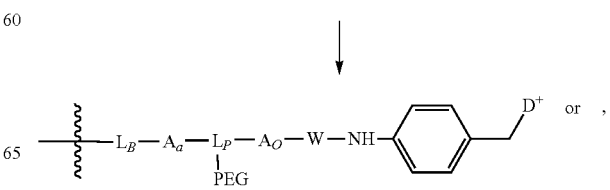

-continued

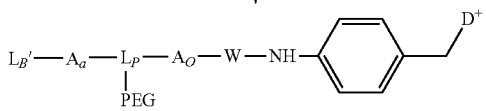

wherein W is a naturally occurring L-amino acid residue or are sequential Amino Acid subunits so that W consists or is comprised of a dipeptide wherein the dipeptide is at the distal end of W wherein the dipeptide and the indicated bond is an amide bond specifically cleavable by an intracellular protease in comparison to freely circulating serum proteases. In preferred embodiments the Amino Acid subunit attached to J/NH of Y is a natural L-amino acid or an un-natural amino acid whose amine-bearing carbon is of the same stereochemical configuration.

In any one of the above embodiments where W is comprised of a dipeptide that is recognized by a intracellular protease, preferably a cathepsin protease, preferred dipeptides have the structure of

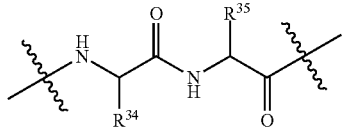

wherein $R^{34}$ is benzyl, methyl, isopropyl, isobutyl, sec-butyl, —CH(OH)CH$_3$ or has the structure of

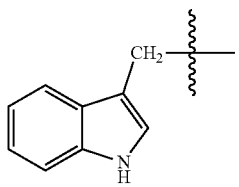 [SMILES: *Cc1c[nH]c2ccccc12]

and $R^{35}$ is methyl, —(CH$_2$)$_4$—NH$_2$, —(CH$_2$)$_3$NH(C=O)NH$_2$, (CH$_2$)$_3$NH(C=NH)NH$_2$, or —(CH$_2$)$_2$CO$_2$H, wherein the wavy line at the dipeptide N-terminal indicates covalent binding to A or to $L_B$ or $L_B'$ and the wavy line at the dipeptide C-terminal indicates covalent binding to J.

In preferred embodiments -$L_B$ and $L_B'$ are succinimide ($M^2$) or maleimide ($M^1$) moieties, respectively. In those embodiments -$L_B$-A- and -$L_B$-A$_1$-A$_2$- are referred to as succinimide-containing moieties, which are representative $L_{SS}$ moieties when A or A$_1$ is comprised of a Basic Unit, and $L_B'$-A, and $L_B'$-A$_1$- are referred to as maleimide-containing moieties, which are precursors to representative $L_{SS}$ moieties when A or A$_1$ is comprised of a Basic Unit.

Preferably, A$_O$, when A$_O$ is present, in any one of the above $L_R$-$L_O$ structures in which W, Y and D$^+$ are in a linear configuration corresponds in structure to an amine-containing acid or is an amine-containing acid residue wherein the carboxylic acid terminus of the amine-containing acid is bonded to W as an ester or amide, preferably as amide, and its N-terminus is bonded to $L_P$ of -$L^P$(PEG)- through a carbonyl-containing functional group.

In other preferred embodiments, -$L_B$-$L_O$-D$^+$ or $L_B'$-$L_O$-D$^+$ has the structure of:

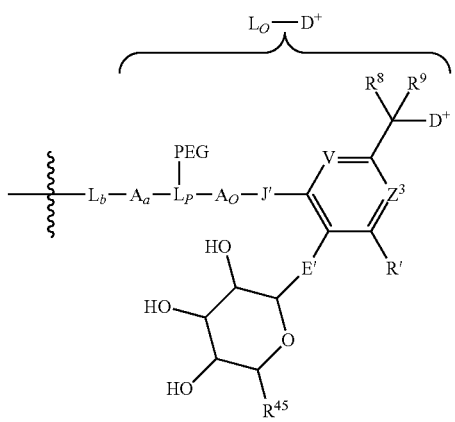

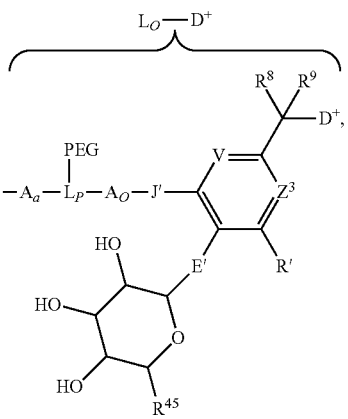

wherein V and $Z^3$ independently are =N— or =C($R^{24}$)—, wherein $R^{24}$, independently selected, is hydrogen, optionally substituted alkyl or an electron donating group, $R^8$ and $R^9$ independently are hydrogen or optionally substituted alkyl, and J' is —O— or —N($R^{33}$), wherein $R^{33}$ is hydrogen or lower alkyl, and R' is hydrogen or an electron withdrawing group.

In other more preferred embodiments $L_R$-$L_O$-D$^+$ (i.e., -$L_B$-$L_O$-D$^+$ or $L_B'$-$L_O$-D$^+$) has the structure of

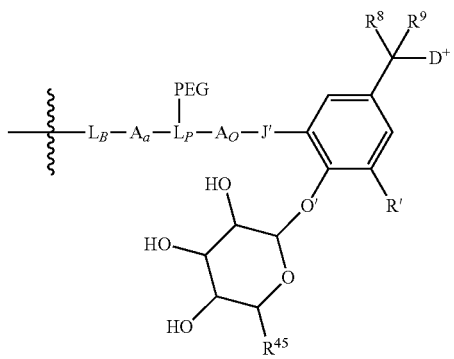

61

-continued

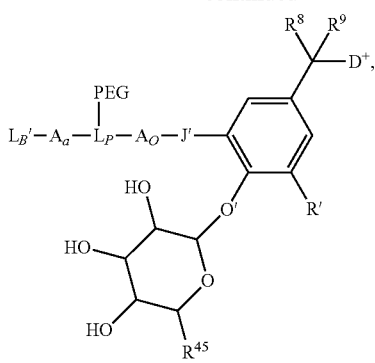

wherein V, $Z^1$ or $Z^3$ is =N— or =C($R^{24}$)—, wherein $R^{24}$, independently selected, is hydrogen, optionally substituted alkyl or an electron donating group, $R^8$ and $R^9$ independently are hydrogen or optionally substituted alkyl, and J' is —O— or —N($R^{33}$) wherein $R^{33}$ is hydrogen or lower alkyl, R' is hydrogen or an electron withdrawing group and O' represents a glycosidic-bonded oxygen, the bond to which is cleavable by a glycosidase. In preferred embodiments J' is —NH—.

Preferably, $A_O$, when $A_O$ is present, in any one of the above $L_R$-$L_O$- structures corresponds in structure to an amine-containing acid wherein the carboxylic acid terminus of the amine-containing acid is bonded to J/J' as an ester or amide, preferably as amide and its N-terminus is bonded to $L_P$ through a carbonyl-containing functional group.

In particularly preferred embodiments, -$L_B$-A- or $L_B$'-A in any one of the above -$L_B$-$L_O$-$D^+$, $L_B$'-$L_O$-$D^+$ or $L_R$-$L_O$-$D^+$ embodiments has the structure of $M^1$-A, $M^1$-$A_1$-$A_2$-, $M^2$-A or $M^2$-$A_1$-$A_2$- represented by:

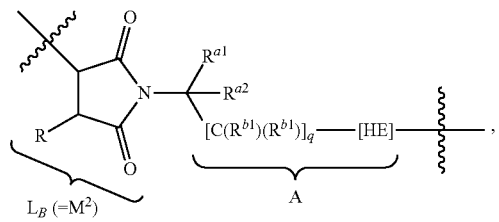

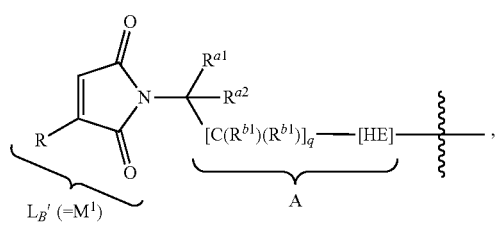

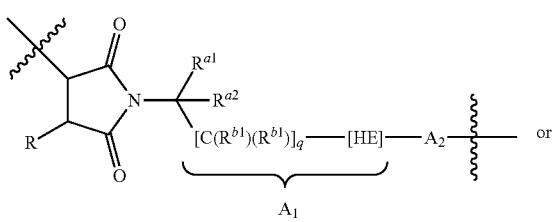

or

62

-continued

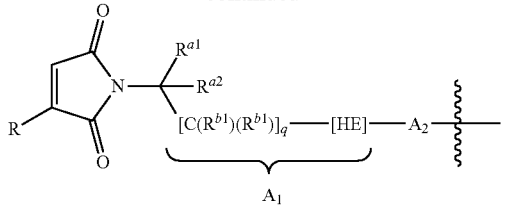

wherein $A_1$ and $A_2$ are subunits of A, $L_B$ is a succinimide ($M^2$) moiety and $L_B$' is a maleimide moiety ($M^1$), wherein —[C($R^{b1}$)($R^{b1}$)]$_q$—[HE]- is A or a subunit ($A_1$) of A; R and $R^{a2}$ independently are hydrogen or optionally substituted alkyl; $R^{a1}$ is hydrogen, lower alkyl or BU; HE is an optional hydrolysis enhancer (HE) unit; subscript q is an integer ranging from 0 to 6; each $R^{b1}$ independently is hydrogen, optionally substituted $C_1$-$C_6$ alkyl, optionally substituted aryl or optionally substituted heteroaryl, or two $R^{b1}$ together with the carbon(s) to which they are attached comprise or define a $C_3$-$C_6$ cycloalkyl or one $R^{b1}$ and HE together with the carbon to which they are attached comprise or define a 5 or 6-membered cycloalkyl or a 5- or 6-membered heterocycloalkyl and the other $R^{b1}$ is hydrogen, optionally substituted $C_1$-$C_6$ alkyl, optionally substituted aryl or optionally substituted heteroaryl; BU is a basic unit having the structure of —[C($R^1$)($R^1$)]—[C($R^2$)($R^2$)]$_n$—N($R^2$)($R^2$), wherein subscript n is 0, 1, 2 or 3, $R^1$ independently are hydrogen or lower alkyl or two $R^1$ together with the carbon to which they are attached comprise or define a $C_3$-$C_6$ cycloalkyl, $R^2$ independently are hydrogen, optionally substituted $C_1$-$C_6$ alkyl, optionally substituted aryl or optionally substituted heteroaryl, or two $R^2$ together with the carbon(s) to which they are attached and any intervening carbons define a $C_3$-$C_6$ cycloalkyl, or one $R^1$ and one $R^2$ together with the carbons to which they are attached and any intervening carbons comprise or define a 5- or 6-membered cycloalkyl and the remaining $R^1$ and $R^2$ are as defined; $R^{22}$ and $R^{23}$ independently are hydrogen or optionally substituted $C_1$-$C_6$ alkyl or $R^{22}$ and $R^{23}$ together with the nitrogen to which they are attached comprise or define a 5- or 6-membered heterocycloalkyl or one of $R^{22}$, $R^{23}$ is hydrogen and the other is an acid-labile protecting group; and wherein a sulfhydryl moiety of a targeting agent is bonded to $M^2$ as a targeting Ligand Unit as indicated by the wavy line to the succinimide moiety and wherein the wavy line to HE (or to [C($R^{b1}$)($R^{b1}$)]$_q$ when HE is not present) indicates covalent binding to another subunit of A or to -$L_P$(PEG)-.

In other particularly preferred embodiments, -$L_B$-A- or -$L_B$-$A_1$-$A_2$- in any one of the above $L_B$-containing embodiments has the structure of -$M^3$-A- or -$M^3$-$A_1$-$A_2$-represented by:

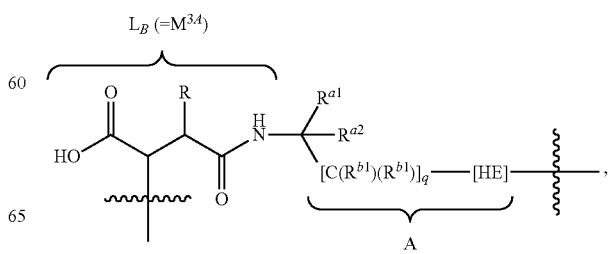

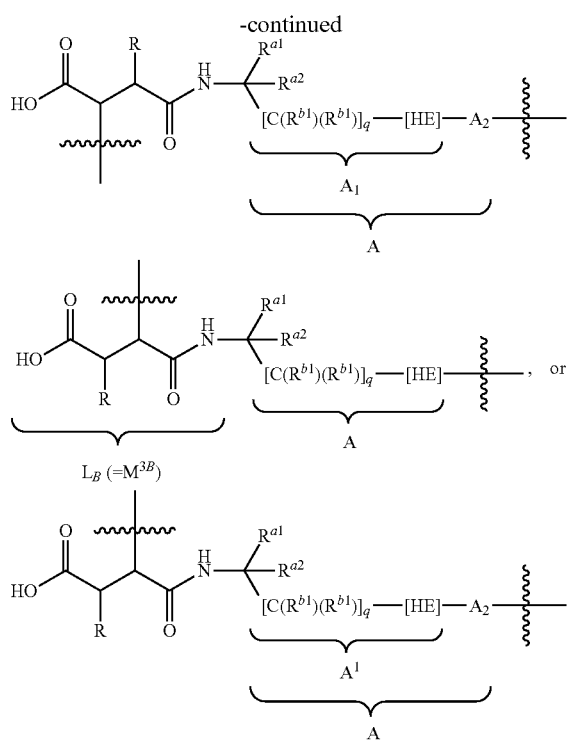

wherein $A_1$ and $A_2$ are subunits of A, and $M^{3A}$ and $M^{3B}$ are regioisomers of $M^3$ and wherein the variable groups and connectivity to a sulfhydryl group of a targeting moiety and HE (or $[C(R^{b1})(R^{b1})]_q$) are as defined for the corresponding succinimide-containing moieties shown immediately above. In the present embodiments $L_B$ is referred to as a succinic acid-amide ($M^3$) moiety and -$L_B$-A-, $L_B'$-A-, -$L_B$-$A_1$- or $L_B'$-$A_1$- are referred to as succinic acid-amide-containing moieties, which are representative Ls moieties.

In those and any one of the above embodiments comprised of HE, HE is preferably —C(=O)—.

In any one of those -$L_B$-A-, $L_B'$-A-, -$L_B$-$A_1$- and $L_B'$-$A_1$- or $M^1$-A, $M^1$-$A_1$-$A_2$-, $M^2$-A-, $M^2$-$A_1$-$A_2$-, $M^3$-A- and $M^3$-$A_1$-$A_2$- embodiments each $R^b$ independently is preferably hydrogen or lower alkyl and subscript m is 0 or 1, $R^{a1}$ is preferably hydrogen, lower alkyl or BU or $R^2$ is preferably hydrogen.

In any one of the above embodiments where W, Y and $D^+$ are in a linear configuration and is comprised of A or $A_1$-$A_2$, preferred embodiments are those where W is bonded to A or $A_2$ through an amide functional group. In those embodiments preferably A, $A_1$ and $A_2$ have independently selected structures corresponding to or incorporating amine-containing acids as described herein for Stretcher Unit embodiments. In any one of the above -$L_B$-A-, $L_B'$-A-, -$L_B$-$A_1$- and $L_B'$-$A_1$- embodiments comprised of A or $A_1$, A and $A_1$ preferably have structures corresponding to incorporating amine-containing acids or are amine-containing acid residues as described herein for Stretcher Unit embodiments wherein A is bonded to W or $A_1$ is bonded to $A_2$ through an amide functional group. In any one of the above M -A-, M -$A_1$-$A_2$-, $M^2$-A-, $M^2$-$A_1$-$A_2$-, $M^3$-A- and $M^3$-$A_1$-$A_2$-embodiments, preferably A, $A_1$ and $A_2$ have independently selected structures corresponding to or incorporating amine-containing acids or are independently selected amino acid residues as described herein for first Stretcher Unit A and second Stretcher Unit $A_O$ embodiments. In any one of the above $L_{SS}$ or Ls embodiments that are comprised of -A(BU)— or -$A_1$(BU)— moieties, A and $A_1$ preferably have structures corresponding to or incorporating amine-containing acids substituted with BU, and are therefore diamino-containing acids as described herein for Stretcher Unit and Basic Unit embodiments. In $M^1$, $M^2$ and $M^3$-containing moieties having A or $A_1$ moieties corresponding in structure to or residue of an amine-containing acid, the amine nitrogen of the amine-containing acid is incorporated as the imine nitrogen of the $M^1$ or $M^2$ ring system or the amide nitrogen of the $M^3$ moiety. In $L_{SS}$ or Ls-containing moieties the N-terminal amine nitrogen of the diamino-containing acid is incorporated as the imine nitrogen of the $M^1$ or $M^2$ ring system or the amide nitrogen of the $M^3$ moiety. Preferably for any one of the above $M^1$-, $M^2$- and $M^3$-containing moieties or $L_{SS}$- or Ls-containing moieties the carboxylic acid of the amine-containing acid or the diamino-containing acid is incorporated into an amide functional group to $A_2$ for those moieties comprised of $A_1$-$A_2$- or to W for those moieties comprised of A when A is a single unit.

In more preferred embodiments A or $A_1$ and $A_2$ in -$A_1$-$A_2$- are independently represented by structures (3) or (4):

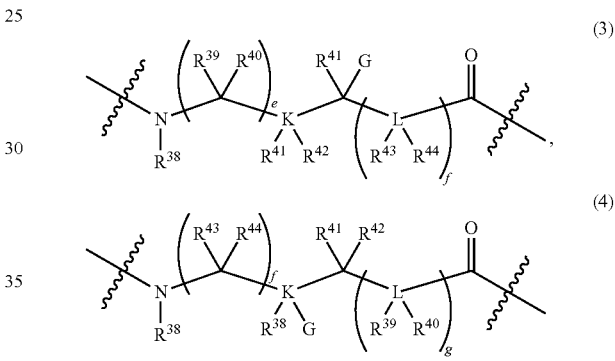

wherein L is absent (i.e., subscript e is 0) and G is hydrogen, BU, —$CO_2H$ or —$NH_2$ or the side chain of a naturally occurring amino acid such as aspartic acid, glutamic acid or lysine and the other variable group are as previously defined. In other preferred embodiments L and K are carbon and $R^{41}$, $R^{42}$, $R^{43}$ and $R^{44}$ in each occurrence is hydrogen and $R^{38}$-$R^{40}$ and subscripts e, f and g are as previously defined. In other preferred embodiments $R^{38}$-$R^{44}$ in each occurrence is hydrogen and K, L and subscripts e, f and g are as previously defined. Other preferred embodiments have structure (3) wherein K is nitrogen and one of $R^{41}$, $R^{42}$ is absent and the other is hydrogen and L, subscripts e, f and g and the remaining $R^{39}$-$R^{42}$ variable groups are as previously defined. Other preferred embodiments have structure (4) wherein subscript g is 1, K is nitrogen and one of $R^{41}$, $R^{42}$ is absent and the other is hydrogen, L, subscripts e and f and the remaining $R^{39}$-$R^{42}$ variable groups are as previously defined. In other preferred embodiments subscripts e and f of structure (3) are each 0 or subscripts f and g of structure (4) are each 0, wherein K, L and the remaining $R^{38}$-$R^{44}$ variable groups are as previously defined. Other preferred embodiments have structure (3) wherein subscripts e and f are both 0 and K together with $R^{41}$ and $R^{42}$ is —C(=O)— and the remaining $R^{38}$-$R^{40}$ variable groups are as previously defined. Other preferred embodiments have structure (4) wherein subscript f is 1 and L together with $R^{43}$ and $R^{44}$ is —C(=O)— and K, L, subscript g and $R^{38}$-$R^{42}$ are as previously defined.

In more preferred embodiments A, or $A_1$ and $A_2$ in -$A_1$-$A_2$-, independently have the structure of (3a) or (4a):

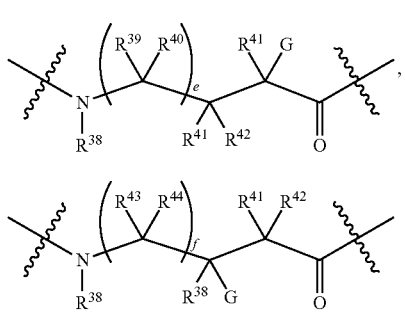
(3a)

(4a)

wherein subscript e or f is 0 or 1 and G and $R^{39}$-$R^{44}$ are as previously defined.

When an $L_{SS}$ or Ls moiety is comprised of A or $A_1$ preferred A or $A_1$ structures correspond to those shown for (3), (3a), (4) and (4a) wherein $R^{38}$ is absent, G is a basic unit (BU) and the N-terminal nitrogen is incorporated into a $M^1$ or $M^2$ moiety as the imine nitrogen of that moiety's ring system or is incorporated into a $M^3$ moiety as the amide nitrogen of the succinic acid amide.

In other more preferred embodiments A or $A_1$ and $A_O$ of A correspond independently in structure to or are independently selected residues of an alpha-amino, beta-amino or other amine-containing acid. When an $L_{SS}$ or Ls moiety is comprised of A or $A_1$, preferred A or $A_1$ moieties correspond in structure to or are residues of an alpha-amino, beta-amino or other amine-containing acid substituted with BU (i.e., is a diamino-containing acid), wherein the N-terminal nitrogen of the BU-substituted alpha-amino, beta-amino or other amine-containing acid, which is represented by A(BU) or $A_1$(BU), is incorporated into a $M^1$ or $M^2$ moiety as the imine nitrogen of that moiety's ring system or is incorporated into $M^3$ as the amide nitrogen of the succinic acid amide moiety.

In those embodiments, particularly preferred A(BU) or $A_1$(BU) have the structure of (3) or (3a) wherein subscript e is 0 and G is BU or have the structure of (4) or (4a) wherein subscript f is 1 and G is BU. In embodiments wherein W, Y and $D^+$ are in linear arrangement wherein $A_O$ is present, particularly preferred amine-containing acids incorporated as $A_O$ have the structure of $NH_2$—$X^1$—$CO_2H$ wherein $X^1$ is an optionally substituted $C_1$-$C_6$-alkylene, including ε-amino-caproic acid and β-amino-propionic acid.

In preferred embodiments where A, W and Y are in an orthogonal configuration in -$L_B$-$L_O$-$D^+$ or $L_B'$-$L_O$-$D^+$ have the structure of:

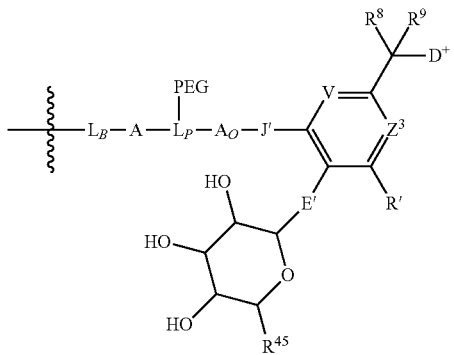

or

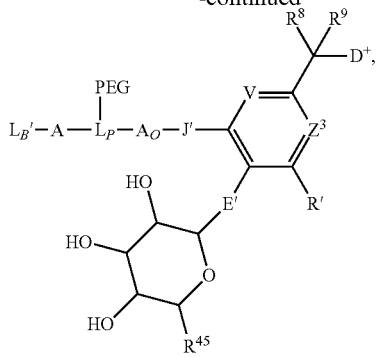

and other preferred embodiments where A, W and Y are in a linear configuration in -$L_B$-$L_O$-$D^+$ or $L_B'$-$L_O$-$D^+$ have the structure of:

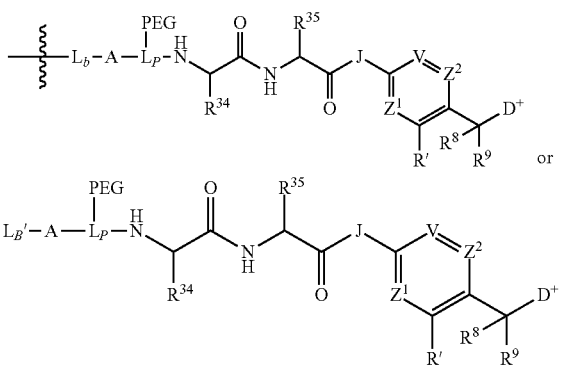

or wherein A is a single unit and $A_O$ is present.

In more preferred embodiments E' is O', J/J' is —NH—, $R^{34}$ is methyl, isopropyl or —CH(OH)CH$_3$ and $R^{35}$ is methyl, —(CH$_2$)$_3$NH(C=O)NH$_2$ or —(CH$_2$)$_2$CO$_2$H, $R^{45}$ is —CO$_2$H and R', $R^8$, $R^9$, J, V, Z, $Z^2$ and $Z^3$ are as previously defined for Formula 1A, 1B, 1D or Formula IA, IB or ID. In more preferred embodiments $R^8$ and $R^9$ are each hydrogen. In still other more preferred embodiments E is O', J/J' is —NH—, V, $Z^1$, $Z^2$ and $Z^3$ are each —CH=. Also more preferred are those embodiments wherein $L_B'$ has the structure of a maleimide moiety ($M^1$) or wherein $L_B$ has the structure of a succinimide moiety ($M^2$) or an succinic acid-amide ($M^3$) moiety.

More preferred are those embodiments in which $L_B'$-A has the structure given above for any one of the $M^1$-A-, and more preferred -$L_B$-A- moieties have the structure given above for any one of the $M^2$-A- or $M^3$-$A_1$- moieties. In any one of those embodiments J/J' is preferably —NH—.

In preferred embodiments in which W', Y and $D^+$ are in a orthogonal relationship $A_O$ is present and has the structure previously defined for (3), (3a), (4) or (4a), wherein the wavy line to the carbonyl moiety of any one of the structure represents the point of attachment of $A_O$ to J' preferably through an amide functional group and wherein the wavy line to the amino moiety of either structure represents the point of attachment to a carbonyl-containing functional group of $L_P$ or -$L_P$(PEG)-, preferably forming an amide functional group; wherein the variable groups are as previously defined for structures representing A, or $A_1$ and $A_2$ in -$A_1$-$A_2$-. In preferred embodiments L is absent (i.e., subscript q is 0) and G is hydrogen, —CO$_2$H or —NH$_2$ or the side chain of a naturally occurring amino acid such as aspartic acid, glutamic acid or lysine. In other preferred embodiments, L and K are carbon and $R^{41}$, $R^{42}$, $R^{43}$ and $R^{44}$ in each occurrence is hydrogen. In other preferred embodiments $R^{38}$-$R^{44}$ in each occurrence is hydrogen. Other preferred embodiments have structure (3) wherein K is nitrogen and one of $R^{41}$, $R^{42}$ is absent and the other is hydrogen. Other preferred embodiments have structure (4) wherein r is 1, K is nitrogen and one of $R^{41}$, $R^{42}$ is absent and the other is hydrogen. In other preferred embodiments subscripts p and q of structure (3) are 0 or subscripts q and r of structure (4) are 0. Other preferred embodiments have structure (3) wherein subscripts p and q are both 0 and K together with $R^{41}$ and $R^{42}$ is —C(=O)—. Other preferred embodiments have structure (4) wherein subscript q is 1 and L together with $R^{43}$ and $R^{44}$ is —C(=O)—.

In more preferred embodiments A or $A_1$ and $A_O$ of A correspond independently in structure to or is a residue of an alpha-amino, beta-amino or other amine-containing acid. In other more preferred embodiments having an $L_{SS}$ or Ls moiety that moiety is comprised of A or $A_1$ with preferred structures corresponding to those shown for (3), (3a), (4) and (4a) wherein $R^{38}$ is absent, G is a basic unit (BU) and the N-terminal nitrogen is incorporated into a $M^1$ or $M^2$ moiety as the imine nitrogen of that moieties ring system or is incorporated into a $M^3$ moiety as the amide nitrogen of the succinic acid amide. Other preferred A or $A_1$ moieties for $L_{SS}$ or Ls correspond in structure to or incorporate an alpha-amino, beta-amino or other amine-containing acid substituted with BU (i.e., is a diamino-containing acid), wherein the N-terminal nitrogen of the BU-substituted alpha-amino, beta-amino or other amine-containing acid, which is represented by A(BU) or $A_1$(BU), is incorporated into a $M^1$ or $M^2$ moiety as the imine nitrogen of that moiety's ring system or is incorporated into $M^3$ as the amide nitrogen of the succinic acid amide moiety.

In embodiments comprised of where A, W' and Y are in an orthogonal configuration in -$L_B$-$L_O$-$D^+$ or $L_B$'-$L_O$-$D^+$ wherein $A_O$ is present, particularly preferred amine-containing acids that correspond to $A_O$ incorporate the structure of $NH_2$—$X^1$—$CO_2H$ wherein $X^1$ is an optionally substituted $C_1$-$C_6$-alkylene, including ε-aminocaproic acid and 3-amino-propionic acid.

Particularly preferred are any one of the above $L_B$-containing embodiments wherein the targeting moiety bonded to $L_B$ is an antibody.

1.3.1 Ligand Unit

In some embodiments of the invention, a Ligand Unit is present. The Ligand Unit (L-) is a targeting moeity that specifically binds to a targeted moiety. The Ligand Unit can specifically bind to a cell component (a Cell Binding Agent) or to other targeted molecules of interest. The Ligand Unit acts to target and present the quaternized tubulysin Drug Units to the particular target cell population with which the Ligand Unit interacts for selective release of $D^+$ as a free tubulysin compound. Targeting agents include, but are not limited to, proteins, polypeptides and peptides. Suitable Ligand Units include those from targeting agent such as antibodies, e.g., full-length antibodies and antigen binding fragments thereof, interferons, lymphokines, hormones, growth factors and colony-stimulating factors, vitamins, nutrient-transport molecules (such as, but not limited to, transferrin), or any other cell binding molecule or substance. The Ligand Unit can be, for example, from non-antibody protein targeting agent. Alternatively, the targeting agent can be, for example, an antibody. Preferred targeting agents are larger molecular weight proteins, e.g., Cell Binding Agents having a molecular weight of at least about 80 Kd.

A targeting agent reacts with a Ligand Covalent Binding Unit precursor $L_B$' to form L-$L_B$- wherein L is a Ligand Unit and $L_B$ is Ligand Covalent Binding Unit. The targeting agent has to have the requisite number of attachment sites to accommodate the drug-linker moieties each comprising a $L_B$, whether they be naturally occurring or non-naturally occurring (e.g., engineered). For example, in order for the value of the subscript p to be from 6 to 14, a targeting agent has to be capable of forming a bond to 6 to 14 drug-linker moieties. A targeting agent can form a bond to $L_B$' in the Linker Unit of a Drug Linker compound via a reactive or activatable heteroatom or a heteroatom-containing functional group of the targeting agent. Reactive or activatable heteroatoms or a heteroatom-containing functional groups that may be present on a targeting agent include sulfur (in one embodiment, from a sulfhydryl group of a targeting agent), C=O or (in one embodiment, from a carbonyl, carboxyl or hydroxyl group of a targeting agent) and nitrogen (in one embodiment, from a primary or secondary amino group of a targeting agent). Those heteroatoms can be present on the targeting agent in the targeting agent's natural state, for example a naturally-occurring antibody, or can be introduced into the targeting agent via chemical modification or biological engineering.

In one embodiment, a targeting agent has a sulfhydryl group and the Ligand Unit therefrom is attached to the Linker Unit via the sulfhydryl group's sulfur atom.

In another embodiment, the targeting agent has lysine residues that can react with activated esters (such esters include, but are not limited to, N-hydroxysuccinimide, pentafluorophenyl, and p-nitrophenyl esters) of $L_B$' of the Linker Unit of a Drug Linker compound and thus form an amide bond between of the nitrogen atom of the Ligand Unit and the C=O group of the Linker Unit.

In yet another aspect, the targeting agent has one or more lysine residues that can be chemically modified to introduce one or more sulfhydryl groups. The Ligand Unit from that targeting agent is attached to the Linker Unit via the introduced sulfhydryl group's sulfur atom. The reagents that can be used to modify lysines in that manner include, but are not limited to, N-succinimidyl S-acetylthioacetate (SATA) and 2-Iminothiolane hydrochloride (Traut's Reagent).

In another embodiment, the targeting agent can have one or more carbohydrate groups that can be chemically modified to have one or more sulfhydryl groups. The Ligand Unit from that targeting agent is attached to the Linker Unit via the introduced sulfhydryl group's sulfur atom In yet another embodiment, the targeting agent can have one or more carbohydrate groups that can be oxidized to provide an aldehyde (—CHO) group (see, e.g., Laguzza, et al., 1989, *J. Med. Chem.* 32(3):548-55). The corresponding aldehyde can then react with a $L_B$' having a nucleophilic nitrogen. Reactive sites on a $L_B$' that can react with a carbonyl group on a targeting agent include, but are not limited to, hydrazine and hydroxylamine. Other protocols for the modification of proteins for the attachment of drug linker moieties are described in Coligan et al., *Current Protocols in Protein Science*, vol. 2, John Wiley & Sons (2002) (incorporated herein by reference).

A targeting agent forms a bond with the reactive group on $L_B$' of a Drug Linker compound to form a LDC in which a drug linker moiety thereof is comprised a $L_B$-containing moiety. A variety of reactive groups are useful and will depend on the nature of the desired Ligand Unit. The reactive group can be a maleimide which is present on $L_B'$ (prior to attachment to L) and covalent attachment of L to $L_B$ is accomplished through a sulfhydryl group of the targeting agent to form a thio-substituted succinimide. The sulfhydryl group can be present on the targeting agent in the targeting agent's natural state, for example a naturally-occurring residue, or can be introduced into the targeting agent via chemical modification.

In still another embodiment, the targeting agent is an antibody and the sulfhydryl group is generated by reduction of an interchain disulfide. Accordingly, in some embodiments, the Linker Unit is conjugated to a cysteine residue of the reduced interchain disulfides of the Ligand Unit.

In yet another embodiment, the targeting agent is an antibody and the sulfhydryl group is chemically introduced into the antibody, for example by introduction of a cysteine residue. Accordingly, in some embodiments, the Linker Unit is conjugated to an introduced cysteine residue.

It has been observed for bioconjugates that the site of drug conjugation can affect a number of parameters including ease of conjugation, drug-linker stability, effects on biophysical properties of the resulting bioconjugates, and in-vitro cytotoxicity. With respect to drug-linker stability, the site of conjugation of a drug-linker to a Ligand Unit can affect the ability of the conjugated drug-linker moiety to undergo an elimination reaction and for the drug linker moiety to be transferred from the Ligand Unit of a bioconjugate to an alternative reactive thiol present in the milieu of the bioconjugate, such as, for example, a reactive thiol in albumin, free cysteine, or glutathione when in plasma. Such sites include, for example, the interchain disulfides as well as select cysteine engineered sites. The Ligand-Drug Conjugates described herein can be conjugated to thiol residues at sites that are less susceptible to the elimination reaction (e.g., positions 239 according to the EU index as set forth in Kabat) in addition to other sites.

When the conjugates comprise non-immunoreactive protein, polypeptide, or peptide ligands instead of an antibody, useful non-immunoreactive protein, polypeptide, or peptide ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, somatostatin, lectins and apoprotein from low density lipoprotein.

Particularly preferred targeting agents are antibodies, including intact antibodies. In fact, in any of the embodiments described herein, the Ligand Unit can be an antibody. Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, or chimeric human-mouse (or other species) monoclonal antibodies. The antibodies include full-length antibodies and antigen binding fragments thereof. Human monoclonal antibodies may be made by any of numerous techniques known in the art (e.g., Teng et al., 1983, *Proc.* *Natl. Acad. Sci. USA.* 80:7308-7312; Kozbor et al., 1983, *Immunology Today* 4:72-79; and Olsson et al., 1982, *Meth. Enzymol.* 92:3-16).

The antibody can be a functionally active fragment, derivative or analog of an antibody that immunospecifically binds to target cells (e.g., cancer cell antigens, viral antigens, or microbial antigens) or other antibodies bound to tumor cells or matrix. In this regard, "functionally active" means that the fragment, derivative or analog is able to immuno-specifically binds to target cells. To determine which CDR sequences bind the antigen, synthetic peptides containing the CDR sequences can be used in binding assays with the antigen by any binding assay method known in the art (e.g., the BIA core assay) (See, e.g., Kabat et al., 1991, *Sequences of Proteins of Immunological Interest*, Fifth Edition, National Institute of Health, Bethesda, Md.; Kabat E et al., 1980, *J. Immunology* 125(3):961-969).

Other useful antibodies include fragments of antibodies such as, but not limited to, F(ab')$_2$ fragments, Fab fragments, Fvs, single chain antibodies, diabodies, tribodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, *Science* 240:1041-1043; Liu et al., 1987, *Proc. Natl. Acad. Sci. USA* 84:3439-3443; Liu et al., 1987, *J. Immunol.* 139:3521-3526; Sun et al., 1987, *Proc. Natl. Acad. Sci. USA* 84:214-218; Nishimura et al., 1987, *Cancer. Res.* 47:999-1005; Wood et al., 1985, *Nature* 314:446-449; and Shaw et al., 1988, *J. Natl. Cancer Inst.* 80:1553-1559; Morrison, 1985, *Science* 229:1202-1207; Oi et al., 1986, *BioTechniques* 4:214; U.S. Pat. No. 5,225,539; Jones et al., 1986, *Nature* 321:552-525; Verhoeyan et al., 1988, *Science* 239:1534; and Beidler et al., 1988, *J. Immunol.* 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes.

Antibodies include analogs and derivatives that are either modified, i.e., by the covalent attachment of any type of molecule as long as such covalent attachment permits the antibody to substantially retain its antigen binding immunospecificity. For example, but not by way of limitation, derivatives and analogs of the antibodies include those that have been further modified, e.g., by glycosylation, acetylation, PEGylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing.

In another specific embodiment, antibodies for the treatment of an autoimmune disease are used in accordance with the compositions and methods of the invention. Antibodies immunospecific for an antigen of a cell that is responsible for producing autoimmune antibodies can be obtained from any organization (e.g., a university scientist or a company) or produced by any method known to one of skill in the art such as, e.g., chemical synthesis or recombinant expression techniques.

In certain embodiments, useful antibodies can bind to a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein.

In some aspects, the antibody will specifically bind CD19, CD20, CD30, CD33, CD70, alpha-v-beta-6, or Lewis Y antigen.

The antibody can be a humanized anti-CD33 antibody (US 2013/0309223 incorporated by reference herein in its entirety and for all purposes), a humanized anti-Beta6 antibody (see, e.g., WO 2013/123152 incorporated by reference herein in its entirety and for all purposes), a humanized anti-Liv-1 antibody (see, e.g., US 2013/0259860 incorporated by reference herein in its entirety and for all purposes), or a humanized AC10 antibody (see, e.g., U.S. Pat. No. 8,257,706 incorporated by reference herein in its entirety and for all purposes).

Exemplary attachment to the Ligand is via thioether linkages. The thioether linkages can be via interchain disulfide bonds, introduced cysteines resides, and combinations thereof.

1.3.2 Parallel Connector Unit

A Ligand Drug Conjugate, and its Drug Linker compound precursor of the present invention, are comprised of a PEG Unit that is in parallel orientation with the quaternized tubulysin Drug Unit in order to influence the pharmacokinetics of the resulting LDC. The parallel orientation of the PEG unit is accomplished by the Parallel Connector Unit ($L_P$). For that purpose the Parallel Connector Unit arranges the Ligand, PEG and Drug Units in a branched configuration. Accordingly, the Parallel Connector Unit can be considered a scaffolding component having attachment sites for other components of the Ligand-Drug Conjugate and Drug Linker compound In order to act as a parallel connector, the $L^P$ Unit is attached via three attachment sites within the Linker Unit. One of the attachment sites connects the $L^P$ Unit to the PEG Unit. In one embodiment a second attachment site connects the $L^P$ Unit to a protease susceptible Cleavable Unit (W), which is the connected to a self-immolative Spacer Unit (Y). In another embodiment a second attachment site of $L_P$ connects directly to a self-immolative Spacer Unit (Y) to which is also attached a glycosidase-susceptible Cleavable Unit (W'), or in such instances indirectly connects to Y through an intervening Stretcher Unit ($A_O$). A third attachment site attaches the L Unit to the remainder of the Linker Unit, which in a LDC is typically connected to the Ligand Unit through another Stretcher Unit (A). The Parallel Connector Unit is a unit that is distinct from the PEG Unit and is attached thereto via the PEG Attachment Unit component of the PEG Unit. In other words, the Parallel Connector Unit is not a subunit of the PEG Unit.

For the Ligand-Drug Conjugates and intermediates thereof having more than one drug per PEG Unit, attachment of the Parallel Connector Unit to W or Y can be through a Branching Unit (B) in place of $A_O$. In all of these embodiments, the $L_P$ unit can be considered a tri-functional chemical moiety that is capable of covalently linking together three spaced chemical moieties. As will be appreciated, for select Intermediate Compounds, a precursor to $L_P$ is represented by $L_P'$ and is not yet completely incorporated into a Linker Unit (e.g. is pending attachment to A, $A_O$, B, W or Y, but has an optionally protected functional group for that attachment). As will also be appreciated, the term "tri-functional" is used to denote the three attachment sites and not the number of functional groups present on any $L_P$, $L_P'$, or subunit thereof.

A Parallel Connector Unit can be prepared from one or more (typically from 1 to 5 or 1 to 4 or 1 to 3 or 1 or 2) natural or non-natural amino acid(s), amino alcohol(s), amino aldehyde(s), or polyamine(s) or some combination thereof.

It will be appreciated that when referring to the natural or non-natural amino acid, amino alcohol, amino aldehyde, or polyamine as present in an LDC or Drug Linker compound of the present invention (whether they be part of a $L_P$ Unit or other component of the LDC or Drug Linker compound described herein), the amino acid, amino alcohol, amino aldehyde, or polyamines will exist in residual form. For example, in embodiments, wherein the Parallel Connector Unit is two amino acids, the two amino acids will exist as residues with a peptide bond between them. In embodiments where the Parallel connector unit is comprised of an amino alcohol, the amino alcohol will exist as a residue where, for example, its amino group is bonded to another residue of the Parallel Connector Unit or another component of the LDC or Drug Linker compound through a carbonyl-containing functional group of that other residue/component while its hydroxyl group is bonded as an ether to, or is bonded through a carbonyl-containing functional group, of yet another residue of the Parallel Connector Unit or another component of the LDC or Drug Linker compound. In embodiments where the Parallel Connector Unit is comprised of an amino aldehyde, the amino aldehyde will exist as a residue where, for example, its amino group is bonded to another residue of the Parallel Connector Unit or another component of the LDC or Drug Linker compound through a carbonyl-containing functional group of that other residue/component while its aldehyde functional group is converted to an imino functional group or through subsequent reduction to provide a nitrogen-carbon bond when bonded to an amino group of yet another residue of the Parallel Connector Unit or another component of the LDC or Drug Linker compound. An amino alcohol or amino aldehyde may be derived from a natural or unnatural amino acid by reduction of its carboxylic acid functional group to an aldehyde or an hydroxyl functional group.

In some embodiments a Parallel Connector Unit or sub-unit thereof having the required tri-functionality is provided by an amino acid or other amine-containing acid residue that has or can be substituted with a functionalized side chain to provide the requisite three points of attachment. For example, serine has three functional groups, i.e., acid, amino and hydroxyl functional groups and may be viewed as a combined amino acid and amino alcohol residue for purposes of its incorporation into a Parallel Connector Unit. Tyrosine also contains a hydroxyl group, in this instance in its phenolic side chain, and may also be view similarly to serine for purposes of its incorporation as a trifunctional component of a Parallel Connector Unit.

In another example, when the three attachment sites of a Parallel Connector Unit or subunit thereof is provided by cysteine, its amino and carboxylic acid group will exist in residual form in a manner previously discussed for amino acids or amine-containing acids to provide two of the three requisite points of attachment while its thiol group will exist in residual form to provide the other requisite attachment point In some instances, the residual thiol group is in its oxidized form (i.e., —S(=O)— or —S(=O)$_2$—) when bonded to another subunit of the Parallel Connector Unit or to another component of the Linker Unit. In yet another example, the alpha amino and carboxylic acid group of a lysine will exist in residual form to provide two of the three requisite points of attachment for a Parallel Connector Unit while it epsilon amino group in its residual form provides the remaining point of attachment. Histidine may also be viewed as an amino acid with two amino groups, where the second amino group is the NH of the imidazole-containing side chain.

In another example, when the three attachment sites of a Parallel Connector unit is provided by aspartic or glutamic acid, the alpha amino and C-terminal carboxylic acid functional groups of the amino acid in their residual forms provide two of the three requisite points of attachment, while its beta or gamma carboxylic acid functional group in its residual form provides the remaining of attachment. In those instances when a naturally occurring amino acid is recited as a Parallel Connector Unit or subunit thereof, but does not naturally contain a functionalized amino acid side chain, yet is required to be a trifunctional component of $L_P$, it is understood that the amino acid structure is modified to have an additional functional group besides its amino and carboxylic acid functional groups when in residual form in order to provide the requisite third point of attachment. For example, an amino acid having an aliphatic side chain may be substituted at a carbon of that side chain with a hydroxyl, amino, aldehyde, thiol, carboxylic acid group or other functional group or other moiety (e.g., an aryl or arylalkyl substituted with any one of these functional groups) to provide an unnatural amino acid having the requisite three points of attachment. Such unnatural amino acids are incorporated into a Parallel Connector Unit as described above for amino acids and residual forms of the introduced functional groups.

Similarly, when an amino aldehyde or amino alcohol is incorporated into a Parallel Connecting Unit that amino aldehyde or amino alcohol will have a third functional group to provide, along with its amino and aldehyde functional groups, the requisite three points of attachment. In those instances, an amino aldehyde or amino alcohol may correspond in structure to a natural amino acid that has a functionalized side chain or an unnatural amino acid having an functional group that was introduced into the side chain of a natural amino acid as described above in which a carboxylic acid of the natural or unnatural amino acid is reduced to an hydroxyl or aldehyde functional group.

An amino acid residue of $L_P$ can be that of an alpha, beta, or gamma amino acid or other amine-containing acid compound and can be in its D- or L-isomer if it contains a chiral carbon to which is bonded a natural or unnatural amino acid side chain that provides the remaining requisite point of attachment. When the Parallel Connector Unit is made up of more than one natural or non-natural amino acid, amino alcohol, amino aldehyde, or polyamine, the amino acids, amino alcohols, amino aldehydes, polyamines or combinations thereof are linked together via covalent bonds to form the Parallel Connector Unit.

The amino acid, amino alcohol, or amino aldehyde can be non-natural and can be modified to have a functionalized side chain for attachment to components of a Ligand Drug Conjugate or Drug Linker compound (as described above for a residue of a Parallel Connector Unit), as the case may be. Exemplary functionalized amino acids, amino alcohols, or amino aldehydes include, for example, azido or alkyne functionalized amino acids, amino alcohols, or amino aldehydes (e.g., amino acid, amino alcohol, or amino aldehyde modified to have an azide group or alkyne group for attachment using click chemistry).

Attachment within the Parallel Connector Unit or with the other components of the conjugate (or linker) can be, for example, via amino, carboxyl, or other functionalities. Methods for the independent activation and reaction of the functional groups present on an amino acid—e.g., the amine portion, the carboxylic acid portion and the side chain portion (whether, for example, an amino moiety, a hydroxyl group, another carboxylic acid, thiol, azide or alkyne) include those adaptable form peptide chemistry.

The Parallel Connector Unit can comprise 1 or more (typically from 1 to 5 or 1 to 4 or 1 to 3 or 1 or 2) amino acids, optionally substituted $C_{1-20}$ heteroalkylenes (preferably optionally substituted $C_{1-12}$ heteroalkylene), optionally substituted $C_{3-8}$ heterocyclos, optionally substituted $C_{6-14}$ arylenes, optionally substituted $C_3$-$C_8$ carbocyclos, or combinations thereof. In some embodiments, the Parallel Connector Unit comprises no more than 2 or no more than one optionally substituted $C_{1-20}$ heteroalkylene, optionally substituted $C_{3-8}$ heterocyclo, optionally substituted $C_{6-14}$ arylene, or optionally substituted $C_3$-$C_8$ carbocyclo. Optional substituents include (=O), —X, —R, —OR, —SR, —NR$_2$, —NR$_3$, =NR, —CX$_3$, —CN, —OCN, —SCN, —N=C=O, —NCS, —NO, —NO$_2$, =N$_2$, —N$_3$, —NRC(=O)R, —C(=O)R, —C(=O)NR$_2$, —SO$_3$—, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO=$_3$, —PO$_3$H$_2$, —AsO$_2$H$_2$, —C(=O)R, —C(=O)X, —C(=S)R, —CO$_2$R, —CO$_2$—, —C(=S)OR, —C(=O)SR, —C(=S)SR, —C(=O)NR$_2$, —C(=S)NR$_2$, or —C(=NR)NR$_2$, where each X is independently a halogen: —F, —Cl, —Br, or —I; and each R is independently —H, —C$_1$ C$_{20}$ alkyl, —C$_6$ C$_{20}$ aryl, —C$_3$ C$_{14}$ heterocycle, a protecting group or a prodrug moiety. Preferred optional substituents are (=O), —X, —R, —OR, —SR, and —NR$_2$.

A Parallel Connector Unit can be represented by Formula AA:

Formula AA

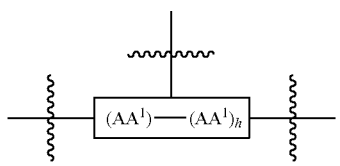

wherein AA$^1$ is a subunit of L$^P$ independently selected from an amino acid, optionally substituted $C_{1-20}$ heteroalkylene (preferably optionally substituted $C_{1-12}$ heteroalkylene), optionally substituted $C_{3-8}$ heterocyclo, optionally substituted $C_{6-14}$ arylene, or optionally substituted $C_3$-$C_8$ carbocyclo;

and subscript h is independently selected from 0 to 4; and the wavy line indicates covalent attachment sites within the Ligand-Drug Conjugate or intermediate thereof. The optionally substituted heteroalkylene, heterocycle, arylene or carbocyclo will have functional groups for attachments between the subunits and within a Ligand-Drug Conjugate or intermediates thereof.

In some embodiments at least one instance of AA$^1$ is an amino acid. The subscript h can be 0, 1, 2, 3, or 4. In some embodiments, AA$^1$ is an amino acid and h is 0. In some embodiments, the Parallel Connector Unit is comprised of no more than 2 optionally substituted $C_{1-20}$ heteroalkylenes, optionally substituted $C_{3-8}$ heterocyclos, optionally substituted $C_{6-14}$ arylenes, or optionally substituted $C_3$-$C_8$ carbocyclos. In some embodiments of formula AA, the Parallel Connector Unit is comprised of no more than 1 optionally substituted $C_{1-20}$ heteroalkylene, optionally substituted $C_{3-8}$ heterocyclo, optionally substituted $C_{6-14}$ arylene, or optionally substituted $C_3$-$C_8$ carbocyclo.

A Parallel Connector Unit or an amino acid subunit thereof can be independently selected from a thiol-containing amino acid. The thiol containing amino acid can be, for example, cysteine, homocysteine, or penicillamine in the D- or L-stereochemical configuration.

A Parallel Connector Unit or an amino acid subunit thereof can be independently selected from the group consisting of the L- or D-isomers of the following amino acids: Alanine (including β-alanine), arginine, aspartic acid, asparagine, cysteine, histidine, glycine, glutamic acid, glutamine phenylalanine, lysine, leucine, methionine, serine, tyrosine, threonine, tryptophan, proline, ornithine, penicillamine, β-alanine, aminoalkynoic acid, aminoalkanedioic acid, heterocyclo-carboxylic acid, citrulline, statine, diaminoalkanoic acid, and derivatives thereof.

Preferred amino acids include cysteine, homocysteine, penicillamine, ornithine, lysine, serine, threonine, glutamine, alanine, aspartic acid, glutamic acid, selenocysteine, proline, glycine, isoleucine, leucine, methionine, valine, and alanine.

Exemplary $L_P$ or AA$^1$ subunits thereof include:

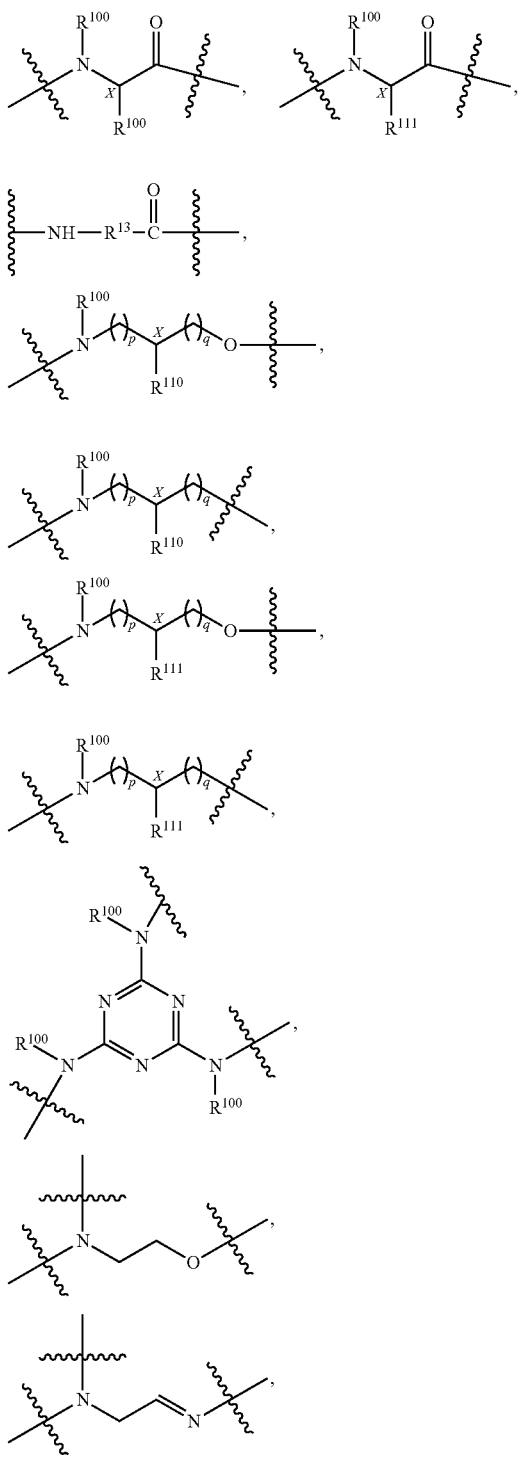

77
-continued

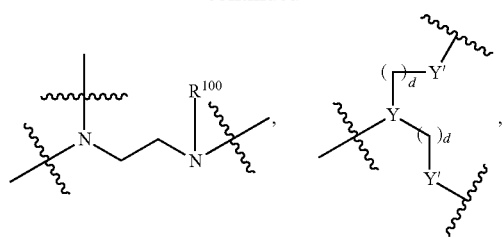

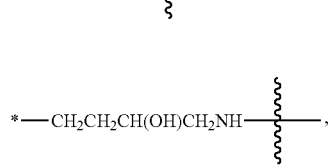

wherein R¹¹⁰ is

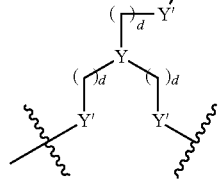

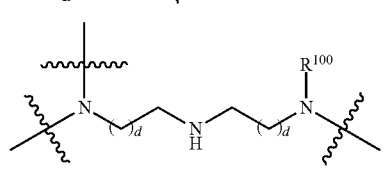

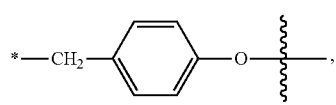

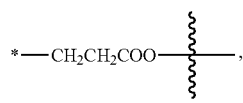

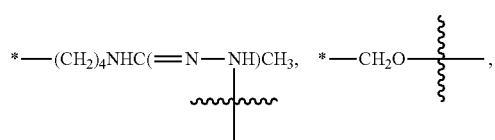

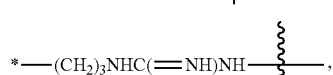

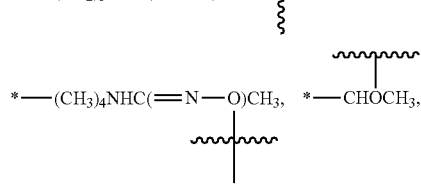

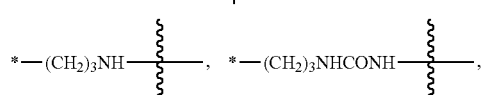

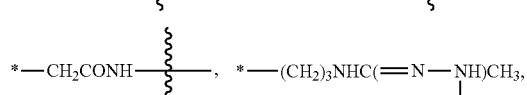

78
-continued

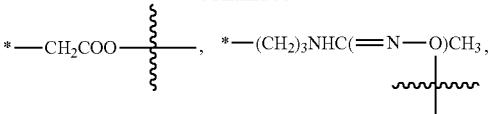

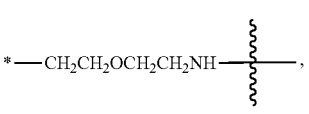

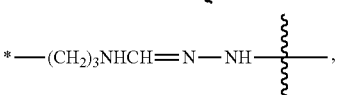

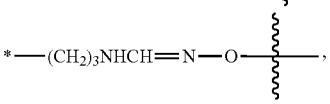

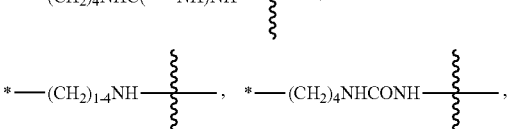

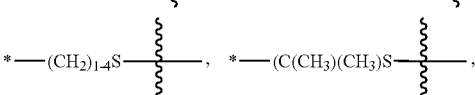

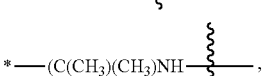

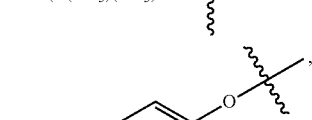

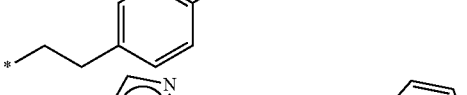

$R^{111}$ is independently selected from hydrogen, p-hydroxybenzyl, methyl, isopropyl, isobutyl, sec-butyl, —CH₂OH, —CH(OH)CH₃, —CH₂CH₂SCH₃, —CH₂CONH₂, —CH₂COOH, —CH₂CH₂CONH₂, —CH₂CH₂COOH, —(CH₂)₃NHC(=NH)NH₂, —(CH₂)₃NH₂, —(CH₂)₃NHCOCH₃, —(CH₂)₃NHCHO, —(CH₂)₄NHC(=NH)NH₂, —(CH₂)₄NH₂, —(CH₂)₄NHCOCH₃, —(CH₂)₄NHCHO, —(CH₂)₃NHCONH₂, —(CH₂)₄NHCONH₂, —CH₂CH₂CH(OH)CH₂NH₂, 2-pyridylmethyl-, 3-pyridylmethyl-, 4-pyridylmethyl-,

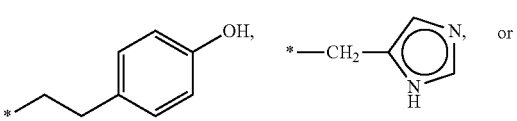

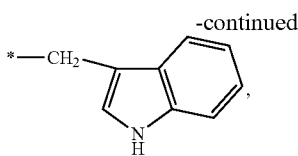

wherein the asterisk indicates attachment to the carbon labeled x;

$R^{100}$ is independently selected from hydrogen or —$C_1$-$C_3$ alkyl (preferably hydrogen or $CH_3$), $R^{13}$ is independently selected from the group consisting of —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, and —($C_3$-$C_8$ heterocyclo)-$C_1$-$C_{10}$ alkylene- (preferably —$CH_2$—$CH_2$—);

Y is

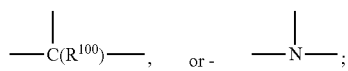

Y' is —C(=O)—, —O—, —S—, —NH—, or —N($CH_3$)—, and the subscripts p, q, and d are integers independently selected from 0 to 5; and the wavy line indicates covalent attachment within the compound, hydrogen, OH or a $C_{1-3}$ unsubstituted alkyl group, provided that at least one of the wavy lines indicates a covalent attachment within the compound. In some aspects, all of the wavy lines indicate covalent attachment within the compound (e.g., when $L^P$ does not comprise any subunits).

In one group of embodiments, $L^P$ is a heterocyclic ring having functional groups that can independently form covalent linkages to the noted components (e.g., a triazole heterocyclic ring formed from cyanuric chloride). In another group of embodiments, $L^P$ is an alkane having attached functional groups as noted above. In still other embodiments, $L^P$ can be a nitrogen atom.

In some embodiments, $L_P$ of -$L_P$(PEG)-, once assembled, has the formula denoted below:

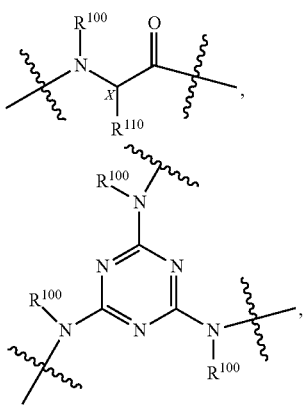

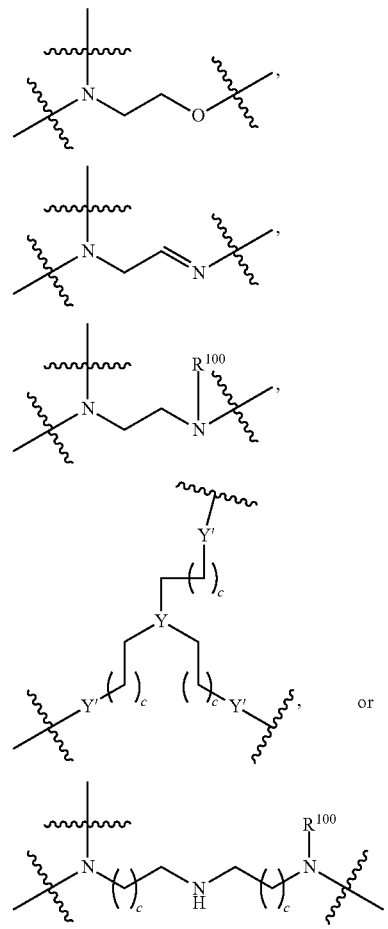

wherein the wavy line indicates the attachment sites within the Ligand-Drug Conjugate or intermediate thereof, $R^{100}$ is as previously defined, the asterisk indicates attachment to the carbon labeled x and the wavy line indicates one of the three attachment sites; Y is independently selected from N or CH, Y' is independently selected from NH, O, or S, and each subscript c is an integer independently selected from 1 to 10, and preferably 1, 2, or 3.

In preferred embodiments, $R^{110}$ is not

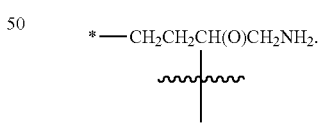

In some embodiments $L^P$ or subunit thereof is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the sulfur substituent is in reduced or oxidized form.

In some embodiments a Parallel Connector Unit or an amino acid subunit thereof has the formula of Formula A or Formula B:

(Formula A)

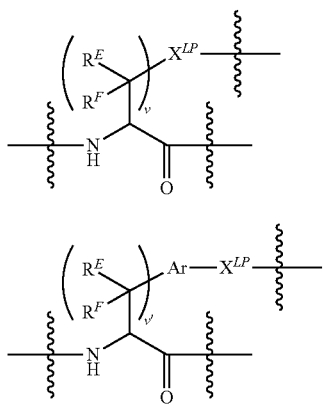

(Formula B)

wherein subscript v is an integer ranging from 1 to 4; subscript v' is an integer ranging from 0 to 4; $X^{LP}$ is provided by a natural or un-natural amino acid side chain or is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N(R$^{LP}$)—, and —N(R$^{LP}$)C(=NR$^{LP}$)N(R$^{LP}$)—, wherein each $R^{LP}$ is independently selected from the group consisting of hydrogen and optionally substituted alkyl or two of $R^{LP}$ together along with their intervening atoms define a heterocycloalkyl and any remaining $R^{LP}$ are as previously defined; Ar is an arylene or heteroarylene, optionally substituted; each $R^E$ and $R^F$ is independently selected from the group consisting of —H, optionally substituted alkyl, optionally substituted aryl and optionally substituted heteroaryl, or $R^E$ and $R^F$ together with the same carbon to which they are attached, or $R^E$ and $R^F$ from adjacent carbons together with these carbons, defines a optionally substituted cycloalkyl with any remaining $R^E$ and $R^F$ substituents as previously defined; and wherein the wavy lines indicates covalent attachment of the Formula A or Formula B structure within the LDC structure.

In some embodiments -L$^P$(PEG)- has the structure of Formula A1 or A2:

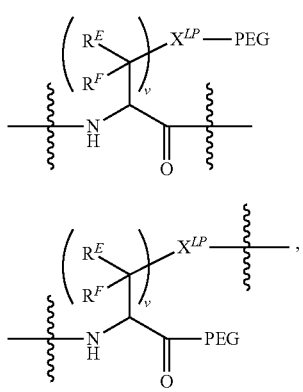

(Formula A1)

(Formula A2)

wherein the variable groups are as defined in Formula A.

In some embodiments, $L_P$ has the structure of Formula $X^P$ is provided by a natural or un-natural amino acid side chain.

In preferred embodiments of Formula A, Formula A1, Formula A2 or Formula B, $R^E$ and $R^F$ are independently selected from the group consisting of —H, and —C$_1$-C$_4$ alkyl. In preferred embodiments of Formula A, Formula A1 or Formula A2, $X^{LP}$ is selected from the group consisting of —O—, —NH, —S— and —C(=O)—

In some embodiments, $L_P$ or a subunit thereof is selected from the group consisting of lysine, glutamic acid, aspartic acid, cysteine, penicillamine, serine or threonine in D- or L-stereochemical configuration.

In other embodiments, $L_P$ or a subunit thereof is selected from the group consisting of lysine, glutamic acid, aspartic acid, cysteine, or penicillamine in D- or L-stereochemical configuration.

In other embodiments, $L_P$ or a subunit thereof is a thiol containing amino acid in the D- or L-stereochemical configuration. The thiol containing amino acid is preferably cysteine, homocysteine, or penicillamine.

In other embodiments, $L_P$ or a subunit thereof is selected from the group consisting of the following amino acids or amine-containing acids: arginine, aspartic acid, asparagine, cysteine, histidine, glutamic acid, glutamine phenylalanine, serine, tyrosine, threonine, tryptophan, ornithine, penicillamine, aminoalkanedioic acid, heterocyclo-carboxylic acid, citrulline, diaminoalkanoic acid, and derivatives thereof in the D- or L-stereochemical configuration.

In other embodiments, $L_P$, or a subunit thereof, is selected from the group consisting of cysteine, homocysteine, penicillamine, ornithine, lysine, serine, threonine, glutamine, aspartic acid, glutamic acid and selenocysteine.

In other embodiments, $L_P$ or $L_P'$, or a subunit thereof, is selected from the group consisting of arginine and arginine derivatives thereof. Illustrative of examples of arginine and derivatives thereof include but are not limited to: arginine (Arg), N-alkyl-arginine, H-Arg(Me)-OH, H-Arg(NH$_2$)—OH, H-Arg(NO$_2$)—OH, H-Arg(Ac)$_2$—OH, H-Arg(Me)$_2$-OH (asymmetrical), H-Arg(Me)$_2$-OH (symmetrical), 2-amino-4-(2'-hydroxyguanidino)-butyric acid (N-ω-hydroxy-nor-arginine) and homoarginine.

In other embodiments, $L_P$ or $L_P'$, or a subunit thereof, is selected from the group consisting of aspartic acid and derivatives thereof. Illustrative of examples of aspartic acid and derivatives thereof include but are not limited to: aspartic acid (Asp), N-alkyl-aspartic acid, and H-Asp(O-tBu)-OH.

In other embodiments, $L_P$ or a subunit thereof is selected from the group consisting of asparagine and derivatives thereof. Illustrative of examples of asparagine and derivatives thereof include but are not limited to: asparagine (Asn), N-alkyl-asparagine, and iso-asparagine (H-Asp-NH$_2$).

In other embodiments, $L_P$ or $L_P'$, or a subunit thereof, is selected from the group consisting of glutamic acid and derivatives thereof. Illustrative of examples of glutamic acid and derivatives thereof include but are not limited to: glutamic acid (Glu), N-alkyl-glutamic acid, H-Glu(OtBu)-OH, H-γ-hydroxy-Glu-OH, H-γ-methylene-Glu-OH, H-γ-carboxy-[Glu(O-tBu)]$_2$—OH, and pyroglutamic acid.

In other embodiments, $L_P$ or $L_P'$, or a subunit thereof, is selected from the group consisting of glutamine and derivatives thereof. Illustrative of examples of glutamine and derivatives thereof include but are not limited to: glutamine (Gln), N-alkyl-glutamine, isoglutamine (H-Glu-NH$_2$), H-Gln(Trt)-OH, and H-Gln(isopropyl)-OH.

In other embodiments, $L_P$ or $L_P'$, or a subunit thereof, is selected from the group consisting of lysine and derivatives thereof. Illustrative of examples of lysine and derivatives thereof include but are not limited to: lysine (Lys), N-alkyl-lysine, H-Lys(Boc)-OH, H-Lys(Ac)—OH, H-Lys(Formyl)-OH, H-Lys(Me)$_2$-OH, H-Lys(nicotinoyl)-OH, H-Lys(Me)$_3$-OH, H-trans-4,5-dehydro-Lys-OH, H-Lys(Alloc)-OH, H—H-δ-hydroxy-Lys-OH, H-δ-hydroxy-Lys(Boc)-OH, H-Lys(acetamidoyl)-OH, and H-Lys(isopropyl)-OH.

In other embodiments, $L_P$ or $L_P'$, or a subunit thereof, is selected from the group consisting of serine and derivatives thereof. Illustrative of examples of serine and derivatives thereof include but are not limited to: serine (Ser), N-alkyl-serine, H-Ser(O—Ac)—OH, H—Ser(O-t-Bu)-OH, H—Ser(O-Bzl)-OH, H—Ser(p-chloro-O-Bzl)-OH, H-β-(3,4-dihydroxyphenyl)-Ser-OH, H-β-(2-thienyl)-Ser-OH, isoserine N-alkyl-isoserine, and 3-phenylisoserine.

In other embodiments, $L_P$ or $L_P'$, or a subunit thereof, is selected from the group consisting of tyrosine and derivatives thereof. Illustrative of examples of tyrosine and derivatives thereof include but are not limited to: tyrosine (Tyr), N-alkyl-tyrosine, H-3,5-dinitro-Tyr-OH, H-3-amino-Tyr-OH, H-3,5-dibromo-Tyr-OH, H-3,5-diiodo-Tyr-OH, H-Tyr(OMe)-OH, H-Tyr(O-t-Bu)-OH, H-Tyr(O-Boc)-OH, H-Tyr(O-Bzl)-OH, H-Tyr(O-Et)-OH, H-3-iodo-Tyr-OH, and H-3-nitro-Tyr-OH.

In other embodiments, $L_P$, $L_P'$, or a subunit thereof, is selected from the group consisting of threonine and derivatives thereof. Illustrative of examples of threonine and derivatives thereof include but are not limited to: threonine (Thr), N-alkyl-threonine, allothreonine, H-Thr(OAc)—OH, H-Thr(O-t-Bu)-OH, and H-Thr(OBzl)-OH.

In other embodiments, $L_P$, $L_P'$, or a subunit thereof, is selected from the group consisting of tryptophan and derivatives thereof. Illustrative of examples of tryptophan and derivatives thereof include but are not limited to: tryptophan (Trp), N-alkyl-tryptophan, H-5-Me-Trp-OH, H-5-hydroxy-Trp-OH, H-4-Me-Trp-OH, H-α-Me-Trp-OH, H-Trp(Boc)-OH, H-Trp(Formyl)-OH, and H-Trp(Mesitylene-2-sulfonyl)-OH.

In other embodiments, $L_P$, $L_{P'}$, or a subunit thereof, is selected from the group consisting of ornithine and derivatives thereof. Illustrative of examples of ornithine and derivatives thereof include but are not limited to: ornithine (Orn), N-alkyl-ornithine, H-Orn(Boc)-OH, H—Orn(Z)—OH, H-α-difluoro-Me-Orn-OH (Eflornitine), and H-Orn(Alloc)-OH.

In other embodiments, $L_P$, $L_{P'}$, or a subunit thereof, is selected from the group consisting of penicillamine and derivatives thereof. Illustrative of examples of penicillamine and derivatives thereof include but are not limited to: penicillamine, H-penicillamine(Acm)-OH (H-β,β-dimethyl-cys(Acm)-OH) and N-alkyl-penicillamine.

In other embodiments, $L_P$, or a subunit thereof, is selected from the group consisting of aminoalkanedioic acid and derivatives thereof. Illustrative of examples of an aminoalkanedioic acid and derivatives thereof include but are not limited to: N-alkylaminoalkanedioic acid, 2-aminohexanedioic acid, 2-aminoheptanedioic acid, 2-aminooctanedioic acid (H-Asu-OH).

In other embodiments, $L_P$, or a subunit thereof, is selected from the group consisting of citrulline and derivatives thereof. Illustrative of examples of citrulline and derivatives thereof include but are not limited to: citrulline (cit), N-alkyl-citrulline, thiocitrulline, S-methyl-thiocitrulline, and homocitrulline.

In other embodiments, $L_P$, $L_P'$, or a subunit thereof, is selected from the group consisting of diaminoalkanoic acid and derivatives thereof. Illustrative of examples of diaminoalkanoic acid (Dab) and derivatives thereof include but are not limited to: N-alkyl-diamino-alkanoic acids, N,N-dialkylamino-alkanoic acids, α,γ-diaminobutyric acid (H-Dab-OH), H-Dab(Alloc)-OH, H-Dab(Boc)-OH, H-Dab(Z)—OH, α,β-diaminopropionic acid and its side-chain protected versions.

An exemplary $L_P$ unit or subunit thereof of, lysine or cysteine or penicillamine, is shown below. The wavy line indicates attachment sites to PEG and of $L_P$ of $L_P$(PEG)-within the Linker Unit. L- and D-isomers of the amino acids are suitable for use herein.

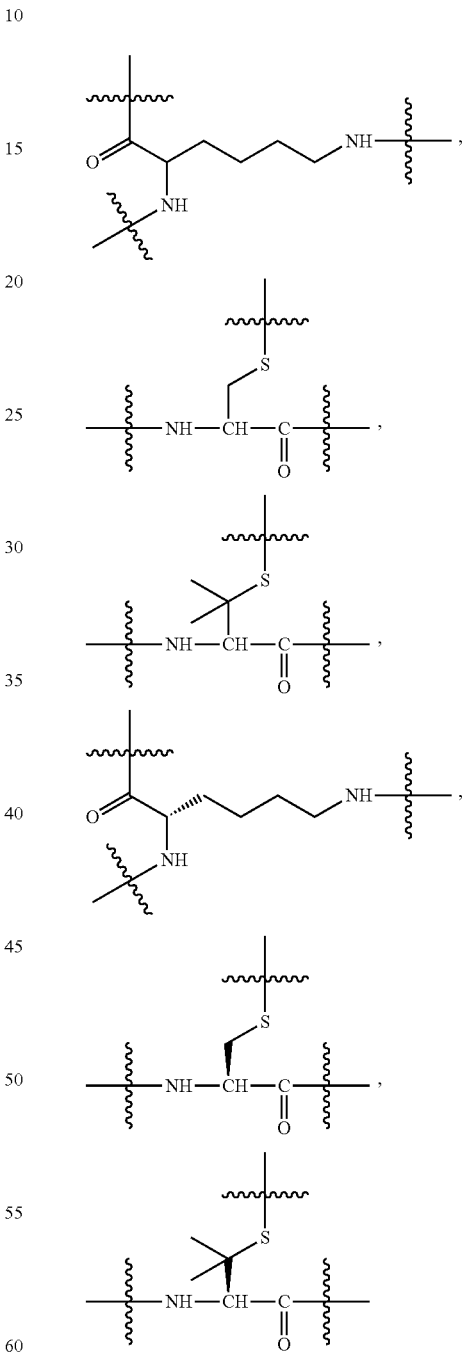

An exemplary Ligand-Drug Conjugate having lysine as the $L_P$ unit is shown below wherein $L_B$, A, $A_O$, L, W, W', Y, $D^+$, PEG, subscripts a and p, and PEG are as described herein. L- and D-isomers of the amino acids are suitable for use herein.

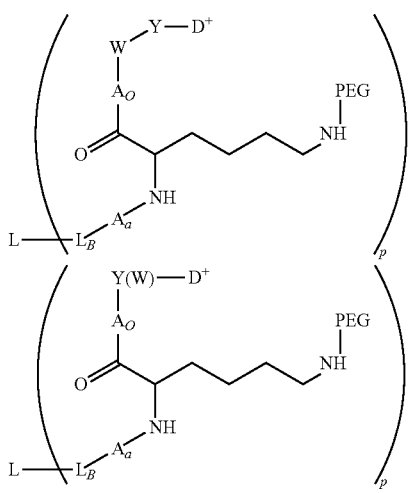

An exemplary Ligand-Drug Conjugate having cysteine or penicillamine as the $L^P$ unit is shown below wherein $L_B$, A, $A_O$, L, W, W', Y, $D^+$, PEG, subscripts a and p, and PEG are as described herein. L- and D-isomers isomers of the amino acids are suitable for use herein.

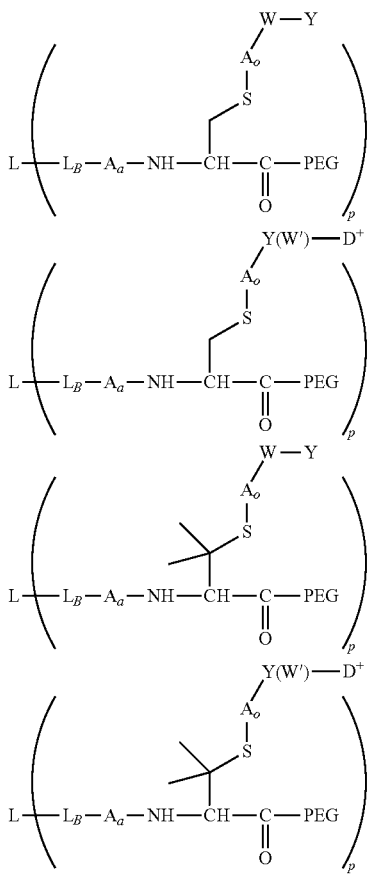

1.3.3 PEG Unit

The PEG Units as taught herein are designed to impart an appropriate level of hydrophobicity masking of hydrophobic quaternized tubulysin Drug Units and other hydrophobic components of the quaternized drug-linker moiety of a Ligand Drug Conjugate. For that reason, the incorporation of PEG Unit as taught herein is particularly suitable for quaternized tubulysin-linkers that otherwise would impart sufficient hydrophobicity to negatively impact the pharmacokinetics of the resultant conjugate as compared to the Ligand Unit's unconjugated targeting agent. Those poorer pharmokinetics include greater plasma clearance, which can be attributed to the hydrophobicity of the tubulysin compound that is quaternized in the Ligand Drug Conjugate. Thus, Ligand Drug Conjugates having a quaternized tubulysin Drug Unit that display significantly greater plasma clearance and correspondingly lower plasma exposure relative to the Ligand Unit's unconjugated targeting agent will be benefited by the present invention. Ligand-Drug Conjugates of the present invention have those more favorable pharmokinetic properties due to the parallel orientation within a hydrophobic drug-linker moiety of a quaternized tubulysin Drug Unit and a PEG Unit whereby the negative impact of hydrophobicity of the quaternized Drug Unit, which may be further aggravated by other hydrophobic components of the quaternized tubulysin drug-linker moiety, on plasma clearance is sufficiently reduced or eliminated (i.e., hydrophobicity of a drug-linker moiety is masked).

Polydisperse PEGS, monodisperse PEGS and discrete PEGs can be used to make the Compounds of the present invention. Polydisperse PEGs are a heterogeneous mixture of sizes and molecular weights whereas monodisperse PEGs are typically purified from heterogeneous mixtures and are therefore provide a single chain length and molecular weight. Preferred PEG Units are discrete PEGs, compounds that are synthesized in step-wise fashion and not via a polymerization process. Discrete PEGs provide a single molecule with defined and specified chain length.

The PEG Unit provided herein comprises one or multiple polyethylene glycol chains. The polyethylene glycol chains can be linked together, for example, in a linear, branched or star shaped configuration. Typically, at least one of the PEG chains is derivitized at one end for covalent attachment to the Parallel Connector Unit. Exemplary attachments to the Parallel Connector Unit are by means of non-conditionally cleavable linkages or via conditionally cleavable linkages. Exemplary attachments are via amide linkage, ether linkages, ester linkages, hydrazone linkages, oxime linkages, disulfide linkages, peptide linkages or triazole linkages. In some aspects, attachment to $L_P$ is by means of a non-conditionally cleavable linkage. In some aspects, attachment to $L_P$ is not via an ester linkage, hydrazone linkage, oxime linkage, or disulfide linkage. In some aspects, attachment to $L^P$ is not via a hydrazone linkage.

A conditionally cleavable linkage refers to a linkage that is not substantially sensitive to cleavage while circulating in the plasma but is sensitive to cleavage in an intracellular or intratumoral environment. A non-conditionally cleavable linkage is one that is not substantially sensitive to cleavage in any biological environment. Chemical hydrolysis of a hydrazone, reduction of a disulfide, and enzymatic cleavage of a peptide bond or glycosidic linkage are examples of conditionally cleavable linkages.

The PEG Unit will be directly attached to the Ligand-Drug Conjugate (or Intermediate thereof) at the Parallel Connector Unit. The other terminus (or termini) of the PEG Unit will be free and untethered and may take the form of a methoxy, carboxylic acid, alcohol or other suitable functional group. The methoxy, carboxylic acid, alcohol or other suitable functional group acts as a cap for the terminal PEG subunit of the PEG Unit. By untethered, it is meant that the PEG Unit will not be attached at that untethered site to a Drug Unit, to a Ligand Unit, or to a linking component linking a Drug Unit and/or a Ligand Unit. For those embodiments wherein the PEG Unit comprises more than one PEG chain, the multiple PEG chains may be the same or different chemical moieties (e.g., PEGs of different molecular weight or number of subunits). The multiple PEG chains are attached to the Parallel Connector Unit at a single attachment site. The skilled artisan will understand that the PEG Unit in addition to comprising repeating polyethylene glycol subunits may also contain non-PEG material (e.g., to facilitate coupling of multiple PEG chains to each other or to facilitate coupling to the Parallel Connector Unit). Non-PEG material refers to the atoms in the PEG Unit that are not part of the repeating —$CH_2CH_2O$-subunits. In embodiments provided herein, the PEG Unit can comprise two monomeric PEG chains linked to each other via non-PEG elements. In other embodiments provided herein, the PEG Unit can comprise two linear PEG chains attached to a central core that is attached to the Parallel Connector Unit (i.e., the PEG unit itself is branched).

There are a number of PEG attachment methods available to those skilled in the art, [see, e.g., Goodson, et al. (1990) *Bio/Technology* 8:343 (PEGylation of interleukin-2 at its glycosylation site after site-directed mutagenesis); EP 0 401 384 (coupling PEG to G-CSF); Malik, et al., (1992) *Exp. Hematol.* 20:1028-1035 (PEGylation of GM-CSF using tresyl chloride); ACT Pub. No. WO 90/12874 (PEGylation of erythropoietin containing a recombinantly introduced cysteine residue using a cysteine-specific mPEG derivative); U.S. Pat. No. 5,757,078 (PEGylation of EPO peptides); U.S. Pat. No. 5,672,662 (Poly(ethylene glycol) and related polymers monosubstituted with propionic or butanoic acids and functional derivatives thereof for biotechnical applications); U.S. Pat. No. 6,077,939 (PEGylation of an N-terminal .alpha.-carbon of a peptide); Veronese et al., (1985) *Appl. Biochem. Bioechnol* 11:141-142 (PEGylation of an N-terminal α-carbon of a peptide with PEG-nitrophenylcarbonate ("PEG-NPC") or PEG-trichlorophenylcarbonate); and Veronese (2001) *Biomaterials* 22:405-417 (Review article on peptide and protein PEGylation)].

For example, PEG may be covalently bound to amino acid residues via a reactive group. Reactive groups are those to which an activated PEG molecule may be bound (e.g., a free amino or carboxyl group). For example, N-terminal amino acid residues and lysine (K) residues have a free amino group; and C-terminal amino acid residues have a free carboxyl group. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide have been described (see Schwarz, et al. (1990) *Methods Enzymol.* 184:160; Rose, et al. (1991) *Bioconjugate Chem.* 2:154; and Gaertner, et al. (1994) *J. Biol. Chem.* 269:7224].

In some embodiments, PEG molecules may be attached to amino groups using methoxylated PEG ("mPEG") having different reactive moieties. Non-limiting examples of such reactive moieties include succinimidyl succinate (SS), succinimidyl carbonate (SC), mPEG-imidate, para-nitrophenylcarbonate (NPC), succinimidyl propionate (SPA), and cyanuric chloride. Non-limiting examples of such mPEGs include mPEG-succinimidyl succinate (mPEG-SS), $mPEG_2$-succinimidyl succinate ($mPEG_2$-SS); mPEG-succinimidyl carbonate (mPEG-SC), $mPEG_2$-succinimidyl carbonate ($mPEG_2$-SC); mPEG-imidate, mPEG-para-nitrophenylcarbonate (mPEG-NPC), mPEG-imidate; $mPEG_2$-para-nitrophenylcarbonate ($mPEG_2$-NPC); mPEG-succinimidyl propionate (mPEG-SPA); $mPEG_2$-succinimidyl propionate (mPEG, —SPA); mPEG-N-hydroxy-succinimide (mPEG-NHS); $mPEG_2$-N-hydroxy-succinimide ($mPEG_2$-NHS); mPEG-cyanuric chloride; $mPEG_2$-cyanuric chloride; $mPEG_2$-Lysinol-NPC, and $mPEG_2$-Lys-NHS.

Generally, at least one of the PEG chains that make up the PEG Unit is functionalized so that it can attach to the Parallel Connector Unit. Functionalization can be, for example, via an amine, thiol, NHS ester, maleimide, alkyne, azide, carbonyl, or other functional group. The PEG Unit can further comprise non-PEG material (i.e., material not comprised of —$CH_2CH_2O$—) to facilitate coupling to the Parallel Connector Unit or to facilitate coupling of two or more PEG chains.

A wide variety of polyethylene glycol (PEG) species can be used, and substantially any suitable reactive PEG reagent can be used. In some embodiments, the reactive PEG reagent will result in formation of a carbamate or amide bond upon attachment to $L_P$. The following PEG reagents are useful in various embodiments: $mPEG_2$-NHS, $mPEG_2$-ALD, multi-Arm PEG, mPEG($MAL)_2$, $mPEG_2$(MAL), mPEG-$NH_2$, mPEG-SPA, mPEG-SBA, mPEG-thioesters, mPEG-Double Esters, mPEG-BTC, mPEG-ButyrALD, mPEG-ACET, heterofunctional PEGs ($NH_2$—PEG-COOH, Boc-PEG-NHS, Fmoc-PEG-NHS, NHS-PEG-VS, NHS-PEG-MAL), PEG acrylates (ACRL-PEG-NHS), PEG-phospholipids (e.g., mPEG-DSPE), multiarmed PEGs of the SUNBRITE™ series including the GL series of glycerin-based PEGs activated by a chemistry chosen by those skilled in the art, any of the SUNBRITE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOK hydroxyl-PEG-aldehyde, carboxylic anhydride type-PEG, functionalized PEG-phospholipid, and other similar and/or suitable reactive PEGs as selected by those skilled in the art for their particular application and usage.

The addition of the PEG Unit may have two potential impacts upon the pharmacokinetics of the resulting Ligand-Drug Conjugate. The desired impact is the decrease in clearance (and consequent in increase in exposure) that arises from the reduction in non-specific interactions induced by the exposed hydrophobic elements of the drug-linker. The second impact is undesired impact and is the decrease in volume and rate of distribution that may arise from the increase in the molecular weight of the Ligand-Drug Conjugate. Increasing the number of PEG subunits increases the hydrodynamic radius of a conjugate, resulting in decreased diffusivity. In turn, decreased diffusivity may diminish the ability of the Ligand-Drug Conjugate to penetrate into a tumor (Schmidt and Wittrup, *Mol. Cancer Ther.* 2009; 8:2861-2871). Because of these two competing pharmacokinetic effects, it is desirable to use a PEG that is sufficiently large to decrease the LDC clearance thus increasing plasma exposure, but not so large as to greatly diminish its diffusivity, which may reduce the ability of the Ligand-Drug Conjugate to reach the intended target cell population.

In one group of embodiments, the PEG Unit comprises at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. As used herein a subunit when referring to the PEG Unit refers to a polyethylene glycol subunit having the formula:

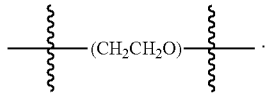

In another group of embodiments, the PEG Unit comprises one or more linear PEG chains each having at least 2 subunits, at least 3 subunits, at least 4 subunits, at least 5 subunits, at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. In preferred embodiments, the PEG Unit comprises a combined total of at least 6 subunits, at least 8, at least 10 subunits, or at least 12 subunits. In some such embodiments, the PEG Unit comprises no more than a combined total of about 72 subunits, preferably no more than a combined total of about 36 subunits.

In another group of embodiments, the PEG Unit is a derivitized linear single PEG chain having from 2 to 72, 2 to 60, 2 to 48, 2 to 36 or 2 to 24 subunits, from 2 to 72, 2 to 60, 2 to 48, 2 to 36 or 2 to 24 subunits, from 3 to 72, 3 to 60, 3 to 48, 3 to 36 or 3 to 24 subunits, from 3 to 72, 3 to 60, 3 to 48, 3 to 36 or 3 to 24 subunits, from 4 to 72, 4 to 60, 4 to 48, 4 to 36 or 4 to 24 subunits, from 5 to 72, 5 to 60, 5 to 48, 5 to 36 or 5 to 24 subunits.

Exemplary linear PEG Units that can be used in any of the embodiments provided herein are as follows:

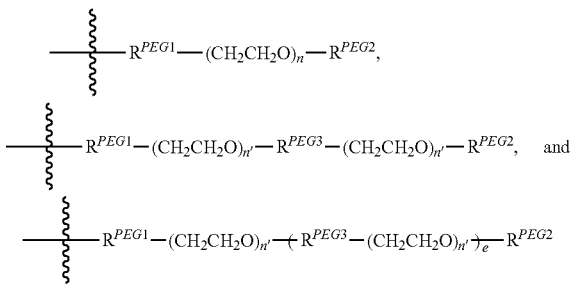

wherein the wavy line indicates site of attachment to the Parallel Connector Unit, $R^{PEG1}$ is a PEG Attachment Unit, $R^{PEG2}$ is a PEG Capping Unit; $R^{PEG3}$ is an PEG Coupling Unit (i.e., for coupling multiple PEG subunit chains together), subscript n is independently selected from 2 to 72 (preferably from 4 to 72, more preferably from 6 to 72, from 8 to 72, from 10 to 72, from 12 to 72 or from 6 to 24); subscript e is 2 to 5, each subscript n' is independently selected from 1 to 72.

In preferred embodiments, there are at least 6, preferably at least 8, at least 10, or at least 12 PEG subunits in the PEG Unit. In some embodiments, there are no more than 72 or 36 PEG subunits in the PEG Unit.

In other preferred embodiments, subscript n is 8 or about 8, 12 or about 12, 24 or about 24.

The PEG Attachment Unit is part of the PEG Unit and acts to link the PEG Unit to the Parallel Connector Unit. In this regard, the Parallel Connector Unit has a functional group that forms a bond with the PEG Unit. Functional groups for attachment of the PEG Unit to the Parallel Connector Unit include sulfhydryl groups to form disulfide bonds or thioether bonds, aldehyde, ketone, or hydrazine groups to form hydrazone bonds, hydroxylamine to form oxime bonds, carboxylic or amino groups to form peptide bonds, carboxylic or hydroxy groups to form ester bonds, sulfonic acids to form sulfonamide bonds, alcohols to form carbamate bonds, and amines to form sulfonamide bonds or carbamate bonds or amide bonds. Accordingly, the PEG unit can be attached to the Parallel Connector Unit, for example, via disulfide, thioether, hydrazone, oxime, peptide, ester, sulfonamide, carbamate, or amide bonds Typically, the PEG Attachment Unit is a product of the cycloaddition, addition, addition/elimination or substitution reaction that occurs when attaching the PEG Unit to the Parallel Connector Unit.

The PEG Coupling Unit is part of the PEG Unit and is non-PEG material that acts to connect two or more chains of repeating $CH_2CH_2O-$ subunits. In exemplary embodiments, the PEG coupling Unit $R^{22}$ is $-C_{1-10}$ alkyl-C(O)—NH—, $-C_{1-10}$ alkyl-NH—C(O)—, $-C_{2-10}$ alkyl-NH—, $-C_{2-10}$ alkyl-O—, $-C_{1-10}$ alkyl-S—, or $-C_{2-10}$ alkyl-NH—.

In exemplary embodiments, the PEG Attachment Unit $R^{20}$ is —C(O)—, —O—, —S—, —S(O)—, —NH—, —C(O)O—, —C(O)C$_{1-10}$alkyl, —C(O)C$_{1-10}$alkyl-O—, —C(O)C$_{1-10}$alkyl-CO$_2$—, —C(O)C$_{1-10}$alkyl-NH—, —C(O)C$_{1-10}$alkyl-S—, —C(O)C$_{1-10}$alkyl-C(O)—NH—, —C(O)C$_{1-10}$alkyl-NH—C(O)—, —C$_{1-10}$alkyl, —C$_{1-10}$alkyl-O—, —C$_{1-10}$alkyl-CO$_2$—, —C$_{1-10}$alkyl-NH—, —C$_{1-10}$alkyl-S—, —C$_{1-10}$alkyl-C(O)—NH—, —C$_{1-10}$alkyl-NH—C(O)—, —CH$_2$CH$_2$SO$_2$—C$_{1-10}$alkyl-, —CH$_2$C(O)—C$_{1-10}$ alkyl-, =N—(O or N)—C$_{1-10}$alkyl-O—, =N—(O or N)—C$_{1-10}$alkyl-NH—, =N—(O or N)—C$_{1-10}$alkyl-CO$_2$—, =N—(O or N)—C$_{1-10}$alkyl-S—,

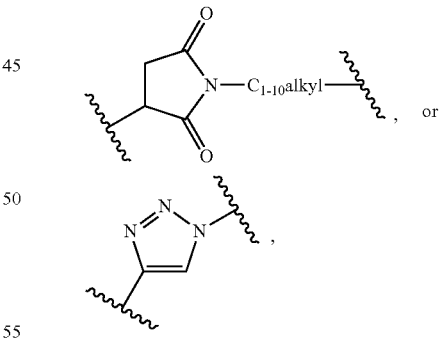

wherein each $R^{21}$ is independently $-C_{1-10}$ alkyl, $-C_{2-10}$ alkyl-CO$_2$H, $-C_{2-10}$ alkyl-OH, $-C_{2-10}$ alkyl-NH$_2$, $C_{2-10}$ alkyl-NH(C$_{1-3}$ alkyl), or C$_{2-10}$ alkyl-N(C$_{1-3}$ alkyl)$_2$; and each $R^{22}$ is independently $-C_{1-10}$ alkyl-C(O)—NH—, $-C_{1-10}$alkyl-NH—C(O)—, $-C_{2-10}$ alkyl-NH—, $-C_{2-10}$ alkyl-O—, $-C_{1-10}$ alkyl-S—, or $-C_{2-10}$ alkyl-NH—.

In some embodiments, $R^{20}$ is —NH—, —C(=O)—, triazole-linked groups, or —S—, or maleimido-linked groups such as

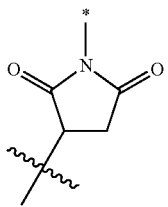 [SMILES: *C1CC(=O)N(C)C1=O]

wherein the wavy line indicates the site of attachment to the Parallel Connector Unit and the asterisk indicates the site of attachment within the PEG Unit. In some such aspects, $R^{21}$ is $C_{1-10}$ alkyl, —$C_{2-10}$ alkyl-$CO_2H$, —$C_{2-10}$ alkyl-OH, or —$C_{2-10}$ alkyl-$NH_2$.

Illustrative linear PEG Units that can be used in any of the embodiments provided herein are as follows:

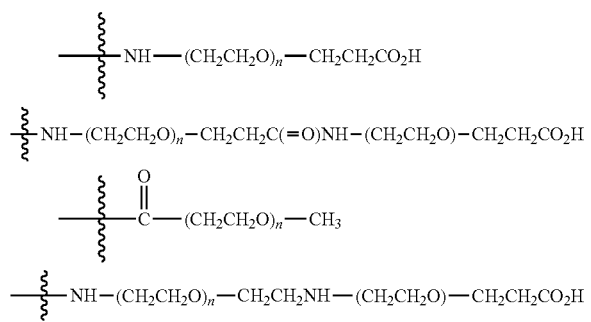

wherein the wavy line indicates site of attachment to the Parallel Connector Unit, and each subunit n is independently selected from 4 to 72, 6 to 72, 8 to 72, 10 to 72, 12 to 72, 6 to 24, or 8 to 24. In some aspects, n is about 8, about 12, or about 24.

As described herein, the PEG unit is selected such that it improves clearance of the resultant Ligand-Drug Conjugate but does not significantly impact the ability of the Conjugate to penetrate into the tumor. In embodiments wherein the quaternized Drug Unit and —W—Y— or —Y(W')— in the Linker Unit of a Ligand-Drug Conjugate has a hydrophobicity comparable to that of a maleimido glucuronide MMAE drug-linker (as shown in the examples), the PEG Unit to be selected for use will preferably have from 8 subunits to about 24 subunits, more preferably about 12 subunits. In embodiments wherein the quaternized Drug Unit and —W—Y— or —Y(W')— in the Linker Unit of a Ligand Drug Conjugate has a hydrophobicity greater than that of a maleimido glucuronide MMAE drug-linker, a PEG unit with more subunits can be selected. The methodology shown in the examples section can be used to identify the ideal number of subunits for a particular drug-linker.

It will be appreciated that when referring to PEG subunits, and depending on context, the number of subunits can represent an average number, e.g., when referring to a population of Ligand-Drug Conjugates or Intermediate Compounds (e.g., Drug Linker compounds), and using polydisperse PEGs.

1.3.4 Quaternized Tubulysins

In one group of embodiments, the quaternized tubulysin Drug Unit incorporates or corresponds in structure to a tubulysin having a tertiary amine at the N-terminus, wherein the nitrogen atom of that tertiary amine is in quaternized form.

In some embodiments, the quaternized Drug Unit is that of a tubulysin represented by the structure of Formula $D_G$, $D_H$ or $D_H'$ wherein the indicated nitrogen (†) is the site of quaternization when such compounds are incorporated into an LDC or a Drug Linker compound as a quaternized drug unit ($D^+$):

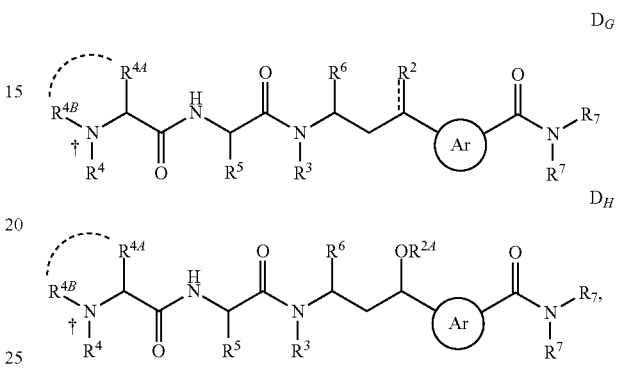

wherein the indicated nitrogen (†) is the site of quaternization when such a tubulysin compound is incorporated into an LDC or a Drug Linker compound as a quaternized tubulysin drug unit ($D^+$); the circle represents an 5-membered or 6-membered nitrogen-containing heteroaryl, wherein the indicated required substituents to that heteroaryl are in a 1,3- or meta-relationship to each other with optional substitution at the remaining positions; the curved dashed line represents optional cyclization; the straight dashed line to $R^2$ represent an optional double bond or optionally two instances of $R^2$ independently selected or a divalent O-linked moiety; $R^2$ is $X^A$—$R^{2A}$, wherein $R^{2A}$ is hydrogen, optionally substituted alkyl, saturated or unsaturated, or —$C(=O)R^B$, wherein $R^B$ is hydrogen, optionally substituted alkyl, saturated or unsaturated, optionally substituted alkenyl or optionally substituted aryl; $X^A$ is —O—, —S—, —N($R^{2C}$)—, —$CH_2$—, —C(=O)—, —(C=O)N($R^{2C}$)— or —O(C=O)N($R^{2C}$)—, wherein $R^{2C}$ is hydrogen or optionally substituted alkyl, or $R^2$ is an monovalent O-linked substituent, and the double bond to $R^2$ is absent, or $R^2$ is O and the double bond to $R^2$ is present; $R^3$ is hydrogen or optionally substituted alkyl; $R^4$, $R^{4A}$, $R^{4B}$, $R^5$ and $R^6$ are optionally substituted alkyl, independently selected, or $R^{4A}$ and $R^{4B}$, along with the atoms to which they are attached define an optionally substituted heterocycloalkyl, as indicated by the curved dashed line between $R^{4A}$ and $R^{4B}$ and $R^4$, $R^5$ and $R^6$ are as previously defined; one $R^7$ is hydrogen or optionally substituted alkyl and the other $R^7$ is optionally substituted arylalkyl, or optionally substituted heteroarylalkyl.

In other embodiments the quaternized drug is a tubulysin represented by structure of Formula $D_G$ wherein one $R^7$ is hydrogen or optionally substituted alkyl, preferably hydrogen or $C_1$-$C_4$, and the other $R^7$ is an independently selected optionally substituted alkyl, preferably $C_1$-$C_6$ alkyl substituted by optionally substituted phenyl or —$CO_2H$ or an ester prodrug thereof; $R^{4A}$ and $R^{4B}$, along with the atoms to which they are attached define an optionally substituted $C_5$-$C_6$ heterocycloalkyl; and the other variable groups are as previously defined.

In some embodiments of Formula $D_G$, $R^2$ is $X^A$—$R^{2A}$, wherein $X^A$ is —O— and $R^{2A}$ is —C(=O)$R^C$, wherein $R^C$ is hydrogen, optionally substituted alkyl, preferably, methyl, ethyl, vinyl or a branched alkyl or $R^2$ is an monovalent O-linked substituent selected from the group consisting of esters.

In other embodiment of Formula $D_G$, $R^2$ is $X^A$—$R^{2A}$, wherein $X^A$ is —O—; and $R^{2A}$ is hydrogen or optionally substituted alkyl, saturated or unsaturated, or $R^2$ is a monovalent O-linked substituent selected from the group consisting of ethers.

In preferred embodiments, the quaternized Drug Unit is that of a tubulysin represented by the structure of Formula $D_G'$:

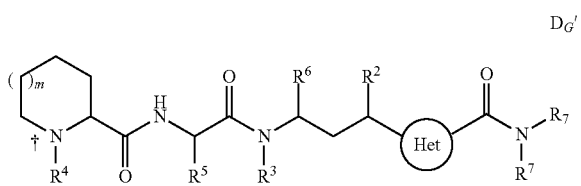

wherein subscript m is 0 or 1, one $R^7$ is hydrogen and the other $R^7$ is an optionally substituted arylalkyl, wherein the alkyl moiety is substituted by —$CO_2H$ or an ester thereof and the remaining variable groups are as defined for Formula $D_G$.

In other preferred embodiments —N($R^7$)($R^7$) of Formula $D_G$ is replaced by —N($R^7$)—CH($R^{10}$)(CH$_2$$R^{11}$) to define quaternized tubulysin drugs of Formula $D_H'$:

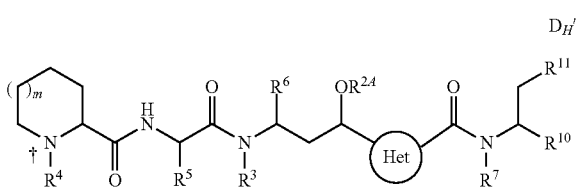

wherein $R^{10}$ is $C_1$-$C_6$ alkyl substituted with —$CO_2H$, or ester thereof, and $R^7$ is hydrogen or a $C_1$-$C_6$ alkyl independently selected from $R^{10}$, or $R^7$ and $R^{10}$ together with the atoms to which they are attached define a 5 or 6-membered heterocycle; and $R^{11}$ is aryl or 5- or 6-membered heteroaryl, optionally substituted with one or more, preferably 1 or 2, more preferably 1, substituent(s) independently selected from the group consisting of halogen, lower alkyl, —OH and —O—$C_1$-$C_6$ alkyl, preferably —F, —$CH_3$, and —$OCH_3$; and the remaining variable groups are as defined for Formula $D_H$.

In still other aspects one $R^7$ in —N($R^7$)($R^7$) in Formula $D_G$, Formula $D_G'$ or Formula $D_H$ is hydrogen or $C_1$-$C_6$ alkyl, and the other $R^7$ is an independently selected $C_1$-$C_6$ alkyl optionally substituted by —$CO_2H$ or an ester thereof, or by an optionally substituted phenyl.

In some embodiments of Formula $D_G$, Formula $D_G'$ or Formula $D_H$ one $R^7$ is hydrogen and the other $R^7$ is an optionally substituted arylalkyl having the structure of:

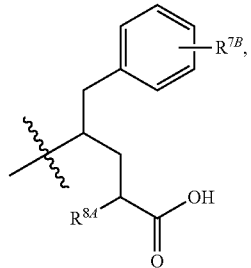

wherein $R^{7B}$ is hydrogen or an O-linked substituent, preferably hydrogen or —OH in the para position, and $R^{8A}$ is hydrogen or lower alkyl, preferably methyl; and wherein the wavy line indicates the point of attachment to the remainder of $D_G$, $D_G'$ or $D_H$.

In preferred embodiments of Formula $D_G$, Formula $D_G'$ or Formula $D_H$, one $R^7$ is hydrogen, and the other $R^7$ is an optionally substituted arylalkyl having the structure of

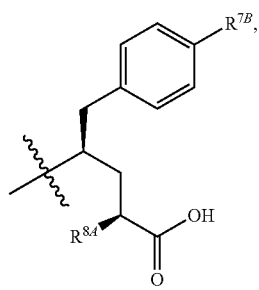

wherein $R^{7B}$ is —H or —OH; and wherein the wavy line indicates the point of attachment to the remainder of $D_G$ or $D_G'$.

In other embodiments of structure Formula $D_G$, Formula $D_G'$ or Formula $D_H$, one $R^7$ is hydrogen or $C_1$-$C_4$ alkyl, preferably hydrogen or methyl, more preferably hydrogen, and the other $R^7$ is optionally substituted arylalkyl having the structure of one of:

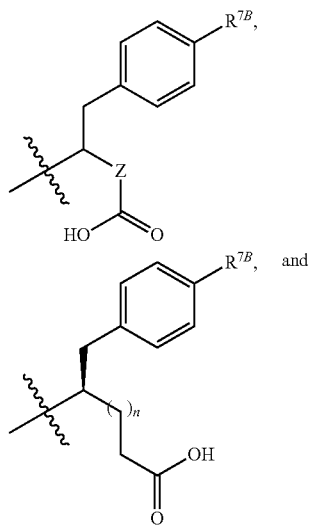

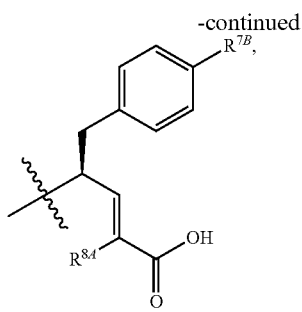

wherein Z is an optionally substituted alkylene or an optionally substituted alkenylene, $R^{7B}$ is hydrogen or an O-linked substituent, preferably hydrogen or —OH in the para position, $R^{8A}$ is hydrogen or lower alkyl, preferably methyl, and subscript n is 0, 1 or 2, preferably 0 or 1; and wherein the wavy line indicates the point of attachment to the remainder of $D_G$ or $D_H$.

In still other embodiments of Formula $D_G$, Formula $D_G'$ or Formula $D_H$, —N($R^7$)($R^7$) is —NH($C_1$-$C_6$ alkyl) wherein the $C_1$-$C_6$ alkyl is optionally substituted by —CO$_2$H or an ester thereof, or by an optionally substituted phenyl, with —N($R^7$)($R^7$) is selected from the group consisting of —NH(CH$_3$), —CH$_2$CH$_2$Ph, and —CH$_2$—CO$_2$H, —CH$_2$CH$_2$CO$_2$H and —CH$_2$CH$_2$CH$_2$CO$_2$H preferred.

In some embodiments of structure $D_H'$, $R^7$ and $R^{10}$ together with the atoms to which they are attached define an optionally substituted 5 or 6-membered heterocycle wherein —N($R^7$)—CH($R^{10}$)(CH$_2$$R^{11}$) has the structure of:

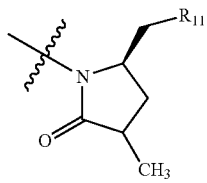

wherein the wavy line indicates the point of attachment to the remainder of $D_H'$.

Some preferred quaternized Drug Units are that of a tubulysin represented by Formula $D_{H-1}$, wherein the indicated nitrogen (†) is the site of quaternization when such a tubulysin compound is incorporated into an LDC or Drug Linker compound as a quaternized drug unit (D$^+$):

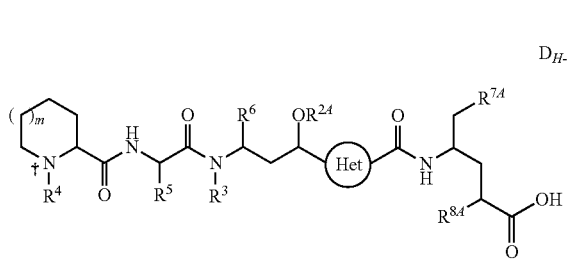

wherein the circle represents an 5-membered or 6-membered nitrogen-heteroaryl wherein the indicated required substituents to that heteroaryl are in a 1,3- or meta-relationship to each other with optional substitution at the remaining positions; $R^{24}$ is hydrogen or optionally substituted alkyl or $R^{24}$ along with the oxygen atom to which it is attached defines an O-linked substituent other than —OH; $R^3$ is hydrogen or optionally substituted alkyl; $R^4$, $R^{4A}$, $R^{4B}$, $R^5$ and $R^6$ are optionally substituted alkyl, independently selected; $R^{7A}$ is optionally substituted aryl or optionally substituted heteroaryl, $R^{8A}$ is hydrogen or optionally substituted alkyl and subscript m is 0 or 1.

In some preferred embodiments of Formula $D_G$, $D_G'$, $D_H$, $D_H'$, or $D_{H-1}$, $R^4$ is methyl or ethyl, $R^3$ is optionally substituted alkyl and $R^5$ and $R^6$ are independently selected side chain residues of natural hydrophobic amino acids and the remaining variable groups are as defined.

In other preferred embodiments of Formula $D_{H-1}$, $R^{7A}$ is optionally substituted phenyl. In other preferred embodiment $R^{8A}$ is methyl in the (S)-configuration. In other preferred embodiments of $D_H$, $D_H'$ or $D_{H-1}$, $R^{24}$ along with the oxygen atom to which it is attached defines an O-linked substituent other than —OH, more preferably an ester, ether or an O-linked carbamate. In more preferred embodiments the circle represents a 5-membered nitrogen-containing heteroarylene with a divalent oxazole or thiazole moiety particularly preferred. In other preferred embodiments $R^4$ is methyl or $R^{4A}$ and $R^{4B}$ are methyl. In other preferred embodiments $R^7$ is optionally substituted arylalkyl, wherein aryl is phenyl and $R^{7A}$ is optionally substituted phenyl.

In other embodiments of Formula $D_G$, $D_G'$, $D_H$, $D_H'$ or $D_{H-1}$ the circle represents a 5-membered nitrogen heteroarylene, preferably represented by the structure

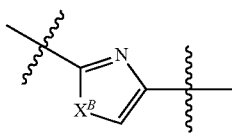

wherein $X^B$ is O, S, or N—$R^B$ wherein $R^B$ is hydrogen or lower alkyl. Preferably the quaternized drug is that of a tubulysin represented by structure Formula $D_G'$, $D_H$, $D_H'$ or $D_{H-1}$, wherein subscript m is 1. More preferred are tubulysins represented by structure Formula $D_G'$, $D_H$, $D_H'$ or $D_{H-1}$, wherein subscript m is 1 and the circle represents an optionally substituted divalent thiazole moiety.

Other quaternized Drug Units are that of a tubulysin represented by the structure of Formula $D_I$:

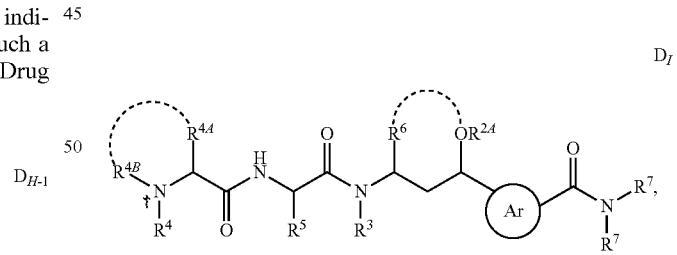

wherein the indicated nitrogen (†) is the site of quaternization when such a tubulysin compound corresponds to or is incorporated into an LDC or a Drug Linker compound as a quaternized drug unit (D$^+$); the curved dashed lines indicate optional cyclizations; $R^{24}$ is hydrogen or optionally substituted alkyl, or $R^{24}$ along with the oxygen atom to which it is attached defines an O-linked substituent other than —OH, or $R^{24}$ is absent when $R^6$ is bonded to that oxygen atom, as indicated by the curved dash line between $R^6$ and the oxygen atom, to define an oxygen-containing heterocycloalkyl; the circled Ar represents a 5-membered nitrogen-heteroarylene, wherein the indicated required substituents to that heteroarylene are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the $-OR^{2A}$ moiety in which $R^{2A}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached, as indicated by the curved dotted line between $R^{4A}$ and $R^{4B}$, define a quaternized nitrogen heterocycloalkyl, optionally substituted; one $R^7$ is hydrogen or optionally substituted alkyl and the other $R^7$ is optionally substituted aralkyl or heteroaralkyl; wherein the wavy line indicates covalent bonding of the $D^+$ structure to the remainder of the LDC structure.

In those embodiments the tubulysin compound preferably has the structure of Formula $D_{I-1}$:

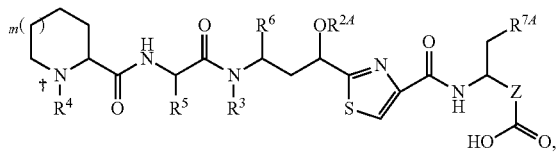

wherein subscript m is 0 or 1; Z is an optionally substituted alkylene or an optionally substituted alkenylene; $R^{7A}$ is optionally substituted aryl or optionally substituted heteroaryl; and the other variable groups are as previously defined for Formula $D_I$.

In preferred embodiments of Formula $D_I$ the tubulysin compound has the structure of Formula $D_{I-2}$:

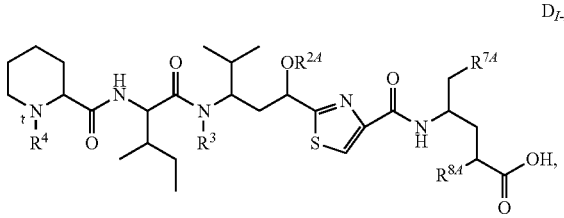

wherein $R^{7A}$ is optionally substituted phenyl; $R^{8A}$ is hydrogen or methyl; and the other variable groups are as previously defined for Formula $D_I$.

In other preferred embodiments of Formula $D_I$ the tubulysin compound has the structure of Formula $D_{I-3}$:

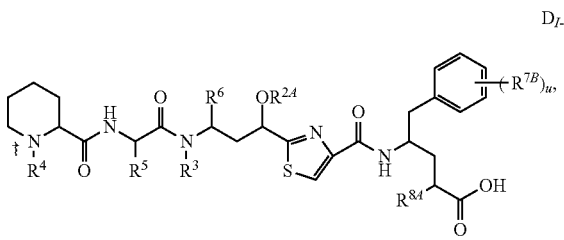

wherein $R^5$ and $R^6$ are alkyl side chain residues of natural or unnatural hydrophobic amino acids, independently selected; subscript u, indicating the number of $R^{7B}$ substituents, is 0, 1, 2 or 3; each $R^{7B}$, when present, is an independently selected O-linked substituent; $R^{8A}$ is hydrogen or optionally substituted alkyl; and the other variable groups are as previously defined for Formula $D_I$.

In more preferred embodiments of Formula $D_I$ the tubulysin compound has the structure of Formula $D_{I-4}$:

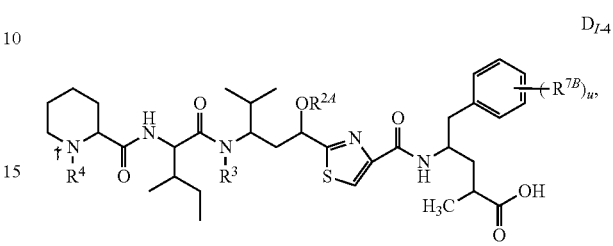

wherein the indicated nitrogen (†) is the site of quaternization when such a tubulysin compound corresponds to or is incorporated into an LDC or a Drug Linker compound as a quaternized drug unit ($D^+$); $R^4$ is methyl; subscript u is 0, 1 or 2; $R^3$ is H, methyl, ethyl, propyl, $-CH_2-OC(O)R^{3A}$, $-CH_2CH(R^{3B})C(O)R^{3A}$ or $-CH(R^{3B})C(O)NHR^{3A}$, wherein $R^{3A}$ is $C_1$-$C_6$ alkyl and $R^{3B}$ is H or $C_1$-$C_6$ alkyl, independently selected from $R^{3A}$; $R^{2A}$ along with the oxygen atom to which it is attached is an O-linked substituent selected from the group consisting of $-OCH_2OCH_2R^{2B}$, $-OCH_2R^{2B}$, $-OC(O)R^{2B}$, $-CH_2OC(O)R^{2B}$, $-OC(O)N(R^{2B})(R^{2C})$, and $-OCH_2C(O)N(R^{2B})(R^{2C})$, wherein $R^{2B}$ and $R^{2C}$ are independently selected from the group consisting of H, $C_1$-$C_6$ alkyl and $C_2$-$C_6$ alkenyl; and each $R^{7B}$, when present, independently is $-OH$ or $-OCH_3$.

In other more preferred embodiments of Formula $D_I$ the tubulysin compound has the structure of Formula $D_{I-5}$:

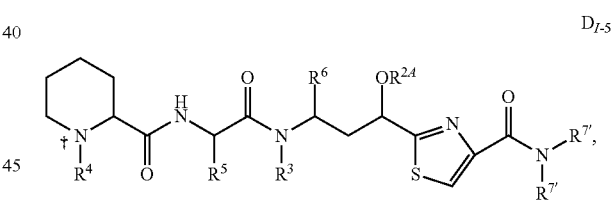

wherein the indicated nitrogen (†) is the site of quaternization when such a tubulysin compound corresponds to or is incorporated into an LDC or a Drug Linker compound as a quaternized drug unit ($D^+$); $R^{2A}$ is hydrogen, an optionally substituted alkyl, saturated or unsaturated, or $R^2$ along with the oxygen atom to which it is attached defines an O-linked substituent other than $-OH$; $R^3$ is optionally substituted $C_1$-$C_6$ alkyl; $R^4$ is methyl; $R^5$ and $R^6$ are alkyl side chain residues of natural hydrophobic amino acids; and the $-N(R^7)(R^{7'})$ moiety is $-NH(C_1$-$C_6$ alkyl) or $-NH-N(C_1$-$C_6$ alkyl)$_2$, wherein one and only one $C_1$-$C_6$ alkyl is optionally substituted by $-CO_2H$, or an ester thereof, or by an optionally substituted phenyl with the $-N(R^7)(R^{7'})$ moiety preferably selected from the group consisting of $-NH(CH_3)$, $-NHCH_2CH_2Ph$, and $-NHCH_2-CO_2H$, $-NHCH_2CH_2CO_2H$ and $-NHCH_2CH_2CH_2CO_2H$.

In any one of Formula $D_H$, $D_H'$, $D_{H-1}$, $D_I$, $D_{I-1}$, $D_{I-2}$, $D_{I-3}$, $D_{I-4}$ and $D_{I-5}$, preferably $R^{2A}$ is $-CH_2CH_3$, $-CH_2-CH=CH_2$ or $-CH_2-C(CH_3)=CH_2$.

In particularly preferred embodiments of Formula D₁ the tubulysin compound has the structure of

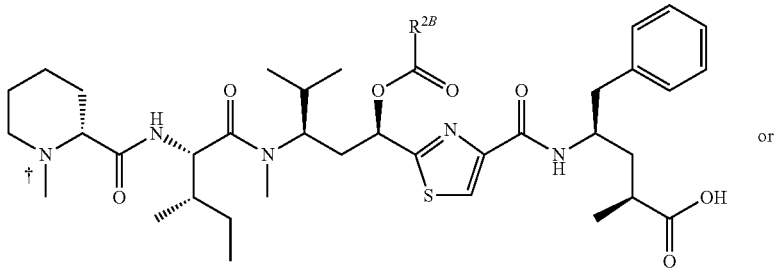

or

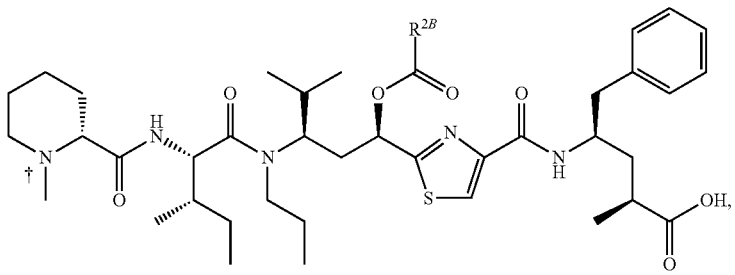

wherein R²ᴮ is —CH₃, —CH₂CH₃, —CH₂CH₂CH₃, —CH(CH₃)₂, —CH₂CH(CH₃)₂, —CH₂C(CH₃)₃; and the indicated nitrogen (†) is the site of quaternization when such a tubulysin compound corresponds to or is incorporated into an LDC or a Drug Linker compound as a quaternized drug unit (D⁺).

In other particularly preferred embodiments of Formula D₁ the tubulysin compound has the structure of

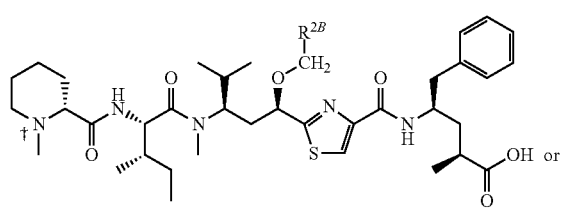

or

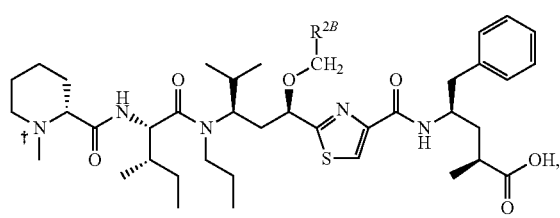

wherein R²ᴮ is hydrogen, methyl or —OCH₃ (i.e., —OCH₂R²ᴮ is a methyl, ethyl, or methoxymethyl ether substituent), or —OCH₂R²ᴮ is —OCH₂CH=CH₂ or —OCH₂C(CH₃)=CH₂; and the indicated nitrogen (†) is the site of quaternization when such a tubulysin compound corresponds to or is incorporated into an LDC or a Drug Linker compound as a quaternized drug unit (D⁺).

In other preferred embodiments of any one of Formula $D_{I-1}$, $D_{I-2}$, $D_{I-2}$, $D_{I-4}$ or $D_{I-5}$: the thiazole core heterocycle

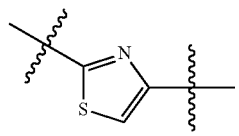 [SMILES: *c1csc(*)n1]

is replaced with

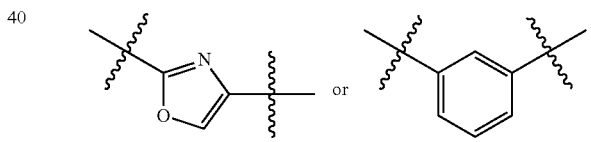

In some preferred embodiments of any one of Formula DH, $D_{H'}$, $D_{H-1}$, $D_I$, $D_{I-1}$, $D_{I-2}$, $D_{I-3}$, $D_{I-4}$ and $D_{I-5}$, $R^3$ is methyl or is —CH₂OC(=O)$R^{3A}$, wherein $R^{3A}$ is optionally substituted alkyl. In other preferred embodiments of any one of those structures $R^3$ is —C($R^{3A}$)($R^{3A}$)C(=O)—$X^C$, wherein $X^C$ is —O$R^{3B}$ or —N($R^{3C}$)($R^{3C}$), wherein each $R^{3A}$, $R^{3B}$ and $R^{3C}$ independently is hydrogen, optionally substituted alkyl or optionally substituted cycloalkyl. Preferably $R^3$ is —C($R^{3A}$)($R^{3A}$)C(=O)—N($R^{3C}$)($R^{3C}$), with each $R^{3A}$ hydrogen, one $R^{3C}$ hydrogen and the other $R^{3C}$ n-butyl or isopropyl more preferred.

In other preferred embodiments the tubulysin corresponding to or incorporated as D⁺ in an LDC is a naturally occurring tubulysin including Tubulysin A, Tubulysin B, Tubulysin C, Tubulysin D, Tubulysin E, Tubulysin F, Tubulysin G, Tubulysin H, Tubulysin I, Tubulysin U, Tubulysin V, Tubulysin W, Tubulysin X or Tubulysin Z, whose structures are given by the following structure and variable group definitions wherein the indicated nitrogen (†) is the site of quaternization when such compounds are incorporated into an LDC as a quaternized drug unit (D⁺):

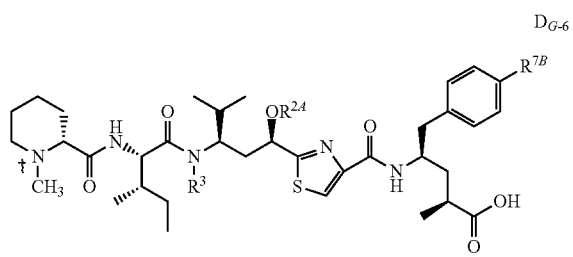

TABLE 1
Some Naturally Occurring Tubulysins

| Tubulysin | $R^{7B}$ | $R^{2A}$ | $R^3$ |
|---|---|---|---|
| A | OH | C(=O)CH$_3$ | CH$_2$O(C=O)i-Bu |
| B | OH | C(=O)CH$_3$ | CH$_2$O(C=O)n-Pr |

TABLE 1-continued
Some Naturally Occurring Tubulysins

| Tubulysin | $R^{7B}$ | $R^{2A}$ | $R^3$ |
|---|---|---|---|
| C | OH | C(=O)CH$_3$ | CH$_2$O(C=O)Et |
| D | H | C(=O)CH$_3$ | CH$_2$O(C=O)i-Bu |
| E | H | C(=O)CH$_3$ | CH$_2$O(C=O)n-Pr |
| F | H | C(=O)CH$_3$ | CH$_2$O(C=O)Et |
| G | OH | C(=O)CH$_3$ | CH$_2$O(C=O)CH=CH$_2$ |
| H | H | C(=O)CH$_3$ | CH$_2$O(C=O)Me |
| I | OH | C(=O)CH$_3$ | CH$_2$O(C=O)Me |
| U | H | C(=O)CH$_3$ | H |
| V | H | OH | H |
| Z | OH | OH | H |

In particularly preferred embodiments the quaternized tubulysin is that of Tubulysin M.

1.4.1 Drug Linker Compounds $L_B'\text{-}L_O\text{-}D^+$

In other preferred embodiments $L_B'\text{-}L_O\text{-}D^+$ or $L_B\text{-}L_O\text{-}D^+$ has the structure of:

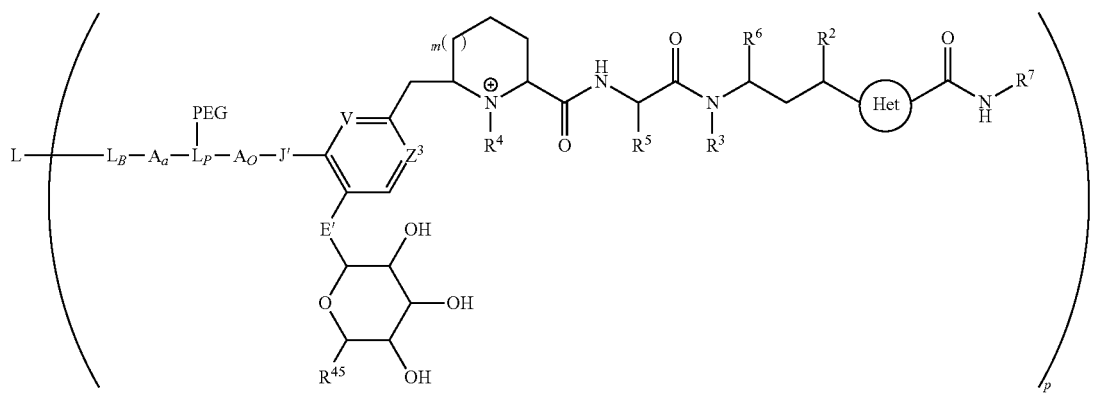

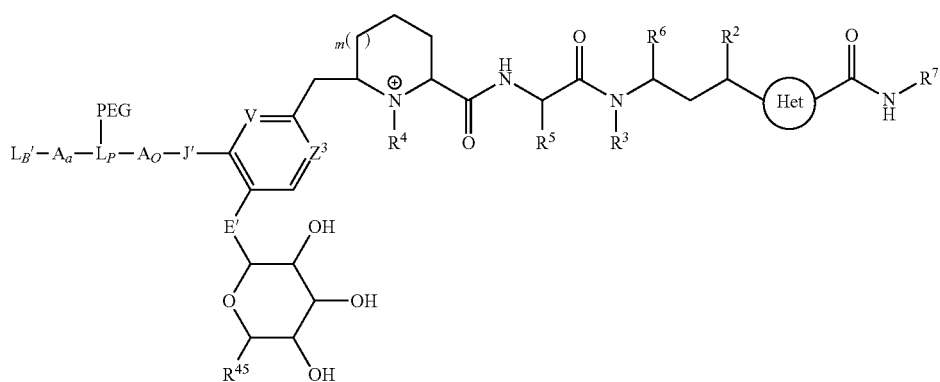

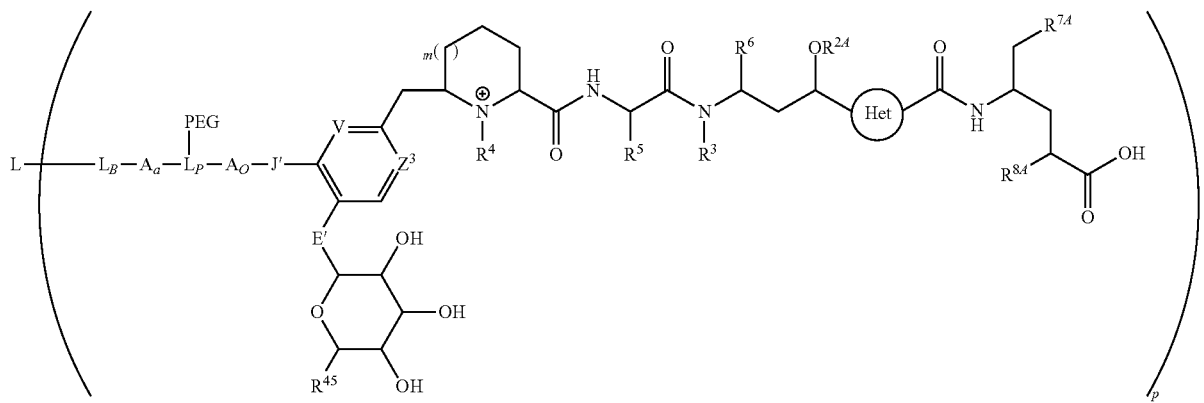

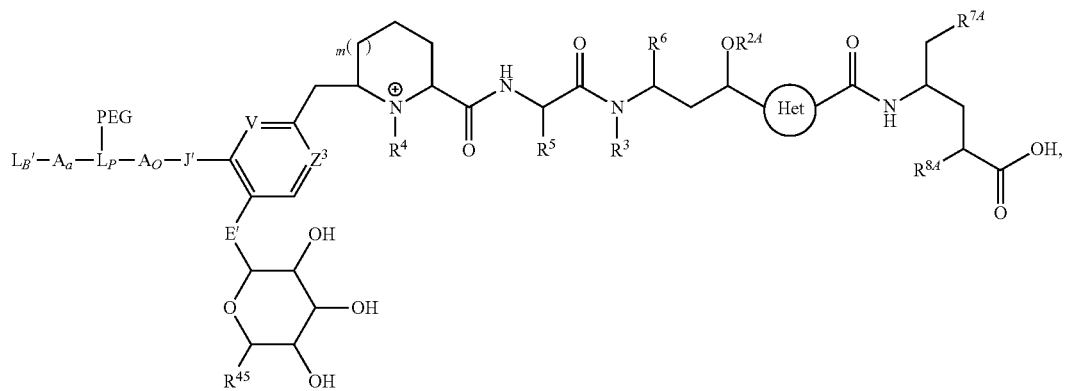

wherein $R^2$, $R^{2A}$, $R^3$, $R^4$, $R^{4A}$, $R^{4B}$, $R^5$, $R^6$, $R^7$, $R^{7A}$ an $R^{8A}$ are as described for tubulysin drugs in free form in structure $D_G'$, $D_H$, $D_H'$, $D_{H-1}$, $D_I$, $D_{I-1}$, $D_{I-2}$, $D_{I-3}$, $D_{I-4}$ and $D_{I-5}$, and $L_B$, $L_A'$, $L_P$, PEG, A, $A_O$, V and $Z^3$, and subscripts m and p are as previously described for $L_B$- and $L_B'$-containing moieties described herein; E' and J' are independently —O—, —S— or —N($R^{33}$), wherein $R^{33}$ is hydrogen or optionally substituted alkyl; and $R^{45}$ is $CO_2H$ or $CH_2OH$. In more preferred embodiments J' is —NH—. In other preferred embodiments E' is —O—.

More preferred are those embodiments where $L_B'$ is a maleimide ($M^1$) moiety or $L_B$ is a succinimide ($M^2$) or amide-acid ($M^3$) moiety.

In other more preferred embodiments $L_B'$-$L_O$-$D^+$ has the structure of:

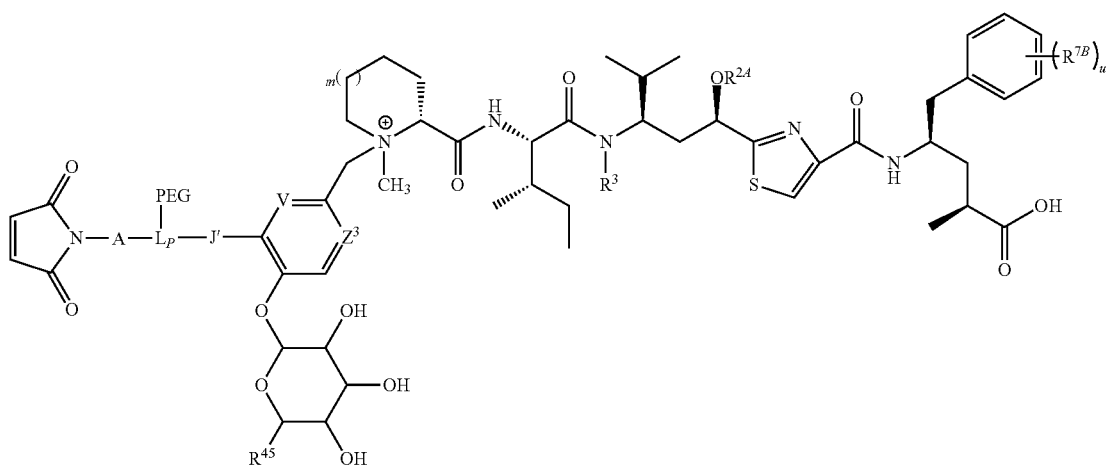

wherein A, $R^{2A}$, $R^3$, $R^{45}$, $R^{7B}$, $R^{45}$, and subscript u are as previously defined. In more preferred embodiments one or both of V, $Z^3$ are =CH—.
In more preferred embodiments a $L_B{}'$-$L_O$-$D^+$ or -$L_B$-$L_O$-$D^+$ moiety comprised of a quaternized tubulysin drug unit has the structure of:
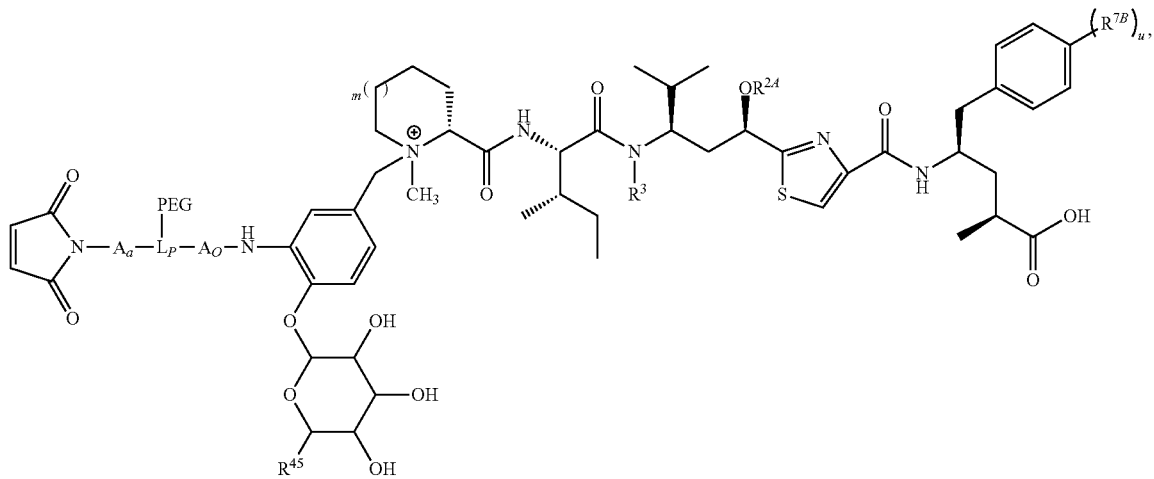
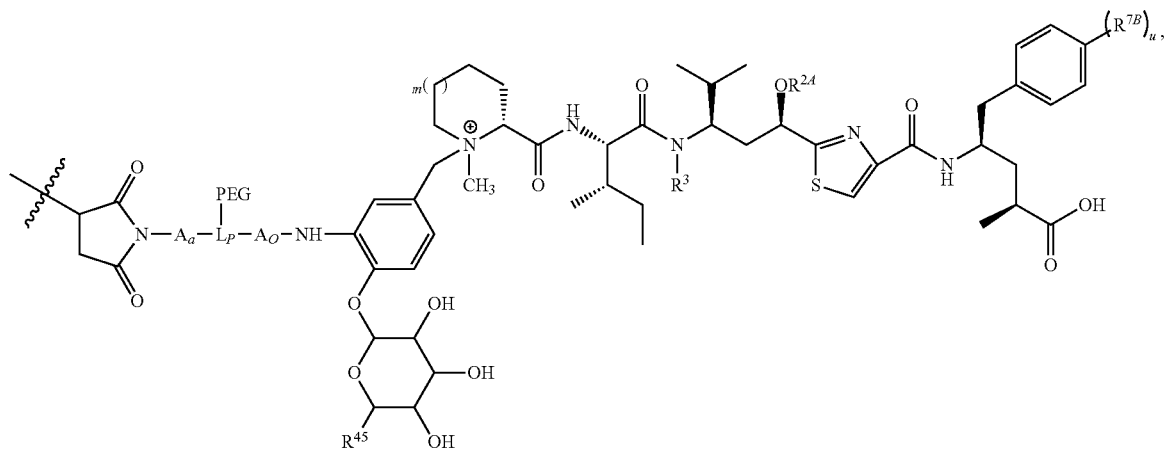
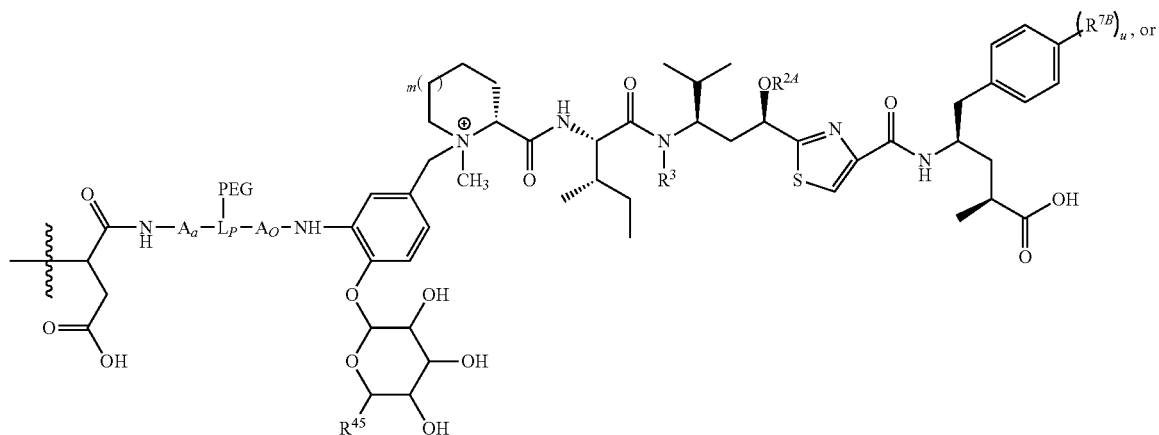

-continued

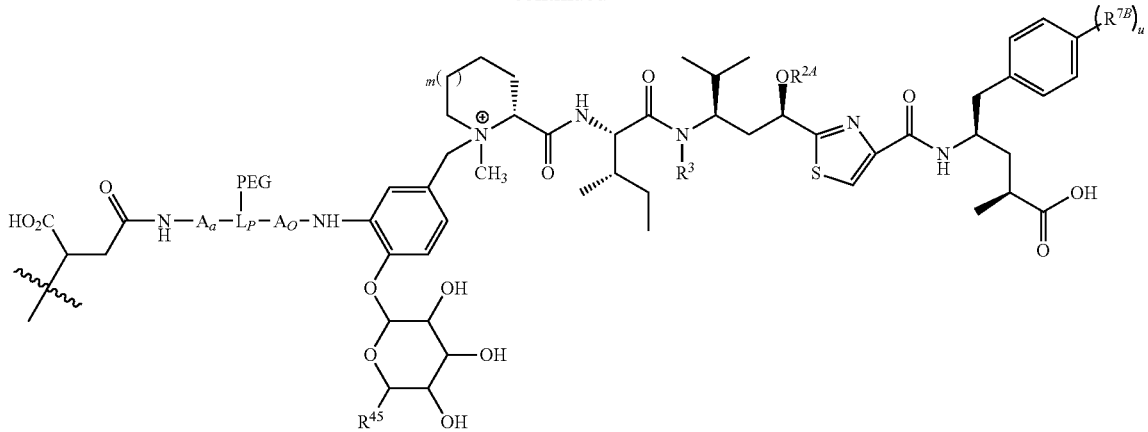

wherein the wavy line indicates covalent bonding to a sulfhydryl group of a Ligand Unit. In more preferred embodiments the carbohydrate moiety covalently attached to a self-immolative moeity of Y through a glycoside bond has its anomeric carbon in the β-configuration. In other more preferred embodiments $R^{45}$ is —$CH_2OH$ or —$CO_2H$.

In any one of the above embodiments for $L_B$-, $L_B'$-, $M^1$-, $M^2$- or $M^3$-containing moieties comprised of a quaternized tubulysin drug, $R^3$ is preferably methyl or $R^2$ is preferably acetate or subscript m is preferably 1. Also, preferred for such $L_B$-, $L_B'$-, $M^1$-, $M^2$- or $M^3$-containing moieties are those wherein $R^3$ is methyl, ethyl or propyl and —$OR^{2A}$ is —$OC(O)CH_3$, —$OCH_3$, —$OCH_2CH_3$, —$OCH_2CH_2CH_3$, —$OCH_2CH=CH_2$, or —$OCH_2C(CH_3)=CH_2$. In any one of those embodiments subscript u is 0 or is 1 and $R^{7B}$ is —OH 1.51 Treatment of Hyper-Proliferating Conditions The Ligand-Drug Conjugates are useful for inhibiting the multiplication of a tumor cell or cancer cell, causing apoptosis in a tumor or cancer cell, or for treating cancer in a patient. The Ligand-Drug Conjugates can be used accordingly in a variety of settings for the treatment of cancers. The Ligand-Drug Conjugates can be used to deliver a drug to a tumor cell or cancer cell. Without being bound by theory, in one embodiment, the Ligand unit of a Ligand-Drug Conjugate binds to or associates with a cell-surface cancer-cell or a tumor-cell-associated antigen or receptor, and upon binding the Ligand-Drug Conjugate can be taken up (internalized) inside a tumor cell or cancer cell through antigen- or receptor-mediated endocytosis or other internalization mechanism. The antigen can be attached to a tumor cell or cancer cell or can be an extracellular matrix protein associated with the tumor cell or cancer cell. Once inside the cell, via a enzymatic or non-enzymatic cleavable mechanism, depending upon the components of the linker system, the drug is released within the cell. In an alternative embodiment, the Drug or Drug unit is cleaved from the Ligand-Drug Conjugate within the vicinity of the tumor cell or cancer cell, and the Drug or Drug unit subsequently penetrates the cell.

The Ligand-Drug Conjugates can provide conjugation-specific tumor or cancer drug targeting, thus reducing general toxicity of the drug.

In some embodiments, the Linker units stabilize the Ligand-Drug Conjugates in blood, yet are capable of liberating drug once inside the cell.

In one embodiment, the Ligand unit binds to the tumor cell or cancer cell.

In another embodiment, the Ligand unit binds to a tumor cell or cancer cell antigen which is on the surface of the tumor cell or cancer cell.

In another embodiment, the Ligand unit binds to a tumor cell or cancer cell antigen which is an extracellular matrix protein associated with the tumor cell or cancer cell.

The specificity of the Ligand unit for a particular tumor cell or cancer cell can be important for determining those tumors or cancers that are most effectively treated. For example, a ligand drug conjugate having a BR96 Ligand Unit can be useful for treating antigen positive carcinomas including those of the lung, breast, colon, ovaries, and pancreas. Ligand-Drug Conjugates having an anti-CD30 or an anti-CD70 binding Ligand unit can be useful for treating hematologic malignancies.

Other particular types of cancers that can be treated with a ligand drug conjugates include, but are not limited to the following solid tumors, blood-borne cancers, acute and chronic leukemias, and lymphomas.

Solid tumors include but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Blood-borne cancers include but are not limited to acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia "CML", chronic lymphocytic leukemia "CLL", hairy cell leukemia, and multiple myeloma.

Acute and chronic leukemias include but are not limited to lymphoblastic, myelogenous, lymphocytic, and myelocytic leukemias.

Lymphomas include but are not limited to Hodgkin's disease, non-Hodgkin's Lymphoma, Multiple myeloma, Waldenström's macroglobulinemia, Heavy chain disease, and Polycythemia vera.

Cancers, including, but not limited to, a tumor, metastasis, or other diseases or disorders characterized by hyper-proliferating cells, can be treated or its progression inhibited by administration of an ADC composition.

In other embodiments, methods for treating cancer are provided, including administering to a patient in need thereof an effective amount of an LDC composition and a chemotherapeutic agent. In one embodiment the cancer to be treated with a chemotherapeutic in combination with an LDC has not been found to be refractory to the chemotherapeutic agent. In another embodiment, the cancer to be treated with a chemotherapeutic in combination with an ADC is refractory to the chemotherapeutic agent. The LDC compositions can be administered to a patient that has also undergone surgery as treatment for the cancer.

In some embodiments, the patient also receives an additional treatment, such as radiation therapy. In a specific embodiment, the Ligand-Drug Conjugate is administered concurrently with the chemotherapeutic agent or with radiation therapy. In another specific embodiment, the chemotherapeutic agent or radiation therapy is administered prior or subsequent to administration of a ligand drug conjugate.

A chemotherapeutic agent can be administered over a series of sessions. Any one or a combination of the chemotherapeutic agents, such a standard of care chemotherapeutic agent(s), can be administered.

Additionally, methods of treatment of cancer with a Ligand Drug Conjugate are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

1.6.1 Pharmaceutical Compositions

The present invention provides pharmaceutical compositions comprising an LDC composition described herein, or a pharmaceutically acceptable salt thereof, and one or more pharmaceutically acceptable excipients, or from one to four pharmaceutically acceptable excipients, which is some embodiments includes a pharmaceutically acceptable carrier. The pharmaceutical compositions can be in any form that allows for an Antibody Drug Conjugate as the LDC to be administered to a patient for treatment of a disorder associated with expression of the antigen to which the antibody of the ADC binds. For example, the pharmaceutical compositions can be in the form of a liquid or a lyophilized solid. The preferred route of administration is parenteral. Parenteral administration includes subcutaneous injections, intravenous, intramuscular, and intrasternal injection or infusion techniques. In preferred embodiments, a pharmaceutical composition comprising an ADC is administered intravenously in the form of a liquid solution. Preferably the liquid solution is prepared from reconstitution of a solid pre-formulation from lyophilization of a liquid pre-formulation comprising the ADC using a suitable pharmaceutically acceptable carrier.

Pharmaceutical compositions can be formulated so as to allow a compound to be bioavailable upon administration of the composition to a patient. Such compositions can take the form of one or more dosage units, where for example, a lyophilized solid may provide a single dosage unit when reconstituted as a solution or suspension on addition of a suitable liquid carrier.

Materials used in preparing the pharmaceutical compositions are preferably non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the pharmaceutical composition, the manner of administration, and the LDC composition employed.

The pharmaceutical composition can be, for example, in the form of a liquid. The liquid can be useful for delivery by injection. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as amino acids, acetates, citrates or phosphates; detergents, such as nonionic surfactants, polyols; and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable pharmaceutical composition is preferably sterile.

The amount of the conjugate that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The pharmaceutical composition comprises an effective amount of an LDC composition such that a suitable dosage will be obtained for administration to a subject in need thereof. Typically, this amount is at least about 0.01% by weight of the pharmaceutical composition.

For intravenous administration, the pharmaceutical composition can comprise from about 0.01 to about 100 mg of an LDC composition per kg of the animal's body weight. In one aspect, the pharmaceutical composition can include from about 1 to about 100 mg of a ADC composition per kg of the animal's body weight. In another aspect, the amount administered will be in the range from about 0.1 to about 25 mg/Kg of body weight of an ADC composition.

Generally, the dosage of an LDC composition administered to a patient is typically about 0.01 mg/Kg to about 100 mg/Kg of the subject's body weight. In some embodiments, the dosage administered to a patient is between about 0.01 mg/Kg to about 15 mg/Kg of the subject's body weight. In some embodiments, the dosage administered to a patient is between about 0.1 mg/Kg and about 15 mg/Kg of the subject's body weight. In some embodiments, the dosage administered to a patient is between about 0.1 mg/Kg and about 20 mg/kg of the subject's body weight. In other embodiments, the dosage administered is between about 0.1 mg/Kg to about 5 mg/Kg or about 0.1 mg/Kg to about 10 mg/Kg of the subject's body weight. In other embodiments, the dosage administered is between about 1 mg/Kg to about 15 mg/Kg of the subject's body weight. In other embodiments, the dosage administered is between about 1 mg/Kg to about 10 mg/Kg of the subject's body weight. In some embodiments, the dosage administered is between about 0.1 to 4 mg/Kg, preferably 0.1 to 3.2 mg/Kg, or more preferably 0.1 to 2.7 mg/Kg of the subject's body weight over a treatment cycle.

An LDC can be administered by any convenient route, for example by infusion or bolus injection, by absorption through epithelial or mucocutaneous linings (e.g., oral mucosa, rectal and intestinal mucosa). Administration can be systemic or local. Various delivery systems are known, e.g., encapsulation in liposomes, microparticles, microcapsules, capsules, and can be used to administer a compound. In certain embodiments, more than one compounds or composition is administered to a patient.

In an embodiment, the conjugates are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where a conjugate is to be administered by infusion, it can be dispensed, for example, with an infusion bottle containing sterile pharmaceutical grade water or saline. Where the conjugate is administered by injection, an ampoule of sterile water for injection or saline can be provided so that the ingredients can be mixed prior to administration.

The pharmaceutical compositions are generally formulated as sterile, substantially isotonic and in full compliance with all Good Manufacturing Practice (GMP) regulations of the U.S. Food and Drug Administration.

1.71 Numbered Embodiments

The following numbered embodiments further describe the invention without limiting thereto.

1. A Ligand Drug Conjugate composition, wherein the composition is represented by the structure of Formula 1:

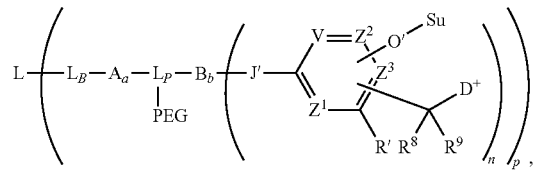

(Formula 1)

preferably in pharmaceutically acceptable salt form, wherein L is a Ligand Unit; $L_B$ is a Ligand Covalent Binding Unit; $L_P$ is a Parallel Connector Unit; PEG is a Polyethylene Glycol Unit; subscripts a and b independently are 0 or 1; subscript n is 1, 2, 3 or 4; A is a first optional Stretcher Unit so that subscript a is 0 when A is absent or 1 when A is present and is optionally comprised of two, three or four independently selected subunits ($A_1$, $A_2$, $A_3$, $A_4$); B is an Branching Unit or a second optional Stretcher Unit ($A_O$) so that subscript b is 0 when B is absent or 1 when B is present and is optionally comprised of two, three or four subunits independently of A, wherein subscript b is 1 and B is a Branching when subscript n is 2, 3 or 4, or subscript b is 0, or subscript b is 1 so that B is $A_O$, when subscript and is 1; Su is a carbohydrate moiety; —O'— represents an oxygen atom of an O-glycosidic bond cleavable by a glycosidase; -J'- represents a heteroatom, optionally substituted when nitrogen, preferably —NH—, or a nitrogen atom substituted by an optionally substituted alkyl, or an optionally substituted (heteroaryl)arylalkyl, from a functional group of B, when B is present, or from $L_P$, when B is absent; V, $Z^1$, $Z^2$ and $Z^3$ are =N— or =C($R^{24}$)—, wherein $R^{24}$ is hydrogen or alkyl, alkenyl or alkynyl, optionally substituted, or halogen, —$NO_2$, —CN or other electron withdrawing group, or —$OCH_3$ or other electron donating group, —O'-Su, or —C($R^8$)($R^9$)-$D^+$, wherein at least at least two of V, $Z^1$, $Z^2$ and $Z^3$ are =C($R^{24}$)—, provided, one any only one $R^{24}$ is —C($R^8$)($R^9$)-$D^+$ so that —C($R^8$)($R^9$)-$D^+$ is bonded to one of V, Z, Z, $Z^3$ when that variable group is =C($R^{24}$)— and one and only one other $R^{24}$ is so that —O'-Su is bonded to another one of V, Z, Z, $Z^3$ when that variable group is =C($R^{24}$)—, and the —O'-Su and —C($R^8$)($R^9$)-$D^+$ substituents are ortho or para to each other; $R^8$ and $R^9$ independently are hydrogen, alkyl, alkenyl or alkynyl, optionally substituted, or aryl or heteroaryl, optionally substituted; R' is hydrogen or is halogen, —$NO_2$, —CN or other electron withdrawing group; $D^+$ is a quaternized tubulysin Drug Unit; subscript p is an average drug loading having a number ranging from 1 to 24; and wherein said glycosidase cleavage results in release of a tubulysin compound (D) from a Ligand Drug Conjugate compound of the composition.

2. The Ligand Drug Conjugate composition of embodiment 1 wherein -$D^+$ is a quaternized tubulysin compound preferably having the structure of:

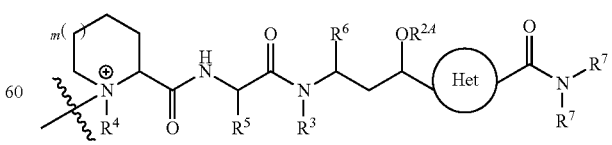

wherein the circle represents an 5-membered nitrogen-heteroarylene and wherein the indicated required substituents to that heteroarylene are in a 1,3-relationship with each other with optional substitution at the remaining positions;

subscript m is 0 or 1; $R^{24}$ is hydrogen or optionally substituted alkyl, or $R^{24}$ along with the oxygen atom to which it is attached defines an O-linked substituent; $R^3$ is hydrogen or optionally substituted alkyl; $R^4$, $R^5$ and $R^6$ are optionally substituted alkyl; one $R^7$ is an optionally substituted alkyl, an optionally substituted arylalkyl, optionally substituted heteroarylalkyl and the other $R^7$ is hydrogen or an optionally substituted alkyl; and $R^{8A}$ is hydrogen or optionally substituted alkyl, wherein the wavy line indicates covalent bonding of $D^+$ to the remainder of the Ligand Drug Conjugate structure and wherein each optionally substituted alkyl is independently selected.

3. The Ligand Drug Conjugate composition of embodiment 2 wherein the composition is represented by the structure of one of Formula 2A-2F:

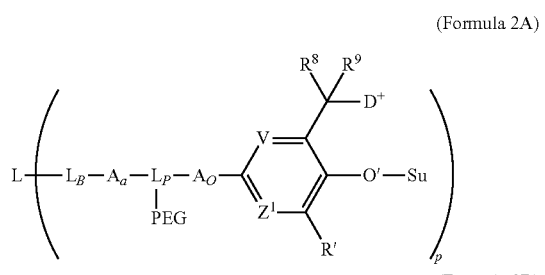
(Formula 2A)

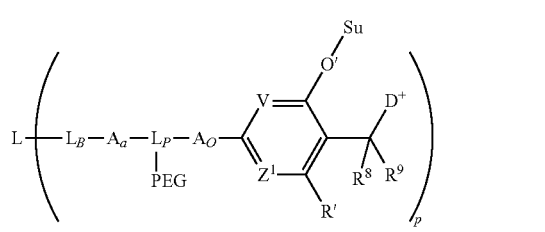
(Formula 2B)

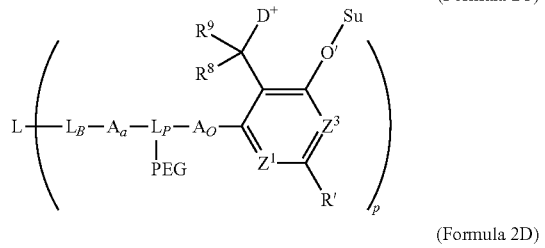
(Formula 2C)

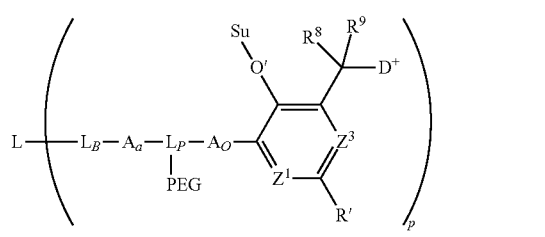
(Formula 2D)

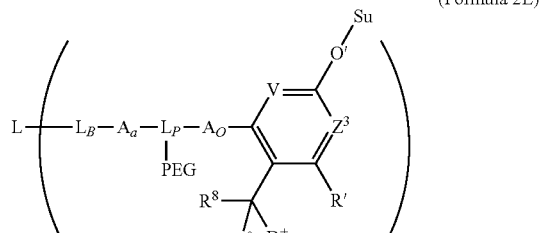
(Formula 2E)

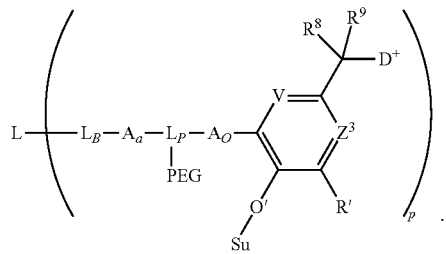
(Formula 2F)

4. The Ligand Drug Conjugate composition of embodiment 3 wherein L is an antibody Ligand Unit, thereby defining an antibody drug conjugate (ADC), wherein the antibody Ligand Unit selectively binds, or preferentially is capable of binding, to an accessible cell-surface antigen of targeted abnormal or other unwanted cells that is capable of cellular internalization of bound ADC, wherein the antigen is preferentially present on the abnormal or other unwanted cells in comparison to normal cells.

5. The Ligand Drug Conjugate composition of embodiment 3 wherein L is a cognate ligand of an accessible cell-surface receptor targeting that cell-surface receptor, wherein the targeted receptor on abnormal cells or other unwanted cells is capable of cellular internalization of bound LDC, and wherein the receptor is preferentially present on the abnormal cells in comparison to normal cells.

6. The Ligand Drug Conjugate composition of embodiment 3 wherein L is an antibody Ligand Unit, thereby defining an antibody drug conjugate (ADC), wherein the antibody Ligand Unit selectively, or preferentially binds to, an accessible cell-surface antigen of vascular epithelial cells in the vicinity of abnormal cells or other unwanted cells, wherein said antigen is preferably more abundant on said cells in comparison to epithelial cells in the periphery and is capable of cellular internalization of bound ADC.

7. The Ligand Drug Conjugate composition of any one of embodiments 1 to 6 wherein —O'-Su has the structure of Formula 3:

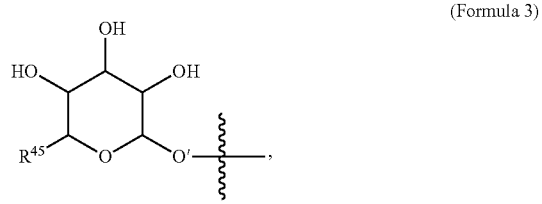
(Formula 3)

wherein the wavy line represents covalent bonding of O' to the remainder of the LDC structure; and $R^{45}$ is —CH$_2$OH or —CO$_2$H.

8. The Ligand Drug Conjugate composition of embodiment 7 wherein the composition is represented by the structure of Formula 4:

(Formula 4)

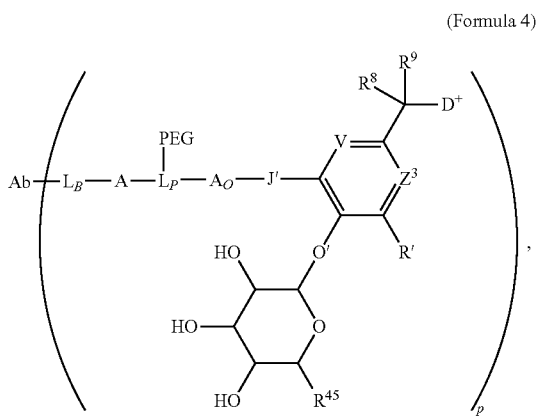

wherein Ab is an antibody Ligand Unit; J' is —N($R^{33}$)—, wherein $R^{33}$ is hydrogen or methyl; V and $Z^3$ independently are =CH— or =N—; R' is hydrogen or an electron withdrawing group; $R^8$ is hydrogen; $R^9$ is hydrogen, optionally substituted $C_1$-$C_6$ alkyl or optionally substituted phenyl; $R^{45}$ is —$CO_2H$; and subscript p is a number ranging from 1 to 24.

9. The Ligand Drug Conjugate composition of embodiment 1 wherein a is 1; and -$L_B$-A- of Formula 1 has the structure of:

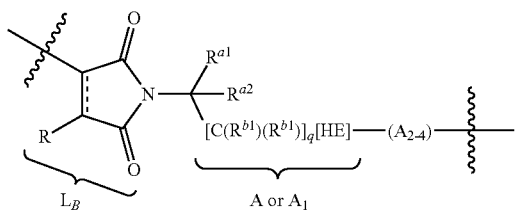

wherein the —[C($R^{b1}$)($R^{b1}$)]$_q$—[HE]- moiety is A or $A_1$, wherein $A_1$ is a subunit of A; $A_{2-4}$ are optional subunits of A; R is hydrogen or $C_1$-$C_4$ alkyl; $R^{a1}$ is hydrogen, optionally substituted alkyl or a Basic Unit (BU); and $R^{a2}$ is hydrogen or optionally substituted alkyl, or $R^{a1}$ and $R^{a2}$ together with the carbon atom to which they are attached define a substituted or unsubstituted nitrogen-containing heterocycloalkyl; HE is an optional Hydrolysis Enhancer (HE) Unit; subscript q is an integer ranging from 0 to 6; each $R^{b1}$ independently is hydrogen, optionally substituted $C_1$-$C_6$ alkyl, optionally substituted aryl or optionally substituted heteroaryl, or two $R^{b1}$ together with the carbon(s) to which they are attached comprise or preferably define a substituted or unsubstituted $C_3$-$C_6$ cycloalkyl or one $R^{b1}$ and HE together with the carbon to which they are attached define a substituted or unsubstituted 5 or 6-membered cycloalkyl or a substituted or unsubstituted 5- or 6-membered heterocycloalkyl and the other $R^{b1}$ is hydrogen, optionally substituted $C_1$-$C_6$ alkyl, optionally substituted aryl or optionally substituted heteroaryl; BU has the structure of —[C($R^1$)($R^1$)]—[C($R^2$)($R^2$)]r-N($R^{22}$)($R^{23}$), or an acid addition salt thereof, wherein subscript r is 0, 1, 2 or 3; each $R^1$ independently is hydrogen or lower alkyl or two $R^1$ together with the carbon to which they are attached comprise, or preferably define, a substituted or unsubstituted $C_3$-$C_6$ cycloalkyl, and each $R^2$ independently is hydrogen, optionally substituted $C_1$-$C_6$ alkyl, optionally substituted aryl or optionally substituted heteroaryl, or two $R^2$ together with the carbon(s) to which they are attached and any intervening carbons define a substituted or unsubstituted $C_3$-$C_6$ cycloalkyl, or one $R^1$ and one $R^2$ together with the carbons to which they are attached and any intervening carbons define a substituted or unsubstituted 5- or 6-membered cycloalkyl and the remaining $R^1$ and $R^2$ are as defined; $R^{22}$ and $R^{23}$ independently are hydrogen or optionally substituted $C_1$-$C_6$ alkyl or together with the nitrogen to which they are attached define a substituted or unsubstituted 5- or 6-membered heterocycloalkyl, or one of $R^{22}$, $R^{23}$ is hydrogen and the other is an acid labile protecting group; and wherein the dotted line is an optional double bond and the wavy line to the succinimide (double bond is absent) or maleimide ring (double bond is present) of $L_B$ indicates covalent bonding of sulfur derived from a sulfhydryl group of a targeting moiety and the other wavy line indicates covalent bonding to the remainder of the Ligand Drug Conjugate structure.

10. The Ligand Drug Conjugate composition of embodiment 1 wherein subscript a is 1; and -$L_B$-A- of Formula 1 or a compound thereof has the structure of:

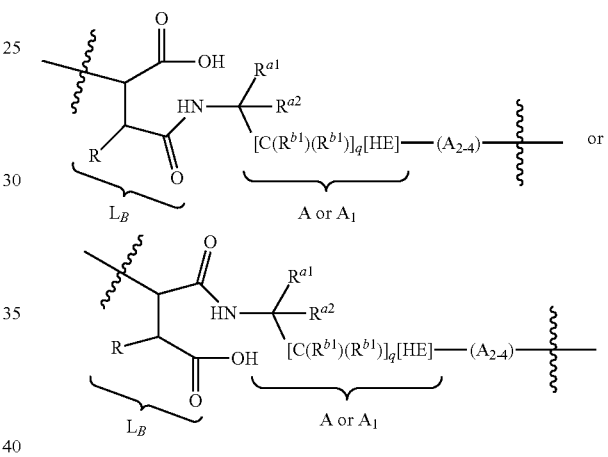

wherein the —[C($R^{b1}$)($R^{b1}$)]$_q$—[HE]- moiety is A or $A_1$, wherein $A_1$ is a subunit of A; $A_{2-4}$ are optional subunits of A; R is hydrogen or $C_1$-$C_4$ alkyl; $R^{a1}$ is hydrogen, optionally substituted alkyl or a Basic Unit (BU); and $R^{a2}$ is hydrogen or optionally substituted alkyl, or $R^{a1}$ and $R^{a2}$ together with the carbon atom to which they are attached defines a substituted or unsubstituted nitrogen-containing heterocycloalkyl; HE is an optional Hydrolysis Enhancer (HE) Unit; subscript q is an integer ranging from 0 to 6; each $R^{b1}$ independently is hydrogen, optionally substituted $C_1$-$C_6$ alkyl, optionally substituted aryl or optionally substituted heteroaryl, or two $R^{b1}$ together with the carbon(s) to which they are attached comprise, or preferably define, a substituted or unsubstituted $C_3$-$C_6$ cycloalkyl or one $R^{b1}$ and HE together with the carbon to which they are attached define a substituted or unsubstituted 5 or 6-membered cycloalkyl or a substituted or unsubstituted 5- or 6-membered heterocycloalkyl and the other $R^{b1}$ is hydrogen, optionally substituted $C_1$-$C_6$ alkyl, optionally substituted aryl or optionally substituted heteroaryl; BU has the structure of —[C($R^1$)($R^1$)]—[C($R^2$)($R^2$)]r-N($R^{22}$)($R^{23}$), or an acid addition salt thereof, wherein subscript r is 0, 1, 2 or 3; each $R^1$ independently is hydrogen or lower alkyl or two $R^1$ together with the carbon to which they are attached comprise, or preferably define, an a substituted or unsubstituted $C_3$-$C_6$ cycloalkyl, and each $R^2$ independently is hydrogen, optionally substituted $C_1$-$C_6$ alkyl, optionally substituted aryl or optionally substituted heteroaryl, or two $R^2$ together with the carbon(s) to which they are attached and any intervening carbons define a substituted or unsubstituted $C_3$-$C_6$ cycloalkyl, or one $R^1$ and one $R^2$ together with the carbons to which they are attached and any intervening carbons define a substituted or unsubstituted 5- or 6-membered cycloalkyl and the remaining $R^1$ and $R^2$ are as defined; $R^{22}$ and $R^{23}$ independently are hydrogen or optionally substituted $C_1$-$C_6$ alkyl or together with the nitrogen to which they are attached define a substituted or unsubstituted 5- or 6-membered heterocycloalkyl, or one of $R^{22}$, $R^{23}$ is hydrogen and the other is an acid labile protecting group; and wherein the dotted line is an optional double bond and the wavy line to the succinimide (double bond is absent) or maleimide ring (double bond is present) of $L_B$ indicates covalent bonding of sulfur derived from a sulfhydryl group of a targeting moiety and the other wavy line indicates covalent bonding to the remainder of the Ligand Drug Conjugate structure.

11. The Ligand Drug Conjugate composition of embodiment 9 wherein -$L_B$-A- of Formula 1 has the structure of:

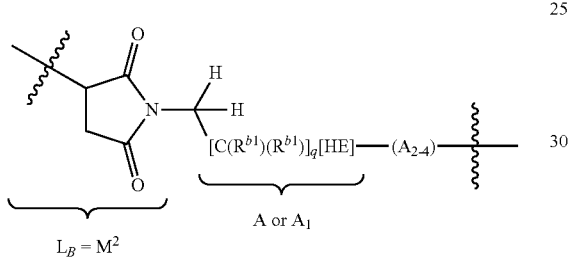

wherein subscript q is an integer ranging from 0 to 4.

12. The Ligand Drug Conjugate composition of embodiment 10 wherein -$L_B$-A- of Formula 1 or a compound thereof has the structure of:

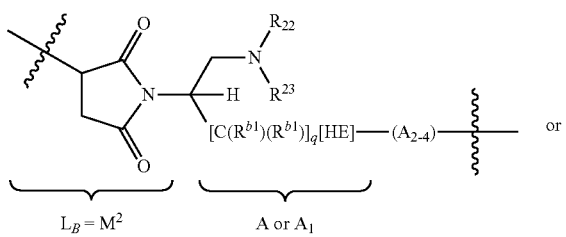

or

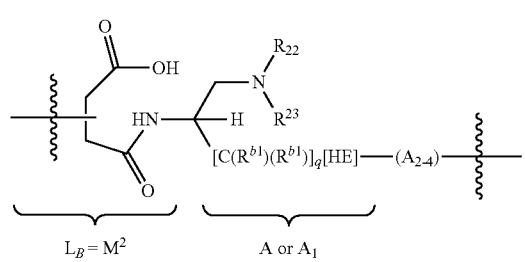

or an acid addition salt thereof, wherein $R^{22}$ and $R^{23}$ are each hydrogen or one of $R^{22}$, $R^{23}$ is hydrogen and the other is an acid labile carbamate protecting group; and subscript q is an integer ranging from 0 to 4.

13. The Ligand Drug Conjugate composition of embodiment 12 wherein -$L_B$-A- of Formula 1 has the structure of:

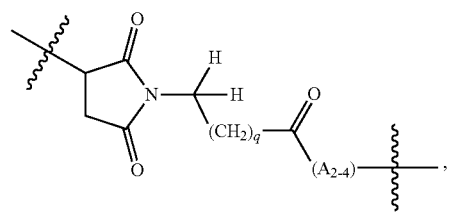

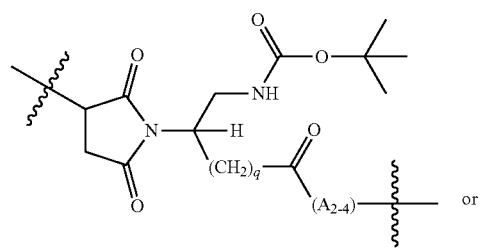

or

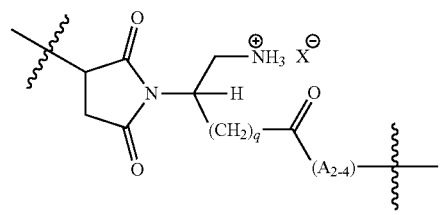

wherein $X^-$ is chloride, acetate, trifluoroacetate or dihydrogen phosphate.

14. The Ligand Drug Conjugate composition of embodiment 12 wherein -$L_B$-A- of Formula 1 or a compound thereof has the structure of:

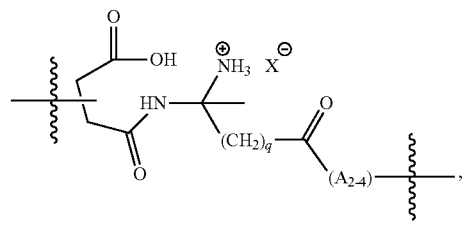

wherein $X^-$ is the counter anion of an acid addition salt.

15. The Ligand Drug Conjugate composition of embodiment 9 wherein the composition is represented by the structure of Formula 6:

(Formula 6)

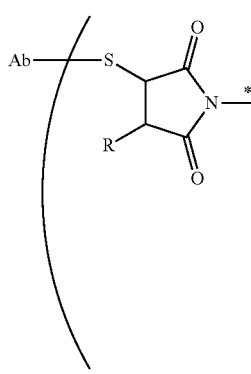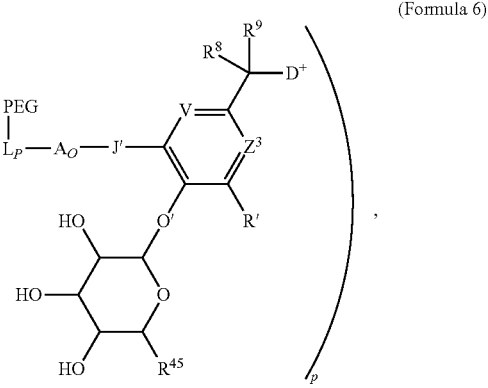

wherein Ab is an antibody Ligand Unit and S is a sulfur atom of the antibody Ligand Unit; the asterisk (*) designates chirality or absence thereof at the indicated carbon; $A_{2-4}$ are independently selected optional subunits of A, wherein —[C($R^{b1}$)($R^{b1}$)]$_q$—[HE]- is $A_1$ when one or more such subunits of A are present; R is hydrogen; R' is hydrogen or an electron withdrawing group; $R^{a1}$ is hydrogen or BU wherein BU is a Basic Unit having the structure of —CH$_2$—N($R^{22}$)($R^{23}$), or an acid addition salt thereof, wherein $R^{22}$ and $R^{23}$ independently are hydrogen, methyl or ethyl or both together with the nitrogen atom to which they are attached comprise, or preferably define, a substituted or unsubstituted 5- or 6-membered heterocycloalkyl, or one of $R^{22}$, $R^{23}$ is hydrogen and the other is an acid labile carbamate protecting group; $R^{a2}$ is hydrogen; subscript q is an integer ranging from 0 to 5 when HE is present or 1 to 5 when HE is absent; each $R^{b1}$ independently is hydrogen or optionally substituted $C_1$-$C_6$ alkyl; HE is absent or is —C(=O)—; $R^{45}$ is —CO$_2$H; J' is —NH—; V and $Z^3$ are =CH—; $R^8$ is hydrogen; $R^9$ is hydrogen or methyl; and subscript p is a number ranging from 1 to 16.

16. The Ligand Drug Conjugate composition of embodiment 1 wherein Ligand Drug Conjugate compounds of the composition are independently represented by the structures of Formula 9A or Formula 9B:

(Formula 9A)

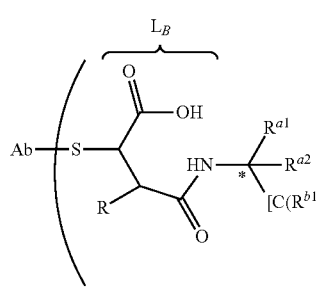

(Formula 9B)

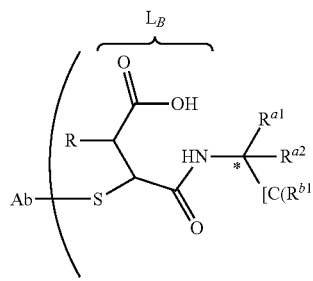

wherein Ab is an antibody Ligand Unit; S is a sulfur atom of the antibody Ligand Unit; $A_{2-4}$ are independently selected optional subunits of A, wherein —[C($R^{b1}$)($R^{b1}$)]$_q$—[HE]- is $A_1$ when one or more such subunits are present; R is hydrogen; R' is hydrogen or an electron withdrawing group; $R^{a1}$ is —H or BU wherein BU is a Basic Unit having the structure of —CH$_2$—N($R^{22}$)($R^{23}$), or an acid addition salt thereof, wherein $R^{22}$ and $R^{23}$ independently are hydrogen or methyl or both together with the nitrogen atom to which they are attached define a substituted or unsubstituted basic nitrogen-containing 5- or 6-membered heterocycloalkyl, or one of $R^{22}$, $R^{23}$ is hydrogen and the other is an acid labile protecting group; $R^{a2}$ is hydrogen; subscript q is an integer ranging from 0 to 5 when HE is present or from 1 to 5 when HE is absent; each $R^{b1}$ independently is hydrogen or optionally substituted $C_1$-$C_6$ alkyl; HE is absent or is —C(=O)—; J' is —O— or —NH—; $R^8$ and $R^9$ are independently —H or optionally substituted alkyl or both together along with the carbon atom to which they are attached define a substituted or unsubstituted cycloalkyl; and subscript p' is an integer ranging from 1 to 24.

17. The Ligand Drug Conjugate composition of embodiment 16 wherein Ligand Drug Conjugate compounds of the composition are independently represented by the structure of Formula 10A or Formula 10B:

18. The Ligand Drug Conjugate composition of embodiment 15, 16 or 17 wherein the indicated starred (*) carbon is predominantly in the same absolute configuration as the alpha carbon of an L-amino acid when that indicated carbon is chiral.

19. The Ligand Drug Conjugate composition of any one of embodiments 1 to 8 wherein A and $A_O$, when present, or any one of embodiments 9 to 18, wherein each of $A_2$-4, when present, independently have the structure of Formula 7 or Formula 8:

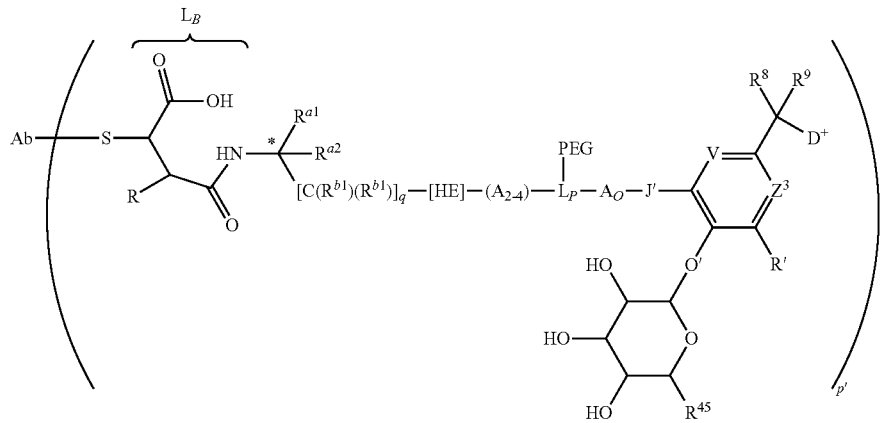

(Formula 10A)

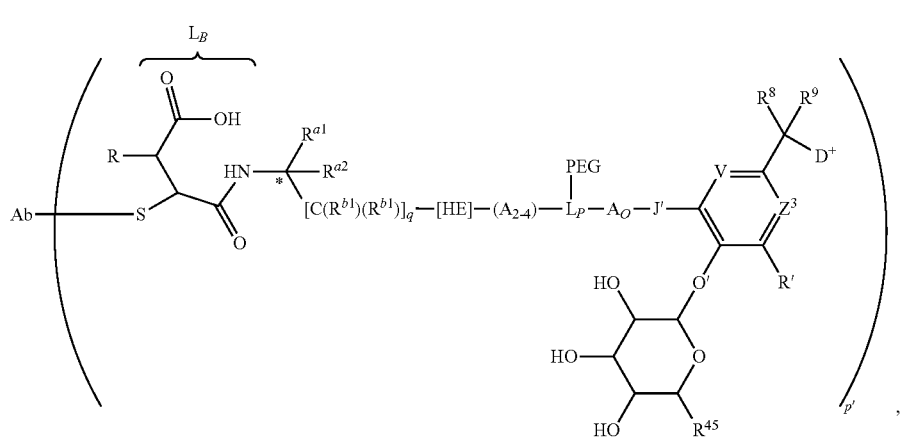

(Formula 10B)

wherein R is hydrogen; R' is hydrogen or —NO$_2$; HE is —C(=O)—; $R^{45}$ is —CO$_2$H; J' is —NH—; V and $Z^3$ are each =CH—; $R^8$ is hydrogen; and $R^9$ is hydrogen or methyl.

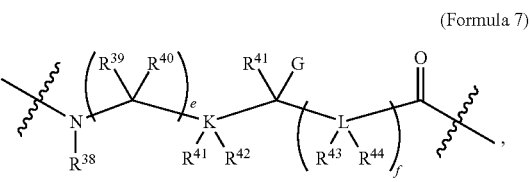

(Formula 7)

123
-continued (Formula 8)

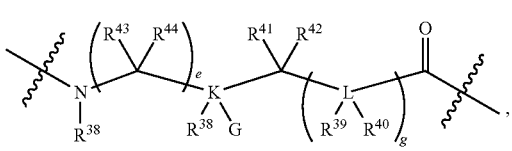

124

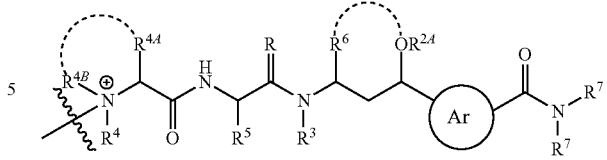

wherein the wavy lines indicated covalent attachment within the remainder of the Ligand Drug Conjugate structure, wherein K and L independently are C, N, O or S, provided that when K or L is O or S, $R^{41}$ and $R^{42}$ to K or $R^{43}$ and $R^{44}$ to L are absent, and when K or L are N, one of $R^{41}$, $R^{42}$ to K or one of $R^{42}$, $R^{43}$ to L are absent, and provided that no two adjacent L are independently selected as N, O, or S; wherein subscripts e and f are independently selected integers that range from 0 to 12, and subscript g is an integer ranging from 1 to 12: wherein G is hydrogen, optionally substituted $C_1$-$C_6$ alkyl, —OH, —$OR^{PR}$, —$CO_2H$, $CO_2R^{PR}$, wherein $R^{PR}$ is a suitable protecting, —$N(R^{PR})(R^{PR})$, wherein $R^{PR}$ are independently a protecting group or $R^{PR}$ together form a suitable protecting group, or —$N(R^{45})(R^{46})$, wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl; wherein $R^{38}$ is hydrogen or optionally substituted $C_1$-$C_6$ alkyl; $R^{39}$-$R^{44}$ independently are hydrogen, optionally substituted $C_1$-$C_6$ alkyl, optionally substituted aryl, or optionally substituted heteroaryl, or both $R^{39}$, $R^{40}$ together with the carbon to which they are attached comprise or preferentially define a substituted or unsubstituted $C_3$-$C_6$ cycloalkyl, or $R^{41}$, $R^{42}$ together with K to which they are attached when K is C, or $R^{43}$, $R^{44}$ together with L to which they are attached when L is a carbon atom comprise or preferentially define a substituted or unsubstituted $C_3$-$C_6$ cycloalkyl, or $R^{40}$ and $R^{41}$, or $R^{40}$ and $R^{43}$, or $R^{41}$ and $R^{43}$ to together with the carbon atom or heteroatom to which they are attached and the atoms intervening between those carbon atoms and/or heteroatoms comprise or preferably define a substituted or unsubstituted 5- or 6-membered cycloalkyl or a substituted or unsubstituted heterocycloalkyl, provided that when K is O or S, $R^{41}$ and $R^{42}$ are absent, when K is N, one of $R^{41}$, $R^{42}$ is absent, when L is O or S, $R^{43}$ and $R^{44}$ are absent, and when L is N, one of $R^{43}$, $R^{44}$ is absent, or wherein $A_O$ is an alpha-amino, beta-amino or another amine-containing acid residue.

20. The Ligand Drug Conjugate composition of any one of embodiments 1 to 19 wherein the quaternized tubulysin Drug Unit (-$D^+$) is a tubulysin compound preferably having the structure of:

wherein the curved dashed lines indicate optional cyclizations; $R^{2A}$ is hydrogen or optionally substituted alkyl, or $R^{2A}$ along with the oxygen atom to which it is attached defines an O-linked substituent other than —OH, or $R^{2A}$ is absent when $R^6$ is bonded to that oxygen atom, as indicated by the curved dash line between $R^6$ and the oxygen atom, to define a substituted or unsubstituted substituted oxygen-containing heterocycloalkyl; the circled Ar represents a 5-membered nitrogen-heteroarylene, wherein the indicated required substituents to that heteroarylene are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{2A}$ moiety in which $R^{2A}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached, as indicated by the curved dotted line between $R^{4A}$ and $R^{4B}$, define a substituted or unsubstituted quaternized nitrogen heterocycloalkyl, one $R^7$ is hydrogen or optionally substituted alkyl and the other $R^7$ is optionally substituted aralkyl or heteroaralkyl; wherein the wavy line indicates covalent bonding of the $D^+$ structure to the remainder of the Ligand Drug Conjugated structure.

21. The Ligand Drug Conjugate composition of embodiment 20 wherein the quaternized tubulysin Drug Unit (-$D^+$) has the structure of:

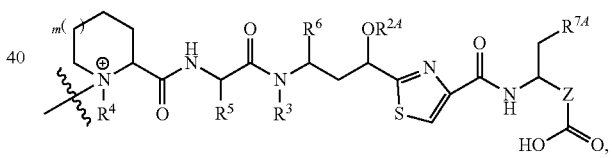

wherein subscript m is 0 or 1; Z is an optionally substituted alkylene or an optionally substituted alkenylene; and $R^{7A}$ is optionally substituted aryl or optionally substituted heteroaryl.

22. The Ligand Drug Conjugate composition of embodiment 21 wherein the quaternized tubulysin Drug Unit (-$D^+$) has the structure of:

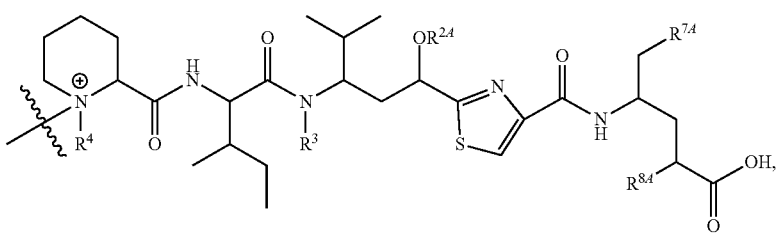

wherein $R^{7A}$ is optionally substituted phenyl and $R^8$ is hydrogen or methyl.

23. The Ligand Drug Conjugate composition of embodiment 21 wherein the quaternized tubulysin Drug Unit (-D$^+$) has the structure of:

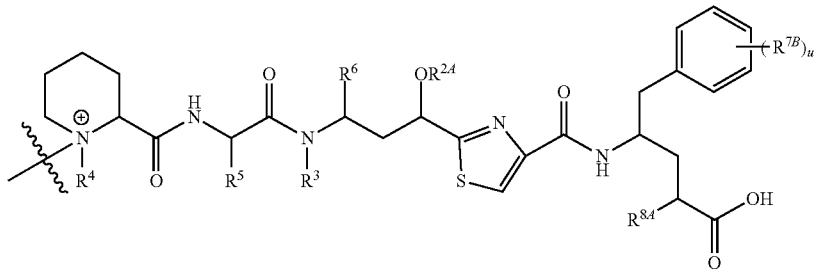

wherein $R^5$ and $R^6$ are alkyl side chain residues of natural or un-natural hydrophobic amino acids, preferably of hydrophobic natural amino acids, independently selected; subscript u, indicating the number of $R^{7B}$ substituents, is 0, 1, 2 or 3; each $R^{7B}$, when present, is an independently selected O-linked substituent; and $R^{8A}$ is hydrogen or optionally substituted alkyl.

24. The Ligand Drug Conjugate composition of embodiment 22 wherein the quaternized tubulysin Drug Unit (-D$^+$) has the structure of:

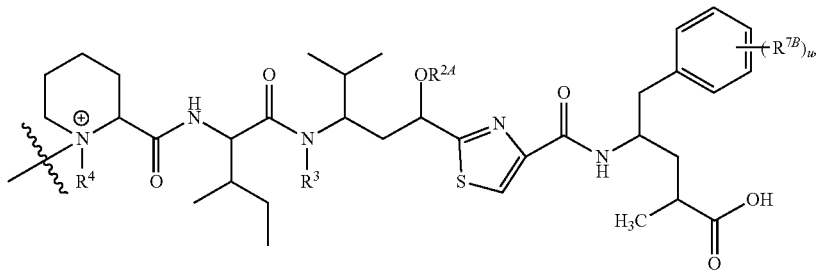

wherein $R^4$ is methyl; subscript u is 0, 1 or 2; $R^3$ is H, methyl, ethyl, propyl, —CH$_2$—OC(O)R$^{3A}$, —CH$_2$CH(R$^{3B}$)C(O)R$^{3A}$ or —CH(R$^{3B}$)C(O)NHR$^{3A}$, wherein $R^{3A}$ is C$_1$-C$_6$ alkyl and $R^{3B}$ is H or C$_1$-C$_6$ alkyl, independently selected from $R^{3A}$; $R^{2A}$ along with the oxygen atom to which it is attached is an O-linked substituent selected from the group consisting of —OCH$_2$OCH$_2$R$^{2B}$, —OCH$_2$R$^{2B}$, —OC(O)R$^{2B}$, —CH$_2$OC(O)R$^{2B}$, —OC(O)N(R$^{2B}$)(R$^{2C}$), and —OCH$_2$C(O)N(R$^{2B}$)(R$^{2C}$), wherein $R^{2B}$ and $R^{2C}$ are independently selected from the group consisting of H, C$_1$-C$_6$ alkyl and C$_2$-C$_6$ alkenyl; and each $R^{7B}$, when present, independently is —OH or —OCH$_3$.

25. The Ligand Drug Conjugate composition of embodiment 20 wherein the quaternized tubulysin Drug Unit (-D$^+$) has the structure of:

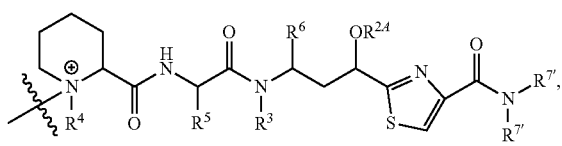

wherein $R^{2A}$ is hydrogen, an optionally substituted alkyl, saturated or unsaturated, or $R^2$ along with the oxygen atom to which it is attached defines an O-linked substituent other than —OH; $R^3$ is optionally substituted C$_1$-C$_6$ alkyl; $R^4$ is methyl; $R^5$ and $R^6$ are alkyl side chain residues of a hydrophobic natural or unnatural amino acids, preferably of natural hydrophobic amino acids; and the —N(R$^{7'}$)(R$^{7'}$) moiety is —NH(C$_1$-C$_6$ alkyl), optionally substituted by —CO$_2$H or an ester thereof, or by an optionally substituted phenyl, or is —N(C$_1$-C$_6$ alkyl)$_2$, wherein one and only one C$_1$-C$_6$ alkyl is optionally substituted by —CO$_2$H, or an ester thereof, or by an optionally substituted phenyl.

26. The Ligand Drug Conjugate composition of embodiment 25 wherein the —N(R$^{7'}$)(R$^{7'}$) moiety is selected from the group consisting of —NH(CH$_3$), —NHCH$_2$CH$_2$Ph, and —NHCH$_2$—CO$_2$H, —NHCH$_2$CH$_2$CO$_2$H and —NHCH$_2$CH$_2$CH$_2$CO$_2$H.

27. The Ligand Drug Conjugate composition of any one of embodiments 21 to 26 wherein $R^{2A}$ is —CH$_2$CH$_3$.

28. The Ligand Drug Conjugate composition of any one of embodiments 21 to 26 wherein $R^{2A}$ is —CH$_2$—CH=CH$_2$.

29. The Ligand Drug Conjugate composition of embodiment 24 wherein $R^{2A}$ is —CH$_2$CH$_3$, —CH$_2$—CH=CH$_2$ or —CH$_2$C(CH$_3$)=CH$_2$, $R^{2B}$ is —CH$_3$, $R^3$ is —CH$_3$ and subscript u is 0.

30. The Ligand Drug Conjugate composition of embodiment 24 wherein $R^{2A}$ is —CH$_2$CH$_3$ or —CH$_2$—CH=CH$_2$, or —CH$_2$C(CH$_3$)=CH$_2$, $R^{2B}$ is —CH$_3$, $R^3$ is —CH$_3$ and subscript u is 1, wherein $R^{7B}$ is —OH.

31. The Ligand Drug Conjugate composition of embodiment 24 wherein the quaternized tubulysin Drug Unit (-D$^+$) has the structure of:

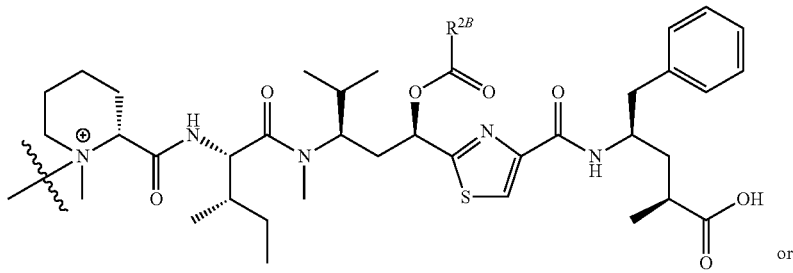
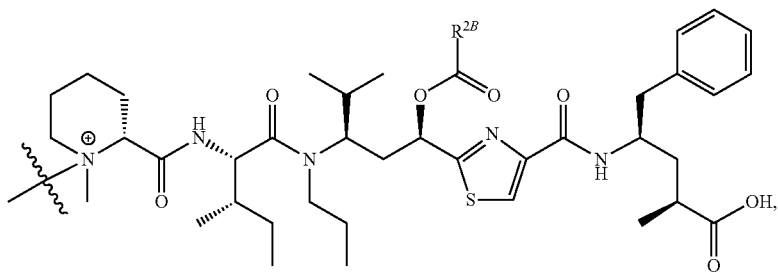
wherein $R^{2B}$ is —CH$_3$, —CH$_2$CH$_3$, —CH$_2$CH$_2$CH$_3$, —CH(CH$_3$)$_2$, —CH$_2$CH(CH$_3$)$_2$, or —CH$_2$C(CH$_3$)$_3$.
32. The Ligand Drug Conjugate composition of embodiment 24 wherein the quaternized tubulysin Drug Unit (-D$^+$) has the structure of:
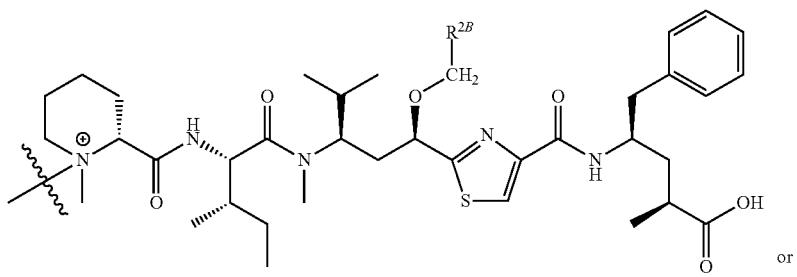
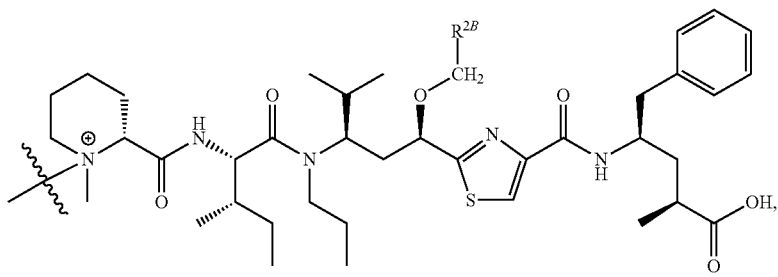

wherein $R^{2B}$ is hydrogen, methyl or —OCH$_3$, or —OCH$_2$R$^{2B}$ is —OCH$_2$CH=CH$_2$ or —OCH$_2$C(CH$_3$)=CH$_2$.

33. The Ligand Drug Conjugate composition of embodiment 24 wherein the quaternized tubulysin Drug Unit (-D$^+$) is that of tubulysin M, for which D$^+$ has the structure of:

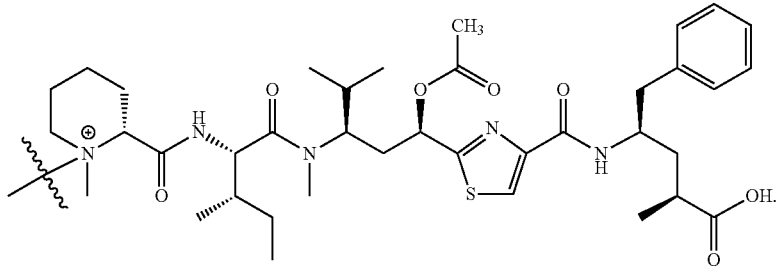

34. The Ligand Drug Conjugate composition of any one of embodiments 1 to 33 wherein $L_P$ is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the sulfur substituent is in reduced or oxidized form.

35. The Ligand Drug Conjugate composition of any one of embodiments 1 to 33 wherein $L_P$ is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

36. The Ligand Drug Conjugate composition of embodiment 34 wherein the aminoalkanedioic acid, diaminoalkanoic acid, sulfur-substituted aminoalkanoic acid or hydroxyl substituted aminoalkanoic acid residue has the structure of Formula A or B:

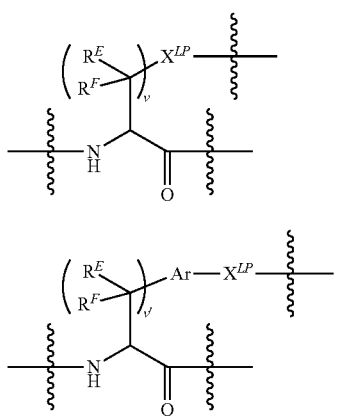

(Formula A)

(Formula B)

wherein subscript v is an integer ranging from 1 to 4; subscript v' is an integer ranging from 0 to 4; $X^{LP}$ is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N(R$^{LP}$)—, and —N(R$^{LP}$)C(=NR$^{LP}$)N(R$^{LP}$)— wherein each R$^{LP}$ is independently selected from the group consisting of hydrogen and optionally substituted alkyl or two of R$^{LP}$ together along with their intervening atoms define an optionally substituted heterocycloalkyl and any remaining R$^{LP}$ are as previously defined; Ar is an arylene or heteroarylene, optionally substituted; each R$^E$ and R$^F$ is independently selected from the group consisting of —H, optionally substituted alkyl, optionally substituted aryl and optionally substituted heteroaryl, or R$^E$ and R$^F$ together with the same carbon to which they are attached, or R$^E$ and R$^F$ from adjacent carbons together with these carbons define a substituted or unsubstituted cycloalkyl, with any remaining R$^E$ and R$^F$ substituents as previously defined; and wherein the wavy lines indicates covalent attachment of the Formula A or Formula B structure within the Ligand Drug Conjugate structure.

37. The Ligand Drug Conjugate composition of any one of embodiments 1 to 16 wherein -L$_P$(PEG)- has the structure of Formula A1 or A2:

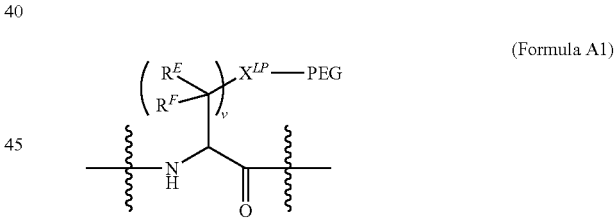

(Formula A1)

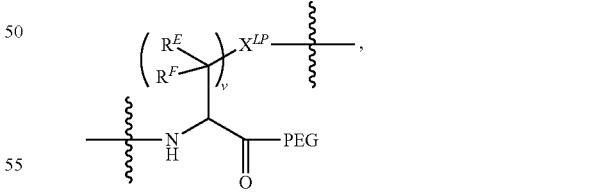

(Formula A2)

wherein $X^{LP}$ is selected from the group consisting of —O—, —NH, —S— and —C(=O)—; R$^E$ and R$^F$ are independently selected from the group consisting of —H and —C$_{1-4}$ alkyl; and wherein the wavy line indicates covalent attachment of Formula A1 or Formula A2 within the Ligand Drug Conjugate structure.

38. The Ligand Drug Conjugate composition of embodiment 1 wherein the composition is represented by the structure(s) of:

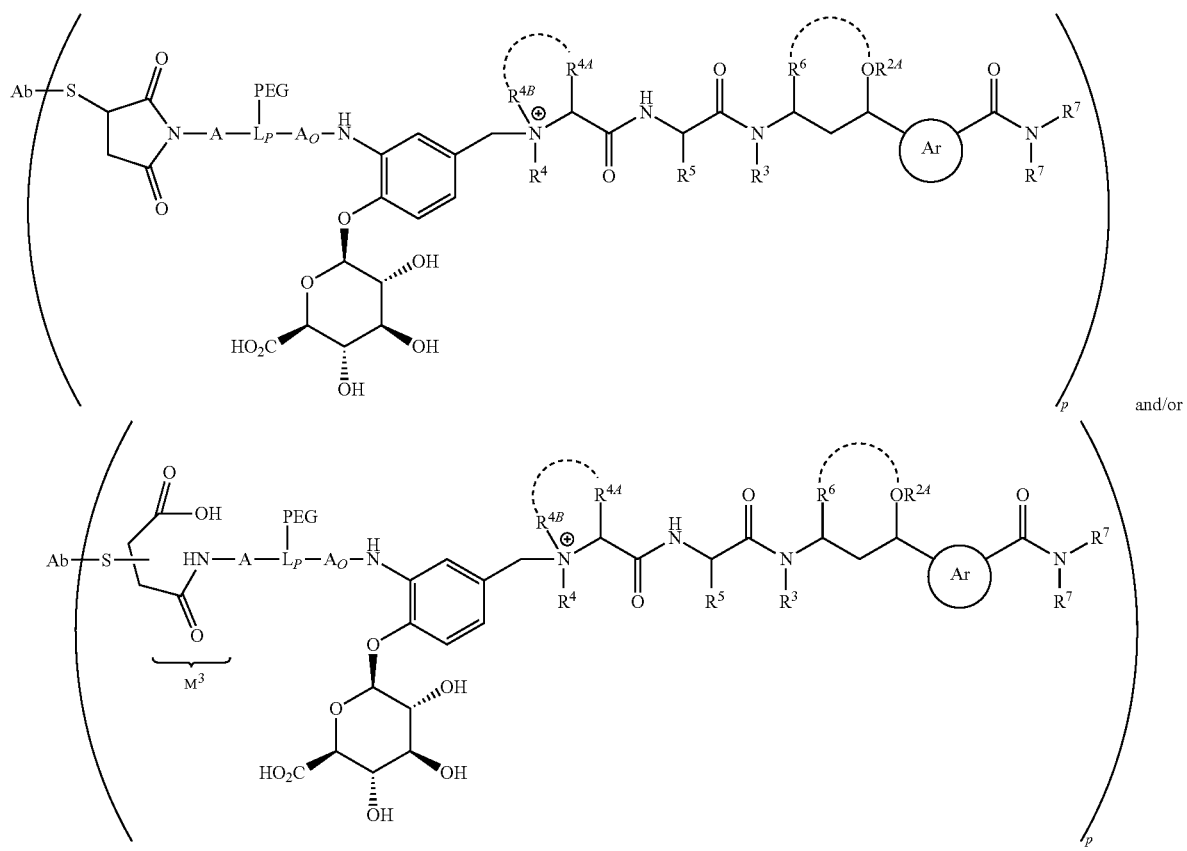

wherein the curved dashed lines indicate optional cyclizations; Ab is an antibody Ligand Unit; S is a sulfur atom of the antibody Ligand Unit; the Ab-S— moiety is bonded to the carbon α or β to the indicated $M^3$ carboxylic acid; $R^{2A}$ is hydrogen or optionally substituted alkyl, or $R^{2A}$ along with the oxygen atom to which it is attached defines an O-linked substituent other than —OH, or $R^{2A}$ is absent when $R^6$ is bonded to that oxygen atom, as indicated by the curved dash line between $R^6$ and the oxygen atom, to define a substituted or unsubstituted oxygen-containing heterocycloalkyl; the circled Ar represents a 5-membered nitrogen-heteroarylene, wherein the indicated required substituents to that heteroarylene are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{2A}$ moiety in which $R^{2A}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached define a substituted or unsubstituted nitrogen quaternized heterocycloalkyl as indicated by the curved dashed line between $R^{4A}$ and $R^{4B}$; one $R^7$ is hydrogen or optionally substituted alkyl and the other $R^7$ is optionally substituted aralkyl or heteroaralkyl; and subscript p is a number ranging from 1 to 16.

39. The Ligand Drug Conjugate composition of embodiment 38 wherein the composition is represented by the structure(s) of:

-continued
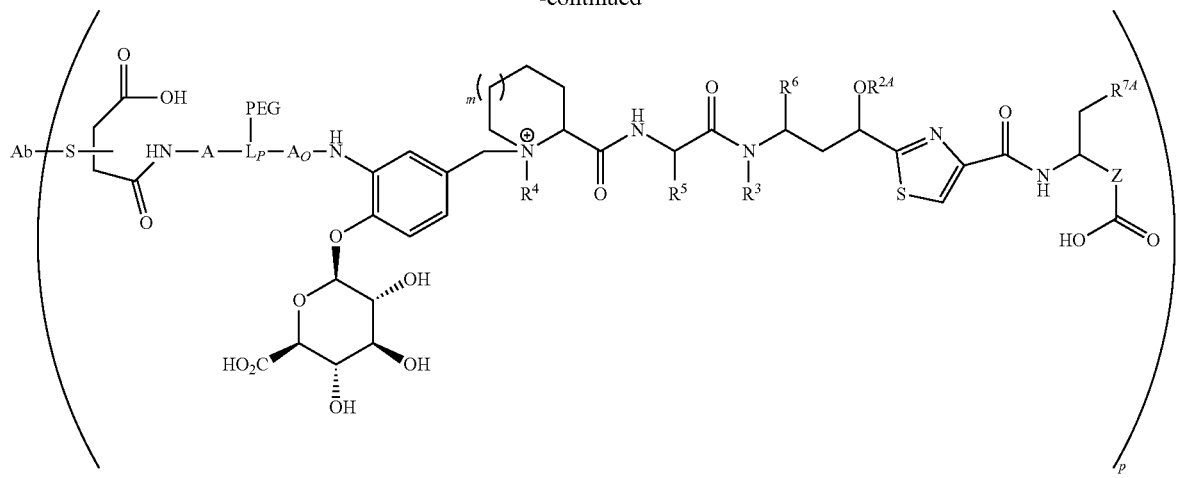
wherein subscript m is 0 or 1; subscript p is a number ranging from 1 to 8; Z is an optionally alkylene or an optionally substituted alkenylene; and $R^{7A}$ is optionally substituted aryl or optionally substituted heteroaryl.
40. The Ligand Drug Conjugate composition of embodiment 39 wherein the composition is represented by the structure(s) of:
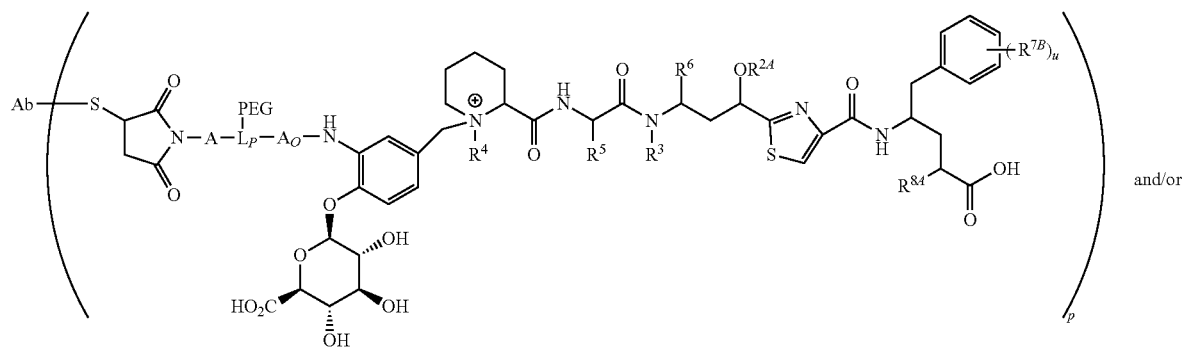
and/or
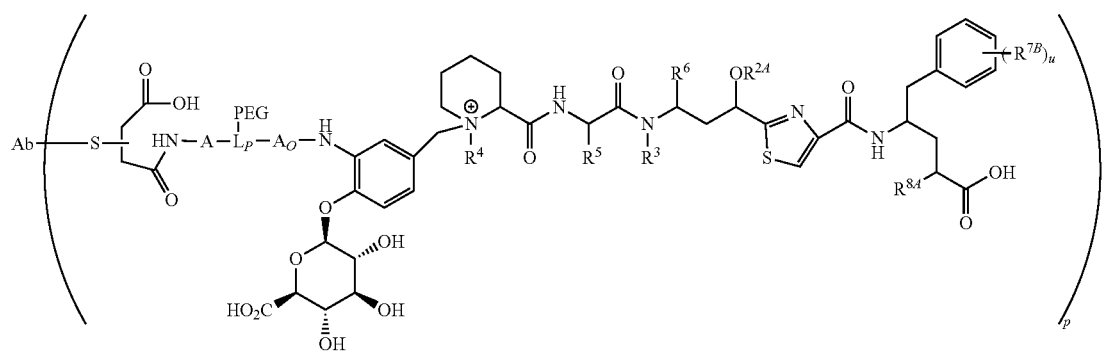

wherein $R^3$ is optionally substituted alkyl; $R^4$ is methyl; $R^5$ and $R^6$ are alkyl side chain residues of natural or un-natural hydrophobic amino acids, preferably of natural hydrophobic amino acids, independently selected; subscript p is a number ranging from 1 to 8; subscript u, indicating the number of $R^{7B}$ substituents, is 0, 1, 2 or 3; wherein each $R^{7B}$, when present, is an independently selected O-linked substituent; and $R^{8A}$ is hydrogen or optionally substituted alkyl.

41. The Ligand Drug Conjugate composition of embodiment 40 wherein the composition is represented by the structure(s) of:

alkyl and $R^{3B}$ is H or $C_1$-$C_6$ alkyl, independently selected from $R^{3A}$; $R^{2A}$ along with the oxygen atom to which it is attached is an O-linked substituent selected from the group consisting of —OCH$_2$OCH$_2$R$^{2B}$, —OCH$_2$R$^{2B}$, —OC(O)R$^{2B}$, —CH$_2$OC(O)R$^{2B}$, —OC(O)N(R$^{2B}$)(R$^{2C}$), and —OCH$_2$C(O)N(R$^{2B}$)(R$^{2C}$), wherein $R^{2B}$ and $R^{2C}$ are independently selected from the group consisting of H, $C_1$-$C_6$ alkyl and $C_2$-$C_6$ alkenyl; and each $R^{7B}$, when present, independently is —OH or —OCH$_3$.

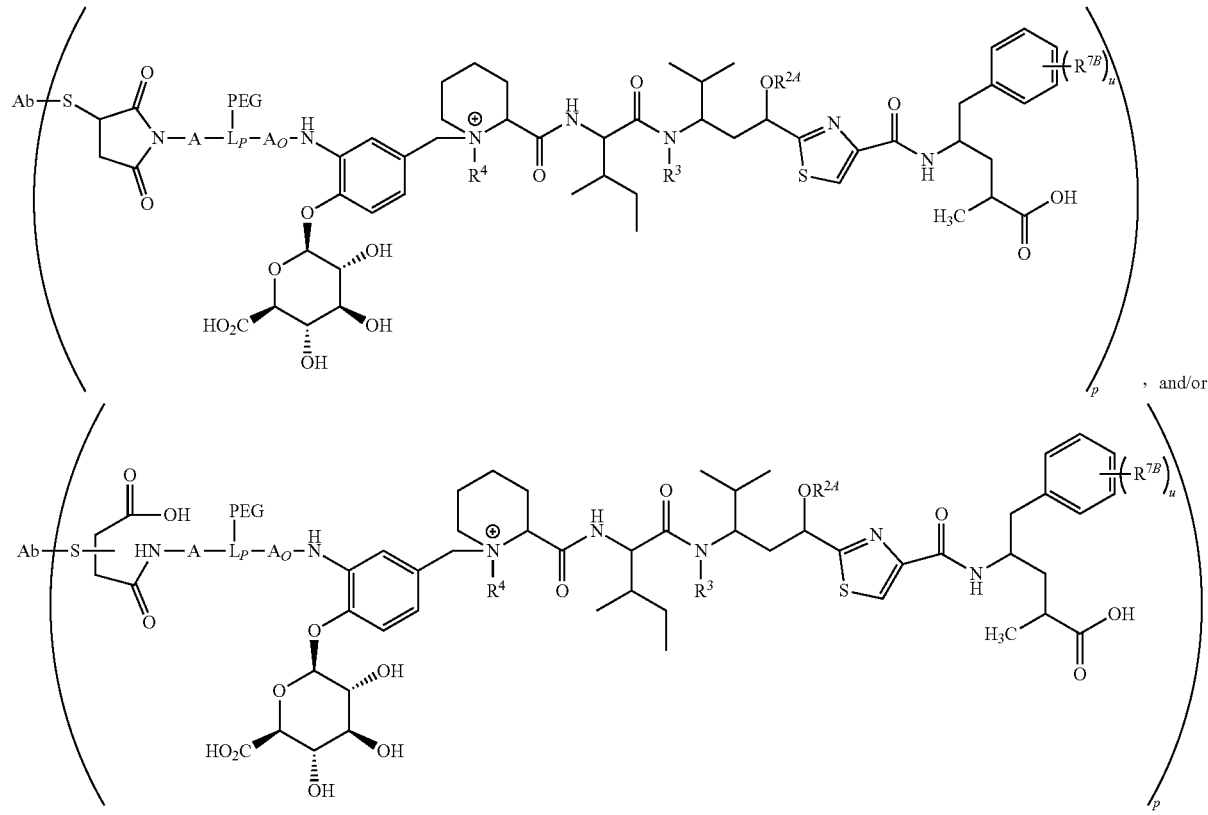

wherein $R^4$ is methyl; subscript u is 0, 1 or 2; $R^3$ is H, methyl, ethyl, propyl, —CH$_2$—OC(O)R$^{3A}$, —CH$_2$CH(R$^{3B}$)C(O)R$^{3A}$ or —CH(R$^{3B}$)C(O)NHR$^{3A}$, wherein $R^{3A}$ is $C_1$-$C_6$ 42. The Ligand Drug Conjugate composition of embodiment 38 wherein the composition is represented by the structure(s) of:

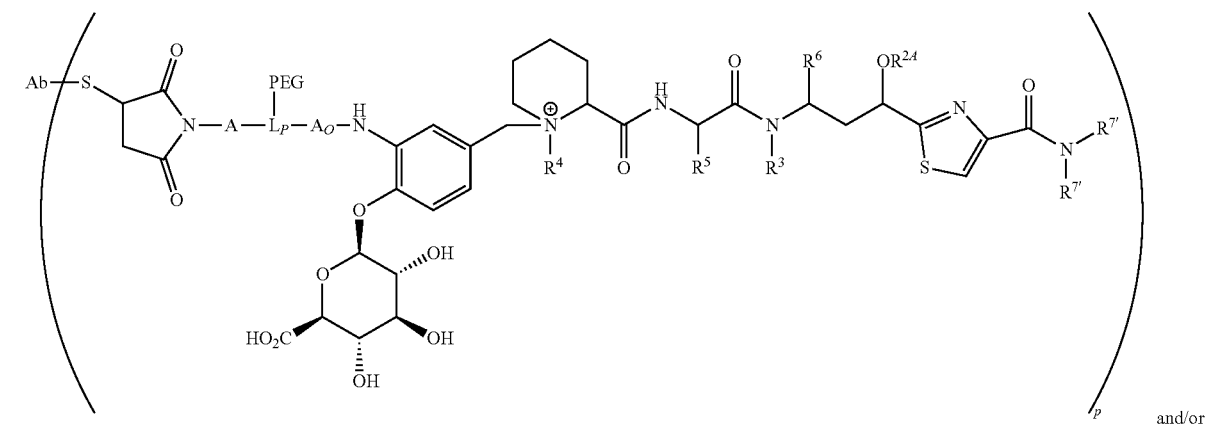

and/or

-continued

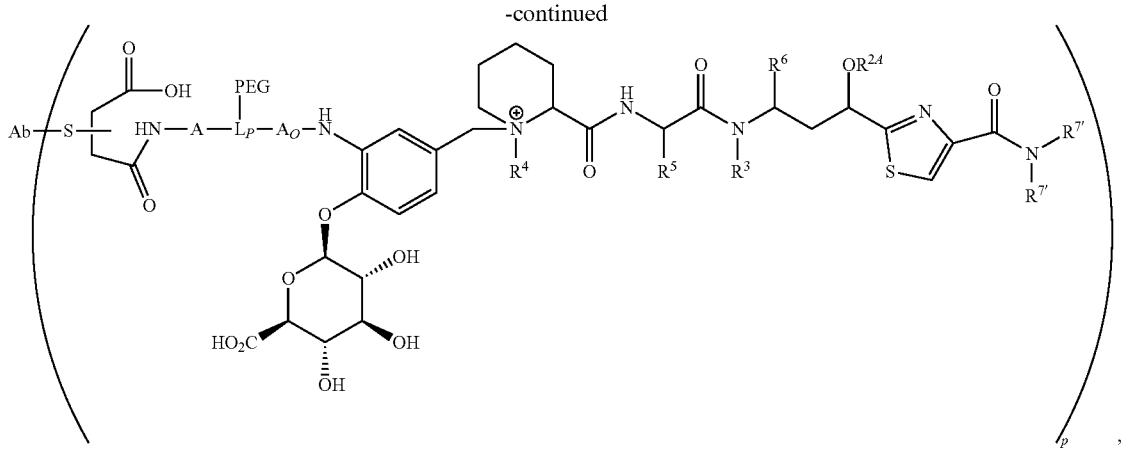

wherein $R^{24}$ is hydrogen, an optionally substituted alkyl, saturated or unsaturated, or $R^2$ along with the oxygen atom to which it is attached defines an O-linked substituent other than —OH; $R^3$ is optionally substituted $C_1$-$C_6$ alkyl; $R^4$ is methyl; $R^5$ and $R^6$ are side chain residues of natural or un-natural hydrophobic amino acids, preferably of natural hydrophobic amino acids, independently selected; and the —$N(R^{7'})(R^{7'})$ moiety is —$NH(C_1$-$C_6$ alkyl), optionally substituted by —$CO_2H$, or an ester thereof, or by an optionally substituted phenyl, or is —NH—$N(C_1$-$C_6$ alkyl)$_2$, wherein one and only one $C_1$-$C_6$ alkyl is optionally substituted by —$CO_2H$, or an ester thereof, or by an optionally substituted phenyl.

43. The Ligand Drug Conjugate composition of embodiment 42 wherein the —$N(R^{7'})(R^{7'})$ moiety is selected from the group consisting of —$NH(CH_3)$, —$NHCH_2CH_2Ph$, and —$NHCH_2$—$CO_2H$, —$NHCH_2CH_2CO_2H$ and —$NHCH_2CH_2CH_2CO_2H$.

44. The Ligand Drug Conjugate composition of embodiment 1 wherein Ligand Drug Conjugate compounds of the composition are independently represented by the structure of:

with the oxygen atom to which it is attached defines an O-linked substituent other than —OH, or $R^{24}$ is absent when $R^6$ is bonded to that oxygen atom to define a substituted or unsubstituted oxygen-containing heterocycloalkyl as indicated by the dash curved line; the circled Ar represents a 5-membered nitrogen-heteroarylene, wherein the indicated required substituents to that heteroarylene are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{24}$ moiety in which $R^{24}$ is absent, as indicated by the curved dashed line between $R^6$ and that oxygen atom, and $R^4$ and $R^5$ are as previously defined; $R^{4a}$ is hydrogen or optionally substituted alkyl and $R^{4B}$ is optionally substituted alkyl, or both together with the nitrogen to which they are attached define a substituted or unsubstituted nitrogen quaternized heterocycloalkyl, as indicated by the curved dash line between $R^{4A}$ and $R^{4B}$; one $R^7$ is hydrogen or optionally substituted alkyl and the other $R^7$ is optionally substituted aralkyl or heteroaralkyl; and subscript p' is an integer

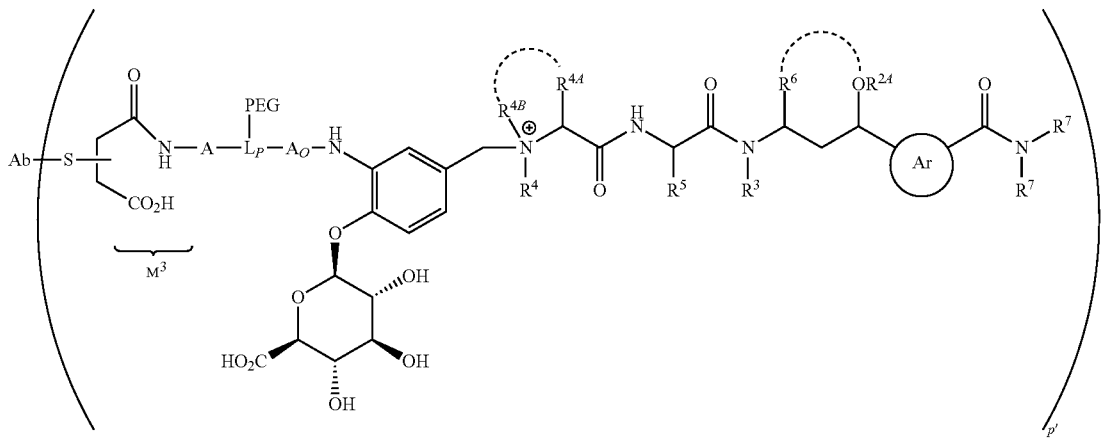

wherein the curved dashed lines indicate optional cyclizations; Ab is an antibody Ligand Unit; S is a sulfur atom of the antibody Ligand Unit; the Ab-S— moiety is bonded to the carbon α or β to the indicated $M^3$ carboxylic acid; $R^{24}$ is hydrogen or optionally substituted alkyl, or $R^{24}$ along ranging from 1 to 24, preferably 1 to 20, or more preferably from 1 to 16.

45. The Ligand Drug Conjugate composition of embodiment 44 wherein Ligand Drug Conjugate compounds of the composition are independently represented by the structure of:

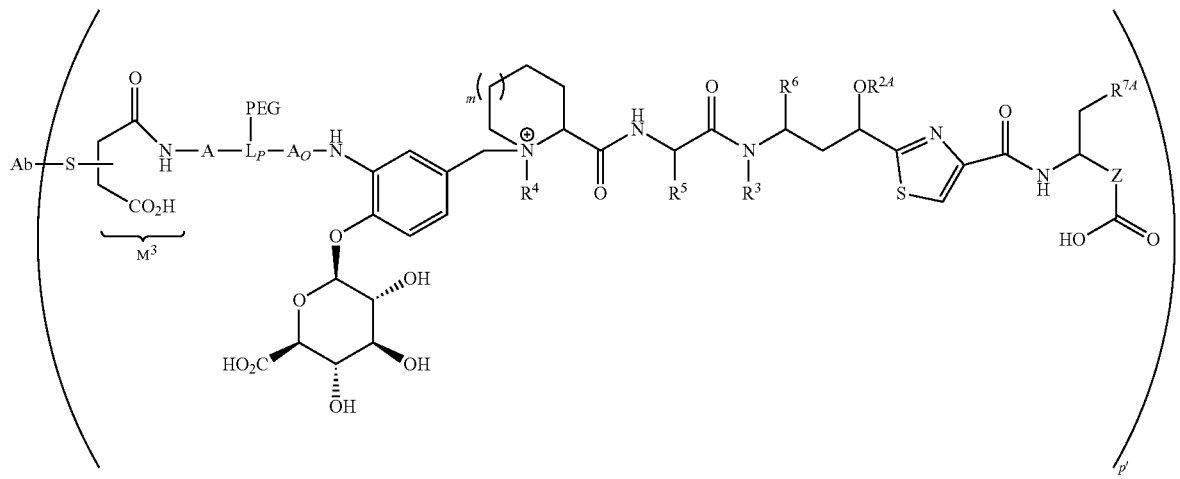

wherein subscript m is 0 or 1, preferably 1; Z is an optionally alkylene or an optionally substituted alkenylene; $R^{2A}$ is hydrogen or optionally substituted alkyl or $R^{2A}$ along with the oxygen atom to which it is attached defines an O-linked substituent other than —OH; $R^3$ is hydrogen or optionally substituted alkyl; $R^4$, $R^5$ and $R^6$ are optionally substituted alkyl, independently selected; and $R^{7A}$ is optionally substituted aryl or optionally substituted heteroaryl.

46. The Ligand Drug Conjugate composition of embodiment 45 wherein Ligand Drug Conjugate compounds of the composition are independently represented by the structure of:

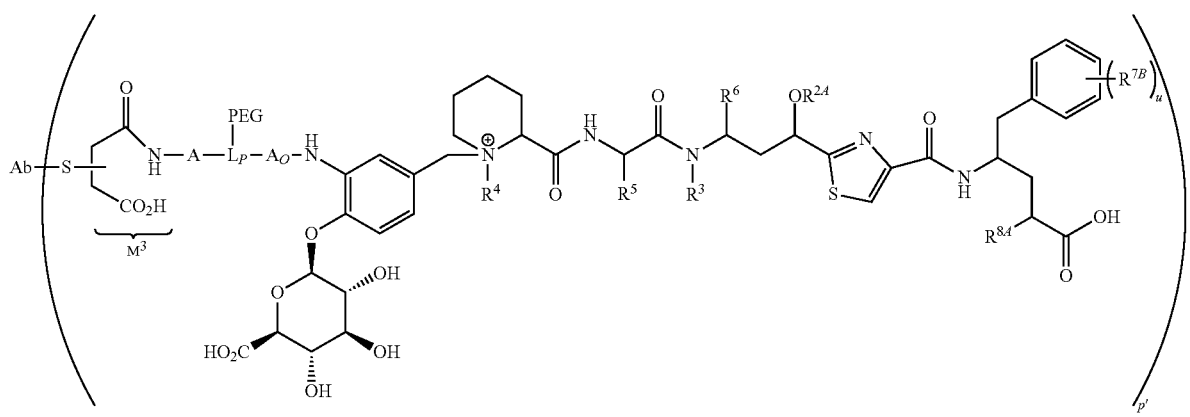

wherein $R^3$ is optionally substituted alkyl; $R^4$ is methyl; $R^5$ and $R^6$ are side chain residues of natural or un-natural hydrophobic amino acids, preferably of natural hydrophobic amino acids, independently selected; subscript p' is an integer ranging from 1 to 8; subscript u, indicating the number of $R^{7B}$ substituents, is 0, 1, 2 or 3, wherein each $R^{7B}$, when present, is an independently selected O-linked substituent; and $R^{8A}$ is hydrogen or optionally substituted alkyl.

47. The Ligand Drug Conjugate composition of embodiment 46 wherein Ligand Drug Conjugate compounds of the composition are independently represented by the structure of:

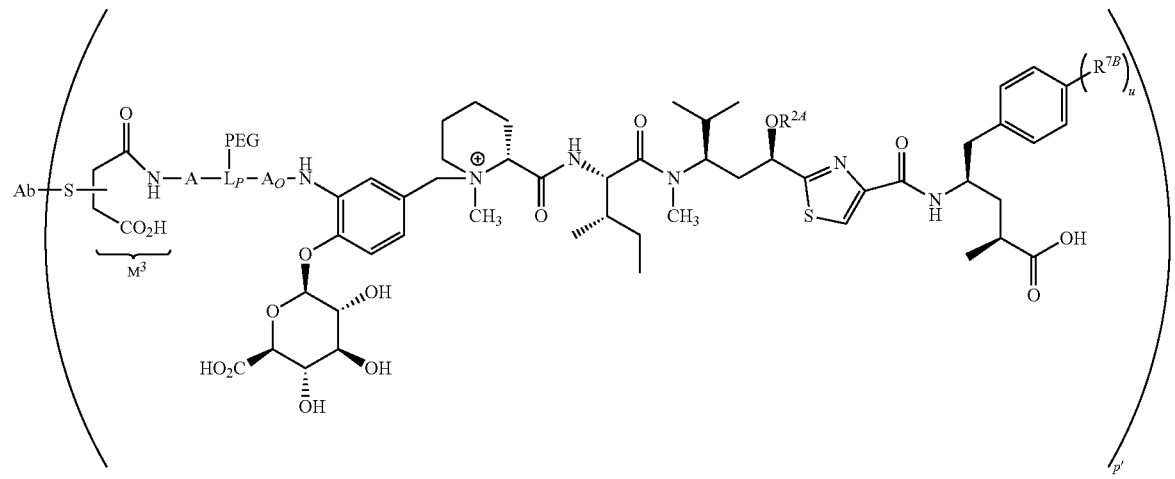

wherein subscript u is 0, 1 or 2; each $R^{7B}$, when present, is independently —OH or —OCH$_3$; and $R^{2A}$ is $C_1$-$C_6$ alkyl, —CH$_2$OR$^{2B}$, —CH$_2$R$^{2B}$, —C(=O)R$^{2B}$, —CH$_2$C(=O)R$^{2B}$, —C(=O)NHR$^{2B}$ or —CH$_2$C(=O)NHR$^{2B}$, wherein $R^{2B}$ is $C_1$-$C_6$ alkyl or $C_2$-$C_6$ alkenyl.

48. The Ligand Drug Conjugate composition of embodiment 1 wherein Ligand Drug Conjugate compounds of the composition are represented by the structure of:

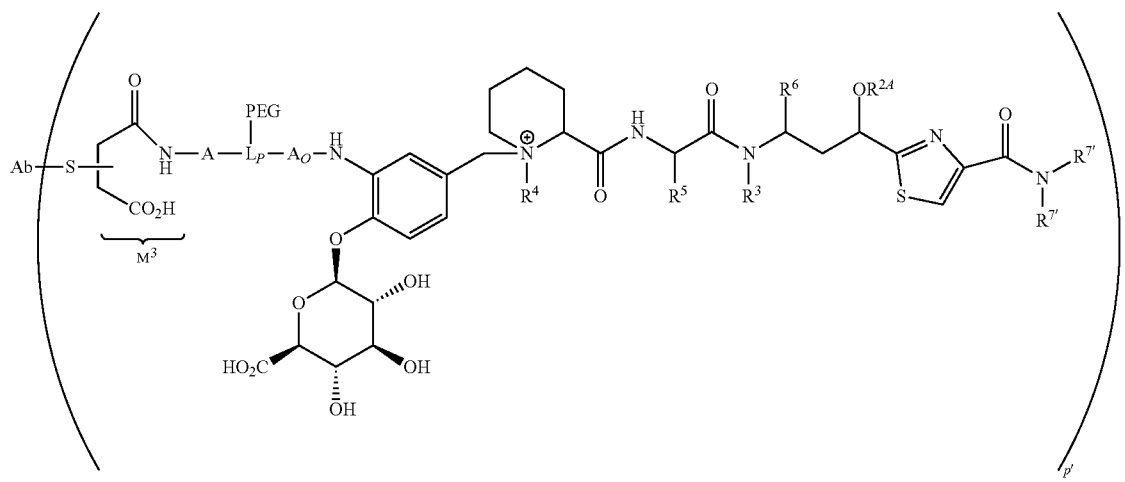

wherein Ab is an antibody Ligand Unit, S is a sulfur atom from the antibody Ligand Unit; the Ab-S— moiety is bonded to the carbon α or β to the indicated $M^3$ carboxylic acid; $R^{2A}$ is hydrogen, an optionally substituted alkyl, saturated or unsaturated, or $R^2$ along with the oxygen atom to which it is attached defines an O-linked substituent other than —OH; $R^3$ is optionally substituted $C_1$-$C_6$ alkyl; $R^4$ is methyl; $R^5$ and $R^6$ are side chain residues of natural or un-natural hydrophobic amino acids, preferably of natural hydrophobic amino acids, independently selected; and the —N(R$^{7'}$)(R$^{7'}$) moiety is —NH(C$_1$-C$_6$ alkyl), optionally substituted by —CO$_2$H, or an ester thereof, or by an optionally substituted phenyl, or is —N(C$_1$-C$_6$ alkyl)$_2$, wherein one and only one $C_1$-$C_6$ alkyl is optionally substituted by —CO$_2$H, or an ester thereof, or by an optionally substituted phenyl; and subscript p' is an integer ranging from 1 to 8.

49. The Ligand Drug Conjugate composition of any one of embodiments 38 to 48 wherein $R^{2A}$ is saturated $C_1$-$C_4$ alkyl, unsaturated $C_2$-$C_4$ alkyl, —C(=O)R$^{2B}$, wherein $R^{2B}$ is $C_1$-$C_4$ alkyl; and subscript p is a number ranging from 1 to 8 or subscript p' is an integer ranging from 1 to 8.

50. The Ligand Drug Conjugate composition of embodiment 49 wherein $R^{2A}$ is saturated $C_1$-$C_4$ alkyl or unsaturated $C_3$-$C_4$ alkyl, wherein saturated $C_1$-$C_4$ alkyl is —CH$_3$, —CH$_2$CH$_3$, or —CH$_2$CH$_2$CH$_3$ and unsaturated C$_3$-C$_4$ alkyl is —CH$_2$CH═CH$_2$ or —CH(CH$_3$)CH═CH$_2$.

51. The Ligand Drug Conjugate composition of any one of embodiments 38 to 50 wherein L$_P$ is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration 52. The Ligand Drug Conjugate composition of embodiment 38 wherein the composition is represented by the structure(s) of:

wherein A$_O$ is absent or is an amine-containing acid residue; subscript p is an number ranging from 1 to 8; subscript q is an integer ranging from 1 to 4; subscript u is 0 or 1; subscript v is an integer ranging from 1 to 4; R$^{7B}$, when present, is —OH; X$^{LP}$ is selected from the group consisting of —O—, —NH, —S— and —C(═O)—; and R$^E$ and R$^F$ are independently selected from the group consisting of —H and C$_1$-C$_4$ alkyl.

53. The Ligand Drug Conjugate composition of any one of embodiments 42 to 44 wherein Ligand Drug Conjugate compounds of the composition are independently represented by the structure(s) of:

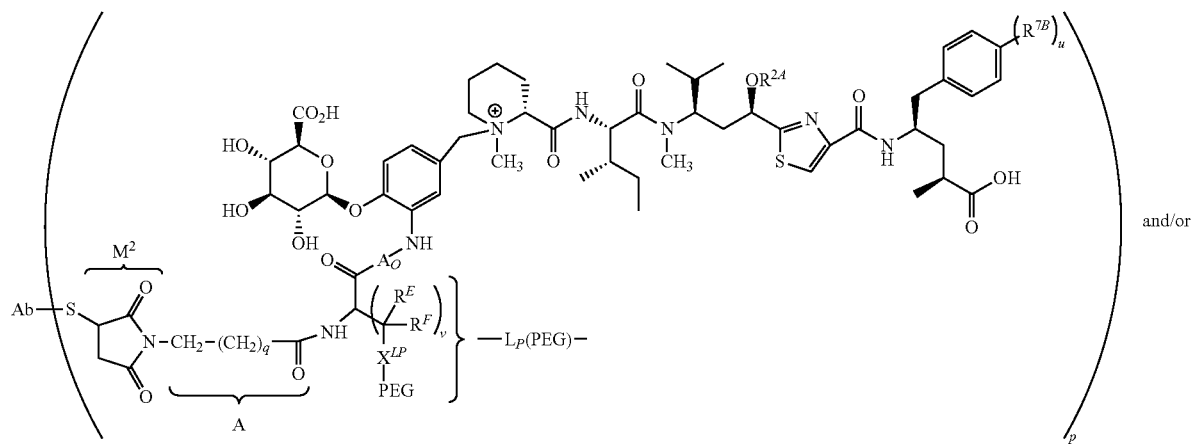

and/or

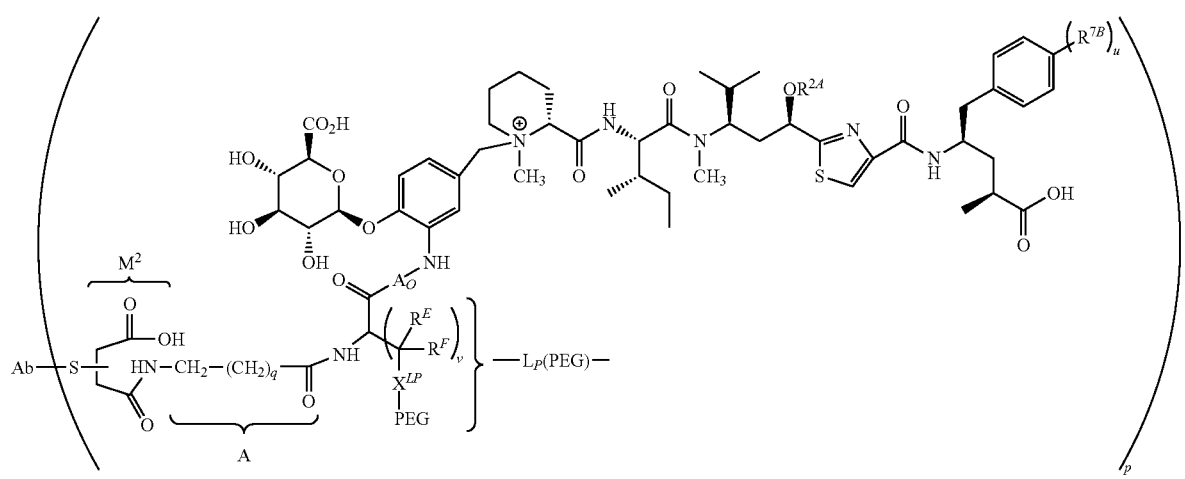

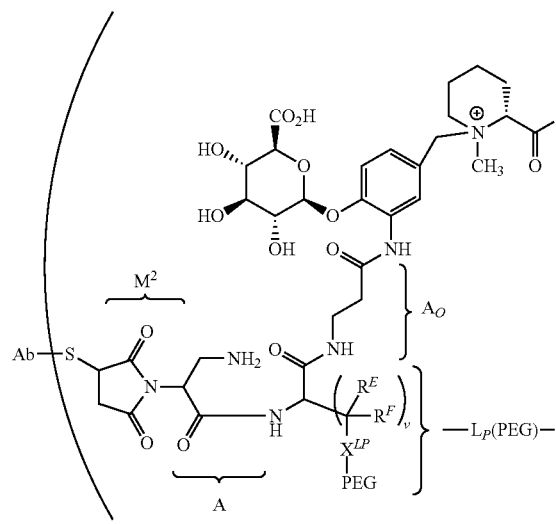

and/or

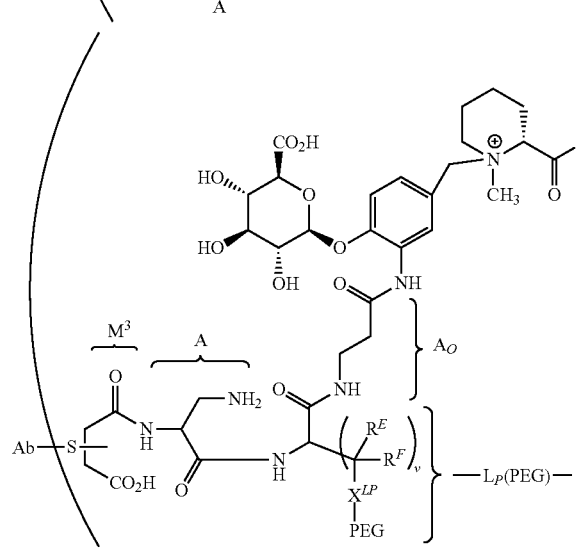

wherein $A_O$ is absent or is an amine-containing acid residue; subscript p' is an integer ranging from 1 to 8; subscript q is an integer ranging from 1 to 4; subscript u is 0 or 1; subscript v is an integer ranging from 1 to 4; $R^{7B}$, when present, is —OH; $X^{LP}$ is selected from the group consisting of —O—, —NH, —S— and —C(=O)—; and $R^E$ and $R^F$ are independently selected from the group consisting of —H, and —$C_1$-$C_4$ alkyl.

54. The Ligand Drug Conjugate composition of any one of embodiments 38 to 48 wherein A is —$CH_2(CH_2)_4$(C=O)— or —$CH_2(CH_2)_4$(C=O)$NHCH_2CH_2$(C=O)—.

55. The Ligand Drug Conjugate composition of any one of embodiments 38 to 49 and 52 to 54 wherein $R^{24}$ is —C(O)$CH_3$.

56. The Ligand Drug Conjugate composition of any one of embodiments 39 to 54 wherein $R^{24}$ is ethyl.

57. The Ligand Drug Conjugate composition of any one of embodiments 38 to 54 wherein $R^{24}$ is —$CH_2CH=CH_2$.

58. The Ligand Drug Conjugate composition of any one of embodiments 38 to 57 wherein $A_O$ is a β-amino acid residue.

59. The Ligand Drug Conjugate composition of any one of embodiments 1 to 58 wherein PEG has the structure selected from the group consisting of:

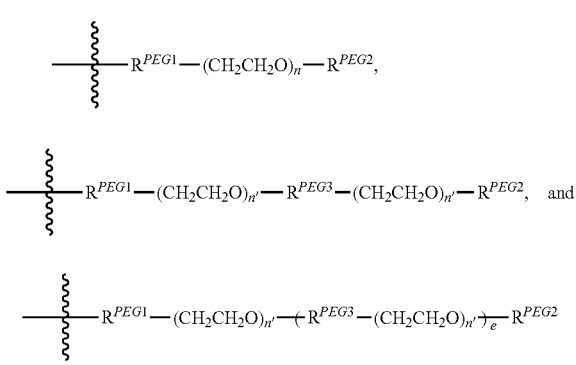

wherein the wavy line indicates site of attachment to $X^{LP}$ of the Parallel Connector Unit ($L_P$); $R^{PEG1}$ is an optional PEG Attachment Unit; $R^{PEG2}$ is a PEG Capping Unit; $R^{PEG3}$ is an PEG Coupling Unit; subscript n ranges from 2 to 72; each subscript n' is independently selected from 1 to 72; and subscript e ranges from 2 to 5.

60. The Ligand Drug Conjugate composition of embodiment 52 or 53 wherein —$X^{LP}$—PEG has the structure of:

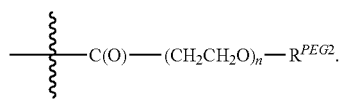

61. The Ligand Drug Conjugate composition of embodiment 60 wherein subscript n is 12 and $R^{PEG2}$ is hydrogen or —$CH_3$.

62. The Ligand Drug Conjugate composition of embodiment 1 wherein Ligand Drug Conjugate compounds of the composition are independently represented by the structure of:

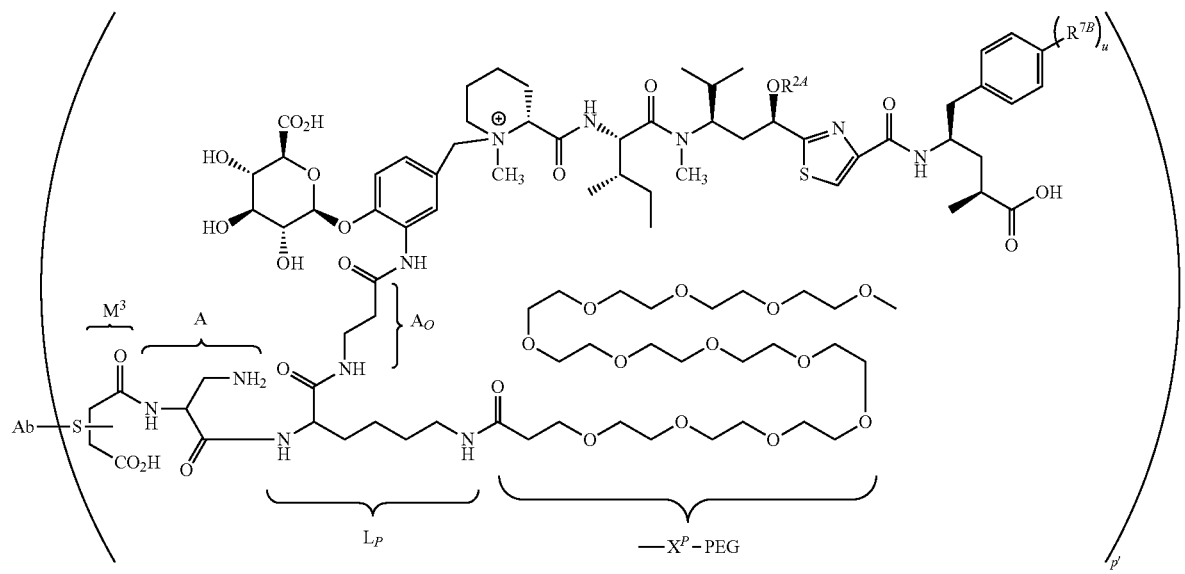

wherein Ab is an antibody Ligand Unit; S is a sulfur atom of the antibody Ligand Unit; the Ab-S— moiety is bonded to the carbon α or β to the indicated $M^3$ carboxylic acid; subscript u is 0 or 1; $R^{7B}$, when present, is —OH; and $R^{24}$ along with the oxygen atom to which it is attached is —OC(O)$CH_3$, —$CH_2CH_3$ or —$CH_2CH=CH_2$.

63. The Ligand Drug Conjugate composition of embodiment 1 wherein Ligand Drug Conjugate compounds of the composition are independently represented by the structure of:

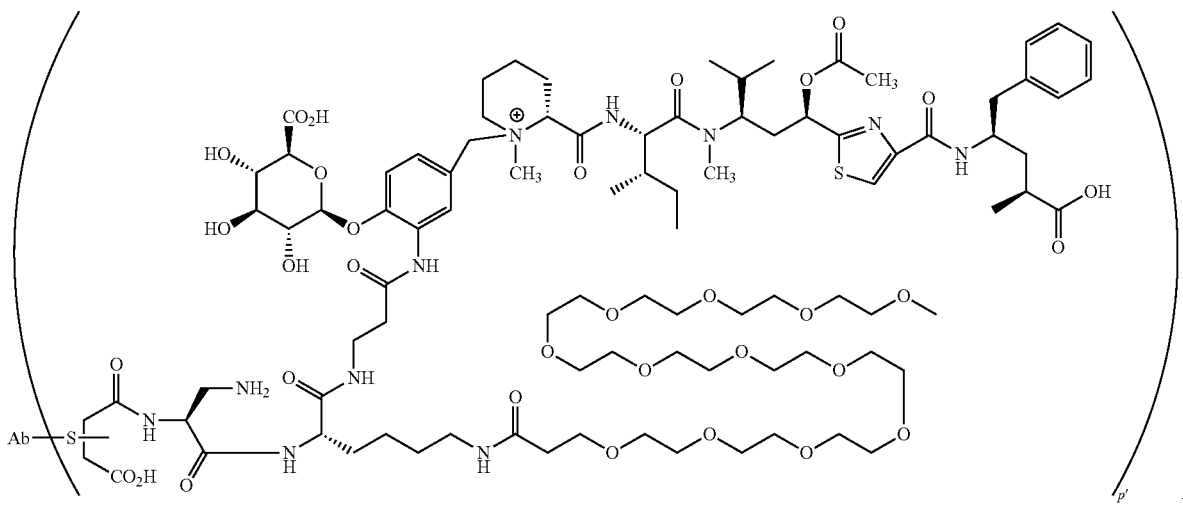

64. A Drug Linker compound, wherein the compound has the structure of Formula I:

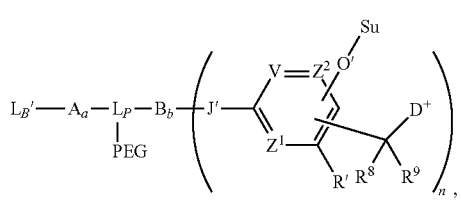

(Formula I)

wherein $L_B'$ is a Ligand Covalent Binding Unit precursor; $L_P$ is a Parallel Connector Unit; PEG is a Polyethylene Glycol Unit; subscripts a and b independently are 0 or 1; subscript n is 1, 2, 3 or 4; A is a first optional Stretcher Unit so that subscript a is 0 when A is absent or 1 when A is present and is optionally comprised of two, three or four subunits; B is an Branching Unit or a second optional Stretcher Unit ($A_O$) so that subscript b is 0 when B is absent or 1 when B is present and is optionally comprised of two, three or four other subunits, wherein subscript b is 1 and B is a Branching when subscript n is 2, 3 or 4, or subscript b is 0, or subscript b is 1 so that B is $A_O$, when subscript and is 1; Su is a carbohydrate moiety; —O'— represents an oxygen atom of an O-glycosidic bond cleavable by a glycosidase; -J'- represents a heteroatom, optionally substituted when nitrogen, preferably —NH—, or a nitrogen atom substituted by an optionally substituted alkyl, or an optionally substituted (heteroaryl)arylalkyl, from a functional group of B, when B is present, or from $L_P$, when B is absent; V, $Z^1$, $Z^2$ and $Z^3$ are =N— or =C($R^{24}$)—, wherein $R^{24}$ is hydrogen or alkyl, alkenyl or alkynyl, optionally substituted, or halogen, —$NO_2$, —CN or other electron withdrawing group, an electron donating group, —O'-Su, or —C($R^8$)($R^9$)-$D^+$, wherein at least at least two of V, Z, $Z^2$ and $Z^3$ are =C($R^{24}$)—, provided, one any only one $R^{24}$ is —C($R^8$)($R^9$)-$D^+$ so that —C($R^8$)($R^9$)-$D^+$ is bonded to one of V, Z, Z, $Z^3$ when that variable group is =C($R^{24}$)— and one and only one other $R^{24}$ is so that —O'-Su is bonded to another one of V, $Z^1$, $Z^2$, $Z^3$ when that variable group is =C($R^{24}$)—, and the —O'Su and —C($R^8$)($R^9$)-$D^+$ substituents are ortho or para to each other; $R^8$ and $R^9$ independently are hydrogen, alkyl, alkenyl or alkynyl, optionally substituted, or aryl or heteroaryl, optionally substituted; R' is hydrogen or is halogen, —$NO_2$, —CN or other electron withdrawing group; $D^+$ is a quaternized tubulysin Drug Unit; and wherein said glycosidase cleavage results in release of tubulysin compound (D) from a Ligand Drug Conjugate compound prepared from the Linker Drug compound.

65. The Drug-Linker compound of embodiment 65 wherein $L_B'$- has a structure selected from the group consisting of:

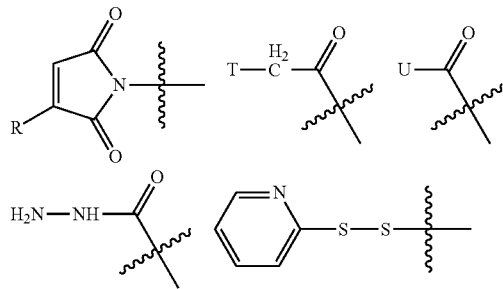

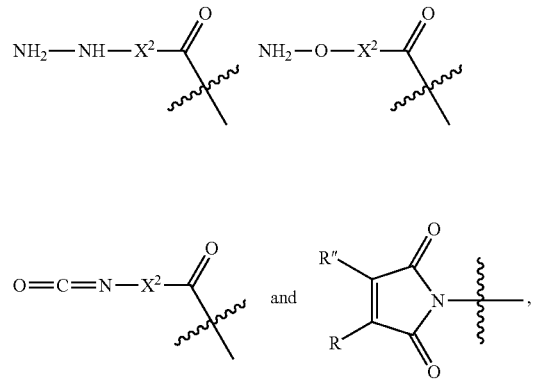

wherein R is hydrogen or $C_1$-$C_6$ optionally substituted alkyl; R" is hydrogen or halogen or R and R' are independently selected halogen; T is —Cl, —Br, —I, —O-mesyl or —O— tosyl or other sulfonate leaving group; U is —F, —Cl, —Br, —I, —O—N-succinimide, —O-(4-nitrophenyl), —O-pentafluorophenyl, —O-tetrafluorophenyl or —O—C(=O)—$OR^{57}$; and $X^2$ is $C_1$-$C_{10}$ alkylene, $C_3$-$C_8$-carbocycle, —O—($C_1$-$C_6$ alkyl), -arylene-, $C_1$-$C_{10}$ alkylene-arylene, -arylene-$C_1$-$C_{10}$ alkylene, —$C_1$-$C_{10}$ alkylene-($C_3$-$C_6$-carbocycle)-, —($C_3$-$C_8$ carbocycle)-$C_1$-$C_{10}$ alkylene-, $C_3$-$C_8$-heterocycle, —$C_1$-$C_{10}$ alkylene-($C_3$-$C_8$ heterocyclo)-, —$C_3$-$C_8$-heterocyclo)-$C_1$-$C_{10}$ alkylene, —($CH_2CH_2O)_u$, or —$CH_2CH_2O)_u$—$CH_2$—, wherein subscript u is an integer ranging from 1 to 10 and $R^{57}$ is $C_1$-$C_6$ alkyl or aryl.

66. The Drug-Linker compound of embodiment 64 or 65 wherein -$D^+$ is a quaternized tubulysin compound preferably having the structure of:

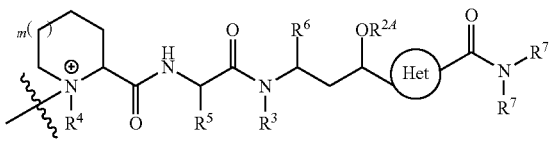

wherein the circle represents an 5-membered nitrogen-heteroarylene and wherein the indicated required substituents to that heteroarylene are in a 1,3-relationship with each other with optional substitution at the remaining positions; subscript m is 0 or 1; $R^{2A}$ is hydrogen or optionally substituted alkyl or $R^{2A}$ along with the oxygen atom to which it is attached defines an O-linked substituent other than —OH; $R^3$ is hydrogen or optionally substituted alkyl; $R^4$, $R^5$ and $R^6$ are optionally substituted alkyl; one $R^7$ is an optionally substituted alkyl, an optionally substituted arylalkyl, optionally substituted heteroarylalkyl and the other $R^7$ is hydrogen or an optionally substituted alkyl; and $R^{8A}$ is hydrogen or optionally substituted alkyl, wherein the wavy line indicates covalent bonding of $D^+$ to the remainder of the Drug Linker compound structure and wherein optionally substituted alkyl are independently selected.

67. The Drug-Linker compound of embodiment 66 wherein the compound has the structure of one of Formula IIA-IIF:

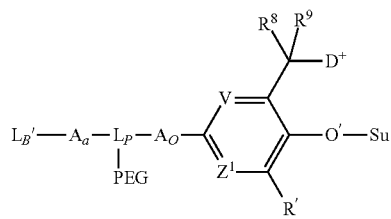
(Formula IIA)

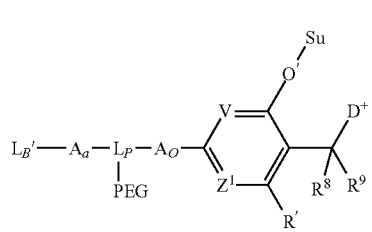
(Formula IIB)

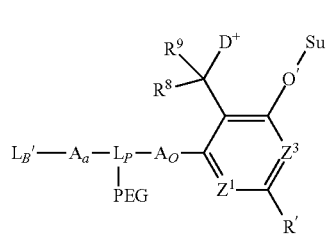
(Formula IIC)

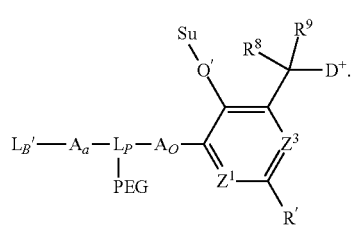
(Formula IID)

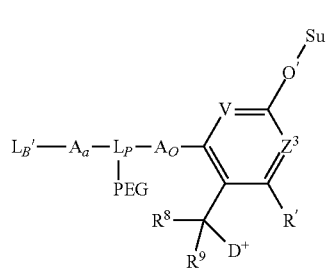
(Formula IIE)

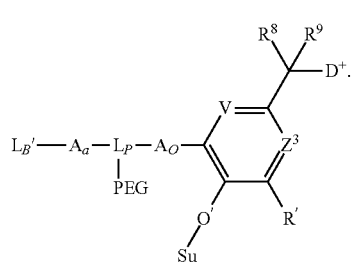
(Formula IIF)

68. The Drug-Linker compound of any one of embodiments 64 to 67 wherein —O'-Su has the structure of Formula III:

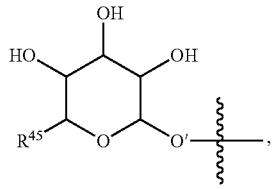
(Formula 3)

wherein the wavy line represents covalent bonding of O' to the remainder of the Drug Linker compound; and $R^{45}$ is —$CH_2OH$ or —$CO_2H$.

69. The Drug-Linker compound of embodiment 68 wherein the compound has the structure of Formula IV:

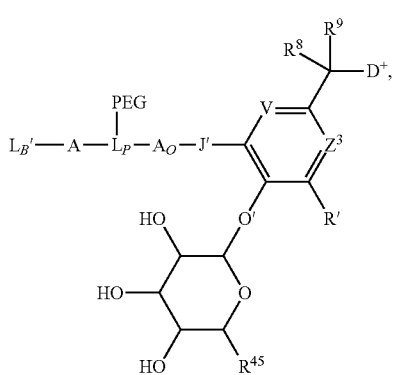
(Formula IV)

wherein J' is —$N(R^{33})$—, wherein $R^{33}$ is hydrogen or methyl; V and $Z^3$ independently are =CH— or =N—; R' is hydrogen or an electron withdrawing group; $R^8$ is hydrogen; $R^9$ is hydrogen, optionally substituted $C_1$-$C_6$ alkyl or optionally substituted phenyl; and $R^{45}$ is —$CO_2H$.

70. The Drug-Linker compound of embodiment 64 wherein a is 1; and $L_B$'-A- of Formula I has the structure of Formula V:

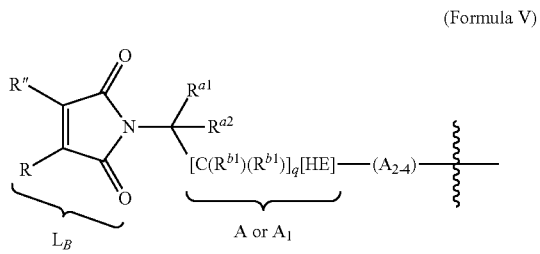
(Formula V)

wherein the —$[C(R^{b1})(R^{b1})]_q$—[HE]- moiety is A or $A_1$, wherein $A_1$ is a subunit of A; $A_{2-4}$ are optional subunits of A; R is hydrogen, chloro or $C_1$-$C_4$ alkyl; R" is hydrogen or chloro; $R^{a1}$ is hydrogen, optionally substituted alkyl or a Basic Unit (BU), optionally protected; and $R^{a2}$ is hydrogen or optionally substituted alkyl, or $R^{a1}$ and $R^{a2}$ together with the carbon atom to which they are attached defines a substituted or unsubstituted nitrogen-containing heterocycloalkyl; HE is an optional Hydrolysis Enhancer (HE) Unit;

subscript q is an integer ranging from 0 to 6; each $R^{b1}$ independently is hydrogen, optionally substituted $C_1$-$C_6$ alkyl, optionally substituted aryl or optionally substituted heteroaryl, or two $R^{b1}$ together with the carbon(s) to which they are attached comprise or preferably define, a substituted or unsubstituted $C_3$-$C_6$ cycloalkyl or one $R^{b1}$ and HE together with the carbon to which they are attached define a substituted or unsubstituted 5 or 6-membered cycloalkyl or a substituted or unsubstituted 5- or 6-membered heterocycloalkyl and the other $R^{b1}$ is hydrogen, optionally substituted $C_1$-$C_6$ alkyl, optionally substituted aryl or optionally substituted heteroaryl; BU, optionally protected, has the structure of —[C($R^1$)($R^1$)]—[C($R^2$)($R^2$)]r-N($R^{22}$)($R^{23}$), or an acid addition salt thereof, wherein subscript r is 0, 1, 2 or 3; each $R^1$ independently is hydrogen or lower alkyl or two $R^1$ together with the carbon to which they are attached comprise, or preferably define, a substituted or unsubstituted $C_3$-$C_6$ cycloalkyl, and each $R^2$ independently is hydrogen, optionally substituted $C_1$-$C_6$ alkyl, optionally substituted aryl or optionally substituted heteroaryl, or two $R^2$ together with the carbon(s) to which they are attached and any intervening carbons define a substituted or unsubstituted $C_3$-$C_6$ cycloalkyl, or one $R^1$ and one $R^2$ together with the carbons to which they are attached and any intervening carbons define a substituted or unsubstituted 5- or 6-membered cycloalkyl, and the remaining $R^1$ and $R^2$ are as defined; and $R^{22}$ and $R^{23}$ independently, hydrogen, optionally substituted $C_1$-$C_6$ alkyl, or an acid-labile protecting group, or together with the nitrogen to which they are attached define a substituted or unsubstituted 5- or 6-membered heterocycloalkyl, one of $R^{22}$, $R^{23}$ is hydrogen and the other is an acid labile protecting group.

71. The Drug Linker compound of embodiment 70 wherein Formula V has the structure of Formula VA:

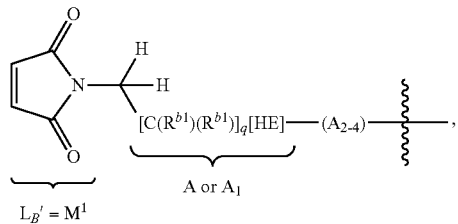

(Formula VA)

wherein subscript q is an integer ranging from 0 to 4.

72. The Drug Linker compound of embodiment 70 wherein Formula V has the structure of Formula VB:

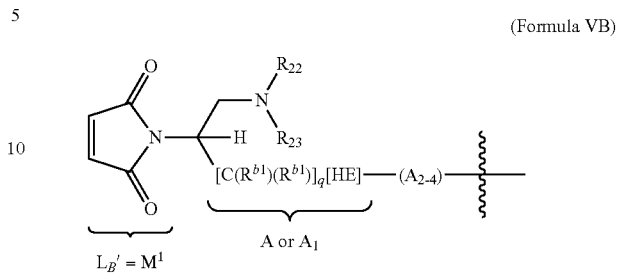

(Formula VB)

wherein one of $R^{22}$, $R^{23}$ is hydrogen and the other is an acid labile carbamate protecting group; and subscript q is an integer ranging from 0 to 4.

73. The Drug Linker compound of embodiment 71 or 72 wherein Formula VA or Formula VB has the structure of:

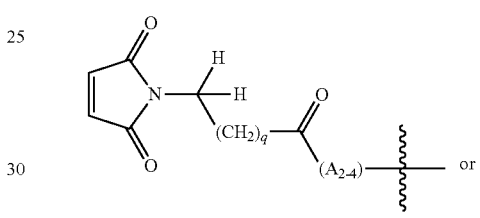

or

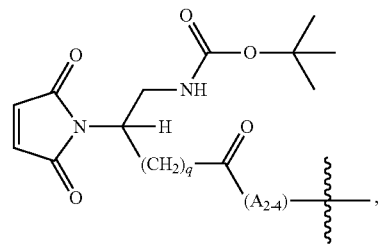

respectively.

74. The Drug Linker compound of embodiment 70 wherein the compound has the structure of Formula VI:

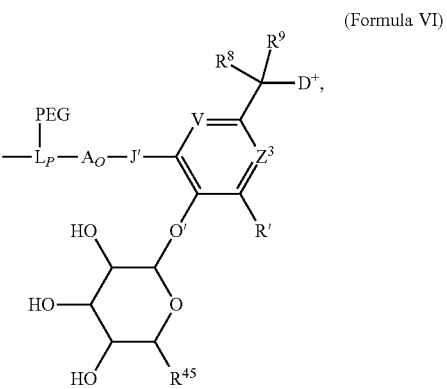

(Formula VI)

wherein the asterisk (*) designates chirality or absence thereof at the indicated carbon; $A_{2-4}$ are independently selected optional subunits of A, wherein —[C($R^{b1}$)($R^{b1}$)]$_q$—[HE]- is $A_1$ when one or more such subunits are present; one of R and R" is hydrogen and the other is hydrogen or chloro; R' is hydrogen or an electron withdrawing group; $R^{a1}$ is hydrogen or a basic unit (BU), optionally protected, having the structure of —$CH_2$—N($R^{22}$)($R^{23}$), or an acid addition salt thereof, wherein $R^{22}$ and $R^{23}$ independently are hydrogen, methyl or ethyl or both together with the nitrogen atom to which they are attached comprise a substituted or unsubstituted 5- or 6-membered heterocycloalkyl, or one of $R^{22}$, $R^{23}$ is hydrogen and the other is an acid labile carbamate protecting group; $R^{a2}$ is hydrogen; subscript q is an integer ranging from 0 to 5 when HE is present or 1 to 5 when HE is absent; each $R^{b1}$ independently is hydrogen or optionally substituted $C_1$-$C_6$ alkyl; HE is absent or is —C(=O)—; $R^{45}$ is —$CO_2H$; J' is —NH—; V and $Z^3$ are =$CH_2$—; $R^8$ is hydrogen; and $R^9$ is hydrogen or methyl.

75. The Drug Linker compound of embodiment 74 wherein the indicated starred (*) carbon is predominantly in the same absolute configuration as the alpha carbon of an L-amino acid when that indicated carbon is chiral.

76. The Drug Linker compound of any one of embodiments 67 to 69 wherein A and $A_O$, when present, independently has the structure of Formula 7 or Formula 8, or any one of embodiments 68 to 73, wherein each of $A_2$-4, when present, independently has the structure of Formula 7 or Formula 8:

(Formula 7)

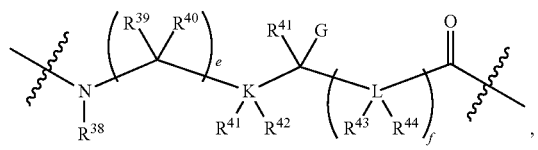

(Formula 8)

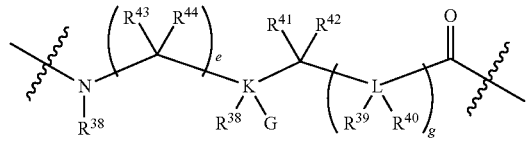

wherein the wavy line indicates covalent bonding of the Formula 7 or Formula 8 structure within the Drug Linker structure; wherein K and L independently are C, N, O or S, provided that when K or L is O or S, $R^{41}$ and $R^{42}$ to K or $R^{43}$ and $R^{44}$ to L are absent, and when K or L are N, one of $R^{41}$, $R^{42}$ to K or one of $R^{43}$, $R^{44}$ to L are absent, and provided that no two adjacent L are independently selected as N, O, or S; wherein subscript s is an integer ranging from 0 to 12, and subscript t is an integer ranging from 1 to 12; wherein G is hydrogen, optionally substituted $C_1$-$C_6$ alkyl, —OH, —$OR^G$, —$CO_2H$, $CO_2R^G$, wherein $R^G$ is $C_1$-$C_6$ alkyl, aryl or heteroaryl, optionally substituted, or $R^{PR}$ wherein $R^{PR}$ is a suitable protecting group, —$NH_2$, or —N($R^G$)($R^{PG}$), wherein $R^G$ independently selected is as previously defined or both $R^G$ together with the nitrogen to which they are attached comprise, or preferably define, a substituted or unsubstituted 5- or 6-membered heterocycloalkyl or both $R^{PR}$ together form a suitable protecting group; wherein $R^{38}$ is hydrogen or optionally substituted $C_1$-$C_6$ alkyl; $R^{39}$-$R^{44}$ independently are hydrogen, optionally substituted $C_1$-$C_6$ alkyl, optionally substituted, or optionally substituted heteroaryl, or both $R^{39}$, $R^{40}$ together with the carbon to which they are attached comprise, or preferably define, a substituted or unsubstituted $C_3$-$C_6$ cycloalkyl, or $R^{41}$, $R^{42}$ together with K to which they are attached when K is C, or $R^{43}$, $R^{44}$ together with L to which they are attached when L is C, comprise, or preferably define a substituted or unsubstituted $C_3$-$C_6$ cycloalkyl, or $R^{40}$ and $R^{41}$, or $R^{40}$ and $R^{43}$, or $R^{41}$ and $R^{43}$ to together with the carbon or heteroatom to which they are attached and atoms intervening between those carbon and/or heteroatoms comprise, or preferably define, a substituted or unsubstituted 5- or 6-membered cycloalkyl or heterocycloalkyl, or wherein $A_O$ is an alpha-amino, beta-amino or another amine-containing acid residue.

77. The Drug Linker compound of any one of embodiments 64 to 76 wherein -$D^+$ is a quaternized tubulysin compound preferably having the structure of:

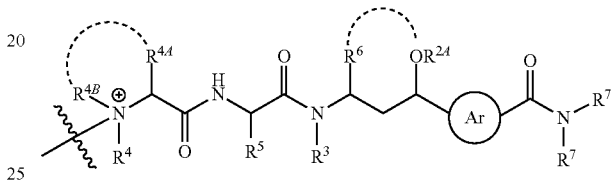

wherein the dashed curved lines indicate optional cyclizations; $R^{24}$ is hydrogen or optionally substituted alkyl, or $R^{24}$ is hydrogen or optionally substituted alkyl, or $R^{24}$ along with the oxygen atom to which it is attached defines an O-linked substituent other than —OH, or $R^{24}$ is absent when $R^6$ is bonded to that oxygen atom, as indicated by the curved dash line between $R^6$ and the oxygen atom, to define a substituted or unsubstituted oxygen-containing heterocycloalkyl; the circled Ar represents a 5-membered nitrogen-heteroaryl, wherein the indicated required substituents to that heteroaryl are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{24}$ moiety in which $R^{24}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached, as indicated by the curved dashed line between $R^{4A}$ and $R^{4B}$, define a substituted or unsubstituted quaternized nitrogen heterocycloalkyl; one $R^7$ is hydrogen or optionally substituted alkyl and the other $R^7$ is optionally substituted aralkyl or heteroaralkyl; wherein the wavy line indicates covalent bonding of the $D^+$ structure to the remainder of the Drug Linker structure.

78. The Drug Linker compound of embodiment 77 wherein the quaternized tubulysin Drug Unit (-$D^+$) has the structure of:

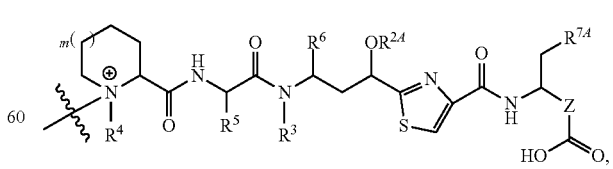

subscript m is 0 or 1, preferably 1; Z is an optionally substituted alkylene or an optionally substituted alkenylene; and $R^{7A}$ is optionally substituted aryl or optionally substituted heteroaryl.

79. The Drug Linker compound of embodiment 78 wherein the quaternized tubulysin Drug Unit (-D⁺) has the structure of:

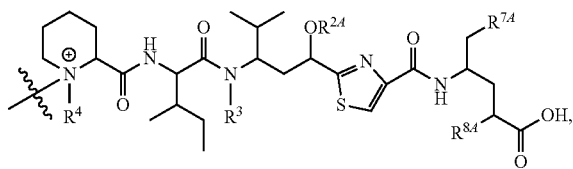

wherein $R^{7A}$ is optionally substituted phenyl and $R^8$ is hydrogen or methyl.

80. The Drug Linker compound of embodiment 78 wherein the quaternized tubulysin Drug Unit (-D⁺) has the structure of:

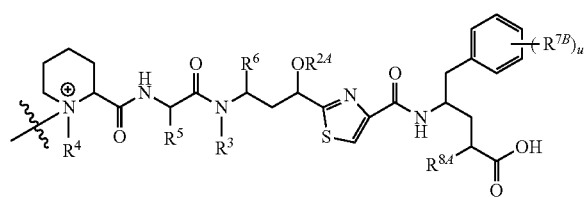

wherein $R^5$ and $R^6$ are alkyl side chain residues of natural hydrophobic amino acids, independently selected; subscript u, indicating the number of $R^{7B}$ substituents, is 0, 1, 2 or 3; each $R^{7B}$, when present, is an independently selected O-linked substituent; and $R^{8A}$ is hydrogen or optionally substituted alkyl.

81. The Drug Linker compound of embodiment 79 wherein the quaternized tubulysin Drug Unit (-D⁺) has the structure of:

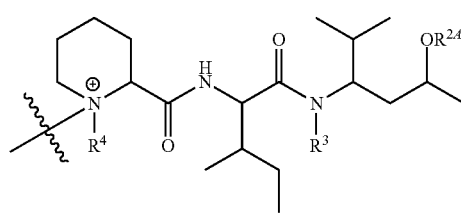

wherein $R^4$ is methyl; subscript u is 0, 1 or 2; $R^3$ is H, methyl, ethyl, propyl, —CH₂—OC(O)$R^{3A}$, —CH₂CH($R^{3B}$)C(O)$R^{3A}$ or —CH($R^{3B}$)C(O)NH$R^{3A}$, wherein $R^{3A}$ is C₁-C₆ alkyl and $R^{3B}$ is H or C₁-C₆ alkyl, independently selected from $R^{3A}$; $R^{2A}$ along with the oxygen atom to which it is attached is an O-linked substituent selected from the group consisting of —OCH₂OCH₂$R^{2B}$, —OCH₂$R^{2B}$, —OC(O)$R^{2B}$, —CH₂OC(O)$R^{2B}$, —OC(O)N($R^{2B}$)($R^{2C}$), and —OCH₂C(O)N($R^{2B}$)($R^{2C}$), wherein $R^{2B}$ and $R^{2C}$ are independently selected from the group consisting of H, C₁-C₆ alkyl and C₂-C₆ alkenyl; and each $R^{7B}$, when present, independently is —OH or —OCH₃.

82. The Drug Linker compound of embodiment 77 wherein the quaternized tubulysin Drug Unit (-D⁺) has the structure of:

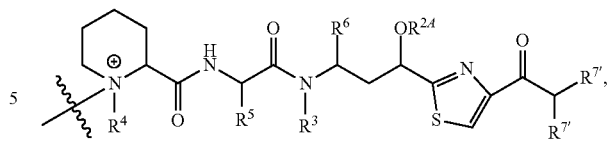

wherein $R^{2A}$ is hydrogen, an optionally substituted alkyl, saturated or unsaturated, or $R^2$ along with the oxygen atom to which it is attached defines an O-linked substituent other than —OH; $R^3$ is optionally substituted C₁-C₆ alkyl; $R^4$ is methyl; $R^5$ and $R^6$ are alkyl side chain residues of natural hydrophobic amino acids; and the —N($R^{7'}$)($R^{7'}$) moiety is —NH(C₁-C₆ alkyl), optionally substituted by —CO₂H, or an ester thereof, or by an optionally substituted phenyl, or is —N(C₁-C₆ alkyl)₂, wherein one and only one C₁-C₆ alkyl is optionally substituted by —CO₂H, or an ester thereof, or by an optionally substituted phenyl.

83. The Drug Linker compound of embodiment 82 wherein the —N($R^{7'}$)($R^{7'}$) moiety is selected from the group consisting of —NH(CH₃), —NHCH₂CH₂Ph, and —NHCH₂—CO₂H, —NHCH₂CH₂CO₂H and —NHCH₂CH₂CH₂CO₂H.

84. The Drug Linker compound of any one of embodiments 78 to 83 wherein $R^{2A}$ is —CH₂CH₃.

85. The Drug Linker compound of any one of embodiments 78 to 83 wherein $R^{2A}$ is —CH₂—CH=CH₂ or —CH₂C(CH₃)=CH₂.

86. The Drug Linker compound of embodiment 81 wherein $R^{2A}$ is —CH₂CH₃ or —CH₂—CH=CH₂, or —CH₂C(CH₃)=CH₂, $R^{2B}$ is —CH₃, $R^3$ is —CH₃ and subscript u is 0.

87. The Drug Linker compound of embodiment 81 wherein $R^{2A}$ is —CH₂CH₃ or —CH₂—CH=CH₂, $R^{2B}$ is —CH₃, $R^3$ is —CH₃ and subscript u is 1, wherein $R^{7B}$ is —OH.

88. The Drug Linker compound of embodiment 81 wherein the quaternized tubulysin Drug Unit (-D⁺) has the structure of:

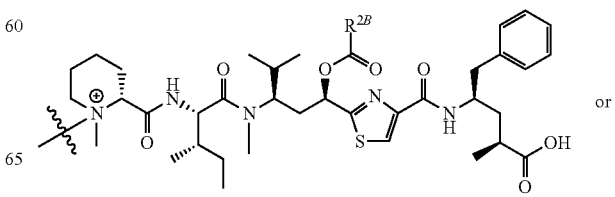

or

-continued

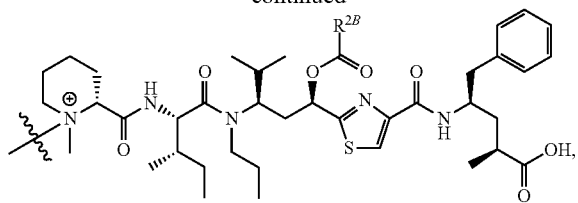

wherein R$^{2B}$ is —CH$_3$, —CH$_2$CH$_3$, —CH$_2$CH$_2$CH$_3$, —CH(CH$_3$)$_2$, —CH$_2$CH(CH$_3$)$_2$, or —CH$_2$C(CH$_3$)$_3$.

89. The Drug Linker compound of embodiment 81 wherein the quaternized tubulysin Drug Unit (-D$^+$) has the structure of:

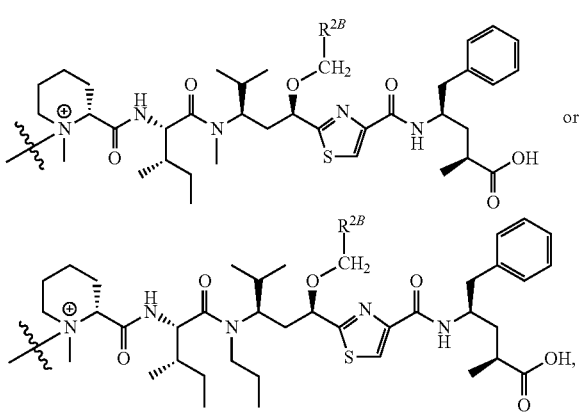

wherein R$^{2B}$ is hydrogen, methyl or —OCH$_3$, or —OCH$_2$R$^{2B}$ is —OCH$_2$CH=CH$_2$ or —OCH$_2$C(CH$_3$)=CH$_2$.

90. The Drug Linker compound of embodiment 81 wherein the quaternized tubulysin Drug Unit (-D$^+$) is that of tubulysin M, the structure of which is:

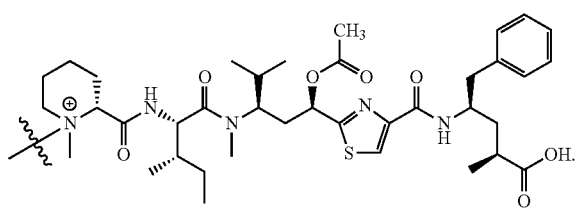

91. The Drug Linker compound of any one of embodiments 70 to 90 wherein L$^P$ is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the sulfur substituent is in reduced or oxidized form.

92. The Drug Linker compound of any one of embodiments 70 to 90 wherein L$^P$ is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

93. The Drug Linker compound of embodiment 91 wherein the aminoalkanedioic acid, diaminoalkanoic acid, sulfur-substituted aminoalkanoic acid or hydroxyl substituted aminoalkanoic acid residue has the structure of Formula A or Formula B:

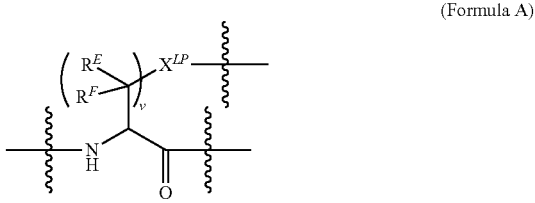
(Formula A)

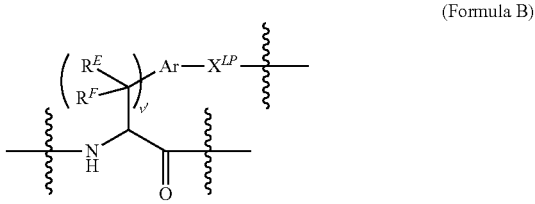
(Formula B)

wherein subscript v is an integer ranging from 1 to 4; subscript v' is an integer ranging from 0 to 4; X$^{LP}$ is selected from the group consisting of —O—, —NR$^{LP}$—, —S—, —S(=O)—, —S(=O)$_2$—, and —C(=O)—, —C(=O)N(R$^{LP}$)—, —N(R$^{LP}$)C(=O)N(R$^{LP}$)—, —N(R$^{LP}$)C(=NR$^{LP}$)N(R$^{LP}$)—, wherein each R$^{LP}$ is independently selected from the group consisting of hydrogen and optionally substituted alkyl or two of R$^{LP}$ together along with intervening atoms define a heterocycloalkyl with any remaining R$^{LP}$ as previously defined; Ar is an arylene or heteroarylene, optionally substituted; each R$^E$ and R$^F$ is independently selected from the group consisting of —H, optionally substituted alkyl, optionally substituted aryl and optionally substituted heteroaryl, or R$^E$ and R$^F$ together with the same carbon to which they are attached, or R$^E$ and R$^F$ from adjacent carbons together with these carbons, define a substituted or unsubstituted cycloalkyl, with any remaining R$^E$ and R$^F$ substituents as previously defined; and wherein the wavy lines indicates covalent attachment of the Formula A or Formula B structure within the Drug Linker compound structure.

94. The Drug Linker compound of embodiment 93 wherein -L$^P$(PEG)- has the structure of Formula A1 or A2:

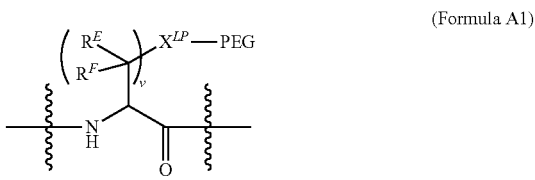
(Formula A1)

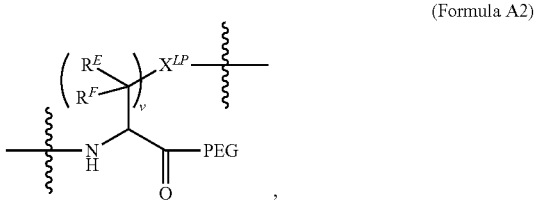
(Formula A2)

wherein X$^{LP}$ is selected from the group consisting of —O—, —NH, —S— and —C(=O)—; R$^E$ and R$^F$ are independently selected from the group consisting of —H and —C$_{1-4}$ alkyl; and wherein the wavy line indicates covalent attachment of Formula A1 or Formula A2 within the Drug Linker compound structure.

95. The Drug Linker compound of embodiment 70 wherein the compound has the structure of:

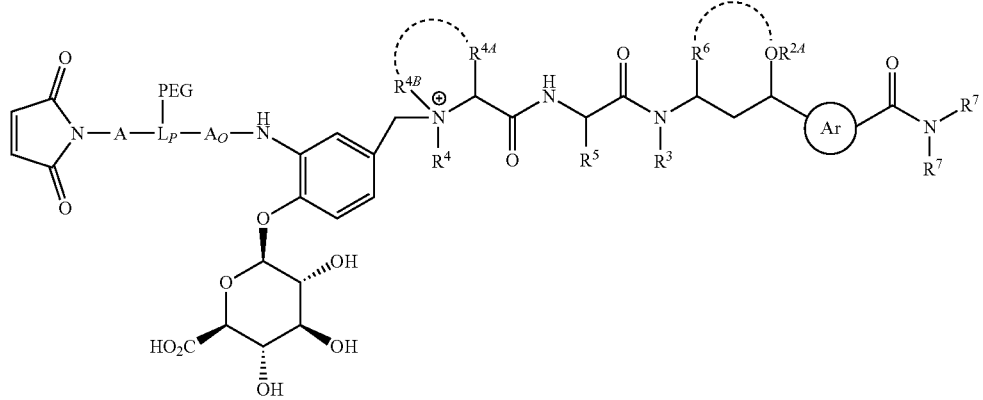

wherein the curved dashed lines indicate optional cyclizations; $R^{2A}$ is hydrogen or optionally substituted alkyl, or $R^{2A}$ is hydrogen or optionally substituted alkyl, or $R^{2A}$ along with the oxygen atom to which it is attached defines an O-linked substituent other than —OH, or $R^{2A}$ is absent when $R^6$ is bonded to that oxygen atom, as indicated by the curved dash line between $R^6$ and the oxygen atom, to define a substituted or unsubstituted oxygen-containing heterocycloalkyl; the circled Ar represents a 5-membered nitrogen-heteroaryl, wherein the indicated required substituents to that heteroaryl are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{2A}$ moiety in which $R^{2A}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached define a substituted or unsubstituted nitrogen quaternized heterocycloalkyl, as indicated by the curved dashed line between $R^{4A}$ and $R^{4B}$; and one $R^7$ is hydrogen or optionally substituted alkyl and the other $R^7$ is optionally substituted aralkyl or heteroaralkyl.

96. The Drug Linker compound of embodiment 95 wherein the compound has the structure of:

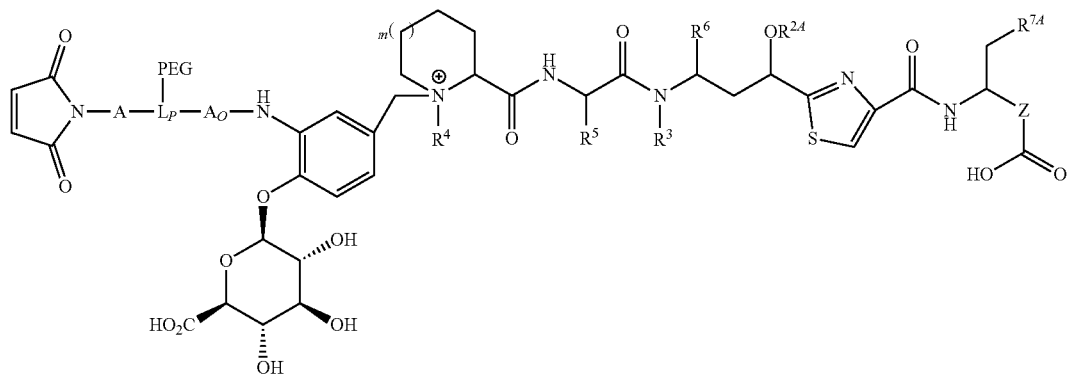

subscript m is 0 or 1, preferably 0; Z is an optionally alkylene or an optionally substituted alkenylene; and $R^{7A}$ is optionally substituted aryl or optionally substituted heteroaryl.

97. The Drug Linker compound of embodiment 96 wherein the compound has the structure of:

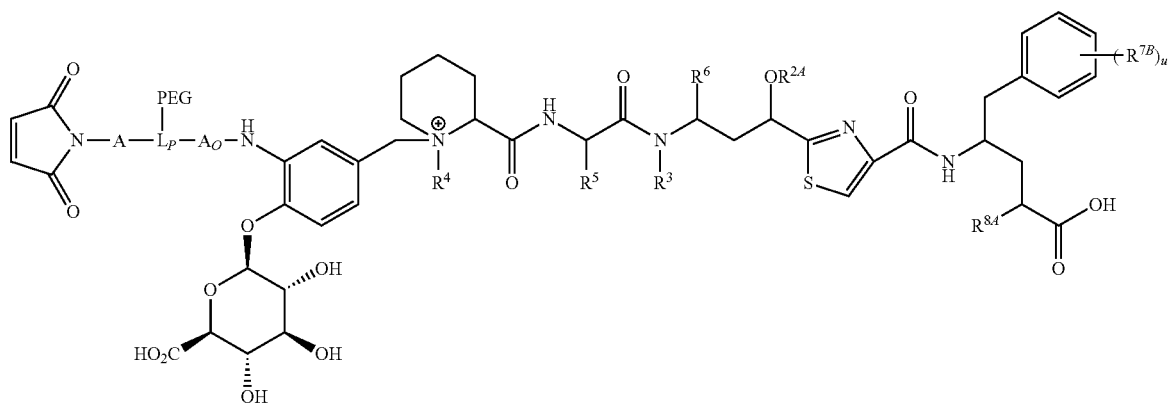

$R^3$ is optionally substituted alkyl; $R^4$ is methyl; $R^5$ and $R^6$ are alkyl side chain residues of natural or un-natural hydrophobic amino acids, preferably of natural hydrophobic amino acids, independently selected; subscript u, indicating the number of $R^{7B}$ substituents, is 0, 1, 2 or 3; wherein each $R^{7B}$, when present, is an independently selected O-linked substituent; and $R^{8A}$ is hydrogen or optionally substituted alkyl.

98. The Drug Linker compound of embodiment 97 wherein compound has the structure of:

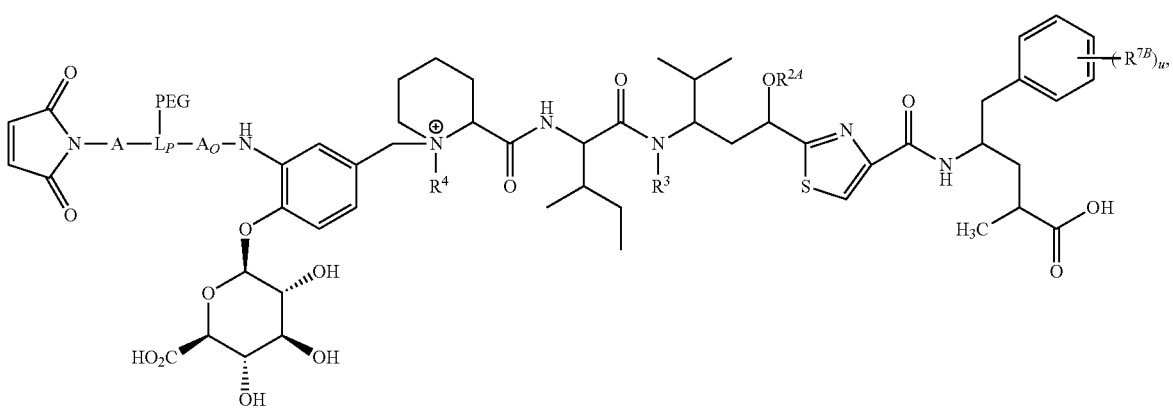

wherein R⁴ is methyl; subscript u is 0, 1 or 2; R³ is H, methyl, ethyl, propyl, —CH₂—OC(O)R³ᴬ, —CH₂CH(R³ᴮ)C(O)R³ᴬ or —CH(R³ᴮ)C(O)NHR³ᴬ, wherein R³ᴬ is C₁-C₆ alkyl and R³ᴮ is H or C₁-C₆ alkyl, independently selected from R³ᴬ; R²ᴬ along with the oxygen atom to which it is attached is an O-linked substituent selected from the group consisting of —OCH₂OCH₂R²ᴮ, —OCH₂R²ᴮ, —OC(O)R²ᴮ, —CH₂OC(O)R²ᴮ, —OC(O)N(R²ᴮ)(R²ᶜ), and —OCH₂C(O)N(R²ᴮ)(R²ᶜ), wherein R²ᴮ and R²ᶜ are independently selected from the group consisting of H, C₁-C₆ alkyl and C₂-C₆ alkenyl; and each R⁷ᴮ, when present, independently is —OH or —OCH₃.

99. The Drug Linker compound of embodiment 70 wherein the compound has the structure of:

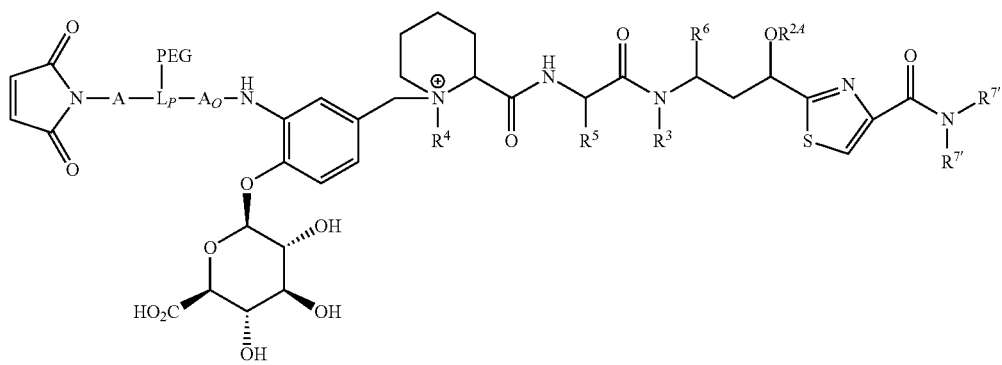

R²ᴬ is hydrogen, an optionally substituted alkyl, saturated or unsaturated, or R² along with the oxygen atom to which it is attached defines an O-linked substituent other than —OH; R³ is optionally substituted C₁-C₆ alkyl; R⁴ is methyl; R⁵ and R⁶ are side chain residues of natural or un-natural hydrophobic amino acids, preferably of natural hydrophobic amino acids, independently selected; and the —N(R⁷')(R⁷') moiety is —NH(C₁-C₆ alkyl), optionally substituted by —CO₂H, or an ester thereof, or by an optionally substituted phenyl, or is —NH(C₁-C₆ alkyl)₂, wherein one and only one C₁-C₆ alkyl is optionally substituted by —CO₂H, or an ester thereof, or by an optionally substituted phenyl.

100. The Drug Linker compound of embodiment 99 wherein the —N(R⁷')(R⁷') moiety is selected from the group consisting of —NH(CH₃), —NHCH₂CH₂Ph, and —NHCH₂—CO₂H, —NHCH₂CH₂CO₂H and —NHCH₂CH₂CH₂CO₂H.

101. The Drug Linker compound of any one of embodiments 98 to 101 wherein R²ᴬ is C₁-C₄ saturated alkyl, C₂-C₄ unsaturated alkyl, —C(=O)R²ᴮ, wherein R²ᴮ is C₁-C₄ alkyl.

102. The Drug Linker compound of embodiment 100 wherein R²ᴬ is saturated C₁-C₄ alkyl or unsaturated C₃-C₄ alkyl, wherein saturated C₁-C₄ alkyl is —CH₃, —CH₂CH₃, or —CH₂CH₂CH₃ and unsaturated C₃-C₄ alkyl is —CH₂CH=CH₂ or —CH(CH₃)CH=CH₂.

103. The Drug Linker compound of any one of embodiments 95 to 102 wherein Lₚ is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

104. The Drug Linker compound of embodiment 64 wherein the compound has the structure of:

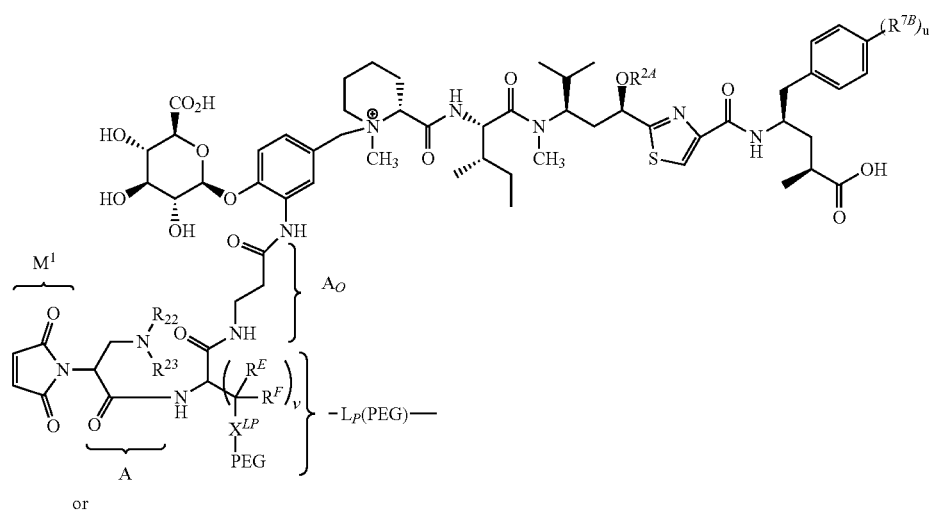

or

-continued

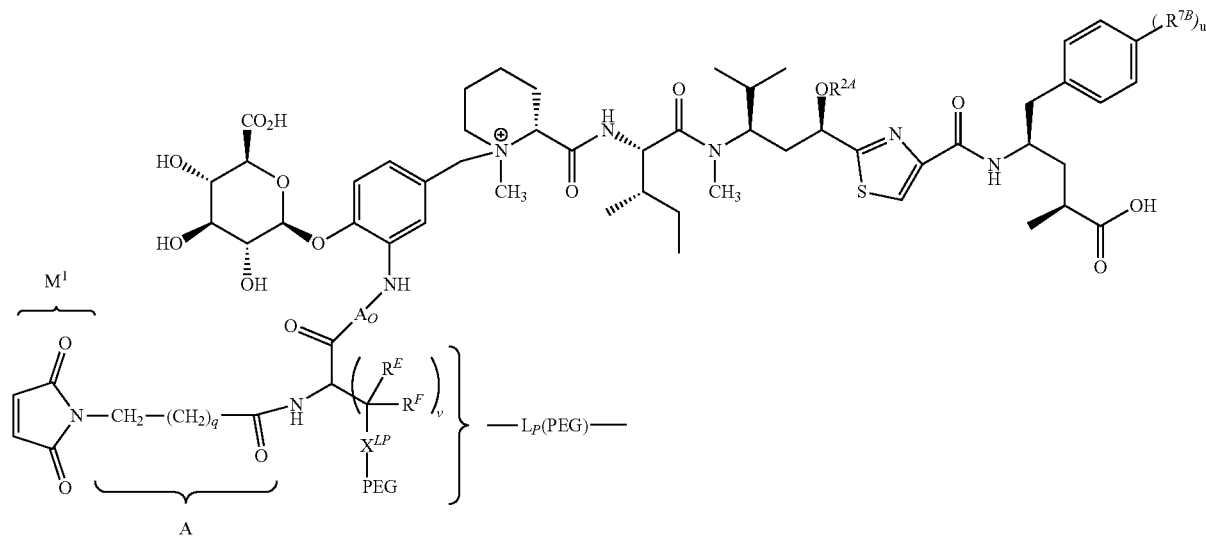

wherein $A_O$ is absent or is an amine-containing acid residue; subscript q is an integer ranging from 1 to 4; subscript u is 0 or 1; subscript v is an integer ranging from 1 to 4; $R^{7B}$, when present, is —OH; $X^{LP}$ is selected from the group consisting of —O—, —NH, —S— and —C(=O)—; $R^E$ and $R^F$ are independently selected from the group consisting of —H, and $C_1$-$C_4$ alkyl; and one of $R^{22}$, $R^{23}$ is hydrogen and the other is an acid labile protecting group or $R^{22}$ and $R^{23}$ are each hydrogen with the nitrogen to which they are attached optionally protonated as an acid addition salt.

105. The Drug Linker compound of any one of embodiments 70 to 103 wherein A is —$CH_2(CH_2)_4(C=O)$— or —$CH_2(CH_2)_4(C=O)NHCH_2CH_2(C=O)$—.

106. The Drug Linker compound of any one of embodiments 95 to 104 wherein $R^{24}$ is —$C(=O)CH_3$.

107. The Drug Linker compound of any one of embodiments 95 to 104 wherein $R^{24}$ is ethyl.

108. The Drug Linker compound of any one of embodiments 95 to 104 wherein $R^{24}$ is —$CH_2CH=CH_2$.

109. The Drug Linker compound of any one of embodiments 95 to 104 wherein $A_O$ is a β-amino acid residue.

110. The Drug Linker compound of any one of embodiments 96 to 109 wherein PEG has the structure selected from the group consisting of:

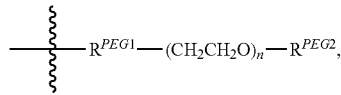

-continued

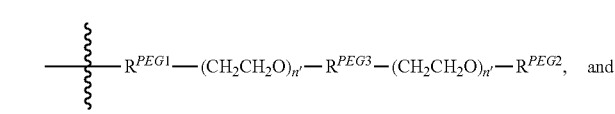

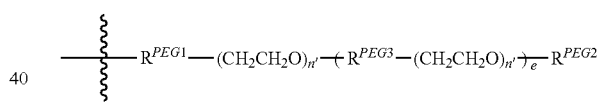

wherein the wavy line indicates site of attachment to $X^{LP}$ of the Parallel Connector Unit ($L_P$); $R^{PEG1}$ is an optional PEG Attachment Unit; $R^{PEG2}$ is a PEG Capping Unit; $R^{PEG3}$ is an PEG Coupling Unit; subscript n ranges from 2 to 72; each subscript n' is independently selected from 1 to 72; and subscript e ranges from 2 to 5.

111. The Drug Linker compound of embodiment 104 wherein —$X^{LP}$—PEG has the structure of:

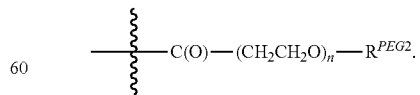

112. The Drug Linker compound of embodiment 111 wherein subscript n is 12 and $R^{PEG2}$ is hydrogen or —$CH_3$.

113. The Drug Linker compound of embodiment 104 wherein the compound has the structure of:

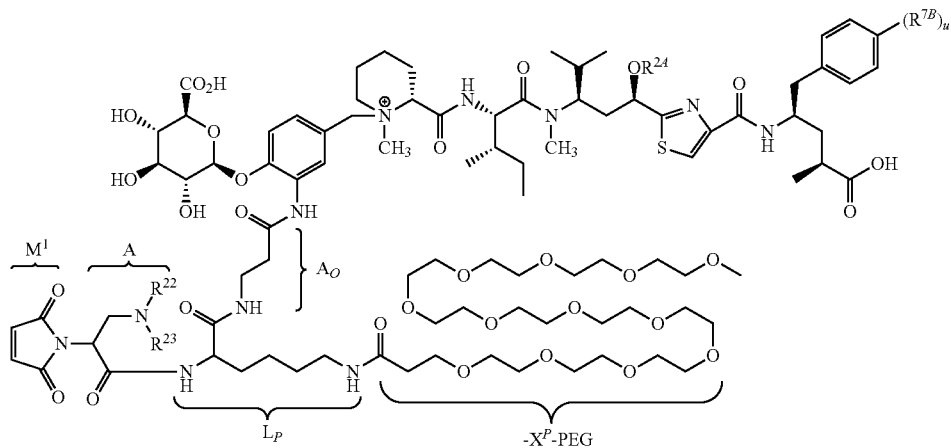

wherein subscript u is 0 or 1; $R^{7B}$, when present, is —OH; $R^{24}$ along with the oxygen atom to which it is attached is —OC(=O)CH$_3$, CH$_2$CH$_3$ or —CH$_2$CH=CH$_2$; and one of $R^{22}$, $R^{23}$ is hydrogen and the other is an acid labile carbamate protecting group or $R^{22}$ and $R^{23}$ are each hydrogen with the nitrogen to which they are attached optionally protonated as an acid addition salt.

114. The Drug Linker compound of embodiment 113 wherein the compound has the structure of:

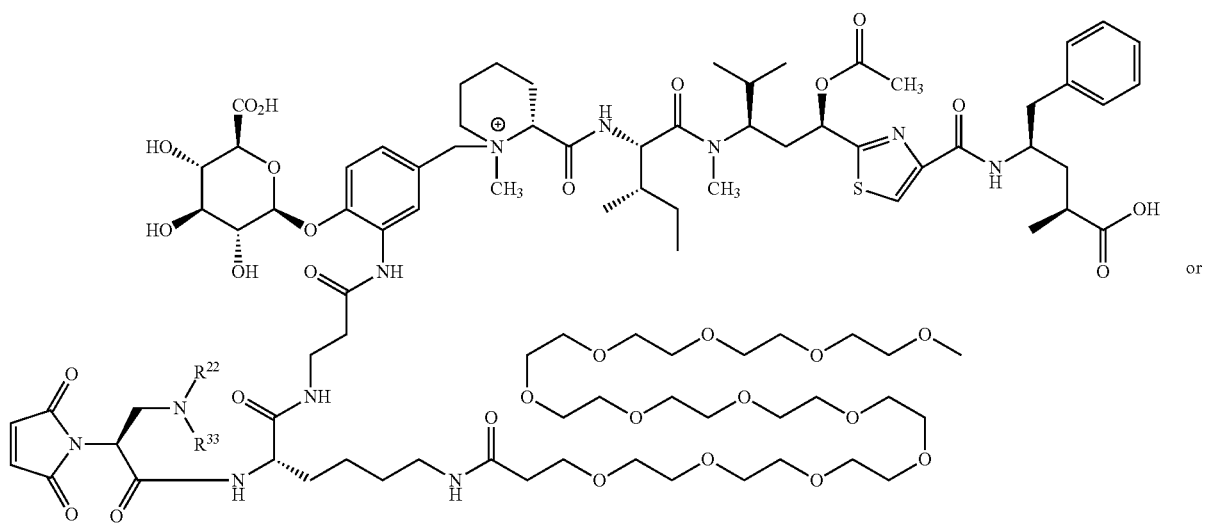

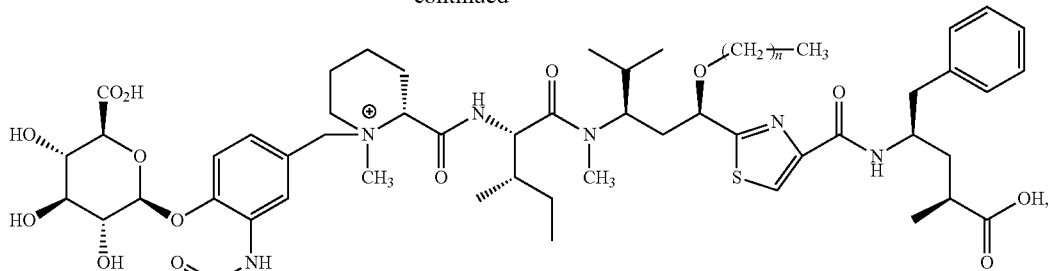

wherein subscript n is 0, 1 or 2.

115. A tubulysin compound having the structure of:

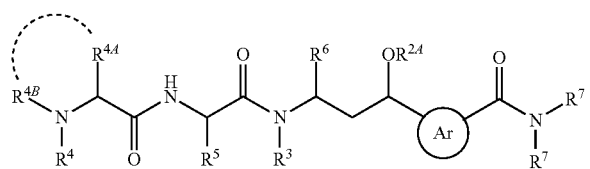

wherein the curved dashed line indicates optional cyclization; $R^{2A}$ is unsaturated alkyl, optionally substituted; the circled Ar represents a 5-membered nitrogen-containing heteroarylene, wherein the indicated required substituents to that heteroarylene are in a 1,3-relationship with each other with optional substitution at the remaining positions; $R^3$ is hydrogen or optionally substituted alkyl; $R^4$, $R^5$ and $R^6$ are optionally substituted alkyl, independently selected; $R^{4a}$ is hydrogen or optionally substituted alkyl and $R^{4B}$ is optionally substituted alkyl, or both together with the nitrogen to which they are attached, as indicated by the curved dashed line, define a substituted or unsubstituted quaternized nitrogen heterocycloalkyl; and one $R^7$ is hydrogen or optionally substituted alkyl and the other $R^7$ is optionally substituted aralkyl or heteroaralkyl.

116. The tubulysin compound of embodiment 115 wherein the compound has the structure of:

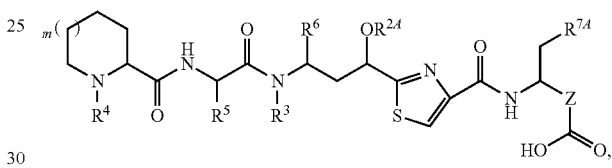

subscript m is 0 or 1; $R^{2A}$ is unsaturated $C_3$-$C_6$ alkyl; Z is an optionally substituted alkylene or an optionally substituted alkenylene; and $R^{7A}$ is optionally substituted aryl or optionally substituted heteroaryl.

117. The tubulysin compound of embodiment 116 wherein the compound has the structure of:

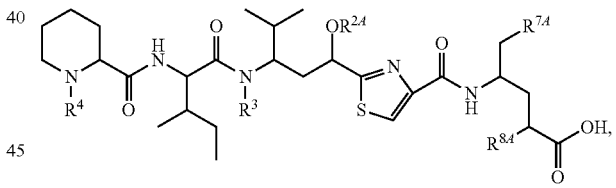

wherein $R^{7A}$ is optionally substituted phenyl and $R^8$ is hydrogen or methyl.

118. The tubulysin compound of embodiment 116 wherein the compound has the structure of:

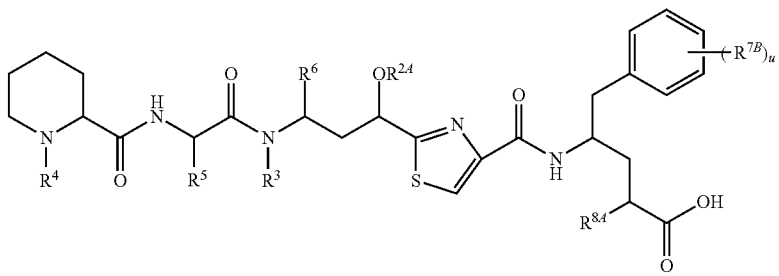

wherein $R^{2A}$ is unsaturated $C_3$-$C_6$ alkyl; $R^5$ and $R^6$ are alkyl side chain residues of natural or un-natural hydrophobic amino acids, preferably of natural hydrophobic amino acids, independently selected; subscript u, indicating the number of $R^{7B}$ substituents, is 0, 1, 2 or 3; each $R^{7B}$, when present, is an independently selected O-linked substituent; and $R^{8A}$ is hydrogen or optionally substituted alkyl.

119. The tubulysin compound of embodiment 117 wherein the compound has the structure of:

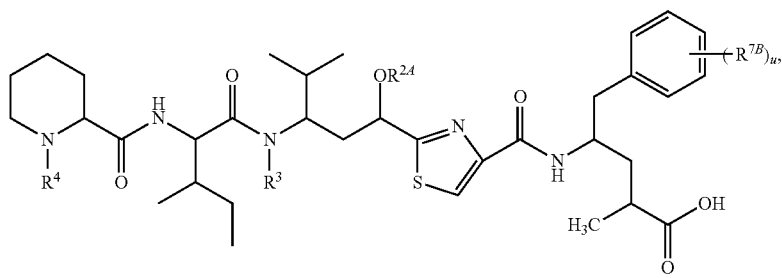

wherein $R^4$ is methyl; subscript u is 0, 1 or 2; $R^3$ is H, methyl, ethyl, propyl, —$CH_2$—OC(O)$R^{3A}$, —$CH_2CH(R^{3B})$C(O)$R^{3A}$ or —CH($R^{3B}$)C(O)NH$R^{3A}$, wherein $R^{3A}$ is $C_1$-$C_6$ alkyl and $R^{3B}$ is H or $C_1$-$C_6$ alkyl, independently selected from $R^{3A}$; and each $R^{7B}$, when present, independently is —OH or —OCH$_3$.

120. The tubulysin compound of embodiment 115 wherein the compound has the structure of:

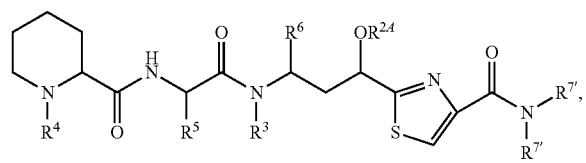

wherein $R^{2A}$ is unsaturated alkyl, optionally substituted; $R^3$ is optionally substituted $C_1$-$C_6$ alkyl; $R^4$ is methyl; $R^5$ and $R^6$ are alkyl side chain residues of natural or un-natural hydrophobic amino acids, preferably of natural amino acids; and the —N($R^{7'}$)($R^{7'}$) moiety is —NH($C_1$-$C_6$ alkyl), optionally substituted by —$CO_2H$, or an ester thereof, or by an optionally substituted phenyl, or is —N($C_1$-$C_6$ alkyl)$_2$, wherein one and only one $C_1$-$C_6$ alkyl is optionally substituted by —$CO_2H$, or an ester thereof, or by an optionally substituted phenyl.

121. The tubulysin compound of embodiment 119 wherein the —N($R^{7'}$)($R^{7'}$) moiety is selected from the group consisting of —NH(CH$_3$), —NHCH$_2$CH$_2$Ph, and —NHCH$_2$—$CO_2$H, —NHCH$_2$CH$_2$CO$_2$H and —NHCH$_2$CH$_2$CH$_2$CO$_2$H.

122. The tubulysin compound of any one of embodiments 115 to 121 wherein $R^{2A}$ is —CH$_2$—CH=CH$_2$.

123. The tubulysin compound of embodiment 115, wherein the compound has the structure of:

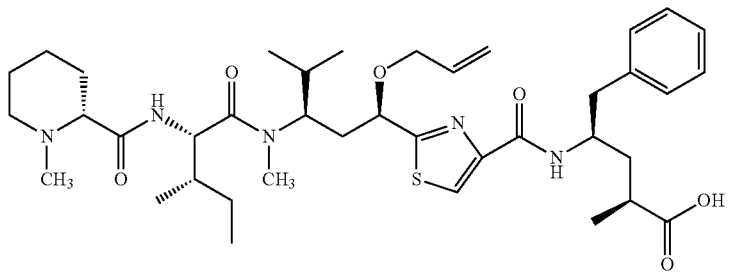

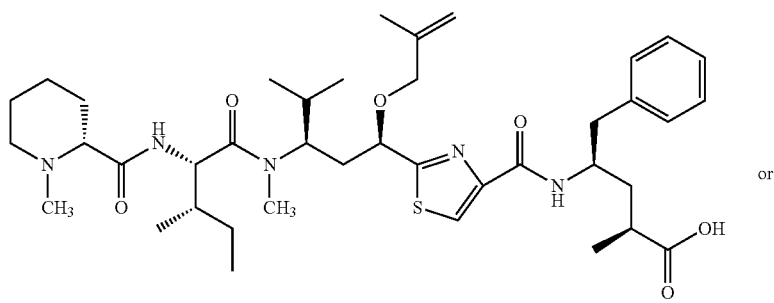
or
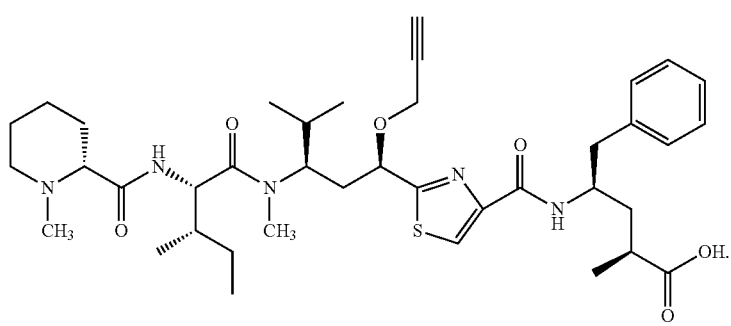
124. A tubulysin compound having the structure of:
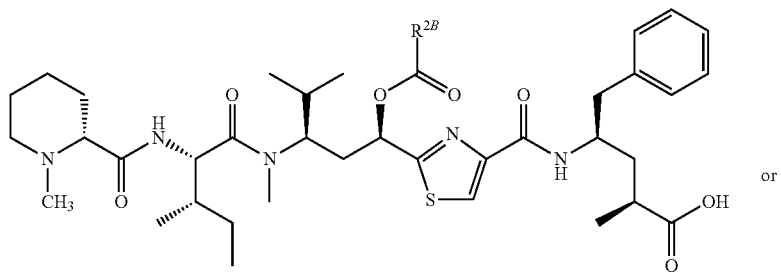
or
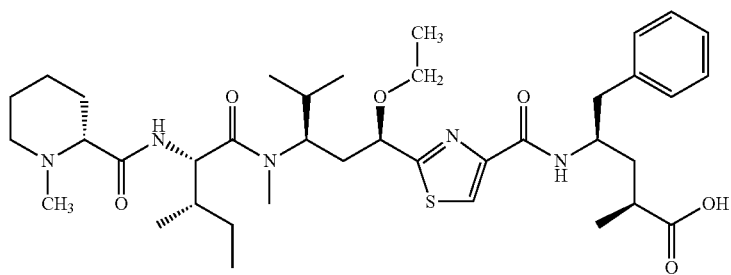

wherein $R^{2B}$ is —CH$_2$CH$_3$, —CH$_2$CH$_2$CH$_3$, —CH(CH$_3$)$_2$, —CH$_2$CH(CH$_3$)$_2$ or —CH$_2$C(CH$_3$)$_3$.

125. A method of preparing a Drug Linker compound comprising the step of quaternizing a tubulysin compound of any one of embodiments 115 to 124 with a Linker Unit precursor.

126. A Ligand Drug Conjugate composition, wherein the composition is represented by the structure of:

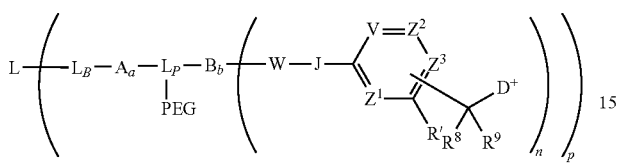

wherein L is a Ligand Unit; $L_B$ is a Ligand Covalent Binding Unit; $L_P$ is a Parallel Connector Unit; PEG is a Polyethylene Glycol Unit; subscripts a and b independently are 0 or 1; subscript n is 1, 2, 3 or 4; A is a first optional Stretcher Unit so that subscript a is 0 when A is absent or 1 when A is present and is optionally comprised of two, three or four independently selected subunits (A$_1$, A$_2$, A$_3$, A$_4$); B is an Branching Unit or a second optional Stretcher Unit (A$_O$) so that subscript b is 0 when B is absent or subscript b is 1 when B is present and is optionally comprised of two, three or four subunits independently of A, wherein subscript b is 1 and B is a Branching when subscript n is 2, 3 or 4, or subscript b is 0, or subscript b is 1 so that B is A$_O$, when subscript n is 1; V, Z$^1$, Z$^2$ and Z$^3$ are =N— or =C(R$^{24}$)—, wherein R$^{24}$ is hydrogen or alkyl, alkenyl or alkynyl, optionally substituted, or halogen, —NO$_2$, —CN or other electron withdrawing group, or —OCH$_3$ or other an electron donating group, or —C(R$^8$)(R$^9$)-D$^+$, wherein at least one of V, Z$^1$, and Z$^3$ is =C(R$^{24}$)—, provided that one any only one R$^{24}$ is —C(R$^8$)(R$^9$)-D$^+$ so that —C(R$^8$)(R$^9$)-D$^+$ is bonded to one of V, Z, and Z$^3$ when that variable group is =C(R$^{24}$)—; R' is hydrogen or —OCH$_3$ or other electron donating group; D$^+$ is a quaternized tubulysin compound; J is a heteroatom, optionally substituted when nitrogen, preferably —NH—, or a nitrogen atom substituted by an optionally substituted alkyl, or an optionally substituted (heteroaryl)arylalkyl; W is a peptide comprised of an amino acid sequence covalently attached to J through an amide bond wherein that amide bond is cleavable by a protease, wherein said protease cleavage initiates release of a tubulysin compound (D) from a Ligand Drug Conjugate compound of the composition; and subscript p is a number ranging from 1 to 24.

127. The Ligand Drug Conjugate composition of embodiment 126, wherein the composition is represented by the structure of:

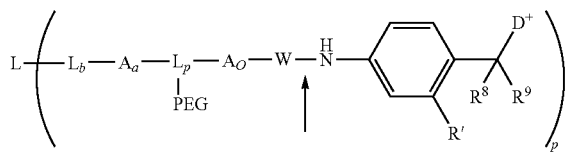

wherein W consists or is comprised of a dipeptide, wherein the dipeptide is at the distal end of W and the indicated bond is an amide bond specifically or preferentially cleavable by an intracellular protease in comparison to freely circulating serum proteases.

128. The Ligand Drug Conjugate composition of embodiment 127, wherein the dipeptide has the structure of;

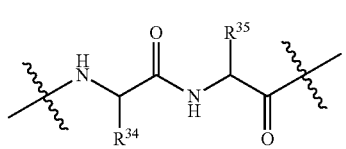

wherein $R^{34}$ is benzyl, methyl, isopropyl, isobutyl, sec-butyl, —CH(OH)CH$_3$ or has the structure of

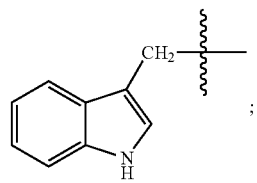 [SMILES: *Cc1c[nH]c2ccccc12]

and $R^{35}$ is methyl, —(CH$_2$)$_4$—NH$_2$, —(CH$_2$)$_3$NH(C=O)NH$_2$, (CH$_2$)$_3$NH(C=NH)NH$_2$, or —(CH$_2$)$_2$CO$_2$H, wherein the wavy line at the dipeptide N-terminus indicates covalent binding to A$_O$ or to L$_P$, depending on the presence or absence of A$_O$, respectively, and the wavy line at the dipeptide C-terminus indicates covalent binding to J.

129. The Ligand Drug Conjugate composition of embodiment 126, 127 or 128 wherein D$^+$ is a tubulysin compound preferably having the structure of:

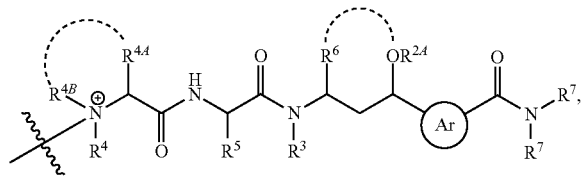

wherein the curved dashed lines indicate optional cyclizations; $R^{24}$ is hydrogen or optionally substituted alkyl, or $R^{24}$ along with the oxygen atom to which it is attached defines an O-linked substituent other than —OH, or $R^{24}$ is absent when $R^6$ is bonded to that oxygen atom, as indicated by the curved dash line between $R^6$ and the oxygen atom, to define a substituted or unsubstituted oxygen-containing heterocycloalkyl; the circled Ar represents a 5-membered nitrogen-heteroaryl, wherein the indicated required substituents to that heteroaryl are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{2A}$ moiety in which $R^{2A}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached, as indicated by the curved dotted line between $R^{4A}$ and $R^{4B}$, define a substituted or unsubstituted quaternized nitrogen heterocycloalkyl; one $R^7$ is hydrogen or optionally substituted alkyl and the other $R^7$ is optionally substituted aralkyl or heteroaralkyl; wherein the wavy line indicates covalent bonding of the $D^+$ structure to the remainder of the Ligand Drug Conjugate structure.

130. The Ligand Drug Conjugate composition of embodiment 129 wherein the quaternized tubulysin Drug Unit (-$D^+$) has the structure of:

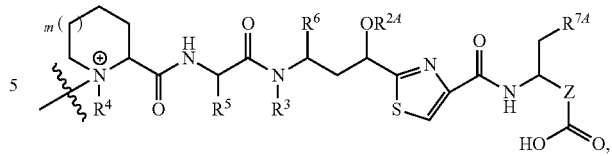

subscript m is 0 or 1, preferably 0; Z is an optionally substituted alkylene or an optionally substituted alkenylene; and $R^{7A}$ is optionally substituted aryl or optionally substituted heteroaryl.

131. The Ligand Drug Conjugate composition of embodiment 130 wherein the quaternized tubulysin Drug Unit (-$D^+$) has the structure of:

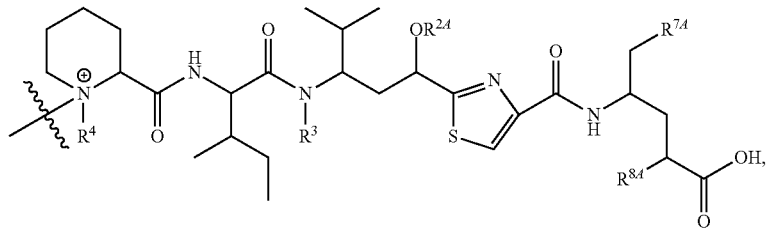

wherein $R^{7A}$ is optionally substituted phenyl and $R^8$ is hydrogen or methyl.

132. The Ligand Drug Conjugate composition of embodiment 130 wherein the quaternized tubulysin Drug Unit (-$D^+$) has the structure of:

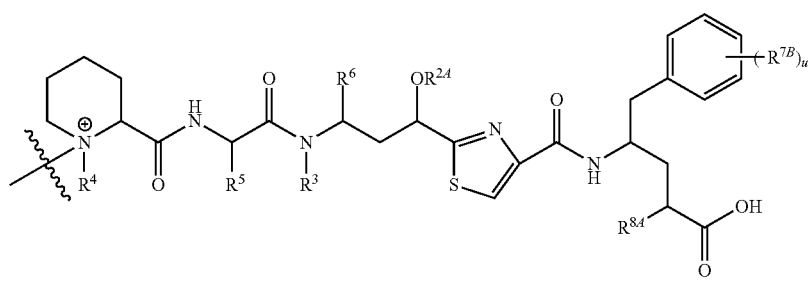

wherein $R^5$ and $R^6$ are alkyl side chain residues of natural or un-natural hydrophobic amino acids, preferably of natural amino acids, independently selected; subscript u, indicating the number of $R^{7B}$ substituents, is 0, 1, 2 or 3; each $R^{7B}$, when present, is an independently selected O-linked substituent; and $R^{8A}$ is hydrogen or optionally substituted alkyl.

133. The Ligand Drug Conjugate composition of embodiment 131 wherein the quaternized tubulysin Drug Unit (-D$^+$) has the structure of:

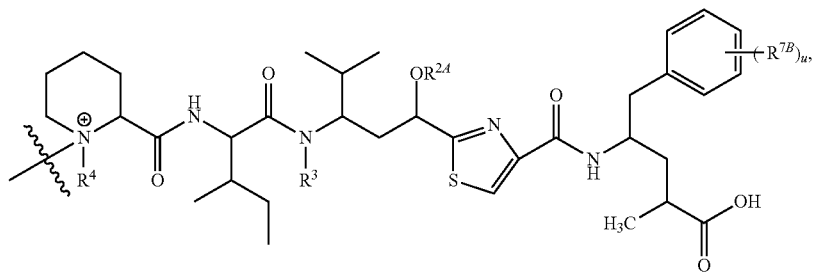

wherein $R^4$ is methyl; subscript u is 0, 1 or 2; $R^3$ is H, methyl, ethyl, propyl, —CH$_2$—OC(O)R$^{3A}$, —CH$_2$CH(R$^{3B}$)C(O)R$^{3A}$ or —CH(R$^{3B}$)C(O)NHR$^{3A}$, wherein R$^{3A}$ is C$_1$-C$_6$ alkyl and R$^{3B}$ is H or C$_1$-C$_6$ alkyl, independently selected from R$^{3A}$; R$^{2A}$ along with the oxygen atom to which it is attached is an O-linked substituent selected from the group consisting of —OCH$_2$OCH$_2$R$^{2B}$, —OCH$_2$R$^{2B}$, —OC(O)R$^{2B}$, —CH$_2$OC(O)R$^{2B}$, —OC(O)N(R$^{2B}$)(R$^{2C}$), and —OCH$_2$C(O)N(R$^{2B}$)(R$^{2C}$), wherein R$^{2B}$ and R$^{2C}$ are independently selected from the group consisting of H, C$_1$-C$_6$ alkyl and C$_2$-C$_6$ alkenyl; and each R$^{7B}$, when present, independently is —OH or —OCH$_3$.

134. The Ligand Drug Conjugate composition of embodiment 133, wherein the quaternized tubulysin Drug Unit (-D$^+$) has the structure of:

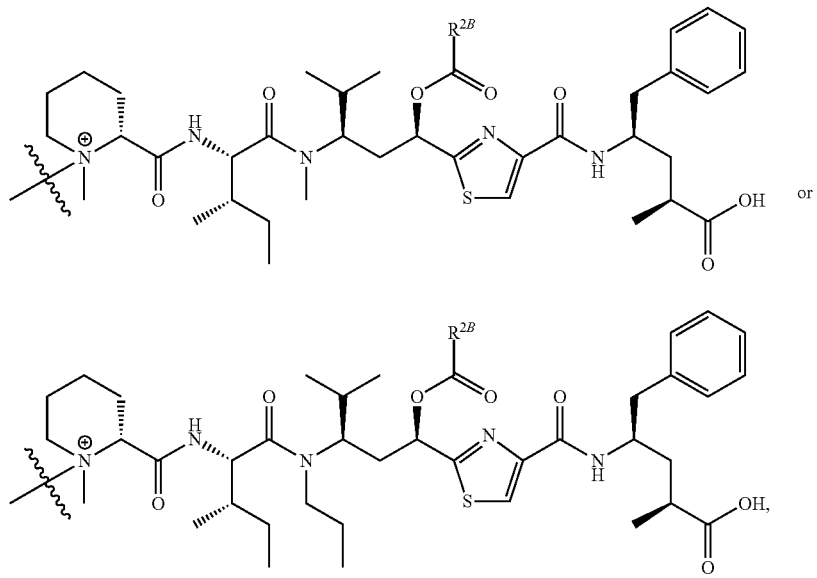

wherein $R^{2B}$ is —CH$_3$, —CH$_2$CH$_3$, —CH$_2$CH$_2$CH$_3$, —CH(CH$_3$)$_2$, —CH$_2$CH(CH$_3$)$_2$, —CH$_2$C(CH$_3$)$_3$.

135. The Ligand Drug Conjugate composition of embodiment 133, wherein the quaternized tubulysin Drug Unit (-D$^+$) has the structure of:

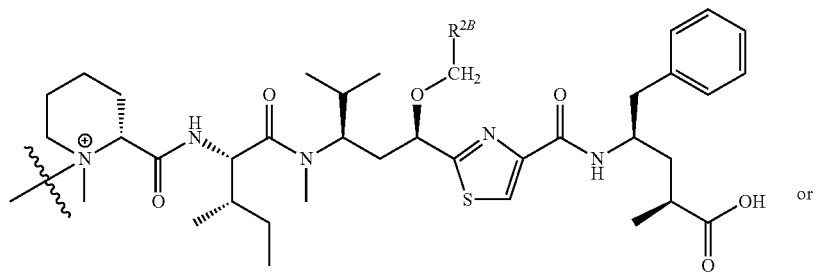

or

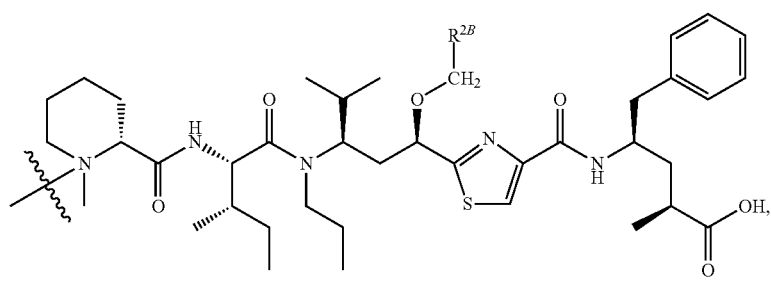

wherein $R^{2B}$ is hydrogen, methyl or —OCH$_3$, or —OCH$_2$R$^{2B}$ is —OCH$_2$CH=CH$_2$ or —OCH$_2$C(CH$_3$)=CH$_2$.

136. The Ligand Drug Conjugate composition of embodiment 126, wherein the Ligand Drug Conjugate composition is represented by the structure(s) of

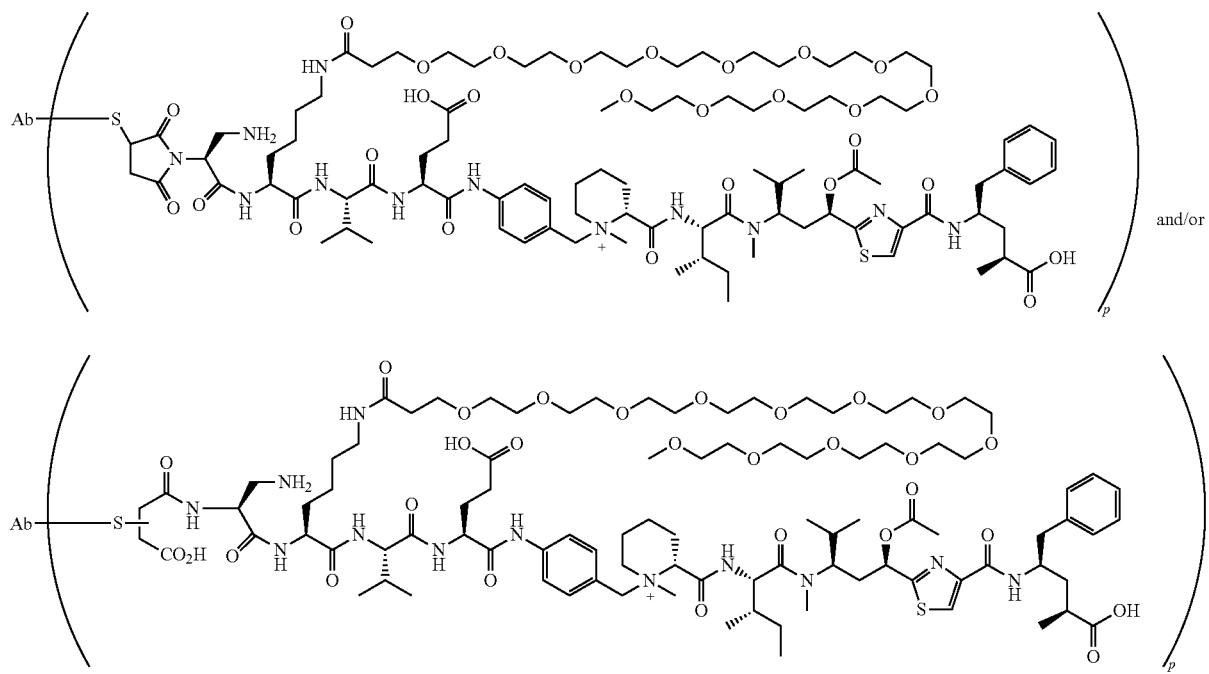

and/or

137. A Drug Linker compound, wherein the compound is represented by the structure of:

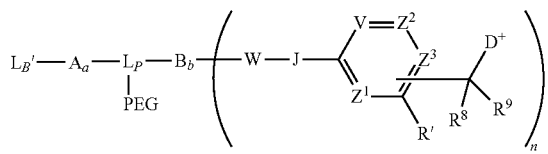

wherein $L_B'$ is a Ligand Covalent Binding Unit precursor; $L_P$ is a Parallel Connector Unit; PEG is a Polyethylene Glycol Unit; subscripts a and b independently are 0 or 1; subscript n is 1, 2, 3 or 4; A is a first optional Stretcher Unit so that subscript a is 0 when A is absent or 1 when A is present and is optionally comprised of two, three or four independently selected subunits ($A_1$, $A_2$, $A_3$, $A_4$); B is an Branching Unit or a second optional Stretcher Unit ($A_O$) so that subscript b is 0 when B is absent or 1 when B is present and is optionally comprised of two, three or four subunits independently of A, wherein subscript b is 1 and B is a Branching when subscript n is 2, 3 or 4 or subscript b is 0, or subscript b is 1 so that B is $A_O$, when subscript n is 1; V, $Z^1$, $Z^2$ and $Z^3$ are =N— or =C($R^{24}$)—, wherein $R^{24}$ is hydrogen or alkyl, alkenyl or alkynyl, optionally substituted, or halogen, —$NO_2$, —CN or other electron withdrawing group, or —$OCH_3$ or other an electron donating group, or —C($R^8$)($R^9$)-$D^+$, wherein at least one of V, $Z^1$, and $Z^3$ is =C($R^{24}$)—, provided that one any only one $R^{24}$ is —C($R^8$)($R^9$)-$D^+$ so that —C($R^8$)($R^9$)-$D^+$ is bonded to one of V, Z, and $Z^3$ when that variable group is =C($R^{24}$)—; R' is hydrogen or —$OCH_3$ or other electron donating group; $D^+$ is a quaternized tubulysin compound; J is a heteroatom, optionally substituted when nitrogen, preferably —NH—, or a nitrogen atom substituted by an optionally substituted alkyl, or an optionally substituted (heteroaryl)arylalkyl; W is a peptide comprised of an amino acid sequence covalently attached to J through an amide bond wherein that amide bond is cleavable by a protease, wherein said protease cleavage initiates release of a tubulysin compound (D) from a Ligand Drug Conjugate compound of the composition.

138. The Drug Linker compound of embodiment 137, wherein the compound is represented by the structure of:

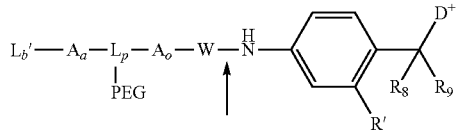

wherein W consists or is comprised of a dipeptide, wherein the dipeptide is at the distal end of W and the indicated bond is an amide bond specifically cleavable by an intracellular protease in comparison to freely circulating serum proteases.

139. The Drug Linker compound of embodiment 138, wherein the dipeptide has the structure of:

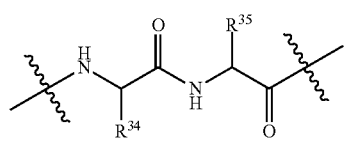

wherein $R^{34}$ is benzyl, methyl, isopropyl, isobutyl, sec-butyl, —CH(OH)$CH_3$ or has the structure of

and $R^{35}$ is methyl, —($CH_2$)$_4$—$NH_2$, —($CH_2$)$_3$NH(C=O)$NH_2$, ($CH_2$)$_3$NH(C=NH)$NH_2$, or —($CH_2$)$_2$$CO_2$H, wherein the wavy line at the dipeptide N-terminus indicates covalent binding to $A_O$ or to $L_P$, depending on the presence or absence of $A_O$, respectively, and the wavy line at the dipeptide C-terminus indicates covalent binding to J.

140. The Drug Linker compound of embodiment 137, 138 or 139 wherein $D^+$ is a tubulysin compound preferably having the structure of:

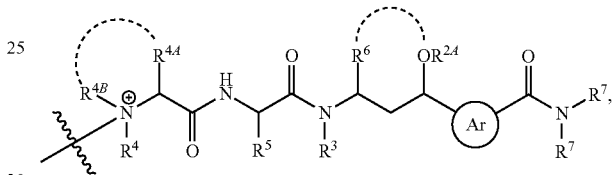

wherein the curved dashed lines indicate optional cyclizations; $R^{24}$ is hydrogen or optionally substituted alkyl, or $R^{24}$ along with the oxygen atom to which it is attached defines an O-linked substituent other than —OH, or $R^{24}$ is absent when $R^6$ is bonded to that oxygen atom, as indicated by the curved dash line between $R^6$ and the oxygen atom, to define a substituted or unsubstituted oxygen-containing heterocycloalkyl; the circled Ar represents a 5-membered nitrogen-heteroaryl, wherein the indicated required substituents to that heteroaryl are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{24}$ moiety in which $R^{24}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached, as indicated by the curved dotted line between $R^{4A}$ and $R^{4B}$, define a substituted or unsubstituted quaternized nitrogen heterocycloalkyl; one $R^7$ is hydrogen or optionally substituted alkyl and the other $R^7$ is optionally substituted aralkyl or heteroaralkyl; wherein the wavy line indicates covalent bonding of the $D^+$ structure to the remainder of the Ligand Drug Conjugate structure.

141. The Drug Linker compound of embodiment 140 wherein the quaternized tubulysin Drug Unit (-$D^+$) has the structure of:

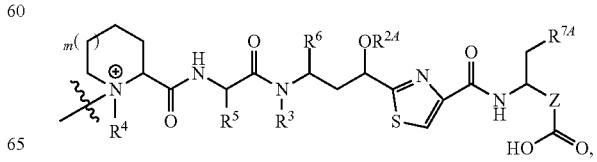

subscript m is 0 or 1, preferably 1; Z is an optionally substituted alkylene or an optionally substituted alkenylene; and $R^{7A}$ is optionally substituted aryl or optionally substituted heteroaryl.

142. The Drug Linker compound of embodiment 141 wherein the quaternized tubulysin Drug Unit (-D⁺) has the structure of:

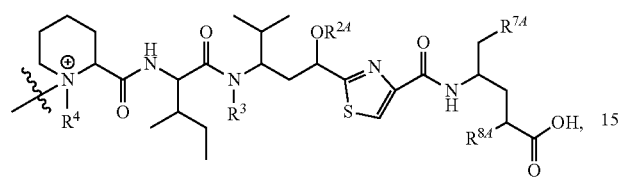

wherein $R^{7A}$ is optionally substituted phenyl and $R^8$ is hydrogen or methyl.

143. Drug Linker compound of embodiment 141 wherein the quaternized tubulysin Drug Unit -D⁺ has the structure of:

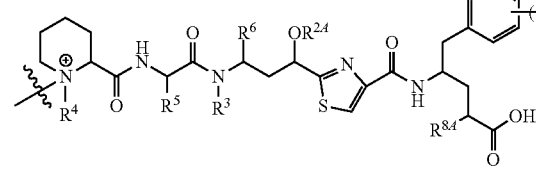

wherein $R^5$ and $R^6$ are alkyl side chain residues of natural or un-natural hydrophobic amino acids, preferably of natural hydrophobic amino acids, independently selected; subscript u, indicating the number of $R^{7B}$ substituents, is 0, 1, 2 or 3; each $R^{7B}$, when present, is an independently selected O-linked substituent; and $R^{8A}$ is hydrogen or optionally substituted alkyl.

144. Drug Linker compound of embodiment 142 wherein the quaternized tubulysin Drug Unit (-D⁺) has the structure of:

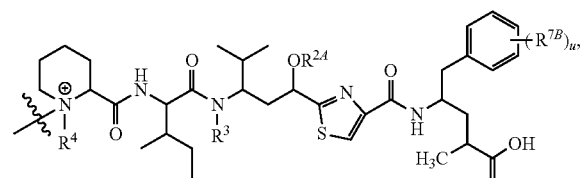

wherein $R^4$ is methyl; subscript u is 0, 1 or 2; $R^3$ is H, methyl, ethyl, propyl, —CH₂—OC(O)$R^{3A}$, —CH₂CH($R^{3B}$)C(O)$R^{3A}$ or —CH($R^{3B}$)C(O)NHR$^{3A}$, wherein $R^{3A}$ is C₁-C₆ alkyl and $R^{3B}$ is H or C₁-C₆ alkyl, independently selected from $R^{3A}$; $R^{2A}$ along with the oxygen atom to which it is attached is an O-linked substituent selected from the group consisting of —OCH₂OCH₂R$^{2B}$, —OCH₂R$^{2B}$, —OC(O)R$^{2B}$, —CH₂OC(O)R$^{2B}$, —OC(O)N(R$^{2B}$)(R$^{2C}$), and —OCH₂C(O)N(R$^{2B}$)(R$^{2C}$), wherein R$^{2B}$ and R$^{2C}$ are independently selected from the group consisting of H, C₁-C₆ alkyl and C₂-C₆ alkenyl; and each R$^{7B}$, when present, independently is —OH or —OCH₃.

145. Drug Linker compound of embodiment 144, wherein the quaternized tubulysin Drug Unit (-D⁺) has the structure of:

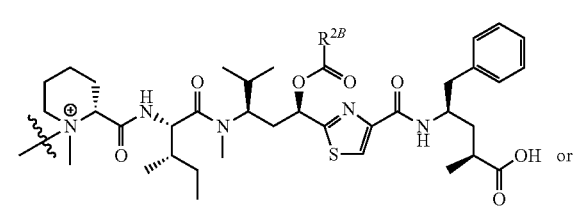

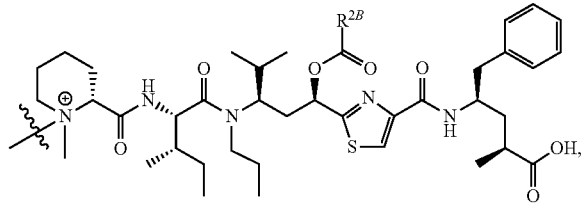

wherein $R^{2B}$ is —CH₃, —CH₂CH₃, —CH₂CH₂CH₃, —CH(CH₃)₂, —CH₂CH(CH₃)₂, —CH₂C(CH₃)₃.

146. Drug Linker compound of embodiment 144, wherein the quaternized tubulysin Drug Unit (-D⁺) has the structure of:

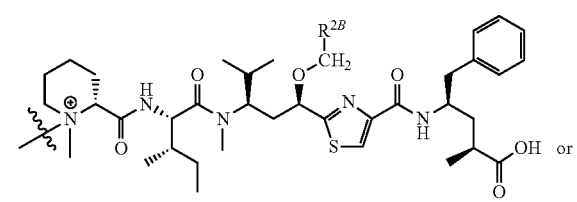

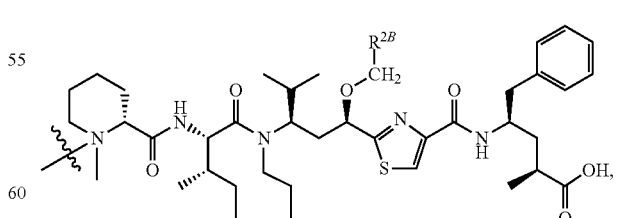

wherein $R^{2B}$ is hydrogen, methyl or —OCH₃, or —OCH₂R$^{2B}$ is —OCH₂CH=CH₂ or —OCH₂C(CH₃)=CH₂.

147. The Drug Linker compound of embodiment 137, wherein the compound has the structure of:

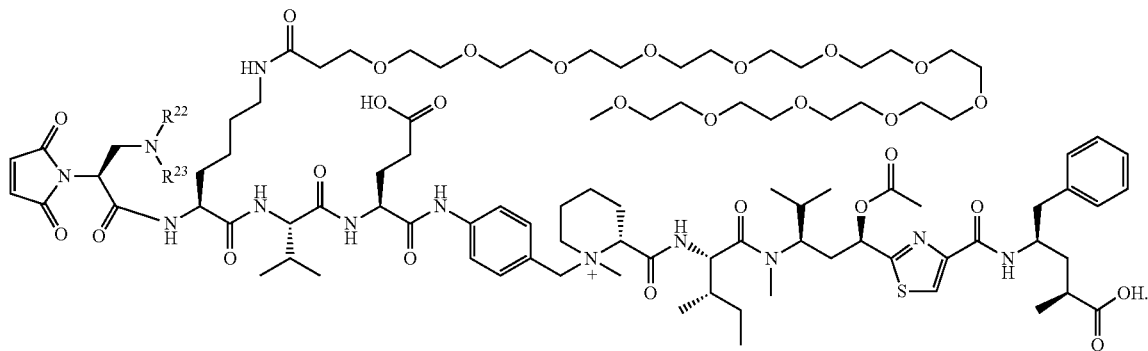

wherein one of $R^{22}$, $R^{23}$ is hydrogen and the other is an acid labile protecting group or $R^{22}$ and $R^{23}$ are each hydrogen with the nitrogen to which they are attached optionally protonated as an acid addition salt.

148. A formulation comprising a Ligand Drug Conjugate of any one of embodiments 1 to 63 and 126 to 136 and one or more excipients.

149. The formulation of embodiment 148 wherein the formulation is a pharmaceutically acceptable formulation or a precursor thereof.

150. The formulation of embodiment 149 wherein the pharmaceutically acceptable formulation precursor is a solid suitable for reconstitution as a solution for intravenous injection to a subject.

151. The formulation of embodiment 149 wherein the pharmaceutically acceptable formulation is a liquid suitable for intravenous injection to a subject.

152. The formulation of embodiments 149, 150 or 151 wherein the Ligand Drug Conjugate is present in the pharmaceutically acceptable formulation or precursor thereof in an effective amount for treatment of a hyperproliferative condition.

153. A method of treating a hyperproliferative disease or condition comprising the step of administering to a patient having said disease or condition an effective amount of a Ligand Drug Conjugate of any one of embodiments 1 to 63 and 126 to 136.

154. The method of embodiment 153 wherein the hyperproliferative disease or condition is a cancer.

155. The method of embodiment 154 wherein the hyperproliferative disease or condition is a leukemia or a lymphoma.

156. A method of inhibiting the multiplication of a tumor cell or cancer cell, or causing apoptosis in a tumor or cancer cell, by exposing said cell with an effective amount of Ligand Drug Conjugate of any one of embodiments 1 to 63 and 126 to 136 or of a tubulysin compound of any one of embodiments 115 to 124.

1A. An Antibody Drug Conjugate having the structure of:

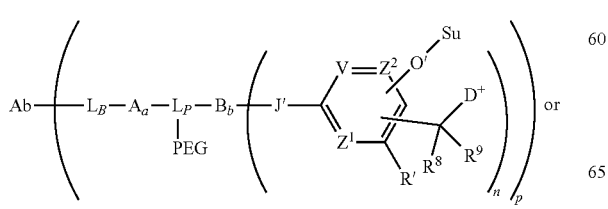

-continued

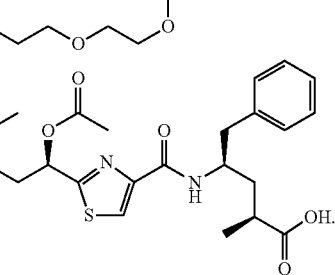

one of Formula 2A-2F:

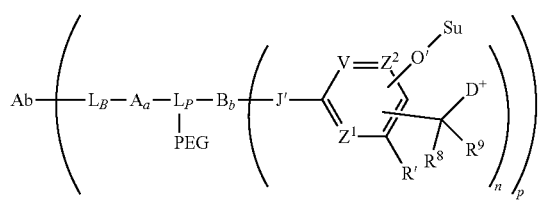

(Formula 2A)

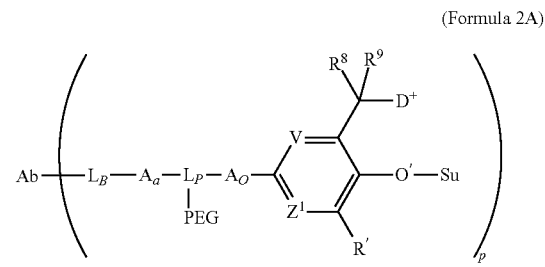

(Formula 2B)

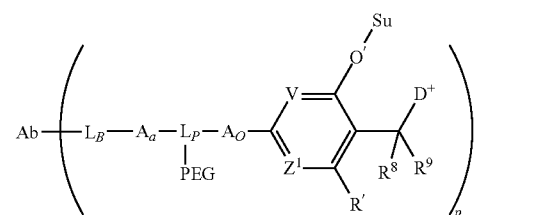

(Formula 2C)

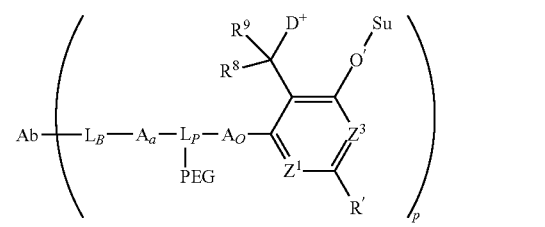

191
-continued

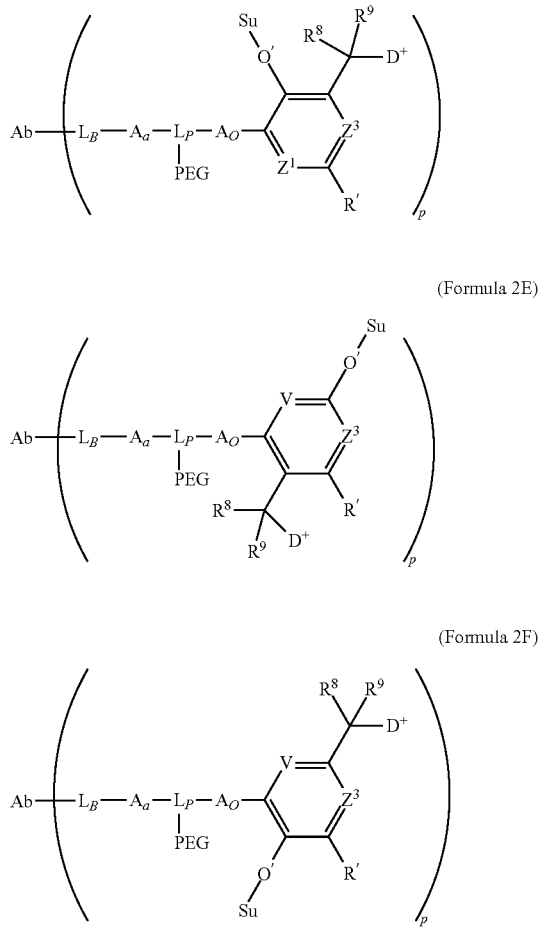

(Formula 2D)

(Formula 2E)

(Formula 2F)

preferably in pharmaceutically acceptable salt form, wherein Ab is an antibody Ligand Unit, wherein a targeted moiety of the antibody Ligand Unit is an accessible cell-surface antigen of targeted abnormal cells, wherein that antigen is preferentially present on the targeted abnormal cells in comparison to normal cells, or the targeted moiety of the antibody Ligand Unit is an accessible cell-surface antigen of a vascular epithelial cell in the vicinity of abnormal cells, wherein that antigen is preferably more abundant on the epithelial cell in comparison to epithelial cells in the periphery; and wherein either cell-surface antigen is capable of cellular internalization of bound ADC; $L_B$ is a Ligand Covalent Binding Unit; $L_P$ is a Parallel Connector Unit; PEG is a Polyethylene Glycol Unit; subscripts a and b independently are 0 or 1; subscript n is 1, 2, 3 or 4; A is a first optional Stretcher Unit so that subscript a is 0 when A is absent or 1 when A is present and is optionally comprised of two, three or four independently selected subunits ($A_1$, $A_2$, $A_3$, $A_4$); B is an Branching Unit or a second optional Stretcher Unit ($A_O$) so that subscript b is 0 when B is absent or subscript b is 1 when B is present and is optionally comprised of two, three or four subunits independently of A, wherein subscript b is 1 and B is a Branching when subscript n is 2, 3 or 4, or subscript b is 0, or subscript b is 1 so that B is $A_O$, when subscript n is 1; Su is a carbohydrate moiety; —O'— represents an oxygen atom of an O-glycosidic bond cleavable by a glycosidase; -J'- represents a heteroatom, optionally substituted when nitrogen, from a functional group of B or $A_O$, when either are present, or from $L_P$, when either are absent; V, $Z^1$, $Z^2$ and $Z^3$ are =N— or =C($R^{24}$)—, wherein $R^{24}$ is hydrogen or alkyl, alkenyl or alkynyl, optionally substituted, or halogen, —$NO_2$, —CN or other electron withdrawing group, an electron donating group, —O'-Su, or —C($R^8$)($R^9$)-$D^+$, wherein at least at least two of V, $Z^1$, $Z^2$ and $Z^3$ are =C($R^{24}$)—, provided, one any only one $R^{24}$ is —C($R^8$)($R^9$)-$D^+$ so that —C($R^8$)($R^9$)-$D^+$ is bonded to one of V, $Z^1$, $Z^2$, $Z^3$ when that variable group is =C($R^{24}$)— and one and only one other $R^{24}$ is so that —O'-Su is bonded to another one of V, $Z^1$, $Z^2$, $Z^3$ when that variable group is =C($R^{24}$)—, and the —O'-Su and —C($R^8$)($R^9$)-$D^+$ substituents are ortho or para to each other; $R^8$ and $R^9$ independently are hydrogen, alkyl, alkenyl or alkynyl, optionally substituted, or aryl or heteroaryl, optionally substituted; R' is hydrogen or is halogen, —$NO_2$, —CN or other electron withdrawing group;

$D^+$ is a quaternized tubulysin Drug Unit preferably having the structure of:

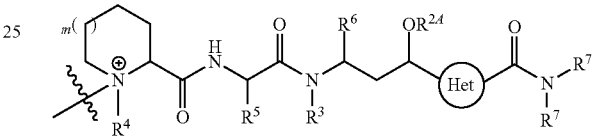

wherein the circle represents an 5-membered nitrogen-heteroarylene and wherein the indicated required substituents to that heteroarylene are in a 1,3-relationship with each other with optional substitution at the remaining positions; subscript m is 0 or 1; $R^{24}$ is hydrogen or optionally substituted alkyl, or $R^{24}$ along with the oxygen atom to which it is attached defines an O-linked substituent; $R^3$ is hydrogen or optionally substituted alkyl; $R^4$, $R^5$ and $R^6$ are optionally substituted alkyl; one $R^7$ is an optionally substituted alkyl, an optionally substituted arylalkyl, optionally substituted heteroarylalkyl and the other $R^7$ is hydrogen or an optionally substituted alkyl; and $R^{8A}$ is hydrogen or optionally substituted alkyl, wherein the wavy line indicates covalent bonding of the quaternized tubulysin Drug Unit to the remainder of the Formula 2A-2F structures and wherein each optionally substituted alkyl is independently selected; and subscript p is an average drug loading having a number ranging from 1 to 24.

2A. The Antibody Drug Conjugate of embodiment 1A wherein —O'-Su has the structure of Formula 3:

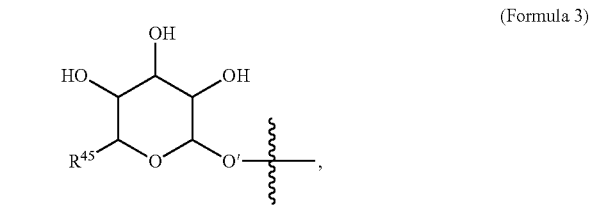

(Formula 3)

wherein the wavy line represents covalent bonding of O' to the remainder of the LDC structure; and $R^{45}$ is —$CH_2OH$ or —$CO_2H$.

3A. The Antibody Drug Conjugate of embodiment 2A having the structure of Formula 4:

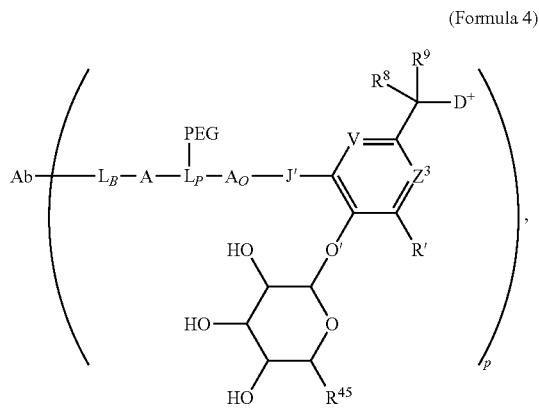

(Formula 4)

J' is —N($R^{33}$)—, wherein $R^{33}$ is hydrogen or methyl; V and $Z^3$ independently are =CH— or =N—; R' is hydrogen or an electron withdrawing group; $R^8$ is hydrogen; $R^9$ is hydrogen, optionally substituted $C_1$-$C_6$ alkyl or optionally substituted phenyl; and $R^{45}$ is —$CO_2$H.

4A. The Antibody Drug Conjugate of embodiment 1A wherein a is 1; and -$L_B$-A- has the structure of Formula 5:

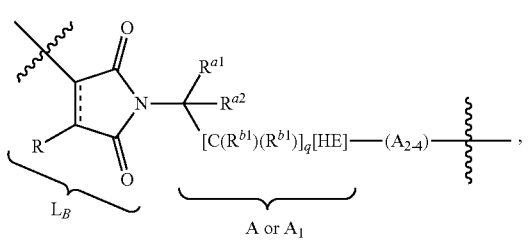

(Formula 5)

wherein the —[C($R^{b1}$)($R^{b1}$)]$_q$—[HE]- moiety is A or $A_1$, wherein $A_1$ is a subunit of A; $A_{2-4}$ are optional subunits of A; R is hydrogen or $C_1$-$C_4$ alkyl; $R^{a1}$ is hydrogen, optionally substituted alkyl or a Basic Unit (BU); and $R^2$ is hydrogen or optionally substituted alkyl, or $R^{a1}$ and $R^{a2}$ together with the carbon atom to which they are attached define a nitrogen-containing heterocycloalkyl; HE is an optional Hydrolysis Enhancer (HE) Unit; subscript q is an integer ranging from 0 to 6; each $R^{b1}$ independently is hydrogen, optionally substituted $C_1$-$C_6$ alkyl, optionally substituted aryl or optionally substituted heteroaryl, or two $R^{b1}$ together with the carbon(s) to which they are attached comprise, or preferentially define, a $C_3$-$C_6$ cycloalkyl or one $R^{b1}$ and HE together with the carbon to which they are attached define a 5 or 6-membered cycloalkyl or a 5- or 6-membered heterocycloalkyl and the other $R^{b1}$ is hydrogen, optionally substituted $C_1$-$C_6$ alkyl, optionally substituted aryl or optionally substituted heteroaryl; BU has the structure of —[C($R^1$)($R^1$)]—[C($R^2$)($R^2$)]r-N($R^{22}$)($R^{23}$), or an acid addition salt thereof, wherein subscript r is 0, 1, 2 or 3; each $R^1$ independently is hydrogen or $C_1$-$C_4$ alkyl or two $R^1$ together with the carbon to which they are attached comprise, or preferably define, a $C_3$-$C_6$ cycloalkyl, and each $R^2$ independently is hydrogen, optionally substituted $C_1$-$C_6$ alkyl, optionally substituted aryl or optionally substituted heteroaryl, or two $R^2$ together with the carbon(s) to which they are attached and any intervening carbons define a $C_3$-$C_6$ cycloalkyl, or one $R^1$ and one $R^2$ together with the carbons to which they are attached and any intervening carbons define a 5- or 6-membered cycloalkyl and the remaining $R^1$ and $R^2$ are as defined; $R^{22}$ and $R^{23}$ independently are hydrogen or optionally substituted $C_1$-$C_6$ alkyl or together with the nitrogen to which they are attached define a 5- or 6-membered heterocycloalkyl, or one of $R^{22}$, $R^{23}$ is hydrogen and the other is an acid labile protecting group; and wherein the dotted line is an optional double bond and the wavy line to the succinimide (double bond is absent) or maleimide ring (double bond is present) of $L_B$ indicates covalent bonding of sulfur derived from a sulfhydryl group of an antibody and the other wavy line indicates covalent bonding to the remainder of the Antibody Drug Conjugate structure.

5A. The Antibody Drug Conjugate of embodiment 4A wherein Formula 5 has the structure of Formula 5A:

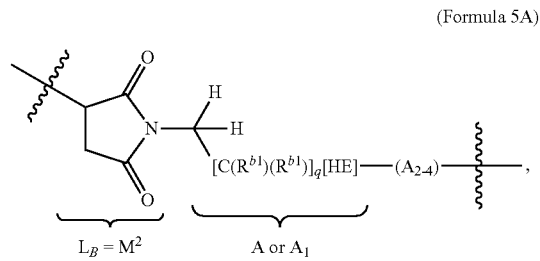

(Formula 5A)

wherein subscript q is an integer ranging from 0 to 4.

6A. The Antibody Drug Conjugate of embodiment 4A wherein Formula 5 has the structure of Formula 5B, or an acid addition salt thereof:

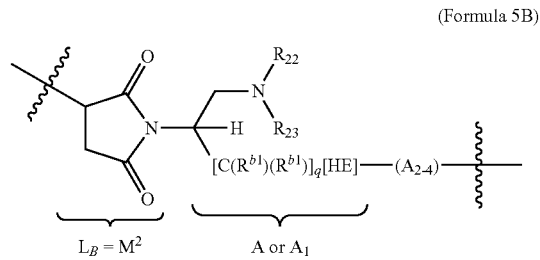

(Formula 5B)

wherein $R^{22}$ and $R^{23}$ are each hydrogen or one of $R^{22}$, $R^{23}$ is hydrogen and the other is an acid labile carbamate protecting group; and subscript q is an integer ranging from 0 to 4.

7A. The Antibody Drug Conjugate of embodiment 5A or 6A wherein Formula 5A or Formula 5B has the structure of:

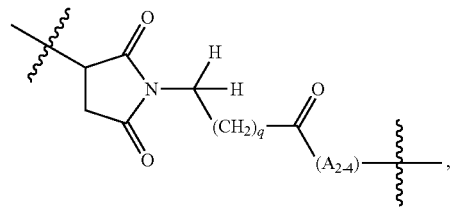

195
-continued

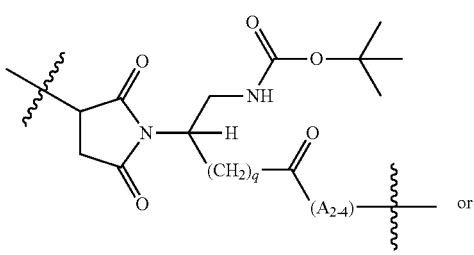

or

196
-continued

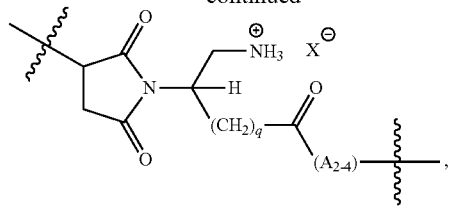

wherein X⁻ is chloride, acetate, trifluoroacetate or dihydrogen phosphate.

8A. The Antibody Drug Conjugate of embodiment 4A having the structure of Formula 6:

(Formula 6)

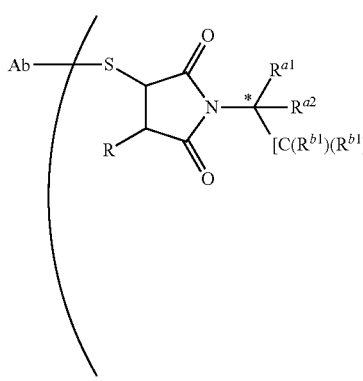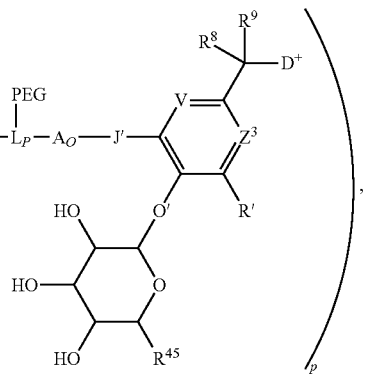

wherein S is a sulfur atom of the antibody Ligand Unit; the asterisk (*) designates chirality or absence thereof at the indicated carbon; $A_{2-4}$ are independently selected optional subunits of A, wherein $—[C(R^{b1})(R^{b1})]_q—[HE]—$ is $A_1$ when one or more such subunits are present; R is hydrogen; R' is hydrogen or an electron withdrawing group; $R^{a1}$ is hydrogen or a basic unit (BU) wherein BU is a Basic Unit having the structure of $—CH_2—N(R^{22})(R^{23})$, or an acid addition salt thereof, wherein $R^{22}$ and $R^{23}$ independently are hydrogen, methyl or ethyl or both together with the nitrogen atom to which they are attached comprise, or preferably define, a 5- or 6-membered heterocycloalkyl, or one of $R^{22}$, $R^{23}$ is hydrogen and the other is an acid labile carbamate protecting group; $R^{a2}$ is hydrogen; subscript q is an integer ranging from 0 to 5 when HE is present or 1 to 5 when HE is absent; each $R^{b1}$ independently is hydrogen or optionally substituted $C_1$-$C_6$ alkyl; HE is absent or is $—C(=O)—$; $R^{45}$ is $—CO_2H$; J' is $—NH—$; V and $Z^3$ are each $=CH_2—$; $R^8$ is hydrogen; $R^9$ is hydrogen or methyl; and subscript p is a number ranging from 1 to 16.

9A. The Antibody Drug Conjugate of embodiment 1A represented by the structure(s) of Formula 9A and/or Formula 9B:

(Formula 9A)

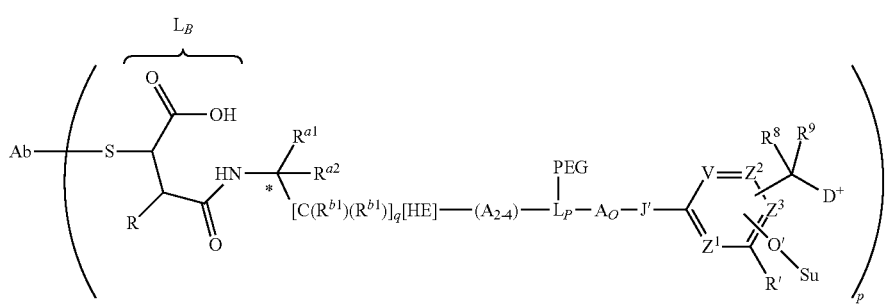

(Formula 9B)

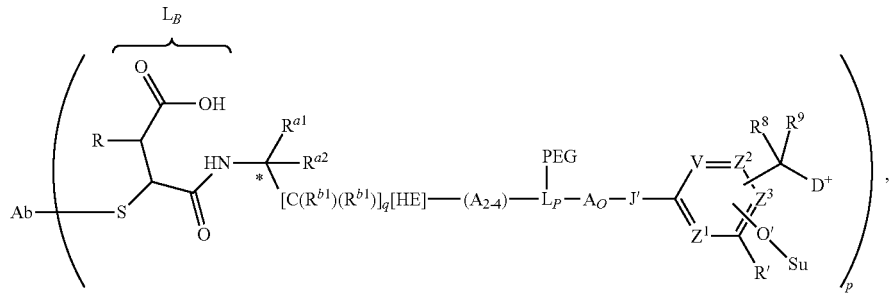

wherein S is a sulfur atom of the antibody Ligand Unit; $A_{2-4}$ are independently selected optional subunits of A, wherein $—[C(R^{b1})(R^{b1})]_q—[HE]-$ is $A_1$ when one or more such subunits are present; R is hydrogen; R' is hydrogen or an electron withdrawing group; $R^{a1}$ is —H or BU wherein BU is a Basic Unit having the structure of $—CH_2—N(R^{22})(R^{23})$, or an acid addition salt thereof, wherein $R^{22}$ and $R^{23}$ independently are hydrogen or methyl or both together with the nitrogen atom to which they are attached define a basic nitrogen-containing 5- or 6-membered heterocycloalkyl, or one of $R^{22}$, $R^{23}$ is hydrogen and the other is an acid labile protecting group; $R^{a2}$ is hydrogen; subscript q is an integer ranging from 0 to 5 when HE is present or from 1 to 5 when HE is absent; each $R^{b1}$ independently is hydrogen or optionally substituted $C_1$-$C_6$ alkyl; HE is absent or is —C(=O)—; J' is —O— or —NH—; and $R^8$ and $R^9$ are independently —H or optionally substituted alkyl or both together along with the carbon atom to which they are attached define a cycloalkyl; and 10A. The Antibody Drug Conjugate of embodiment 9A represented by the structure(s) of Formula 10A and/or Formula 10B:

(Formula 10A)

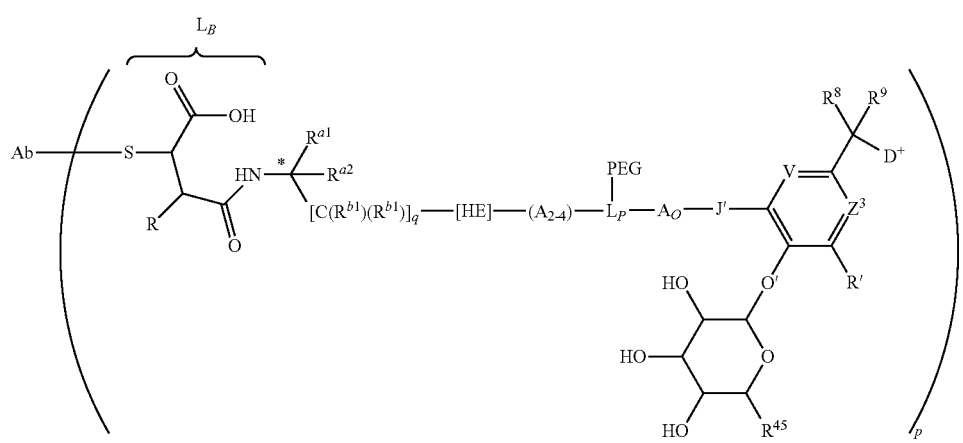

(Formula 10B)

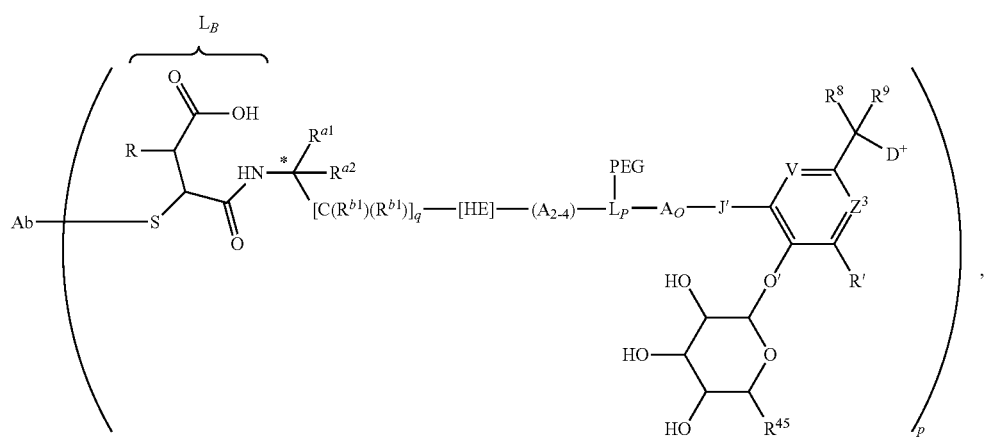

wherein R is hydrogen; R' is hydrogen, —NO₂, —Cl or —F; HE is —C(=O)—; $R^{45}$ is —CO₂H; J' is —NH—; V and $Z^3$ are each =CH—; $R^8$ is hydrogen; and $R^9$ is hydrogen or methyl.

11A. The Antibody Drug Conjugate of embodiment 8A, 9A or 10A wherein the indicated starred (*) carbon is predominantly in the same absolute configuration as the alpha carbon of an L-amino acid when that indicated carbon is chiral.

12A. The Antibody Drug Conjugate of any one of embodiments 1A to 10A, wherein A, $A_O$, and each of $A_2$-4, when present, independently have the structure of Formula 7 or Formula 8:

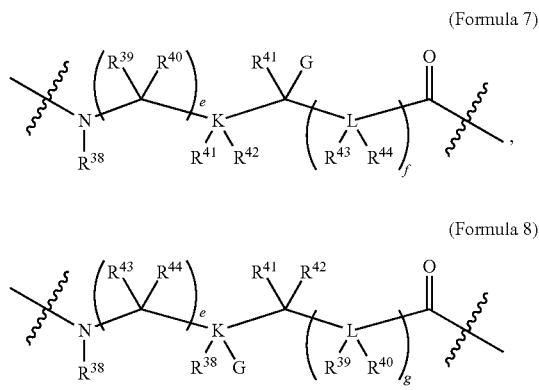

(Formula 7)

(Formula 8)

wherein the wavy lines indicated covalent attachment within the remainder of $L_O$, wherein K and L independently are C, N, O or S, provided that when K or L is O or S, $R^{41}$ and $R^{42}$ to K or $R^{43}$ and $R^{44}$ to L are absent, and when K or L are N, one of $R^{41}$, $R^{42}$ to K or one of $R^{42}$, $R^{43}$ to L are absent, and provided that no two adjacent L are independently selected as N, O, or S; wherein subscripts e and f are independently selected integers that range from 0 to 12, and subscript g is an integer ranging from 1 to 12; G is hydrogen, optionally substituted $C_1$-$C_6$ alkyl, —OH, —$OR^{PR}$, —$CO_2H$, $CO_2R^{PR}$, wherein $R^{PR}$ is a suitable protecting, —$N(R^{PR})(R^{PR})$, wherein $R^{PR}$ are independently a protecting group or $R^{PR}$ together form a suitable protecting group, or —$N(R^{45})(R^{46})$, wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl; wherein $R^{38}$ is hydrogen or optionally substituted $C_1$-$C_6$ alkyl; $R^{39}$-$R^{44}$ independently are hydrogen, optionally substituted $C_1$-$C_6$ alkyl, optionally substituted aryl, or optionally substituted heteroaryl, or both $R^{39}$, $R^{40}$ together with the carbon to which they are attached comprise or preferably define a $C_3$-$C_6$ cycloalkyl, or $R^{41}$, $R^{42}$ together with K to which they are attached when K is C, or $R^{43}$, $R^{44}$ together with L to which they are attached when L is a carbon atom comprise a $C_3$-$C_6$ cycloalkyl, or $R^{40}$ and $R^{41}$, or $R^{40}$ and $R^{43}$, or $R^{41}$ and $R^{43}$ to together with the carbon atom or heteroatom to which they are attached and the atoms intervening between those carbon atoms and/or heteroatoms comprise or preferably define a 5- or 6-membered cycloalkyl or heterocycloalkyl, provided that when K is O or S, $R^{41}$ and $R^{42}$ are absent, when K is N, one of $R^{41}$, $R^{42}$ is absent, when L is O or S, $R^{43}$ and $R^{44}$ are absent, and when L is N, one of $R^{43}$, $R^{44}$ is absent, or wherein $A_O$ has a structure corresponding to an alpha-amino, beta-amino or another amine-containing acid.

13A. The Antibody Drug Conjugate of any one of embodiments 1A to 12A wherein the quaternized tubulysin Drug Unit (-D$^+$) has the structure of:

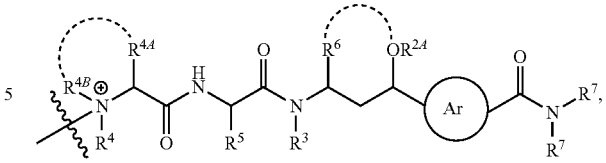

$R^{2A}$ is hydrogen or optionally substituted alkyl, or $R^{2A}$ along with the oxygen atom to which it is attached defines an O-linked substituent other than —OH, or $R^{2A}$ is absent when $R^6$ is bonded to that oxygen atom, as indicated by the curved dash line between $R^6$ and the oxygen atom, to define an oxygen-containing heterocycloalkyl; the circled Ar represents a 5-membered nitrogen-heteroarylene, wherein the indicated required substituents to that heteroarylene are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{2A}$ moiety in which $R^{2A}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached, as indicated by the curved dotted line between $R^{4A}$ and $R^{4B}$, define a quaternized nitrogen heterocycloalkyl, optionally substituted; one $R^7$ is hydrogen or optionally substituted alkyl and the other $R^7$ is optionally substituted aralkyl or heteroaralkyl; wherein the wavy line indicates covalent bonding to the remainder of the Antibody Drug Conjugate structure.

14A. The Antibody Drug Conjugate of embodiment 13A wherein the quaternized tubulysin Drug Unit (-D)D has the structure of:

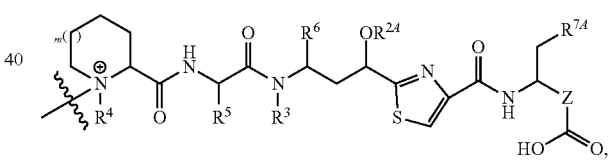

subscript m is 0 or 1; Z is an optionally substituted alkylene or an optionally substituted alkenylene; and $R^{7A}$ is optionally substituted aryl or optionally substituted heteroaryl.

15A. The Antibody Drug Conjugate of embodiment 14A wherein the quaternized tubulysin Drug Unit (-D$^+$) has the structure of:

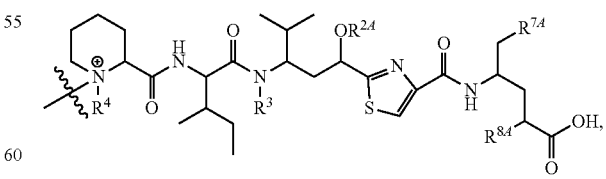

wherein $R^{7A}$ is optionally substituted phenyl and $R^8$ is hydrogen or methyl.

16A. The Antibody Drug Conjugate of embodiment 14A wherein the quaternized tubulysin Drug Unit (-D$^+$) has the structure of:

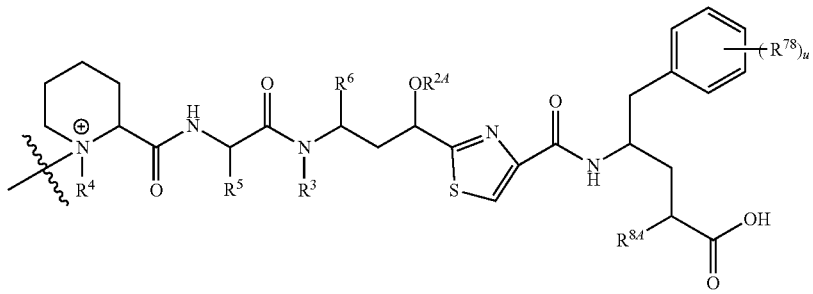

wherein $R^5$ and $R^6$ are alkyl side chain residues of natural hydrophobic amino acids, independently selected; subscript u, indicating the number of $R^{7B}$ substituents, is 0, 1, 2 or 3; each $R^{7B}$, when present, is an independently selected O-linked substituent; and $R^{8A}$ is hydrogen or optionally substituted alkyl.

17A. The Antibody Drug Conjugate of embodiment 15A wherein the quaternized tubulysin Drug Unit (-D) has the structure of:

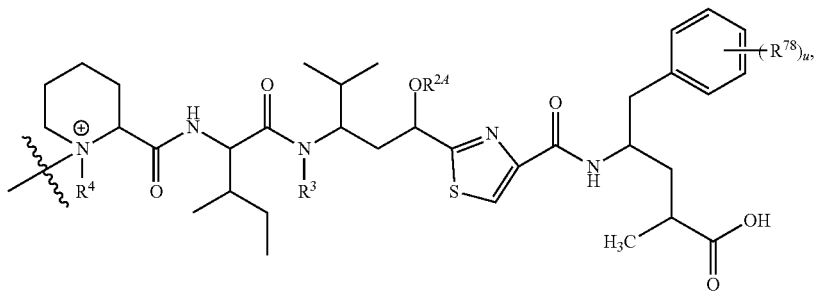

wherein $R^4$ is methyl; subscript u is 0, 1 or 2; $R^3$ is H, methyl, ethyl, propyl, —$CH_2$—$OC(O)R^{3A}$, —$CH_2CH(R^{3B})$ $C(O)R^{3A}$ or —$CH(R^{3B})C(O)NHR^{3A}$, wherein $R^{3A}$ is $C_1$-$C_6$ alkyl and $R^{3B}$ is H or $C_1$-$C_6$ alkyl, independently selected from $R^{3A}$; $R^{2A}$ along with the oxygen atom to which it is attached is an O-linked substituent selected from the group consisting of —$OCH_2OCH_2R^{2B}$, —$OCH_2R^{2B}$, —$OC(O)$ $R^{2B}$, —$CH_2OC(O)R^{2B}$, —$OC(O)N(R^{2B})(R^{2C})$, and —$OCH_2C(O)N(R^{2B})(R^{2C})$, wherein $R^{2B}$ and $R^{2C}$ are independently selected from the group consisting of H, $C_1$-$C_6$ alkyl and $C_2$-$C_6$ alkenyl; and each $R^{7B}$, when present, independently is —OH or —$OCH_3$.

18A. The Antibody Drug Conjugate of embodiment 13A wherein the quaternized tubulysin Drug Unit (-D+) has the structure of:

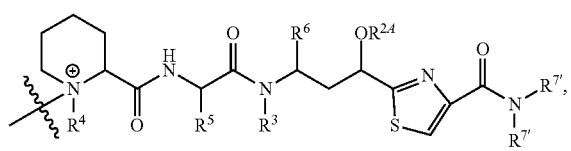

wherein $R^{2A}$ is hydrogen, an optionally substituted alkyl, saturated or unsaturated, or $R^2$ along with the oxygen atom to which it is attached defines an O-linked substituent other than —OH; $R^3$ is optionally substituted $C_1$-$C_6$ alkyl; $R^4$ is methyl; $R^5$ and $R^6$ are alkyl side chain residues of natural hydrophobic amino acids; and the —$N(R^{7'})(R^{7'})$ moiety is —$NH(C_1$-$C_6$ alkyl), optionally substituted by —$CO_2H$, or an ester thereof, or by an optionally substituted phenyl, or is —NH—$N(C_1$-$C_6$ alkyl)$_2$, wherein one and only one $C_1$-$C_6$ alkyl is optionally substituted by —$CO_2H$, or an ester thereof, or by an optionally substituted phenyl.

19A. The Antibody Drug Conjugate of embodiment 18A wherein the —$N(R^{7'})(R^{7'})$ moiety is selected from the group consisting of —$NH(CH_3)$, —$NHCH_2CH_2Ph$, and —$NHCH_2$—$CO_2H$, —$NHCH_2CH_2CO_2H$ and —$NHCH_2CH_2CH_2CO_2H$.

20A. The Antibody Drug Conjugate of any one of embodiments 11A to 18A, wherein $R^{2A}$ is —$CH_2CH_3$.

21A. The Antibody Drug Conjugate of any one of embodiments 11A to 18A wherein $R^{2A}$ is —$CH_2$—$CH=CH_2$.

22A. The Antibody Drug Conjugate of any one of embodiment 17A or 18A wherein $R^{2A}$ is —$CH_2CH_3$, —$CH_2$—$CH=CH_2$ or —$CH_2C(CH_3)=CH_2$, $R^{2B}$ is —$CH_3$, $R^3$ is —$CH_3$ and subscript u is 0.

23A. The Antibody Drug Conjugate of embodiment 17A or 18A wherein $R^{2A}$ is —$CH_2CH_3$ or —$CH_2$—$CH=CH_2$, or —$CH_2C(CH_3)=CH_2$, $R^{2B}$ is —$CH_3$, $R^3$ is —$CH_3$ and subscript u is 1, wherein $R^{7B}$ is —OH.

24A. The Antibody Drug Conjugate of any one of embodiments 1A to 23A wherein $L_P$ is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the sulfur substituent is in reduced or oxidized form.

25A. The Antibody Drug Conjugate of any one of embodiments 1A to 23A wherein $L_P$ is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

26A. The Antibody Drug Conjugate of embodiment 24A wherein the aminoalkanedioic acid, diaminoalkanoic acid, sulfur-substituted aminoalkanoic acid or hydroxyl substituted aminoalkanoic acid residue has the structure of Formula A or Formula B:

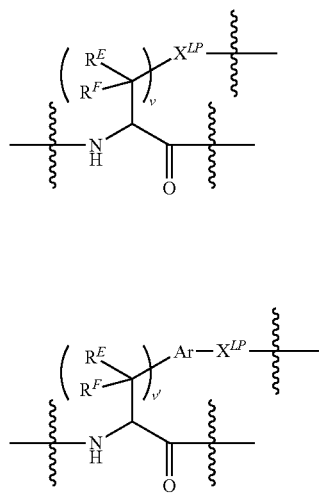

(Formula A)

(Formula B)

wherein subscript v is an integer ranging from 1 to 4; subscript v' is an integer ranging from 0 to 4; $X^{LP}$ is selected from the group consisting of —O—, —$NR^{LP}$—, —S—, —S(=O)—, —S(=O)$_2$—, —C(=O)—, —C(=O)N($R^{LP}$)—, —N($R^{LP}$)C(=O)N($R^{LP}$)—, and —N($R^{LP}$)C(=N$R^{LP}$)N($R^{LP}$)— wherein each $R^{LP}$ is independently selected from the group consisting of hydrogen and optionally substituted alkyl or two of $R^{LP}$ together along with their intervening atoms define a heterocycloalkyl and any remaining $R^{LP}$ are as previously defined; Ar is an arylene or heteroarylene, optionally substituted; each $R^E$ and $R^F$ is independently selected from the group consisting of —H, optionally substituted alkyl, optionally substituted aryl and optionally substituted heteroaryl, or $R^E$ and $R^F$ together with the same carbon to which they are attached, or $R^E$ and $R^F$ from adjacent carbons together with these carbons, defines a optionally substituted cycloalkyl with any remaining $R^E$ and $R^F$ substituents as previously defined; and wherein the wavy lines indicates covalent attachment of the Formula A or Formula B structure within the Antibody Drug Conjugate structure.

27A. The Antibody Drug Conjugate of any one of embodiments 1A to 10A wherein -$L_P$(PEG)- has the structure of Formula A1 or A2:

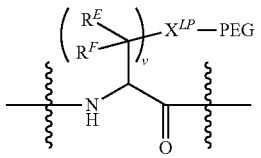

(Formula A1)

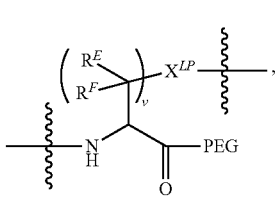

(Formula A2)

wherein $X^{LP}$ is selected from the group consisting of —O—, —NH, —S— and —C(=O)—; $R^E$ and $R^F$ are independently selected from the group consisting of —H, and —$C_1$-$C_4$ alkyl; and wherein the wavy line indicates covalent attachment of Formula A1 or Formula A2 within the Antibody Drug Conjugate structure.

28A. The Antibody Drug Conjugate of embodiment 1A having the structure of:

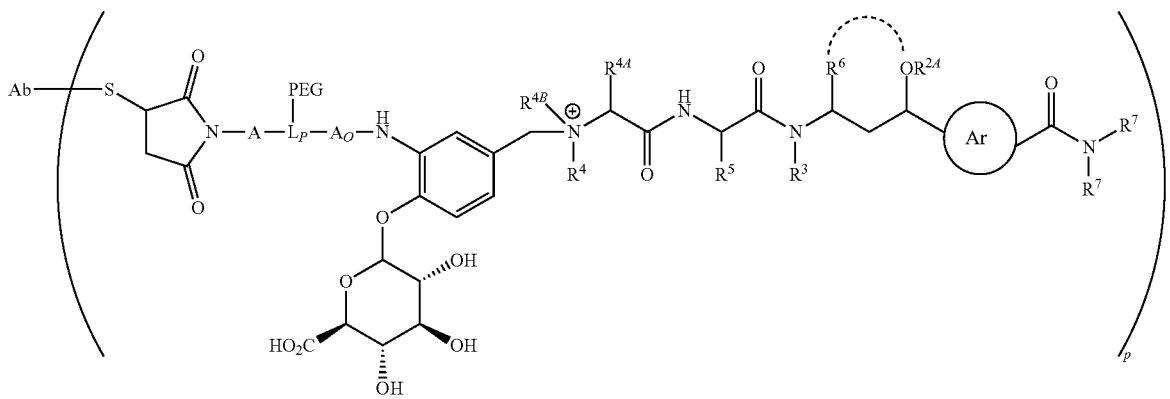

wherein S is a sulfur atom of the antibody Ligand Unit; $R^{2A}$ is hydrogen or optionally substituted alkyl, or $R^{2A}$ along with the oxygen atom to which it is attached defines an O-linked substituent other than —OH, or $R^{2A}$ is absent when $R^6$ is bonded to that oxygen atom, as indicated by the dash curved line, to define an oxygen-containing heterocycloalkyl; the circled Ar represents a 5-membered nitrogen-containing heteroarylene, wherein the indicated required substituents to that heteroaryl are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{2A}$ moiety in which $R^{2A}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached define a nitrogen quaternized heterocycloalkyl, optionally substituted; one $R^7$ is hydrogen or optionally substituted alkyl and the other $R^7$ is optionally substituted aralkyl or heteroaralkyl; and subscript p is a number ranging from 1 to 16.

29A. The Antibody Drug Conjugate of embodiment 28A having the structure of:

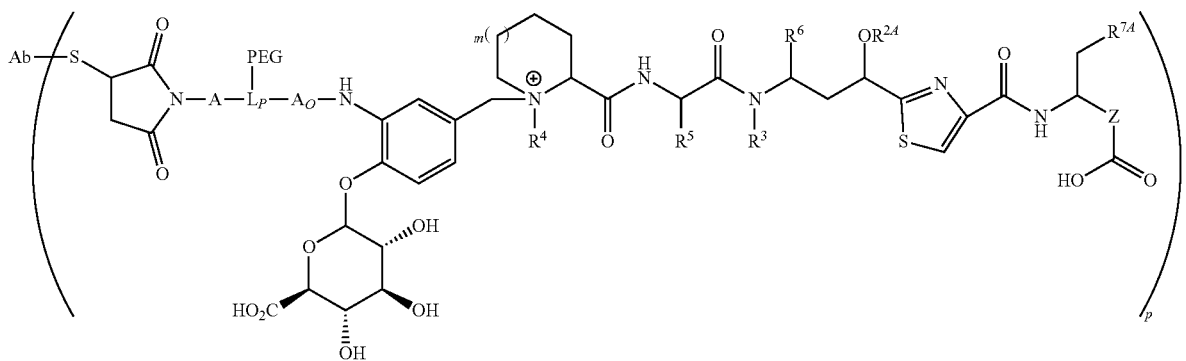

wherein subscript m is 0 or 1; subscript p is a number ranging from 1 to 8; Z is an optionally alkylene or an optionally substituted alkenylene; and $R^{7A}$ is optionally substituted aryl or optionally substituted heteroaryl.

30A. The Antibody Drug Conjugate of embodiment 29A having the structure of:

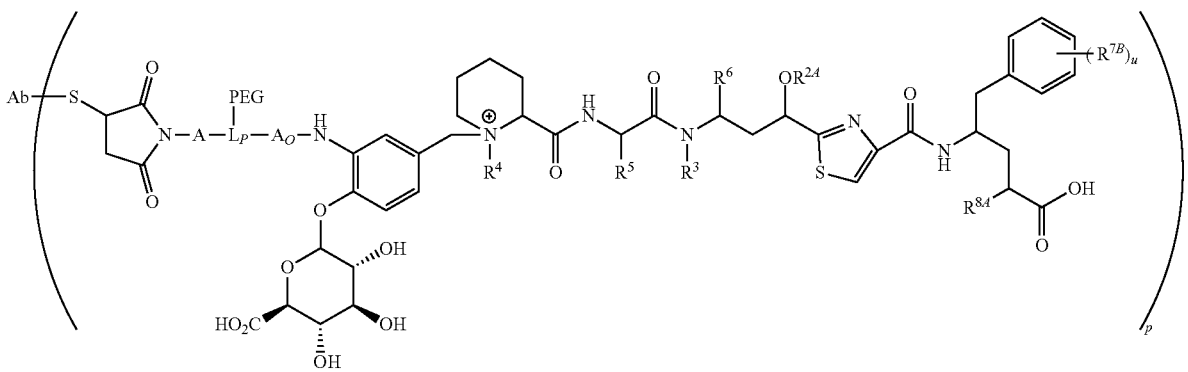

wherein $R^3$ is optionally substituted alkyl; $R^4$ is methyl; $R^5$ and $R^6$ are alkyl side chain residues of natural hydrophobic amino acids, independently selected; subscript p is a number ranging from 1 to 8; subscript u, indicating the number of $R^{7B}$ substituents, is 0, 1, 2 or 3; wherein each $R^{7B}$, when present, is an independently selected O-linked substituent; and $R^{8A}$ is hydrogen or optionally substituted alkyl.

31A. The Antibody Drug Conjugate of embodiment 30A having the structure of:

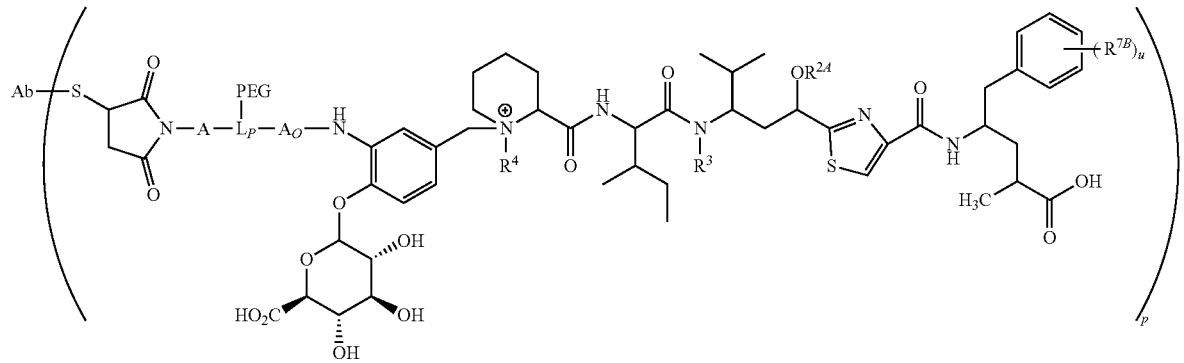

wherein $R^4$ is methyl; subscript u is 0, 1 or 2; $R^3$ is H, methyl, ethyl, propyl, —$CH_2$—$OC(O)R^{3A}$, —$CH_2CH(R^{3B})$$C(O)R^{3A}$ or —$CH(R^{3B})C(O)NHR^{3A}$, wherein $R^{3A}$ is $C_1$-$C_6$ alkyl and $R^{3B}$ is H or $C_1$-$C_6$ alkyl, independently selected from $R^{3A}$; $R^{2A}$ along with the oxygen atom to which it is attached is an O-linked substituent selected from the group consisting of —$OCH_2OCH_2R^{2B}$, —$OCH_2R^{2B}$, —$OC(O)R^{2B}$, —$CH_2OC(O)R^{2B}$, —$OC(O)N(R^{2B})(R^{2C})$, and —$OCH_2C(O)N(R^{2B})(R^{2C})$, wherein $R^{2B}$ and $R^{2C}$ are independently selected from the group consisting of H, $C_1$-$C_6$ alkyl and $C_2$-$C_6$ alkenyl; and each $R^{7B}$, when present, independently is —OH or —$OCH_3$.

32A. The Antibody Drug Conjugate of embodiment 28A having the structure of:

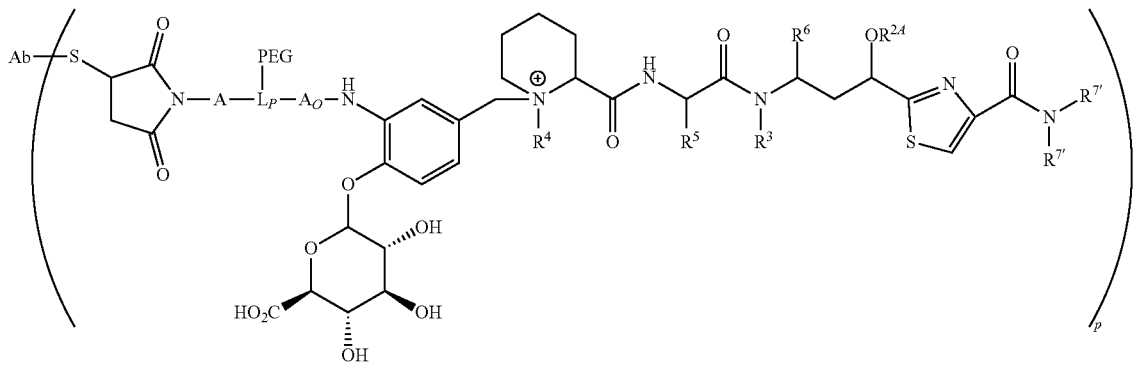

wherein $R^{2A}$ is hydrogen, an optionally substituted alkyl, saturated or unsaturated, or $R^2$ along with the oxygen atom to which it is attached defines an O-linked substituent other than —OH; $R^3$ is optionally substituted $C_1$-$C_6$ alkyl; $R^4$ is methyl; $R^5$ and $R^6$ are side chain residues of natural hydrophobic amino acids, independently selected; and the —N($R^{7'}$)($R^{7'}$) moiety is —NH($C_1$-$C_6$ alkyl) or —NH—N($C_1$-$C_6$ alkyl)$_2$, wherein one and only one $C_1$-$C_6$ alkyl is optionally substituted by —$CO_2H$, or an ester thereof, or by an optionally substituted phenyl.

33A. The Antibody Drug Conjugate of embodiment 32A wherein the —N($R^{7'}$)($R^{7'}$) moiety is selected from the group consisting of —NH($CH_3$), —NHCH$_2$CH$_2$Ph, and —NHCH$_2$—$CO_2H$, —NHCH$_2$CH$_2$CO$_2H$ and —NHCH$_2$CH$_2$CH$_2$CO$_2H$.

34A. The Antibody Drug Conjugate of embodiment 1A having the structure of:

than —OH, or $R^{2A}$ is absent when $R^6$ is bonded to that oxygen atom to define an oxygen-containing heterocycloalkyl as indicated by the dash curved line; the circled Ar represents a 5-membered nitrogen-heteroarylene, wherein the indicated required substituents to that heteroarylene are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{2A}$ moiety in which $R^{2A}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached define a nitrogen quaternized heterocycloalkyl, optionally substituted; one $R^7$ is hydrogen or optionally substituted

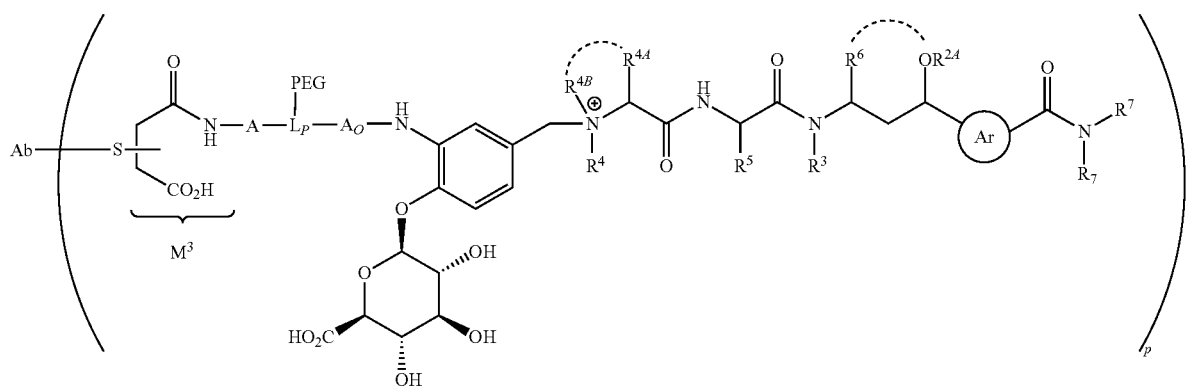

wherein S is a sulfur atom of the antibody Ligand Unit; the Ab-S— moiety is bonded to the carbon α or β to the indicated $M^3$ carboxylic acid; $R^{2A}$ is hydrogen or optionally substituted alkyl, or $R^{2A}$ along with the oxygen atom to which it is attached defines an O-linked substituent other alkyl and the other $R^7$ is optionally substituted aralkyl or heteroaralkyl; and subscript p is number ranging from 1 to 16.

35A. The Antibody Drug Conjugate of embodiment 31A having the structure of:

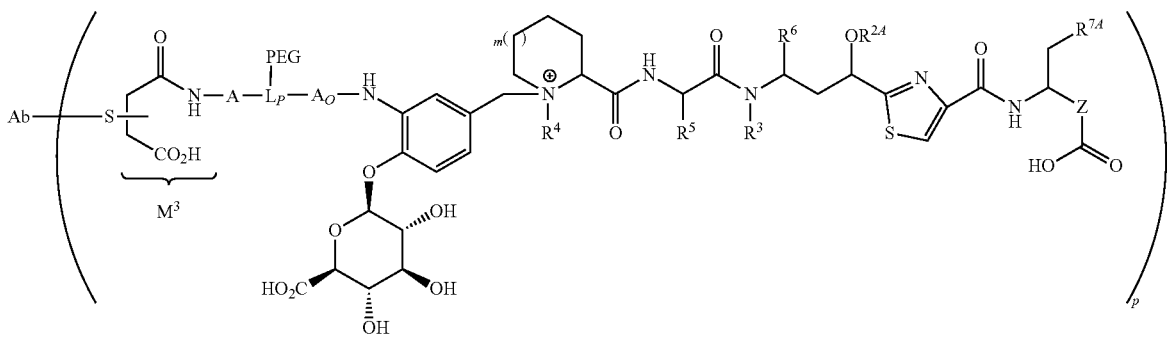

wherein subscript m is 0 or 1; Z is an optionally alkylene or an optionally substituted alkenylene; $R^{2A}$ is hydrogen or optionally substituted alkyl or $R^{2A}$ along with the oxygen atom to which it is attached defines an O-linked substituent other than —OH; $R^3$ is hydrogen or optionally substituted alkyl; $R^4$, $R^5$ and $R^6$ are optionally substituted alkyl, independently selected; and $R^{7A}$ is optionally substituted aryl or optionally substituted heteroaryl.

36A. The Antibody Drug Conjugate of embodiment 35A having the structure of:

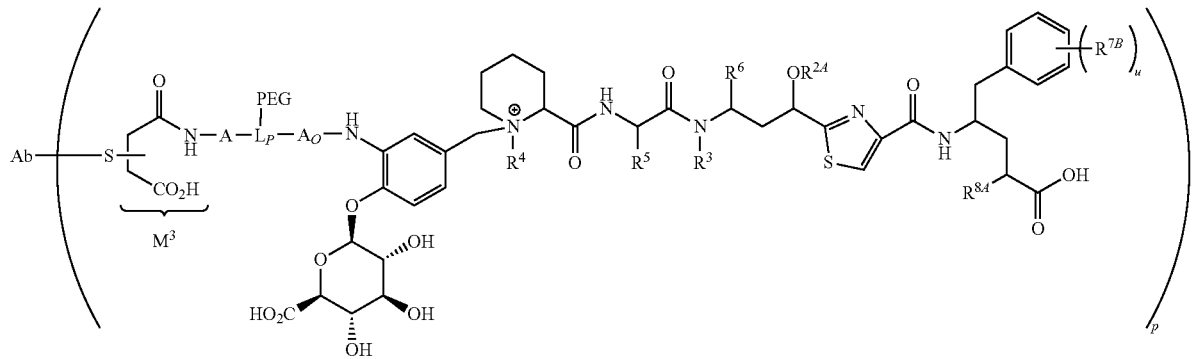

wherein $R^3$ is optionally substituted alkyl; $R^4$ is methyl; $R^5$ and $R^6$ are side chain residues of natural hydrophobic amino acids, independently selected; subscript p' is an integer ranging from 1 to 8; subscript u, indicating the number of $R^{7B}$ substituents, is 0, 1, 2 or 3, wherein each $R^{7B}$, when present, is an independently selected O-linked substituent; and $R^{8A}$ is hydrogen or optionally substituted alkyl.

37A. The Antibody Drug Conjugate of embodiment 36A having the structure of:

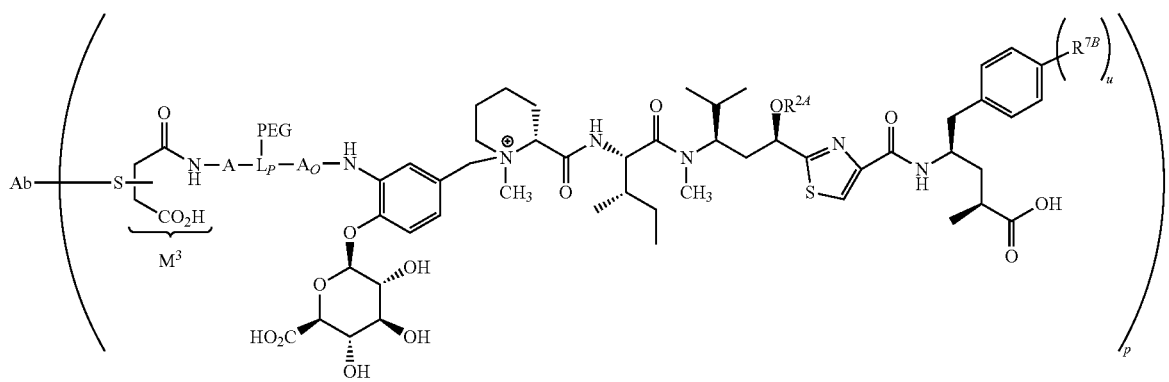

wherein subscript u is 0, 1 or 2; each $R^{7B}$, when present, is independently —OH or —OCH$_3$; and $R^{2A}$ is C$_1$-C$_6$ alkyl, —CH$_2$OR$^{2B}$, —CH$_2$R$^{2B}$, —C(=O)R$^{2B}$, —CH$_2$C(=O)R$^{2B}$, —C(=O)NHR$^{2B}$ or —CH$_2$C(=O)NHR$^{2B}$, wherein $R^{2B}$ is C$_1$-C$_6$ alkyl or C$_2$-C$_6$ alkenyl.

38A. The Antibody Drug Conjugate of embodiment 34A having the structure of:

39A. The Antibody Drug Conjugate of any one of embodiments 33A to 38A wherein $R^{2A}$ is C$_1$-C$_4$, saturated alkyl, C$_2$-C$_4$ unsaturated alkyl, —C(=O)R$^{2B}$, wherein $R^{2B}$ is C$_1$-C$_4$ alkyl; and subscript p is a number ranging from 1 to 8.

40A. The Antibody Drug Conjugate of embodiment 39A wherein $R^{2A}$ is saturated C$_1$-C$_4$ alkyl or unsaturated C$_3$-C$_4$

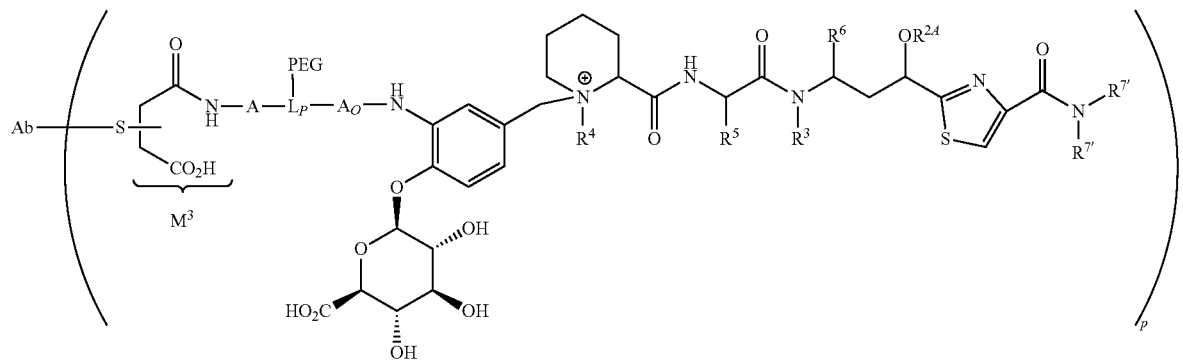

wherein $R^{2A}$ is hydrogen, an optionally substituted alkyl, saturated or unsaturated, or $R^2$ along with the oxygen atom to which it is attached defines an O-linked substituent other than —OH; $R^3$ is optionally substituted C$_1$-C$_6$ alkyl; $R^4$ is methyl; $R^5$ and $R^6$ are side chain residues of hydrophobic amino acids, preferably natural hydrophic amino acids, independently selected; and the —N(R$^{7'}$)(R$^{7'}$) moiety is —NH(C$_1$-C$_6$ alkyl) or —NH—N(C$_1$-C$_6$ alkyl)$_2$, wherein one and only one C$_1$-C$_6$ alkyl is optionally substituted by —CO$_2$H, or an ester thereof, or by an optionally substituted phenyl; and subscript p is a number ranging from 1 to 8.

alkyl, wherein saturated C$_1$-C$_4$ alkyl is —CH$_3$, —CH$_2$CH$_3$, —CH$_2$CH$_2$CH$_3$ and unsaturated C$_3$-C$_4$ alkyl is —CH$_2$CH=CH$_2$ or —CH(CH$_3$)CH=CH$_2$.

41A. The Antibody Drug Conjugate of any one of embodiments 1A to 40A wherein L$_P$ is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration 42A. The Antibody Drug Conjugate of embodiment 31A having the structure of:

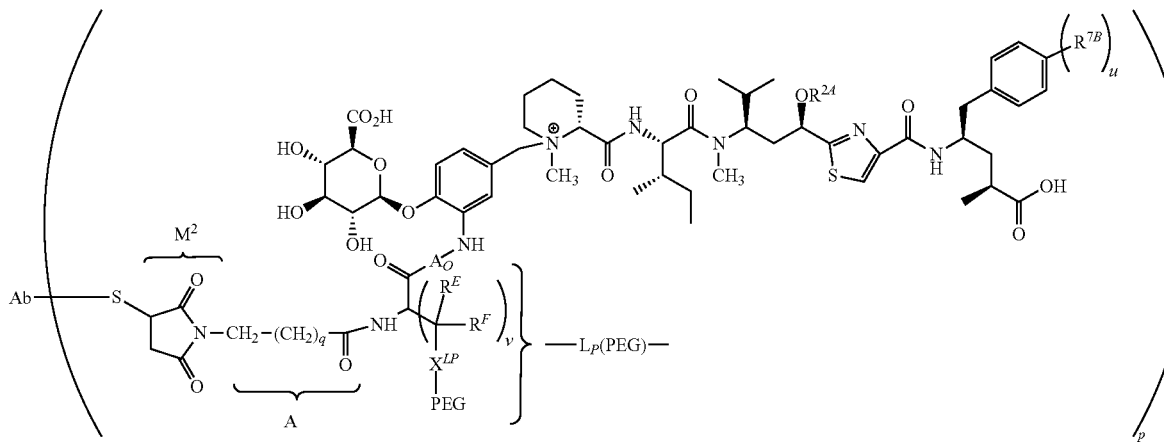

wherein $A_O$ is absent or is an amine-containing acid residue; subscript p is an number ranging from 1 to 8; subscript q is an integer ranging from 1 to 4; subscript u is 0 or 1; subscript v is an integer ranging from 1 to 4; $R^{7B}$, when present, is —OH; $X^{LP}$ is selected from the group consisting of —O—, —NH, —S— and —C(=O)—; and $R^E$ and $R^F$ are independently selected from the group consisting of —H, and $C_1$-$C_4$ alkyl; and subscript p is a number ranging from 1 to 8.

43A. The Antibody Drug Conjugate of embodiment 34A having the structure of:

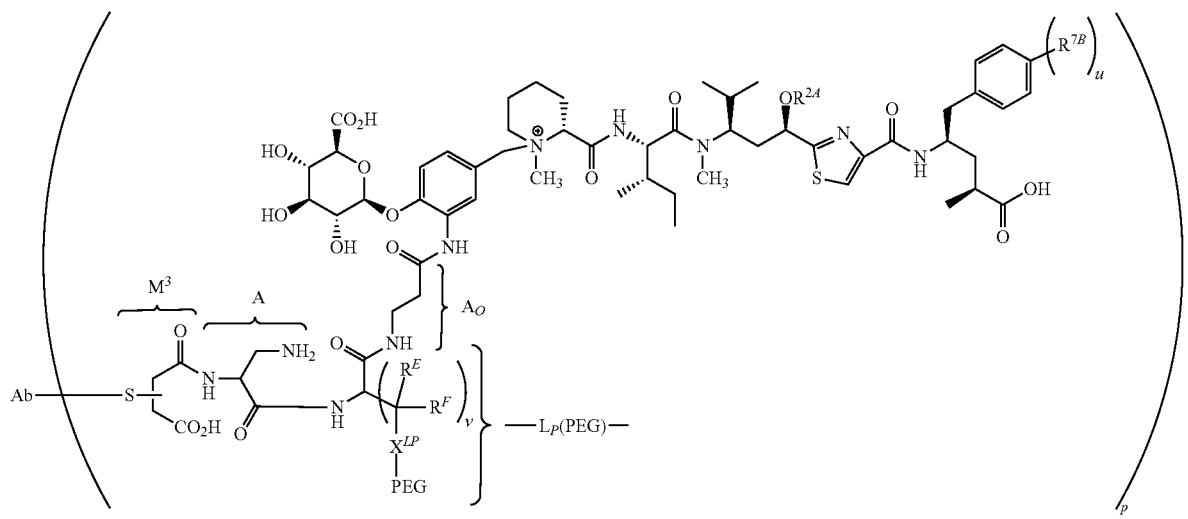

wherein $A_O$ is absent or is an amine-containing acid residue; subscript p is a number ranging from 1 to 8; subscript q is an integer ranging from 1 to 4; subscript u is 0 or 1; subscript v is an integer ranging from 1 to 4; $R^{7B}$, when present, is —OH; $X^{LP}$ is selected from the group consisting of —O—, —NH, —S— and —C(=O)—; and $R^E$ and $R^F$ are independently selected from the group consisting of —H, and —$C_1$-$C_4$ alkyl.

44A. The Antibody Drug Conjugate of any one of embodiments 34A to 41A wherein A is —$CH_2(CH_2)_4$(C=O)— or —$CH_2(CH_2)_4$(C=O)NHCH$_2$CH$_2$(C=O)—.

45A. The Antibody Drug Conjugate of any one of embodiments 34A to 39A, 42A and 43A wherein $R^{2A}$ is —C(O)CH$_3$.

46A. The Antibody Drug Conjugate of any one of embodiments 34A to 43A wherein $R^{2A}$ is ethyl.

47A. The Antibody Drug Conjugate of any one of embodiments 34A to 43A wherein $R^{2A}$ is —CH$_2$CH=CH$_2$.

48A. The Antibody Drug Conjugate of any one of embodiments 34A to 43A wherein $A_O$ is a β-amino acid residue.

49A. The Antibody Drug Conjugate of any one of embodiments 1A to 48A wherein PEG has the structure selected from the group consisting of:

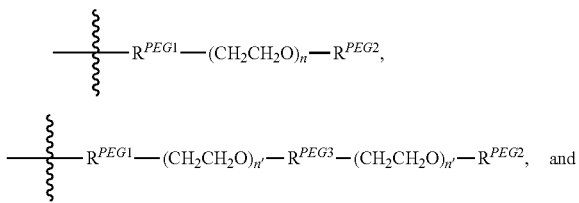

-continued

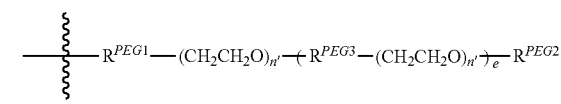

wherein the wavy line indicates site of attachment to $X^{LP}$ of the Parallel Connector Unit ($L_P$): $R^{PEG1}$ is an optional PEG Attachment Unit; $R^{PEG2}$ is a PEG Capping Unit; $R^{PEG3}$ is an PEG Coupling Unit; subscript n ranges from 2 to 72; each subscript n' is independently selected from 1 to 72; and subscript e ranges from 2 to 5.

50A. The Antibody Drug Conjugate of embodiment 42A or 43A wherein —$X^{LP}$—PEG has the structure of:

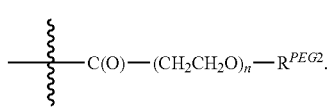

51A. The Antibody Drug Conjugate of embodiment 50A wherein subscript n is 12 and $R^{PEG2}$ is hydrogen or —CH$_3$.

52A. The Antibody Drug Conjugate of embodiment 1A having the structure of:

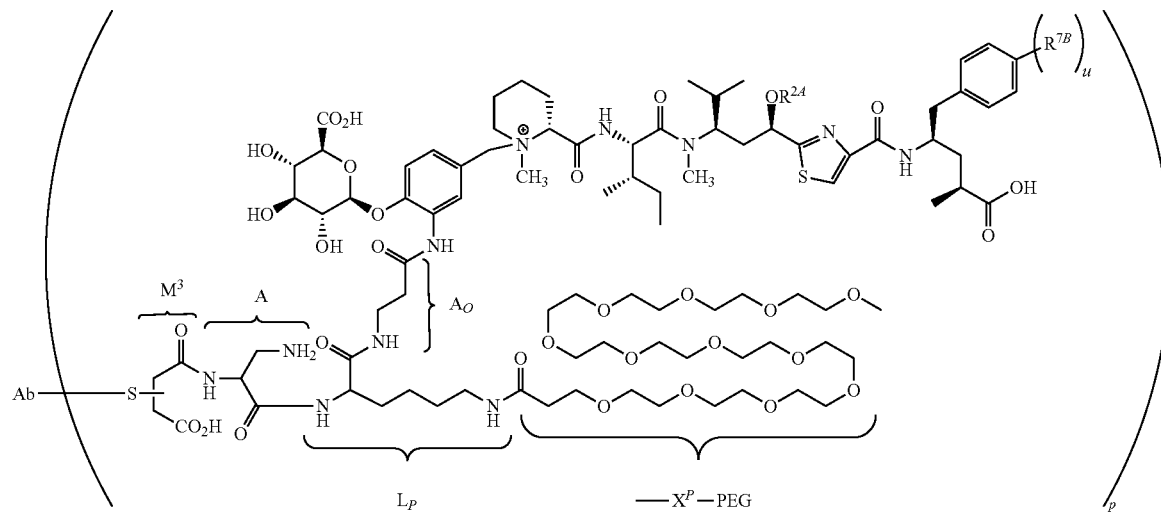

wherein Ab is an antibody Ligand Unit; S is a sulfur atom of the antibody Ligand Unit; the Ab-S— moiety is bonded to the carbon α or β to the indicated $M^3$ carboxylic acid; subscript u is 0 or 1; $R^{7B}$, when present, is —OH; and $R^{2A}$ along with the oxygen atom to which it is attached is —OC(O)CH$_3$, CH$_2$CH$_3$ or —CH$_2$CH=CH$_2$; and p is a number ranging from 1 to 8.

53A. A Drug Linker compound wherein the compound has the structure of Formula IA or Formula IC:

or one of Formula IIA-IIF:

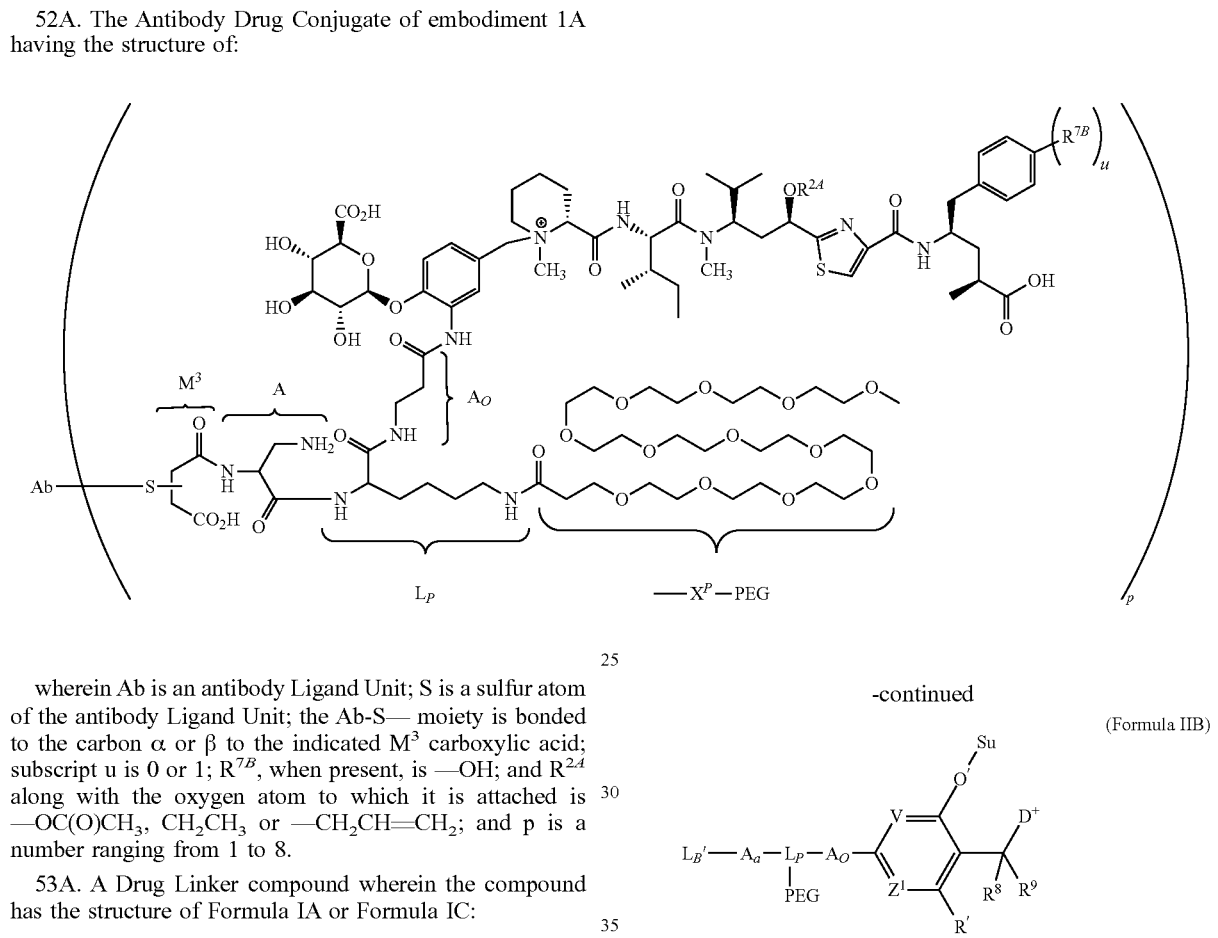

-continued

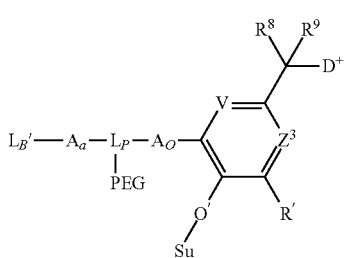

(Formula IIF)

wherein $L_B'$ is a Ligand Covalent Binding Unit precursor; $L_P$ is a Parallel Connector Unit; PEG is a Polyethylene Glycol Unit; subscripts a and b independently are 0 or 1; subscript n is 1, 2, 3 or 4; A is a first optional Stretcher Unit so that subscript a is 0 when A is absent or 1 when A is present and is optionally comprised of two, three or four independently selected subunits ($A_1$, $A_2$, $A_3$, $A_4$); B is an Branching Unit or a second optional Stretcher Unit ($A_O$) so that subscript b is 0 when B is absent or subscript b is 1 when B is present and is optionally comprised of two, three or four subunits independently of A, wherein subscript b is 1 and B is a Branching when subscript n is 2, 3 or 4 or subscript b is 0, or subscript b is 1 so that B is $A_O$, when subscript n is 1; Su is a carbohydrate moiety; —O'— represents an oxygen atom of an O-glycosidic bond cleavable by a glycosidase; -J'- represents a heteroatom, optionally substituted when nitrogen, from a functional group of B, when B or $A_O$ is present, or $L_P$, when B or $A_O$ is absent; V, $Z^1$, $Z^2$ and $Z^3$ are =N— or =C($R^{24}$)—, wherein $R^{24}$ is hydrogen or alkyl, alkenyl or alkynyl, optionally substituted, or halogen, —$NO_2$, —CN or other electron withdrawing group, an electron donating group, —O'-Su, or —C($R^8$)($R^9$)-$D^+$, wherein at least at least two of V, $Z^1$, $Z^2$ and $Z^3$ are =C($R^{24}$)—, provided, one any only one $R^{24}$ is —C($R^8$)($R^9$)-$D^+$ so that —C($R^8$)($R^9$)-$D^+$ is bonded to one of V, $Z^1$, $Z^2$, $Z^3$ when that variable group is =C($R^{24}$)— and one and only one other $R^{24}$ is so that —O'-Su is bonded to another one of V, $Z^1$, $Z^2$, $Z^3$ when that variable group is =C($R^{24}$)—, and the $Q^2$ and —C($R^8$)($R^9$)-$D^+$ substituents are ortho or para to each other; $R^8$ and $R^9$ independently are hydrogen, alkyl, alkenyl or alkynyl, optionally substituted, or aryl or heteroaryl, optionally substituted; R' is hydrogen or is halogen, —$NO_2$, —CN or other electron withdrawing group; $D^+$ is a quaternized tubulysin Drug Unit preferably having the structure of:

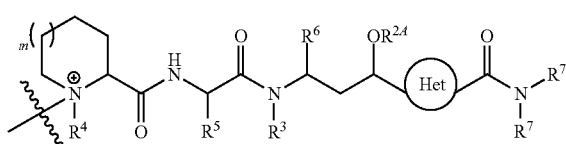

wherein the circle represents an 5-membered nitrogen-heteroarylene and wherein the indicated required substituents to that heteroarylene are in a 1,3-relationship with each other with optional substitution at the remaining positions; subscript m is 0 or 1; $R^{2A}$ is hydrogen or optionally substituted alkyl, or $R^{2A}$ along with the oxygen atom to which it is attached defines an O-linked substituent; $R^3$ is hydrogen or optionally substituted alkyl; $R^4$, $R^5$ and $R^6$ are optionally substituted alkyl; one $R^7$ is an optionally substituted alkyl, an optionally substituted arylalkyl, optionally substituted heteroarylalkyl and the other $R^7$ is hydrogen or an optionally substituted alkyl; and $R^{8A}$ is hydrogen or optionally substituted alkyl, wherein the wavy line indicates covalent bonding of the quaternized tubulysin Drug Unit to the remainder of the Drug Linker compound structures and wherein each optionally substituted alkyl is independently selected.

54A. The Drug Linker compound of embodiment 53A wherein —O'-Su has the structure of Formula 3:

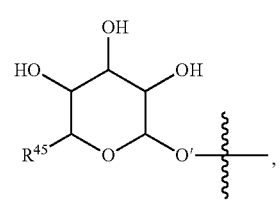

(Formula 3)

wherein the wavy line represents covalent bonding of O' to the remainder of the LDC structure; and $R^{45}$ is —$CH_2OH$ or —$CO_2H$.

55A. The Drug Linker compound of embodiment 54A having the structure of Formula IV:

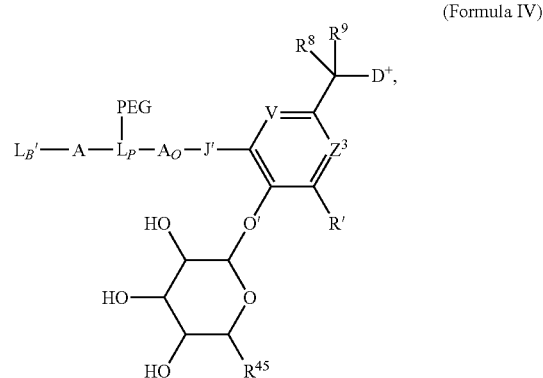

(Formula IV)

wherein J' is —N($R^{33}$)—, wherein $R^{33}$ is hydrogen or methyl; V and $Z^3$ independently are =CH— or =N—; R' is hydrogen or an electron withdrawing group; $R^8$ is hydrogen; $R^9$ is hydrogen, optionally substituted $C_1$-$C_6$ alkyl or optionally substituted phenyl; and $R^{45}$ is —$CO_2H$.

56A. The Drug Linker compound of embodiment 53A wherein a is 1; and $L_B'$-A- has the structure of Formula V:

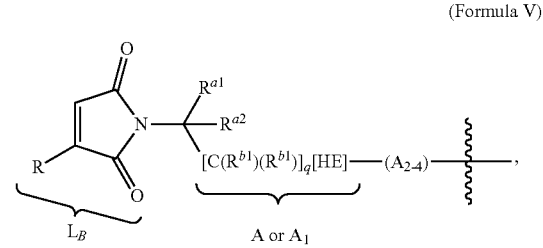

(Formula V)

wherein the —[C($R^{b1}$)($R^{b1}$)]$_q$—[HE]- moiety is A or $A_1$, wherein $A_1$ is a subunit of A; $A_{2-4}$ are optional subunits of A;

R is hydrogen or $C_1$-$C_4$ alkyl; $R^{a1}$ is hydrogen, optionally substituted alkyl or a Basic Unit (BU); and $R^{a2}$ is hydrogen or optionally substituted alkyl, or $R^{a1}$ and $R^{a2}$ together with the carbon atom to which they are attached defines a nitrogen-containing heterocycloalkyl; HE is an optional Hydrolysis Enhancer (HE) Unit; subscript q is an integer ranging from 0 to 6; each $R^{b1}$ independently is hydrogen, optionally substituted $C_1$-$C_6$ alkyl, optionally substituted aryl or optionally substituted heteroaryl, or two $R^{b1}$ together with the carbon(s) to which they are attached comprise a $C_3$-$C_6$ cycloalkyl or one $R^{b1}$ and HE together with the carbon to which they are attached define a 5 or 6-membered cycloalkyl or a 5- or 6-membered heterocycloalkyl and the other $R^{b1}$ is hydrogen, optionally substituted $C_1$-$C_6$ alkyl, optionally substituted aryl or optionally substituted heteroaryl; BU has the structure of —[C($R^1$)($R^1$)]—[C($R^2$)($R^2$)]r-N($R^{22}$)($R^{23}$), or an acid addition salt thereof, wherein subscript r is 0, 1, 2 or 3; each $R^1$ independently is hydrogen or $C_1$-$C_4$ alkyl or two $R^1$ together with the carbon to which they are attached comprise a $C_3$-$C_6$ cycloalkyl, and each $R^2$ independently is hydrogen, optionally substituted $C_1$-$C_6$ alkyl, optionally substituted aryl or optionally substituted heteroaryl, or two $R^2$ together with the carbon(s) to which they are attached and any intervening carbons define a $C_3$-$C_6$ cycloalkyl, or one $R^1$ and one $R^2$ together with the carbons to which they are attached and any intervening carbons define a 5- or 6-membered cycloalkyl and the remaining $R^1$ and $R^2$ are as defined; $R^{22}$ and $R^{23}$ independently are hydrogen or optionally substituted $C_1$-$C_6$ alkyl or together with the nitrogen to which they are attached define a 5- or 6-membered heterocycloalkyl, or one of $R^{22}$, $R^{23}$ is hydrogen and the other is an acid labile protecting group.

57A. The Drug Linker compound of embodiment 56A wherein Formula V has the structure of Formula VA:

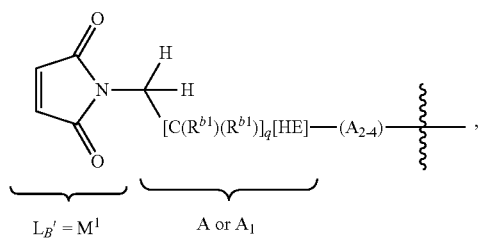

(Formula VA)

wherein subscript q is an integer ranging from 0 to 4.

58A. The Drug Linker compound of embodiment 56A wherein Formula V has the structure of Formula VB, or an acid addition salt thereof

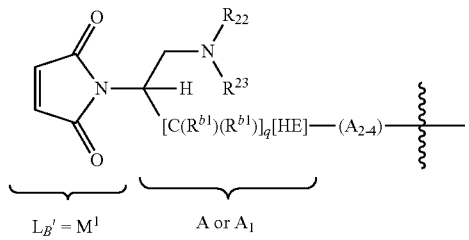

(Formula VB)

wherein $R^{22}$ and $R^{23}$ are each hydrogen or one of $R^{22}$, $R^{23}$ is hydrogen and the other is an acid labile carbamate protecting group; and subscript q is an integer ranging from 0 to 4.

59A. The Drug Linker compound of embodiment 57A or 58A wherein Formula VA or Formula VB has the structure of:

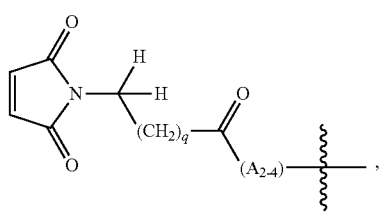

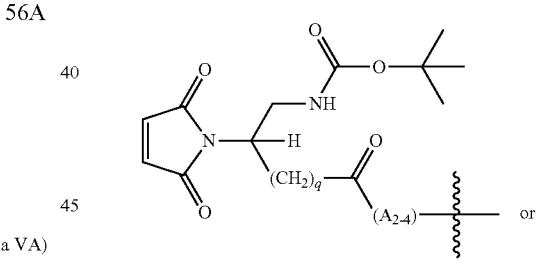

or

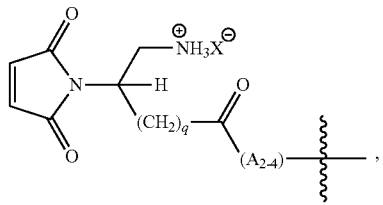

wherein $X^-$ is chloride, acetate, trifluoroacetate or dihydrogen phosphate.

60A. The Drug Linker compound of embodiment 56A having the structure of Formula VI:

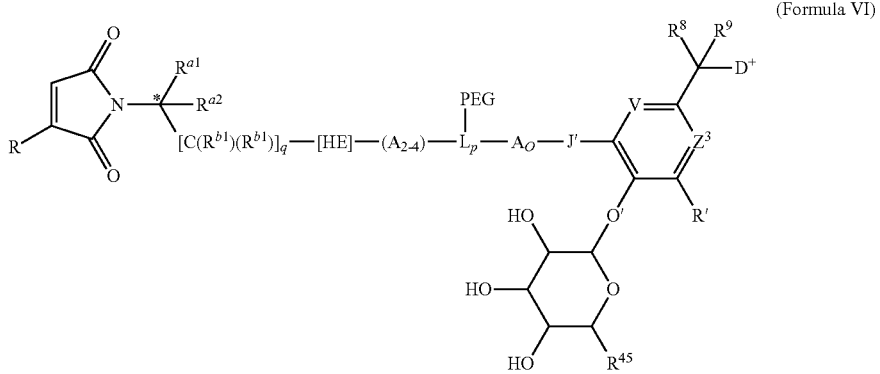

(Formula VI)

wherein the asterisk (*) designates chirality or absence thereof at the indicated carbon; $A_{2-4}$ are independently selected optional subunits of A, wherein —[C($R^{b1}$)($R^{b1}$)]$_q$—[HE]- is $A_1$ when one or more such subunits are present; R is hydrogen; R' is hydrogen or an electron withdrawing group; $R^{a1}$ is hydrogen or a basic unit (BU) wherein BU is a Basic Unit having the structure of —$CH_2$—N($R^{22}$)($R^{23}$), or an acid addition salt thereof, wherein $R^{22}$ and $R^{23}$ independently are hydrogen, methyl or ethyl or both together with the nitrogen atom to which they are attached comprise a 5- or 6-membered heterocycloalkyl, or one of $R^{22}$, $R^{23}$ is hydrogen and the other is an acid labile carbamate protecting group; $R^{a2}$ is hydrogen; subscript q is an integer ranging from 0 to 5 when HE is present or 1 to 5 when HE is absent; each $R^{b1}$ independently is hydrogen or optionally substituted $C_1$-$C_6$ alkyl; HE is absent or is —C(=O)—; $R^{45}$ is —$CO_2$H; J' is —NH—; V and $Z^3$ are each =$CH_2$—; $R^8$ is hydrogen; and $R^9$ is hydrogen or methyl.

61A. The Drug Linker compound of embodiment 60A wherein the indicated starred (*) carbon is predominantly in the same absolute configuration as the alpha carbon of an L-amino acid when that indicated carbon is chiral.

62A. The Drug Linker compound of any one of embodiments 53A to 61A, wherein A, $A_O$, and each of $A_2$-4, when present, independently have the structure of Formula 7 or Formula 8:

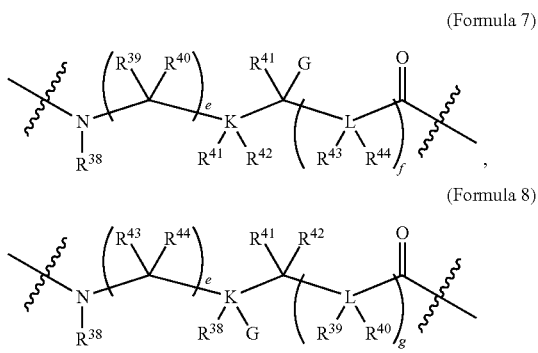

(Formula 7)

(Formula 8)

wherein the wavy lines indicated covalent attachment within the remainder of the Drug Linker compound structure, wherein K and L independently are C, N, O or S, provided that when K or L is O or S, $R^{41}$ and $R^{42}$ to K or $R^{43}$ and $R^4$ to L are absent, and when K or L are N, one of $R^{41}$, $R^{42}$ to K or one of $R^{42}$, $R^{43}$ to L are absent, and provided that no two adjacent L are independently selected as N, O, or S; wherein subscripts e and f are independently selected integers that range from 0 to 12, and subscript g is an integer ranging from 1 to 12; G is hydrogen, optionally substituted $C_1$-$C_6$ alkyl, —OH, —$OR^{PR}$, —$CO_2$H, $CO_2R^{PR}$, wherein $R^{PR}$ is a suitable protecting, —N($R^{PR}$)($R^{PR}$), wherein $R^{PR}$ are independently a protecting group or $R^{PR}$ together form a suitable protecting group, or —N($R^{45}$)($R^{46}$), wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl; wherein $R^{38}$ is hydrogen or optionally substituted $C_1$-$C_6$ alkyl; $R^{39}$-$R^{44}$ independently are hydrogen, optionally substituted $C_1$-$C_6$ alkyl, optionally substituted aryl, or optionally substituted heteroaryl, or both $R^{39}$, $R^{40}$ together with the carbon to which they are attached comprise a $C_3$-$C_6$ cycloalkyl, or $R^{41}$, $R^{42}$ together with K to which they are attached when K is C, or $R^{43}$, $R^{44}$ together with L to which they are attached when L is a carbon atom comprise a $C_3$-$C_6$ cycloalkyl, or $R^{40}$ and $R^{41}$, or $R^{40}$ and $R^{43}$, or $R^{41}$ and $R^{43}$ to together with the carbon atom or heteroatom to which they are attached and the atoms intervening between those carbon atoms and/or heteroatoms comprise a 5- or 6-membered cycloalkyl or heterocycloalkyl, provided that when K is O or S, $R^{41}$ and $R^{42}$ are absent, when K is N, one of $R^{41}$, $R^{42}$ is absent, when L is O or S, $R^{43}$ and $R^{44}$ are absent, and when L is N, one of $R^{43}$, $R^{44}$ is absent, or wherein $A_O$ has a structure corresponding to an alpha-amino, beta-amino or another amine-containing acid.

63A. The Antibody Drug Conjugate of any one of embodiments 53A to 62A wherein $D^+$ is a quaternized tubulysin Drug Unit (-$D^+$) preferably having the structure of

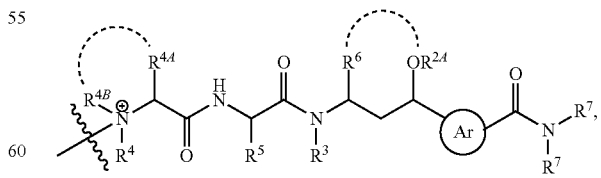

wherein $R^{24}$ is hydrogen or optionally substituted alkyl, or $R^{24}$ along with the oxygen atom to which it is attached defines an O-linked substituent other than —OH, or $R^{24}$ is absent when $R^6$ is bonded to that oxygen atom, as indicated by the curved dash line between $R^6$ and the oxygen atom, to define an oxygen-containing heterocycloalkyl; the circled Ar represents a 5-membered nitrogen-heteroarylene, wherein the indicated required substituents to that heteroarylene are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{2A}$ moiety in which $R^{2A}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached, as indicated by the curved dotted line between $R^{4A}$ and $R^{4B}$, define a quaternized nitrogen heterocycloalkyl, optionally substituted; one $R^7$ is hydrogen or optionally substituted alkyl and the other $R^7$ is optionally substituted aralkyl or heteroaralkyl; wherein the wavy line indicates covalent bonding to the remainder of the Drug Linker compound structure.

64A. The Drug Linker compound of embodiment 63A wherein the quaternized tubulysin Drug Unit (-D$^+$) has the structure of:

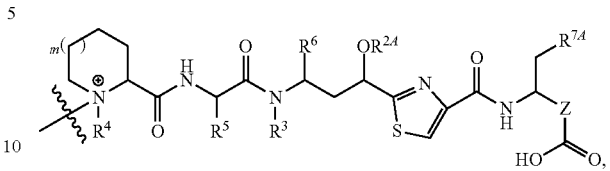

wherein subscript m is 0 or 1; Z is an optionally substituted alkylene or an optionally substituted alkenylene; and $R^{7A}$ is optionally substituted aryl or optionally substituted heteroaryl.

65A. The Drug Linker compound of embodiment 64A wherein the quaternized tubulysin Drug Unit (-D$^+$) has the structure of:

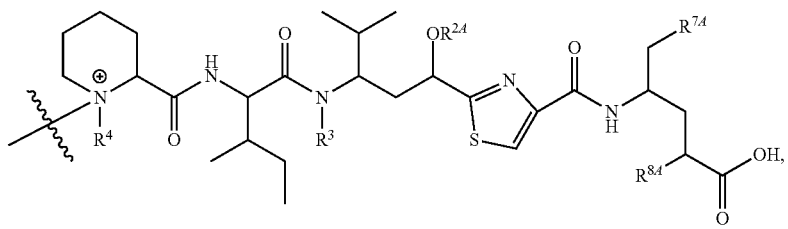

wherein R is optionally substituted phenyl and R is hydrogen or methyl.

66A. The Drug Linker compound of embodiment 14A wherein the quaternized tubulysin Drug Unit (-D$^+$) has the structure of:

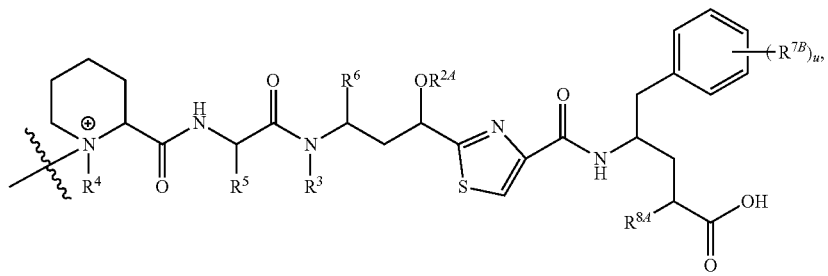

wherein $R^5$ and $R^6$ are alkyl side chain residues of natural hydrophobic amino acids, independently selected; subscript u, indicating the number of $R^{7B}$ substituents, is 0, 1, 2 or 3; each $R^{7B}$, when present, is an independently selected O-linked substituent; and $R^{8A}$ is hydrogen or optionally substituted alkyl.

67A. The Drug Linker compound of embodiment 65A wherein the quaternized tubulysin Drug Unit (-D) has the structure of

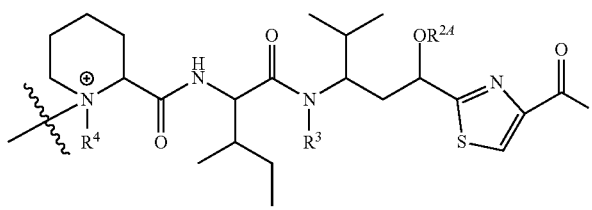

wherein $R^4$ is methyl; subscript u is 0, 1 or 2; $R^3$ is H, methyl, ethyl, propyl, —CH$_2$—OC(O)R$^{3A}$, —CH$_2$CH(R$^{3B}$)C(O)R$^{3A}$ or —CH(R$^{3B}$)C(O)NHR$^{3A}$, wherein R$^{3A}$ is C$_1$-C$_6$ alkyl and R$^{3B}$ is H or C$_1$-C$_6$ alkyl, independently selected from R$^{3A}$; R$^{2A}$ along with the oxygen atom to which it is attached is an O-linked substituent selected from the group consisting of —OCH$_2$OCH$_2$R$^{2B}$, —OCH$_2$R$^{2B}$, —OC(O)R$^{2B}$, —CH$_2$OC(O)R$^{2B}$, —OC(O)N(R$^{2B}$)(R$^{2C}$), and —OCH$_2$C(O)N(R$^{2B}$)(R$^{2C}$), wherein R$^{2B}$ and R$^{2C}$ are independently selected from the group consisting of H, C$_1$-C$_6$ alkyl and C$_2$-C$_6$ alkenyl; and each R$^{7B}$, when present, independently is —OH or —OCH$_3$.

18A. The Drug Linker compound of embodiment 13A wherein the quaternized tubulysin Drug Unit (-D$^+$) has the structure of

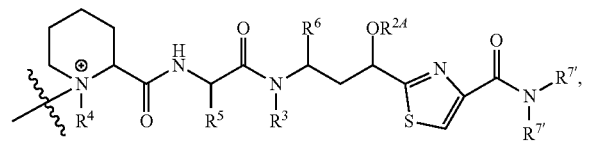

wherein $R^{2A}$ is hydrogen, an optionally substituted alkyl, saturated or unsaturated, or $R^2$ along with the oxygen atom to which it is attached defines an O-linked substituent other than —OH; $R^3$ is optionally substituted C$_1$-C$_6$ alkyl; $R^4$ is methyl; $R^5$ and $R^6$ are alkyl side chain residues of natural hydrophobic amino acids; and the —N(R$^{7'}$)(R$^{7'}$) moiety is —NH(C$_1$-C$_6$ alkyl), wherein C$_1$-C$_6$ alkyl is optionally substituted by —CO$_2$H, or an ester thereof, or by an optionally substituted phenyl, or is —NH—N(C$_1$-C$_6$ alkyl)$_2$, wherein one and only one C$_1$-C$_6$ alkyl is optionally substituted by —CO$_2$H, or an ester thereof, or by an optionally substituted phenyl.

69A. The Drug Linker compound of embodiment 68A wherein the —N(R$^{7'}$)(R$^{7'}$) moiety is selected from the group consisting of —NH(CH$_3$), —NHCH$_2$CH$_2$Ph, —NHCH$_2$—CO$_2$H, —NHCH$_2$CH$_2$CO$_2$H and —NHCH$_2$CH$_2$CH$_2$CO$_2$H.

70A. The Drug Linker compound of any one of embodiments 61A to 68A, wherein $R^{2A}$ is —CH$_2$CH$_3$.

71A. The Drug Linker compound of any one of embodiments 61A to 68A wherein $R^{2A}$ is —CH$_2$—CH=CH$_2$.

72A. The Drug Linker compound of any one of embodiment 67A or 68A wherein $R^{2A}$ is —CH$_2$CH$_3$, —CH$_2$—CH=CH$_2$ or —CH$_2$C(CH$_3$)=CH$_2$, $R^{2B}$ is —CH$_3$, $R^3$ is —CH$_3$ and subscript u is 0.

73A. The Drug Linker compound of embodiment 67A or 68A wherein $R^{2A}$ is —CH$_2$CH$_3$ or —CH$_2$—CH=CH$_2$, or —CH$_2$C(CH$_3$)=CH$_2$, $R^{2B}$ is —CH$_3$, $R^3$ is —CH$_3$ and subscript u is 1, wherein $R^{7B}$ is —OH.

74A. The Drug Linker compound of any one of embodiments 53A to 73A wherein L$_P$ is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the sulfur substituent is in reduced or oxidized form.

75A. The Drug Linker compound of any one of embodiments 53A to 73A wherein L$_P$ is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

76A. The Drug Linker compound of embodiment 74A wherein the aminoalkanedioic acid, diaminoalkanoic acid, sulfur-substituted aminoalkanoic acid or hydroxyl substituted aminoalkanoic acid residue has the structure of Formula A or Formula B:

(Formula A)

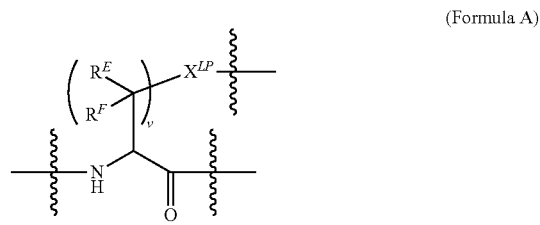

77A. The Drug Linker compound of any one of embodiments 53A to 60A wherein -L$_P$(PEG)- has the structure of Formula A1 or A2:

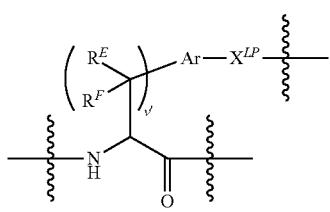

(Formula B)

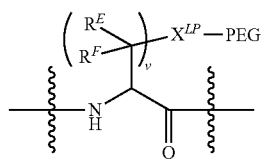

(Formula A1)

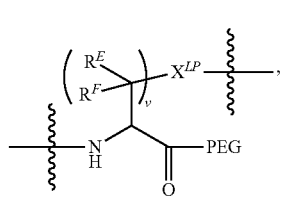

(Formula A2)

wherein subscript v is an integer ranging from 1 to 4; subscript v' is an integer ranging from 0 to 4; $X^{LP}$ is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N(R$^{LP}$)—, and —N(R$^{LP}$)C(=NR$^{LP}$)N(R$^{LP}$)— wherein each R$^{LP}$ is independently selected from the group consisting of hydrogen and optionally substituted alkyl or two of R$^{LP}$ together along with their intervening atoms define a heterocycloalkyl and any remaining R$^{LP}$ are as previously defined; Ar is an arylene or heteroarylene, optionally substituted; each R$^E$ and R$^F$ is independently selected from the group consisting of —H, optionally substituted alkyl, optionally substituted aryl and optionally substituted heteroaryl, or R$^E$ and R$^F$ together with the same carbon to which they are attached, or R$^E$ and R$^F$ from adjacent carbons together with these carbons, defines a optionally substituted cycloalkyl with any remaining R$^E$ and R$^F$ substituents as previously defined; and wherein the wavy lines indicates covalent attachment of the Formula A or Formula B structure within the Drug Linker compound structure.

wherein $X^{LP}$ is selected from the group consisting of —O—, —NH, —S— and —C(=O)—; R$^E$ and R$^F$ are independently selected from the group consisting of —H, and —C$_1$-C$_4$ alkyl; and wherein the wavy line indicates covalent attachment of Formula A1 or Formula A2 within the Drug Linker compound structure.

78A. The Drug Linker compound of embodiment 1A having the structure of:

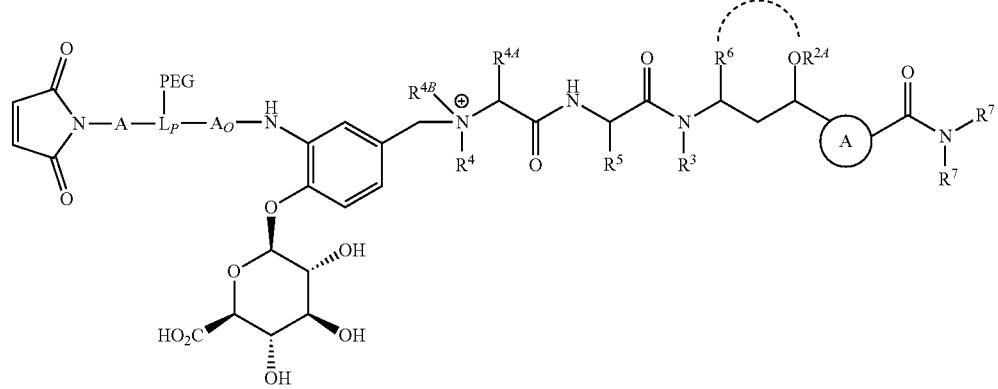

wherein $R^4$ is hydrogen or optionally substituted alkyl, or $R^2$ along with the oxygen atom to which it is attached defines an O-linked substituent other than —OH, or $R^{2A}$ is absent when $R^6$ is bonded to that oxygen atom, as indicated by the dash curved line, to define an oxygen-containing heterocycloalkyl; the circled Ar represents a 5-membered nitrogen-containing heteroarylene, wherein the indicated required substituents to that heteroaryl are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{2A}$ moiety in which $R^{2A}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached define a nitrogen quaternized heterocycloalkyl, optionally substituted; and one $R^7$ is hydrogen or optionally substituted alkyl and the other $R^7$ is optionally substituted aralkyl or heteroaralkyl.

79A. The Drug Linker compound of embodiment 78A having the structure of:

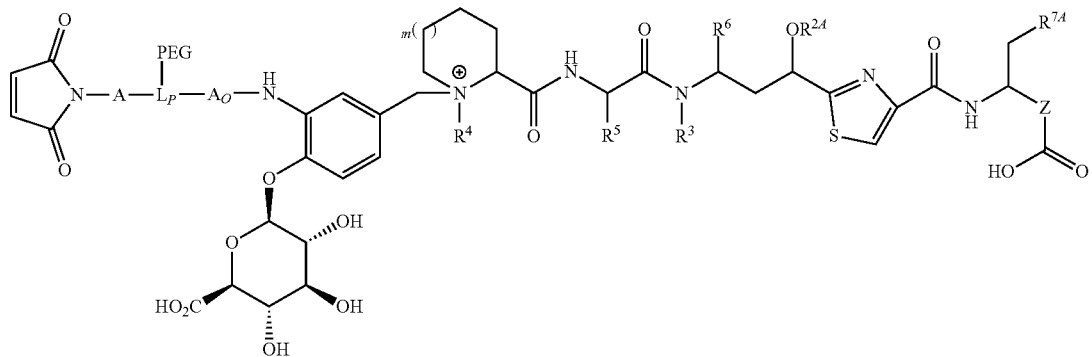

wherein subscript m is 0 or 1; subscript p is a number ranging from 1 to 8; Z is an optionally alkylene or an optionally substituted alkenylene; and $R^{7A}$ is optionally substituted aryl or optionally substituted heteroaryl.

80A. The Drug Linker compound of embodiment 79A having the structure of:

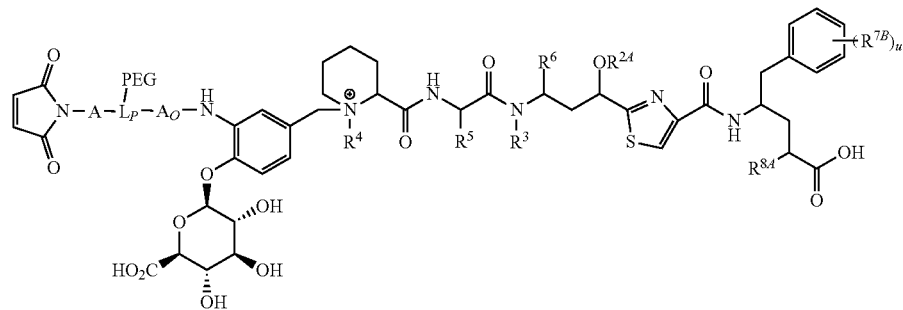

$R^3$ is optionally substituted alkyl; $R^4$ is methyl; $R^5$ and $R^6$ are alkyl side chain residues of hydrophobic amino acids, preferably natural hydrophobic amino acids, independently selected; subscript p is a number ranging from 1 to 8; subscript u, indicating the number of $R^{7B}$ substituents, is 0, 1, 2 or 3; wherein each $R^{7B}$, when present, is an independently selected O-linked substituent; and $R^{8A}$ is hydrogen or optionally substituted alkyl.

81A. The Drug Linker compound of embodiment 80A having the structure of:

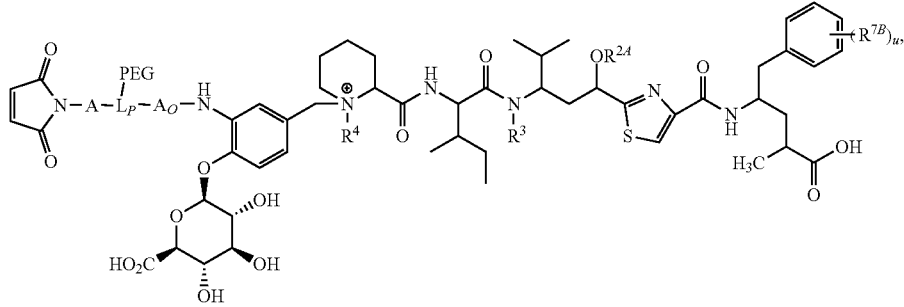

wherein $R^4$ is methyl; subscript u is 0, 1 or 2; $R^3$ is H, methyl, ethyl, propyl, —$CH_2$—OC(O)$R^{3A}$, —$CH_2$CH($R^{3B}$)C(O)$R^{3A}$ or —CH($R^{3B}$)C(O)NHR$^{3A}$, wherein $R^{3A}$ is $C_1$-$C_6$ alkyl and $R^{3B}$ is H or $C_1$-$C_6$ alkyl, independently selected from $R^{3A}$; $R^{2A}$ along with the oxygen atom to which it is attached is an O-linked substituent selected from the group consisting of —OCH$_2$OCH$_2$R$^{2B}$, —OCH$_2$R$^{2B}$, —OC(O)R$^{2B}$, —CH$_2$OC(O)R$^{2B}$, —OC(O)N(R$^{2B}$)(R$^{2C}$), and —OCH$_2$C(O)N(R$^{2B}$)(R$^{2C}$), wherein $R^{2B}$ and $R^{2C}$ are independently selected from the group consisting of H, $C_1$-$C_6$ alkyl and $C_2$-$C_6$ alkenyl; and each $R^{7B}$, when present, independently is —OH or —OCH$_3$.

82A. The Drug Linker compound of embodiment 78A having the structure of:

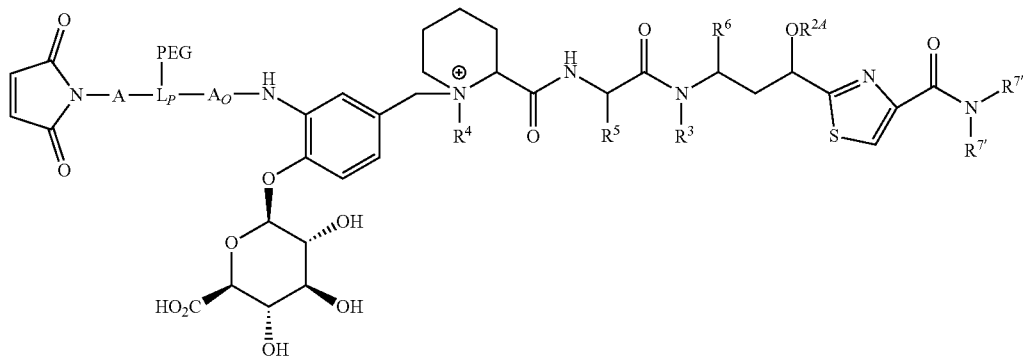

wherein $R^{2A}$ is hydrogen, an optionally substituted alkyl, saturated or unsaturated, or $R^2$ along with the oxygen atom to which it is attached defines an O-linked substituent other than —OH; $R^3$ is optionally substituted $C_1$-$C_6$ alkyl; $R^4$ is methyl; $R^5$ and $R^6$ are side chain residues of hydrophobic amino acids, preferably natural hydrophobic amino acids, independently selected; and the —N(R$^{7'}$)(R$^{7'}$) moiety is —NH(C$_1$-C$_6$ alkyl), wherein C$_1$-C$_6$ alkyl is optionally substituted by —CO$_2$H, or an ester thereof, or by an optionally substituted phenyl, or is —NH—N(C$_1$-C$_6$ alkyl)$_2$, wherein one and only one C$_1$-C$_6$ alkyl is optionally substituted by —CO$_2$H, or an ester thereof, or by an optionally substituted phenyl.

83A. The Drug Linker compound of embodiment 82A wherein the —N(R$^{7'}$)(R$^{7'}$) moiety is selected from the group consisting of —NH(CH$_3$), —NHCH$_2$CH$_2$Ph, and —NHCH$_2$—CO$_2$H, —NHCH$_2$CH$_2$CO$_2$H and —NHCH$_2$CH$_2$CH$_2$CO$_2$H.

84A. The Drug Linker compound of any one of embodiments 72A to 83A wherein $R^{2A}$ is $C_1$-$C_4$, saturated alkyl, $C_2$-$C_4$ unsaturated alkyl, —C(=O)R$^{2B}$, wherein $R^{2B}$ is $C_1$-$C_4$ alkyl.

85A. The Drug Linker compound of embodiment 84A wherein $R^{2A}$ is saturated $C_1$-$C_4$ alkyl or unsaturated $C_3$-$C_4$ alkyl, wherein saturated $C_1$-$C_4$ alkyl is —CH$_3$, —CH$_2$CH$_3$, —CH$_2$CH$_2$CH$_3$ and unsaturated $C_3$-$C_4$ alkyl is —CH$_2$CH=CH$_2$ or —CH(CH$_3$)CH=CH$_2$.

86A. The Drug Linker compound of any one of embodiments 53A to 85A wherein $L_P$ is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

87A. The Drug Linker compound of embodiment 81A having the structure of:

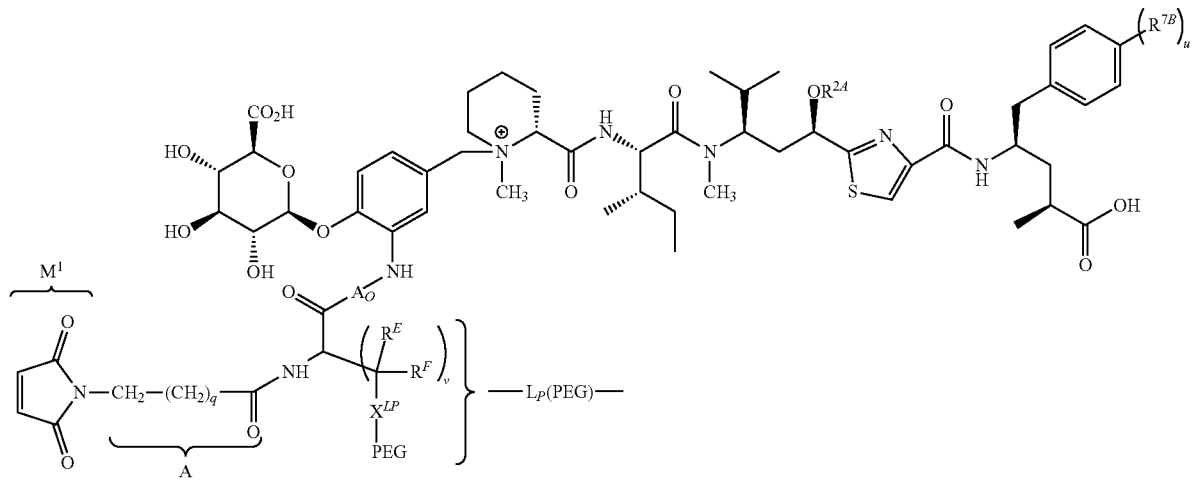

wherein $A_O$ is absent or is an amine-containing acid residue; subscript p is an number ranging from 1 to 8; subscript q is an integer ranging from 1 to 4; subscript u is 0 or 1; subscript v is an integer ranging from 1 to 4; $R^{7B}$, when present, is —OH; $X^{LP}$ is selected from the group consisting of —O—, —NH, —S— and —C(=O)—; and $R^E$ and $R^F$ are independently selected from the group consisting of —H, and $C_1$-$C_4$ alkyl.

88A. The Drug Linker compound of embodiment 81A having the structure of:

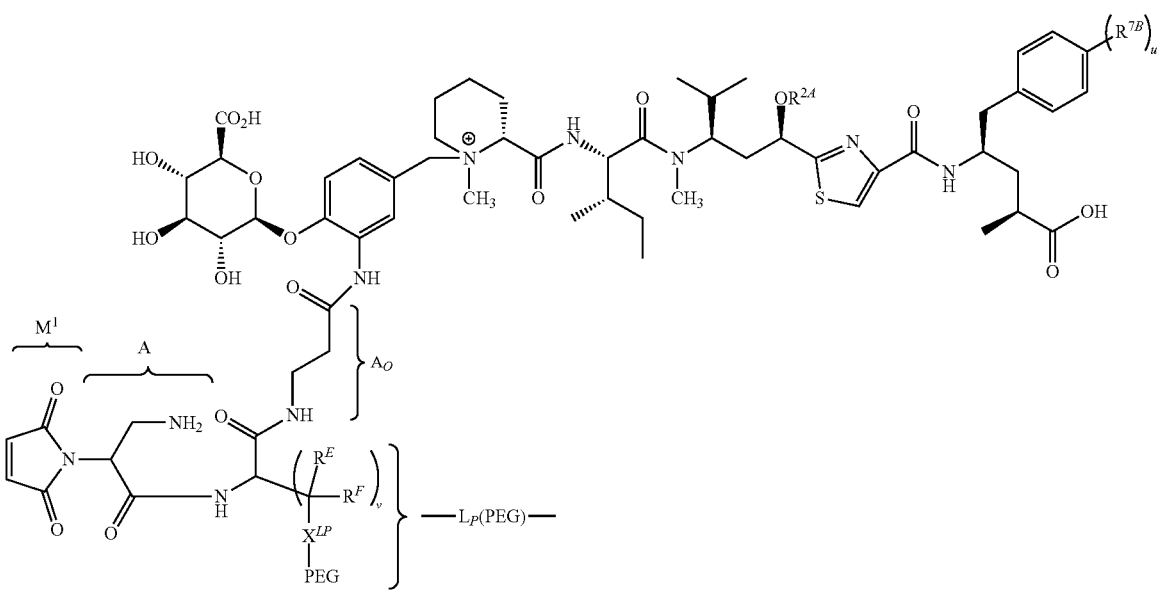

wherein $A_O$ is absent or is an amine-containing acid residue; subscript q is an integer ranging from 1 to 4; subscript u is 0 or 1; subscript v is an integer ranging from 1 to 4; $R^{7B}$, when present, is —OH; $X^{LP}$ is selected from the group consisting of —O—, —NH, —S— and —C(=O)—; and $R^E$ and $R^F$ are independently selected from the group consisting of —H, and —$C_1$-$C_4$ alkyl.

89A. The Drug linker compound of any one of embodiments 73A to 86A wherein A is —$CH_2(CH_2)_4$(C=O)— or —$CH_2(CH_2)_4$(C=O)$NHCH_2CH_2$(C=O)—.

89A. The Drug linker compound of any one of embodiments 78A to 84A, 87A and 88A wherein $R^{2A}$ is —C(=O)$CH_3$.

90A. The Drug linker compound of any one of embodiments 78A to 88A wherein $R^{2A}$ is ethyl.

91A. The Drug linker compound of any one of embodiments 78A to 88A wherein $R^{2A}$ is —$CH_2CH$=$CH_2$.

92A. The Drug linker compound of any one of embodiments 78A to 87A wherein $A_O$ is a β-amino acid residue.

93A. The Drug linker compound of any one of embodiments 53A to 92A wherein PEG has the structure selected from the group consisting of:

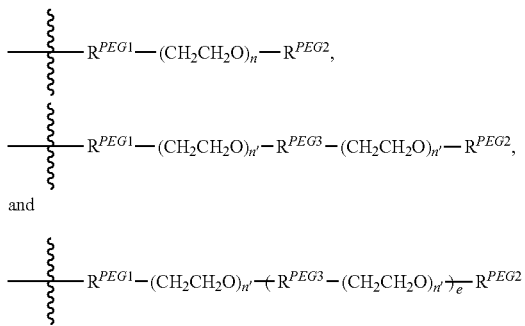

and

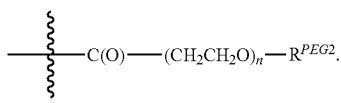

wherein the wavy line indicates site of attachment to $X^{LP}$ of the Parallel Connector Unit ($L_P$): $R^{PEG1}$ is an optional PEG Attachment Unit; $R^{PEG2}$ is a PEG Capping Unit; $R^{PEG3}$ is an PEG Coupling Unit; subscript n ranges from 2 to 72; each subscript n' is independently selected from 1 to 72; and subscript e ranges from 2 to 5.

94A. The Drug linker compound of embodiment 87A or 88A wherein —$X^{LP}$ PEG has the structure of:

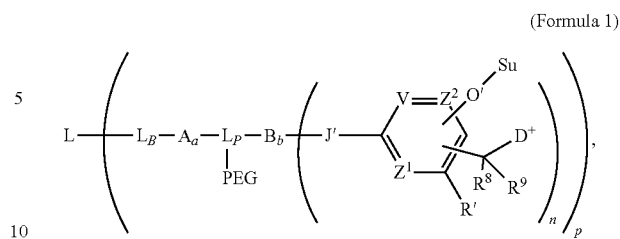

95A. The Drug linker compound of embodiment 94A wherein subscript n is 12 and $R^{PEG2}$ is hydrogen or —$CH_3$.

96A. The Drug linker compound of embodiment 53 having the structure of:

(Formula 1)

$$\left( L \left\{ \left\{ L_B - A_a - L_P - B_b \atop \phantom{L_B - A_a -} PEG \right\} \left\{ J' - V = Z_1^2 \cdot O' - Su \atop Z^1 \phantom{=V} R^8 R^9 \phantom{R'} D^+ \right\}_n \right\}_p \right)$$

wherein L a Ligand Unit from a targeting agent, wherein L selectively binds to a targeted moiety; $L_B$ is a Ligand Covalent Binding Unit; $L_P$ is a Parallel Connector Unit; PEG is a Polyethylene Glycol Unit; subscripts a and b independently are 0 or 1; subscript n is 1, 2, 3 or 4; A is a first optional Stretcher Unit so that subscript a is 0 when A is absent or 1 when A is present and is optionally comprised of two, three or four independently selected subunits ($A_1$, $A_2$, $A_3$, $A_4$); B is an Branching Unit or a second optional Stretcher Unit ($A_O$) so that subscript b is 0 when B is absent or 1 when B is present and is optionally comprised of two, three or four subunits independently of A, wherein subscript b is 1 and B is a Branching when subscript n is 2, 3 or 4 or b is 0 or 1 so that B is $A_O$ when subscript n is 1; Su is a carbohydrate moiety; —O'— represents an oxygen atom of an O-glycosidic bond cleavable by a glycosidase; -J'- represents a heteroatom, optionally substituted when nitrogen, from a functional group of B, when B is present, or $L_B$, when B is absent; V, $Z^1$, and $Z^2$ is =N— or =C($R^{24}$)—, wherein $R^{24}$ is hydrogen or alkyl, alkenyl or alkynyl, optionally substituted, or halogen, —$NO_2$, —CN or other electron withdrawing group, an electron donating group, —O'-Su, or

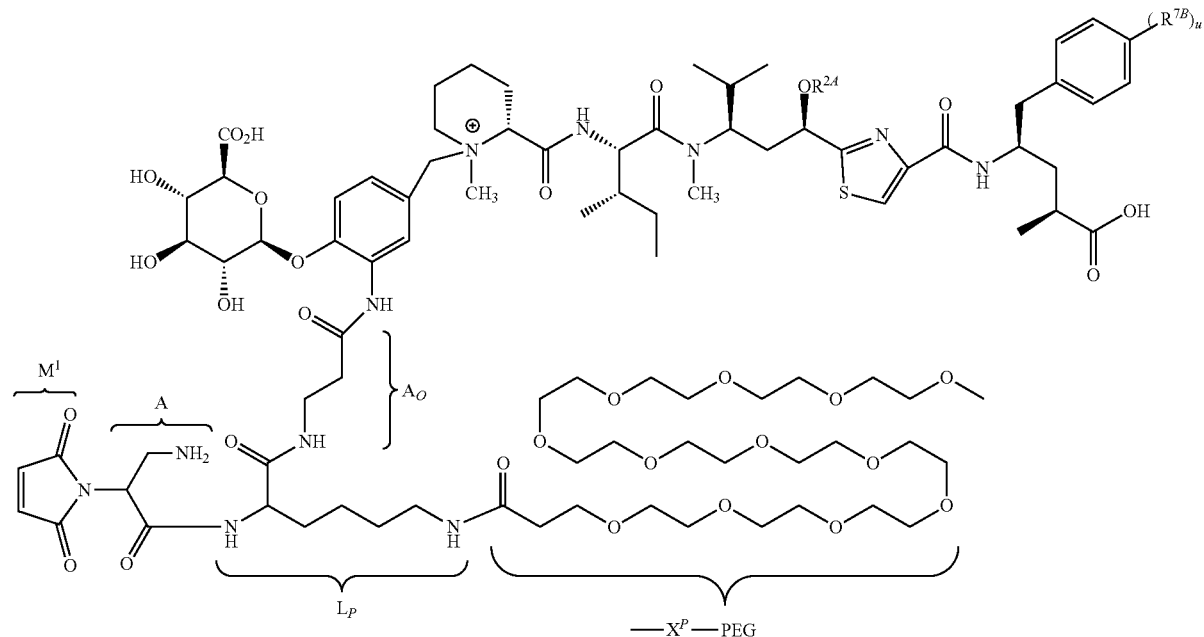

wherein subscript u is 0 or 1; $R^{7B}$, when present, is —OH; and $R^{24}$ along with the oxygen atom to which it is attached is —$OC(O)CH_3$, $CH_2CH_3$ or —$CH_2CH=CH_2$.

1B. A Ligand Drug Conjugate composition, wherein the composition is represented by the structure of Formula 1:

—C($R^8$)($R^9$)-$D^+$, wherein at least at least two of V, $Z^1$ and $Z^2$ are =C($R^{24}$)—, provided, one any only one $R^{24}$ is —C($R^8$)($R^9$)-$D^+$ so that —C($R^8$)($R^9$)-$D^+$ is bonded to one of V, Z, $Z^2$ when that variable group is =C($R^{24}$)— and one and only one other $R^{24}$ is so that —O'-Su is bonded to another one of V, Z, $Z^2$ when that variable group is $=C(R^{24})-$, and the —O'-Su and —$C(R^8)(R^9)$-$D^+$ substituents are ortho or para to each other; $R^8$ and $R^9$ independently are hydrogen, alkyl, alkenyl or alkynyl, optionally substituted, or aryl or heteroaryl, optionally substituted; R' is hydrogen or is halogen, —$NO_2$, —CN or other electron withdrawing group; $D^+$ is a quaternized tubulysin Drug Unit; subscript p is an average drug loading having a number ranging from 1 to 24; and wherein said glycosidase cleavage results in release of a tubulysin compound (D) from a Ligand Drug Conjugate compound of the composition. 2B. The Ligand Drug Conjugate composition of embodiment 1B wherein the quaternized tubulysin Drug Unit (-$D^+$) has the structure of:

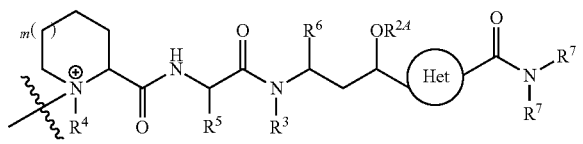

wherein the circle represents an 5-membered nitrogen-heteroarylene and wherein the indicated required substituents to that heteroarylene are in a 1,3-relationship with each other with optional substitution at the remaining positions; subscript m is 0 or 1; $R^{24}$ is hydrogen or optionally substituted alkyl, or $R^{24}$ along with the oxygen atom to which it is attached defines an O-linked substituent; $R^3$ is hydrogen or optionally substituted alkyl; $R^4$, $R^5$ and $R^6$ are optionally substituted alkyl; one $R^7$ is an optionally substituted alkyl, an optionally substituted arylalkyl, optionally substituted heteroarylalkyl and the other $R^7$ is hydrogen or an optionally substituted alkyl; and $R^{8A}$ is hydrogen or optionally substituted alkyl, wherein the wavy line indicates covalent bonding of $D^+$ to the remainder of the Conjugate structure and wherein each optionally substituted alkyl is independently selected.

3B. The Ligand Drug Conjugate composition of embodiment 2B wherein the composition is represented by the structure of one of Formula 2C, 2D, 2E and 2F:

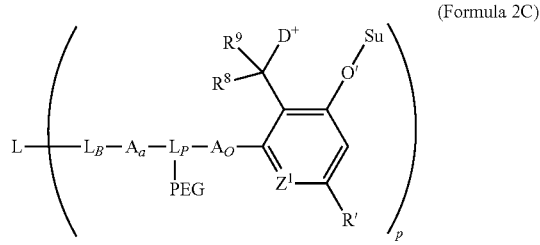
(Formula 2C)

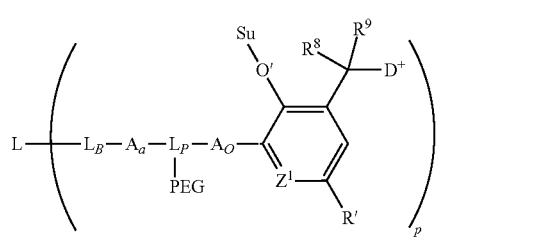
(Formula 2D)

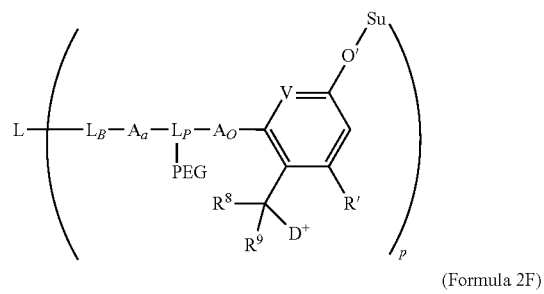
(Formula 2E)

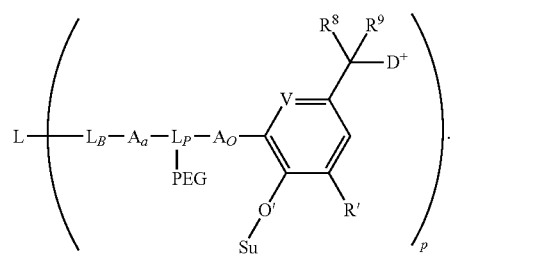
(Formula 2F)

4B. The Ligand Drug Conjugate composition of embodiment 3B wherein the targeting agent is an antibody, thereby defining an antibody drug conjugate (ADC) so that L is an antibody Ligand Unit, wherein the targeted moiety of the antibody Ligand Unit is an accessible cell-surface antigen of targeted abnormal or other unwanted cells that is capable of cellular internalization of bound ADC, wherein the antigen is preferentially present on the abnormal or other unwanted cells in comparison to normal cells.

5B. The Ligand Drug Conjugate composition of embodiment 3B wherein the targeting agent is a cognate ligand of an accessible cell-surface receptor and the targeted moiety is that cell-surface receptor, wherein the targeted receptor on abnormal cells or other unwanted cells is capable of cellular internalization of bound LDC, and wherein the receptor is preferentially present on the abnormal cells in comparison to normal cells.

6B. The Ligand Drug Conjugate composition of embodiment 3B wherein the targeting agent is an antibody, thereby defining an antibody drug conjugate (ADC), wherein the targeted moiety of the antibody Ligand Unit is an accessible cell-surface antigen of a vascular epithelial cell in the vicinity of abnormal cells or other unwanted cells, wherein said antigen is more abundant on said cells in comparison to epithelial cells in the periphery and is capable of cellular internalization of bound ADC.

7B. The Ligand Drug Conjugate composition of any one of embodiments 1B to 6B wherein —O'-Su has the structure of Formula 3:

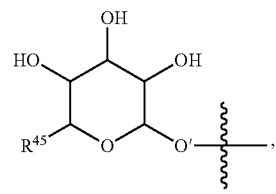
(Formula 3)

wherein the wavy line represents covalent bonding of O' to the remainder of the LDC structure; and $R^{45}$ is —$CH_2OH$ or —$CO_2H$.

8B. The Ligand Drug Conjugate composition of embodiment 7B wherein the composition is represented by the structure of Formula 4

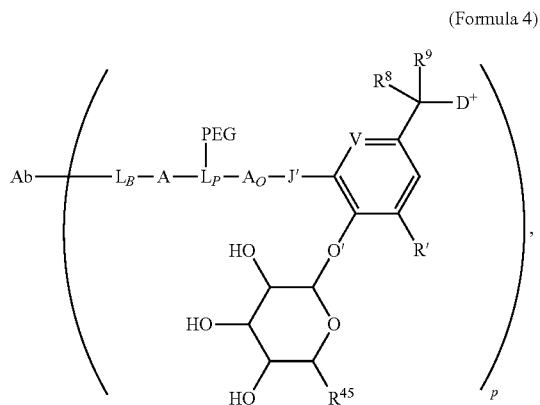

(Formula 4)

wherein Ab is an antibody Ligand Unit; J' is —N($R^{33}$)—, wherein $R^{33}$ is hydrogen or methyl; V is =CH— or =N—; R' is hydrogen or an electron withdrawing group; $R^8$ is hydrogen; $R^9$ is hydrogen, optionally substituted $C_1$-$C_6$ alkyl or optionally substituted phenyl; $R^{45}$ is —$CO_2H$; and subscript p is a number ranging from 1 to 24.

9B. The Ligand Drug Conjugate composition of embodiment 1B wherein subscript a is 1; and -$L_B$-A- of Formula 1 has the structure of Formula 5

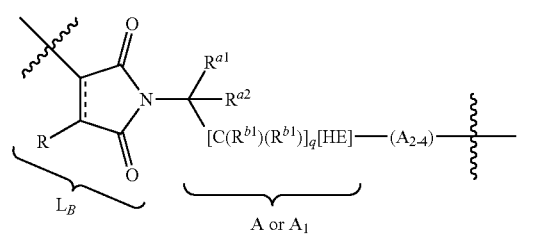

(Formula 5)

wherein the —[C($R^{b1}$)($R^{b1}$)]$_q$—[HE]- moiety is A or $A_1$, wherein $A_1$ is a subunit of A; $A_{2-4}$ are optional subunits of A; R is hydrogen or $C_1$-$C_4$ alkyl; $R^{a1}$ is hydrogen, optionally substituted alkyl or a Basic Unit (BU); and $R^2$ is hydrogen or optionally substituted alkyl, or $R^{a1}$ and $R^{a2}$ together with the carbon atom to which they are attached defines a nitrogen-containing heterocycloalkyl; HE is an optional Hydrolysis Enhancer (HE) Unit; subscript q is an integer ranging from 0 to 6; each $R^{b1}$ independently is hydrogen, optionally substituted $C_1$-$C_6$ alkyl, optionally substituted aryl or optionally substituted heteroaryl, or two $R^{b1}$ together with the carbon(s) to which they are attached comprise a $C_3$-$C_6$ cycloalkyl or one $R^{b1}$ and HE together with the carbon to which they are attached define a 5- or 6-membered cycloalkyl or a 5- or 6-membered heterocycloalkyl and the other $R^{b1}$ is hydrogen, optionally substituted $C_1$-$C_6$ alkyl, optionally substituted aryl or optionally substituted heteroaryl; BU has the structure of —[C($R^1$)($R^1$)]—[C($R^2$)($R^2$)]$_r$—N($R^{22}$)($R^{23}$), or an acid addition salt thereof, wherein subscript r is 0, 1, 2 or 3; each $R^1$ independently is hydrogen or lower alkyl or two $R^1$ together with the carbon to which they are attached comprise a $C_3$-$C_6$ cycloalkyl, and each $R^2$ independently is hydrogen, optionally substituted $C_1$-$C_6$ alkyl, optionally substituted aryl or optionally substituted heteroaryl, or two $R^2$ together with the carbon(s) to which they are attached and any intervening carbons define a $C_3$-$C_6$ cycloalkyl, or one $R^1$ and one $R^2$ together with the carbons to which they are attached and any intervening carbons define a 5- or 6-membered cycloalkyl and the remaining $R^1$ and $R^2$ are as defined; $R^{22}$ and $R^{23}$ independently are hydrogen or optionally substituted $C_1$-$C_6$ alkyl or together with the nitrogen to which they are attached define a 5- or 6-membered heterocycloalkyl, or one of $R^{22}$, $R^{23}$ is hydrogen and the other is an acid labile protecting group; and wherein the dotted line is an optional double bond and the wavy line to the succinimide (double bond is absent) or maleimide ring (double bond is present) of $L_B$ indicates covalent bonding of sulfur derived from a sulfhydryl group of a targeting moiety and the other wavy line indicates covalent bonding of the Formula 4 structure to the remainder of the LDC structure.

10B. The Ligand Drug Conjugate composition of embodiment 9B wherein Formula 5 has the structure of Formula 5A:

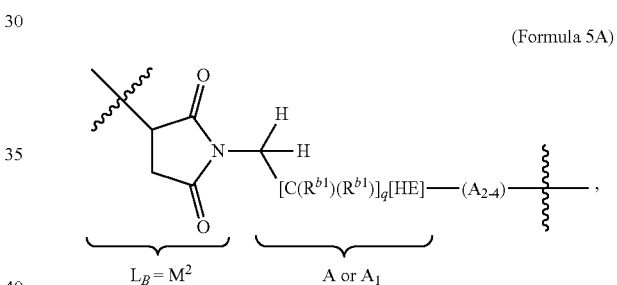

(Formula 5A)

wherein subscript q is an integer ranging from 0 to 4.

11B. The Ligand Drug Conjugate composition of embodiment 9B wherein Formula 4 has the structure of Formula 5B, or an acid addition salt thereof

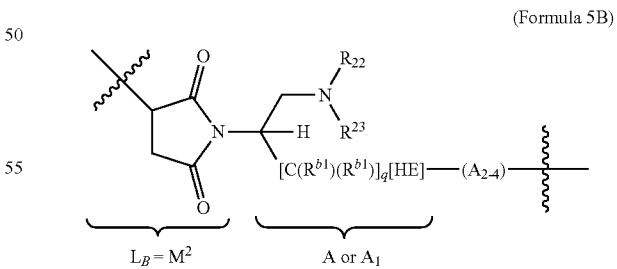

(Formula 5B)

wherein $R^{22}$ and $R^{23}$ are each hydrogen or one of $R^{22}$, $R^{23}$ is hydrogen and the other is an acid labile carbamate protecting group; and subscript q is an integer ranging from 0 to 4.

12B. The Ligand Drug Conjugate composition of embodiment 10B or 11B wherein Formula 5A or Formula 5B has the structure of:

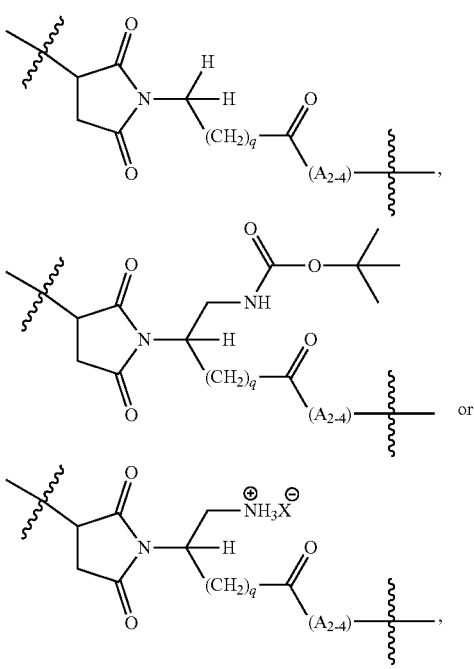

wherein X⁻ is chloride, acetate, trifluoroacetate or dihydrogen phosphate.

13B. The Ligand Drug Conjugate composition of embodiment 9B wherein the composition is represented by the structure of Formula 6:

wherein Ab is an antibody Ligand Unit, S is a sulfur atom of the antibody Ligand Unit; the asterisk (*) designates chirality or absence thereof at the indicated carbon; $A_{2-4}$ are independently selected optional subunits of A, wherein —[C($R^{b1}$)($R^{b1}$)]$_q$—[HE]- is $A_1$ when one or more such subunits are present; R is hydrogen; R' is hydrogen or an electron withdrawing group; $R^{a1}$ is hydrogen or a basic unit (BU) wherein BU is a Basic Unit having the structure of —CH$_2$—N($R^{22}$)($R^{23}$), or an acid addition salt thereof, wherein $R^{22}$ and $R^{23}$ independently are hydrogen, methyl or ethyl or both together with the nitrogen atom to which they are attached comprise a 5- or 6-membered heterocycloalkyl, or one of $R^{22}$, $R^{23}$ is hydrogen and the other is an acid labile carbamate protecting group; $R^{a2}$ is hydrogen; subscript q is an integer ranging from 0 to 5 when HE is present or 1 to 5 when HE is absent; each $R^{b1}$ independently is hydrogen or optionally substituted $C_1$-$C_6$ alkyl; HE is absent or is —C(=O)—; $R^{45}$ is —CO$_2$H; J' is —NH—; V and $Z^3$ are =CH—; $R^8$ is hydrogen; $R^9$ is hydrogen or methyl; and subscript p is a number ranging from 1 to 16.

14B. The Ligand Drug Conjugate composition of embodiment 1B wherein compounds of the composition are independently represented by the structure of Formula 9A or Formula 9B:

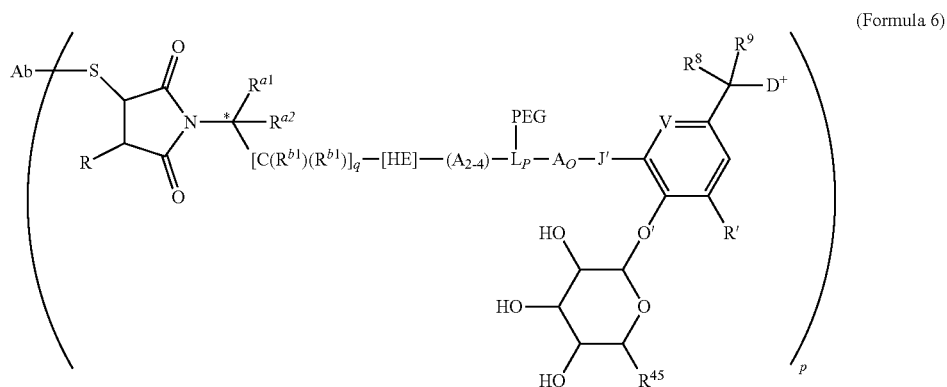

(Formula 6)

(Formula 9A)

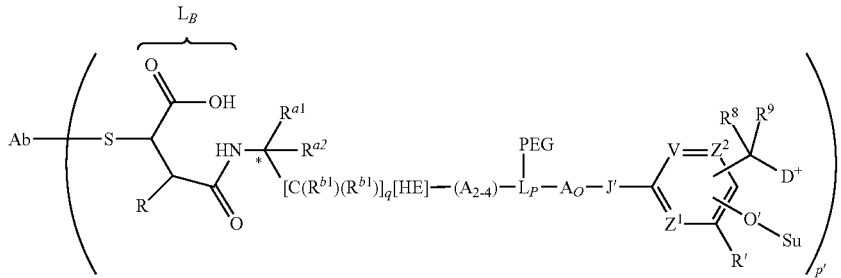

(Formula 9B)

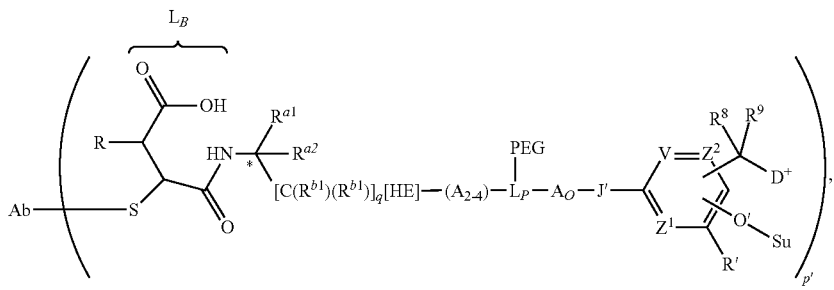

wherein Ab is an antibody Ligand Unit; S is a sulfur atom of the antibody Ligand Unit; $A_{2-4}$ are independently selected optional subunits of A, wherein —$[C(R^{b1})(R^{b1})]_q$—[HE]- is $A_1$ when one or more such subunits are present; R is hydrogen; R' is hydrogen or an electron withdrawing group; $R^{a1}$ is —H or BU wherein BU is a Basic Unit having the structure of —$CH_2$—$N(R^{22})(R^{23})$, or an acid addition salt thereof, wherein $R^{22}$ and $R^{23}$ independently are hydrogen or methyl or both together with the nitrogen atom to which they are attached define a basic nitrogen-containing 5- or 6-membered heterocycloalkyl, or one of $R^{22}$, $R^{23}$ is hydrogen and the other is an acid labile protecting group; $R^{a2}$ is hydrogen; subscript q is an integer ranging from 0 to 5 when HE is present or from 1 to 5 when HE is absent; each $R^{b1}$ independently is hydrogen or optionally substituted $C_1$-$C_6$ alkyl; HE is absent or is —C(=O)—; J' is —O— or —NH—; R and $R^9$ are independently —H or optionally substituted alkyl or both together along with the carbon atom to which they are attached define a cycloalkyl; and subscript p' is an integer ranging from 1 to 24.

15B. The Ligand Drug Conjugate composition of embodiment 14B wherein compounds of the composition are independently represented by the structure of Formula 10A or Formula 10B:

(Formula 10A)

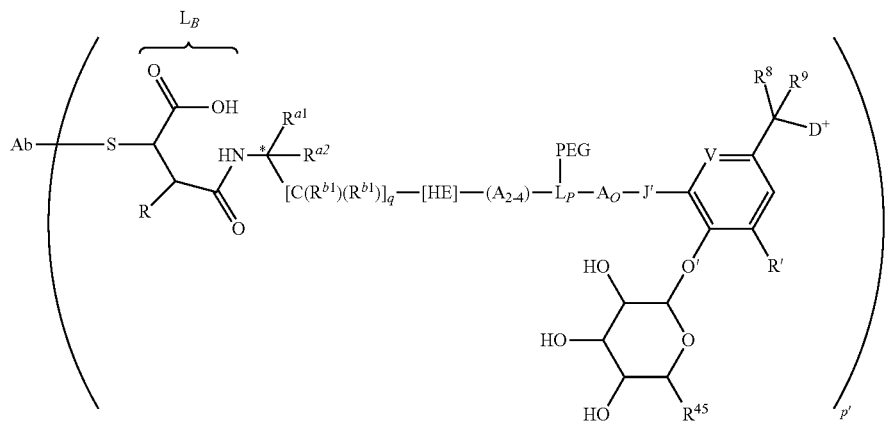

(Formula 10B)

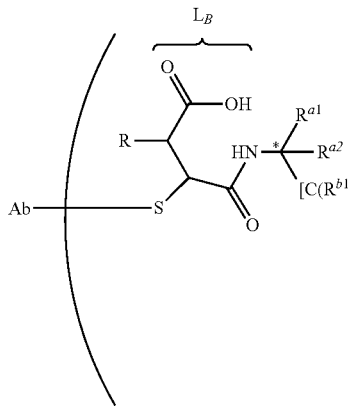
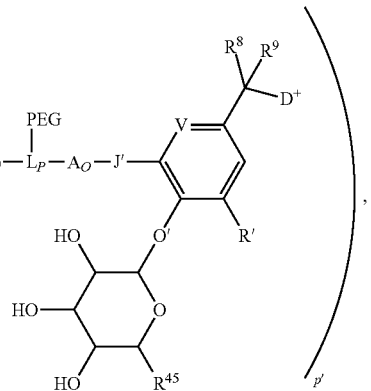

wherein R is hydrogen; R' is hydrogen, —$NO_2$, —Cl or —F; HE is —C(=O)—; $R^{45}$ is —$CO_2H$; J' is —NH—; V is =$CH_2$—; $R^8$ is hydrogen; and $R^9$ is hydrogen or methyl.

16B. The Ligand Drug Conjugate composition of embodiment 13B, 14B or 15B wherein the indicated starred (*) carbon is predominantly in the same absolute configuration as the alpha carbon of an L-amino acid when that indicated carbon is chiral.

17B. The Ligand Drug Conjugate composition of any one of embodiment 1B to 8B wherein A and $A_O$, when present, or any one of embodiments 9B to 16B, wherein each of $A_2$-4, when present, independently have the structure of Formula 7 or Formula 8

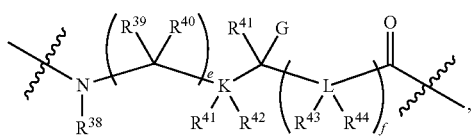

(Formula 7)

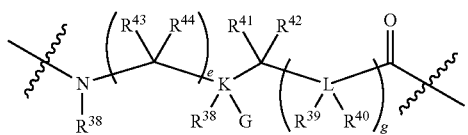

(Formula 8)

wherein the wavy lines indicate covalent attachment within the remainder of $L_O$, wherein K and L independently are C, N, O or S, provided that when K or L is O or S, $R^{41}$ and $R^{42}$ to K or $R^{43}$ and $R^{44}$ to L are absent, and when K or L are N, one of $R^{41}$, $R^{42}$ to K or one of $R^{42}$, $R^{43}$ to L are absent, and provided that no two adjacent L are independently selected as N, O, or S; wherein subscripts e and f are independently selected integers that range from 0 to 12, and subscript g is an integer ranging from 1 to 12; wherein G is hydrogen, optionally substituted $C_1$-$C_6$ alkyl, —OH, —$OR^{PR}$, —$CO_2H$, $CO_2R^{PR}$ wherein $R^{PR}$ is a suitable protecting, —N($R^{PR}$)($R^{PR}$), wherein $R^{PR}$ are independently a protecting group or $R^{PR}$ together form a suitable protecting group, or —N($R^{45}$)($R^{46}$), wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl; wherein $R^{38}$ is hydrogen or optionally substituted $C_1$-$C_6$ alkyl; $R^{39}$-$R^{44}$ independently are hydrogen, optionally substituted $C_1$-$C_6$ alkyl, optionally substituted aryl, or optionally substituted heteroaryl, or both $R^{39}$, $R^{40}$ together with the carbon to which they are attached comprise a $C_3$-$C_6$ cycloalkyl, or $R^{41}$, $R^{42}$ together with K to which they are attached when K is C, or $R^{43}$, $R^{44}$ together with L to which they are attached when L is a carbon atom comprise a $C_3$-$C_6$ cycloalkyl, or $R^{40}$ and $R^{41}$, or $R^{40}$ and $R^{43}$, or $R^{41}$ and $R^{43}$ to together with the carbon atom or heteroatom to which they are attached and the atoms intervening between those carbon atoms and/or heteroatoms comprise a 5- or 6-membered cycloalkyl or heterocycloalkyl, provided that when K is O or S, $R^{41}$ and $R^{42}$ are absent, when K is N, one of $R^{41}$, $R^{42}$ is absent, when L is O or S, $R^{43}$ and $R^{44}$ are absent, and when L is N, one of $R^{43}$, $R^{44}$ is absent, or wherein $A_O$ has a structure corresponding to alpha-amino, beta-amino or another amine-containing acid.

18B. The Ligand Drug Conjugate composition of any one of embodiments 1B to 17B wherein the quaternized tubulysin Drug Unit -$D^+$ has the structure of

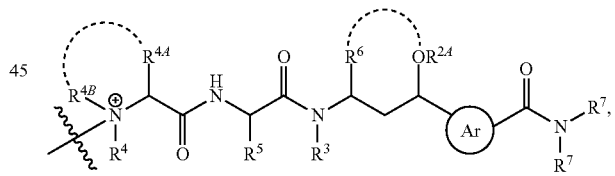

$R^{24}$ is hydrogen or optionally substituted alkyl, or $R^{24}$ along with the oxygen atom to which it is attached defines an O-linked substituent other than —OH, or $R^{24}$ is absent when $R^6$ is bonded to that oxygen atom, as indicated by the curved dash line between $R^6$ and the oxygen atom, to define an oxygen-containing heterocycloalkyl; the circled Ar represents a 5-membered nitrogen-heteroarylene, wherein the indicated required substituents to that heteroarylene are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{24}$ moiety in which $R^{24}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached, as indicated by the curved dotted line between $R^{4A}$ and $R^{4B}$, define a quaternized nitrogen heterocycloalkyl, optionally substituted; one $R^7$ is hydrogen or optionally substituted alkyl and the other $R^7$ is optionally substituted aralkyl or heteroaralkyl; wherein the wavy line indicates covalent bonding of the $D^+$ structure to the remainder of the LDC structure.

19B. The Ligand Drug Conjugate composition of embodiment 18B wherein the quaternized tubulysin Drug Unit -$D^+$ has the structure of:

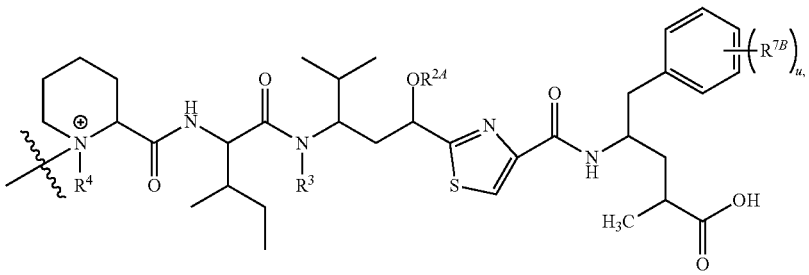

wherein subscript m is 0 or 1; Z is an optionally substituted alkylene or an optionally substituted alkenylene; and $R^{7A}$ is optionally substituted aryl or optionally substituted heteroaryl.

20B. The Ligand Drug Conjugate composition of embodiment 19B wherein the quaternized tubulysin Drug Unit -D has the structure of:

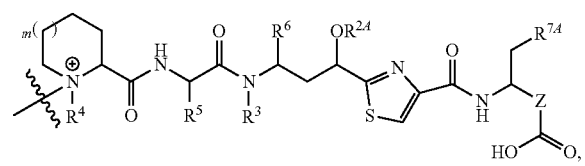

wherein $R^{7A}$ is optionally substituted phenyl and $R^8$ is hydrogen or methyl.

21B. The Ligand Drug Conjugate composition of embodiment 19B wherein the quaternized tubulysin Drug Unit -D has the structure of

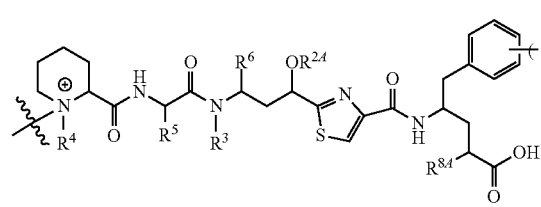

wherein $R^5$ and $R^6$ are alkyl side chain residues of natural hydrophobic amino acids, independently selected; subscript u, indicating the number of $R^{7B}$ substituents, is 0, 1, 2 or 3; each $R^{7B}$, when present, is an independently selected O-linked substituent; and $R^{8A}$ is hydrogen or optionally substituted alkyl.

22B. The Ligand Drug Conjugate composition of embodiment 21B wherein the quaternized tubulysin Drug Unit (-$D^+$) has the structure of:

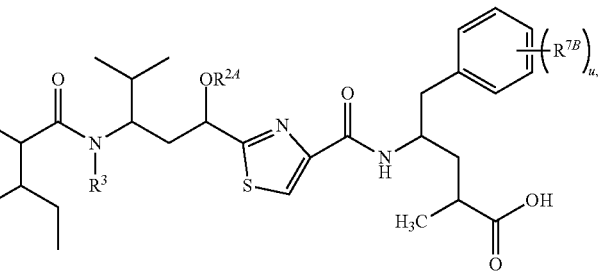

wherein $R^4$ is methyl; subscript u is 0, 1 or 2; $R^3$ is H, methyl, ethyl, propyl, —CH$_2$—OC(O)R$^{3A}$, —CH$_2$CH(R$^{3B}$)C(O)R$^{3A}$ or —CH(R$^{3B}$)C(O)NHR$^{3A}$, wherein R$^{3A}$ is C$_1$-C$_6$ alkyl and R$^{3B}$ is H or C$_1$-C$_6$ alkyl, independently selected from R$^{3A}$; R$^{2A}$ along with the oxygen atom to which it is attached is an O-linked substituent selected from the group consisting of —OCH$_2$OCH$_2$R$^{2B}$, —OCH$_2$R$^{2B}$, —OC(O)R$^{2B}$, —CH$_2$OC(O)R$^{2B}$, —OC(O)N(R$^{2B}$)(R$^{2C}$), and —OCH$_2$C(O)N(R$^{2B}$)(R$^{2C}$), wherein R$^{2B}$ and R$^{2C}$ are independently selected from the group consisting of H, C$_1$-C$_6$ alkyl and C$_2$-C$_6$ alkenyl; and each R$^{7B}$, when present, independently is —OH or —OCH$_3$.

23B. The Ligand Drug Conjugate composition of embodiment 18B wherein the quaternized tubulysin Drug Unit (-$D^+$) has the structure of

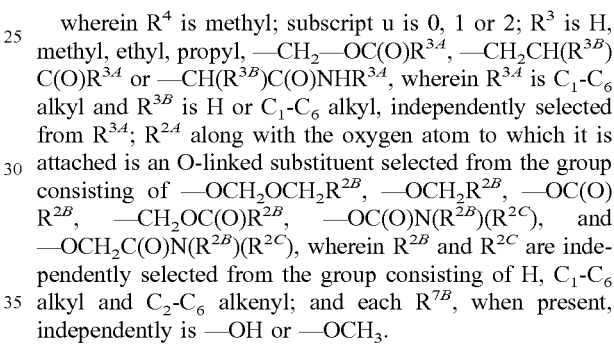

wherein $R^{2A}$ is hydrogen, an optionally substituted alkyl, saturated or unsaturated, or $R^2$ along with the oxygen atom to which it is attached defines an O-linked substituent other than —OH; $R^3$ is optionally substituted C$_1$-C$_6$ alkyl; $R^4$ is methyl; $R^5$ and $R^6$ are alkyl side chain residues of natural hydrophobic amino acids; and the —N(R$^{7'}$)(R$^{7'}$) moiety is —NH(C$_1$-C$_6$ alkyl) or —NH—N(C$_1$-C$_6$ alkyl)$_2$, wherein one and only one C$_1$-C$_6$ alkyl is optionally substituted by —CO$_2$H, or an ester thereof, or by an optionally substituted phenyl.

24B. The Ligand Drug Conjugate composition of embodiment 23B wherein the —N(R$^{7'}$)(R$^{7'}$) moiety is selected from the group consisting of —NH(CH$_3$), —NHCH$_2$CH$_2$Ph, and —NHCH$_2$—CO$_2$H, —NHCH$_2$CH$_2$CO$_2$H and —NHCH$_2$CH$_2$CH$_2$CO$_2$H.

25B. The Ligand Drug Conjugate composition of any one of claims 18B to 24B wherein $R^{2A}$ is —CH$_2$CH$_3$.

26B. The Ligand Drug Conjugate composition of any one of claims 18B to 24B wherein $R^{2A}$ is —CH$_2$—CH=CH$_2$.

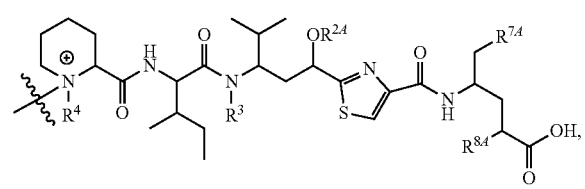

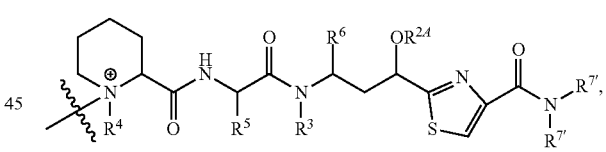

27B. The Ligand Drug Conjugate composition of any one of claim 21B or 22B wherein $R^{2A}$ is —CH$_2$CH$_3$, —CH$_2$—CH=CH$_2$ or —CH$_2$C(CH$_3$)=CH$_2$, $R^{2B}$ is —CH$_3$, $R^3$ is —CH$_3$ and subscript u is 0.

28B. The Ligand Drug Conjugate composition of claim 21B or 22B wherein $R^{2A}$ is —CH$_2$CH$_3$ or —CH$_2$—CH=CH$_2$, or —CH$_2$C(CH$_3$)=CH$_2$, $R^{2B}$ is —CH$_3$, $R^3$ is —CH$_3$ and subscript u is 1, wherein $R^{7B}$ is —OH.

29B. The Ligand Drug Conjugate composition of embodiment 18B wherein the quaternized tubulysin Drug Unit (-D$^+$) has the structure of:

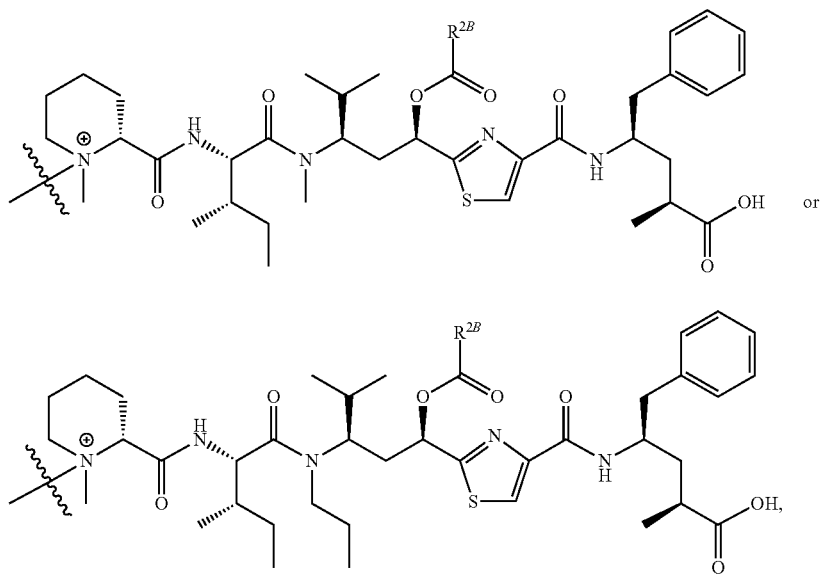

wherein $R^{2B}$ is —CH$_3$, —CH$_2$CH$_3$, —CH$_2$CH$_2$CH$_3$, —CH(CH$_3$)$_2$, —CH$_2$CH(CH$_3$)$_2$, or —CH$_2$C(CH$_3$)$_3$.

30B. The Ligand Drug Conjugate composition of embodiment 18B wherein the quaternized tubulysin Drug Unit (-D$^+$) has the structure of:

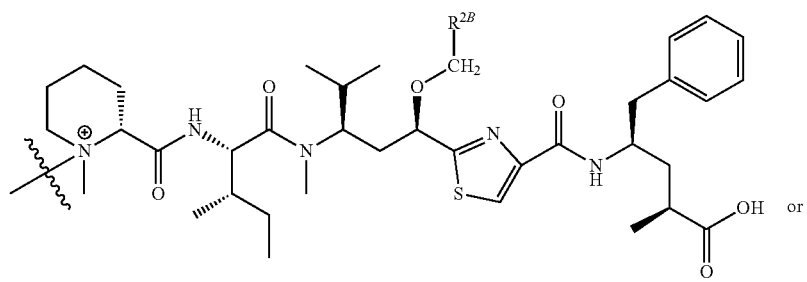

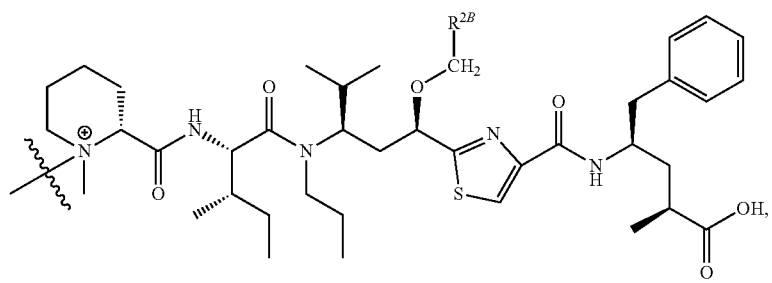

wherein $R^{2B}$ is hydrogen, methyl or —OCH$_3$, or —OCH$_2$R$^{2B}$ is —OCH$_2$CH=CH$_2$ or —OCH$_2$C(CH$_3$)=CH$_2$.
31B. The Ligand Drug Conjugate composition of embodiment 18B wherein the quaternized tubulysin Drug Unit (-D$^+$) is that of tubulysin M, for which D$^+$ has the structure of:
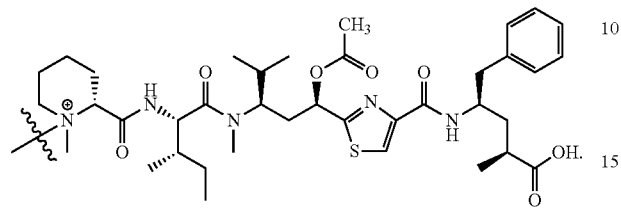
32B. The Ligand Drug Conjugate composition of embodiment 1B represented by the structure of:
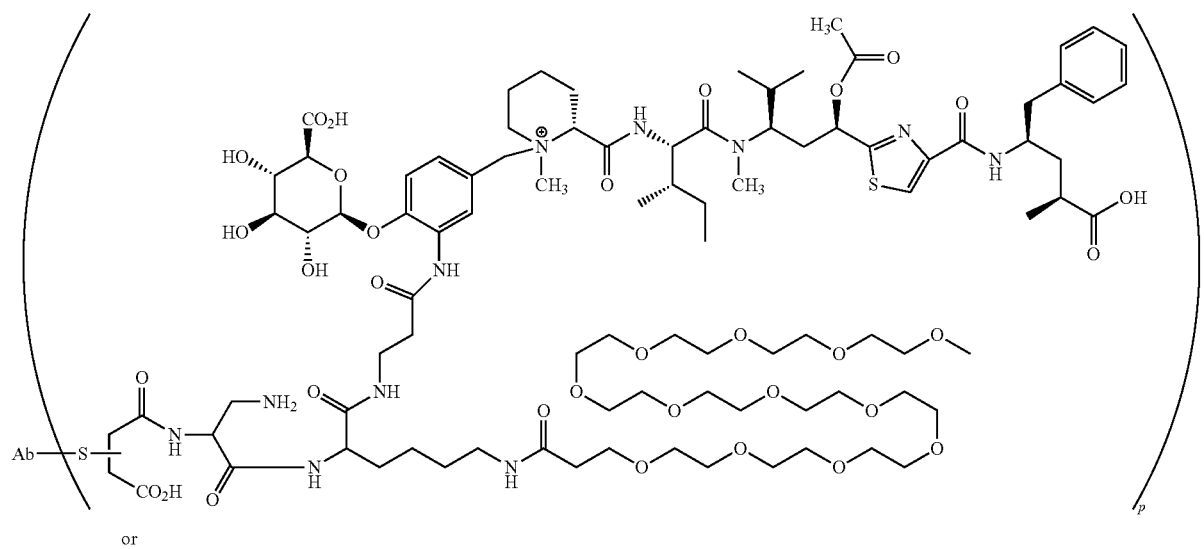
or
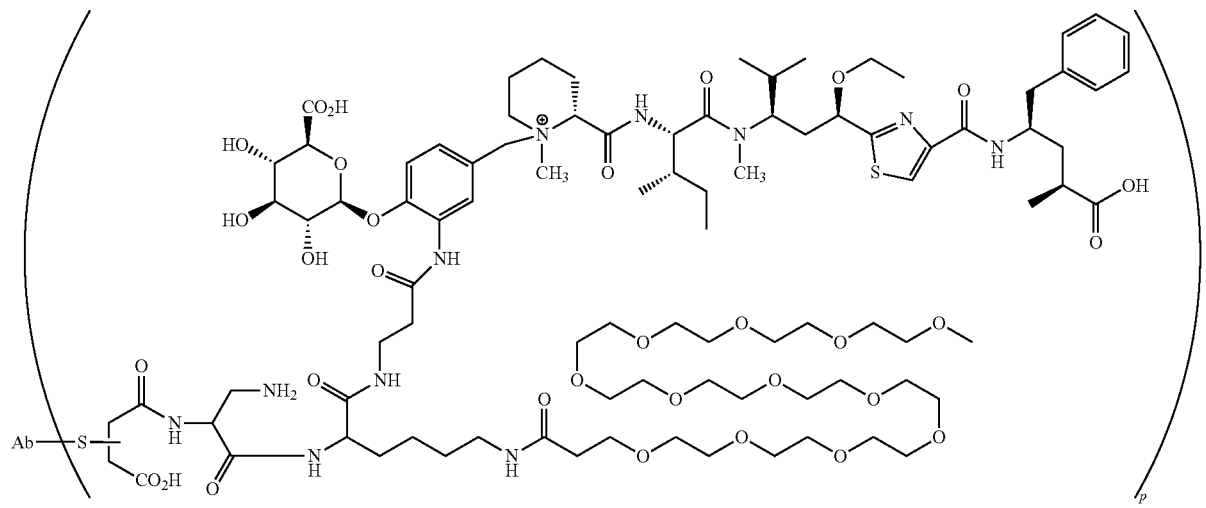

1C. A Ligand Drug Conjugate composition wherein the composition is represented by the structure of Formula 1A or Formula 1C:

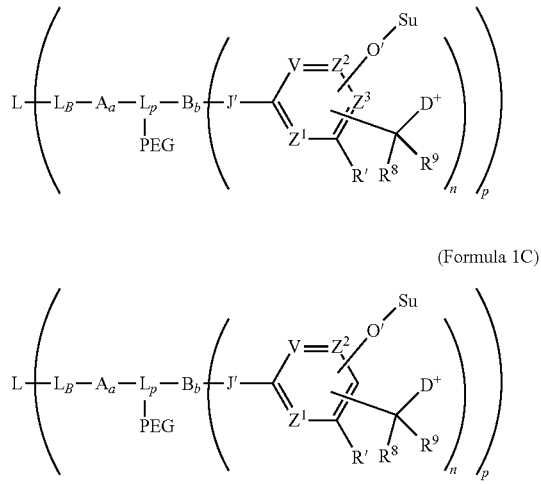

(Formula 1A)

(Formula 1C)

wherein L is an antibody Ligand Unit, thereby defining an Antibody Drug Conjugate (ADC); $L_B$ is a Ligand Covalent Binding Unit; $L_P$ is a Parallel Connector Unit; PEG is a Polyethylene Glycol Unit; subscripts a and b independently are 0 or 1; subscript n is 1, 2, 3 or 4; subscript p is a number ranging from 1 to 24; A is a first optional Stretcher Unit so that subscript a is 0 when A is absent or 1 when A is present and is optionally comprised of two, three or four independently selected subunits ($A_1$, $A_2$, $A_3$, $A_4$); B is an Branching Unit or a second optional Stretcher Unit ($A_O$) so that subscript b is 0 when B is absent or 1 when B is present and is optionally comprised of two, three or four subunits independently of A, wherein subscript b is 1 and B is a Branching when subscript n is 2, 3 or 4 or b is 0 or 1 so that B is $A_O$ when subscript n is 1; Su is a carbohydrate moiety; —O'— represents an oxygen atom of an O-glycosidic bond cleavable by a glycosidase; -J'- represents a heteroatom, optionally substituted when nitrogen, from a functional group of B, when B is present, or $L_B$, when B is absent; V, $Z^1$, $Z^2$ and $Z^3$ are =N— or =C($R^{24}$)—, wherein $R^{24}$ is hydrogen or alkyl, alkenyl or alkynyl, optionally substituted, or halogen, —$NO_2$, —CN or other electron withdrawing group, or —$OCH_3$ or other electron donating group, —O'-Su, or —C($R^8$)($R^9$)-$D^+$, wherein at least at least two of V, Z, $Z^2$ and $Z^3$ are =C($R^{24}$)—, provided, one any only one $R^{24}$ is —C($R^8$)($R^9$)-$D^+$ so that —C($R^8$)($R^9$)-$D^+$ is bonded to one of V, $Z^1$, $Z^2$, $Z^3$ when that variable group is =C($R^{24}$)— and one and only one other $R^{24}$ is so that —O'-Su is bonded to another one of V, $Z^1$, $Z^2$, $Z^3$ when that variable group is =C($R^{24}$)—, and the —O'Su and —C($R^8$)($R^9$)-$D^+$ substituents are ortho or para to each other; $R^8$ and $R^9$ independently are hydrogen, alkyl, alkenyl or alkynyl, optionally substituted, or aryl or heteroaryl, optionally substituted; R' is hydrogen or is halogen, —$NO_2$, —CN or other electron withdrawing group; $D^+$ is a quaternized tubulysin Drug Unit having the structure of:

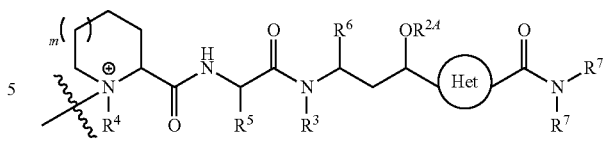

wherein the circle represents an 5-membered nitrogen-heteroarylene and wherein the indicated required substituents to that heteroarylene are in a 1,3-relationship with each other with optional substitution at the remaining positions; subscript m is 0 or 1; $R^{24}$ is hydrogen or optionally substituted alkyl, or $R^{24}$ along with the oxygen atom to which it is attached defines an O-linked substituent; $R^3$ is hydrogen or optionally substituted alkyl; $R^4$, $R^5$ and $R^6$ are optionally substituted alkyl; one $R^7$ is an optionally substituted alkyl, an optionally substituted arylalkyl, optionally substituted heteroarylalkyl and the other $R^7$ is hydrogen or an optionally substituted alkyl; and $R^{8A}$ is hydrogen or optionally substituted alkyl, wherein the wavy line indicates covalent bonding of $D^+$ to the remainder of the LDC structure and wherein each optionally substituted alkyl is independently selected, wherein said glycosidase cleavage results in release of a tubulysin compound (D) from a Ligand Drug Conjugate compound of the composition.

2C. The Ligand Drug Conjugate composition of embodiment 1C wherein the composition is represented by the structure of one of Formula 2A-2F:

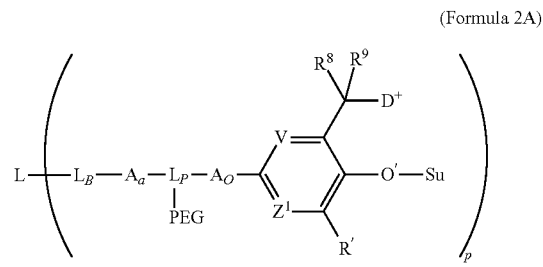

(Formula 2A)

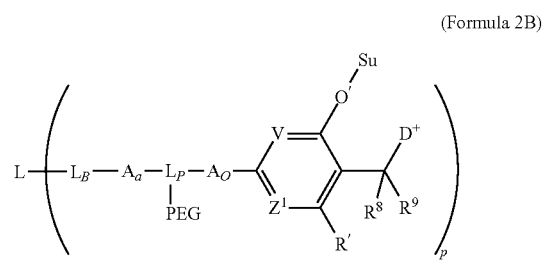

(Formula 2B)

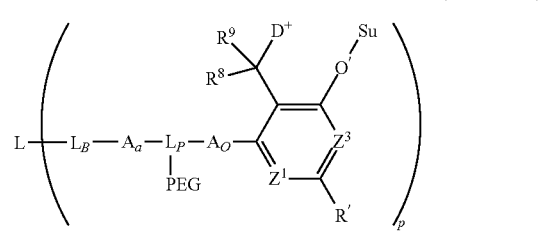

(Formula 2C)

(Formula 2D)

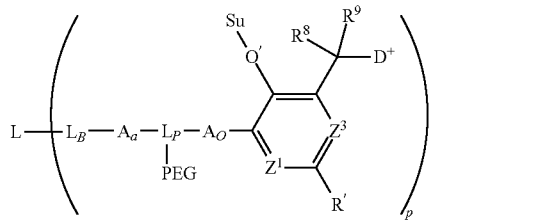

(Formula 2E)

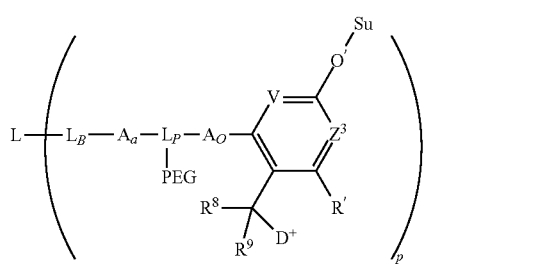

(Formula 2F)

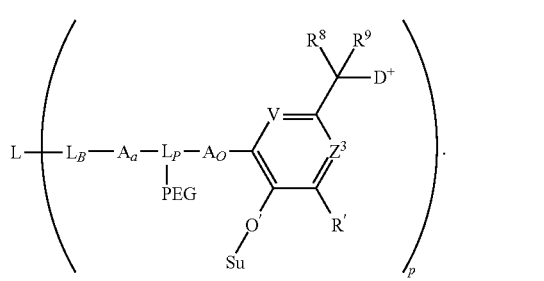

3C. The Ligand Drug Conjugate composition of embodiment 1C or 2C, wherein the antibody Ligand Unit is capable of selectively binding to an accessible cell-surface antigen of abnormal cells, wherein the antigen is capable of cellular internalization of bound ADC and is preferentially present on the abnormal or other unwanted cells in comparison to normal cells.

4C. The Ligand Drug Conjugate composition of embodiment 1C or 2C wherein —O'-Su has the structure of Formula 3:

(Formula 3)

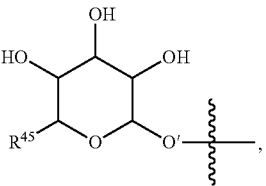

wherein the wavy line represents covalent bonding of O' to the remainder of the LDC structure; and $R^{45}$ is —$CH_2OH$ or —$CO_2H$.

5C. The Ligand Drug Conjugate composition of embodiment 2C wherein the composition is represented by the structure of Formula 4:

(Formula 4)

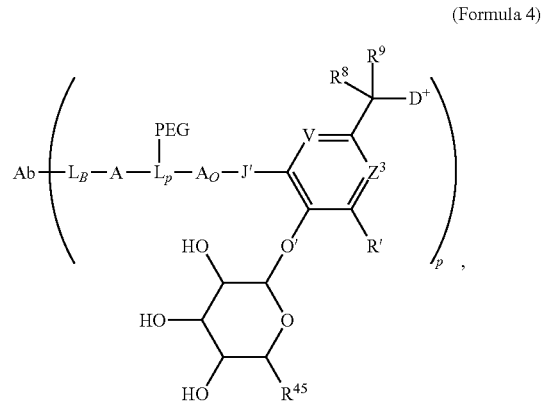

wherein Ab is the antibody Ligand Unit; J' is —$N(R^{33})$—, wherein $R^{33}$ is hydrogen or methyl; V and $Z^3$ independently are =CH— or =N—; R' is hydrogen or an electron withdrawing group; $R^8$ is hydrogen; $R^9$ is hydrogen, optionally substituted $C_1$-$C_6$ alkyl or optionally substituted phenyl; $R^{45}$ is —$CO_2H$; and subscript p is a number ranging from 1 to 24.

6C. The Ligand Drug Conjugate composition of embodiment 5C wherein the composition is represented by the structure of Formula 6:

(Formula 6)

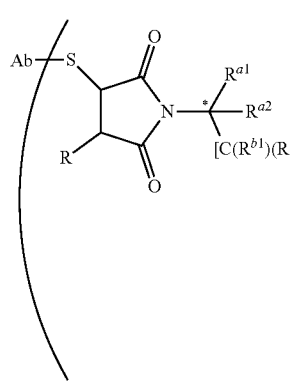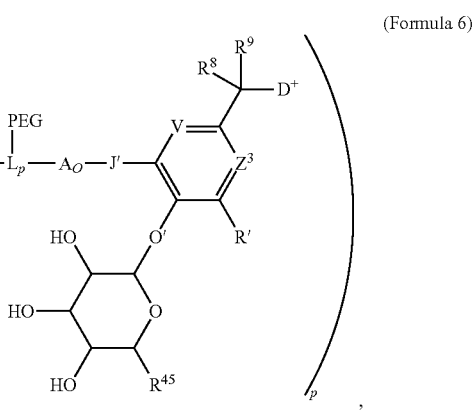

wherein S is a sulfur atom of the antibody Ligand Unit (Ab); the asterisk (*) designates chirality or absence thereof at the indicated carbon; $A_{2-4}$ are independently selected optional subunits of A, wherein —[C($R^{b1}$)($R^{b1}$)]$_q$—[HE]- is $A_1$ when one or more such subunits are present; R is hydrogen; R' is hydrogen or an electron withdrawing group; $R^{a1}$ is hydrogen or a basic unit (BU) wherein BU is a Basic Unit having the structure of —$CH_2$—N($R^{22}$)($R^{23}$), or an acid addition salt thereof, wherein $R^{22}$ and $R^{23}$ independently are hydrogen, methyl or ethyl or both together with the nitrogen atom to which they are attached comprise a 5- or 6-membered heterocycloalkyl, or one of $R^{22}$, $R^{23}$ is hydrogen and the other is an acid labile carbamate protecting group; $R^{a2}$ is hydrogen; subscript q is an integer ranging from 0 to 5 when HE is present or 1 to 5 when HE is absent; each $R^{b1}$ independently is hydrogen or optionally substituted $C_1$-$C_6$ alkyl; HE is absent or is —C(=O)—; $R^{45}$ is —$CO_2H$; J' is —NH—; V and $Z^3$ are =$CH_2$—; $R^8$ is hydrogen; $R^9$ is hydrogen or methyl; subscript p is a number ranging from 1 to 16; and wherein the remaining variable groups are as defined for Formula 1A or Formula 1B.

7C. The Ligand Drug Conjugate composition of embodiment 1C wherein a compound thereof has the structure of Formula 9A or Formula 9B wherein S is a sulfur atom of the antibody Ligand Unit (Ab); the asterisk (*) designates chirality or absence thereof at the indicated carbon; $A_{24}$ are independently selected optional subunits of A, wherein —[C($R^{b1}$)($R^{b1}$)]$_q$—[HE]- is $A_1$ when one or more such subunits are present; R is hydrogen; R' is hydrogen or an electron withdrawing group; $R^{a1}$ is —H or BU wherein BU is a Basic Unit having the structure of —$CH_2$—N($R^{22}$)($R^{23}$), or an acid addition salt thereof, wherein $R^{22}$ and $R^{23}$ independently are hydrogen or methyl or both together with the nitrogen atom to which they are attached define a basic nitrogen-containing 5- or 6-membered heterocycloalkyl, or one of $R^{22}$, $R^{23}$ is hydrogen and the other is an acid labile protecting group; $R^{a2}$ is hydrogen; subscript q is an integer ranging from 0 to 5 when HE is present or from 1 to 5 when HE is absent; each $R^{b1}$ independently is hydrogen or optionally substituted $C_1$-$C_6$ alkyl; HE is absent or is —C(=O)—; J' is —O— or —NH—; $R^8$ and $R^9$ are independently —H or optionally substituted alkyl or both together along with the carbon atom to which they are attached define a cycloalkyl; and subscript p' is an integer ranging from 1 to 24; and wherein the remaining variable groups are as defined for Formula 1A or Formula 1B.

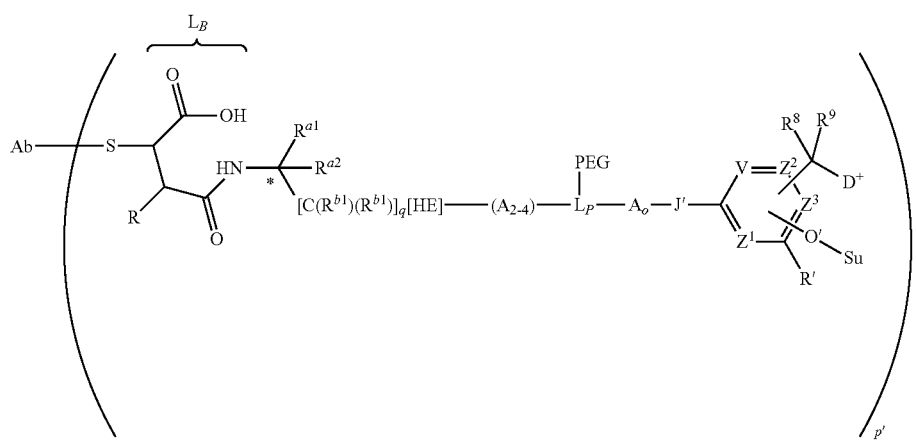

(Formula 9A)

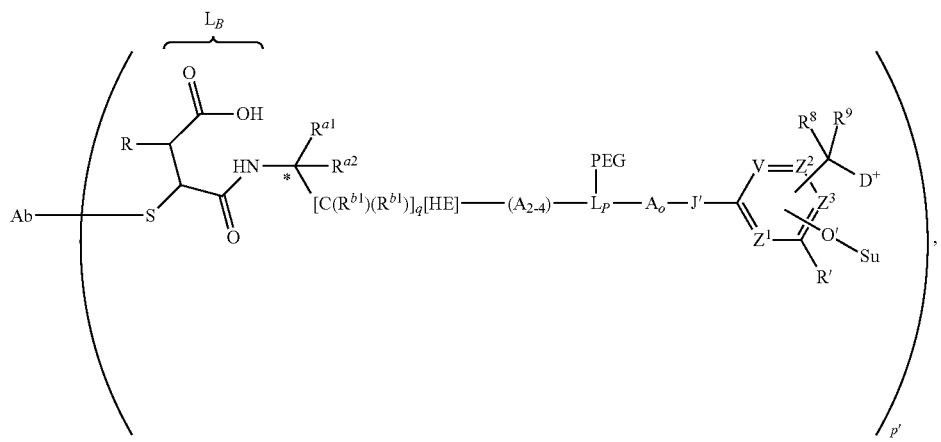

(Formula 9B)

8C. The Ligand Drug Conjugate composition of embodiment 7C, wherein a compound thereof has the structure of Formula 10A or Formula 10B

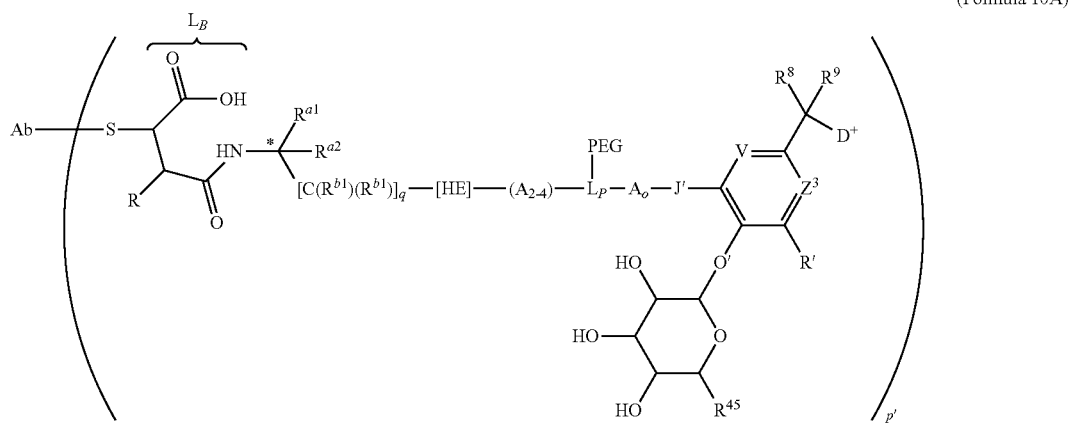
(Formula 10A)

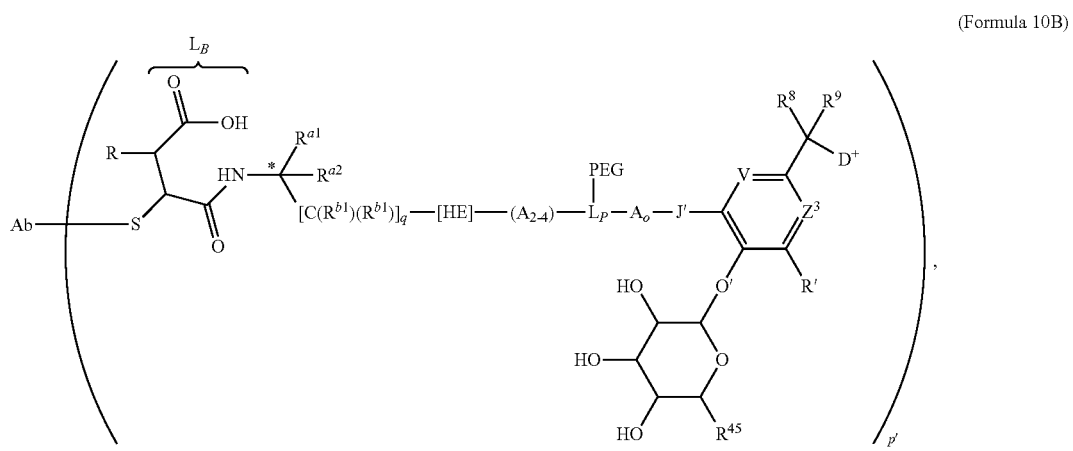
(Formula 10B)

wherein R is hydrogen; R' is hydrogen, —NO$_2$, —Cl or —F; HE is —C(=O)—; R$^{45}$ is —CO$_2$H; J' is —NH—; V and Z$^3$ are each =CH—; R$^8$ is hydrogen; R$^9$ is hydrogen or methyl; p' is an integer ranging from 1 to 12; and wherein the remaining variable groups are as defined for Formula 1A or Formula 1B.

9C. The Ligand Drug Conjugate composition, or compound thereof, of embodiment 6C, 7C or 8C wherein the indicated starred (*) carbon is predominantly in the same absolute configuration as the alpha carbon of an L-amino acid when that indicated carbon is chiral.

10C. The Ligand Drug Conjugate composition, or compound thereof, of any one of embodiments 1C to 5C wherein A and A$_O$, when present, independently has the structure of Formula 7 or Formula 8, or any one of claims 6 to 9, wherein each of A$_2$-4, when present, independently has the structure of Formula 7 or Formula 8:

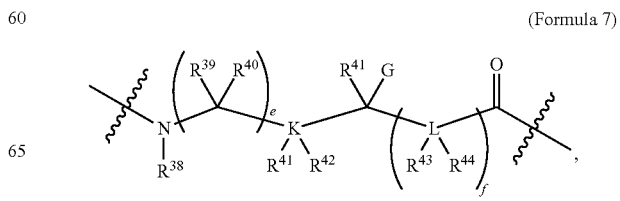
(Formula 7)

263

-continued (Formula 8)

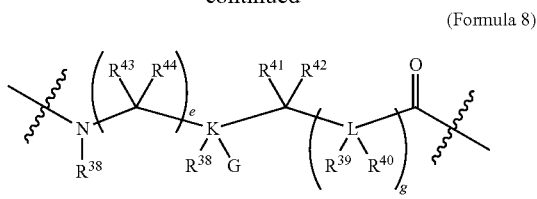

wherein the wavy lines indicated covalent attachment within the Conjugate structure, wherein K and L independently are C, N, O or S, provided that when K or L is O or S, $R^{41}$ and $R^{42}$ to K or $R^{43}$ and $R^{44}$ to L are absent, and when K or L are N, one of $R^{41}$, $R^{42}$ to K or one of $R^{42}$, $R^{43}$ to L are absent, and provided that no two adjacent L are independently selected as N, O, or S; wherein subscripts e and f are independently selected integers that range from 0 to 12, and subscript g is an integer ranging from 1 to 12; wherein G is hydrogen, optionally substituted $C_1$-$C_6$ alkyl, —OH, —$OR^{PR}$, —$CO_2H$, $CO_2R^{PR}$ wherein $R^{PR}$ is a suitable protecting, —$N(R^{PR})(R^{PR})$, wherein $R^{PR}$ are independently a protecting group or $R^{PR}$ together form a suitable protecting group, or —$N(R^{45})(R^{46})$, wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl; wherein $R^{38}$ is hydrogen or optionally substituted $C_1$-$C_6$ alkyl; $R^{39}$-$R^{44}$ independently are hydrogen, optionally substituted $C_1$-$C_6$ alkyl, optionally substituted aryl, or optionally substituted heteroaryl, or both $R^{39}$, $R^{40}$ together with the carbon to which they are attached comprise a $C_3$-$C_6$ cycloalkyl, or $R^{41}$, $R^{42}$ together with K to which they are attached when K is C, or $R^{43}$, $R^{44}$ together with L to which they are attached when L is a carbon atom comprise a $C_3$-$C_6$ cycloalkyl, or $R^{40}$ and $R^{41}$, or $R^{40}$ and $R^{43}$, or $R^{41}$ and $R^{43}$ to together with the carbon atom or heteroatom to which they are attached and the atoms intervening between those carbon atoms and/or heteroatoms comprise a 5- or 6-membered cycloalkyl or heterocycloalkyl, provided that when K is O or S, $R^{41}$ and $R^{42}$ are absent, when K is N, one of $R^{41}$, $R^{42}$ is absent, when L is O or S, $R^{43}$ and $R^{44}$ are absent, and when L is N, one of $R^{43}$, $R^{44}$ is absent, or wherein $A_O$ has a structure corresponding to an alpha-amino, beta-amino or another amine-containing acid.

11C. The Ligand Drug Conjugate composition, or compound thereof, of any one of embodiments 1C to 10C wherein the quaternized tubulysin Drug Unit (-$D^+$) has the structure of:

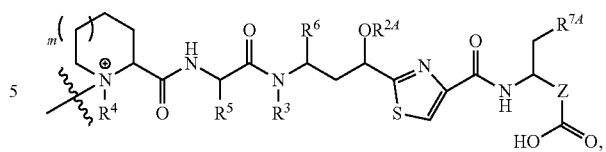

wherein subscript m is 0 or 1; Z is an optionally substituted alkylene or an optionally substituted alkenylene; and $R^{7A}$ is optionally substituted aryl or optionally substituted heteroaryl.

12C. The Ligand Drug Conjugate composition, or compound thereof, of embodiment 11C wherein the quaternized tubulysin Drug Unit (-$D^+$) has the structure of:

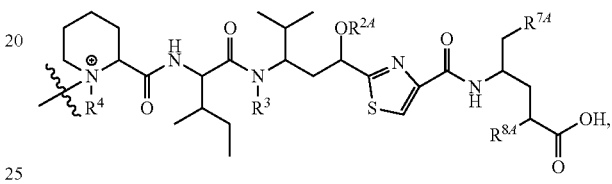

wherein $R^{7A}$ is optionally substituted phenyl and R is hydrogen or methyl.

13C. The Ligand Drug Conjugate composition, or compound thereof, of embodiment 12C wherein the quaternized tubulysin Drug Unit (-$D^+$) has the structure of

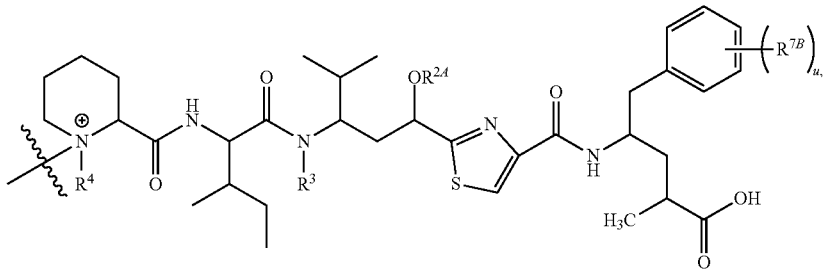

wherein $R^4$ is methyl; subscript u is 0, 1 or 2; $R^3$ is H, methyl, ethyl, propyl, —$CH_2$—$OC(O)R^{3A}$, —$CH_2CH(R^{3B})$ $C(O)R^{3A}$ or —$CH(R^{3B})C(O)NHR^{3A}$, wherein $R^{3A}$ is $C_1$-$C_6$ alkyl and $R^{3B}$ is H or $C_1$-$C_6$ alkyl, independently selected from $R^{3A}$; $R^{2A}$ along with the oxygen atom to which it is attached is an O-linked substituent selected from the group consisting of —$OCH_2OCH_2R^{2B}$, —$OCH_2R^{2B}$, —$OC(O)$ $R^{2B}$, —$CH_2OC(O)R^{2B}$, —$OC(O)N(R^{2B})(R^{2C})$, and —$OCH_2C(O)N(R^{2B})(R^{2C})$, wherein $R^{2B}$ and $R^{2C}$ are independently selected from the group consisting of H, $C_1$-$C_6$ alkyl and $C_2$-$C_6$ alkenyl; and each $R^{7B}$, when present, independently is —OH or —$OCH_3$.

14C. The Ligand Drug Conjugate composition, or compound thereof, of embodiment 13C wherein the quaternized tubulysin Drug Unit (-$D^+$) has the structure of

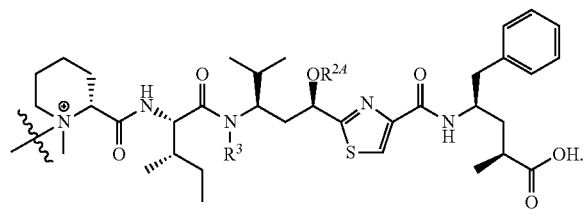

15C. The Ligand Drug Conjugate composition, or compound thereof, of any one of embodiments 11C to 14C wherein $R^{2A}$ is —CH$_2$CH$_3$.

16C. The Ligand Drug Conjugate composition, or compound thereof, of any one of embodiments 11C to 14C wherein $R^{2A}$ is —CH$_2$—CH=CH$_2$.

17C. The Ligand Drug Conjugate composition, or compound thereof, of embodiment 13C, wherein $R^{2A}$ is —CH$_2$CH$_3$, —CH$_2$—CH=CH$_2$ or —CH$_2$C(CH$_3$)=CH$_2$, $R^{2B}$ is —CH$_3$, $R^3$ is —CH$_3$ and subscript u is 0, or $R^{2A}$ is —CH$_2$CH$_3$ or —CH$_2$—CH=CH$_2$, or —CH$_2$C(CH$_3$)=CH$_2$, $R^{2B}$ is —CH$_3$, $R^3$ is —CH$_3$ and subscript u is 1, wherein $R^{7B}$ is —OH.

18C. The Ligand Drug Conjugate composition, or compound thereof, of embodiment 13C wherein the quaternized tubulysin Drug Unit (-D$^+$) has the structure of:

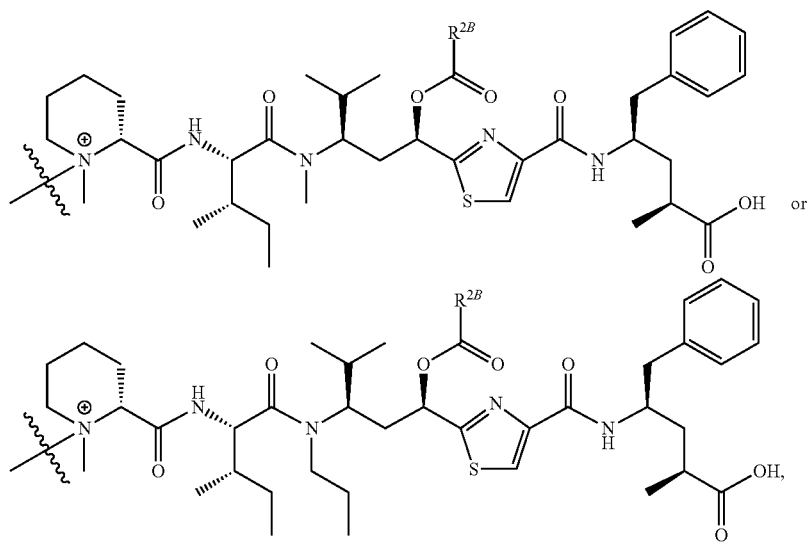

wherein R is —CH$_3$, —CH$_2$CH$_3$, —CH$_2$CH$_2$CH$_3$, —CH(CH$_3$)$_2$, —CH$_2$CH(CH$_3$)$_2$, or —CH$_2$C(CH$_3$)$_3$.

19C. The Ligand Drug Conjugate composition, or compound thereof, of embodiment 13C wherein the quaternized tubulysin Drug Unit (-D$^+$) has the structure of:

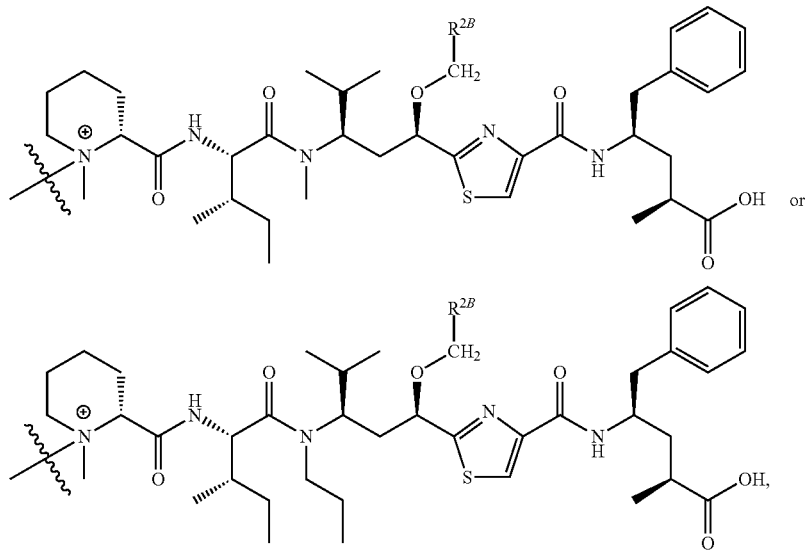

wherein $R^{2B}$ is hydrogen, methyl or —OCH$_3$, or —OCH$_2$R$^{2B}$ is —OCH$_2$CH═CH$_2$ or —OCH$_2$C(CH$_3$)═CH$_2$.

20C. The Ligand Drug Conjugate composition, or compound thereof, of embodiment 13 wherein the quaternized tubulysin Drug Unit (-D$^+$) is that of tubulysin M, which has the structure of:

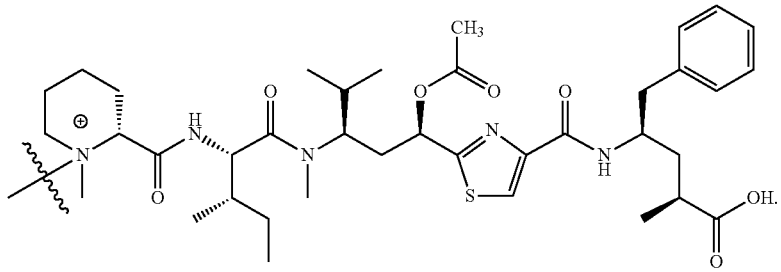

21C. The Ligand Drug Conjugate composition, or compound thereof, of any one of embodiments 1C to 20C wherein L$_P$ is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the sulfur substituent is in reduced or oxidized form, or L$_P$ is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

22C. The Ligand Drug Conjugate composition, or compound thereof, of embodiment 21C wherein the aminoalkanedioic acid, diaminoalkanoic acid, sulfur-substituted aminoalkanoic acid or hydroxyl substituted aminoalkanoic acid residue has the structure of Formula A or Formula B:

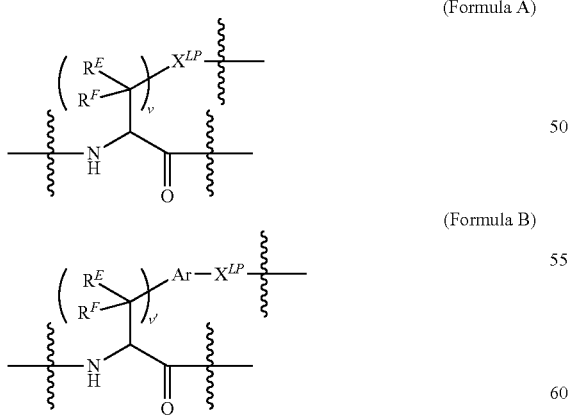

wherein subscript v is an integer ranging from 1 to 4; subscript v' is an integer ranging from 0 to 4; X$^{LP}$ is selected from the group consisting of —O—, —NR$^{LP}$—, —S—, —S(═O)—, —S(═O)$_2$—, —C(═O)—, —C(═O)N(R$^{LP}$)—, —N(R$^{LP}$)C(═O)N(R$^{LP}$)—, and —N(R$^{LP}$)C(═NR$^{LP}$)N(R$^{LP}$)— wherein each R$^{LP}$ is independently selected from the group consisting of hydrogen and optionally substituted alkyl or two of R$^{LP}$ together along with their intervening atoms define a heterocycloalkyl and any remaining R$^{LP}$ are as previously defined; Ar is an arylene or heteroarylene, optionally substituted; each R$^E$ and R$^F$ is independently selected from the group consisting of —H, optionally substituted alkyl, optionally substituted aryl and optionally substituted heteroaryl, or R$^E$ and R$^F$ together with the same carbon to which they are attached, or R$^E$ and R$^F$ from adjacent carbons together with these carbons, defines a optionally substituted cycloalkyl with any remaining R$^E$ and R$^F$ substituents as previously defined; and wherein the wavy lines indicates covalent attachment of the Formula A or Formula B structure within the Conjugate structure.

23C. The Ligand Drug Conjugate composition, or compound thereof, of any one of embodiments 1C to 20C wherein -L$_P$(PEG)- has the structure of Formula A1 or A2:

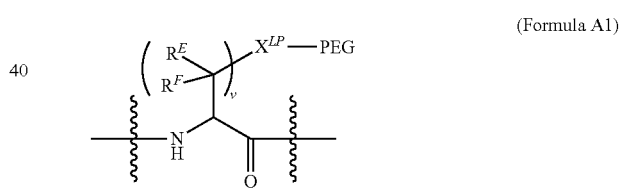

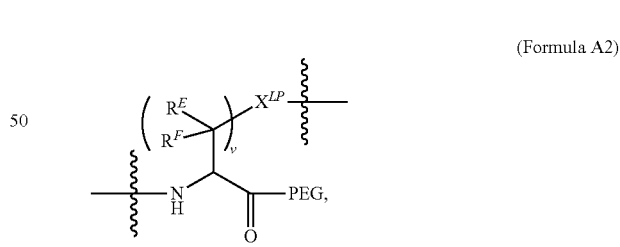

wherein X$^{LP}$ is selected from the group consisting of —O—, —NH, —S— and —C(═O)—; R$^E$ and R$^F$ are independently selected from the group consisting of —H, and —C$_1$-C$_4$ alkyl; and wherein the wavy line indicates covalent attachment of Formula A1 or Formula A2 within the Conjugate structure.

24C. The Ligand Drug Conjugate composition of embodiment 1C wherein the composition is represented by the structure of:

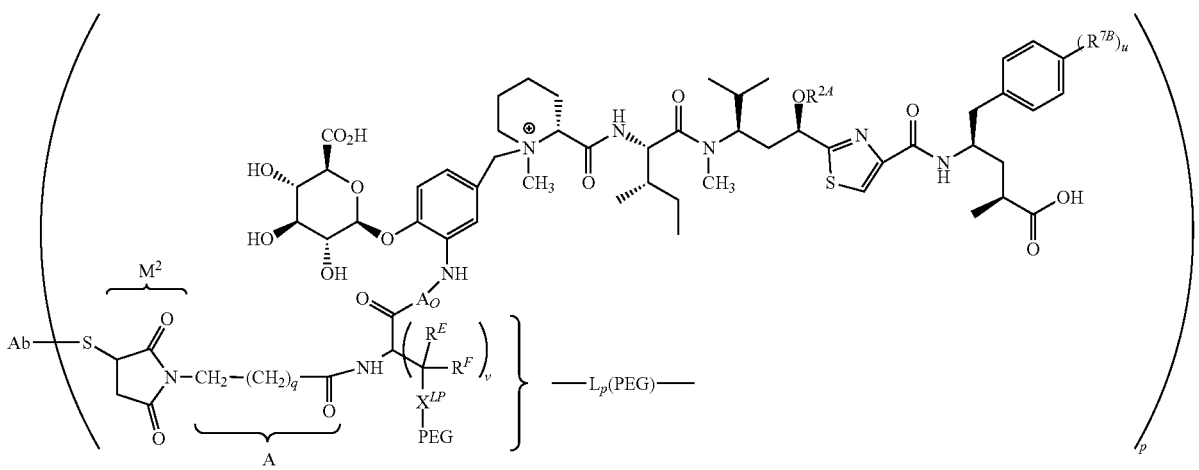

wherein Ab is the antibody Ligand Unit; S is a sulfur atom of the antibody Ligand Unit; $R^{2A}$ is saturated $C_1$-$C_4$ alkyl, unsaturated $C_2$-$C_4$ alkyl, —C(=O)$R^{2B}$, wherein $R^{2B}$ is $C_1$-$C_4$ alkyl; $A_O$ is absent or is an amine-containing acid residue; subscript p is a number ranging from 1 to 8; subscript q is an integer ranging from 1 to 4; subscript u is 0 or 1; subscript v is an integer ranging from 1 to 4; $R^{7B}$, when present, is —OH; $X^{LP}$ is selected from the group consisting of —O—, —NH, —S— and —C(=O)—; and $R^E$ and $R^F$ are independently selected from the group consisting of —H, and $C_1$-$C_4$ alkyl.

25C. The Ligand Drug Conjugate composition of embodiment 1C wherein a compound thereof is represented by the structure of:

from 1 to 4; $R^{7B}$, when present, is —OH; $X^{LP}$ is selected from the group consisting of —O—, —NH, —S— and —C(=O)—; and $R^E$ and $R^F$ are independently selected from the group consisting of —H, and $C_1$-$C_4$ alkyl.

26C. The Ligand Drug Conjugate composition, or compound thereof, of claim 24C or 25, wherein $R^{2A}$ is saturated $C_1$-$C_4$ alkyl or unsaturated $C_3$-$C_4$ alkyl, wherein saturated $C_1$-$C_4$ alkyl is —$CH_3$, —$CH_2CH_3$, —$CH_2CH_2CH_3$ and unsaturated $C_3$-$C_4$ alkyl is —$CH_2CH$=$CH_2$ or —$CH(CH_3)CH$=$CH_2$.

27C. The Ligand Drug Conjugate composition, or compound thereof, of embodiment 24C or 25C wherein $R^{2A}$ is —C(O)$CH_3$.

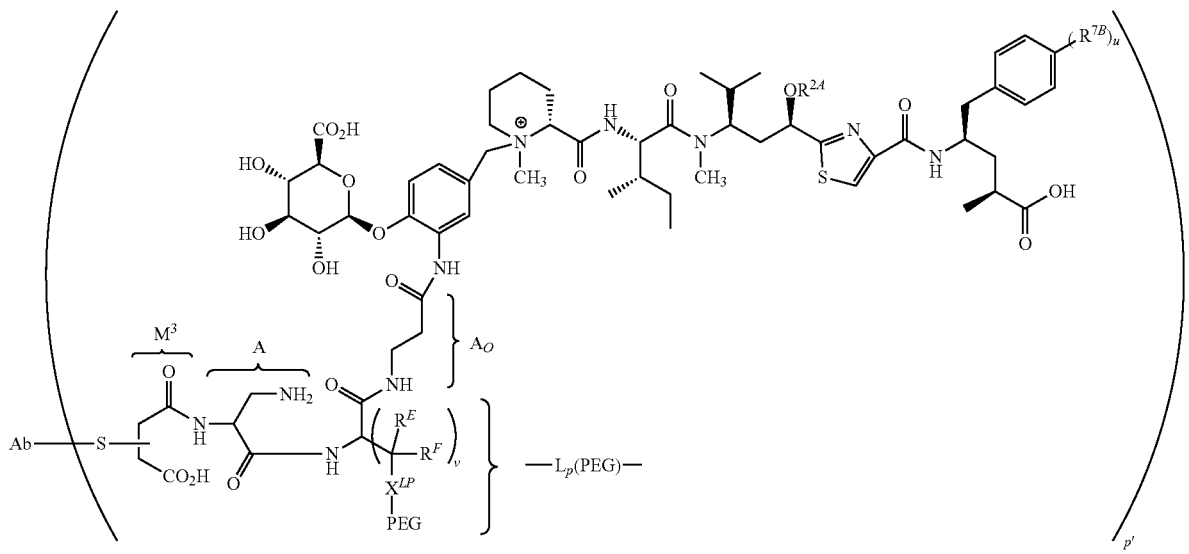

wherein Ab is the antibody Ligand Unit; S is a sulfur atom of the antibody Ligand Unit; the Ab-S— moiety is bonded to the carbon α or 1 to the indicated $M^3$ carboxylic acid; $R^{2A}$ is saturated $C_1$-$C_4$ alkyl, unsaturated $C_2$-$C_4$ alkyl, —C(=O)$R^{2B}$, wherein $R^{2B}$ is $C_1$-$C_4$ alkyl; subscript p' is an integer ranging from 1 to 8; subscript q is an integer ranging from 1 to 4; subscript u is 0 or 1; subscript v is an integer ranging 28C. The Ligand Drug Conjugate composition, or compound thereof, of embodiment 24C or 25C wherein $R^{2A}$ is —$CH_2CH_3$.

29C. The Ligand Drug Conjugate composition, or compound thereof, of embodiment 24C or 25C wherein $R^{2A}$ is —$CH_2CH$=$CH_2$.

30C. The Ligand Drug Conjugate composition, or a compound thereof, of any one of embodiments 1C to 29C wherein PEG has the structure selected from the group consisting of:

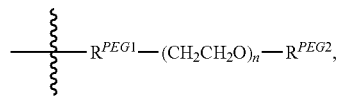

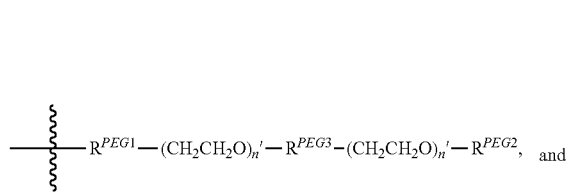 and

31C. The Ligand Drug Conjugate composition, or compound thereof, of embodiment 24C or 25C wherein —$X^{LP}$—PEG has the structure of:

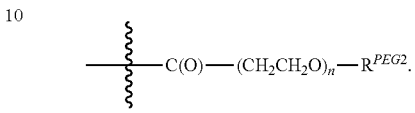

32C. The Ligand Drug Conjugate composition, or a compound thereof, of embodiment 31C wherein subscript n is 12 and $R^{PEG2}$ is hydrogen or —$CH_3$.

33C. The Ligand Drug Conjugate composition of embodiment 1C wherein a compound thereof is represented by the structure of:

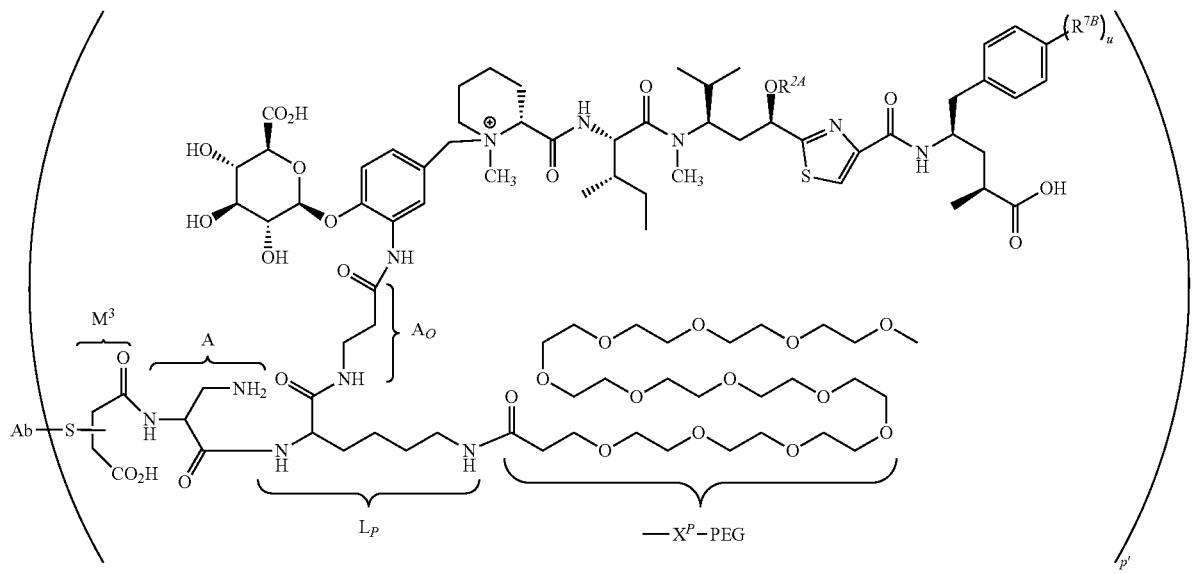

-continued

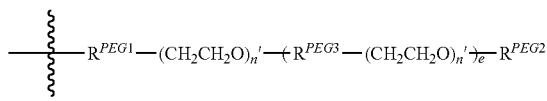

wherein the wavy line indicates site of attachment to $X^{LP}$ of the Parallel Connector Unit ($L_P$); $R^{PEG1}$ is an optional PEG Attachment Unit; $R^{PEG2}$ is a PEG Capping Unit; $R^{PEG3}$ is an PEG Coupling Unit; subscript n ranges from 2 to 72; each subscript n' is independently selected from 1 to 72; and subscript e ranges from 2 to 5.

wherein Ab is the antibody Ligand Unit; S is a sulfur atom of the antibody Ligand Unit; the Ab-S— moiety is bonded to the carbon α or β to the indicated $M^3$ carboxylic acid; subscript p' is an integer ranging from 1 to 8; subscript u is 0 or 1; $R^{7B}$, when present, is —OH; and $R^{2A}$ along with the oxygen atom to which it is attached is —OC(O)$CH_3$, —$CH_2CH_3$ or —$CH_2CH$=$CH_2$.

34C. The Ligand Drug Conjugate composition of embodiment 33C wherein a compound thereof is represented by the structure of:

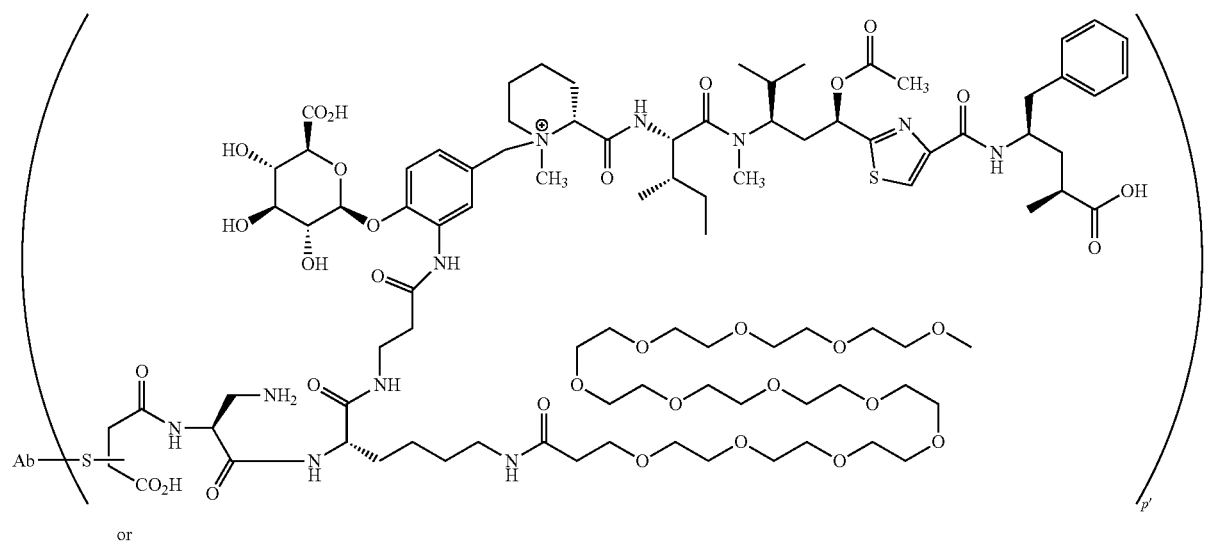

or

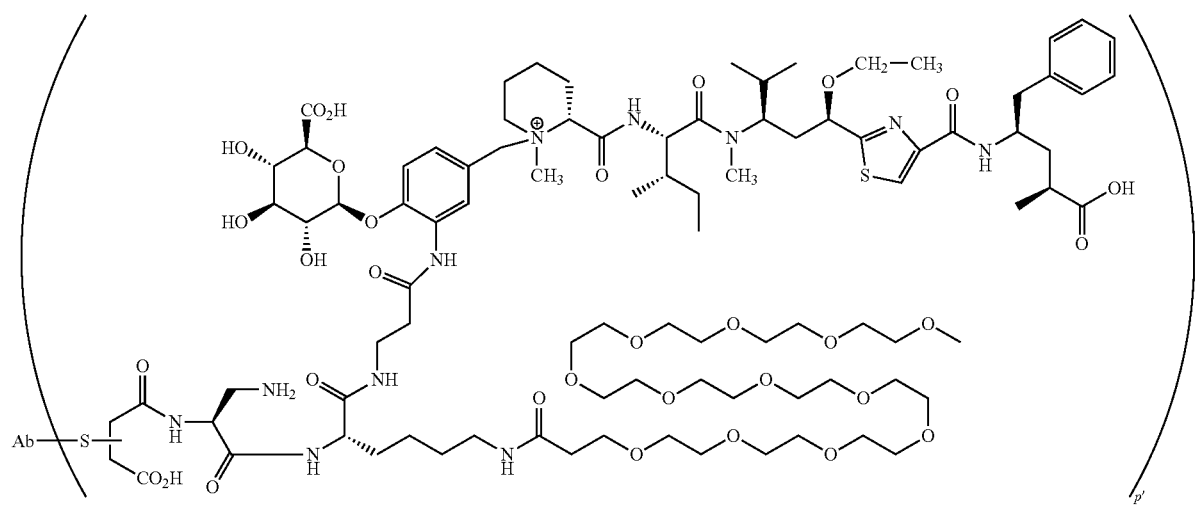

1D. A Ligand Drug Conjugate composition wherein the composition is represented by the structure of Formula 1A

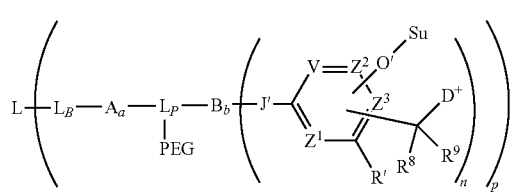

(Formula 1A)

wherein L is an antibody Ligand Unit, thereby defining an Antibody Drug Conjugate (ADC); $L_B$ is a Ligand Covalent Binding Unit; L is a Parallel Connector Unit; PEG is a Polyethylene Glycol Unit; subscript a is 0 or 1; subscript b is 0 or 1; A is a first optional Stretcher Unit so that subscript a is 0 when A is absent or A is present so that subscript a is 1 and is optionally comprised of two, three or four independently selected subunits ($A_1$, $A_2$, $A_3$, $A_4$); B is an Branching Unit or a second optional Stretcher Unit ($A_O$) so that subscript b is 0 when B is absent or B is present so that subscript b is 1 and is optionally comprised of two, three or four subunits independently of A; subscript n is 1, 2, 3 or 4, provided that subscript b is 1 and B is a Branching when subscript n is 2, 3 or 4 and provided that B is $A_O$ or is absent when subscript n is 1; Su is a carbohydrate moiety; —O'— represents an oxygen atom of an O-glycosidic bond cleavable by a glycosidase; -J'-represents a heteroatom, optionally substituted when nitrogen, from a functional group of B, when B is present, or $L_B$, when B is absent; V, $Z^1$, $Z^2$ and $Z^3$ are =N— or =C($R^{24}$)—, wherein $R^{24}$ is hydrogen or alkyl, alkenyl or alkynyl, optionally substituted, or halogen, —$NO_2$, —CN or other electron withdrawing group, or —$OCH_3$ or other electron donating group, —O'-Su, or —C($R^8$)($R^9$)-$D^+$, wherein at least at least two of V, Z, $Z^2$ and $Z^3$ are =C($R^{24}$)—, provided, one any only one $R^{24}$ is —C($R^8$)($R^9$)-$D^+$ so that —C($R^8$)($R^9$)-$D^+$ is bonded to one of V, $Z^1$, Z, $Z^3$ when that variable group is =C($R^{24}$)— and one and only one other $R^{24}$ is so that —O'-Su is bonded to another one of V, Z, Z, $Z^3$ when that variable group is =C($R^{24}$)—, and the —O'Su and —C($R^8$)($R^9$)-$D^+$ substituents are ortho or para to each other; $R^8$ and $R^9$ independently are hydrogen, alkyl, alkenyl or alkynyl, optionally substituted, or aryl or heteroaryl, optionally substituted; R' is hydrogen or is halogen, —$NO_2$, —CN or other electron withdrawing group; $D^+$ is a quaternized tubulysin Drug Unit, preferably having the structure of:

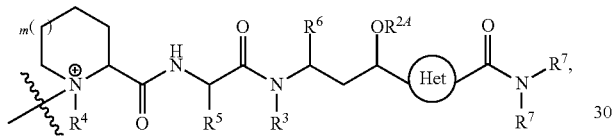

wherein the circle represents an 5-membered nitrogen-heteroarylene and wherein the indicated required substituents to that heteroarylene are in a 1,3-relationship with each other with optional substitution at the remaining positions; subscript m is 0 or 1; $R^{2A}$ is hydrogen or optionally substituted alkyl, or $R^{2A}$ along with the oxygen atom to which it is attached defines an O-linked substituent; $R^3$ is hydrogen or optionally substituted alkyl; $R^4$, $R^5$ and $R^6$ are optionally substituted alkyl; one $R^7$ is an optionally substituted alkyl, an optionally substituted arylalkyl, optionally substituted heteroarylalkyl and the other $R^7$ is hydrogen or an optionally substituted alkyl; and $R^{8A}$ is hydrogen or optionally substituted alkyl; subscript p is a number ranging from 1 to 24; and wherein the wavy line indicates covalent bonding of $D^+$ to the remainder of the Ligand Drug Conjugate structure and wherein each optionally substituted alkyl is independently selected, and wherein said glycosidase cleavage results in release of a tubulysin compound (D) from a Ligand Drug Conjugate compound of the composition, wherein said glycosidase cleavage results in release of a tubulysin compound (D) from a Ligand Drug Conjugate compound of the composition, wherein the Ligand Drug Conjugate compound has the structure of Formula IA in which subscript p is replaced by subscript p' wherein subscript p' is an integer ranging from 1 to 24.

2D. The Ligand Drug Conjugate composition of embodiment 1D wherein the composition of Formula 1A is represented by the structure of one of Formula 2A-2F:

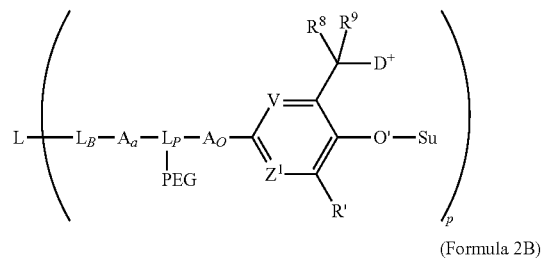

(Formula 2A)

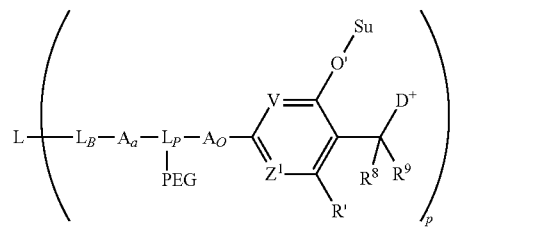

(Formula 2B)

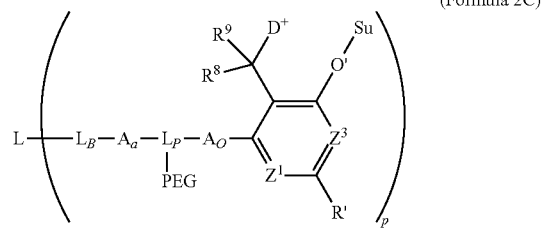

(Formula 2C)

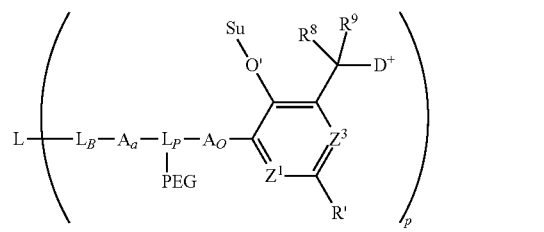

(Formula 2D)

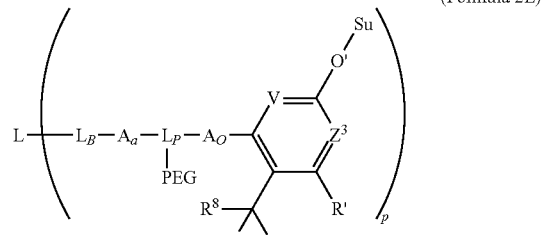

(Formula 2E)

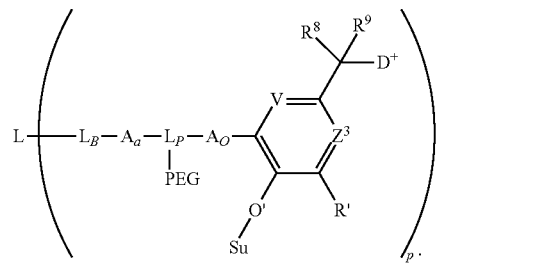

(Formula 2F)

3D. The Ligand Drug Conjugate composition of embodiment 1D or 2D, wherein the antibody Ligand Unit is capable of selectively binding to an accessible cell-surface antigen of abnormal cells, wherein the antigen is capable of cellular internalization of bound ADC and is preferentially present on the abnormal or other unwanted cells in comparison to normal cells.

4D. The Ligand Drug Conjugate composition of embodiment 1D or 2D wherein —O'-Su has the structure of Formula 3:

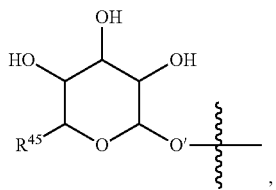

(Formula 3)

wherein the wavy line represents covalent bonding of O' to the remainder of the LDC structure; and $R^{45}$ is —CH$_2$OH or —CO$_2$H.

5D. The Ligand Drug Conjugate composition of embodiment 2D wherein the composition is represented by the structure of Formula 4:

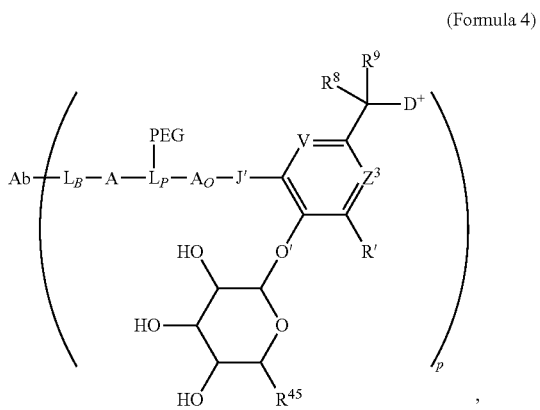

(Formula 4)

wherein Ab is the antibody Ligand Unit; J' is —N($R^{33}$)—, wherein $R^{33}$ is hydrogen or methyl; V and $Z^3$ independently are =CH— or =N—; R' is hydrogen or an electron withdrawing group; $R^8$ is hydrogen; $R^9$ is hydrogen, optionally substituted $C_1$-$C_6$ alkyl or optionally substituted phenyl; $R^{45}$ is —CO$_2$H; and subscript p is a number ranging from 1 to 24.

6D. The Ligand Drug Conjugate composition of embodiment 5D wherein the composition is represented by the structure of Formula 6:

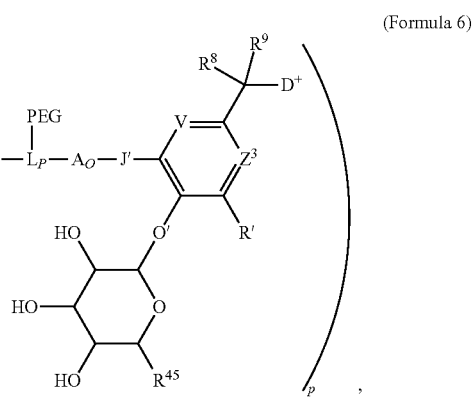

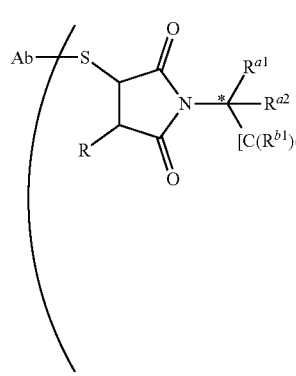

(Formula 6)

wherein S is a sulfur atom of the antibody Ligand Unit (Ab); the asterisk (*) designates chirality or absence thereof at the indicated carbon; $A_{2-4}$ are independently selected optional subunits of A, wherein —[C($R^{b1}$)($R^{b1}$)]$_q$—[HE]- is $A_1$ when one or more such subunits are present; R is hydrogen; R' is hydrogen or an electron withdrawing group; $R^{a1}$ is hydrogen or a basic unit (BU) wherein BU is a Basic Unit having the structure of —CH$_2$—N($R^{22}$)($R^{23}$), or an acid addition salt thereof, wherein $R^{22}$ and $R^{23}$ independently are hydrogen, methyl or ethyl or both together with the nitrogen atom to which they are attached comprise a 5- or 6-membered heterocycloalkyl, or one of $R^{22}$, $R^{23}$ is hydrogen and the other is an acid labile carbamate protecting group; $R^{a2}$ is hydrogen; subscript q is an integer ranging from 0 to 5 when HE is present or 1 to 5 when HE is absent; each $R^{b1}$ independently is hydrogen or optionally substituted $C_1$-$C_6$ alkyl; HE is absent or is —C(=O)—; $R^{45}$ is —CO$_2$H; J' is —NH—; V and $Z^3$ are =CH$_2$—; $R^8$ is hydrogen; $R^9$ is hydrogen or methyl; subscript p is a number ranging from 1 to 16; and wherein the remaining variable groups are as defined for Formula 1A.

7D. The Ligand Drug Conjugate composition of embodiment 1D wherein a compound thereof has the structure of Formula 9A or Formula 9B (Formula 9A)

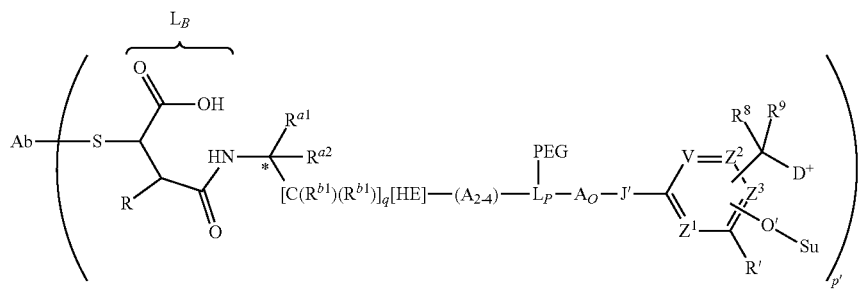

(Formula 9B)

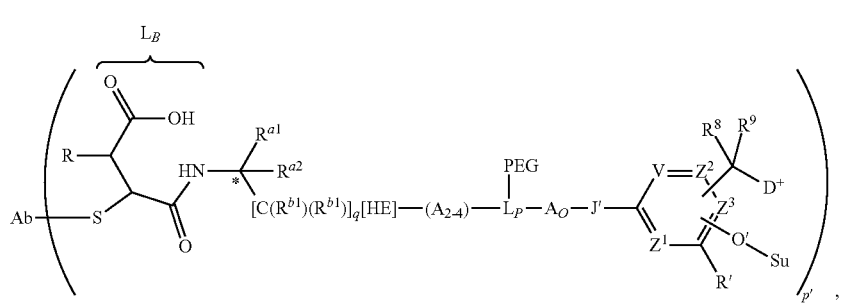

wherein S is a sulfur atom of the antibody Ligand Unit (Ab); the asterisk (*) designates chirality or absence thereof at the indicated carbon; $A_{2-4}$ are independently selected optional subunits of A, wherein $—[C(R^{b1})(R^{b1})]_q—[HE]—$ is $A_1$ when one or more such subunits are present; R is hydrogen; R' is hydrogen or an electron withdrawing group; $R^{a1}$ is —H or BU wherein BU is a Basic Unit having the structure of $—CH_2—N(R^{22})(R^{23})$, or an acid addition salt thereof, wherein $R^{22}$ and $R^{23}$ independently are hydrogen or methyl or both together with the nitrogen atom to which they are attached define a basic nitrogen-containing 5- or 6-membered heterocycloalkyl, or one of $R^{22}$, $R^{23}$ is hydrogen and the other is an acid labile protecting group; $R^{a2}$ is hydrogen; subscript q is an integer ranging from 0 to 5 when HE is present or from 1 to 5 when HE is absent; each $R^{b1}$ independently is hydrogen or optionally substituted $C_1$-$C_6$ alkyl; HE is absent or is —C(=O)—; J' is —O— or —NH—; $R^8$ and $R^9$ are independently —H or optionally substituted alkyl, or both together along with the carbon atom to which they are attached define a cycloalkyl; and subscript p' is an integer ranging from 1 to 24; and wherein the remaining variable groups are as defined for Formula 1A.

8D. The Ligand Drug Conjugate composition of embodiment 7D, wherein a compound thereof has the structure of Formula 10A or Formula 10B:

(Formula 10A)

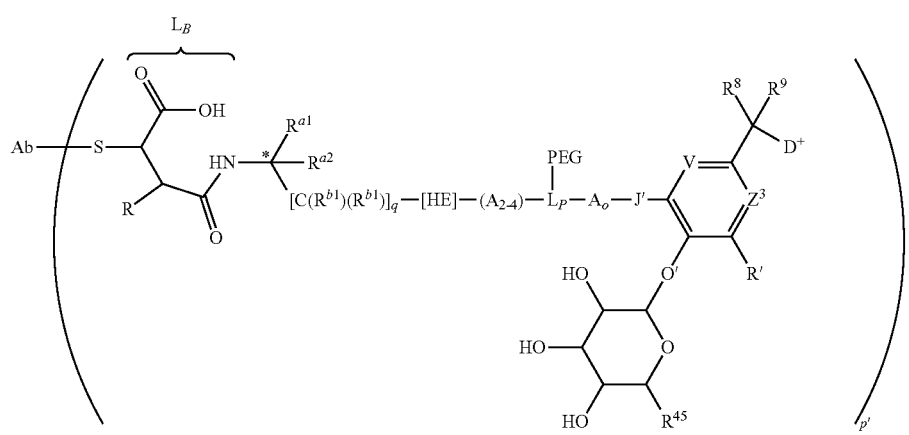

-continued (Formula 10B)

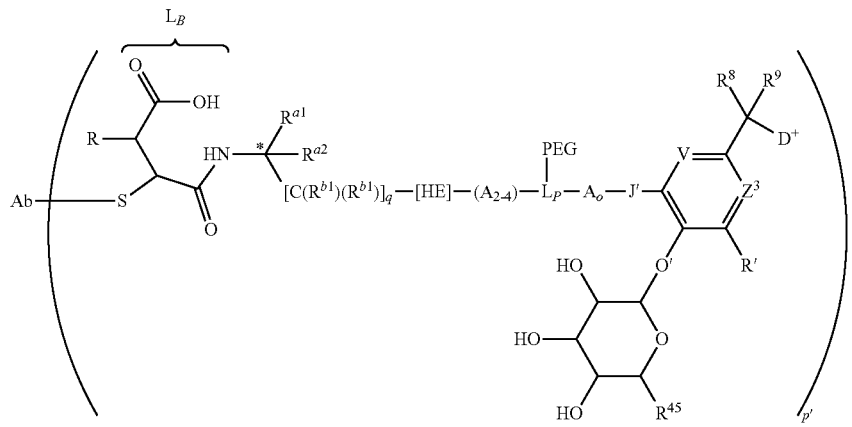

wherein R is hydrogen; R' is hydrogen, —NO$_2$, —Cl or —F; HE is —C(=O)—; R$^{45}$ is —CO$_2$H; J' is —NH—; V and Z$^3$ are each =CH$_2$—; R$^8$ is hydrogen; R$^9$ is hydrogen or methyl; p' is an integer ranging from 1 to 12; and wherein the remaining variable groups are as defined for Formula 1A.

9D. The Ligand Drug Conjugate composition, or compound thereof, of embodiment 6D, 7D or 8D wherein the indicated starred (*) carbon is predominantly in the same absolute configuration as the alpha carbon of an L-amino acid when that indicated carbon is chiral.

10D. The Ligand Drug Conjugate composition, or compound thereof, of any one of embodiments 1D to 5D wherein A and A$_O$, when present, independently has the structure of Formula 7 or Formula 8, or any one of embodiments 6D to 9D, wherein each of A$_2$-4, when present, independently has the structure of Formula 7 or Formula 8:

(Formula 7)

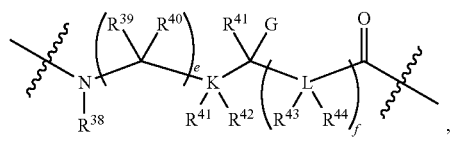

(Formula 8)

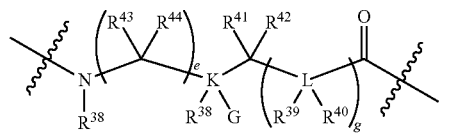

wherein the wavy lines indicated covalent attachment within the Conjugate structure, wherein K and L independently are C, N, O or S, provided that when K or L is O or S, R$^{41}$ and R$^{42}$ to K or R$^{43}$ and R$^{44}$ to L are absent, and when K or L are N, one of R$^{41}$, R$^{42}$ to K or one of R$^{42}$, R$^{43}$ to L are absent, and provided that no two adjacent L are independently selected as N, O, or S; wherein subscripts e and f are independently selected integers that range from 0 to 12, and subscript g is an integer ranging from 1 to 12; wherein G is hydrogen, optionally substituted C$_1$-C$_6$ alkyl, —OH, —OR$^{PR}$, —CO$_2$H, CO$_2$R$^{PR}$ wherein R$^{PR}$ is a suitable protecting, —N(R$^{PR}$)(R$^{PR}$), wherein R$^{PR}$ are independently a protecting group or R$^{PR}$ together form a suitable protecting group, or —N(R$^{45}$)(R$^{46}$), wherein one of R$^{45}$, R$^{46}$ is hydrogen or R$^{PR}$, wherein R$^{PR}$ is a suitable protecting group, and the other is hydrogen or optionally substituted C$_1$-C$_6$ alkyl; wherein R$^{38}$ is hydrogen or optionally substituted C$_1$-C$_6$ alkyl; R$^{39}$-R$^{44}$ independently are hydrogen, optionally substituted C$_1$-C$_6$ alkyl, optionally substituted aryl, or optionally substituted heteroaryl, or both R$^{39}$, R$^{40}$ together with the carbon to which they are attached comprise a C$_3$-C$_6$ cycloalkyl, or R$^{41}$, R$^{42}$ together with K to which they are attached when K is C, or R$^{43}$, R$^{44}$ together with L to which they are attached when L is a carbon atom comprise a C$_3$-C$_6$ cycloalkyl, or R$^{40}$ and R$^{41}$, or R$^{40}$ and R$^{43}$, or R$^{41}$ and R$^{43}$ to together with the carbon atom or heteroatom to which they are attached and the atoms intervening between those carbon atoms and/or heteroatoms comprise a 5- or 6-membered cycloalkyl or heterocycloalkyl, provided that when K is O or S, R$^{41}$ and R$^{42}$ are absent, when K is N, one of R$^{41}$, R$^{42}$ is absent, when L is O or S, R$^{43}$ and R$^{44}$ are absent, and when L is N, one of R$^{43}$, R$^{44}$ is absent, or wherein A$_O$ has a structure corresponding to an alpha-amino, beta-amino or another amine-containing acid.

11D. The Ligand Drug Conjugate composition, or compound thereof, of any one of embodiments 1D to 10D wherein the quaternized tubulysin Drug Unit (-D$^+$) has the structure of

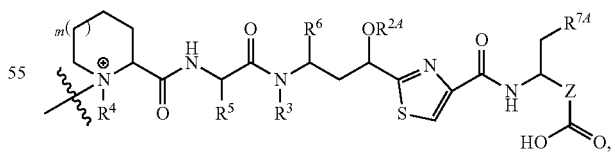

wherein subscript m is 0 or 1; Z is an optionally substituted alkylene or an optionally substituted alkenylene; and R$^{7A}$ is optionally substituted aryl or optionally substituted heteroaryl.

12D. The Ligand Drug Conjugate composition, or compound thereof, of embodiment 11D wherein the quaternized tubulysin Drug Unit (-D$^+$) has the structure of

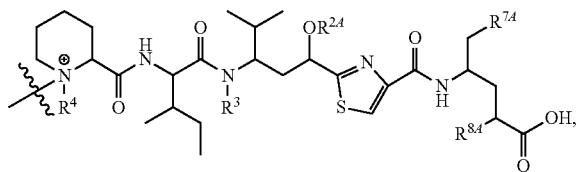

wherein $R^{7A}$ is optionally substituted phenyl and $R^8$ is hydrogen or methyl.

13D. The Ligand Drug Conjugate composition, or compound thereof, of embodiment 12D wherein the quaternized tubulysin Drug Unit (-D⁺) has the structure of:

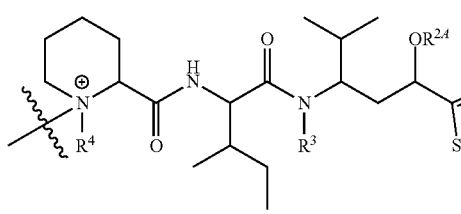

wherein $R^4$ is methyl; subscript u is 0, 1 or 2; $R^3$ is H, methyl, ethyl, propyl, —CH₂—OC(O)$R^{3A}$, —CH₂CH($R^{3B}$)C(O)$R^{3A}$ or —CH($R^{3B}$)C(O)NH$R^{3A}$, wherein $R^{3A}$ is C₁-C₆ alkyl and $R^{3B}$ is H or C₁-C₆ alkyl, independently selected from $R^{3A}$; $R^{2A}$ along with the oxygen atom to which it is attached is an O-linked substituent selected from the group consisting of —OCH₂OCH₂$R^{2B}$, —OCH₂$R^{2B}$, —OC(O)$R^{2B}$, —CH₂OC(O)$R^{2B}$, —OC(O)N($R^{2B}$)($R^{2C}$), and —OCH₂C(O)N($R^{2B}$)($R^{2C}$), wherein $R^{2B}$ and $R^{2C}$ are independently selected from the group consisting of H, C₁-C₆ alkyl and C₂-C₆ alkenyl; and each $R^{7B}$, when present, independently is —OH or —OCH₃.

14D. The Ligand Drug Conjugate composition, or compound thereof, of embodiment 13D wherein the quaternized tubulysin Drug Unit (-D⁺) has the structure of:

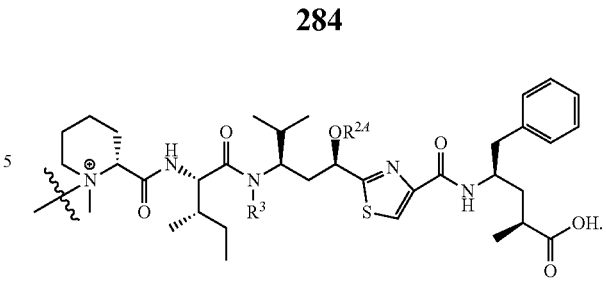

15D. The Ligand Drug Conjugate composition, or compound thereof, of any one of embodiments 11D to 14D wherein $R^{2A}$ is —CH₂CH₃.

16D. The Ligand Drug Conjugate composition, or compound thereof, of any one of embodiments 11 to 14 wherein $R^{2A}$ is —CH₂—CH=CH₂.

17D. The Ligand Drug Conjugate composition, or compound thereof, of embodiment 13D, wherein $R^{2A}$ is —CH₂CH₃, —CH₂—CH=CH₂ or —CH₂C(CH₃)=CH₂, $R^{2B}$ is —CH₃, $R^3$ is —CH₃ and subscript u is 0, or $R^{2A}$ is —CH₂CH₃ or —CH₂—CH=CH₂, or —CH₂C(CH₃)=CH₂, $R^{2B}$ is —CH₃, $R^3$ is —CH₃ and subscript u is 1, wherein $R^{7B}$ is —OH.

18D. The Ligand Drug Conjugate composition, or compound thereof, of embodiment 13D wherein the quaternized tubulysin Drug Unit (-D⁺) has the structure of

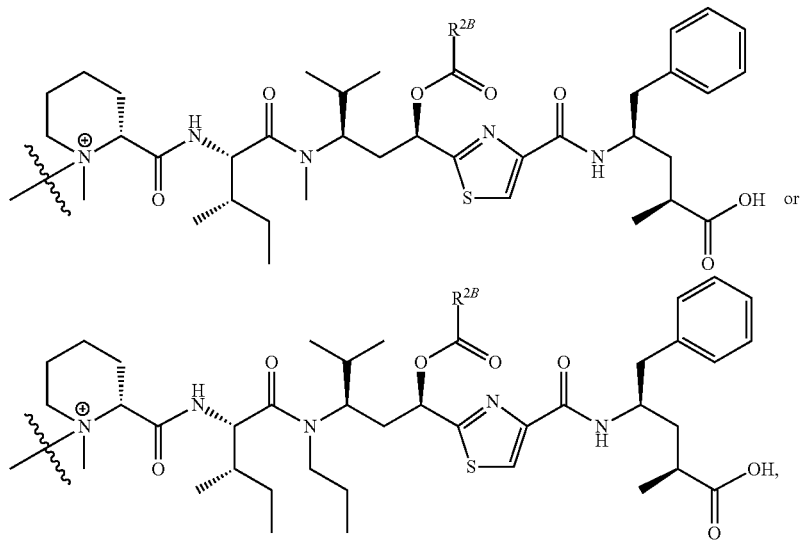

wherein $R^{2B}$ is —CH$_3$, —CH$_2$CH$_3$, —CH$_2$CH$_2$CH$_3$, —CH(CH$_3$)$_2$, —CH$_2$CH(CH$_3$)$_2$, or —CH$_2$C(CH$_3$)$_3$.

19D. The Ligand Drug Conjugate composition, or compound thereof, of embodiment 13D wherein the quaternized tubulysin Drug Unit (-D$^+$) has the structure of

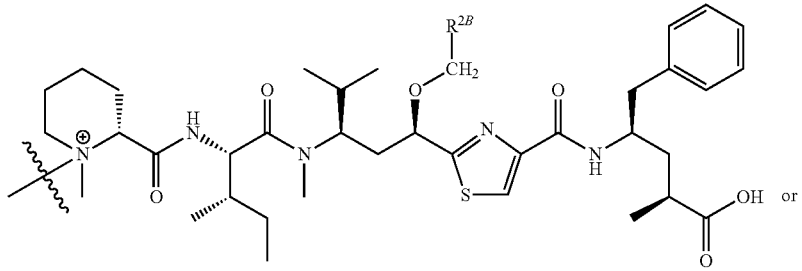

or

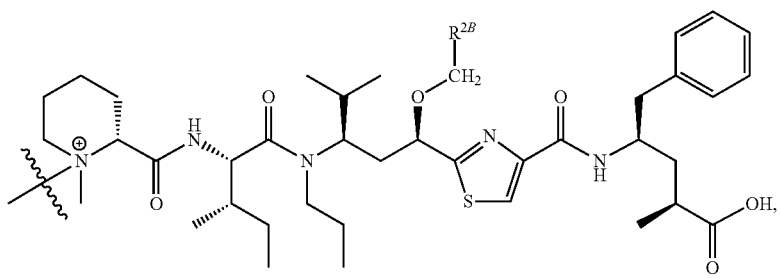

wherein $R^{2B}$ is hydrogen, methyl or —OCH$_3$, or —OCH$_2$R$^{2B}$ is —OCH$_2$CH=CH$_2$ or —OCH$_2$C(CH$_3$)=CH$_2$.

20D. The Ligand Drug Conjugate composition, or compound thereof, of embodiment 13D wherein the quaternized tubulysin Drug Unit -D$^+$ is that of tubulysin M, which has the structure of:

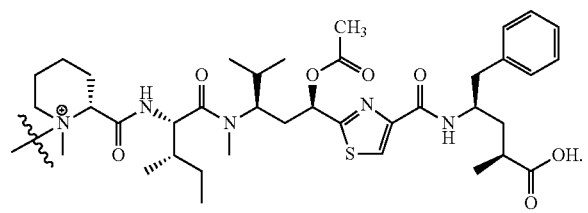

21D. The Ligand Drug Conjugate composition, or compound thereof, of any one of embodiments 1D to 20D wherein $L_P$ is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the sulfur substituent is in reduced or oxidized form, or $L_P$ is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

22D. The Ligand Drug Conjugate composition, or compound thereof, of embodiment 21D wherein the aminoalkanedioic acid, diaminoalkanoic acid, sulfur-substituted aminoalkanoic acid or hydroxyl substituted aminoalkanoic acid residue has the structure of Formula A or Formula B:

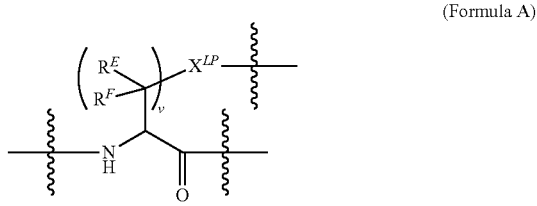

(Formula A)

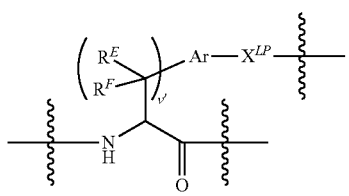

(Formula B)

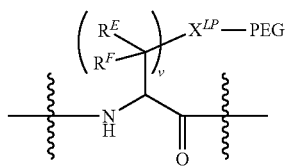

(Formula A1)

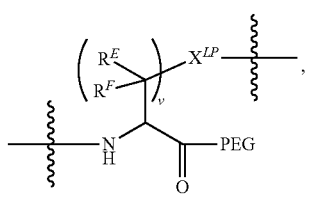

(Formula A2)

wherein subscript v is an integer ranging from 1 to 4; subscript v' is an integer ranging from 0 to 4; $X^{LP}$ is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N(R$^{LP}$)—, and —N(R$^{LP}$)C(=NR$^{LP}$)N(R$^{LP}$)— wherein each $R^{LP}$ is independently selected from the group consisting of hydrogen and optionally substituted alkyl or two of $R^{LP}$ together along with their intervening atoms define a heterocycloalkyl and any remaining $R^{LP}$ are as previously defined; Ar is an arylene or heteroarylene, optionally substituted; each $R^E$ and $R^F$ is independently selected from the group consisting of —H, optionally substituted alkyl, optionally substituted aryl and optionally substituted heteroaryl, or $R^E$ and $R^F$ together with the same carbon to which they are attached, or $R^E$ and $R^F$ from adjacent carbons together with these carbons, defines a optionally substituted cycloalkyl with any remaining $R^E$ and $R^F$ substituents as previously defined; and wherein the wavy lines indicates covalent attachment of the Formula A or Formula B structure within the Conjugate structure.

23D. The Ligand Drug Conjugate composition, or compound thereof, of any one of embodiments 1D to 20D wherein -L$_P$(PEG)- has the structure of Formula A1 or A2:

wherein $X^{LP}$ is selected from the group consisting of —O—, —NH, —S— and —C(=O)—; $R^E$ and $R^F$ are independently selected from the group consisting of —H, and —C$_1$-C$_4$ alkyl; and wherein the wavy line indicates covalent attachment of Formula A1 or Formula A2 within the Conjugate structure.

24D. The Ligand Drug Conjugate composition of embodiment 1D wherein the composition is represented by the structure of:

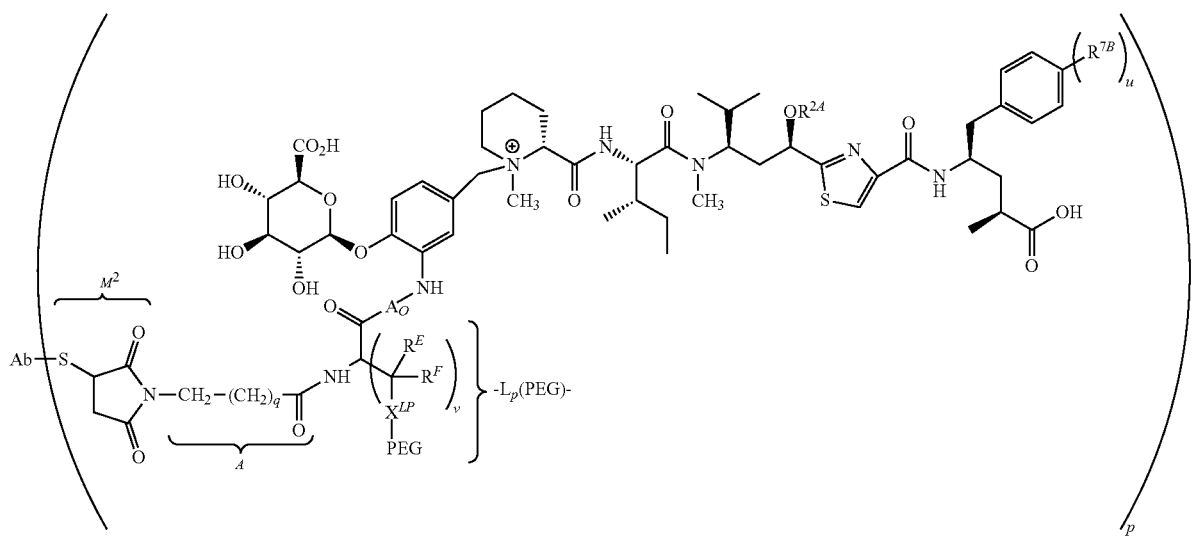

wherein Ab is the antibody Ligand Unit; S is a sulfur atom of the antibody Ligand Unit; $R^{24}$ is saturated C$_1$-C$_4$ alkyl, unsaturated C$_2$-C$_4$ alkyl, —C(=O)R$^{2B}$, wherein R$^{2B}$ is C$_1$-C$_4$ alkyl; A$_O$ is absent or is an amine-containing acid residue; subscript p is a number ranging from 1 to 8; subscript q is an integer ranging from 1 to 4; subscript u is 0 or 1; subscript v is an integer ranging from 1 to 4; R$^{7B}$, when present, is —OH; $X^{LP}$ is selected from the group consisting of —O—, —NH, —S— and —C(=O)—; and $R^E$ and $R^F$ are independently selected from the group consisting of —H, and C$_1$-C$_4$ alkyl.

25D. The Ligand Drug Conjugate composition of embodiment 1D wherein a compound thereof is represented by the structure of:

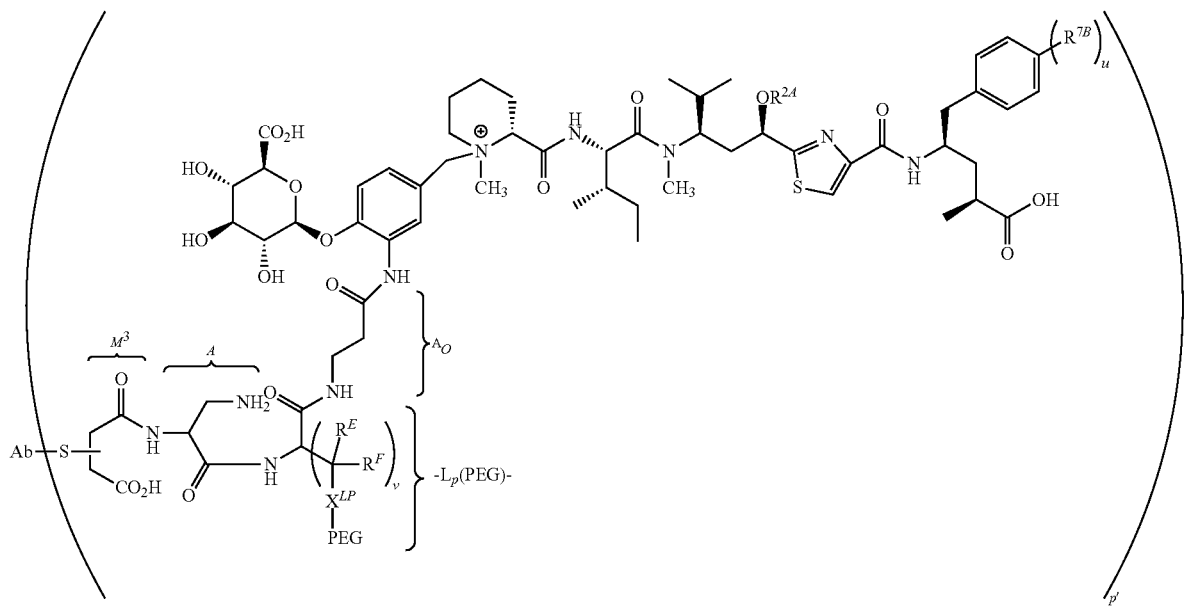

wherein Ab is the antibody Ligand Unit; S is a sulfur atom of the antibody Ligand Unit; the Ab-S— moiety is bonded to the carbon α or 1 to the indicated $M^3$ carboxylic acid; $R^{2A}$ is saturated $C_1$-$C_4$ alkyl, unsaturated $C_2$-$C_4$ alkyl, —C(=O)$R^{2B}$, wherein $R^{2B}$ is $C_1$-$C_4$ alkyl; subscript p' is an integer ranging from 1 to 8; subscript q is an integer ranging from 1 to 4; subscript u is 0 or 1; subscript v is an integer ranging from 1 to 4; $R^{7B}$, when present, is —OH; $X^{LP}$ is selected from the group consisting of —O—, —NH, —S— and —C(=O)—; and $R^E$ and $R^F$ are independently selected from the group consisting of —H, and $C_1$-$C_4$ alkyl.

26D. The Ligand Drug Conjugate composition, or compound thereof, of embodiment 24D or 25D, wherein $R^{2A}$ is saturated $C_1$-$C_4$ alkyl or unsaturated $C_3$-$C_4$ alkyl, wherein saturated $C_1$-$C_4$ alkyl is —$CH_3$, —$CH_2CH_3$, —$CH_2CH_2CH_3$ and unsaturated $C_3$-$C_4$ alkyl is —$CH_2CH=CH_2$ or —$CH(CH_3)CH=CH_2$.

27D. The Ligand Drug Conjugate composition, or compound thereof, of embodiment 24D or 25D wherein $R^{2A}$ is —C(O)$CH_3$.

28D. The Ligand Drug Conjugate composition, or compound thereof, of embodiment 24D or 25D wherein $R^{2A}$ is —$CH_2CH_3$.

29D. The Ligand Drug Conjugate composition, or compound thereof, of embodiment 24D or 25D wherein $R^{2A}$ is —$CH_2CH=CH_2$.

30D. The Ligand Drug Conjugate composition, or a compound thereof, of any one of embodiments 1D to 29D wherein PEG has the structure selected from the group consisting of:

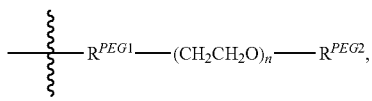

-continued

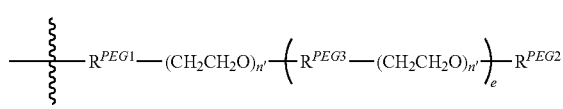

wherein the wavy line indicates site of attachment to $X^{LP}$ of the Parallel Connector Unit ($L_P$); $R^{PEG1}$ is an optional PEG Attachment Unit; $R^{PEG2}$ is a PEG Capping Unit; $R^{PEG3}$ is an PEG Coupling Unit; subscript n ranges from 2 to 72; each subscript n' is independently selected from 1 to 72; and subscript e ranges from 2 to 5.

31D. The Ligand Drug Conjugate composition, or compound thereof, of embodiment 24D or 25D wherein —$X^{LP}$—PEG has the structure of:

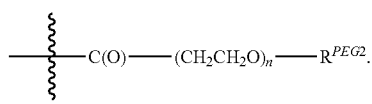

32D. The Ligand Drug Conjugate composition, or a compound thereof, of embodiment 31D wherein subscript n is 12 and $R^{PEG2}$ is hydrogen or —$CH_3$.

33D. The Ligand Drug Conjugate composition of embodiment 1D wherein a compound thereof is represented by the structure of:

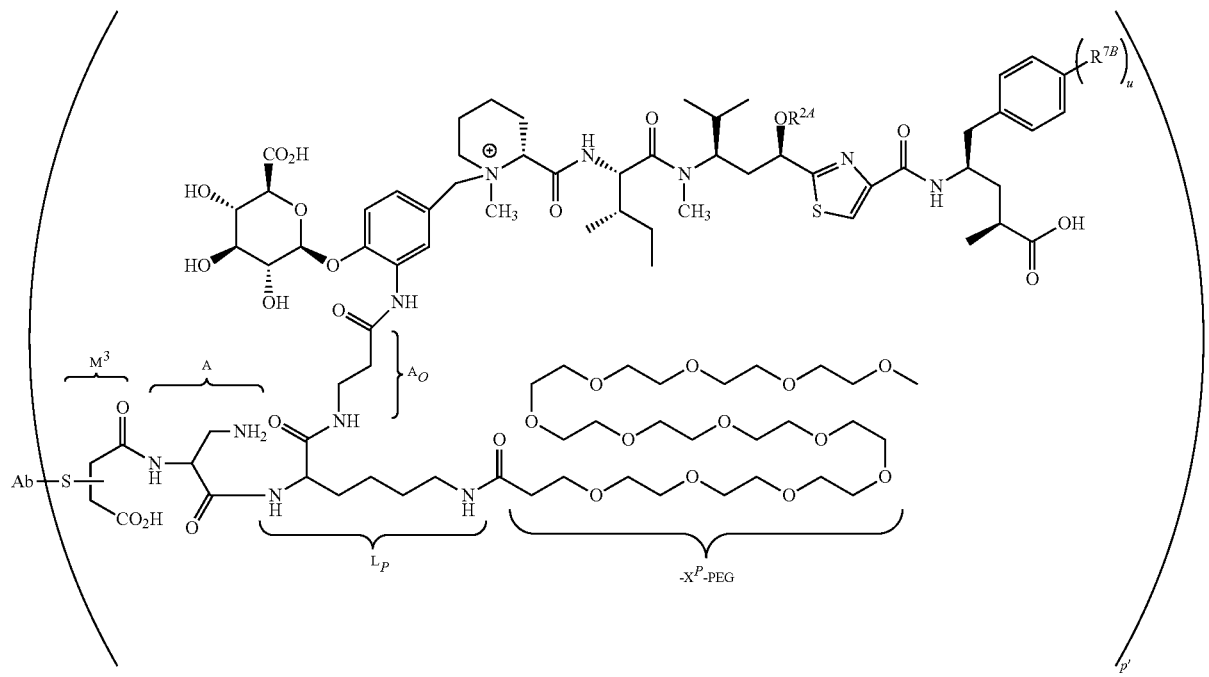

wherein Ab is the antibody Ligand Unit; S is a sulfur atom of the antibody Ligand Unit; the Ab-S— moiety is bonded to the carbon α or β to the indicated $M^3$ carboxylic acid; subscript p' is an integer ranging from 1 to 8; subscript u is 0 or 1; $R^{7B}$, when present, is —OH; and $R^{2A}$ along with the oxygen atom to which it is attached is —OC(O)CH$_3$, —CH$_2$CH$_3$ or —CH$_2$CH=CH$_2$.

34D. The Ligand Drug Conjugate composition of embodiment 33D wherein a compound thereof is represented by the structure of:

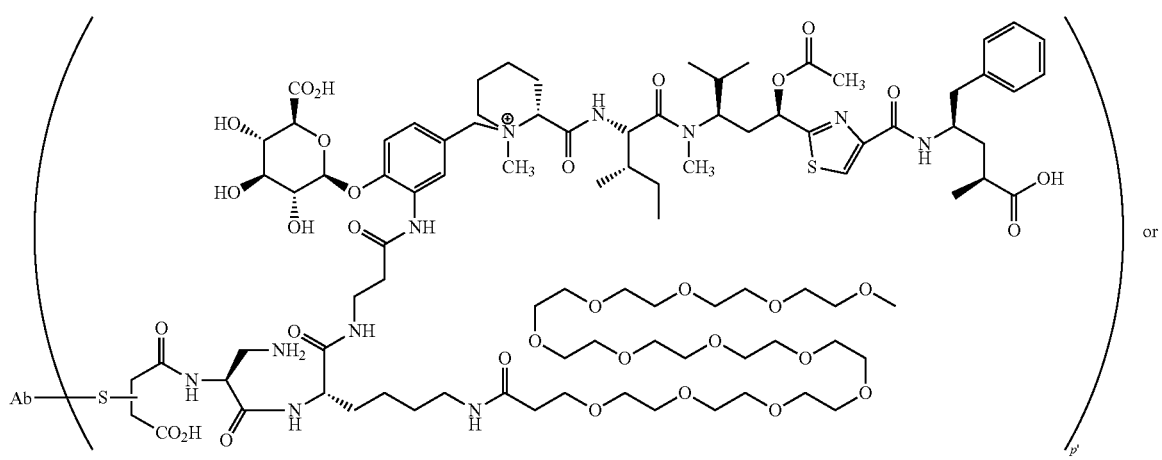

-continued

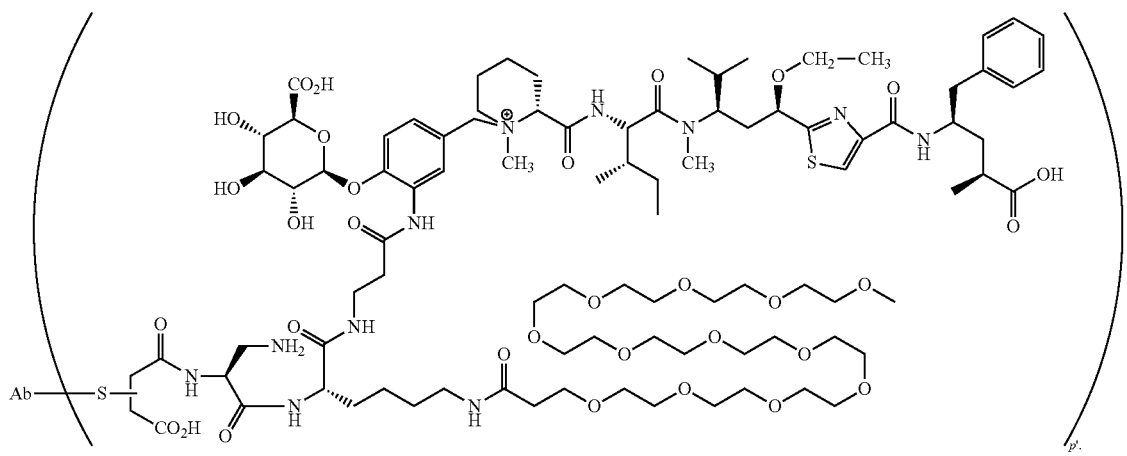

35D. A Drug Linker compound, wherein the compound has the structure of Formula IA:

(Formula IA)

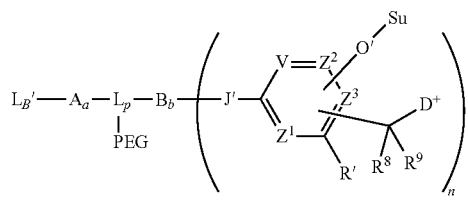

wherein $L_B'$ is a Ligand Covalent Binding Unit precursor; $L_P$ is a Parallel Connector Unit; PEG is a Polyethylene Glycol Unit; subscript a is 0 or 1; subscript b is 0 or 1; A is a first optional Stretcher Unit so that subscript a is 0 when A is absent or A is present so that subscript a is 1 and is optionally comprised of two, three or four independently selected subunits ($A_1$, $A_2$, $A_3$, $A_4$); B is an Branching Unit or a second optional Stretcher Unit ($A_O$) so that subscript b is 0 when B is absent or B is present so that subscript b is 1 and is optionally comprised of two, three or four subunits independently of A; subscript n is 1, 2, 3 or 4, provided that subscript b is 1 and B is a Branching when subscript n is 2, 3 or 4 and provided that B is $A_O$ or is absent when subscript n is 1; Su is a carbohydrate moiety; —O'— represents an oxygen atom of an O-glycosidic bond cleavable by a glycosidase; -J'- represents a heteroatom, optionally substituted when nitrogen, from a functional group bonding B, when B is present, or $L_B$, when B is absent to the remainder of the LDC; V, Z, $Z^2$ and $Z^3$ are =N— or =C($R^{24}$)—, wherein $R^{24}$ is hydrogen or alkyl, alkenyl or alkynyl, optionally substituted, or halogen, —$NO_2$, —CN or other electron withdrawing group, an electron donating group, —O'-Su, or —C($R^8$)($R^9$)-$D^+$, wherein at least at least two of V, $Z^1$, $Z^2$ and $Z^3$ are =C($R^{24}$)—, provided, one any only one $R^{24}$ is —C($R^8$)($R^9$)-$D^+$ so that —C($R^8$)($R^9$)-$D^+$ is bonded to one of V, $Z^1$, $Z^2$, $Z^3$ when that variable group is =C($R^{24}$)— and one and only one other $R^{24}$ is so that —O'-Su is bonded to another one of V, $Z^1$, $Z^2$, $Z^3$ when that variable group is =C($R^{24}$)—, and the —O'Su and —C($R^8$)($R^9$)-$D^+$ substituents are ortho or para to each other; $R^8$ and $R^9$ independently are hydrogen, alkyl, alkenyl or alkynyl, optionally substituted, or aryl or heteroaryl, optionally substituted; R' is hydrogen or is halogen, —$NO_2$, —CN or other electron withdrawing group; $D^+$ is a quaternized tubulysin Drug Unit preferentially having the structure of:

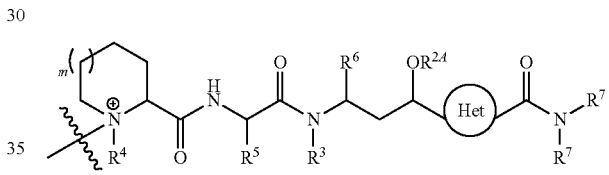

wherein the circle represents an 5-membered nitrogen-heteroarylene and wherein the indicated required substituents to that heteroarylene are in a 1,3-relationship with each other with optional substitution at the remaining positions; subscript m is 0 or 1; $R^{24}$ is hydrogen or optionally substituted alkyl or $R^{24}$ along with the oxygen atom to which it is attached defines an O-linked substituent other than —OH; $R^3$ is hydrogen or optionally substituted alkyl; $R^4$, $R^5$ and $R^6$ are optionally substituted alkyl; one $R^7$ is an optionally substituted alkyl, an optionally substituted arylalkyl, optionally substituted heteroarylalkyl and the other $R^7$ is hydrogen or an optionally substituted alkyl; and $R^{8A}$ is hydrogen or optionally substituted alkyl, wherein the wavy line indicates covalent bonding of $D^+$ to the remainder of the Drug Linker structure and wherein optionally substituted alkyl are independently selected; and wherein said glycosidase cleavage results in release of tubulysin compound (D) from a Ligand Drug Conjugate compound prepared from the Linker Drug compound wherein said glycosidase cleavage results in release of a tubulysin compound (D) from a Ligand Drug Conjugate compound of the composition, wherein the Ligand Drug Conjugate compound has the Formula 1A structure of embodiment 1D in which subscript p is replaced by subscript p', wherein subscript p' is an integer ranging from 1 to 24.

36D. The Drug-Linker compound of embodiment 35D wherein $L_B'$- has a structure selected from the group consisting of:

295

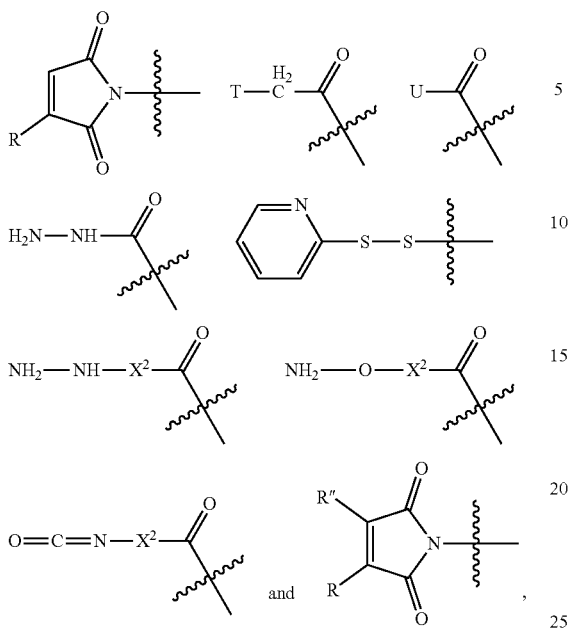

wherein R is hydrogen or $C_1$-$C_6$ optionally substituted alkyl; R" is hydrogen or halogen or R and R' are independently selected halogen; T is —Cl, —Br, —I, —O-mesyl or —O— tosyl or other sulfonate leaving group; U is —F, —Cl, —Br, —I, —O—N-succinimide, —O-(4-nitrophenyl), —O-pentafluorophenyl, —O-tetrafluorophenyl or —O—C(=O)—OR$^{57}$; and X$^2$ is $C_{1-10}$ alkylene, $C_3$-$C_8$-carbocycle, —O—($C_1$-$C_6$ alkyl), -arylene-, $C_1$-$C_{10}$ alkylene-arylene, -arylene-$C_1$-$C_{10}$ alkylene, —$C_1$-$C_{10}$ alkylene-($C_3$-$C_6$-carbocycle)-, —($C_3$-$C_8$ carbocycle)-$C_1$-$C_{10}$ alkylene-, $C_3$-$C_8$-heterocycle, —$C_1$-$C_{10}$ alkylene-($C_3$-$C_8$ heterocyclo)-, —$C_3$-$C_8$-heterocyclo)-$C_1$-$C_{10}$ alkylene, —(CH$_2$CH$_2$O)$_u$, or —(CH$_2$CH$_2$O)$_u$—CH$_2$—, wherein subscript u is an integer ranging from 1 to 10 and R$^{57}$ is $C_1$-$C_6$ alkyl or aryl.

37D. The Drug-Linker compound of embodiment 35D wherein the compound has the structure of one of Formula IIA-IIF:

(Formula IIA)

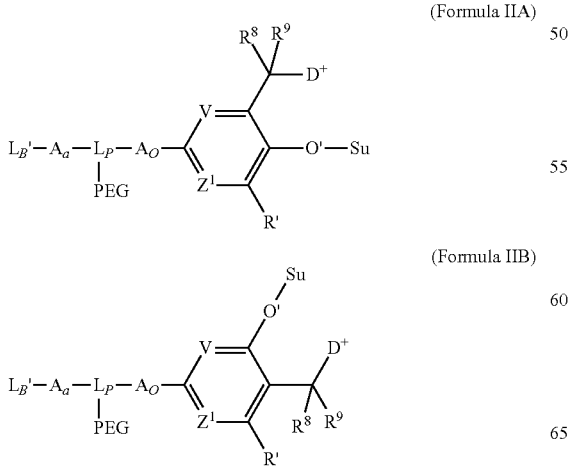

(Formula IIB)

(Formula IIC)

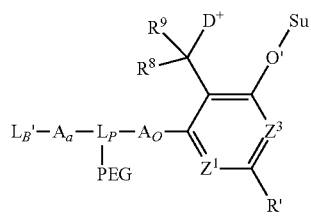

(Formula IID)

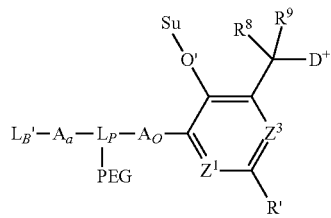

(Formula IIE)

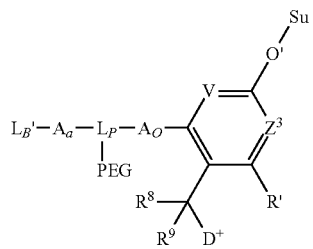

(Formula IIF)

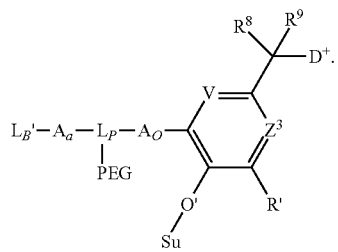

38D. The Drug-Linker compound of any one of embodiments 35D to 37D wherein —O'-Su has the structure of Formula 3:

(Formula 3)

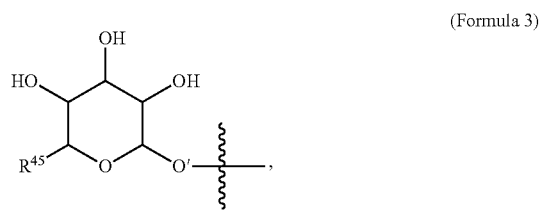

wherein the wavy line represents covalent bonding of O' to the remainder of the Drug Linker compound structure; and R$^{45}$ is —CH$_2$OH or —CO$_2$H.

39D. The Drug-Linker compound of embodiment 35D wherein the compound has the structure of Formula IV:

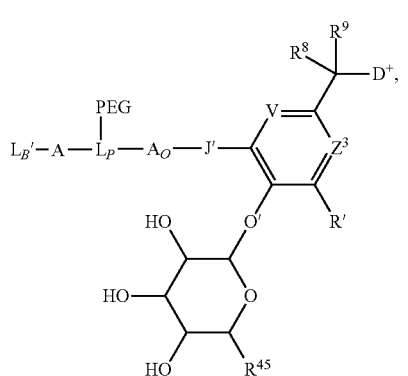

(Formula IV)

wherein J' is —N($R^{33}$)—, wherein $R^{33}$ is hydrogen or methyl; V and $Z^3$ independently are =CH— or =N—; R' is hydrogen or an electron withdrawing group; $R^8$ is hydrogen; $R^9$ is hydrogen, optionally substituted $C_1$-$C_6$ alkyl or optionally substituted phenyl; and $R^{45}$ is —$CO_2H$.

40D. The Drug-Linker compound of embodiment 35 wherein subscript a is 1; and $L_B'$-A- of Formula IA has the structure of Formula V:

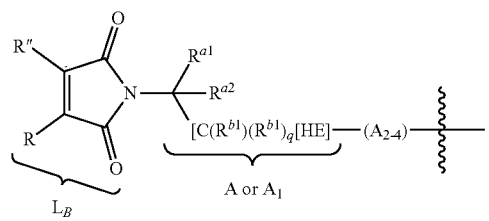

(Formula V)

wherein the —[C($R^{b1}$)($R^{b1}$)]$_q$—[HE]- moiety is A or $A_1$, wherein $A_1$ is a subunit of A; $A_{2-4}$ are optional subunits of A; R is hydrogen, chloro or $C_1$-$C_4$ alkyl; R" is hydrogen or chloro; $R^{a1}$ is hydrogen, optionally substituted alkyl or a Basic Unit (BU), optionally protected; and $R^{a2}$ is hydrogen or optionally substituted alkyl, or $R^{a1}$ and $R^{a2}$ together with the carbon atom to which they are attached defines a nitrogen-containing heterocycloalkyl; HE is an optional Hydrolysis Enhancer (HE) Unit; subscript q is an integer ranging from 0 to 6; each $R^{b1}$ independently is hydrogen, optionally substituted $C_1$-$C_6$ alkyl, optionally substituted aryl or optionally substituted heteroaryl, or two $R^{b1}$ together with the carbon(s) to which they are attached comprise a $C_3$-$C_6$ cycloalkyl or one $R^{b1}$ and HE together with the carbon to which they are attached define a 5 or 6-membered cycloalkyl or a 5- or 6-membered heterocycloalkyl and the other $R^{b1}$ is hydrogen, optionally substituted $C_1$-$C_6$ alkyl, optionally substituted aryl or optionally substituted heteroaryl; BU, optionally protected, has the structure of —[C($R^1$)($R^1$)]—[C($R^2$)($R^2$)]$_r$—N($R^{22}$)($R^{23}$), or an acid addition salt thereof, wherein subscript r is 0, 1, 2 or 3; each $R^1$ independently is hydrogen or lower alkyl or two $R^1$ together with the carbon to which they are attached comprise a $C_3$-$C_6$ cycloalkyl, and each $R^2$ independently is hydrogen, optionally substituted $C_1$-$C_6$ alkyl, optionally substituted aryl or optionally substituted heteroaryl, or two $R^2$ together with the carbon(s) to which they are attached and any intervening carbons define a $C_3$-$C_6$ cycloalkyl, or one $R^1$ and one $R^2$ together with the carbons to which they are attached and any intervening carbons define a 5- or 6-membered cycloalkyl and the remaining $R^1$ and $R^2$ are as defined; and $R^{22}$ and $R^{23}$ independently, hydrogen, optionally substituted $C_1$-$C_6$ alkyl, or an acid-labile protecting group, or together with the nitrogen to which they are attached define a 5- or 6-membered heterocycloalkyl, one of $R^{22}$, $R^{23}$ is hydrogen and the other is an acid labile protecting group; and wherein the wavy line indicates the site of covalent attachment to the remainder of the Drug Linker compound structure.

41D. The Drug Linker compound of embodiment 40D wherein Formula V has the structure of Formula VA:

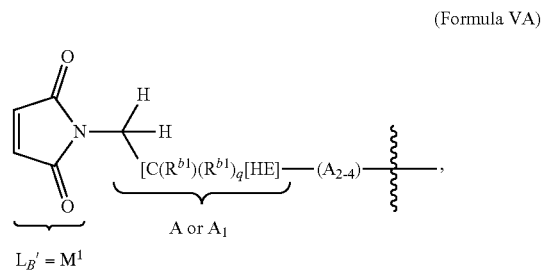

(Formula VA)

wherein subscript q is an integer ranging from 0 to 4.

42D. The Drug Linker compound of embodiment 40D wherein Formula V has the structure of Formula VB:

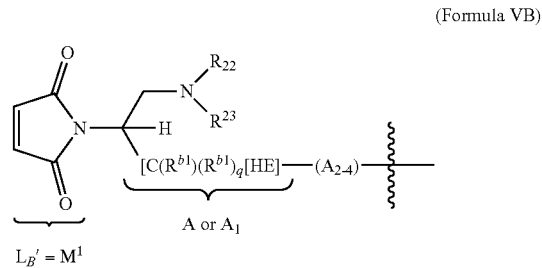

(Formula VB)

wherein one of $R^{22}$, $R^{23}$ is hydrogen and the other is an acid labile carbamate protecting group; and subscript q is an integer ranging from 0 to 4.

43D. The Drug Linker compound of embodiment 41D or 42D wherein Formula VA or Formula VB respectively has the structure of:

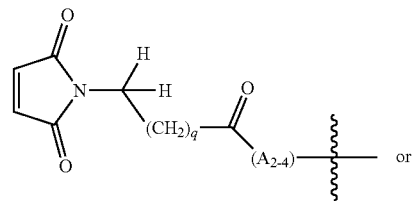

or

-continued

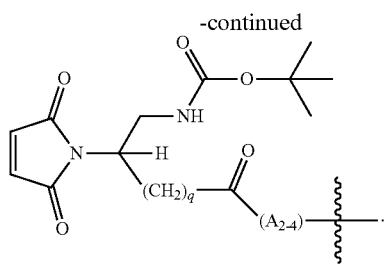

44D. The Drug Linker compound of embodiment 40D wherein the compound has the structure of Formula VI (Formula VI)

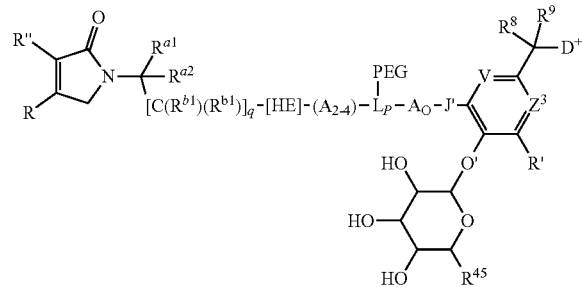

wherein the asterisk (*) designates chirality or absence thereof at the indicated carbon; $A_{2-4}$ are independently selected optional subunits of A, wherein $-[C(R^{b1})(R^{b1})]_q-[HE]-$ is $A_1$ when one or more such subunits are present; one of R and R'' is hydrogen and the other is hydrogen or chloro; R' is hydrogen or an electron withdrawing group; $R^{a1}$ is hydrogen or a basic unit (BU), optionally protected, having the structure of $-CH_2-N(R^{22})(R^{23})$, or an acid addition salt thereof, wherein $R^{22}$ and $R^{23}$ independently are hydrogen, methyl or ethyl or both together with the nitrogen atom to which they are attached comprise a 5- or 6-membered heterocycloalkyl, or one of $R^{22}$, $R^{23}$ is hydrogen and the other is an acid labile carbamate protecting group; $R^{a2}$ is hydrogen; subscript q is an integer ranging from 0 to 5 when HE is present or 1 to 5 when HE is absent; each $R^{b1}$ independently is hydrogen or optionally substituted $C_1$-$C_6$ alkyl; HE is absent or is $-C(=O)-$; $R^{45}$ is $-CO_2H$; J' is $-NH-$; V and $Z^3$ are $=CH-$; $R^8$ is hydrogen; and $R^9$ is hydrogen or methyl.

45D. The Drug Linker compound of embodiment 44D wherein the indicated starred (*) carbon is predominantly in the same absolute configuration as the alpha carbon of an L-amino acid when that indicated carbon is chiral.

46D. The Drug Linker compound of any one of embodiments 35D to 39D wherein A and $A_O$, when present, independently has the structure of Formula 7 or Formula 8, or any one of claims 40 to 45, wherein each of $A_2$-4, when present, independently has the structure of Formula 7 or Formula 8:

(Formula 7)

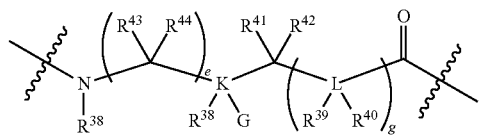

(Formula 8)

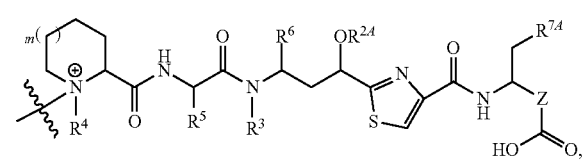

wherein the wavy lines indicated covalent attachment within the Drug Linker compound structure and wherein K and L independently are C, N, O or S, provided that when K or L is O or S, $R^{41}$ and $R^{42}$ to K or $R^{43}$ and $R^{44}$ to L are absent, and when K or L are N, one of $R^{41}$, $R^{42}$ to K or one of $R^{42}$, $R^{43}$ to L are absent, and provided that no two adjacent L are independently selected as N, O, or S; wherein subscripts e and f are independently selected integers that range from 0 to 12, and subscript g is an integer ranging from 1 to 12; wherein G is hydrogen, optionally substituted $C_1$-$C_6$ alkyl, $-OH$, $-OR^{PR}$, $-CO_2H$, $CO_2R^{PR}$, wherein $R^{PR}$ is a suitable protecting, $-N(R^{PR})(R^{PR})$, wherein $R^{PR}$ are independently a protecting group or $R^{PR}$ together form a suitable protecting group, or $-N(R^{45})(R^{46})$, wherein one of $R^{45}$, $R^{46}$ is hydrogen or $R^{PR}$, wherein $R^{PR}$ is a suitable protecting group, and the other is hydrogen or optionally substituted $C_1$-$C_6$ alkyl; wherein $R^{38}$ is hydrogen or optionally substituted $C_1$-$C_6$ alkyl; $R^{39}$-$R^{44}$ independently are hydrogen, optionally substituted $C_1$-$C_6$ alkyl, optionally substituted aryl, or optionally substituted heteroaryl, or both $R^{39}$, $R^{40}$ together with the carbon to which they are attached comprise a $C_3$-$C_6$ cycloalkyl, or $R^{41}$, $R^{42}$ together with K to which they are attached when K is C, or $R^{43}$, $R^{44}$ together with L to which they are attached when L is a carbon atom comprise a $C_3$-$C_6$ cycloalkyl, or $R^{40}$ and $R^{41}$, or $R^{40}$ and $R^{43}$, or $R^{41}$ and $R^{43}$ to together with the carbon atom or heteroatom to which they are attached and the atoms intervening between those carbon atoms and/or heteroatoms comprise a 5- or 6-membered cycloalkyl or heterocycloalkyl, provided that when K is O or S, $R^{41}$ and $R^{42}$ are absent, when K is N, one of $R^{41}$, $R^{42}$ is absent, when L is O or S, $R^{43}$ and $R^{44}$ are absent, and when L is N, one of $R^{43}$, $R^{44}$ is absent, or wherein $A_O$ has a structure corresponding to an alpha-amino, beta-amino or another amine-containing acid.

47D. The Drug Linker compound of any one of embodiments 35D to 46D wherein the quaternized tubulysin Drug Unit (-$D^+$) has the structure of:

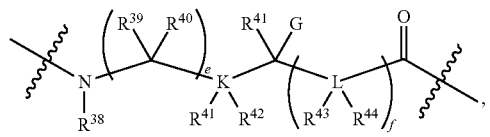

wherein subscript m is 0 or 1; Z is an optionally substituted alkylene or an optionally substituted alkenylene; and $R^{7A}$ is optionally substituted aryl or optionally substituted heteroaryl.

48D. The Drug Linker compound of embodiment 47D wherein the quaternized tubulysin Drug Unit (-Dl) has the structure of:

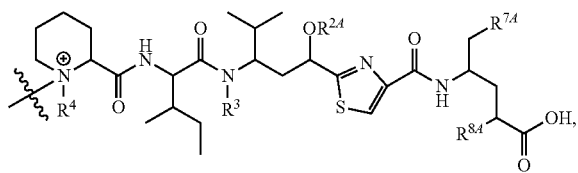

wherein $R^{7A}$ is optionally substituted phenyl and $R^8$ is hydrogen or methyl.

49D. The Drug Linker compound of embodiment 50D wherein the quaternized tubulysin Drug Unit (-D$^+$) has the structure of

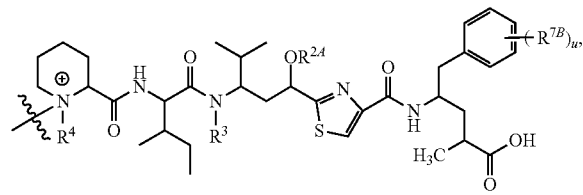

wherein $R^4$ is methyl; subscript u is 0, 1 or 2; $R^3$ is H, methyl, ethyl, propyl, —CH$_2$—OC(O)R$^{3A}$, —CH$_2$CH(R$^{3B}$)C(O)R$^{3A}$ or —CH(R$^{3B}$)C(O)NHR$^{3A}$, wherein R$^{3A}$ is C$_1$-C$_6$ alkyl and R$^{3B}$ is H or C$_1$-C$_6$ alkyl, independently selected from R$^{3A}$; R$^{2A}$ along with the oxygen atom to which it is attached is an O-linked substituent selected from the group consisting of —OCH$_2$OCH$_2$R$^{2B}$, —OCH$_2$R$^{2B}$, —OC(O)R$^{2B}$, —CH$_2$OC(O)R$^{2B}$, —OC(O)N(R$^{2B}$)(R$^{2C}$), and —OCH$_2$C(O)N(R$^{2B}$)(R$^{2C}$), wherein R$^{2B}$ and R$^{2C}$ are independently selected from the group consisting of H, C$_1$-C$_6$ alkyl and C$_2$-C$_6$ alkenyl; and each R$^{7B}$, when present, independently is —OH or —OCH$_3$.

50D. The Drug Linker compound of embodiment 49D wherein the quaternized tubulysin Drug Unit (-D$^+$) has the structure of

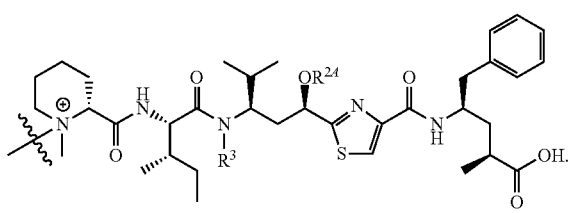

51D. The Drug Linker compound of any one of embodiments 47D to 50D wherein $R^{2A}$ is —CH$_2$CH$_3$.

52D. The Drug Linker compound of any one of embodiments 47D to 50D wherein $R^{2A}$ is —CH$_2$—CH=CH$_2$.

53D. The Drug Linker compound of embodiment 49D, wherein $R^{2A}$ is —CH$_2$CH$_3$, —CH$_2$—CH=CH$_2$ or —CH$_2$C(CH$_3$)=CH$_2$, $R^{2B}$ is —CH$_3$, $R^3$ is —CH$_3$ and subscript u is 0, or $R^{2A}$ is —CH$_2$CH$_3$ or —CH$_2$—CH=CH$_2$, or —CH$_2$C(CH$_3$)=CH$_2$, $R^{2B}$ is —CH$_3$, $R^3$ is —CH$_3$ and subscript u is 1, wherein R$^{7B}$ is —OH.

54D. The Drug Linker compound of embodiment 49D wherein the quaternized tubulysin Drug Unit (-D$^+$) has the structure of:

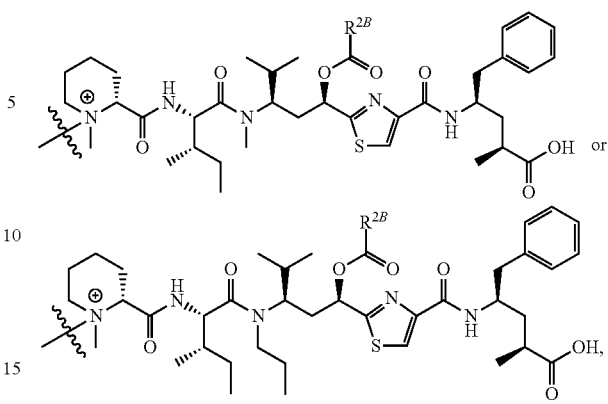

wherein $R^{2B}$ is —CH$_3$, —CH$_2$CH$_3$, —CH$_2$CH$_2$CH$_3$, —CH(CH$_3$)$_2$, —CH$_2$CH(CH$_3$)$_2$, or —CH$_2$C(CH$_3$)$_3$.

55D. Drug Linker compound of embodiment 49D, wherein the quaternized tubulysin Drug Unit (-D$^+$) has the structure of:

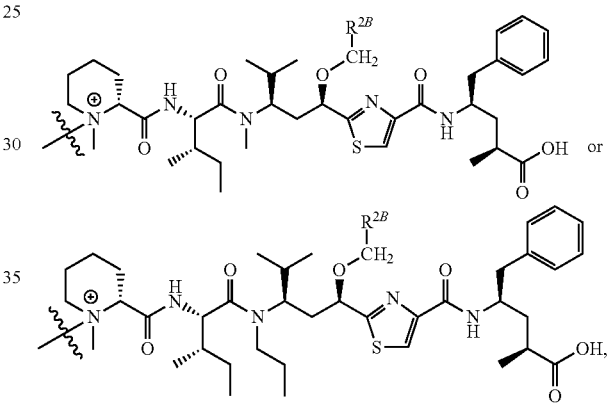

wherein $R^{2B}$ is hydrogen, methyl or —OCH$_3$, or —OCH$_2$R$^{2B}$ is —OCH$_2$CH=CH$_2$ or —OCH$_2$C(CH$_3$)=CH$_2$.

56D. The Drug Linker compound of embodiment 49D, wherein the quaternized tubulysin Drug Unit -D$^+$ is that of tubulysin M, which has the structure of:

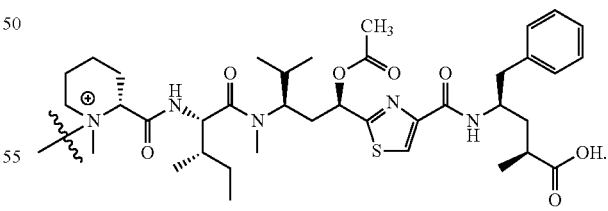

57D. The Drug Linker compound of any one of embodiments 35D to 56D wherein L$_P$ is a aminoalkanedioic acid, a diaminoalkanoic acid, a sulfur-substituted alkanedioic acid, a sulfur-substituted aminoalkanoic acid, a diaminoalkanol, an aminoalkanediol, a hydroxyl substituted alkanedioic acid, a hydroxyl substituted aminoalkanoic acid or a sulfur-substituted aminoalkanol residue, optionally substituted, wherein the sulfur substituent is in reduced or oxidized form, or L$_P$ is an amino acid residue of lysine, arginine, asparagine, glutamine, ornithine, citrulline, cysteine, homocysteine, penicillamine, threonine, serine, glutamic acid, aspartic acid, tyrosine, histidine or tryptophan, wherein the amino acid is in the D- or L-configuration.

58D. The Drug Linker compound of embodiment 57D wherein the aminoalkanedioic acid, diaminoalkanoic acid, sulfur-substituted aminoalkanoic acid or hydroxyl substituted aminoalkanoic acid residue has the structure of Formula A or Formula B:

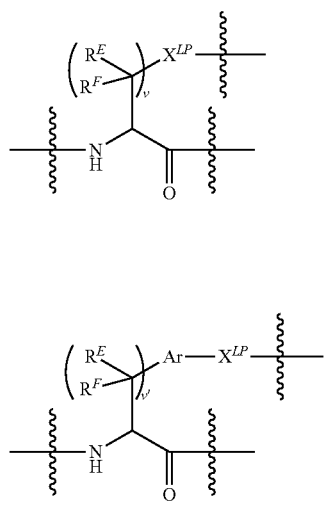

(Formula A)

(Formula B)

wherein subscript v is an integer ranging from 1 to 4; subscript v' is an integer ranging from 0 to 4; $X^{LP}$ is selected from the group consisting of —O—, —$NR^{LP}$—, —S—, —S(=O)—, —S(=O)$_2$—, —C(=O)—, —C(=O)N($R^{LP}$)—, —N($R^{LP}$)C(=O)N($R^{LP}$)—, and —N($R^{LP}$)C(=$NR^{LP}$)N($R^{LP}$)— wherein each $R^{LP}$ is independently selected from the group consisting of hydrogen and optionally substituted alkyl or two of $R^{LP}$ together along with their intervening atoms define a heterocycloalkyl and any remaining $R^{LP}$ are as previously defined; Ar is an arylene or heteroarylene, optionally substituted; each $R^E$ and $R^F$ is independently selected from the group consisting of —H, optionally substituted alkyl, optionally substituted aryl and optionally substituted heteroaryl, or $R^E$ and $R^F$ together with the same carbon to which they are attached, or $R^E$ and $R^F$ from adjacent carbons together with these carbons, defines a optionally substituted cycloalkyl with any remaining $R^E$ and $R^F$ substituents as previously defined; and wherein the wavy lines indicates covalent attachment of the Formula A or Formula B structure within the Drug Linker compound structure.

59D. The Drug Linker compound of any one of embodiment 35D to 56D wherein -$L_P$(PEG)- has the structure of Formula A1 or A2:

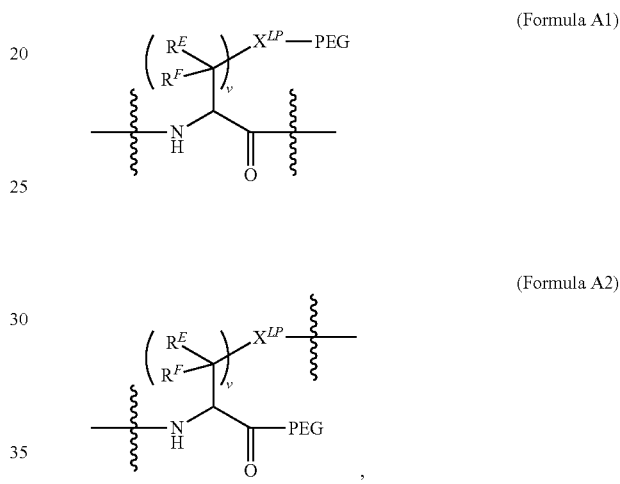

(Formula A1)

(Formula A2)

wherein $X^{LP}$ is selected from the group consisting of —O—, —NH, —S— and —C(=O)—; $R^E$ and $R^F$ are independently selected from the group consisting of —H, and —$C_1$-$C_4$ alkyl; and wherein the wavy line indicates covalent attachment of Formula A1 or Formula A2 within the Drug Linker compound structure.

60D. The Drug Linker compound of embodiment 35D wherein the compound is represented by the structure of

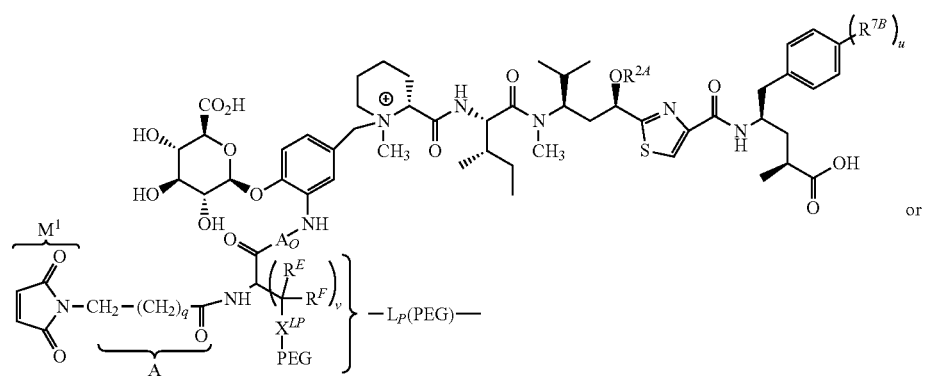

or

-continued

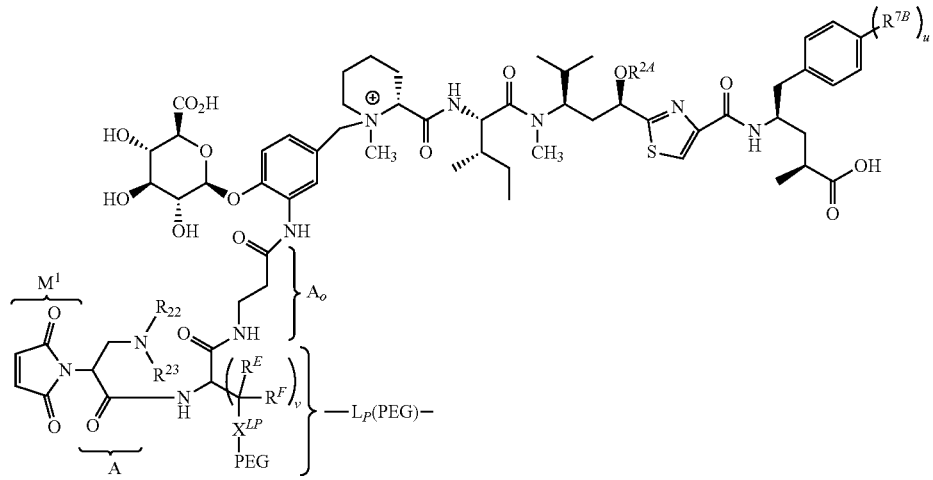

wherein $R^{2A}$ is saturated $C_1$-$C_4$ alkyl, unsaturated $C_2$-$C_4$ alkyl, —C(=O)$R^{2B}$, wherein $R^{2B}$ is $C_1$-$C_4$ alkyl; $A_O$ is absent or is an amine-containing acid residue; subscript q is an integer ranging from 1 to 4; subscript u is 0 or 1; subscript v is an integer ranging from 1 to 4; $R^{7B}$, when present, is —OH; $X^{LP}$ is selected from the group consisting of —O—, —NH, —S— and —C(=O)—; $R^E$ and $R^F$ are independently selected from the group consisting of —H, and $C_1$-$C_4$ alkyl; one of $R^{22}$, $R^{23}$ is hydrogen and the other is an acid labile protecting group or $R^{22}$ and $R^{23}$ are each hydrogen with the nitrogen to which they are attached optionally protonated as an acid addition salt.

61D. The Drug Linker compound of embodiment 60, wherein $R^{2A}$ is saturated $C_1$-$C_4$ alkyl or unsaturated $C_3$-$C_4$ alkyl, wherein saturated $C_1$-$C_4$ alkyl is —$CH_3$, —$CH_2CH_3$, —$CH_2CH_2CH_3$ and unsaturated $C_3$-$C_4$ alkyl is —$CH_2CH=CH_2$ or —$CH(CH_3)CH=CH_2$.

62D. The Drug Linker compound of embodiment 60D wherein $R^{2A}$ is —C(O)$CH_3$.

63D. The Drug Linker compound of embodiment 60D wherein $R^{2A}$ is —$CH_2CH_3$.

64D. The Drug Linker compound of embodiment 60D wherein $R^{2A}$ is —$CH_2CH=CH_2$.

65D. The Drug Linker compound of any one of embodiments 35D to 64D wherein PEG has the structure selected from the group consisting of:

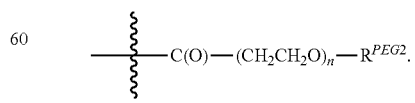

-continued

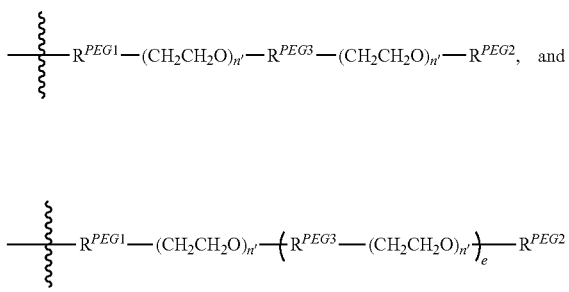

wherein the wavy line indicates site of attachment to $X^{LP}$ of the Parallel Connector Unit ($L_P$); $R^{PEG1}$ is an optional PEG Attachment Unit; $R^{PEG2}$ is a PEG Capping Unit; $R^{PEG3}$ is an PEG Coupling Unit; subscript n ranges from 2 to 72; each subscript n' is independently selected from 1 to 72; and subscript e ranges from 2 to 5.

66D. The Drug Linker compound of embodiment 60D wherein —$X^{LP}$—PEG has the structure of:

$$\text{\{---C(O)---(CH}_2\text{CH}_2\text{O)}_n\text{---R}^{PEG2}.$$

67D. The Drug Linker compound of embodiment 66D wherein subscript n is 12 and $R^{PEG2}$ is hydrogen or —$CH_3$.

68D. The Drug Linker compound of embodiment 60D wherein the compound has the structure of:
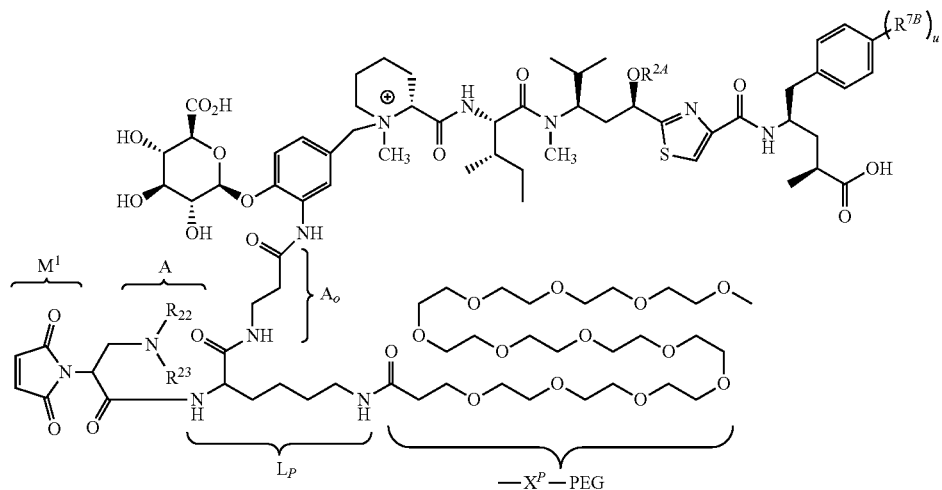
wherein subscript u is 0 or 1; $R^{7B}$, when present, is —OH; and $R^{2A}$ along with the oxygen atom to which it is attached is —OC(O)CH$_3$, —CH$_2$CH$_3$ or —CH$_2$CH=CH$_2$.
69D. The Drug Linker compound of embodiment 68D wherein the compound has the structure of:
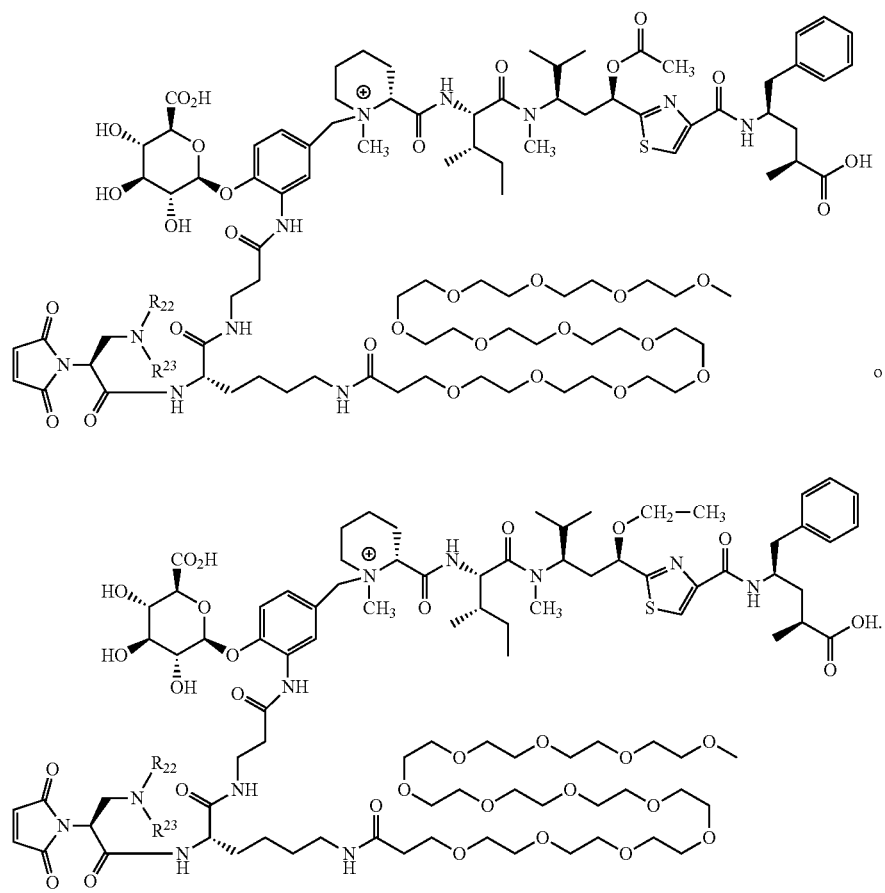

70D. A tubulysin compound having the structure of:

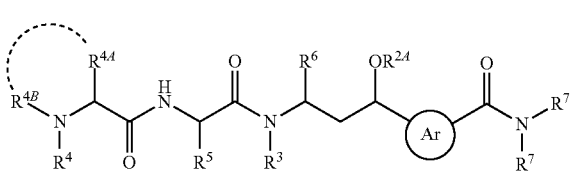

wherein the curved dashed line indicates optional cyclization; $R^{2A}$ is unsaturated alkyl, optionally substituted; the circled Ar represents a 5-membered nitrogen-containing heteroarylene, wherein the indicated required substituents to that heteroarylene are in a 1,3-relationship with each other with optional substitution at the remaining positions; $R^3$ is hydrogen or optionally substituted alkyl; $R^4$, $R^5$ and $R^6$ are optionally substituted alkyl, independently selected; $R^{4a}$ is hydrogen or optionally substituted alkyl and $R^{4B}$ is optionally substituted alkyl, or both together with the nitrogen to which they are attached, as indicated by the curved dashed line, define a quaternized nitrogen heterocycloalkyl, optionally substituted; and one $R^7$ is hydrogen or optionally substituted alkyl and the other $R^7$ is optionally substituted aralkyl or heteroaralkyl.

71D. The tubulysin compound of embodiment 70D, wherein the compound has the structure of:

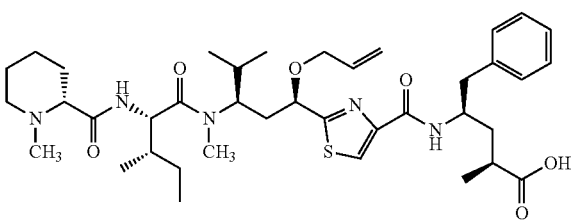

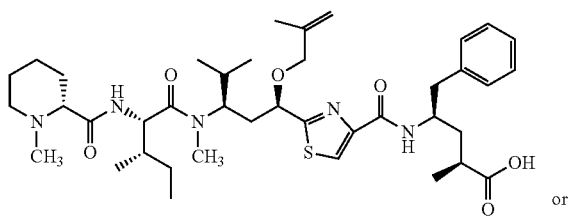

or

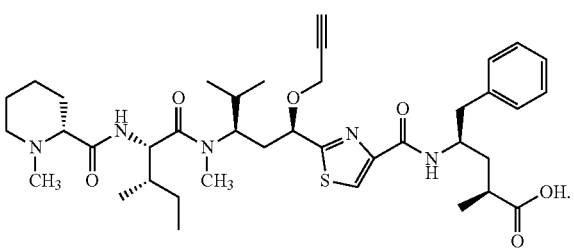

72D. A tubulysin compound having the structure of:

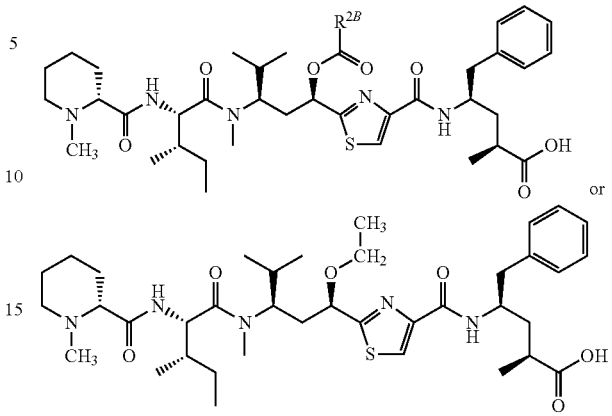

wherein $R^{2B}$ is —CH$_2$CH$_3$, —CH$_2$CH$_2$CH$_3$, —CH(CH$_3$)$_2$, —CH$_2$CH(CH$_3$)$_2$ or —CH$_2$C(CH$_3$)$_3$.

73D. A method of preparing a Drug Linker compound comprising the step of quaternizing a tubulysin compound of embodiment 70D, 71D or 72D with a Linker Unit precursor.

74D. A Ligand Drug Conjugate composition, wherein the composition is represented by the structure of Formula D:

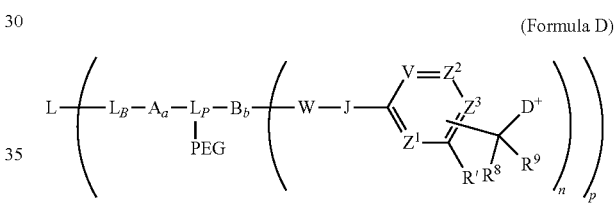

(Formula D)

wherein L is an antibody Ligand Unit, thereby defining an Antibody Drug Conjugate; $L_B$ is a Ligand Covalent Binding Unit; $L_P$ is a Parallel Connector Unit; PEG is a Polyethylene Glycol Unit; subscript a is 0 or 1; subscript b is 0 or 1; A is a first optional Stretcher Unit so that subscript a is 0 when A is absent or A is present so that subscript a is 1 and is optionally comprised of two, three or four independently selected subunits (A$_1$, A$_2$, A$_3$, A$_4$); B is an Branching Unit or a second optional Stretcher Unit (A$_O$) so that subscript b is 0 when B is absent or B is present so that subscript b is 1 and is optionally comprised of two, three or four subunits independently of A; subscript n is 1, 2, 3 or 4, provided that subscript b is 1 and B is a Branching when subscript n is 2, 3 or 4 and provided that B is A$_O$ or is absent when subscript n is 1; V, $Z^1$, $Z^2$ and $Z^3$ are =N— or =C(R$^{24}$)—, wherein $R^{24}$ is hydrogen or alkyl, alkenyl or alkynyl, optionally substituted, or halogen, —NO$_2$, —CN or other electron withdrawing group, or —OCH$_3$ or other an electron donating group, or —C(R$^8$)(R$^9$)-D$^+$, wherein at least one of V, $Z^1$, and $Z^3$ is =C(R$^{24}$)—, provided that one any only one R$^{24}$ is —C(R$^8$)(R$^9$)-D$^+$ so that —C(R$^8$)(R$^9$)-D$^+$ is bonded to one of V, $Z^1$, and $Z^3$ when that variable group is =C(R$^{24}$)—; R' is hydrogen or —OCH$_3$ or other electron donating group; J is a heteroatom, optionally substituted when nitrogen, preferably J is —N(R$^{33}$)—, wherein R$^{33}$ is hydrogen or methyl; D$^+$ is a quaternized tubulysin Drug Unit; W is a peptide comprised of an amino acid sequence covalently attached to J' through an amide bond wherein that amide bond is cleavable by a protease, wherein said protease cleavage initiates release of a tubulysin compound (D) from a Ligand Drug Conjugate compound of the composition; and subscript p is a number ranging from 1 to 24.

75D. The Ligand Drug Conjugate composition of embodiment 74D, wherein the composition is represented by the structure of:

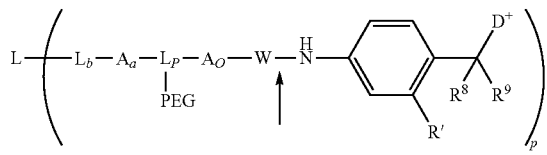

wherein W consists or is comprised of a dipeptide, wherein the dipeptide is at the distal end of W and the indicated bond is an amide bond specifically cleavable by an intracellular protease in comparison to freely circulating serum proteases.

76D. The Ligand Drug Conjugate composition of embodiment 74D, wherein the dipeptide has the structure of;

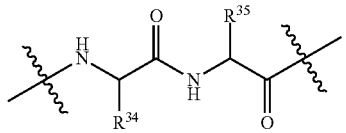

wherein $R^{34}$ is benzyl, methyl, isopropyl, isobutyl, sec-butyl, —CH(OH)CH$_3$ or has the structure of

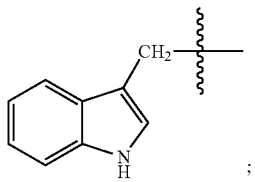 [SMILES: *Cc1c[nH]c2ccccc12]

and $R^{35}$ is methyl, —(CH$_2$)$_4$—NH$_2$, —(CH$_2$)$_3$NH(C=O)NH$_2$, (CH$_2$)$_3$NH(C=NH)NH$_2$, or —(CH$_2$)$_2$CO$_2$H, wherein the wavy line at the dipeptide N-terminus indicates covalent binding to $A_O$ or to $L_P$, depending on the presence or absence of $A_O$, respectively, and the wavy line at the dipeptide C-terminus indicates covalent binding to J.

77D. The Ligand Drug Conjugate composition of embodiment 74D, 75D or 76D wherein the quaternized tubulysin Drug Unit (-D$^+$) preferably has the structure of:

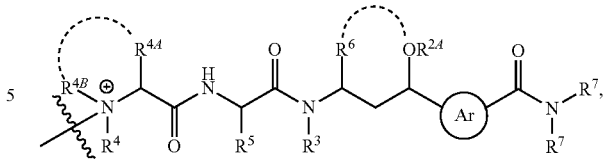

wherein the curved dashed lines indicate optional cyclizations;

$R^{2A}$ is hydrogen or optionally substituted alkyl, or $R^{2A}$ along with the oxygen atom to which it is attached defines an O-linked substituent other than —OH, or $R^{2A}$ is absent when $R^6$ is bonded to that oxygen atom, as indicated by the curved dash line between $R^6$ and the oxygen atom, to define an oxygen-containing heterocycloalkyl; the circled Ar represents a 5-membered nitrogen-heteroarylene, wherein the indicated required substituents to that heteroarylene are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —OR$^{2A}$ moiety in which $R^{2A}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached, as indicated by the curved dotted line between $R^{4A}$ and $R^{4B}$, define a quaternized nitrogen heterocycloalkyl, optionally substituted; one $R^7$ is hydrogen or optionally substituted alkyl and the other $R^7$ is optionally substituted aralkyl or heteroaralkyl; wherein the wavy line indicates covalent bonding of the D$^+$ structure to the remainder of the Conjugate structure.

78D. The Ligand Drug Conjugate composition of embodiment 77D wherein the quaternized tubulysin Drug Unit (-D$^+$) has the structure of:

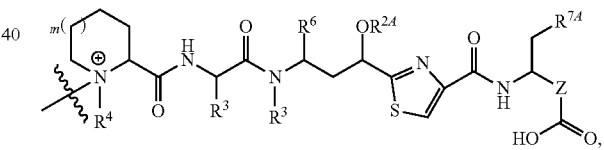

wherein subscript m is 0 or 1; Z is an optionally substituted alkylene or an optionally substituted alkenylene; and $R^{7A}$ is optionally substituted aryl or optionally substituted heteroaryl.

79D. The Ligand Drug Conjugate composition of embodiment 78D wherein the quaternized tubulysin Drug Unit -D$^+$ has the structure of:

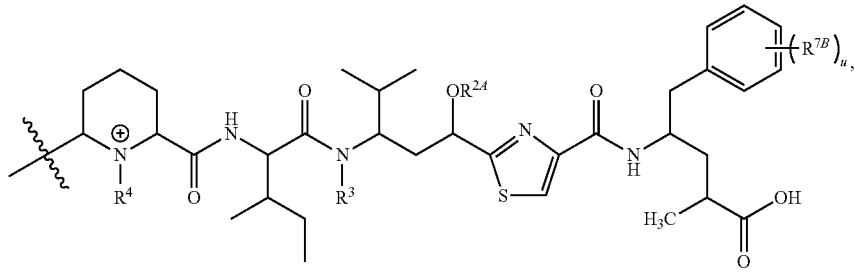

wherein R⁴ is methyl; subscript u is 0, 1 or 2; R³ is H, methyl, ethyl, propyl, —CH₂—OC(O)R³ᴬ, —CH₂CH(R³ᴮ)C(O)R³ᴬ or —CH(R³ᴮ)C(O)NHR³ᴬ, wherein R³ᴬ is C₁-C₆ alkyl and R³ᴮ is H or C₁-C₆ alkyl, independently selected from R³ᴬ; R²ᴬ along with the oxygen atom to which it is attached is an O-linked substituent selected from the group consisting of —OCH₂OCH₂R²ᴮ, —OCH₂R²ᴮ, —OC(O)R²ᴮ, —CH₂OC(O)R²ᴮ, —OC(O)N(R²ᴮ)(R²ᶜ), and —OCH₂C(O)N(R²ᴮ)(R²ᶜ), wherein R²ᴮ and R²ᶜ are independently selected from the group consisting of H, C₁-C₆ alkyl and C₂-C₆ alkenyl; and each R⁷ᴮ, when present, independently is —OH or —OCH₃.

80D. The Ligand Drug Conjugate composition of embodiment 79D, wherein the quaternized tubulysin Drug Unit has the structure of:

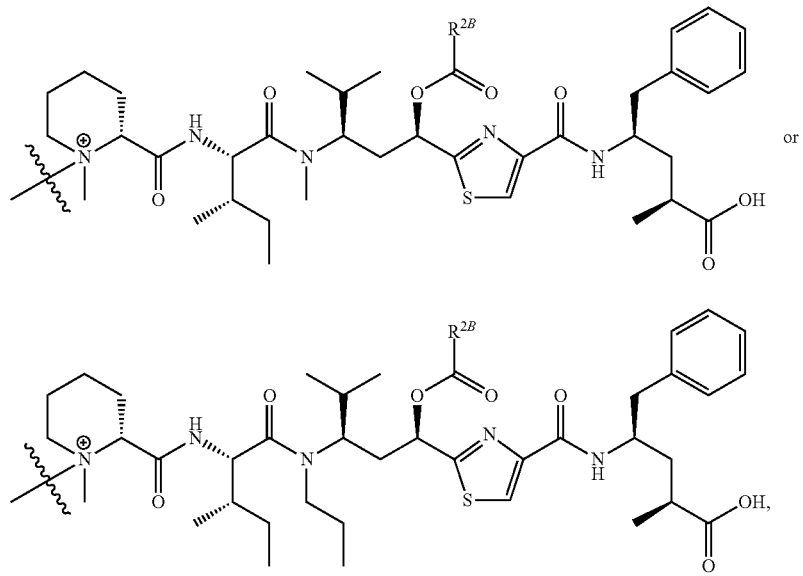

wherein R²ᴮ is —CH₃, —CH₂CH₃, —CH₂CH₂CH₃, —CH(CH₃)₂, —CH₂CH(CH₃)₂, —CH₂C(CH₃)₃.

81D. The Ligand Drug Conjugate composition of embodiment 80D, wherein the quaternized tubulysin Drug Unit has the structure of:

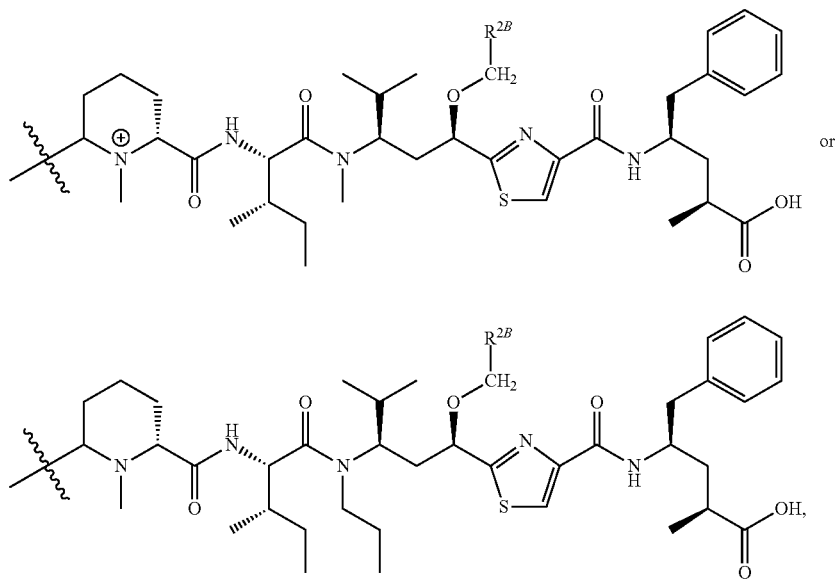

wherein $R^{2B}$ is hydrogen, methyl or —OCH$_3$, or —OCH$_2$R$^{2B}$ is —OCH$_2$CH=CH$_2$ or —OCH$_2$C(CH$_3$)=CH$_2$.

82D. The Ligand Drug Conjugate composition of embodiment 74D, wherein a compound thereof is represented by the structure of:

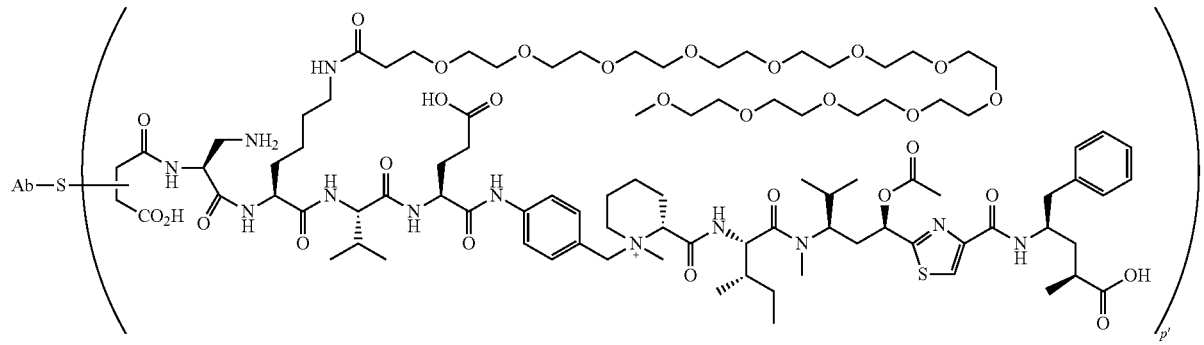

83D. A Drug Linker compound, wherein the compound is represented by the structure of:

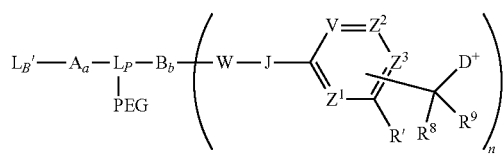

wherein $L_B'$ is a Ligand Covalent Binding Unit precursor; $L_P$ is a Parallel Connector Unit; PEG is a Polyethylene Glycol Unit; subscript a is 0 or 1; subscript b is 0 or 1; A is a first optional Stretcher Unit so that subscript a is 0 when A is absent or A is present so that subscript a is 1 and is optionally comprised of two, three or four independently selected subunits (A$_1$, A$_2$, A$_3$, A$_4$); B is an Branching Unit or a second optional Stretcher Unit (A$_O$) so that subscript b is 0 when B is absent or B is present so that subscript b is 1 and is optionally comprised of two, three or four subunits independently of A; subscript n is 1, 2, 3 or 4, provided that subscript b is 1 and B is a Branching when subscript n is 2, 3 or 4 and provided that B is A$_O$ or is absent when subscript n is 1; V, Z$^1$, Z$^2$ and Z$^3$ are =N— or =C(R$^{24}$)—, wherein R$^{24}$ is hydrogen or alkyl, alkenyl or alkynyl, optionally substituted, or halogen, —NO$_2$, —CN or other electron withdrawing group, or —OCH$_3$ or other an electron donating group, or —C(R$^8$)(R$^9$)-D$^+$, wherein at least one of V, Z$^1$, and Z$^3$ is =C(R$^{24}$)—, provided that one any only one R$^{24}$ is —C(R$^8$)(R$^9$)-D$^+$ so that —C(R$^8$)(R$^9$)-D$^+$ is bonded to one of V, Z, and Z$^3$ when that variable group is =C(R$^{24}$)—; R' is hydrogen or —OCH$_3$ or other electron donating group; D$^+$ is a quaternized tubulysin Drug Unit; J is a heteroatom, optionally substituted when nitrogen, preferably J is —N(R$^{33}$)—, wherein R$^{33}$ is hydrogen or methyl; W is a peptide comprised of an amino acid sequence covalently attached to J through an amide bond wherein that amide bond is cleavable by a protease, wherein said protease cleavage initiates release of a tubulysin compound (D) from the Drug Linker compound or from a Ligand Drug Conjugate compound prepared from the Drug Linker compound, wherein the Ligand Drug Conjugate compound has the Formula 1D structure of embodiment 74D in which subscript p is replaced by subscript p', wherein subscript p' is an integer ranging from 1 to 24.

84D. The Drug Linker compound of embodiment 83D, wherein the compound is represented by the structure of:

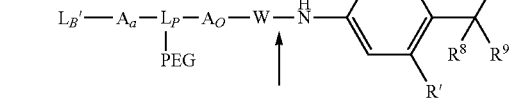

wherein W consists or is comprised of a dipeptide, wherein the dipeptide is at the distal end of W and the indicated bond is an amide bond specifically cleavable by an intracellular protease in comparison to freely circulating serum proteases.

85D. The Drug Linker compound of embodiment 84D, wherein the dipeptide has the structure of;

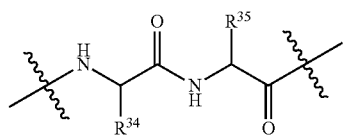

wherein $R^{34}$ is benzyl, methyl, isopropyl, isobutyl, sec-butyl, —CH(OH)CH$_3$ or has the structure of

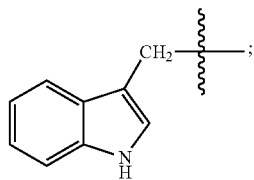 [SMILES: *Cc1c[nH]c2ccccc12]

and $R^{35}$ is methyl, —(CH$_2$)$_4$—NH$_2$, —(CH$_2$)$_3$NH(C=O)NH$_2$, (CH$_2$)$_3$NH(C=NH)NH$_2$, or —(CH$_2$)$_2$CO$_2$H, wherein the wavy line at the dipeptide N-terminus indicates covalent binding to A$_O$ or L$_P$, depending on the presence or absence of A$_O$, respectively, and the wavy line at the dipeptide C-terminus indicates covalent bonding to the nitrogen atom of said amide bond.

86D. The Drug Linker compound of embodiment 83D, 84D or 85D wherein the quaternized tubulysin Drug Unit (-D$^+$) preferably the structure of:

317

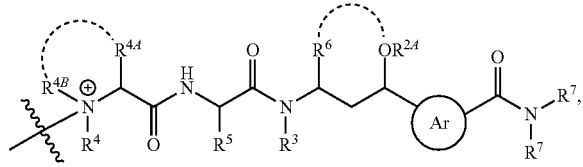

wherein the curved dashed lines indicate optional cyclizations; $R^{2A}$ is hydrogen or optionally substituted alkyl, or $R^{2A}$ along with the oxygen atom to which it is attached defines an O-linked substituent other than —OH, or $R^{2A}$ is absent when $R^6$ is bonded to that oxygen atom, as indicated by the curved dash line between $R^6$ and the oxygen atom, to define an oxygen-containing heterocycloalkyl; the circled Ar represents a 5-membered nitrogen-heteroarylene, wherein the indicated required substituents to that heteroarylene are in a 1,3-relationship with each other with optional substitution at the remaining positions; $R^3$ is hydrogen or optionally substituted alkyl; $R^4$, $R^5$ and $R^6$ are optionally substituted alkyl, independently selected, or $R^6$ is bonded to the oxygen atom of the —$OR^{2A}$ moiety in which $R^{2A}$ is absent and $R^4$ and $R^5$ are as previously defined; $R^{4a}$ is hydrogen or optionally substituted alkyl and $R^{4B}$ is optionally substituted alkyl, or both together with the nitrogen to which they are attached, as indicated by the curved dotted line between $R^{4A}$ and $R^{4B}$, define a quaternized nitrogen heterocycloalkyl, optionally substituted; one $R^7$ is hydrogen or optionally substituted alkyl and the other $R^7$ is optionally substituted aralkyl or heteroaralkyl; wherein the wavy line indicates covalent bonding of the $D^+$ structure to the remainder of the Drug Linker compound structure.

87D. The Drug Linker compound of embodiment 86D wherein the quaternized tubulysin Drug Unit (-$D^+$) has the structure of:

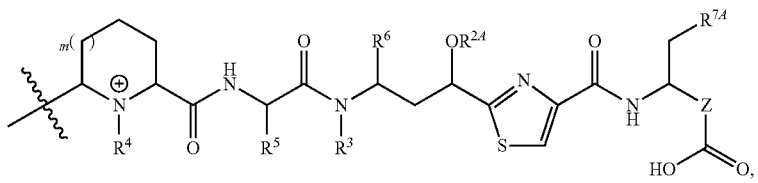

subscript m is 0 or 1; Z is an optionally substituted alkylene or an optionally substituted alkenylene; and $R^{7A}$ is optionally substituted aryl or optionally substituted heteroaryl.

88D. The Drug Linker compound of embodiment 87D wherein the quaternized tubulysin Drug Unit (-$D^+$) has the structure of:

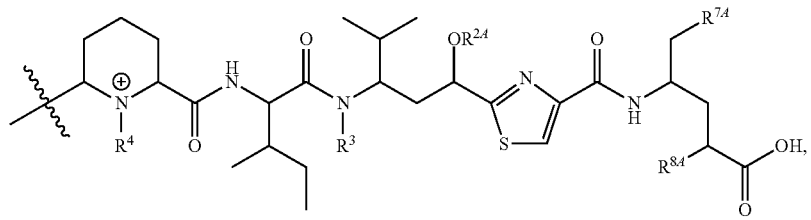

wherein $R^{7A}$ is optionally substituted phenyl and $R^8$ is hydrogen or methyl.

89D. The Drug Linker compound of embodiment 88D wherein the quaternized tubulysin Drug Unit (-$D^+$) has the structure of:

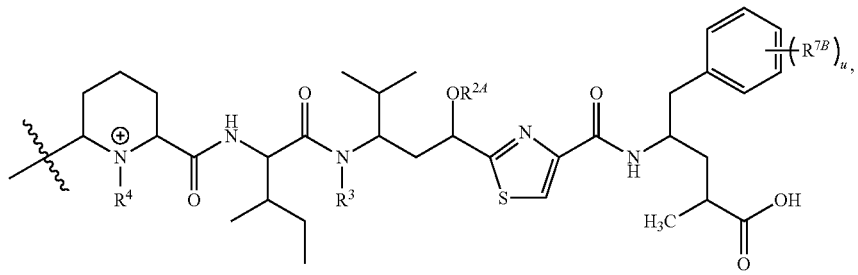

wherein $R^4$ is methyl; subscript u is 0, 1 or 2; $R^3$ is H, methyl, ethyl, propyl, —$CH_2$—$OC(O)R^{3A}$, —$CH_2CH(R^{3B})C(O)R^{3A}$ or —$CH(R^{3B})C(O)NHR^{3A}$, wherein $R^{3A}$ is $C_1$-$C_6$ alkyl and $R^{3B}$ is H or $C_1$-$C_6$ alkyl, independently selected from $R^{3A}$; $R^{2A}$ along with the oxygen atom to which it is attached is an O-linked substituent selected from the group consisting of —$OCH_2OCH_2R^{2B}$, —$OCH_2R^{2B}$, —$OC(O)R^{2B}$, —$CH_2OC(O)R^{2B}$, —$OC(O)N(R^{2B})(R^{2C})$, and —$OCH_2C(O)N(R^{2B})(R^{2C})$, wherein $R^{2B}$ and $R^{2C}$ are independently selected from the group consisting of H, $C_1$-$C_6$ alkyl and $C_2$-$C_6$ alkenyl; and each $R^{7B}$, when present, independently is —OH or —$OCH_3$.

90D. The Drug Linker compound of embodiment 89D, wherein the quaternized tubulysin Drug Unit (-$D^+$) has the structure of:

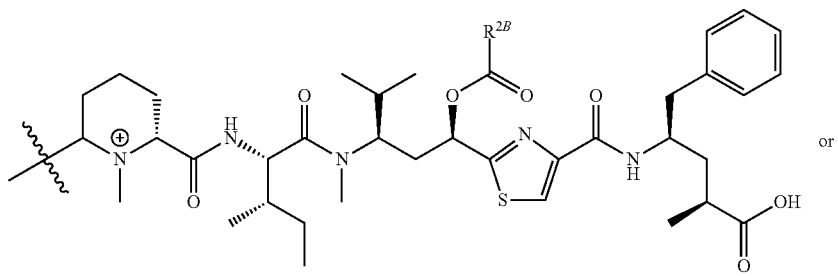

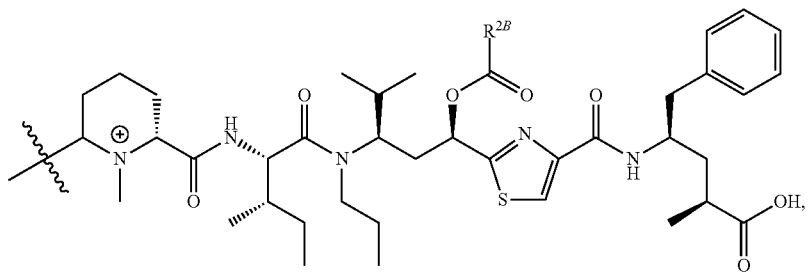

wherein $R^{2B}$ is —$CH_3$, —$CH_2CH_3$, —$CH_2CH_2CH_3$, —$CH(CH_3)_2$, —$CH_2CH(CH_3)_2$, —$CH_2C(CH_3)_3$.

91D. The Drug Linker compound of embodiment 89D, wherein the quaternized tubulysin Drug Unit (-$D^+$) has the structure of:

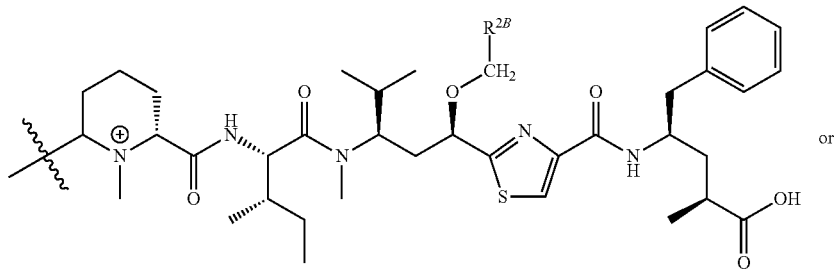

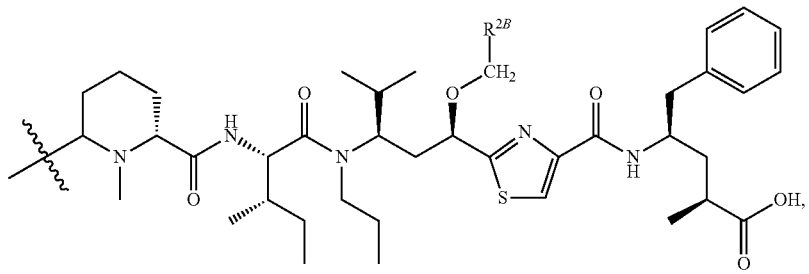

wherein $R^{2B}$ is hydrogen, methyl or —$OCH_3$, or —$OCH_2R^{2B}$ is —$OCH_2CH=CH_2$ or —$OCH_2C(CH_3)=CH_2$.

92D. The Drug Linker compound of embodiment 83D, wherein the compound has the structure of:

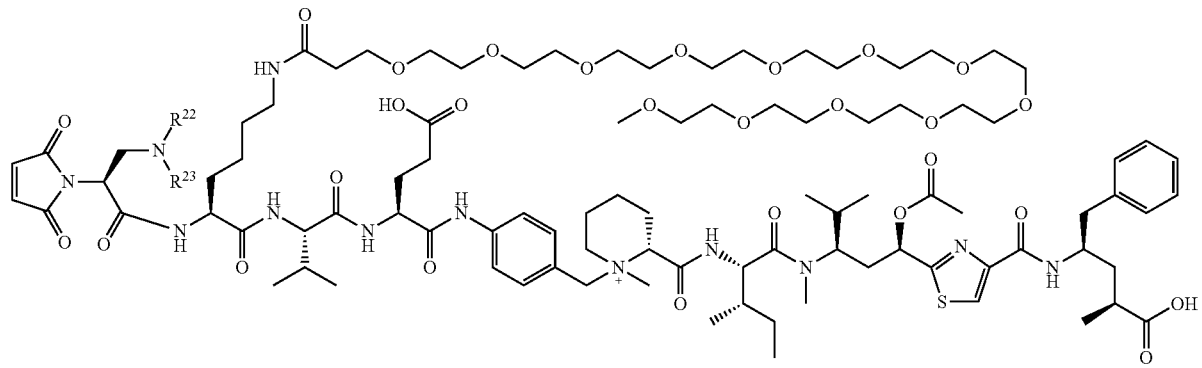

wherein one of $R^{22}$, $R^{23}$ is hydrogen and the other is an acid labile protecting group or $R^{22}$ and $R^{23}$ are each hydrogen with the nitrogen to which they are attached optionally protonated as an acid addition salt.

93D. A formulation comprising a Ligand Drug Conjugate of any one of embodiments 1D to 34D and 78D to 86D and one or more excipients.

94D. The formulation of embodiment 93D wherein the formulation is a pharmaceutically acceptable formulation or a precursor thereof.

95D. The formulation of embodiment 94D wherein the pharmaceutically acceptable formulation precursor is a solid suitable for reconstitution as a solution for intravenous injection to a subject.

96D. The formulation of embodiment 94D wherein the pharmaceutically acceptable formulation is a liquid suitable for intravenous injection to a subject.

97D. The formulation of embodiments 94D, 95D or 96D wherein the Ligand Drug Conjugate is present in the pharmaceutically acceptable formulation or precursor thereof in an effective amount for treatment of a hyperproliferative condition.

98D. A method of treating a hyperproliferative disease or condition comprising the step of administering to a patient having said disease or condition an effective amount of a Ligand Drug Conjugate of any one of embodiments 1D to 34D and 74D to 82D.

99D. The method of embodiment 98D wherein the hyperproliferative disease or condition is a cancer.

100D. The method of embodiment 98D wherein the hyperproliferative disease or condition is a leukemia or a lymphoma.

101D. A method of inhibiting the multiplication of a tumor cell or cancer cell, or causing apoptosis in a tumor or cancer cell, by exposing said cell with an effective amount of Ligand Drug Conjugate of any one of embodiments 1D to 34D and 74D to 82D or of a tubulysin compound of any one of embodiments 70D to 72D.

Examples

General Information.

All commercially available anhydrous solvents were used without further purification. Analytical thin layer chromatography was performed on silica gel 60 F254 aluminum sheets (EMD Chemicals, Gibbstown, N.J.). Radial chromatography was performed on Chromatotron apparatus (Harris Research, Palo Alto, Calif.). Column chromatography was performed on a Biotage Isolera One flash purification system (Charlotte, N.C.). Analytical HPLC was performed on a Varian ProStar 210 solvent delivery system configured with a Varian ProStar 330 PDA detector. Samples were eluted over a C12 Phenomenex Synergi 2.0×150 mm, 4 m, 80 Å reverse-phase column. The acidic mobile phase consisted of acetonitrile and water both containing either 0.05% trifluoroacetic acid or 0.1% formic acid (denoted for each compound). Compounds were eluted with a linear gradient of acidic acetonitrile from 5% at 1 min post injection, to 95% at 11 min, followed by isocratic 95% acetonitrile to 15 min (flow rate=1.0 mL/min). LC-MS was performed on two different systems. LC-MS system 1 consisted of a ZMD Micromass mass spectrometer interfaced to an HP Agilent 1100 HPLC instrument equipped with a C12 Phenomenex Synergi 2.0×150 mm, 4 m, 80 Å reverse phase column. The acidic eluent consisted of a linear gradient of acetonitrile from 5% to 95% in 0.1% aqueous formic acid over 10 min, followed by isocratic 95% acetonitrile for 5 min (flow rate=0.4 mL/min). LC-MS system 2 consisted of a Waters Xevo G2 ToF mass spectrometer interfaced to a Waters 2695 Separations Module with a Waters 2996 Photodiode Array Detector; the column, mobile phases, gradient, and flow rate were same as for LC-MS system 1. UPLC-MS system 1 consisted of a Waters SQ mass detector interfaced to an Acquity Ultra Performance LC equipped with an Acquity UPLC BEH C18 2.1×50 mm, 1.7 μm reverse phase column. The acidic mobile phase (0.1% formic acid) consisted of a gradient of 3% acetonitrile/97% water to 100% acetonitrile (flow rate=0.5 mL/min). UPLC-MS system 2 consisted of a Waters Xevo G2 ToF mass spectrometer interfaced to a Waters Acquity H-Class Ultra Performance LC equipped with an Acquity UPLC BEH C18 2.1×50 mm, 1.7 μm reverse phase column. The acidic mobile phase (0.1% formic acid) consisted of a gradient of 3% acetonitrile/97% water to 100% acetonitrile (flow rate=0.7 mL/min). Preparative HPLC was carried out on a Varian ProStar 210 solvent delivery system configured with a Varian ProStar 330 PDA detector. Products were purified over a C12 Phenomenex Synergi 10.0×250 mm, 4 μm, 80 Å reverse phase column eluting with 0.1% trifluoroacetic acid in water (solvent A) and 0.1% trifluoroacetic acid in acetonitrile (solvent B). The purification methods generally consisted of linear gradients of solvent A to solvent B, ramping from 90% aqueous solvent A to 10% solvent A. The flow rate was 4.6 mL/min with monitoring at 254 nm. NMR spectral data were collected on a Varian Mercury 400 MHz spectrometer. Coupling constants (J) are reported in hertz.

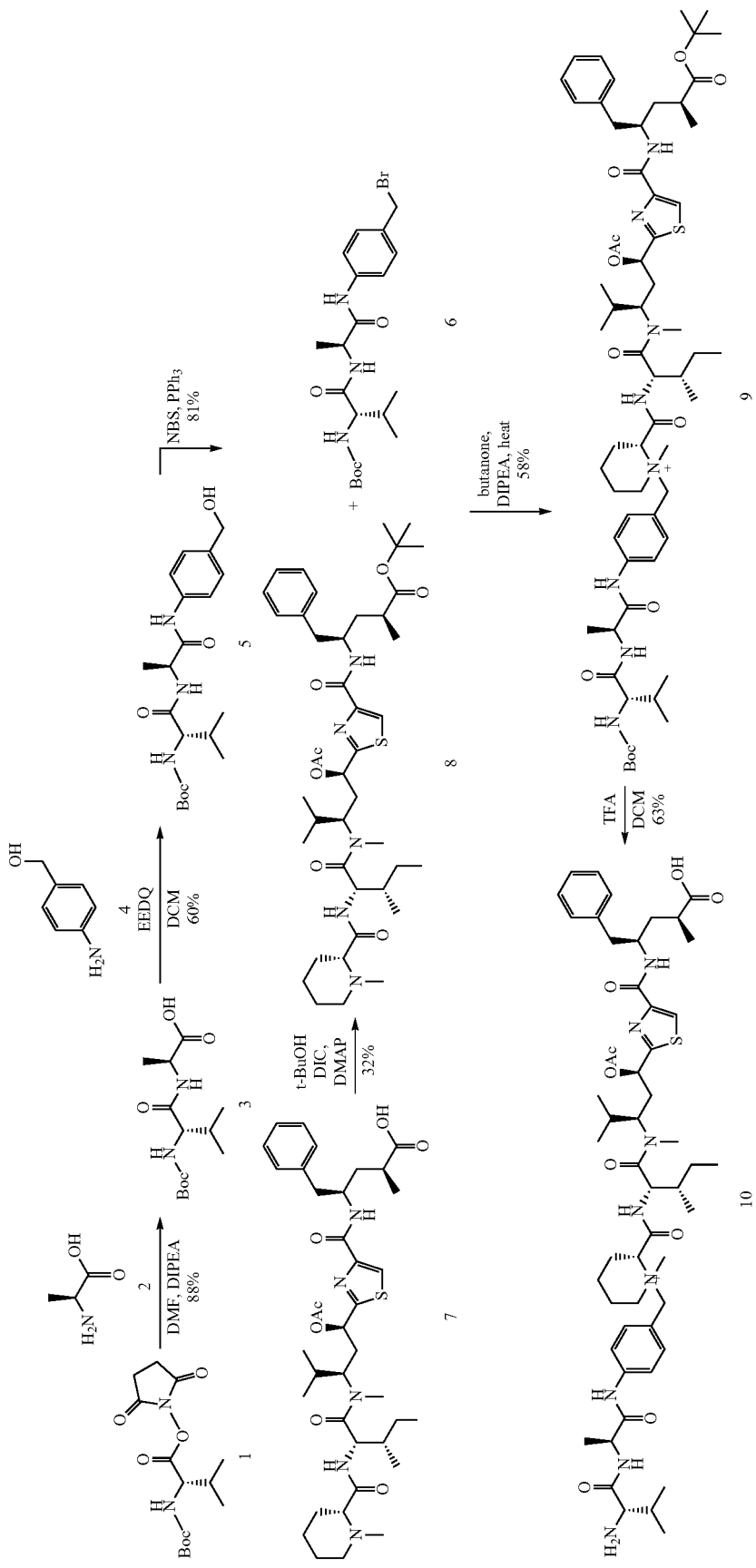

(S)-2-((S)-2-((tert-butoxycarbonyl)amino)-3-methylbutanamido)-propanoic Acid (3)

A flask was charged with Boc-Val-OSu (1, 1.0 g, 3.18 mmol) and H-Ala-OH (2, 312 mg, 3.5 mmol) in anhydrous dimethylformamide (10.6 mL). N,N-diisopropylethylamine (1.1 mL, 6.4 mmol) was added and the solution was stirred under $N_2$ at 50° C. for 12 hours. The reaction was taken up in DMSO and purified by preparative HPLC to yield 3 (808 mg, 88%). Analytical UPLC-MS (system 1): $t_r$=1.38 min, m/z (ES+) found 289.60.

tert-butyl ((S)-1-(((S)-1-((4-(hydroxymethyl)phenyl)amino)-1-oxopropan-2-yl)amino)-3-methyl-1-oxobutan-2-yl)carbamate (5)

A flame-dried flask was charged with dipeptide 3 (808 mg, 2.8 mmol) and 4-aminobenzoic alcohol 4 (345 mg, 2.8 mmol) in anhydrous dichloromethane (14 mL). EEDQ (762 mg, 3.1 mmol) was added as a solid and stirred under nitrogen at room temperature for 12 h. The reaction was then condensed and purified over silica via a Biotage column ($CH_2Cl_2$/MeOH, 0%-10%) to provide 5 (660 mg, 60%). Analytical UPLC-MS (system 1): $t_r$=1.51 min, m/z (ES+) found 394.51.

tert-butyl ((S)-1-(((S)-1-((4-(bromomethyl)phenyl)amino)-1-oxopropan-2-yl)amino)-3-methyl-1-oxobutan-2-yl)carbamate (6)

A flask containing Boc-Val-Ala-PABA-OH (5, 100 mg, 254 µmol), N-bromosuccinimide (68 mg, 381 µmol), and triphenylphosphine (100 mg, 381 µmol) was flushed with nitrogen. The reaction was taken up in THF (4 mL) and stirred for 12 hours. The reaction was condensed and purified over silica via a Biotage column (Hexanes/EtOAc, 10%-100%) to provide 6 (94 mg, 81%). Analytical UPLC-MS (system 1): $t_r$=2.09 min, m/z (ES+) found 456.10.

(2S,4R)-tert-butyl 4-(2-((1R,3R)-1-acetoxy-3-((2S,3S)—N,3-dimethyl-2-((R)-1-methylpiperidine-2-carboxamido)pentanamido)-4-methylpentyl)thiazole-4-carboxamido)-2-methyl-5-phenylpentanoate (8)

A flame A flame dried flask was charged with a tubulysin analog (7, 10 mg, 14 µmol) in anhydrous DCM (0.7 mL) and t-butanol (0.7 mL). Diisopropylcarbodiimide (3.2 µL, 21 µmol) and DMAP (0.08 mg, 0.7 mol) were added and the reaction was stirred at room temperature for 48 hours. The reaction was condensed, taken up in DMSO, and purified by preparative HPLC to yield 8 (3.5 mg, 32%). Analytical UPLC-MS (system 1): $t_r$=1.35 min, m/z (ES+) found 784.56.

(2R)-2-(((2S,3S)-1-(((1R,3R)-1-acetoxy-1-(4-(((2R,4S)-5-(tert-butoxy)-4-methyl-5-oxo-1-phenylpentan-2-yl)carbamoyl)thiazol-2-yl)-4-methylpentan-3-yl)(methyl)amino)-3-methyl-1-oxopentan-2-yl)carbamoyl)-1-(4-((S)-2-((S)-2-((tert-butoxycarbonyl)amino)-3-methylbutanamido)propanamido)benzyl)-1-methylpiperidin-1-ium (9)

A pressure vessel was charged with Boc-Val-Ala-PAB-Br (6, 3.5 mg, 7.7 µmol) and protected tubulysin 8 (4.0 mg, 5.1 µmol) in anhydrous butanone (0.765 mL). N,N-diisopropylethylamine was added (1.8 µL, 10 µmol) and the reaction was flushed with nitrogen. The vessel was sealed and allowed to stir at 80° C. for 12 hours. The reaction was condensed, taken up in DMSO, and purified by preparative HPLC to yield 9 (3.5 mg, 58%). Analytical UPLC-MS (system 1): $t_r$=1.51 min, m/z (ES+) found 1159.58.

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(4-((S)-2-((S)-2-amino-3-methylbutanamido)propanamido)benzyl)-1-methylpiperidin-1-ium (10)

A flask containing Boc-Val-Ala-PAB-TubM-OtBu (9, 3.5 mg, 3 µmol) was cooled to 0° C. under nitrogen. A solution of 10% TFA in $CH_2Cl_2$ (0.3 mL) was added dropwise and stirred for 4 hours. The reaction was condensed, taken up in DMSO, and purified by preparative HPLC to yield 10 (1.9 mg, 63%). Analytical UPLC-MS (system 1): $t_r$=1.05 min, m/z (ES+) found 1003.60.

Scheme 2.

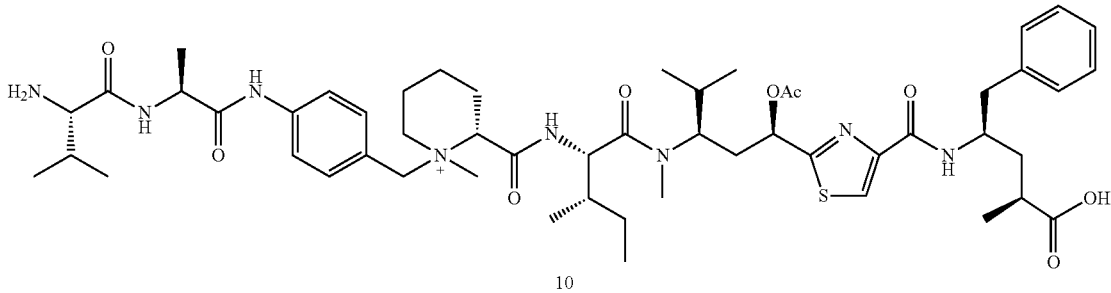

10

-continued
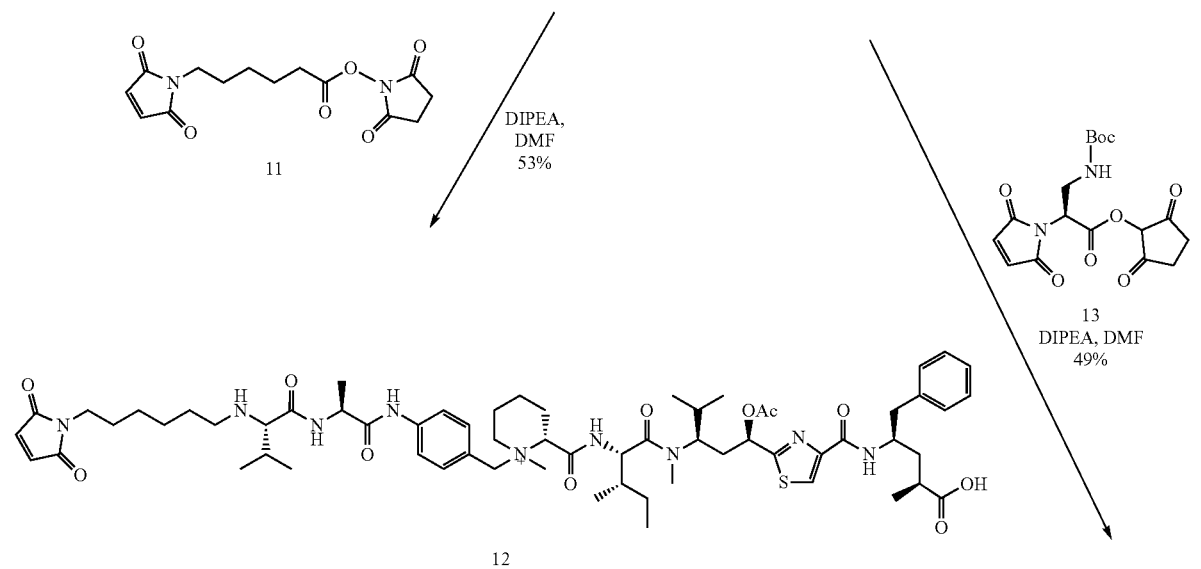
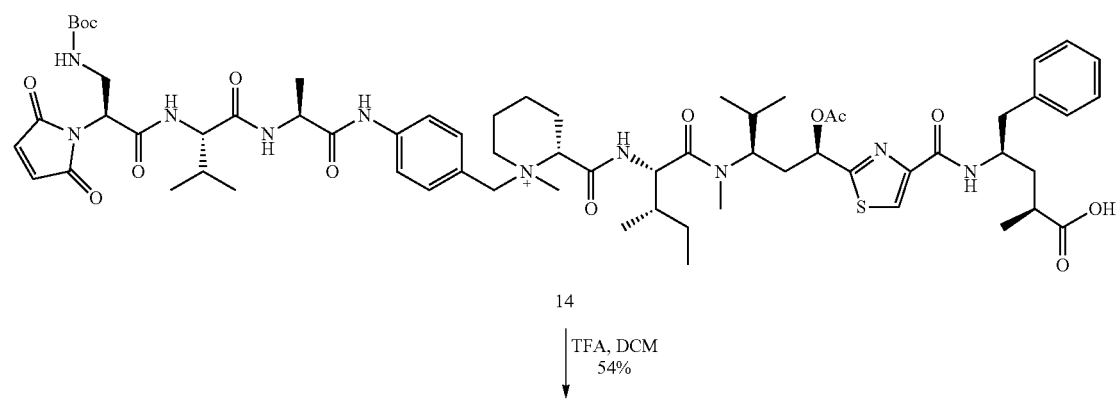
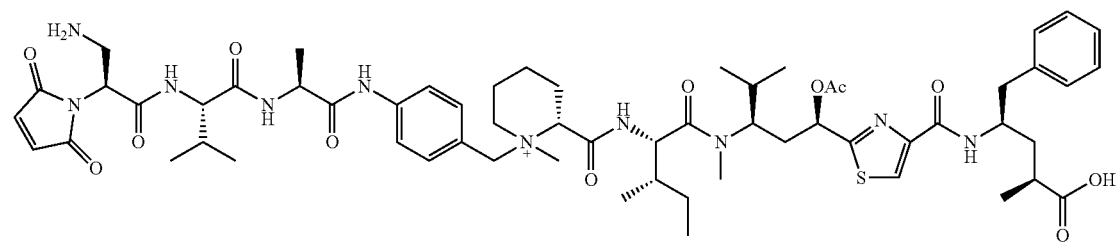

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(4-((S)-2-((S)-2-(6-(2,5-dioxo-2,5-dihydro-1H-pyrrol-1-yl)hexanamido)-3-methylbutanamido)propanamido)benzyl)-1-methylpiperidin-1-ium (12)

MC-OSu (11, 0.6 mg, 2 μmol) was taken up in anhydrous dimethylformamide (0.2 mL) and added to a flask containing Val-Ala-PAB-Tub (10, 1.9 mg, 2 μmol). N,N-diisopropylethylamine (1.0 mg, 8 μmol) was added and the reaction was stirred under nitrogen for 3 hours. The reaction was taken up in DMSO, and purified by preparative HPLC to yield quaternary amine tubulysin linker 12 (1.2 mg, 53%). Analytical UPLC-MS (system 1): $t_r$=1.25 min, m/z (ES+) found 1196.45.

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(4-(((7S,10S,13S)-7-(2,5-dioxo-2,5-dihydro-1H-pyrrol-1-yl)-10-isopropyl-2,2,13-trimethyl-4,8,11-trioxo-3-oxa-5,9,12-triazatetradecanamido)benzyl)-1-methylpiperidin-1-ium (14)

MDPR(Boc)-OSu (13, 1.3 mg, 3.5 μmol) was taken up in anhydrous dimethylformamide (0.3 mL) and added to a flask containing Val-Ala-PAB-TubM (10, 3.2 mg, 3.2 μmol). N,N-diisopropylethylamine (1.6 mg, 13 μmol) was added and the reaction was stirred under nitrogen for 3 hours. The reaction was taken up in DMSO, and purified by preparative HPLC to yield 14 (2.0 mg, 49%). Analytical UPLC-MS (system 2): $t_r$=1.35 min, m/z (ES+) found 1269.76.

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(4-((S)-2-((S)-2-((S)-3-amino-2-(2,5-dioxo-2,5-dihydro-1H-pyrrol-1-yl)propanamido)-3-methylbutanamido)propanamido)benzyl)-1-methylpiperidin-1-ium (15)

A flask containing MDPR(Boc)-Val-Ala-PAB-TubM (14, 2 mg, 1.6 μmol) was cooled to 0° C. under nitrogen. A solution of 10% TFA in $CH_2Cl_2$ (1.6 mL) was added dropwise and stirred for 4 hours. The reaction was condensed, taken up in DMSO, and purified by preparative HPLC to yield 15 (1.0 mg, 54%). Analytical UPLC-MS (system 2): $t_r$=1.02 min, m/z (ES+) found 1169.72.

Tubulysin analogs in which the tubuvaline acetate was replaced with an alkyl ether were prepared as shown in Schemes 3.

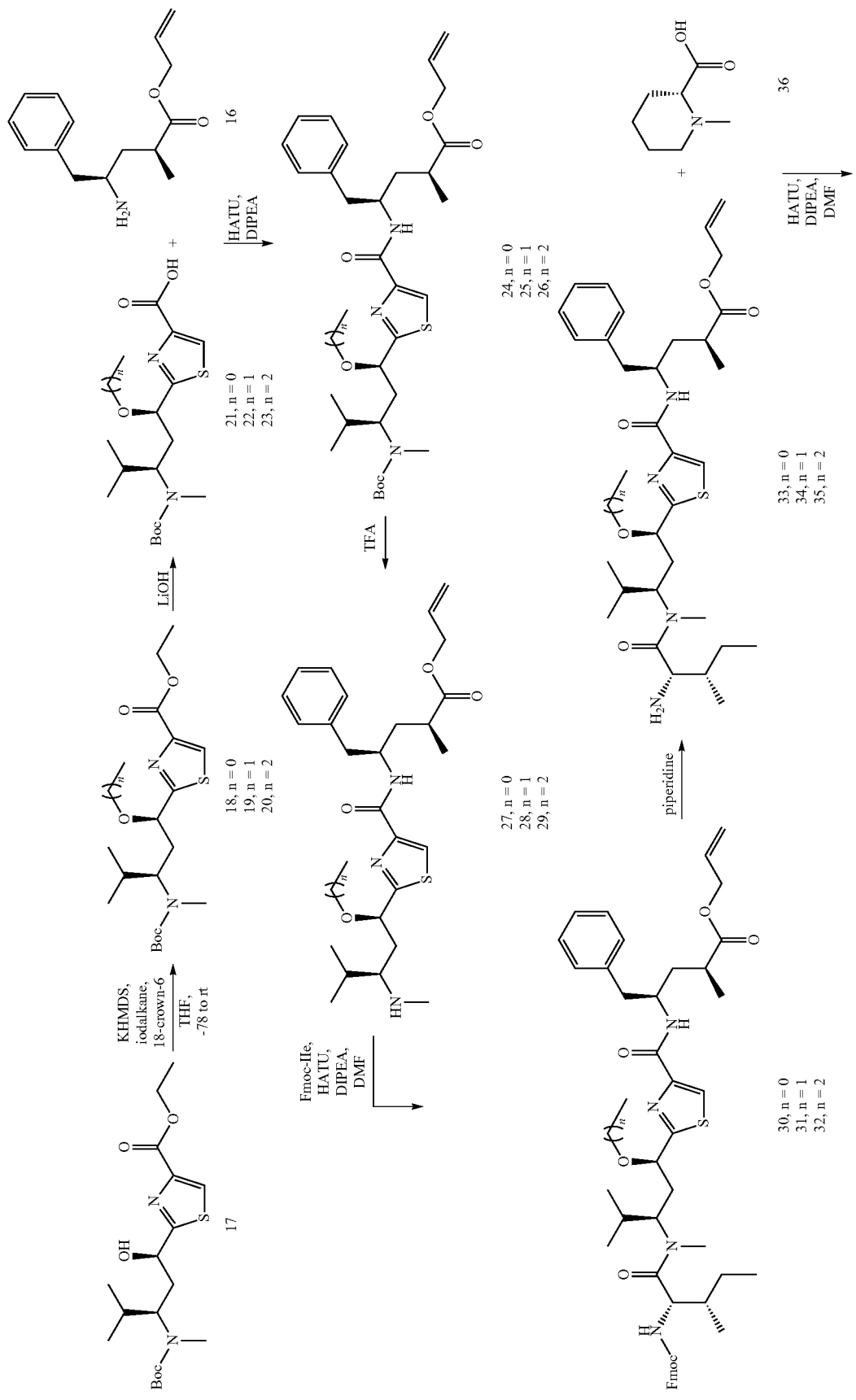

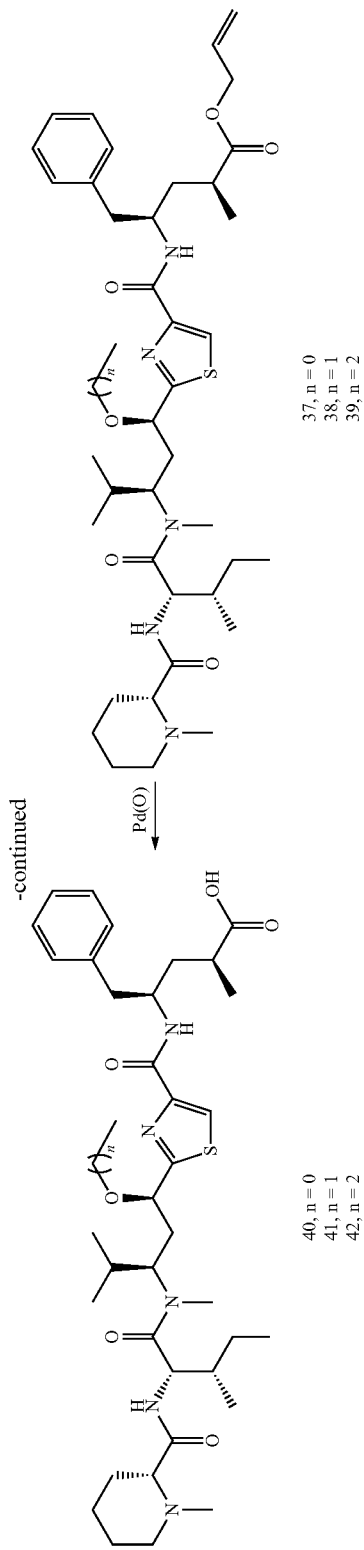

General Procedure for the Etherification of Tubuvaline.

A flame-dried flask was charged with the Boc-protected known tubuvaline (*J. Org. Chem.*, 2008, 73, 4362-4369) intermediate 17 in anhydrous tetrahydrofuran (50 mM), to which was added 18-crown-6 (2.0 equivalents) and cooled to −78 C. Potassium hexamethyldisilazide (1.5 equivalents) as a 1 M solution in tetrahydrofuran was added dropwise and the reaction was then stirred for 1 hour at -78 C under nitrogen. Iodoalkane (2-5 equivalents) was then added and the reaction slowly warmed to room temperature and followed by UPLC/MS. Once the starting material was consumed, the reaction was cooled on ice and quenched with saturated ammonium chloride and diluted in dichloromethane (10 volumes). The organic layer was washed with 0.1 M HCl and the resulting aqueous phase extracted twice with dichloromethane. The combined organics were then dried over sodium sulfate, filtered, and concentrated to dryness. Purification of the crude O-alkylated products was achieved by flash chromatography over silica gel or preparative HPLC.

Ethyl 2-((1R,3R)-3-((tert-butoxycarbonyl)(methyl) amino)-1-methoxy-4-methylpentyl)thiazole-4-carboxylate (18)

Tubuvaline intermediate 17 (170 mg, 440 μmol) was O-methylated as described above with iodomethane (89 μl, 880 μmol) to provide 170 mg (97%) of the title compound after silica gel purification eluting methanol and dichloromethane mixtures. UPLC-MS (system 2): $t_r$=1.62 min, m/z (ES+) calculated 401.21, found 401.28.

Ethyl 2-((1R,3R)-3-((tert-butoxycarbonyl)(methyl) amino)-1-ethoxy-4-methylpentyl)thiazole-4-carboxylate (19)

Tubuvaline intermediate 17 (392 mg, 1.01 mmol) was O-ethylated as described above with iodoethane (791 mg, 5.05 mmol) to provide 407 mg (97%) of the title compound after silica gel purification eluting methanol and dichloromethane mixtures. UPLC-MS (system 2): $t_r$=1.66 min, m/z (ES+) calculated 415.23 (M+H)+, found 415.29.

Ethyl 2-((1R,3R)-3-((tert-butoxycarbonyl)(methyl) amino)-4-methyl-1-propoxypentyl)thiazole-4-carboxylate (20)

Tubuvaline intermediate 17 (22 mg, 57 μmol) was O-propylated as described above with 1-iodopropane (28 μl, 285 μmol) to provide 9 mg (37%) of the title compound after purification by preparative HPLC. UPLC-MS (system 2): $t_r$=1.77 min, m/z (ES+) calculated 428.23 (M+H)+, found 451.30 (M+Na)+. $^1$H NMR (1:1 mix of rotamers, CDCl$_3$) δ (ppm) 0.91 (m, 9H), 1.40 (t, J=7.0 Hz, 3H), 1.47 (two s from rotamers, 9H), 1.64 (m, 3H), 1.87 (m, 2H), 2.74 (m, 3H), 3.42 (m, 2H), 4.10 (m, 1H), 4.42 (q, J=7.0 Hz, 2H), 4.50 (m, 1H), 8.14 (two s from rotamers, 1H).

General Procedure for the Saponification of O-Alkylated Tubuvaline Esters.

Saponification reactions were carried out at 20 mM reaction concentration using a 1:1:1 mixture of tetrahydrofuran:methanol:water solvent mixture. O-alkylated tubuvaline intermediates 18-20 were dissolved in 1 volume each tetrahydrofuran and methanol. The mixture was then cooled in an ice bath at 0 C. Lithium hydroxide monohydrate (2-3 equivalents) was dissolved in 1 volume of distilled water and added dropwise to the reaction flask, with stirring at 0 C. The reaction was then allowed to warm up to room temperature and monitored by UPLC/MS. Once the starting material had converted to free acid, the reaction was quenched with glacial acetic acid (2-3 equivalents) and concentrated by rotary evaporation. The crude carboxylic acids were then purified by preparative HPLC.

Ethyl 2-((1R,3R)-3-((tert-butoxycarbonyl)(methyl) amino)-1-methoxy-4-methylpentyl)thiazole-4-carboxylate (21)

Tubuvaline methyl ether intermediate 18 (170 mg, 425 μmol) was saponified as described above with lithium hydroxide monohydrate (19 mg, 1.28 mmol) to provide 140 mg (89%) of the title compound. UPLC-MS (system 1): $t_r$=1.47 min, m/z (ES+) calculated 373.18, found 373.41. $^1$H NMR (1:1 mix of rotamers, CDCl$_3$) δ (ppm) 0.87 (dd, J=6.7, 2.0 Hz, 3H), 0.96 (dd, J=6.7, 1.2 Hz, 3H), 1.49 (two s from rotamers, 9H), 1.67 (m, 1H), 1.85 (m, 1H), 2.01 (m, 1H), 2.70 (m, 3H), 3.41 (s, 3H), 4.12 (m, 1H), 4.36 (first rotamer, dd, J=10.5, 2.3 Hz, 0.5H), 4.48 (second rotamer, d, J=8.6 Hz, 0.5H), 8.28 (two s from rotamers, 1H).

Ethyl 2-((1R,3R)-3-((tert-butoxycarbonyl)(methyl) amino)-1-ethoxy-4-methylpentyl)thiazole-4-carboxylate (22)

Tubuvaline ethyl ether intermediate 19 (170 mg, 425 μmol) was saponified as described above with lithium hydroxide monohydrate (19 mg, 1.28 mmol) to provide 140 mg (89%) of the title compound. UPLC-MS (system 2): $t_r$=1.48 min, m/z (ES+) calculated 387.20 (M+H)+, found 387.26. $^1$H NMR (CDCl$_3$) δ (ppm) 0.88 (dd, J=6.7, 2.0 Hz, 3H), 0.96 (d, J=6.6 Hz, 3H), 1.49 (two s from rotamers, 9H), 1.68 (m, 1H), 1.86 (m, 1H), 2.00 (m, 1H), 2.69 (m, 3H), 3.53 (m, 2H), 4.09 (m, 1H), 4.43 (first rotamer, dd, J=10.2, 2.7 Hz, 0.5H), 4.54 (second rotamer, d, J=7.0 Hz, 0.5H), 8.24 (two s from rotamers, 1H).

Ethyl 2-((1R,3R)-3-((tert-butoxycarbonyl)(methyl) amino)-4-methyl-1-propoxypentyl)thiazole-4-carboxylate (23)

Tubuvaline propyl ether intermediate 20 (9 mg, 20 μmol) was saponified as described above with lithium hydroxide monohydrate (1.7 mg, 40 μmol) to provide 7.6 mg (95%) of the title compound. UPLC-MS (system 2): $t_r$=1.58 min, m/z (ES+) calculated 401.21 (M+H)+, found 401.28 (M+Na)+.

General Procedure for the Amide Coupling of O-Alkylated Tubuvaline Free Acids and Tubuphenylalanine Allyl Ester.

O-alkylated tubuvaline free acids 21-23 were pre-activated by dissolution in anhydrous dimethylformamide (25-50 mM) and addition of HATU (2.4 equivalents) and DIPEA (5 equivalents); the mixture was then stirred under nitrogen at room temperature for 10 minutes. The activated acid was then added to the known (*Org. Lett.*, 2007, 9, 1605-1607) tubuphenylalanine allyl ester 16 and the reaction was then stirred at an ambient temperature under nitrogen, with progress monitored by UPLC/MS. Upon reaction completion, glacial acetic acid (14 equivalents) was then added and the product was purified by preparative HPLC.

(2S,4R)-allyl 4-(2-((1R,3R)-3-((tert-butoxycarbonyl) (methyl)amino)-1-methoxy-4-methylpentyl)thiazole-4-carboxamido)-2-methyl-5-phenylpentanoate (24)

Tubuvaline methyl ether (TuvOMe) intermediate 21 (140 mg, 380 μmol) was coupled to tubuphenylalanine (Tup) allyl ester 16 (188 mg, 760 µmol) to provide 164 mg (72%) of the title compound. UPLC-MS (system 1): $t_r$=1.96 min, m/z (ES+) calculated 602.33 (M+H)$^+$, found 602.26.

(2S,4R)-allyl 4-(2-((1R,3R)-3-((tert-butoxycarbonyl)
(methyl)amino)-1-ethoxy-4-methylpentyl)thiazole-4-
carboxamido)-2-methyl-5-phenylpentanoate (25)

Tubuvaline ethyl ether (TuvOEt) intermediate 22 (140 mg, 380 µmol) was coupled to tubuphenylalanine (Tup) allyl ester 16 (188 mg, 760 µmol) to provide 164 mg (72%) of the title compound. UPLC-MS (system 2): $t_r$=1.84 min, m/z (ES+) calculated 616.34 (M+H)$^+$, found 616.43.

(2S,4R)-allyl 4-(2-((1R,3R)-3-((tert-butoxycarbonyl)
(methyl)amino)-4-methyl-1-propoxypentyl)thiazole-
4-carboxamido)-2-methyl-5-phenylpentanoate (26)

Tubuvaline propyl ether (TuvOPr) intermediate 23 (7.6 mg, 19 µmol) was coupled to tubuphenylalanine (Tup) allyl ester 16 (9.4 mg, 38 µmol) to provide 8 mg (67%) of the title compound. UPLC-MS (system 2): $t_r$=2.00 min, m/z (ES+) calculated 630.36 (M+H)$^+$, found 630.45. $^1$H NMR (CDCl$_3$) δ (ppm) 0.94 (m, 9H), 1.19 (d, J=7.4 Hz, 3H), 1.49 (s, 9H), 1.64 (m, 5H), 1.84 (m, 1H), 2.03 (m, 2H), 2.63 (m, 1H), 2.73 (m, 3H), 2.93 (m, 2H), 3.41 (m, 2H), 4.07 (m, 2H), 4.29 (m, 1H), 4.41 (m, 2H), 4.55 (m, 2H), 5.25 (m, 2H), 5.88 (m, 1H), 7.24 (m, 5H), 8.05 (two s from rotamers, 1H).

General Procedure for the Boc Deprotection of Tuv(O-Alk)-Tup Intermediates.

O-alkylated tubuvaline-tubuphenylalanine intermediates 24-26 were deprotected to reveal the secondary amine functional group under acidic conditions with 10% TFA in dichloromethane (25 mM). Specifically, the starting material was dissolve in anhydrous dichloromethane (9 volumes) and stirred under nitrogen at 0 C. Trifluoroacetic acid (1 volume) was then added dropwise to the stirred solution. The reaction was warmed slowly to room temperature and monitored by UPLC/MS. Upon completion, the reaction was concentrated by rotary evaporation and pumped down on a vacuum line overnight. The free amines 27-29 were carried forward without further purification.

(2S,4R)-allyl 4-(2-((1R,3R)-1-methoxy-4-methyl-3-
(methylamino)pentyl)thiazole-4-carboxamido)-2-
methyl-5-phenylpentanoate (27)

Boc-protected TuvOMe-Tup intermediate 24 (160 mg, 267 µmol) was deprotected as described above to provide 133 mg (99%) of the title compound. UPLC-MS (system 1): $t_r$=1.17 min, m/z (ES+) calculated 524.26 (M+Na)$^+$, found 524.27.

(2S,4R)-allyl 4-(2-((1R,3R)-1-ethoxy-4-methyl-3-
(methylamino)pentyl)-thiazole-4-carboxamido)-2-
methyl-5-phenylpentanoate (28)

Boc-protected TuvOEt-Tup intermediate 25 (160 mg, 267 µmol) was deprotected as described above to provide 133 mg (99%) of the title compound. UPLC-MS (system 2): $t_r$=1.11 min, m/z (ES+) calculated 516.29 (M+H)$^+$, found 516.37.

(2S,4R)-allyl 2-methyl-4-(2-((1R,3R)-4-methyl-3-
(methylamino)-1-propoxypentyl)thiazole-4-carbox-
amido)-5-phenylpentanoate (29)

Boc-protected TuvOEt-Tup intermediate 26 (8 mg, 13 µmol) was deprotected as described above to provide 7 mg (quant.) of the title compound. UPLC-MS (system 2): $t_r$=1.16 min, m/z (ES+) calculated 530.31 (M+H)$^+$, found 530.40.

General Procedure for the Amide Coupling of O-Alkylated Tubuvaline-Tubuphenylalanine Dipeptides with Fmoc-Protected L-Isoleucine.

Commercially available Fmoc-L-Isoleucine (1.3-2 equivalents) was dissolved in anhydrous dimethylformamide (50-200 mM) and pre-activated with HATU (1.5-2 equivalents) and DIPEA (2 equivalents); the mixture was stirred for 10 minutes at room temperature under nitrogen. The activated acid was then added to the Tuv(O-ether)-Tup dipeptides 27-29; the reaction was stirred at room temperature under nitrogen and monitored by UPLC/MS. Once the reaction had stopped progressing or had reached completion, glacial acetic acid (13 equivalents) was added and the reaction was purified by prep HPLC.

(2S,4R)-allyl 4-(2-((5S,8R,10R)-5-((S)-sec-butyl)-1-
(9H-fluoren-9-yl)-8-isopropyl-7-methyl-3,6-dioxo-2,
11-dioxa-4,7-diazadodecan-10-yl)thiazole-4-carbox-
amido)-2-methyl-5-phenylpentanoate (30)

TuvOMe-Tup intermediate 27 (160 mg, 265 µmol) was coupled to Fmoc-L-Ile as described above to provide 67 mg (30%) of the title compound. UPLC-MS (system 1): $t_r$=2.07 min, m/z (ES+) calculated 837.43 (M+H)$^+$, found 837.20.

(2S,4R)-allyl 4-(2-((5S,8R,10R)-5-((S)-sec-butyl)-1-
(9H-fluoren-9-yl)-8-isopropyl-7-methyl-3,6-dioxo-2,
11-dioxa-4,7-diazatridecan-10-yl)thiazole-4-carbox-
amido)-2-methyl-5-phenylpentanoate (31)

TuvOEt-Tup intermediate 28 (160 mg, 265 µmol) was coupled to Fmoc-L-Ile as described above to provide 133 mg (99%) of the title compound. UPLC-MS (system 2): $t_r$=1.95 min, m/z (ES+) calculated 851.44 (M+H)$^+$, found 851.54.

(2S,4R)-allyl 4-(2-((5S,8R,10R)-5-((S)-sec-butyl)-1-
(9H-fluoren-9-yl)-8-isopropyl-7-methyl-3,6-dioxo-2,
11-dioxa-4,7-diazatetradecan-10-yl)thiazole-4-car-
boxamido)-2-methyl-5-phenylpentanoate (32)

TuvOPr-Tup intermediate 29 (7 mg, 13 µmol) was coupled to Fmoc-L-Ile as described above to provide 9 mg (82%) of the title compound. UPLC-MS (system 2): $t_r$=2.25 min, m/z (ES+) calculated 865.46 (M+H)$^+$, found 865.65.

General Procedure for the Fmoc-Deprotection of Isoleucine-O-Alkylated Tubuvaline-Tubuphenylalanine Tripeptides.

Fmoc-Ile-Tuv(O-ether)-Tup allyl ester (30-32) was treated with 20% piperidine in dimethylformamide (20 mM), with stirring under nitrogen at room temperature. Once complete deprotection had been achieved, as monitored by UPLC/MS, the reaction mixture was concentrated by rotary evaporation. The crude product was then purified by preparative HPLC to provide free amine tripeptides 33-35.

(2S,4R)-allyl 4-(2-((1R,3R)-3-((2S,3S)-2-amino-N,
3-dimethyl-pentanamido)-1-methoxy-4-methylpen-
tyl)thiazole-4-carboxamido)-2-methyl-5-phenylpen-
tanoate (33)

Fmoc-Ile-TuvOMe-Tup intermediate 30 (67 mg, 80 µmol) was deprotected as described above to provide 30 mg (61%)

of the title compound. UPLC-MS (system 1): $t_r$=1.30 min, m/z (ES+) calculated 637.34 (M+Na)$^+$, found 637.57.

(2S,4R)-allyl 4-(2-((1R,3R)-3-((2S,3S)-2-amino-N,3-dimethyl-pentanamido)-1-ethoxy-4-methylpentyl)thiazole-4-carboxamido)-2-methyl-5-phenylpentanoate (34)

Fmoc-Ile-TuvOEt-Tup intermediate 31 (67 mg, 80 μmol) was deprotected as described above to provide 30 mg (61%) of the title compound. UPLC-MS (system 2): $t_r$=1.18 min, m/z (ES+) calculated 629.38 (M+H)$^+$, found 629.45.

(2S,4R)-allyl 4-(2-((1R,3R)-3-((2S,3S)-2-amino-N,3-dimethyl-pentanamido)-4-methyl-1-propoxypentyl)thiazole-4-carboxamido)-2-methyl-5-phenylpentanoate (35)

Fmoc-Ile-TuvOPr-Tup intermediate 32 (9 mg, 10 μmol) was deprotected as described above to provide 7 mg (quant.) of the title compound. UPLC-MS (system 2): $t_r$=1.29 min, m/z (ES+) calculated 643.39 (M+H)$^+$, found 643.55.

General procedure for the amide coupling of isoleucine-tubuvaline(ether)-tubuphenylalanine tripeptides with (R)—N-methyl-pipecolic acid.

Commercially available (R)—N-methyl-pipecolic acid (D-Mep) 36 (1.5-2 equivalents) was dissolved in anhydrous dimethylformamide (25-50 mM) and pre-activated with HATU (2 equivalents) and DIPEA (4 equivalents); the mixture was stirred for 10 minutes at room temperature under nitrogen. The activated acid was then added to the Ile-Tuv(O-ether)-Tup tripeptides 33-35; the reaction was stirred at room temperature under nitrogen and monitored by UPLC/MS. Upon reaction completion, glacial acetic acid (14 equivalents) was then added and the product was purified by preparative HPLC.

(2S,4R)-allyl 4-(2-((1R,3R)-3-((2S,3S)—N,3-dimethyl-2-((R)-1-methylpiperidine-2-carboxamido)pentanamido)-1-methoxy-4-methylpentyl)thiazole-4-carboxamido)-2-methyl-5-phenylpentanoate (37)

Ile-TuvOMe-Tup intermediate 33 (20 mg, 33 μmol) was coupled to D-Mep 36 as described above to provide 17 mg (71%) of the title compound. UPLC-MS (system 1): $t_r$=1.29 min, m/z (ES+) calculated 762.42 (M+Na)$^+$, found 762.32.

(2S,4R)-allyl 4-(2-((1R,3R)-3-((2S,3S)—N,3-dimethyl-2-((R)-1-methylpiperidine-2-carboxamido)pentanamido)-1-ethoxy-4-methylpentyl)thiazole-4-carboxamido)-2-methyl-5-phenylpentanoate (38)

Ile-TuvOEt-Tup intermediate 34 (20 mg, 33 μmol) was coupled to D-Mep 36 as described above to provide 17 mg (71%) of the title compound. UPLC-MS (system 2): $t_r$=1.25 min, m/z (ES+) calculated 754.46 (M+H)$^+$, found 754.55.

(2S,4R)-allyl 4-(2-((1R,3R)-3-((2S,3S)—N,3-dimethyl-2-((R)-1-methylpiperidine-2-carboxamido)pentanamido)-4-methyl-1-propoxypentyl)thiazole-4-carboxamido)-2-methyl-5-phenylpentanoate (39)

Ile-TuvOPr-Tup intermediate 35 (7 mg, 11 μmol) was coupled to D-Mep 36 as described above to provide 4.5 mg (53%) of the title compound. UPLC-MS (system 2): $t_r$=1.36 min, m/z (ES+) calculated 768.48 (M+H)$^+$, found 768.55.

General Procedure for the Allyl Ester Removal from D-Methylpipecolic Acid-Isoleucine-Tubuvaline(Ether)-Tubuphenylalanine Tubulysin Intermediates.

Allyl ester-protected tubulysin ether intermediate (37-39) was dissolved in anhydrous dichloromethane (20 mM) treated with palladium tetrakis(triphenylphosphine) (0.1 equiv.), triphenylphosphine (0.2 equivalents), and anhydrous pyrrolidine (8 equivalents), and the reaction was stirred at an ambient temperature under nitrogen. Once UPLC/MS revealed conversion to the product free acid, the reaction was quenched with glacial acetic acid (22 equivalents), diluted with acetonitrile and dimethylformamide, and then concentrated by rotary evaporation. The crude tubulysin ether was then purified by preparative HPLC.

(2S,4R)-4-(2-((1R,3R)-3-((2S,3S)—N,3-dimethyl-2-((R)-1-methylpiperidine-2-carboxamido)pentanamido)-1-methoxy-4-methylpentyl)thiazole-4-carboxamido)-2-methyl-5-phenylpentanoic Acid (40)

Allyl ester-protected tubulysin methyl ether (TubOMe) intermediate 37 (2.9 mg, 4 μmol) was deprotected as described above to provide 2.5 mg (93%) of tubulysin methyl ether 40 (TubOMe). UPLC-MS (system 2): $t_r$=1.05 min, m/z (ES+) calculated 700.41 (M+H)$^+$, found 700.50.

(2S,4R)-4-(2-((1R,3R)-3-((2S,3S)—N,3-dimethyl-2-((R)-1-methylpiperidine-2-carboxamido)pentanamido)-1-ethoxy-4-methylpentyl)thiazole-4-carboxamido)-2-methyl-5-phenylpentanoic Acid (41)

Allyl ester-protected tubulysin ethyl ether (TubOEt) intermediate 38 (2.9 mg, 4 μmol) was deprotected as described above to provide 2.5 mg (93%) of tubulysin ethyl ether 41 (TubOEt). UPLC-MS (system 2): $t_r$=1.09 min, m/z (ES+) calculated 714.43 (M+H)$^+$, found 714.51.

(2S,4R)-4-(2-((1R,3R)-3-((2S,3S)—N,3-dimethyl-2-((R)-1-methylpiperidine-2-carboxamido)pentanamido)-4-methyl-1-propoxypentyl)thiazole-4-carboxamido)-2-methyl-5-phenylpentanoic Acid (42)

Allyl ester-protected tubulysin propyl ether (TubOPr) intermediate 39 (6 mg, 8 μmol) was deprotected as described above to provide 6 mg (quant.) of tubulysin propyl ether 42 (TubOPr). UPLC-MS (system 2): $t_r$=1.19 min, m/z (ES+) calculated 728.44 (M+H)$^+$, found 728.54.

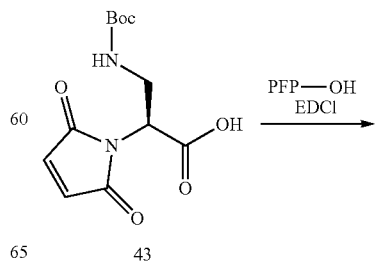

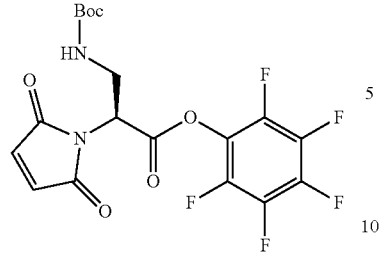

44

(S)-perfluorophenyl 3-((tert-butoxycarbonyl)amino)-2-(2,5-dioxo-2,5-dihydro-1H-pyrrol-1-yl)propanoate (44)

A flask charged with mDPR(Boc)-OH (*Nature Biotech*, 2014, 32, 1059-1062) 43 (500 mg, 1.76 mmol), to which PFP-OH (324 mg, 1.76 mmol) was added a solution in DMF (8.8 mL) followed by 1-Ethyl-3-(3-dimethylaminopropyl) carbodiimide (371 mg, 1.93 mmol) as a solid. The reaction was stirred for 1 hour at room temperature then quenched with 50 mL saturated $NH_4Cl$ in $H_2O$ and 50 mL $H_2O$. The aqueous layer was extracted with DCM twice, the organics were then washed with brine, dried over $NaSO_4$, and condensed under reduced pressure to provide 44 (589 mg, 74%). Analytical UPLC-MS (system 2): $t_r$=1.51 min, m/z (ES+) calculated 473.07 $(M+Na)^+$, found 473.14.

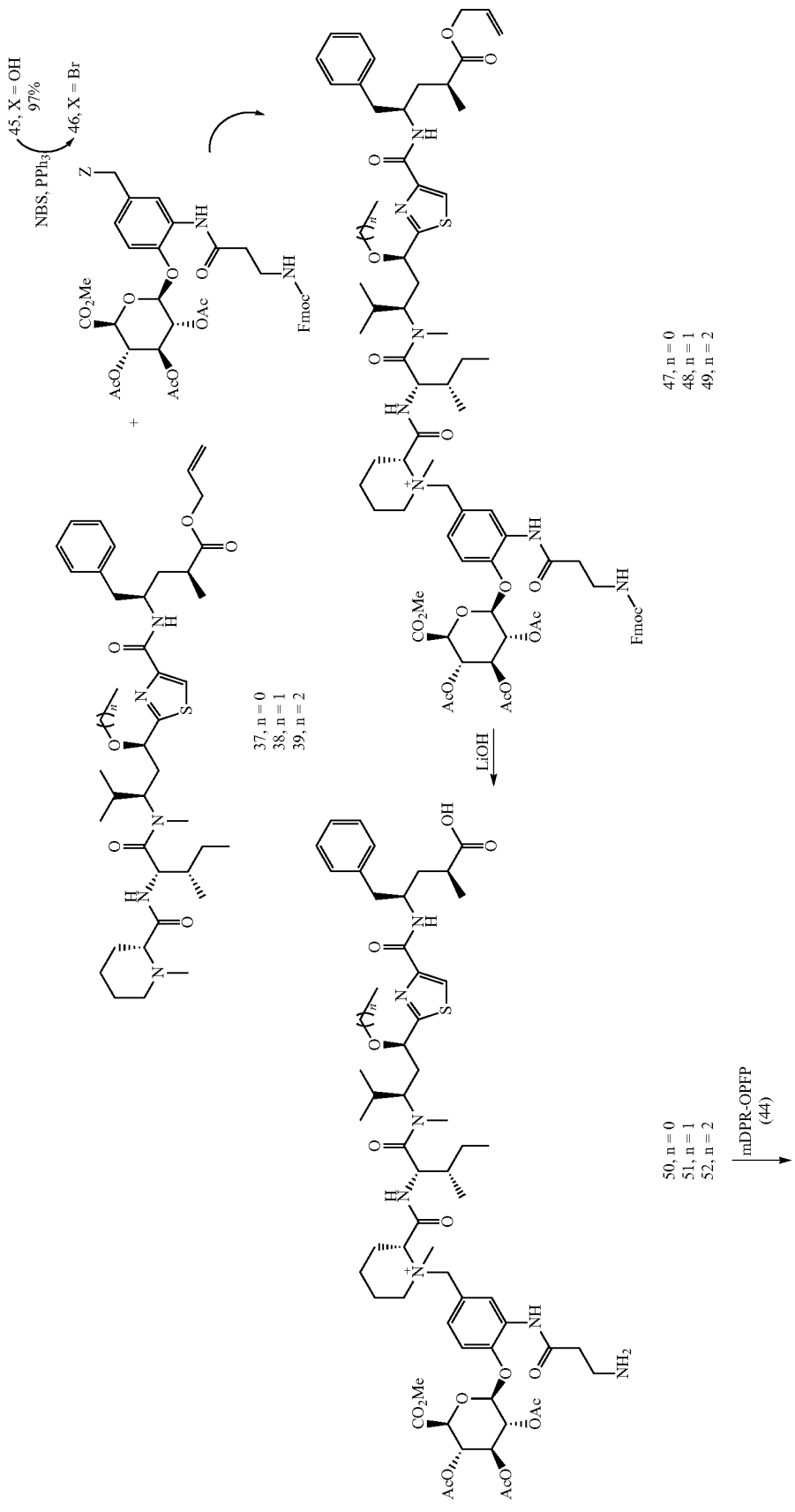

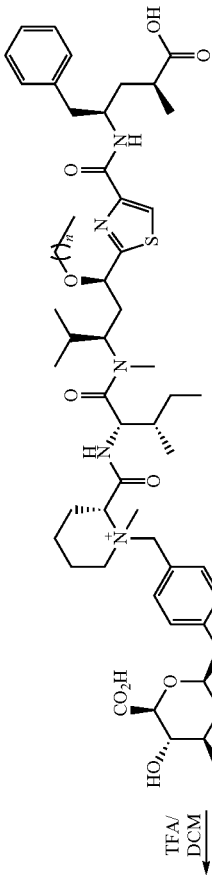
56, n = 0
57, n = 1
58, n = 2
TFA/ DCM
-continued
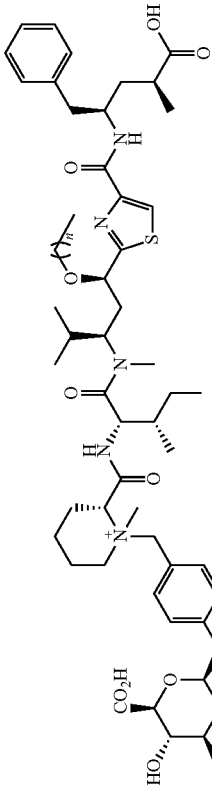
53, n = 0
54, n = 1
55, n = 2

(2S,3R,4S,5S,6S)-2-(2-(3-((((9H-fluoren-9-yl)methoxy)carbonyl)amino)propanamido)-4-(bromomethyl)phenoxy)-6-(methoxycarbonyl)tetrahydro-2H-pyran-3,4,5-triyl Triacetate (46)

A flame dried flask was charged with known (*Bioconjugate Chem.* 2006, 17, 831-840) glucuronide linker fragment (45, 210 mg, 281 µmol) in 4.5 mL anhydrous THF. The solution was stirred at room temperature under $N_2$. Triphenylphosphine (111 mg, 421.5 µmol) and N-bromosuccinimide (75 mg, 421.5 µmol) were added sequentially and the solution was stirred for 2 hours. The reaction was condensed under reduced pressure and purified over silica via a Biotage column (Hexanes/EtOAc, 30%-50%-70%) to provide 46 (222 mg, 97%). Analytical UPLC-MS (system 1): $t_r$=2.36 min, m/z (ES+) found 811.34.

General Procedure for Quaternization of Tub(OR)-OAllyl to Fmoc-Gluc-Br:

A pressure vessel was charged with Tub(OR)-OAllyl (37-39, 1 equivalent) and brominated glucuronide linker fragment (46, 1.5 equivalents) in anhydrous 2-butanone (50 mM). The reaction vessel was flushed with $N_2$ and sealed. The reaction was then stirred and heated to 60° C. for 18 hours. The resulting mixture was cooled, condensed to residue under reduced pressure, then carried forward crude or taken up in minimal DMSO to be purified by preparative HPLC.

(2R)-1-(3-(3-(((((9H-fluoren-9-yl)methoxy)carbonyl)amino)propanamido)-4-(((2S,3R,4S,5S,6S)-3,4,5-triacetoxy-6-(methoxycarbonyl)tetrahydro-2H-pyran-2-yl)oxy)benzyl)-2-(((2S,3S)-1-(((1R,3R)-1-(4-(((2R,4S)-5-(allyloxy)-4-methyl-5-oxo-1-phenylpentan-2-yl)carbamoyl)thiazol-2-yl)-1-methoxy-4-methylpentan-3-yl)(methyl)amino)-3-methyl-1-oxopentan-2-yl)carbamoyl)-1-methylpiperidin-1-ium (47)

Tub(OMe)-OAllyl 37 (13 mg, 18 µmol) was quaternized as above with Gluc-Br 46 (17 mg, 28 µmol) to be carried forward without further purification. Analytical UPLC-MS (system 1): $t_r$=1.61 min, m/z (ES+) calculated 1470.68 (M)$^+$, found 1471.68.

(2R)-1-(3-(3-(((((9H-fluoren-9-yl)methoxy)carbonyl)amino)propanamido)-4-(((2S,3R,4S,5S,6S)-3,4,5-triacetoxy-6-(methoxycarbonyl)tetrahydro-2H-pyran-2-yl)oxy)benzyl)-2-(((2S,3S)-1-(((1R,3R)-1-(4-(((2R,4S)-5-(allyloxy)-4-methyl-5-oxo-1-phenylpentan-2-yl)carbamoyl)thiazol-2-yl)-1-ethoxy-4-methylpentan-3-yl)(methyl)amino)-3-methyl-1-oxopentan-2-yl)carbamoyl)-1-methylpiperidin-1-ium (48)

Tub(OEt)-OAllyl 38 (148 mg, 196 µmol) was quaternized as above with Gluc-Br 46 (175 mg, 216 µmol) to be carried forward without further purification. Analytical UPLC-MS (system 2): $t_r$=1.49 min, m/z (ES+) calculated 1484.69 (M)$^+$, found 1484.84.

(2R)-1-(3-(3-(((((9H-fluoren-9-yl)methoxy)carbonyl)amino)propanamido)-4-(((2S,3R,4S,5S,6S)-3,4,5-triacetoxy-6-(methoxycarbonyl)tetrahydro-2H-pyran-2-yl)oxy)benzyl)-2-(((2S,3S)-1-(((1R,3R)-1-(4-(((2R,4S)-5-(allyloxy)-4-methyl-5-oxo-1-phenylpentan-2-yl)carbamoyl)thiazol-2-yl)-4-methyl-1-propoxypentan-3-yl)(methyl)amino)-3-methyl-1-oxopentan-2-yl)carbamoyl)-1-methylpiperidin-1-ium (49)

Tub(OPr)-OAllyl 39 (43 mg, 56 µmol) was quaternized as above with Gluc-Br 46 (50 mg, 62 µmol) to provide 49 (68%) after preparative LC. Analytical UPLC-MS (system 2): $t_r$=1.47 min, m/z (ES+) calculated 1498.71 (M)$^+$, found 1498.85.

General Procedure for Global Deprotection of Fmoc-GlucQ-Tub(OR)-OAllyl:

A flask was charged with Fmoc-GlucQ-Tub(OR)-OAllyl (47-49) in THF and MeOH and cooled to 0° C. LiOH.$H_2O$ (6.0 equivalents) in $H_2O$ was added dropwise (1:1:1 THF:MeOH:$H_2O$, 50 mM end concentration) and the reaction was allowed to warm to room temperature and stir overnight. THF and MeOH were removed under reduced pressure, the resulting precipitate was resolubilized using minimal DMSO and the mixture was purified by preparative HPLC.

(2R)-1-(3-(3-aminopropanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-methoxy-4-methylpentan-3-yl)(methyl)amino)-3-methyl-1-oxopentan-2-yl)carbamoyl)-1-methylpiperidin-1-ium (50)

Fmoc-GlucQ-Tub(OMe)-OAllyl 47 (17 mg, 12 µmol) was deprotected as above to provide 50 (4.3 mg, 34%). Analytical UPLC-MS (system 1): $t_r$=1.08 min, m/z (ES+) calculated 1068.53 (M)$^+$, found 1068.66.

(2R)-1-(3-(3-aminopropanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-ethoxy-4-methylpentan-3-yl)(methyl)amino)-3-methyl-1-oxopentan-2-yl)carbamoyl)-1-methylpiperidin-1-ium (51)

Fmoc-GlucQ-Tub(OEt)-OAllyl 48 (292 mg, 197 µmol) was deprotected as above to provide 51 (116 mg, 54%). Analytical UPLC-MS (system 2): $t_r$=0.95 min, m/z (ES+) calculated 1082.55 (M)$^+$, found 1082.68.

(2R)-1-(3-(3-aminopropanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-4-methyl-1-propoxypentan-3-yl)(methyl)amino)-3-methyl-1-oxopentan-2-yl)carbamoyl)-1-methylpiperidin-1-ium (52)

Fmoc-GlucQ-Tub(OPr)-OAllyl 49 (57 mg, 38 µmol) was deprotected as above to provide 52 (34 mg, 41%). Analytical UPLC-MS (system 2): $t_r$=0.98 min, m/z (ES+) calculated 1096.56 (M)$^+$, found 1096.67.

General Procedure for Coupling of H-GlucQ-Tub(OR) to mDPR-OPFP:

A flask was charged with H-Gluc-Tub(OR) (50-52) to which mDPR(Boc)-OPFP (44, 1.2 equivalents) was added as a solution in DMF (10 mM). N,N-Diisopropylethylamine (4.0 equivalents) was added and the reaction was stirred at room temperature for 3 hours. The reaction was quenched with AcOH (4.0 equivalents) then diluted in DMSO (1 volume) and purified by preparative HPLC.

(2R)-1-(3-(3-((S)-3-((tert-butoxycarbonyl)amino)-2-(2,5-dioxo-2,5-dihydro-1H-pyrrol-1-yl)propanamido)propanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-methoxy-4-methylpentan-3-yl)(methyl)amino)-3-methyl-1-oxopentan-2-yl)carbamoyl)-1-methylpiperidin-1-ium (53)

H-GlucQ-Tub(OMe) 50 (4.3 mg, 4 μmol) was coupled to mDPR-OPFP 44 (2.2 mg, 4.8 μmol) as above to provide 53 (4 mg, 75%). Analytical UPLC-MS (system 1): $t_r$=1.22 min, m/z (ES+) calculated 1334.62 (M)$^+$, found 1334.68.

(2R)-1-(3-(3-((S)-3-((tert-butoxycarbonyl)amino)-2-(2,5-dioxo-2,5-dihydro-1H-pyrrol-1-yl)propanamido)propanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-ethoxy-4-methylpentan-3-yl)(methyl)amino)-3-methyl-1-oxopentan-2-yl)carbamoyl)-1-methylpiperidin-1-ium (54)

H-GlucQ-Tub(OEt) 51 (29 mg, 27 μmol) was coupled to mDPR-OPFP 44 (14 mg, 32 μmol) as above to provide 54 (26 mg, 72%). Analytical UPLC-MS (system 2): $t_r$=1.19 min, m/z (ES+) calculated 1348.64 (M)$^+$, found 1348.79.

(2R)-1-(3-(3-((S)-3-((tert-butoxycarbonyl)amino)-2-(2,5-dioxo-2,5-dihydro-1H-pyrrol-1-yl)propanamido)propanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-4-methyl-1-propoxypentan-3-yl)(methyl)amino)-3-methyl-1-oxopentan-2-yl)carbamoyl)-1-methylpiperidin-1-ium (55)

H-GlucQ-Tub(OPr) 52 (6 mg, 5 μmol) was coupled to mDPR-OPFP 44 (3 mg, 6 μmol) as above to provide 55 (6 mg, 84%). Analytical UPLC-MS (system 2): $t_r$=1.24 min, m/z (ES+) calculated 1362.65 (M)$^+$, found 1362.78.

General Procedure for Deprotection of mDPR(Boc)-GlucQ-Tub(OR):

A flask was charged with mDPR(Boc)-GlucQ-Tub(OR) (53-55) and cooled to 0° C. A 10% solution of TFA in DCM (50 mM) was added and the reaction was allowed to warm to room temperature while stirring for 1 hour. The reaction was then diluted with DMSO (1 volume), DCM removed via reduced pressure, then purified by preparative HPLC.

(2R)-1-(3-(3-((S)-3-amino-2-(2,5-dioxo-2,5-dihydro-1H-pyrrol-1-yl)propanamido)propanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-methoxy-4-methylpentan-3-yl)(methyl)amino)-3-methyl-1-oxopentan-2-yl)carbamoyl)-1-methylpiperidin-1-ium (56)

mDPR(Boc)-GlucQ-Tub(OMe) 53 (4 mg, 3 μmol) was deprotected as above to provide 56 (2 mg, 54%). Analytical UPLC-MS (system 2): $t_r$=1.09 min, m/z (ES+) calculated 1234.57 (M)$^+$, found 1234.65.

(2R)-1-(3-(3-((S)-3-amino-2-(2,5-dioxo-2,5-dihydro-1H-pyrrol-1-yl)propanamido)propanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-ethoxy-4-methylpentan-3-yl)(methyl)amino)-3-methyl-1-oxopentan-2-yl)carbamoyl)-1-methylpiperidin-1-ium (57)

mDPR(Boc)-GlucQ-Tub(OEt) 54 (26 mg, 19 μmol) was deprotected as above to provide 57 (24 mg, 99%). Analytical UPLC-MS (system 2): $t_r$=0.95 min, m/z (ES+) calculated 1248.59 (M)$^+$, found 1248.72.

(2R)-1-(3-(3-((S)-3-amino-2-(2,5-dioxo-2,5-dihydro-1H-pyrrol-1-yl)propanamido)propanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-4-methyl-1-propoxypentan-3-yl)(methyl)amino)-3-methyl-1-oxopentan-2-yl)carbamoyl)-1-methylpiperidin-1-ium (58)

mDPR(Boc)-GlucQ-Tub(OPr) 55 (6 mg, 4 μmol) was deprotected as above to provide 58 (4 mg, 75%). Analytical UPLC-MS (system 2): $t_r$=1.03 min, m/z (ES+) calculated 1262.60 (M)$^+$, found 1262.73.

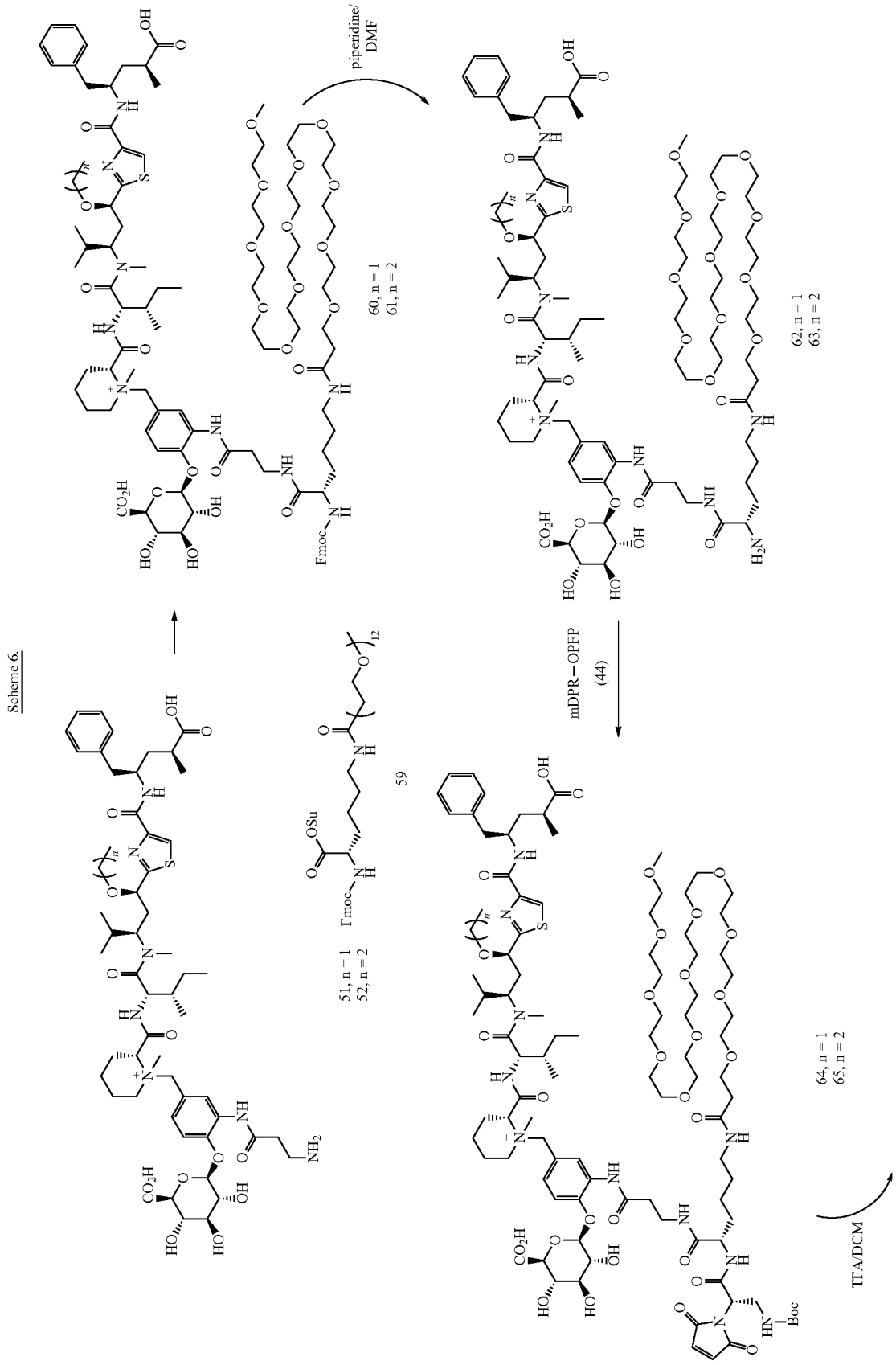

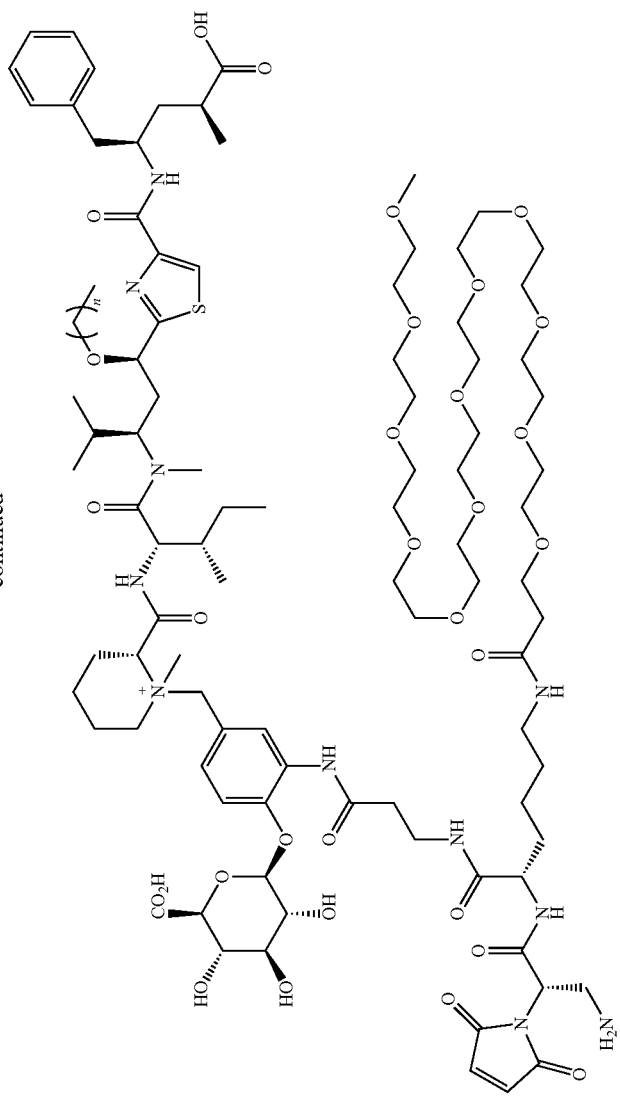
66, n = 1
67, n = 2

General Procedure for Coupling of H-GlucQ-Tub(OR) to Fmoc-Lys(PEG12)-OSu:

A was flask charged with H-GlucQ-Tub(OR) (51 or 52), to which Fmoc-Lys(PEG12)-OSu (WO 2015057699) (1.2 equivalents) was added a solution in DMF (20 mM) followed by N,N-Diisopropylethylamine (4.0 equivalents). The reaction was stirred at room temperature for 4 hours then quenched with AcOH (4.0 equivalents), diluted in DMSO (1 volume) and purified by preparative HPLC.

(2R)-1-(3-((S)-44-(((((9H-fluoren-9-yl)methoxy)carbonyl)amino)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-ethoxy-4-methylpentan-3-yl)(methyl)amino)-3-methyl-1-oxopentan-2-yl)carbamoyl)-1-methylpiperidin-1-ium (60)

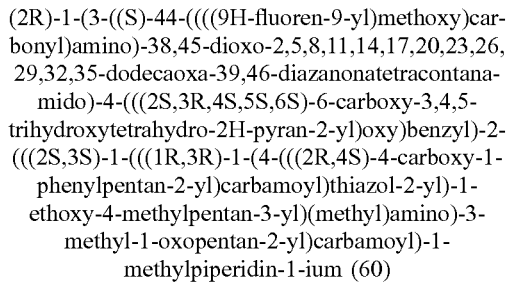

H-GlucQ-Tub(OEt) 51 (87 mg, 80 μmol) was coupled to Fmoc-Lys(PEG12)-OSu 59 (100 mg, 96 μmol) as above to provide 60 (108 mg, 67%). Analytical UPLC-MS (system 2): $t_r$=1.29 min, m/z (ES+) calculated 2003.04 $(M)^+$, found 2003.24.

(2R)-1-(3-((S)-44-(((((9H-fluoren-9-yl)methoxy)carbonyl)amino)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-4-methyl-1-propoxypentan-3-yl)(methyl)amino)-3-methyl-1-oxopentan-2-yl)carbamoyl)-1-methylpiperidin-1-ium (61)

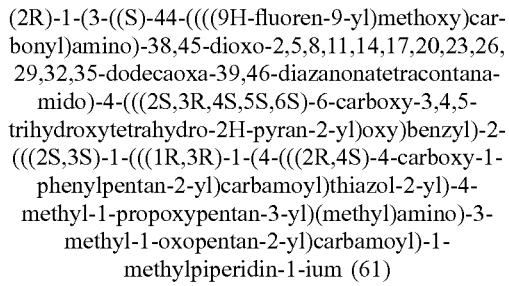

H-GlucQ-Tub(OPr) 52 (20 mg, 18 μmol) was coupled to Fmoc-Lys(PEG12)-OSu 59 (23 mg, 22 μmol) as above to provide 61 (27 mg, 73%). Analytical UPLC-MS (system 2): $t_r$=1.31 min, m/z (ES+) calculated 2017.05 $(M)^+$, found 2017.22.

General Procedure Deprotection of Fmoc-Lys(PEG12)-GlucQ-Tub(OR):

A flask was charged with Fmoc-Lys(PEG12)-GlucQ-Tub(OR) (60 or 61), to which a 20% solution of piperidine in DMF (20 mM) was added. The reaction was stirred for 30 minutes then diluted in DMSO (1 volume) and purified by preparative HPLC.

(2R)-1-(3-((S)-44-amino-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-ethoxy-4-methylpentan-3-yl)(methyl)amino)-3-methyl-1-oxopentan-2-yl)carbamoyl)-1-methylpiperidin-1-ium (62)

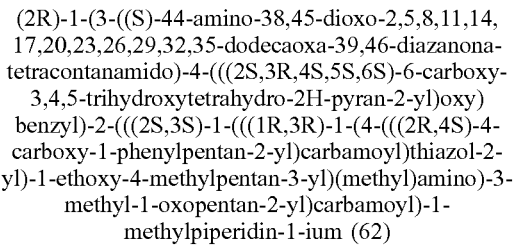

Fmoc-Lys(PEG12)-GlucQ-Tub(OEt) 60 (108 mg, 54 μmol) was deprotected as above to provide 62 (83 mg, 86%). Analytical UPLC-MS (system 2): $t_r$=0.99 min, m/z (ES+) calculated 1780.97 $(M)^+$, found 1781.14.

(2R)-1-(3-((S)-44-amino-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-4-methyl-1-propoxypentan-3-yl)(methyl)amino)-3-methyl-1-oxopentan-2-yl)carbamoyl)-1-methylpiperidin-1-ium (63)

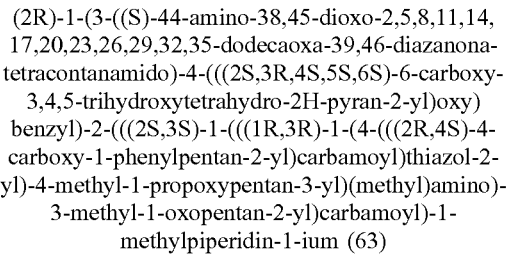

Fmoc-Lys(PEG12)-GlucQ-Tub(OPr) 61 (27 mg, 13 μmol) was deprotected as above to provide 63 (17 mg, 71%). Analytical UPLC-MS (system 2): $t_r$=1.03 min, m/z (ES+) calculated 1794.98 $(M)^+$, found 1795.14.

General Procedure for Coupling H-Lys(PEG12)-GlucQ-Tub(OR) to mDPR-OPFP:

A flask was charged with H-Lys(PEG12)-GlucQ-Tub(OR) (62 or 63), to which mDPR-OPFP (44, 1.2 equivalents) was added as a solution in DMF (10 mM) followed by N,N-Diisopropylethylamine (4.0 equivalents). The reaction was stirred at room temperature for 4 hours then quenched with AcOH (4.0 equivalents), diluted in DMSO (1 volume) and purified by preparative HPLC.

(2R)-1-(3-((S)-44-((S)-3-((tert-butoxycarbonyl)amino)-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-ethoxy-4-methylpentan-3-yl)(methyl)amino)-3-methyl-1-oxopentan-2-yl)carbamoyl)-1-methylpiperidin-1-ium (64)

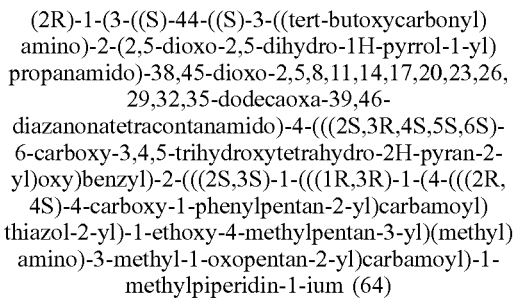

H-Lys(PEG12)-GlucQ-Tub(OEt) (83 mg, 46 μmol) was coupled to mDPR-OPFP 44 (25 mg, 56 μmol) as above to provide 64 (43 mg, 45%). Analytical UPLC-MS (system 2): $t_r$=1.22 min, m/z (ES+) calculated 2047.06 $(M)^+$, found 2047.25.

(2R)-1-(3-((S)-44-((S)-3-((tert-butoxycarbonyl)amino)-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-4-methyl-1-propoxypentan-3-yl)(methyl)amino)-3-methyl-1-oxopentan-2-yl)carbamoyl)-1-methylpiperidin-1-ium (65)

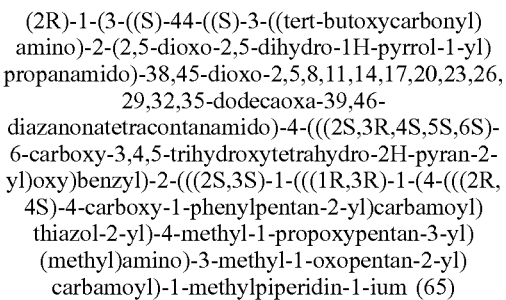

H-Lys(PEG12)-GlucQ-Tub(OPr) (17 mg, 9 μmol) was coupled to mDPR-OPFP 44 (5 mg, 11 μmol) as above to provide 65 (14 mg, 74%). Analytical UPLC-MS (system 2): $t_r$=1.22 min, m/z (ES+) calculated 2061.07 $(M)^+$, found 2061.26.

General procedure for deprotection of mDPR(Boc)-Lys(PEG12)-GlucQ-Tub(OR):

A flask was charged with mDPR(Boc)-Lys(PEG12)-GlucQ-Tub(OR) (64 or 65) and cooled to 0° C. A 10% solution of TFA in DCM (50 mM) was added and the reaction was allowed to warm to room temperature while stirring for 1 hour. The reaction was then diluted with DMSO (1 volume), DCM removed via reduced pressure, then purified by preparative HPLC.

(2R)-1-(3-((S)-44-((S)-3-amino-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-ethoxy-4-methylpentan-3-yl)(methyl)amino)-3-methyl-1-oxopentan-2-yl)carbamoyl)-1-methylpiperidin-1-ium (66)

mDPR(Boc)-Lys(PEG12)-GlucQ-Tub(OEt) 64 (43 mg, 21 µmol) was deprotected as above to provide 66 (34 mg, 83%). Analytical UPLC-MS (system 2): $t_r$=0.96 min, m/z (ES+) calculated 1947.01 (M)$^+$, found 1947.22.

(2R)-1-(3-((S)-44-((S)-3-amino-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-4-methyl-1-propoxypentan-3-yl)(methyl)amino)-3-methyl-1-oxopentan-2-yl)carbamoyl)-1-methylpiperidin-1-ium (67)

mDPR(Boc)-Lys(PEG12)-GlucQ-Tub(OPr) 65 (14 mg, 7 µmol) was deprotected as above to provide 67 (12 mg, 92%). Analytical UPLC-MS (system 2): $t_r$=1.05 min, m/z (ES+) calculated 1961.02 (M)$^+$, found 1961.20.

(2S,4R)-4-(2-((1R,3R)-3-((tert-butoxycarbonyl)(methyl)amino)-1-hydroxy-4-methylpentyl)thiazole-4-carboxamido)-2-methyl-5-phenylpentanoic Acid (69)

A flask was charged with commercially available Boc-Tuv(OAc)-Tup-OEt (68, 50 mg, 81 µmol) in THF (1.35 mL) and MeOH (1.35 mL) and cooled to 0° C. LiOH.H$_2$O (27 mg, 647 µmol) was solubilized in H$_2$O (1.35 mL) then added dropwise. The reaction was allowed to warm to room temperature and stirred for 3 hours. The reaction was then quenched with acetic acid (37 µL, 647 µmol) and condensed under reduced pressure. The residue was taken up in minimal DMSO and purified by preparative HPLC to provide 69 (44 mg, quant.). Analytical UPLC-MS (system 2): $t_r$=1.53 min, m/z (ES+) calculated 548.28 (M+H)$^+$, found 548.24.

(2S,4R)-allyl 4-(2-((1R,3R)-1-acetoxy-3-((tert-butoxycarbonyl)(methyl)amino)-4-methylpentyl)thiazole-4-carboxamido)-2-methyl-5-phenylpentanoate (70)

Boc-Tuv(OH)-Tup-OH (69, 44 mg, 81 µmol) was solubilized in anhydrous pyridine (1.6 mL) and stirred at room temperature under N$_2$. Acetic anhydride (15.4 µL, 162 µmol) was added dropwise. 1.0 additional equivalent of acetic anhydride was added after one hour of stirring and the reaction was complete by LCMS after 2 hours. The reaction was concentrated to dryness under reduced pressure then resolubilized in anhydrous allyl alcohol (1.6 mL). Diallyl pyrocarbonate (54 µL, 325 µmol) was added followed by solid DMAP (3.0 mg, 24 µmol). The reaction was allowed to stir at room temperature and monitored by LCMS, additional diallyl pyrocarbonate added as needed to push reac- Scheme 7.

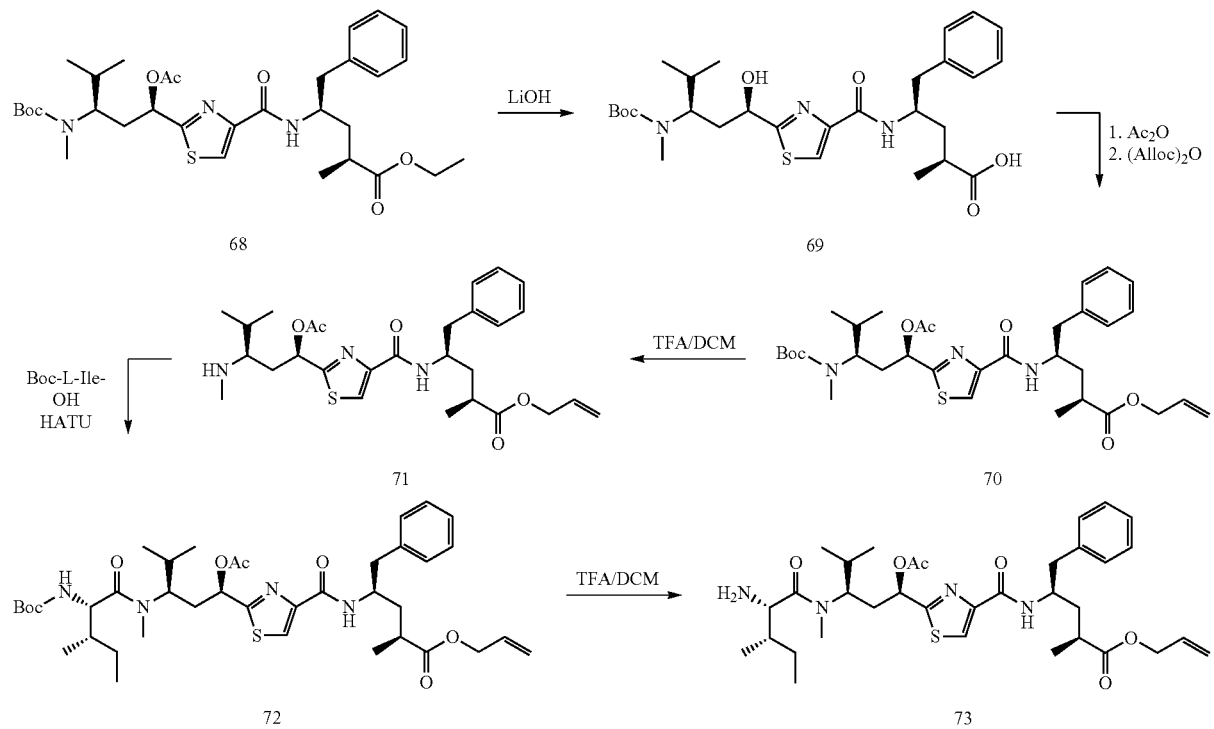

tion to completion (4.0 additional equivalents). The reaction was then taken up in DMSO, condensed under reduced pressure, and purified by preparative HPLC to provide 70 (33 mg, 65%). Analytical UPLC-MS (system 2): $t_r$=1.75 min, m/z (ES+) calculated 630.32 (M+H)$^+$, found 630.42.

(2S,4R)-allyl 4-(2-((1R,3R)-1-acetoxy-4-methyl-3-(methylamino)pentyl)thiazole-4-carboxamido)-2-methyl-5-phenylpentanoate (71)

A flask charged with Boc-Tuv(OAc)-Tup-OEt (70, 33 mg, 21 µmol) was cooled to 0° C. under N$_2$. A solution of 10% TFA in CH$_2$Cl$_2$ (0.52 mL) was added dropwise and stirred for 4 hours. The reaction was concentrated under reduced pressure, resolubilized in DCM, and condensed 3 times to remove TFA then carried forward without further purification. Analytical UPLC-MS (system 2): $t_r$=1.03 min, m/z (ES+) calculated 530.27 (M+H)$^+$, found 530.36.

(2S,4R)-allyl 4-(2-((6S,9R,11R)-6-((S)-sec-butyl)-9-isopropyl-2,2,8-trimethyl-4,7,13-trioxo-3,12-dioxa-5,8-diazatetradecan-11-yl)thiazole-4-carboxamido)-2-methyl-5-phenylpentanoate (72)

To a flask charged with H-Tuv(OAc)-Tup-OAllyl (71, 28 mg, 53 µmol) was added Boc-L-Ile-OH (15 mg, 63 µmol) and HATU (40 mg, 106 µmol) as solids followed by DMF (1.0 mL). N,N-Diisopropylethylamine (37 µL, 211 µmol) was added and the reaction was stirred at room temperature for 48 hours. The reaction was then taken up in DMSO, condensed under reduced pressure, and purified by preparative HPLC to provide 72 (19 mg, 49%). Analytical UPLC-MS (system 2): $t_r$=1.72 min, m/z (ES+) calculated 743.41 (M+H)$^+$, found 743.51.

(2S,4R)-allyl 4-(2-((1R,3R)-1-acetoxy-3-((2S,3S)-2-amino-N,3-dimethylpentanamido)-4-methylpentyl)thiazole-4-carboxamido)-2-methyl-5-phenylpentanoate (73)

A flask charged with Boc-Ile-Tuv(OAc)-Tup-OEt (72, 19 mg, 26 mol) was cooled to 0° C. under N$_2$. A solution of 10% TFA in CH$_2$Cl$_2$ (0.52 mL) was added dropwise and stirred for 4 hours. The reaction was concentrated under reduced pressure, resolubilized in DCM, and condensed 3 times to remove TFA then carried forward without further purification. Analytical UPLC-MS (system 2): $t_r$=1.18 min, m/z (ES+) calculated 643.36 (M+H)+, found 643.42.

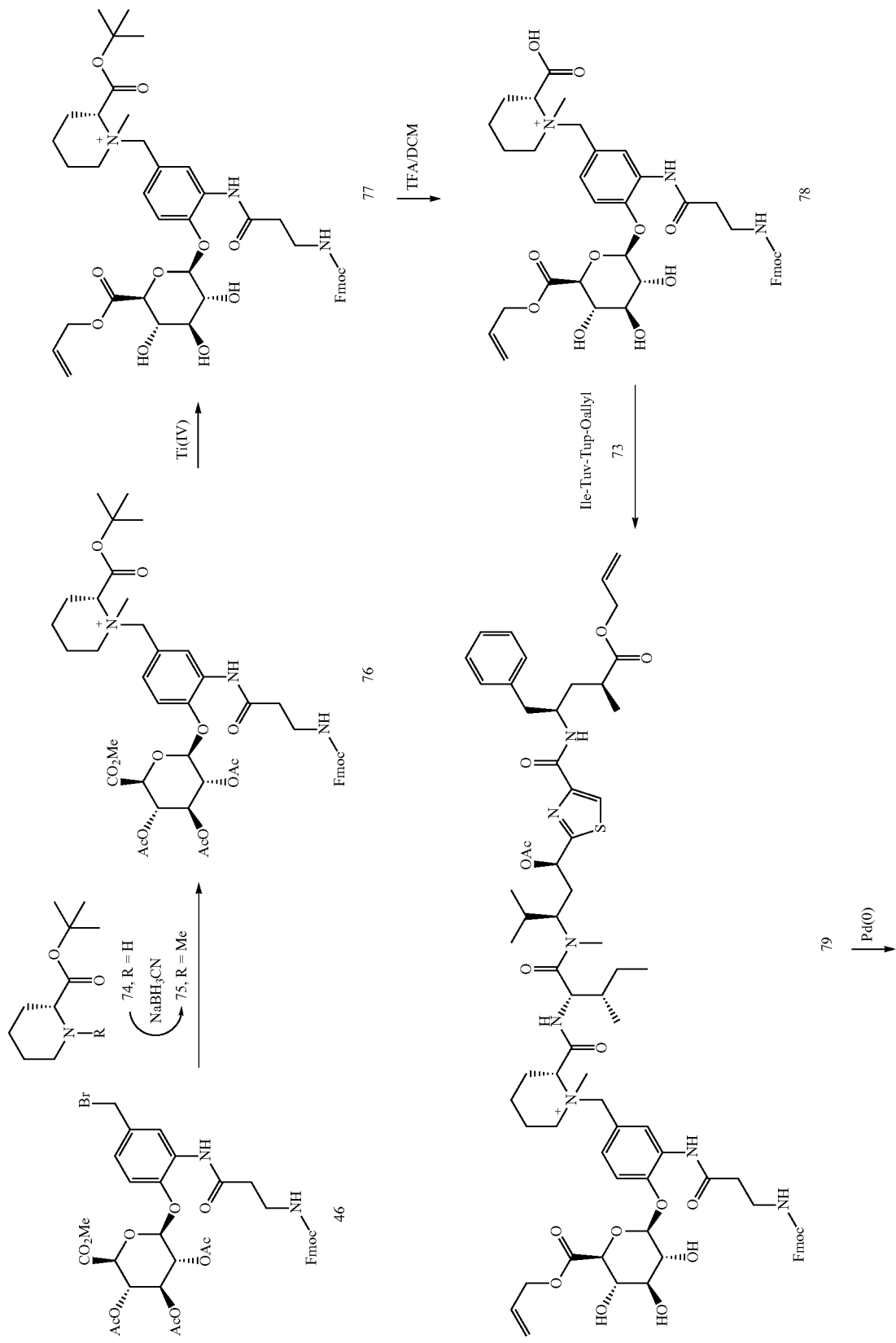

-continued
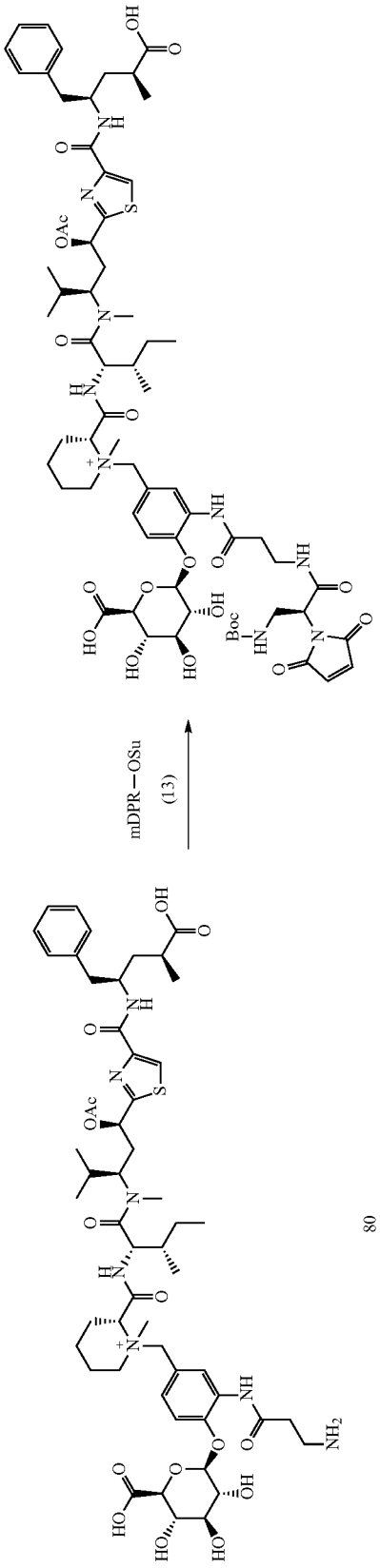
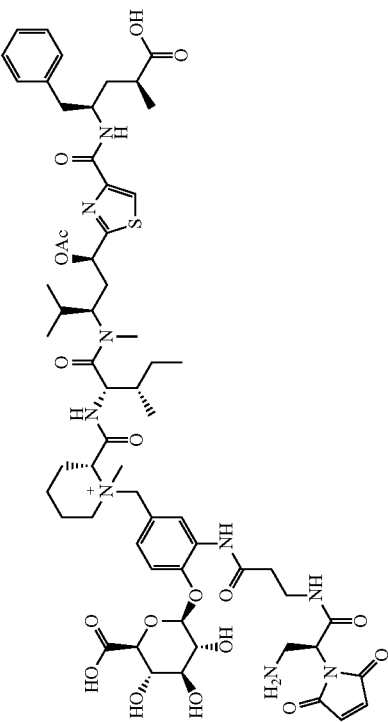

(R)-tert-butyl 1-methylpiperidine-2-carboxylate (75)

Commercially available H-Pip-OtBu (74, 500 mg, 2.70 mmol) was taken up in MeOH (4.50 mL), AcOH (4.50 mL) and 37% $CH_2O$ in $H_2O$ (4.50 mL) and stirred for 20 minutes. $NaBH_3CN$ (509 mg, 8.10 mmol) added slowly as a solid to vigorous bubbling, stir for 30 minutes. The reaction was then poured into 200 mL saturated $NaHCO_3$ solution and extracted 3× with 200 mL DCM. The organic layers were washed with brine, dried over $NaSO_4$, and condensed under reduced pressure to provide 75 (516 mg, 96%) to be carried forward without further purification. Analytical UPLC-MS (system 2): $t_r$=0.53 min, m/z (ES+) calculated 200.17 $(M+H)^+$, found 200.21.

(2R)-1-(3-(3-((((9H-fluoren-9-yl)methoxy)carbonyl)amino)propanamido)-4-(((2S,3R,4S,5S,6S)-3,4,5-triacetoxy-6-(methoxycarbonyl)tetrahydro-2H-pyran-2-yl)oxy)benzyl)-2-(tert-butoxycarbonyl)-1-methylpiperidin-1-ium (76)

A pressure vessel was charged with brominated glucuronide linker fragment (46, 104 mg, 128 µmol) and Mep-OtBu (75, 34 mg, 171 µmol) in anhydrous 2-butanone (1.71 mL). The reaction vessel was flushed with $N_2$ and sealed. The reaction was then stirred and heated to 60° C. for 12 hours. The resulting mixture was cooled, condensed under reduced pressure, taken up in minimal DMSO and purified by preparative HPLC to provide 76 (97 mg, 82%). Analytical UPLC-MS (system 2): $t_r$=1.32 min, m/z (ES+) calculated 930.40 $(M)^+$, found 930.49.

(2R)-1-(3-(3-((((9H-fluoren-9-yl)methoxy)carbonyl)amino)propanamido)-4-(((2S,3R,4S,5S,6S)-6-((allyloxy)carbonyl)-3,4,5-trihydroxytetrahydro-2H-pyran-2-yl)oxy)benzyl)-2-(tert-butoxycarbonyl)-1-methylpiperidin-1-ium (77)

A flame dried flask was charged with Fmoc-GlucQ-Mep-OtBu (76, 97 mg, 104 µmol) in anhydrous allyl alcohol (2.09 mL) under $N_2$. $Ti(OC_2H_5)_4$ (87 µL, 417 µmol) was added and the reaction was heated to 80° C. with stirring for 2 hours. The reaction was then cooled to room temperature and poured into 50 mL 1M HCl. After resting for 45m, the HCl was extracted 3× with 50 mL DCM. Resulting organics were washed with brine, dried over $NaSO_4$, condensed, and purified by preparative HPLC to provide 77 (42 mg, 48%). Analytical UPLC-MS (system 2): $t_r$=1.18 min, m/z (ES+) calculated 830.39 $(M)^+$, found 830.49.

(2R)-1-(3-(3-((((9H-fluoren-9-yl)methoxy)carbonyl)amino)propanamido)-4-(((2S,3R,4S,5S,6S)-6-((allyloxy)carbonyl)-3,4,5-trihydroxytetrahydro-2H-pyran-2-yl)oxy)benzyl)-2-carboxy-1-methylpiperidin-1-ium (78)

A flask containing Fmoc-Gluc(Allyl)Q-Mep-OtBu (77, 42 mg, 50 µmol) was cooled to 0° C. under $N_2$. A solution of 30% TFA in $CH_2Cl_2$ (2.5 mL) was added dropwise and stirred for 18 hours. The reaction was concentrated under reduced pressure, taken up in minimal DMSO and purified by preparative HPLC to provide 78 (25 mg, 64%). Analytical UPLC-MS (system 2): $t_r$=1.05 min, m/z (ES+) calculated 774.32 $(M)^+$, found 774.42.

(2R)-1-(3-(3-((((9H-fluoren-9-yl)methoxy)carbonyl)amino)propanamido)-4-(((2S,3R,4S,5S,6S)-6-((allyloxy)carbonyl)-3,4,5-trihydroxytetrahydro-2H-pyran-2-yl)oxy)benzyl)-2-(((2S,3S)-1-(((1R,3R)-1-acetoxy-1-(4-(((2R,4S)-5-(allyloxy)-4-methyl-5-oxo-1-phenylpentan-2-yl)carbamoyl)thiazol-2-yl)-4-methylpentan-3-yl)(methyl)amino)-3-methyl-1-oxopentan-2-yl)carbamoyl)-1-methylpiperidin-1-ium (79)

To a flask charged with H-Ile-Tuv(OAc)-Tup-OAllyl (73, 23 mg, 36 µmol) was added Fmoc-Gluc(Allyl)Q-Mep-OH (78, 28 mg, 36 µmol) and HATU (27 mg, 72 µmol) as solids followed by DMF (0.714 mL). N,N-Diisopropylethylamine (25 µL, 143 µmol) was added and the reaction was stirred at room temperature for 1 hour. The reaction was then taken up in DMSO and purified by preparative LC to provide 79 (23 mg, 46%). Analytical UPLC-MS (system 2): $t_r$=1.39 min, m/z (ES+) calculated 1398.66 $(M)^+$, found 1398.81.

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(3-(3-aminopropanamido)-4-(((2S,3R,4S,5S,6S)-6-carboxy-3,4,5-trihydroxytetrahydro-2H-pyran-2-yl)oxy)benzyl)-1-methylpiperidin-1-ium (80)

Fmoc-Gluc(Allyl)Q-TubM-OAllyl (79, 21 mg, 15 µmol) was taken up in DCM (1.5 mL) stirring under $N_2$. $Pd(PPh_3)_4$ (3.5 mg, 3.1 µmol) and $PPh_3$ (1.6 mg, 6.1 µmol) were added as solids followed by pyrrolidine (20.1 µL, 245 µmol). The reaction was stirred to 2 hours at room temperature then taken up in 1 mL DMSO, condensed under reduced pressure, and purified by preparative LC to provide 80 (13 mg, 79%). Analytical UPLC-MS (system 2): $t_r$=0.94 min, m/z (ES+) calculated 1096.53 $(M)^+$, found 1096.65.

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(3-(3-((S)-3-((tert-butoxycarbonyl)amino)-2-(2,5-dioxo-2,5-dihydro-1H-pyrrol-1-yl)propanamido)propanamido)-4-(((2S,3R,4S,5S,6S)-6-carboxy-3,4,5-trihydroxytetrahydro-2H-pyran-2-yl)oxy)benzyl)-1-methylpiperidin-1-ium (81)

A flask was charged with H-GlucQ-TubM (80, 13.1 mg, 11.9 µmol) in anhydrous DMF (0.595 mL) to which mDPR(Boc)-OSu (13, 4.6 mg, 11.9 µmol) was added under $N_2$. N,N-Diisopropylethylamine (8.3 µL, 47.8 µmol) was added and the reaction was stirred at room temperature for 3 hours. The reaction was then quenched with acetic acid (8.3 µL) and purified by preparative HPLC to provide 81 (5.2 mg, 33%). Analytical UPLC-MS (system 2): $t_r$=1.20 min, m/z (ES+) calculated 1362.62 $(M)^+$, found 1362.75.

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(3-(3-((S)-3-amino-2-(2,5-dioxo-2,5-dihydro-1H-pyrrol-1-yl)propanamido)propanamido)-4-(((2S,3R,4S,5S,6S)-6-carboxy-3,4,5-trihydroxytetrahydro-2H-pyran-2-yl)oxy)benzyl)-1-methylpiperidin-1-ium (82)

A flask charged with mDPR(Boc)-GlucQ-TubM (81, 5.2 mg, 3.8 µmol) was cooled to 0° C. under $N_2$. A solution of 10% TFA in $CH_2Cl_2$ (0.84 mL) was added dropwise and stirred for 4 hours. The reaction was then taken up in DMSO, condensed under reduced pressure, and purified by preparative HPLC to provide 82 (4.8 mg, 81%). Analytical UPLC-MS (system 2): $t_r$=0.95 min, m/z (ES+) calculated 1262.56 $(M)^+$, found 1262.68.

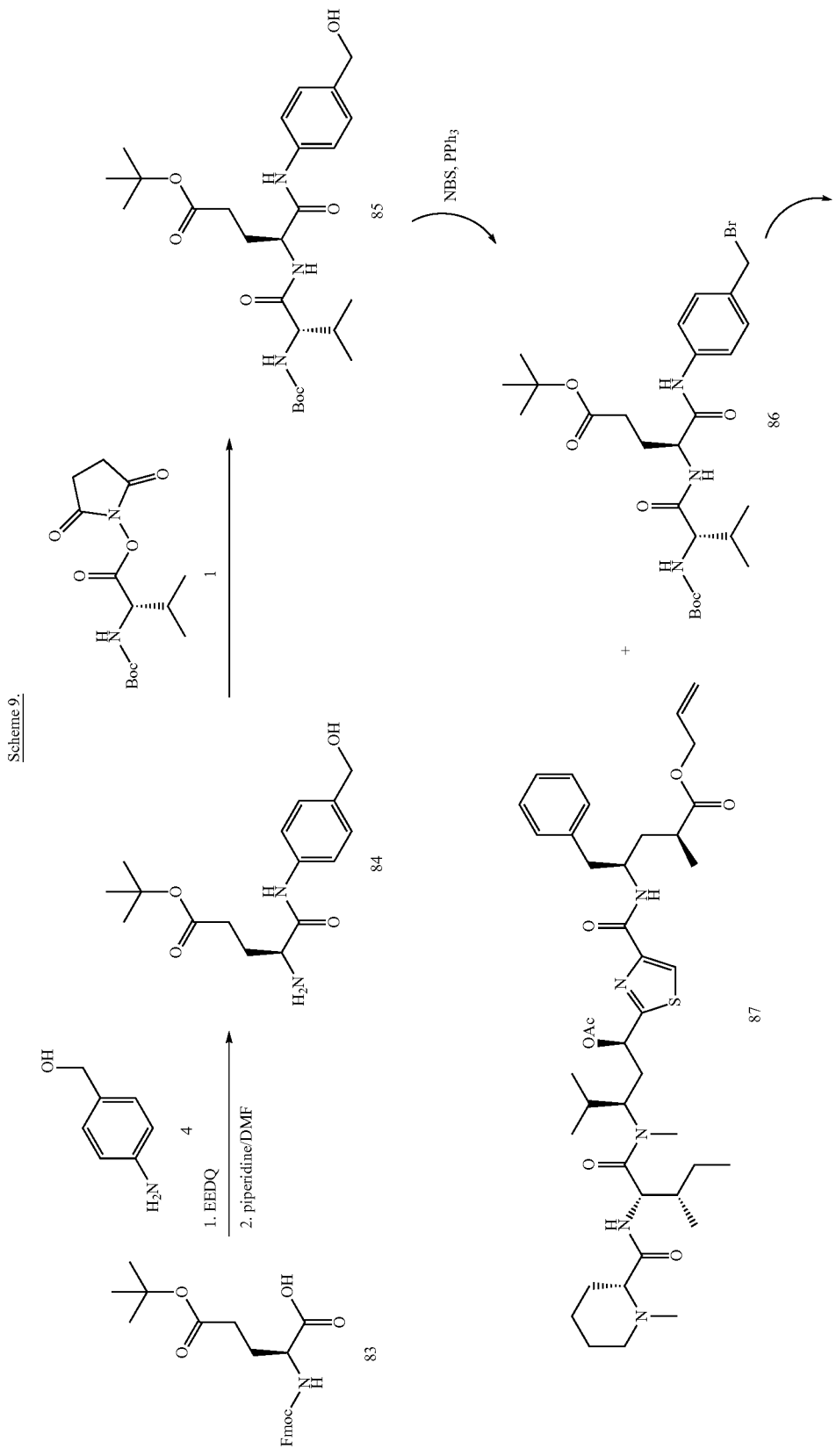

-continued
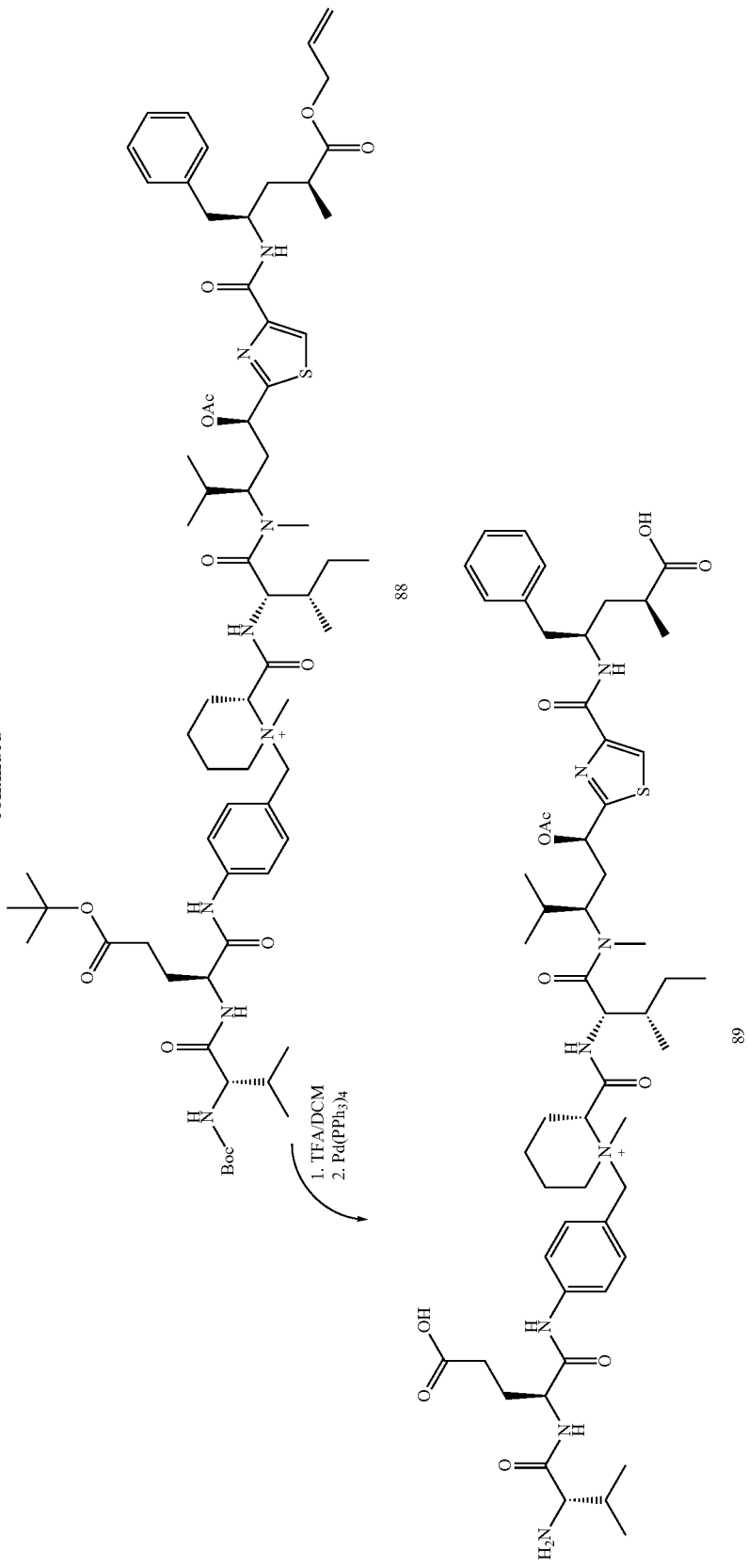

(S)-tert-butyl 4-amino-5-((4-(hydroxymethyl)phenyl)amino)-5-oxopentanoate (84)

A flask charged with Fmoc-Glu(OtBu)-OH (83, 2.0 g, 4.7 mmol), H-PABA (4, 579 mg, 4.7 mmol), and Cl$_2$CH$_2$ (25 mL) was stirred at room temperature. EEDQ (1.40 g, 5.6 mmol) was added as a solid and the mixture was stirred overnight. Product was eluted from a 4 mm chromatotron plate with EtOAc, product containing fractions were condensed. The resulting residue was taken up in 20% piperidine in DCM, stirred for 15 minutes, then condensed to an oil. The oil was dissolved in DCM and eluted from a 2 mm chromatotron plate using 10%-20% MeOH in DCM gradient to provide 84 (860 mg, 60%). Analytical UPLC-MS (system 2): t$_r$=0.65 min, m/z (ES+) calculated 309.18 (M+H)$^+$, found 309.24.

(S)-tert-butyl 4-((S)-2-((tert-butoxycarbonyl)amino)-3-methylbutanamido)-5-((4-(hydroxymethyl)phenyl)amino)-5-oxopentanoate (85)

To a flask charged with H-Glu(OtBu)-PABA (84, 860 mg, 2.78 mmol) in DMF (10 mL) was added Boc-Val-OSu 1 (1.13 g, 3.60 mmol) and DIPEA (0.75 mL). After 30 minutes the reaction mixture was poured into 100 mL EtOAc and washed with H$_2$O 3×, brine 1×, and dried over NaSO$_4$. The solution was dried under reduced pressure, solubilized in 50 mL EtOAc, and precipitated by 10% EtOAc in hexanes (50 mL). The solids were collected and dried to provide 85 as a white solid (0.97 g, 70%). Analytical UPLC-MS (system 2): t$_r$=1.37 min, m/z (ES+) calculated 508.30 (M+H)$^+$, found 508.38.

(S)-tert-butyl 5-((4-(bromomethyl)phenyl)amino)-4-((S)-2-((tert-butoxycarbonyl)amino)-3-methylbutanamido)-5-oxopentanoate (86)

A flask charged with Boc-Val-Glu(OtBu)-PABA-OH (85, 200 mg, 394 µmol), N-bromosuccinimide (105 mg, 591 µmol), and triphenylphosphine (155 mg, 591 µmol) was flushed with N$_2$. The reaction was taken up in THF (4 mL) and stirred for 12 hours. The reaction was condensed and purified over silica via a Biotage column (Hexanes/EtOAc, 10%-100%) to provide 86 (210 mg, 93%). Analytical UPLC-MS (system 2): t$_r$=1.56 min, m/z (ES+) calculated 570.22 (M+H)$^+$, found 570.30.

(2R)-2-(((2S,3S)-1-(((1R,3R)-1-acetoxy-1-(4-(((2R,4S)-5-(allyloxy)-4-methyl-5-oxo-1-phenylpentan-2-yl)carbamoyl)thiazol-2-yl)-4-methylpentan-3-yl)(methyl)amino)-3-methyl-1-oxopentan-2-yl)carbamoyl)-1-(4-((S)-5-(tert-butoxy)-2-((S)-2-((tert-butoxycarbonyl)amino)-3-methylbutanamido)-5-oxopentanamido)benzyl)-1-methylpiperidin-1-ium (88)

A flask charged with Boc-Val-Glu(OtBu)-PABA-Br (86, 40 mg, 70 µmol) and Tub-OAllyl (Org. Lett., 2007, 9, 1605-1607) (87, 45 mg, 59 µmol) was flushed with N$_2$. Butanone (1.17 mL) was added and the reaction was heated to 60° C. while stirring. After 18 hours the reaction was condensed to dryness, taken up in minimal DCM, and purified via Biotage (0-20% DCM/MeOH) to provide 88 (62 mg, 85%). Analytical UPLC-MS (system 2): t$_r$=1.47 min, m/z (ES+) calculated 1257.72 (M)$^+$, found 1257.85.

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(4-((S)-2-((S)-2-amino-3-methylbutanamido)-4-carboxybutanamido)benzyl)-1-methylpiperidin-1-ium (89)

A flask charged with Boc-Val-Glu(OtBu)-PABQ-Tub-OAllyl (88, 42 mg, 50 µmol) was cooled to 0° C. under N$_2$. A solution of 30% TFA in CH$_2$Cl$_2$ (0.99 mL) was added dropwise and stirred for 18 hours. The reaction was concentrated under reduced pressure, taken up in DCM and recondensed 3 times. The residue was then taken up in DCM (0.98 mL) to which Pd(PPh$_3$)$_4$ (5.7 mg, 4.9 µmol) and PPh$_3$ (2.6 mg, 9.8 µmol) were added as solids followed by pyrrolidine (32 µL, 392 µmol). After 1 hour the reaction was taken up in minimal DMSO, condensed, and purified by preparative HPLC to provide 89 (47 mg, 90%). Analytical UPLC-MS (system 2): t$_r$=0.95 min, m/z (ES+) calculated 1061.57 (M)$^+$, found 1061.69.

Scheme 10.

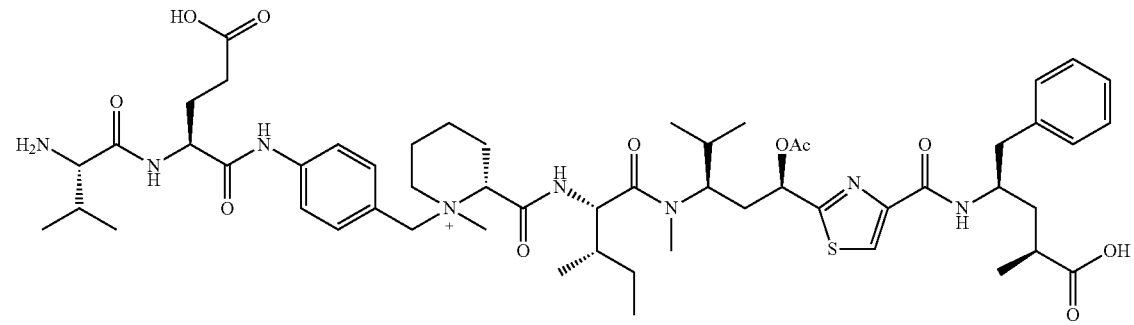

89

| mDPR(Boc)—OSu
13

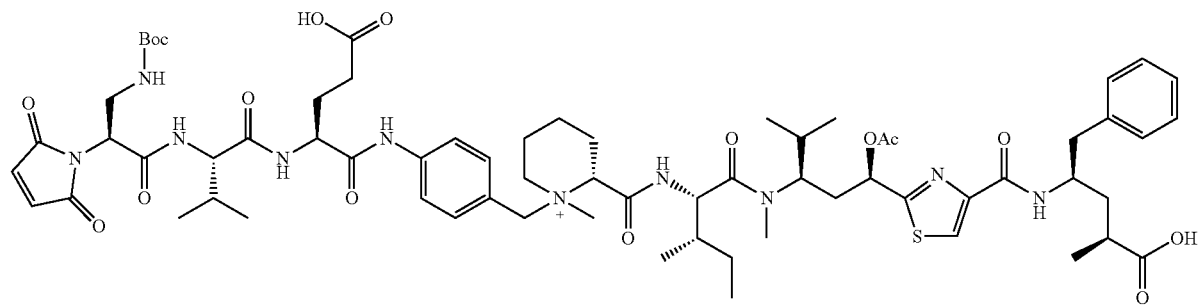

90

↓ TFA/DCM

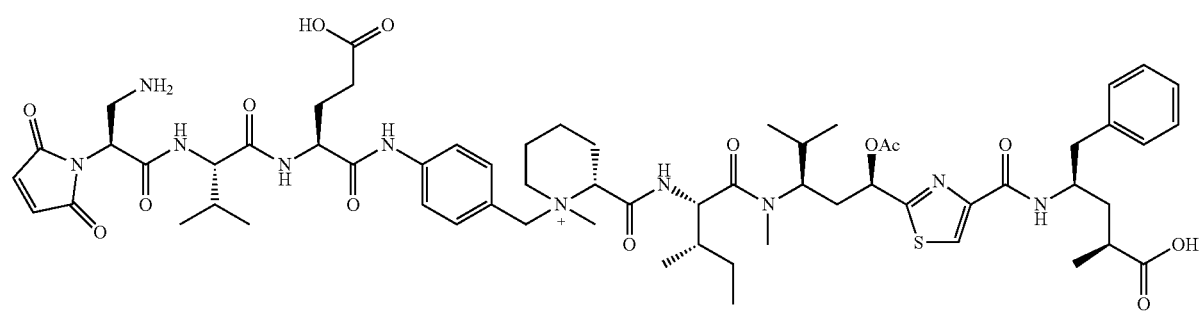

91

(2R)-2-(((2S,3S)-1-(((1R,3R)-1-acetoxy-1-(4-(((2R, 4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(4-(((7S,10S,13S)-13-(2-carboxyethyl)-7-(2,5-dioxo-2,5-dihydro-1H-pyrrol-1-yl)-10-isopropyl-2,2-dimethyl-4,8,11-trioxo-3-oxa-5,9,12-triazatetradecanamido)benzyl)-1-methylpiperidin-1-ium (90)

A flask was charged with H-ValGluPABQ-Tub (89, 22.5 mg, 21.2 μmol) in anhydrous DMF (0.420 mL), to which mDPR(Boc)-OSu (13, 8.9 mg, 23.3 μmol) was added as a solid under $N_2$. N,N-Diisopropylethylamine (14.8 μL, 84.7 μmol) was added and the reaction was stirred at room temperature for 3 hours. The reaction was then quenched with acetic acid (14.8 μL) and purified by preparative HPLC to provide 90 (11.5 mg, 40%). Analytical UPLC-MS (system 2): $t_r$=1.31 min, m/z (ES+) calculated 1327.66 (M)$^+$, found 1327.94.

(2R)-2-(((2S,3S)-1-(((1R,3R)-1-acetoxy-1-(4-(((2R, 4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(4-(((S)-2-((S)-2-((S)-3-amino-2-(2,5-dioxo-2,5-dihydro-1H-pyrrol-1-yl)propanamido)-3-methylbutanamido)-4-carboxybutanamido)benzyl)-1-methylpiperidin-1-ium (91)

A flask charged with mDPR(Boc)-ValGluPABQ-Tub (90, 11.5 mg, 8.6 μmol) was cooled to 0° C. under $N_2$. A solution of 10% TFA in $CH_2Cl_2$ (0.86 mL) was added dropwise and stirred for 2 hours. The reaction was then taken up in DMSO, condensed under reduced pressure, and purified by preparative HPLC to provide 91 (9.9 mg, 93%). Analytical UPLC-MS (system 2): $t_r$=0.99 min, m/z (ES+) calculated 1227.61 (M)$^+$, found 1227.83.

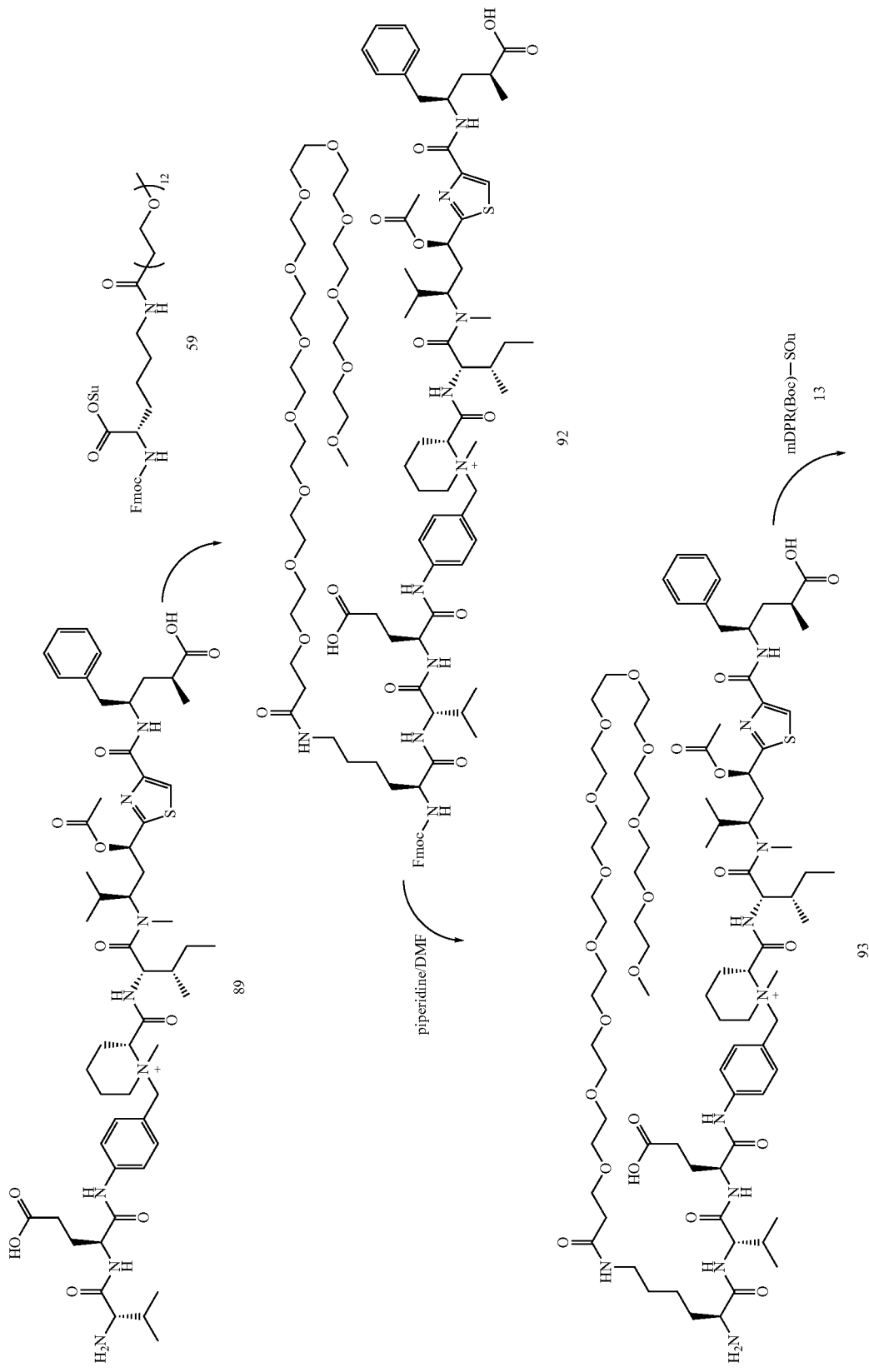

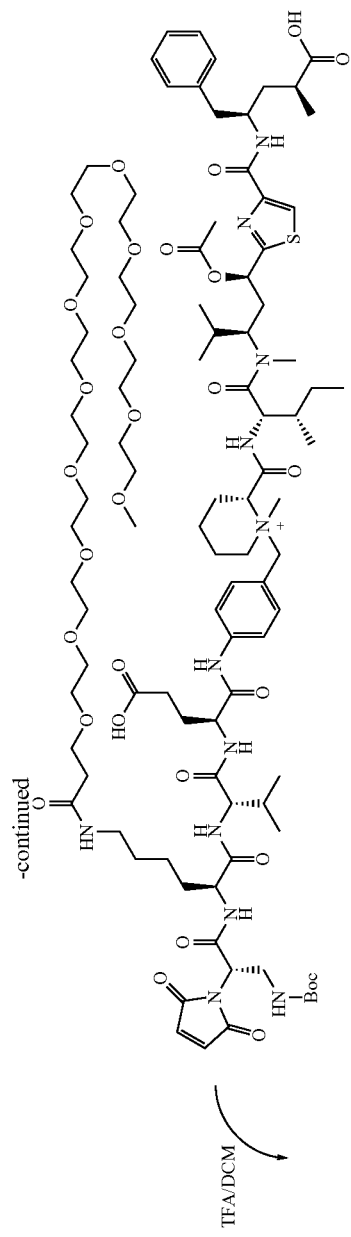
94
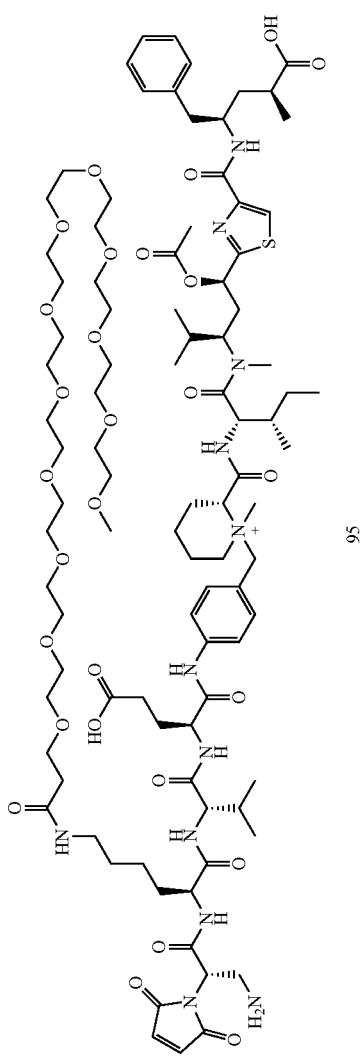
95
TFA/DCM →

(2R)-1-(4-(((44S,47S,50S)-44-((((9H-fluoren-9-yl)methoxy)carbonyl)amino)-50-(2-carboxyethyl)-47-isopropyl-38,45,48-trioxo-2,5,8,11,14,17,20,23,26,29,32,35-dodecaoxa-39,46,49-triazahenpentacontanamido)benzyl)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-methylpiperidin-1-ium (92)

Fmoc-Lys(PEG12)-OSu (59, 26 mg, 25 µmol) was added to a flask charged with H-ValGluPABQ-Tub (89, 24 mg, 23 µmol) as a solution in anhydrous DMF (0.457 mL) under $N_2$. N,N-Diisopropylethylamine (16 µL, 91 µmol) was added and the reaction was stirred at room temperature for 3 hours. The reaction was then quenched with acetic acid (16 µL) and purified by preparative HPLC to provide 92 (34 mg, 75%). Analytical UPLC-MS (system 2): $t_r$=1.35 min, m/z (ES+) calculated 1982.06 (M)$^+$, found 1982.37.

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(4-((44S,47S,50S)-44-amino-50-(2-carboxyethyl)-47-isopropyl-38,45,48-trioxo-2,5,8,11,14,17,20,23,26,29,32,35-dodecaoxa-39,46,49-triazahenpentacontanamido)benzyl)-1-methylpiperidin-1-ium (93)

To a flask charged with Fmoc-Lys(PEG12)-ValGluPABQ-Tub (92, 34 mg, 17 µmol) was added 20% piperidine in DMF (1.7 mL). The reaction was stirred under $N_2$ at room temperature for 30 minutes. The reaction was then diluted with DMSO/$H_2O$ and purified by preparative HPLC to provide 93 (26 mg, 86%). Analytical UPLC-MS (system 2): $t_r$=1.01 min, m/z (ES+) calculated 1759.99 (M)$^+$, found 1760.26.

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(4-((44S,47S,50S)-44-((S)-3-((tert-butoxycarbonyl)amino)-2-(2,5-dioxo-2,5-dihydro-1H-pyrrol-1-yl)propanamido)-50-(2-carboxyethyl)-47-isopropyl-38,45,48-trioxo-2,5,8,11,14,17,20,23,26,29,32,35-dodecaoxa-39,46,49-triazahenpentacontanamido)benzyl)-1-methylpiperidin-1-ium (94)

A flask was charged with H-Lys(PEG12)-ValGluPABQ-Tub (93, 26 mg, 15 µmol) in anhydrous DMF (0.735 mL), to which mDPR(Boc)-OSu (13, 6 mg, 16 µmol) was added as a solid under $N_2$. N,N-Diisopropylethylamine (10 µL, 59 µmol) was added and the reaction was stirred at room temperature for 3 hours. The reaction was then quenched with acetic acid (10 µL), diluted with DMSO, and purified by preparative HPLC to provide 94 (16 mg, 46%). Analytical UPLC-MS (system 2): $t_r$=1.26 min, m/z (ES+) calculated 2026.08 (M)$^+$, found 2026.38.

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(4-((44S,47S,50S)-44-((S)-3-amino-2-(2,5-dioxo-2,5-dihydro-1H-pyrrol-1-yl)propanamido)-50-(2-carboxyethyl)-47-isopropyl-38,45,48-trioxo-2,5,8,11,14,17,20,23,26,29,32,35-dodecaoxa-39,46,49-triazahenpentacontanamido)benzyl)-1-methylpiperidin-1-ium (95)

A flask charged with mDPR(Boc)-Lys(PEG12)-ValGluPABQ-Tub (94, 14 mg, 7 µmol) was cooled to 0° C. under $N_2$. A solution of 10% TFA in $CH_2Cl_2$ (1.03 mL) was added dropwise and stirred for 2 hours. The reaction was then taken up in DMSO, condensed under reduced pressure, and purified by preparative HPLC to provide 95 (9 mg, 70%). Analytical UPLC-MS (system 2): $t_r$=1.03 min, m/z (ES+) calculated 1926.03 (M)$^+$, found 1926.32.

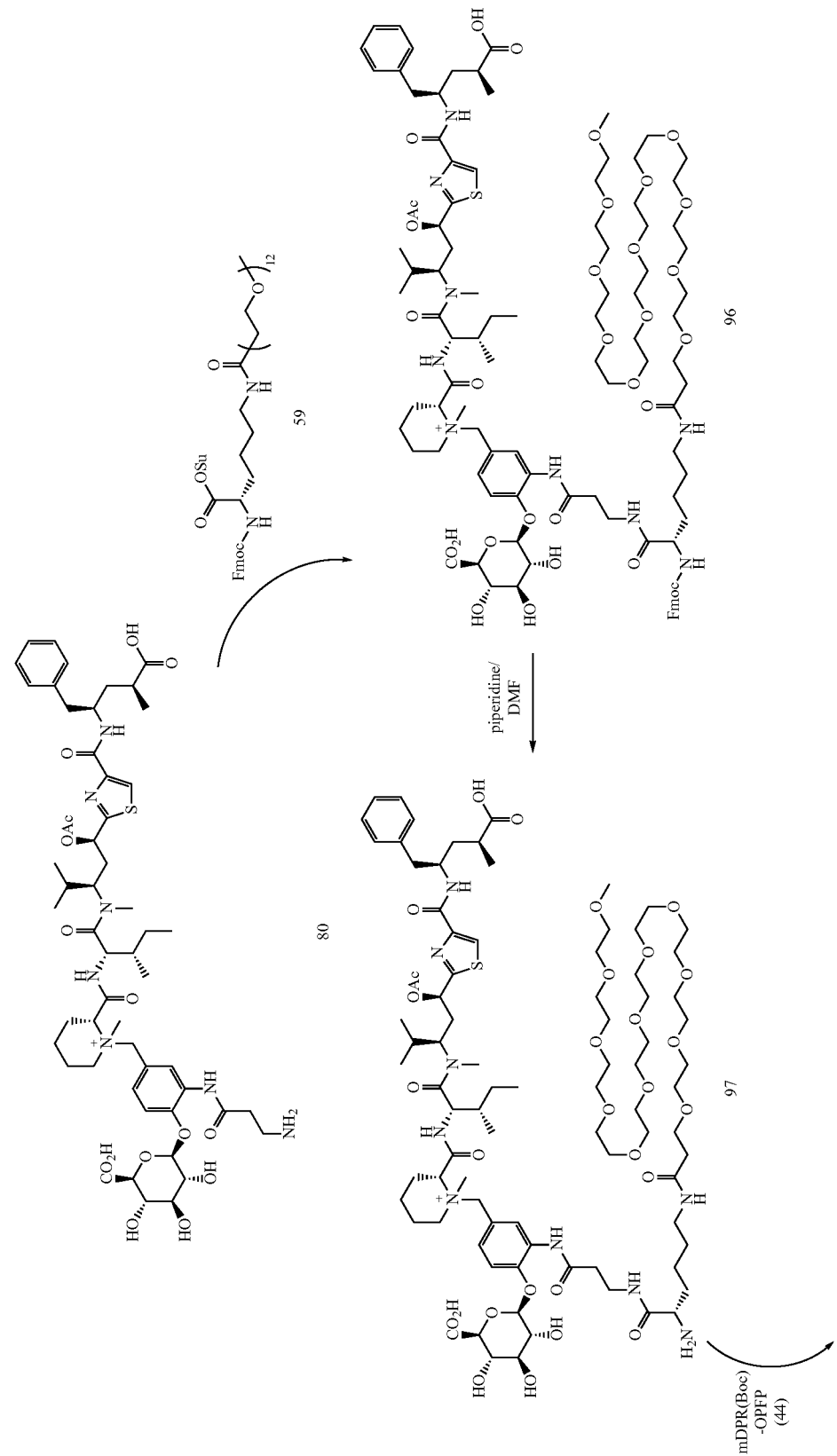

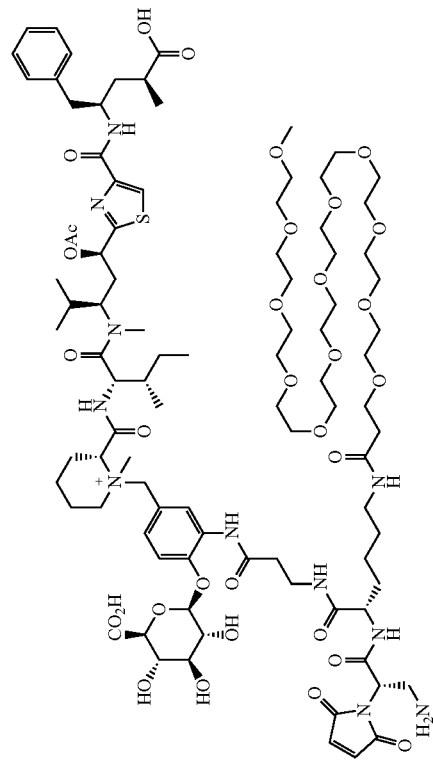
99
↑ TFA/DCM
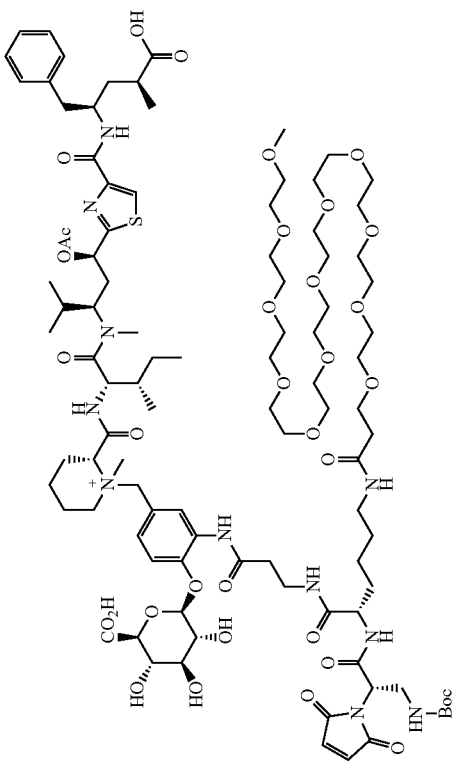
98
-continued

(2R)-1-(3-((S)-44-((((9H-fluoren-9-yl)methoxy)carbonyl)amino)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-methylpiperidin-1-ium (96)

Fmoc-Lys(PEG12)-OSu (59, 4.4 mg, 4.3 µmol) was added to a flask charged with H-GlucQ-Tub (80, 3.9 mg, 3.6 µmol) as a solution in anhydrous DMF (0.355 mL) under $N_2$. N,N-Diisopropylethylamine (1.9 µL, 10.7 µmol) was added and the reaction was stirred at room temperature for 3 hours. The reaction was then quenched with acetic acid (1.9 µL) and purified by preparative HPLC to provide 96 (5.0 mg, 70%). Analytical UPLC-MS (system 2): $t_r$=1.29 min, m/z (ES+) calculated 2017.02 $(M)^+$, found 2017.21.

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(3-((S)-44-amino-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-1-methylpiperidin-1-ium (97)

To a flask charged with Fmoc-Lys(PEG12)-GlucQ-Tub (96, 5.0 mg, 2.5 µmol) was added 20% piperidine in DMF (0.248 mL). The reaction was stirred under $N_2$ at room temperature for 30 minutes. The reaction was then diluted with DMSO/$H_2O$ and purified by preparative HPLC to provide 97 (3.6 mg, 82%). Analytical UPLC-MS (system 2): $t_r$=0.99 min, m/z (ES+) calculated 1794.95 $(M)^+$, found 1795.12.

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(3-((S)-44-((S)-3-((tert-butoxycarbonyl)amino)-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-1-methylpiperidin-1-ium (98)

A flask was charged with H-Lys(PEG12)-GlucQ-Tub (97, 3.8 mg, 2.14 µmol) in anhydrous DMF (0.212 mL), to which mDPR(Boc)-OPFP (44, 1.4 mg, 3.2 µmol) was added as a solid under $N_2$. N,N-Diisopropylethylamine (0.74 µL, 4.2 µmol) was added and the reaction was stirred at room temperature for 3 hours. The reaction was then quenched with acetic acid (0.74 µL), diluted with DMSO, and purified by preparative HPLC to provide 98 (2.7 mg, 61%). Analytical UPLC-MS (system 2): $t_r$=1.20 min, m/z (ES+) calculated 2061.04 $(M)^+$, found 2061.20.

(2R)-2-(((2S,3S)-1-(((1R,3R)-1-acetoxy-1-(4-(((2R,4S)-4-carboxy-1-phenylpentan-2-yl)carbamoyl)thiazol-2-yl)-4-methylpentan-3-yl)(methyl)amino)-3-methyl-1-oxopentan-2-yl)carbamoyl)-1-(3-((S)-44-((S)-3-amino-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-1-methylpiperidin-1-ium (99)

A flask charged with mDPR(Boc)-Lys(PEG12)-GlucQ-Tub (98, 2.7 mg, 1.3 µmol) was cooled to 0° C. under $N_2$. A solution of 10% TFA in $CH_2Cl_2$ (0.26 mL) was added dropwise and stirred for 2 hours. The reaction was then taken up in DMSO, condensed under reduced pressure, and purified by preparative HPLC to provide 99 (2.5 mg, 97%). Analytical UPLC-MS (system 2): $t_r$=1.00 min, m/z (ES+) calculated 1960.99 $(M)^+$, found 1961.17.

Scheme 13.

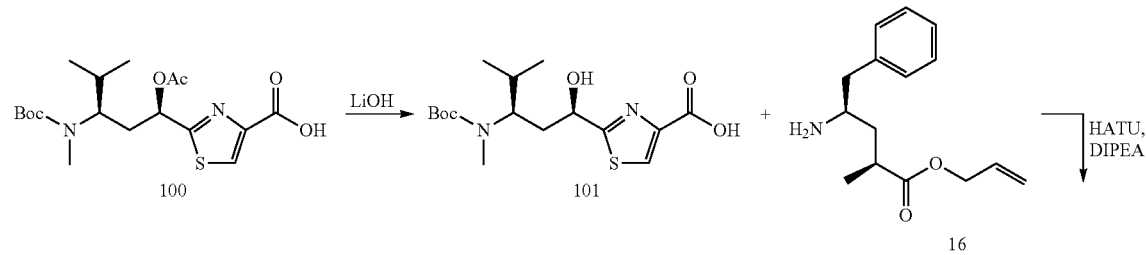

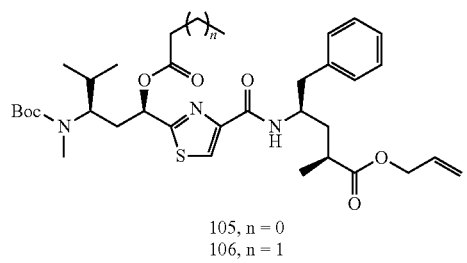
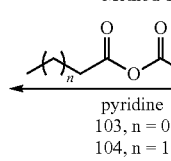
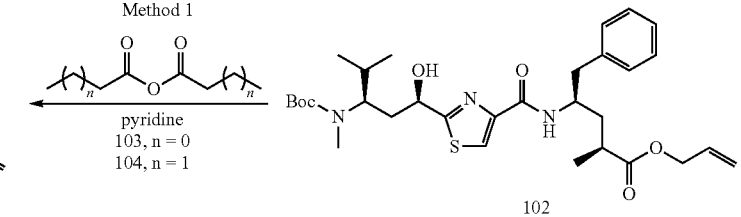

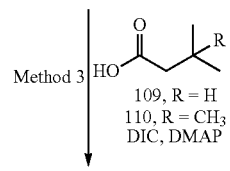

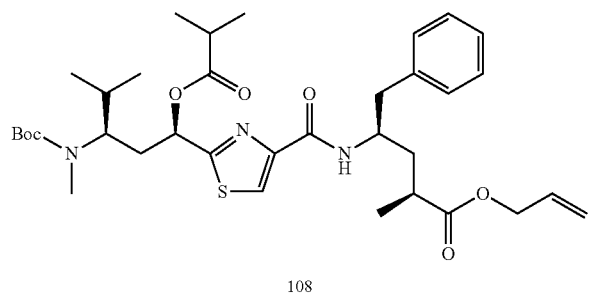
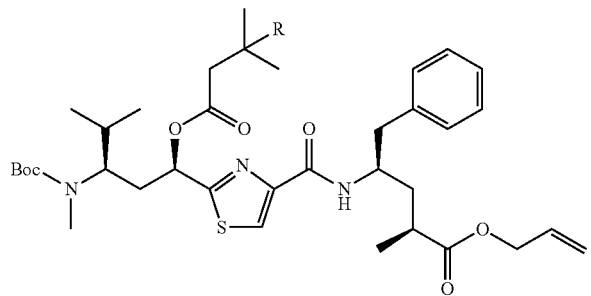

2-((1R,3R)-3-((tert-butoxycarbonyl)(methyl)amino)-1-hydroxy-4-methylpentyl)thiazole-4-carboxylic Acid (101)

A flask was charged with tubuvaline acetate (*Org. Lett.*, 2007, 9, 1605-1607) 100 (225 mg, 560 μmol) dissolved in methanol (5 ml) and tetrahydrofuran (5 ml), then cooled under nitrogen to 0° C. in an ice bath. Lithium hydroxide monohydrate (71 mg, 1680 μmol) was dissolved in water (5 ml) and the solution added dropwise to the reaction flask. The reaction was then stirred at room temperature until UPLC/MS revealed complete conversion to product. The material was the diluted with dichloromethane and washed with 0.1 M HCl. The aqueous layer was extracted twice with dichloromethane, then the combined organics were dried over sodium sulfated, filtered, and concentrated to provide free acid 101 (200 mg, quant.). Analytical UPLC-MS (system 1): $t_r$=1.33 min, m/z (ES+) calculated 359.17 $(M+H)^+$, found 359.14.

(2S,4R)-allyl 4-(2-((1R,3R)-3-((tert-butoxycarbonyl)(methyl)amino)-1-hydroxy-4-methylpentyl)thiazole-4-carboxamido)-2-methyl-5-phenylpentanoate (102)

Tubuvaline free acid 101 (200 mg, 560 μmol) was pre-activated by dissolution in anhydrous dimethylformamide (5.4 ml, 100 mM) and addition of HATU (250 mg, 670 μmol) and DIPEA (0.59 ml, 3.36 mmol); the mixture was then stirred under nitrogen at room temperature for 10 minutes. The activated acid was then added to the known (*Org. Lett.*, 2007, 9, 1605-1607) tubuphenylalanine allyl ester 16 and the reaction was then stirred at an ambient temperature under nitrogen, with progress monitored by UPLC/MS. Upon reaction completion, glacial acetic acid (14 equivalents) was then added and the product was purified by preparative HPLC to provide Tuv(OH)-Tup-O-allyl dipeptide 102 (272 mg, 83%). Analytical UPLC-MS (system 1): $t_r$=1.84 min, m/z (ES+) calculated 588.31 $(M+H)^+$, found 588.29.

(2S,4R)-allyl 4-(2-((1R,3R)-3-((tert-butoxycarbonyl)(methyl)amino)-4-methyl-1-(propionyloxy)pentyl)thiazole-4-carboxamido)-2-methyl-5-phenylpentanoate (105)

Tuv(OH)-Tup-O-allyl dipeptide 102 (26 mg, 44 μmol) was dissolved in anhydrous pyridine (1.8 ml, 25 mM) and stirred under a nitrogen atmosphere at room temperature. Propionic anhydride 103 (113 μl, 20 equivalents) was added dropwise and the reaction was then monitored by UPLC/MS. Additional propionic anhydride (20 equivalents) was added to achieve conversion to product. The material was the diluted with dichloromethane and washed with 0.1 M HCl. The aqueous layer was extracted twice with dichloromethane, then the combined organics were dried over sodium sulfated, filtered, and concentrated to provide the crude product, which was subsequently purified by preparative HPLC to provide the esterified product 105 (17 mg, 61%). Analytical UPLC-MS (system 1): $t_r$=1.99 min, m/z (ES+) calculated 644.34 $(M+H)^+$, found 644.26.

(2S,4R)-allyl 4-(2-((1R,3R)-3-((tert-butoxycarbonyl)(methyl)amino)-1-(butyryloxy)-4-methylpentyl)thiazole-4-carboxamido)-2-methyl-5-phenylpentanoate (106)

Tuv(OH)-Tup-O-allyl dipeptide 102 (27 mg, 46 μmol) was dissolved in anhydrous pyridine (0.9 ml, 50 mM) and stirred under a nitrogen atmosphere at room temperature. Butyric anhydride 104 (225 µl, 30 equivalents) was added dropwise and the reaction was then monitored by UPLC/MS. Additional butyric anhydride (40 equivalents) was added in three portions to achieve conversion to product. The material was the diluted with dichloromethane and washed with 0.1 M HCl. The aqueous layer was extracted twice with dichloromethane, then the combined organics were dried over sodium sulfated, filtered, and concentrated to provide the crude product, which was subsequently purified by preparative HPLC to provide the esterified product 106 (24 mg, 80%). Analytical UPLC-MS (system 1): $t_r$=2.13 min, m/z (ES+) calculated 658.35 (M+H)$^+$, found 658.23.

(2S,4R)-allyl 4-(2-((1R,3R)-3-((tert-butoxycarbonyl) (methyl)amino)-1-(isobutyryloxy)-4-methylpentyl) thiazole-4-carboxamido)-2-methyl-5-phenylpentanoate (108)

Tuv(OH)-Tup-O-allyl dipeptide 102 (26 mg, 44 µmol) was dissolved in anhydrous pyridine (1.8 ml, 25 mM) and stirred under a nitrogen atmosphere at room temperature. Isobutyryl chloride 107 (93 µl, 20 equivalents) was added dropwise and the reaction was then monitored by UPLC/MS. Upon conversion to product, the material was then diluted with dichloromethane and washed with 0.1 M HCl. The aqueous layer was extracted twice with dichloromethane, then the combined organics were dried over sodium sulfated, filtered, and concentrated to provide the crude product, which was subsequently purified by preparative HPLC to provide the esterified product 108 (29 mg, quant.). Analytical UPLC-MS (system 1): $t_r$=2.13 min, m/z (ES+) calculated 658.35 (M+H)$^+$, found 658.33.

(2S,4R)-allyl 4-(2-((1R,3R)-3-((tert-butoxycarbonyl) (methyl)amino)-4-methyl-1-((3-methylbutanoyl)oxy) pentyl)thiazole-4-carboxamido)-2-methyl-5-phenyl-pentanoate (111)

A flask was charged with isovaleric acid 109 (94 µl, 851 µmol) dissolved in anhydrous dichloromethane (5.6 ml, 15 mM) and the solution was stirred at 0 C under a nitrogen atmosphere. DMAP (10 mg, 85 µmol) was then added, followed by DCC (88 mg, 425 µmol), and the reaction was allowed to warm to room temperature over 2 hours. The resulting activated acid was then added to Tuv(OH)-Tup-O-allyl dipeptide 102 (50 mg, 85 µmol) and the reaction was stirred overnight, at which time UPLC/MS revealed conversion to product. The reaction was then diluted with dichloromethane and washed with 0.1 M HCl. The aqueous layer was extracted twice with dichloromethane, then the combined organics were dried over sodium sulfated, filtered, and concentrated to provide the crude product, which was subsequently purified by preparative HPLC to provide the esterified product 111 (52 mg, 91%). Analytical UPLC-MS (system 2): $t_r$=1.91 min, m/z (ES+) calculated 672.37 (M+H)$^+$, found 672.46.

(2S,4R)-allyl 4-(2-((1R,3R)-3-((tert-butoxycarbonyl) (methyl)amino)-1-((3,3-dimethylbutanoyl)oxy)-4-methylpentyl)thiazole-4-carboxamido)-2-methyl-5-phenylpentanoate (112)

A flask was charged with gem-dimethylbutyric acid 110 (98 µl, 766 µmol) dissolved in anhydrous dichloromethane (5.1 ml, 15 mM) and the solution was stirred at 0 C under a nitrogen atmosphere. DMAP (9 mg, 77 µmol) was then added, followed by DCC (79 mg, 383 µmol), and the reaction was allowed to warm to room temperature over 2 hours. The resulting activated acid was then added to Tuv(OH)-Tup-O-allyl dipeptide 102 (45 mg, 77 µmol) and the reaction was stirred overnight, at which time UPLC/MS revealed conversion to product. The reaction was then diluted with dichloromethane and washed with 0.1 M HCl. The aqueous layer was extracted twice with dichloromethane, then the combined organics were dried over sodium sulfated, filtered, and concentrated to provide the crude product, which was subsequently purified by preparative HPLC to provide the esterified product 112 (49 mg, 93%). Analytical UPLC-MS (system 2): $t_r$=1.88 min, m/z (ES+) calculated 686.39 (M+H)$^+$, found 686.47.

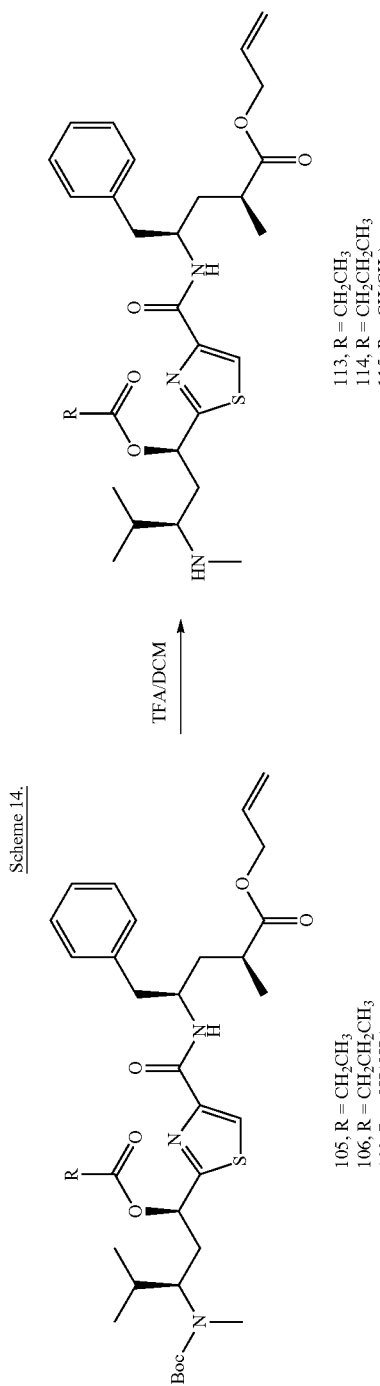

-continued
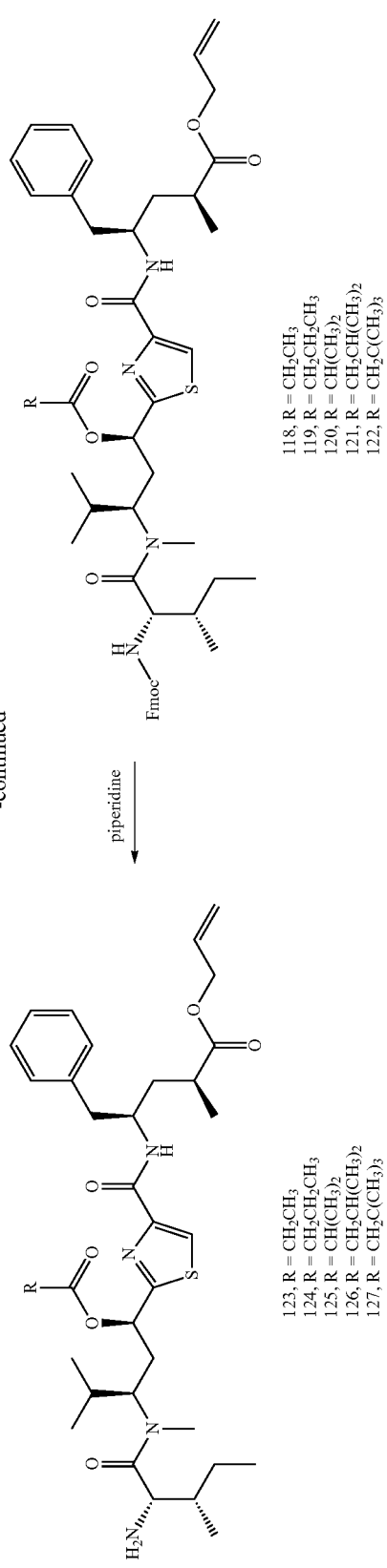
118, R = CH$_2$CH$_3$
119, R = CH$_2$CH$_2$CH$_3$
120, R = CH(CH$_3$)$_2$
121, R = CH$_2$CH(CH$_3$)$_2$
122, R = CH$_2$C(CH$_3$)$_3$
piperidine ↓
123, R = CH$_2$CH$_3$
124, R = CH$_2$CH$_2$CH$_3$
125, R = CH(CH$_3$)$_2$
126, R = CH$_2$CH(CH$_3$)$_2$
127, R = CH$_2$C(CH$_3$)$_3$
HATU, DIPEA, DMF
36
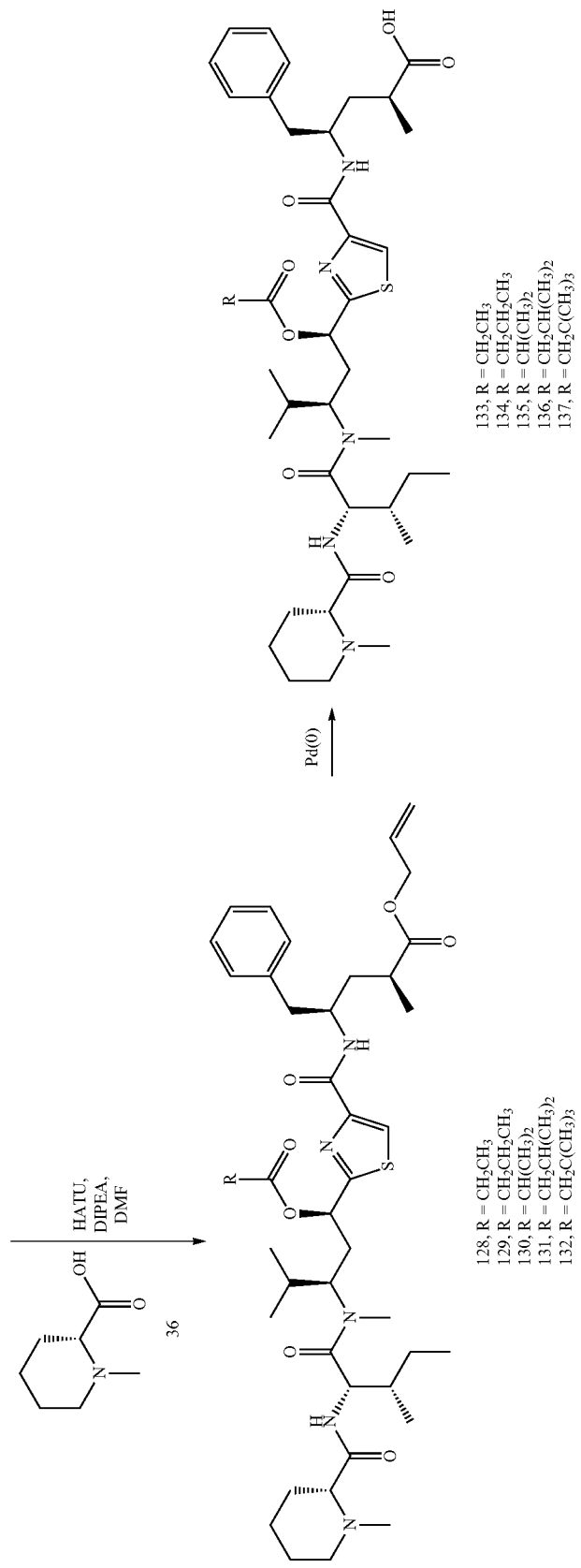
128, R = CH$_2$CH$_3$
129, R = CH$_2$CH$_2$CH$_3$
130, R = CH(CH$_3$)$_2$
131, R = CH$_2$CH(CH$_3$)$_2$
132, R = CH$_2$C(CH$_3$)$_3$
Pd(0) ↑
133, R = CH$_2$CH$_3$
134, R = CH$_2$CH$_2$CH$_3$
135, R = CH(CH$_3$)$_2$
136, R = CH$_2$CH(CH$_3$)$_2$
137, R = CH$_2$C(CH$_3$)$_3$ General Procedure for the Boc Deprotection of Tuv(O-Ester)-Tup Intermediates.

Esterified tubuvaline-tubuphenylalanine intermediates 105, 106, 108, 111, or 112 were deprotected to reveal the secondary amine functional group under acidic conditions with 10% TFA in dichloromethane (25 mM). Specifically, the starting material was dissolve in anhydrous dichloromethane (9 volumes) and stirred under nitrogen at 0 C. Trifluoroacetic acid (1 volume) was then added dropwise to the stirred solution. The reaction was warmed slowly to room temperature and monitored by UPLC/MS. Upon completion, the reaction was concentrated by rotary evaporation and pumped down on a vacuum line overnight. The free amines 135-139 were carried forward without further purification.

(2S,4R)-allyl 2-methyl-4-(2-((1R,3R)-4-methyl-3-(methylamino)-1-(propionyloxy)pentyl)thiazole-4-carboxamido)-5-phenylpentanoate (113)

Boc-protected Tuv-Tup intermediate 105 (17 mg, 26 μmol) was deprotected as described above to provide 14 mg (quant.) of the title compound. UPLC-MS (system 1): $t_r$=1.24 min, m/z (ES+) calculated 544.29 (M+H)$^+$, found 544.25.

(2S,4R)-allyl 4-(2-((1R,3R)-1-(butyryloxy)-4-methyl-3-(methylamino)pentyl)thiazole-4-carboxamido)-2-methyl-5-phenylpentanoate (114)

Boc-protected Tuv-Tup intermediate 106 (24 mg, 37 μmol) was deprotected as described above to provide 21 mg (quant.) of the title compound. UPLC-MS (system 2): $t_r$=1.20 min, m/z (ES+) calculated 558.30 (M+H)$^+$, found 558.38.

(2S,4R)-allyl 4-(2-((1R,3R)-1-(isobutyryloxy)-4-methyl-3-(methylamino)pentyl)thiazole-4-carboxamido)-2-methyl-5-phenylpentanoate (115)

Boc-protected Tuv-Tup intermediate 108 (29 mg, 44 μmol) was deprotected as described above to provide 25 mg (quant.) of the title compound. UPLC-MS (system 1): $t_r$=1.30 min, m/z (ES+) calculated 558.30 (M+H)+, found 557.93.

(2S,4R)-allyl 2-methyl-4-(2-((1R,3R)-4-methyl-3-(methylamino)-1-((3-methylbutanoyl)oxy)pentyl)thiazole-4-carboxamido)-5-phenylpentanoate (116)

Boc-protected Tuv-Tup intermediate 111 (52 mg, 78 μmol) was deprotected as described above to provide 45 mg (quant.) of the title compound. UPLC-MS (system 2): $t_r$=1.23 min, m/z (ES+) calculated 572.32 (M+H)$^+$, found 572.40.

(2S,4R)-allyl 4-(2-((1R,3R)-1-((3,3-dimethylbutanoyl)oxy)-4-methyl-3-(methylamino)pentyl)thiazole-4-carboxamido)-2-methyl-5-phenylpentanoate (117)

Boc-protected Tuv-Tup intermediate 112 (49 mg, 71 μmol) was deprotected as described above to provide 46 mg (quant.) of the title compound. UPLC-MS (system 2): $t_r$=1.27 min, m/z (ES+) calculated 586.33 (M+H)$^+$, found 586.42.

General Procedure for the Amide Coupling of O-Esterified Tubuvaline-Tubuphenylalanine Dipeptides with Fmoc-Protected L-Isoleucine.

Commercially available Fmoc-L-Isoleucine (4 equivalents) was dissolved in anhydrous dimethylformamide (50 mM) and pre-activated with HATU (4 equivalents) and DIPEA (8 equivalents); the mixture was stirred for 10 minutes at room temperature under nitrogen. The activated acid was then added to the Tuv(O-ester)-Tup dipeptides 113-117; the reaction was stirred at room temperature under nitrogen and monitored by UPLC/MS. Once the reaction had stopped progressing or had reached completion, glacial acetic acid (13 equivalents) was added and the reaction was purified by prep HPLC.

(2S,4R)-allyl 4-(2-((5S,8R,10R)-5-((S)-sec-butyl)-1-(9H-fluoren-9-yl)-8-isopropyl-7-methyl-3,6,12-trioxo-2,11-dioxa-4,7-diazatetradecan-10-yl)thiazole-4-carboxamido)-2-methyl-5-phenylpentanoate (118)

Tuv-Tup intermediate 113 (14 mg, 25 μmol) was coupled to Fmoc-L-Ile as described above to provide 17 mg (77%) of the title compound. UPLC-MS (system 1): $t_r$=2.11 min, m/z (ES+) calculated 879.44 (M+H)$^+$, found 879.60.

(2S,4R)-allyl 4-(2-((5S,8R,10R)-5-((S)-sec-butyl)-1-(9H-fluoren-9-yl)-8-isopropyl-7-methyl-3,6,12-trioxo-2,11-dioxa-4,7-diazapentadecan-10-yl)thiazole-4-carboxamido)-2-methyl-5-phenylpentanoate (119)

Tuv-Tup intermediate 114 (21 mg, 37 μmol) was coupled to Fmoc-L-Ile as described above to provide 24 mg (73%) of the title compound. UPLC-MS (system 2): $t_r$=1.94 min, m/z (ES+) calculated 893.45 (M+H)$^+$, found 893.56.

(2S,4R)-allyl 4-(2-((5S,8R,10R)-5-((S)-sec-butyl)-1-(9H-fluoren-9-yl)-8-isopropyl-7,13-dimethyl-3,6,12-trioxo-2,11-dioxa-4,7-diazatetradecan-10-yl)thiazole-4-carboxamido)-2-methyl-5-phenylpentanoate (120)

Tuv-Tup intermediate 115 (25 mg, 44 μmol) was coupled to Fmoc-L-Ile as described above to provide 26 mg (67%) of the title compound. UPLC-MS (system 2): $t_r$=1.85 min, m/z (ES+) calculated 893.45 (M+H)$^+$, found 893.56.

(2S,4R)-allyl 4-(2-((5S,8R,10R)-5-((S)-sec-butyl)-1-(9H-fluoren-9-yl)-8-isopropyl-7,14-dimethyl-3,6,12-trioxo-2,11-dioxa-4,7-diazapentadecan-10-yl)thiazole-4-carboxamido)-2-methyl-5-phenylpentanoate (121)

Tuv-Tup intermediate 116 (45 mg, 79 μmol) was coupled to Fmoc-L-Ile as described above to provide 54 mg (75%) of the title compound. UPLC-MS (system 2): $t_r$=2.06 min, m/z (ES+) calculated 907.47 (M+H)$^+$, found 907.58.

(2S,4R)-allyl 4-(2-((5S,8R,10R)-5-((S)-sec-butyl)-1-(9H-fluoren-9-yl)-8-isopropyl-7,14,14-trimethyl-3,6,12-trioxo-2,11-dioxa-4,7-diazapentadecan-10-yl)thiazole-4-carboxamido)-2-methyl-5-phenylpentanoate (122)

Tuv-Tup intermediate 117 (46 mg, 79 μmol) was coupled to Fmoc-L-Ile as described above to provide 55 mg (75%) of the title compound. UPLC-MS (system 2): $t_r$=2.50 min, m/z (ES+) calculated 921.49 (M+H)$^+$, found 921.59.

General Procedure for the Fmoc-Deprotection of Isoleucine-O-Esterified Tubuvaline-Tubuphenylalanine Tripeptides.

Fmoc-Ile-Tuv(O-ester)-Tup allyl ester (118-122) was treated with 20% piperidine in dimethylformamide (20 mM), with stirring under nitrogen at room temperature. Once complete deprotection had been achieved, as monitored by UPLC/MS, the reaction mixture was concentrated by rotary evaporation. The crude product was then purified by preparative HPLC to provide free amine tripeptides 145-149.

(2S,4R)-allyl 4-(2-((1R,3R)-3-((2S,3S)-2-amino-N,3-dimethylpentanamido)-4-methyl-1-(propionyloxy)pentyl)thiazole-4-carboxamido)-2-methyl-5-phenylpentanoate (123)

Fmoc-Ile-Tuv-Tup intermediate 118 (17 mg, 19 mol) was deprotected as described above to provide 15 mg (quant.) of the title compound. UPLC-MS (system 1): $t_r$=1.29 min, m/z (ES+) calculated 657.37 (M+H)$^+$, found 658.04.

(2S,4R)-allyl 4-(2-((1R,3R)-3-((2S,3S)-2-amino-N,3-dimethylpentanamido)-1-(butyryloxy)-4-methylpentyl)thiazole-4-carboxamido)-2-methyl-5-phenylpentanoate (124)

Fmoc-Ile-Tuv-Tup intermediate 119 (23 mg, 26 mol) was deprotected as described above to provide 15 mg (86%) of the title compound. UPLC-MS (system 2): $t_r$=1.24 min, m/z (ES+) calculated 671.39 (M+H)$^+$, found 671.48.

(2S,4R)-allyl 4-(2-((1R,3R)-3-((2S,3S)-2-amino-N,3-dimethylpentanamido)-1-(isobutyryloxy)-4-methylpentyl)thiazole-4-carboxamido)-2-methyl-5-phenylpentanoate (125)

Fmoc-Ile-Tuv-Tup intermediate 120 (26 mg, 29 mol) was deprotected as described above to provide 20 mg (quant.) of the title compound. UPLC-MS (system 1): $t_r$=1.33 min, m/z (ES+) calculated 671.39 (M+H)$^+$, found 671.33.

(2S,4R)-allyl 4-(2-((1R,3R)-3-((2S,3S)-2-amino-N,3-dimethylpentanamido)-4-methyl-1-((3-methylbutanoyl)oxy)pentyl)thiazole-4-carboxamido)-2-methyl-5-phenylpentanoate (126)

Fmoc-Ile-Tuv-Tup intermediate 121 (54 mg, 60 µmol) was deprotected as described above to provide 41 mg (quant.) of the title compound. UPLC-MS (system 2): $t_r$=1.31 min, m/z (ES+) calculated 685.40 (M+H)$^+$, found 685.49.

(2S,4R)-allyl 4-(2-((1R,3R)-3-((2S,3S)-2-amino-N,3-dimethylpentanamido)-1-((3,3-dimethylbutanoyl)oxy)-4-methylpentyl)thiazole-4-carboxamido)-2-methyl-5-phenylpentanoate (127)

Fmoc-Ile-Tuv-Tup intermediate 122 (55 mg, 60 µmol) was deprotected as described above to provide 36 mg (86%) of the title compound. UPLC-MS (system 2): $t_r$=1.30 min, m/z (ES+) calculated 699.42 (M+H)$^+$, found 699.51.

General Procedure for the Amide Coupling of Isoleucine-Tubuvaline(O-Ester)-Tubuphenylalanine Tripeptides with (R)—N-Methyl-Pipecolic Acid.

Commercially available (R)—N-methyl-pipecolic acid (D-Mep) 36 (2 equivalents) was dissolved in anhydrous dimethylformamide (20-25 mM) and pre-activated with HATU (2 equivalents) and DIPEA (4 equivalents); the mixture was stirred for 10 minutes at room temperature under nitrogen. The activated acid was then added to the Ile-Tuv(O-ester)-Tup tripeptides 123-127; the reaction was stirred at room temperature under nitrogen and monitored by UPLC/MS. Upon reaction completion, glacial acetic acid (14 equivalents) was then added and the product was purified by preparative HPLC.

(2S,4R)-allyl 4-(2-((1R,3R)-3-((2S,3S)—N,3-dimethyl-2-((R)-1-methylpiperidine-2-carboxamido)pentanamido)-4-methyl-1-(propionyloxy)pentyl)thiazole-4-carboxamido)-2-methyl-5-phenylpentanoate (128)

Ile-Tuv-Tup intermediate 123 (5 mg, 8 µmol) was coupled to D-Mep 36 as described above to provide 6 mg (97%) of the title compound. UPLC-MS (system 1): $t_r$=1.33 min, m/z (ES+) calculated 782.45 (M+H)$^+$, found 781.82.

(2S,4R)-allyl 4-(2-((1R,3R)-1-(butyryloxy)-3-((2S,3S)—N,3-dimethyl-2-((R)-1-methylpiperidine-2-carboxamido)pentanamido)-4-methylpentyl)thiazole-4-carboxamido)-2-methyl-5-phenylpentanoate (129)

Ile-Tuv-Tup intermediate 124 (6 mg, 9 µmol) was coupled to D-Mep 36 as described above to provide 7 mg (98%) of the title compound. UPLC-MS (system 2): $t_r$=1.31 min, m/z (ES+) calculated 796.47 (M+H)$^+$, found 796.57.

(2S,4R)-allyl 4-(2-((1R,3R)-3-((2S,3S)—N,3-dimethyl-2-((R)-1-methylpiperidine-2-carboxamido)pentanamido)-1-(isobutyryloxy)-4-methylpentyl)thiazole-4-carboxamido)-2-methyl-5-phenylpentanoate (130)

Ile-Tuv-Tup intermediate 125 (5 mg, 8 µmol) was coupled to D-Mep 36 as described above to provide 6 mg (94%) of the title compound. UPLC-MS (system 1): $t_r$=1.37 min, m/z (ES+) calculated 796.47 (M+H)$^+$, found 795.78.

(2S,4R)-allyl 4-(2-((1R,3R)-3-((2S,3S)—N,3-dimethyl-2-((R)-1-methylpiperidine-2-carboxamido)pentanamido)-4-methyl-1-((3-methylbutanoyl)oxy)pentyl)thiazole-4-carboxamido)-2-methyl-5-phenylpentanoate (131)

Ile-Tuv-Tup intermediate 126 (7 mg, 10 µmol) was coupled to D-Mep 36 as described above to provide 6 mg (94%) of the title compound. UPLC-MS (system 2): $t_r$=1.35 min, m/z (ES+) calculated 810.49 (M+H)$^+$, found 810.59.

(2S,4R)-allyl 4-(2-((1R,3R)-3-((2S,3S)—N,3-dimethyl-2-((R)-1-methylpiperidine-2-carboxamido)pentanamido)-1-((3,3-dimethylbutanoyl)oxy)-4-methylpentyl)thiazole-4-carboxamido)-2-methyl-5-phenylpentanoate (132)

Ile-Tuv-Tup intermediate 127 (7 mg, 10 µmol) was coupled to D-Mep 36 as described above to provide 6 mg (94%) of the title compound. UPLC-MS (system 2): $t_r$=1.38 min, m/z (ES+) calculated 824.50 (M+H)$^+$, found 824.60.

General Procedure for the Allyl Ester Removal from D-Methylpipecolic Acid-Isoleucine-Tubuvaline(O-Ester)-Tubuphenylalanine Intermediates.

Allyl ester-protected tubulysin intermediate (128-132) was dissolved in anhydrous dichloromethane (20 mM) treated with palladium tetrakis(triphenylphosphine) (0.1 equiv.), triphenylphosphine (0.2 equivalents), and anhydrous pyrrolidine (8 equivalents), and the reaction was stirred at an ambient temperature under nitrogen. Once UPLC/MS revealed conversion to the product free acid, the reaction was quenched with glacial acetic acid (22 equivalents), diluted with acetonitrile and dimethylformamide, and then concentrated by rotary evaporation. The crude tubulysin ether was then purified by preparative HPLC.

(2S,4R)-4-(2-((1R,3R)-3-((2S,3S)—N,3-dimethyl-2-((R)-1-methylpiperidine-2-carboxamido)pentanamido)-4-methyl-1-(propionyloxy)pentyl)thiazole-4-carboxamido)-2-methyl-5-phenylpentanoic Acid (133)

Allyl ester-protected tubulysin intermediate 128 (6 mg, 8 μmol) was deprotected as described above to provide 3.8 mg (67%) of tubulysin 133 (Tub propionate). UPLC-MS (system 2): $t_r$=1.11 min, m/z (ES+) calculated 742.42 $(M+H)^+$, found 742.51.

(2S,4R)-4-(2-((1R,3R)-1-(butyryloxy)-3-((2S,3S)—N,3-dimethyl-2-((R)-1-methylpiperidine-2-carboxamido)pentanamido)-4-methylpentyl)thiazole-4-carboxamido)-2-methyl-5-phenylpentanoic Acid (134)

Allyl ester-protected tubulysin intermediate 129 (7 mg, 9 μmol) was deprotected as described above to provide 6 mg (88%) of tubulysin 134 (Tub butyrate). UPLC-MS (system 2): $t_r$=1.16 min, m/z (ES+) calculated 756.44 $(M+H)^+$, found 756.54.

(2S,4R)-4-(2-((1R,3R)-3-((2S,3S)—N,3-dimethyl-2-((R)-1-methylpiperidine-2-carboxamido)pentanamido)-1-(isobutyryloxy)-4-methylpentyl)thiazole-4-carboxamido)-2-methyl-5-phenylpentanoic Acid (135)

Allyl ester-protected tubulysin intermediate 130 (6 mg, 8 μmol) was deprotected as described above to provide 3 mg (50%) of tubulysin 135 (Tub isobutyrate). UPLC-MS (system 1): $t_r$=1.23 min, m/z (ES+) calculated 756.44 $(M+H)^+$, found 756.82.

(2S,4R)-4-(2-((1R,3R)-3-((2S,3S)—N,3-dimethyl-2-((R)-1-methylpiperidine-2-carboxamido)pentanamido)-4-methyl-1-((3-methylbutanoyl)oxy)pentyl)thiazole-4-carboxamido)-2-methyl-5-phenylpentanoic Acid (136)

Allyl ester-protected tubulysin intermediate 131 (7 mg, 9 μmol) was deprotected as described above to provide 7 mg (quant.) of tubulysin 136 (Tub isovalerate). UPLC-MS (system 2): $t_r$=1.22 min, m/z (ES+) calculated 770.45 $(M+H)^+$, found 770.55.

(2S,4R)-4-(2-((1R,3R)-3-((2S,3S)—N,3-dimethyl-2-((R)-1-methylpiperidine-2-carboxamido)pentanamido)-1-((3,3-dimethylbutanoyl)oxy)-4-methylpentyl)thiazole-4-carboxamido)-2-methyl-5-phenylpentanoic Acid (137)

Allyl ester-protected tubulysin intermediate 132 (7 mg, 8.5 μmol) was deprotected as described above to provide 8 mg (quant.) of tubulysin 137 (Tub gem-dimethylbutyrate). UPLC-MS (system 2): $t_r$=1.23 min, m/z (ES+) calculated 784.47 $(M+H)^+$, found 784.57.

Scheme 15.
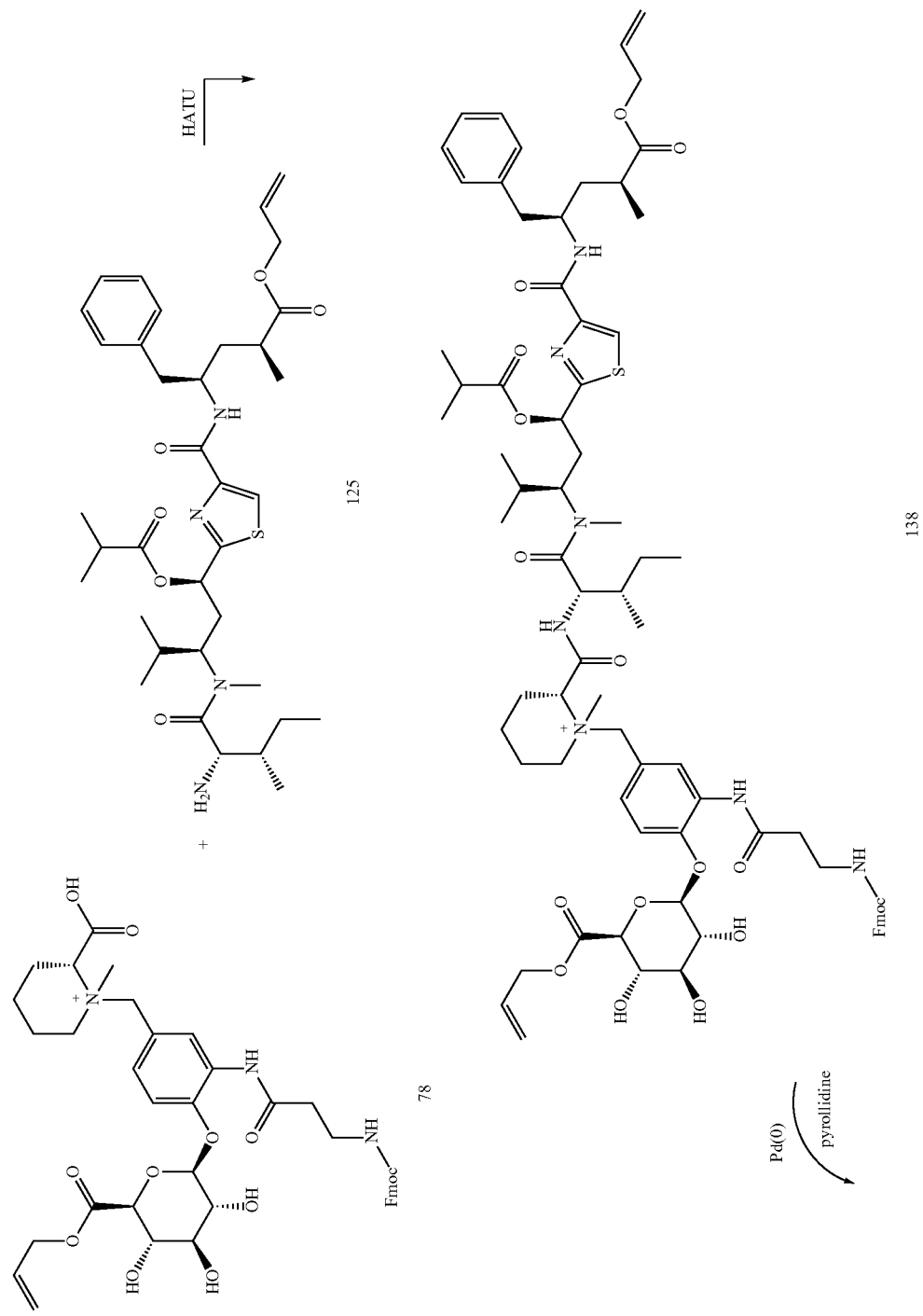

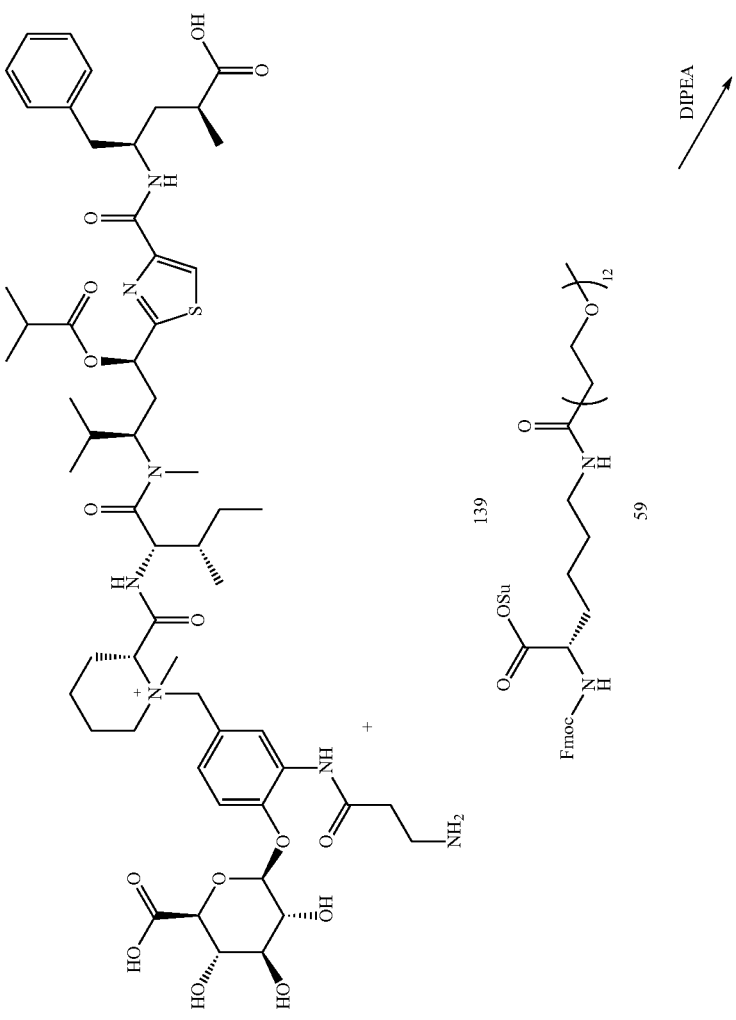

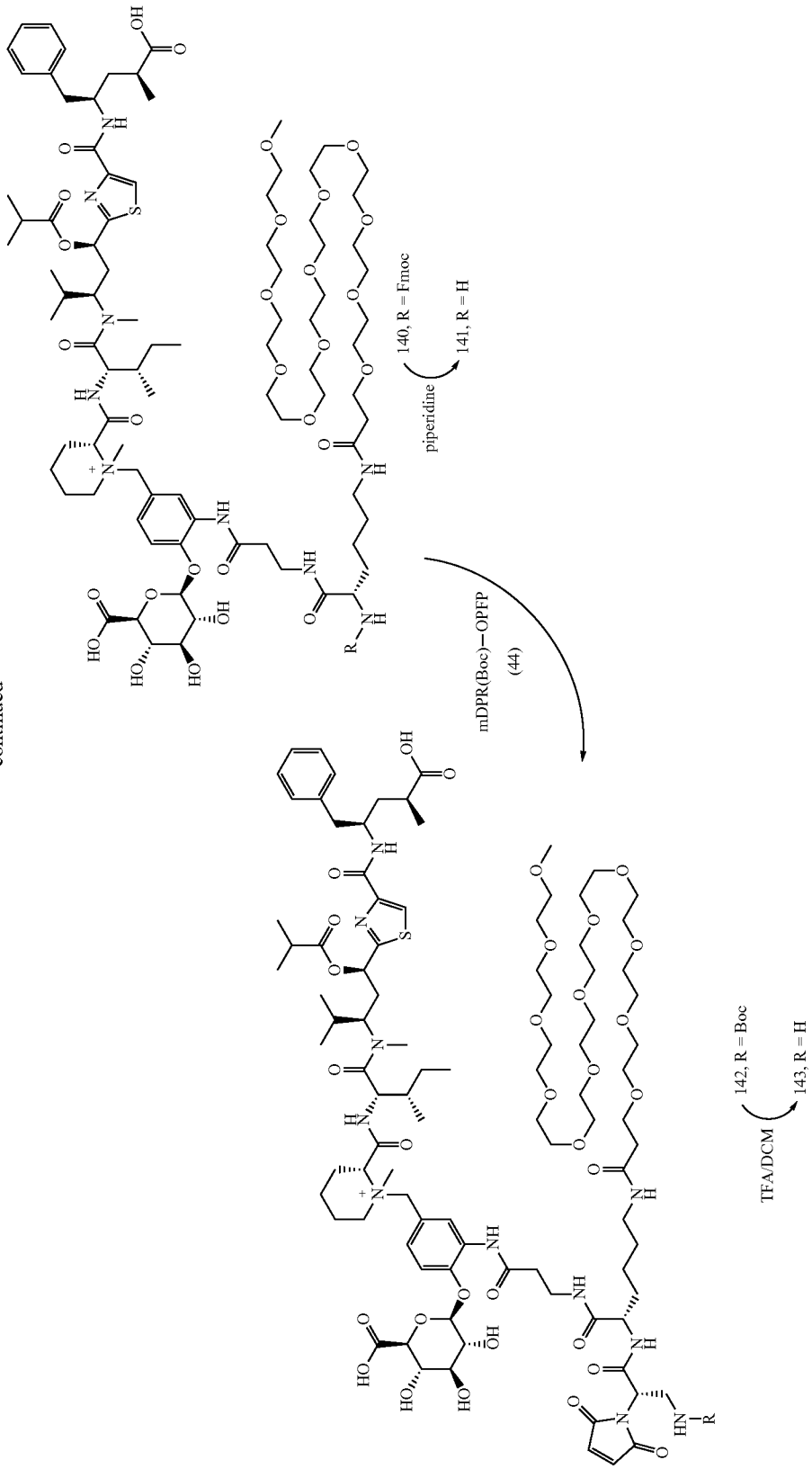

(2R)-1-(3-(3-((((9-fluoren-9-yl)methoxy)carbonyl) amino)propanamido)-4-(((2S,3R,4S,5S,6S)-6-((allyloxy)carbonyl)-3,4,5-trihydroxytetrahydro-2H-pyran-2-yl)oxy)benzyl)-2-(((2S,3S)-1-(((1R,3R)-1-(4-(((2R,4S)-5-(allyloxy)-4-methyl-5-oxo-1-phenylpentan-2-yl)carbamoyl)thiazol-2-yl)-1-(isobutyryloxy)-4-methylpentan-3-yl)(methyl)amino)-3-methyl-1-oxopentan-2-yl)carbamoyl)-1-methylpiperidin-1-ium (138)

To a flask charged with H-Ile-Tuv(O-isobutyrate)-Tup-OAllyl (125, 15 mg, 22 μmol) was added Fmoc-Gluc(Allyl)Q-Mep-OH (78, 17 mg, 22 μmol) and HATU (9 mg, 22 μmol) as solids followed by DMF (0.9 ml). N,N-Diisopropylethylamine (15 μl, 88 μmol) was added and the reaction was stirred at room temperature and monitored by UPLC/MS. The reaction was then taken up in DMSO and purified by preparative HPLC to provide 138 (4 mg, 13%). Analytical UPLC-MS (system 1): $t_r$=1.53 min, m/z (ES+) calculated 1426.69 $(M)^+$, found 1426.17.

(2R)-1-(3-(3-aminopropanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-(isobutyryloxy)-4-methylpentan-3-yl)(methyl)amino)-3-methyl-1-oxopentan-2-yl)carbamoyl)-1-methylpiperidin-1-ium (139)

Fmoc-Gluc(Allyl)Q-Tub(iso-O-Allyl) (138, 4 mg, 3 μmol) was taken up in DCM (0.3 ml) stirring under $N_2$. $Pd(PPh_3)_4$ (0.4 mg, 0.3 μmol) and $PPh_3$ (0.2 mg, 0.6 μmol) were added as solids followed by pyrrolidine (2 μl, 24 μmol). The reaction was stirred to 2 hours at room temperature, then taken up in DMSO, condensed under reduced pressure, and purified by preparative HPLC to provide 139 (3 mg, 88%). Analytical UPLC-MS (system 1): $t_r$=1.04 min, m/z (ES+) calculated 1124.56 $(M)^+$, found 1124.69.

(2R)-1-(3-((S)-44-((((9H-fluoren-9-yl)methoxy)carbonyl)amino)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-(isobutyryloxy)-4-methylpentan-3-yl)(methyl)amino)-3-methyl-1-oxopentan-2-yl)carbamoyl)-1-methylpiperidin-1-ium (140)

Fmoc-Lys(PEG12)-OSu (59, 10 mg, 9 μmol) was added to a flask charged with H-GlucQ-Tub(iso-O-allyl) (139, 3 mg, 3 μmol) as a solution in anhydrous DMF (0.3 ml) under $N_2$. N,N-Diisopropylethylamine (2 μl, 9 μmol) was added and the reaction was stirred at room temperature for 3 hours. The reaction was then quenched with acetic acid and purified by preparative HPLC to provide 140 (0.8 mg, 13%). Analytical UPLC-MS (system 2): $t_r$=1.35 min, m/z (ES+) calculated 1023.03 $(M+H)^{2+}$, found 1023.15.

(2R)-1-(3-((S)-44-amino-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-(isobutyryloxy)-4-methylpentan-3-yl)(methyl)amino)-3-methyl-1-oxopentan-2-yl)carbamoyl)-1-methylpiperidin-1-ium (141)

To a flask charged with Fmoc-Lys(PEG12)-GlucQ-Tub-(O-iso-allyl) (140, 0.8 mg, 0.4 μmol) was added 20% piperidine in DMF (0.2 ml). The reaction was stirred under $N_2$ at room temperature for 2 hours. The reaction was then diluted with $DMSO/H_2O$ and purified by preparative HPLC to provide 141 (3.6 mg, 82%). Analytical UPLC-MS (system 2): $t_r$=1.07 min, m/z (ES+) calculated 1822.98 $(M)^+$, found 1823.15.

(2R)-1-(3-((S)-44-((S)-3-((tert-butoxycarbonyl)amino)-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-(isobutyryloxy)-4-methylpentan-3-yl)(methyl)amino)-3-methyl-1-oxopentan-2-yl)carbamoyl)-1-methylpiperidin-1-ium (142)

A flask was charged with H-Lys(PEG12)-GlucQ-Tub-(O-iso-allyl) (141, 0.5 mg, 0.4 μmol) in anhydrous DMF (0.212 ml), to which mDPR(Boc)-OPFP (44, 1.4 mg, 3.2 μmol) was added as a solid under $N_2$. N,N-Diisopropylethylamine (0.74 μl, 4.2 μmol) was added and the reaction was stirred at room temperature for 3 hours. The reaction was then quenched with acetic acid, diluted with DMSO, and purified by preparative HPLC to provide 142 (0.5 mg, 61%). Analytical UPLC-MS (system 2): $t_r$=1.25 min, m/z (ES+) calculated 1045.04 $(M+H)^{2+}$, found 1045.16.

(2R)-1-(3-((S)-44-((S)-3-amino-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-1-(isobutyryloxy)-4-methylpentan-3-yl)(methyl)amino)-3-methyl-1-oxopentan-2-yl)carbamoyl)-1-methylpiperidin-1-ium (143)

A flask charged with mDPR(Boc)-Lys(PEG12)-GlucQ-Tub(O-iso-allyl) (142, 0.5 mg, 0.24 μmol) was cooled to 0° C. under $N_2$. A solution of 10% TFA in $CH_2Cl_2$ (0.26 ml) was added dropwise and stirred for 2 hours. The reaction was then taken up in DMSO, condensed under reduced pressure, and purified by preparative HPLC to provide 143 (0.7 mg, quant.). Analytical UPLC-MS (system 2): $t_r$=1.06 min, m/z (ES+) calculated 1989.02 $(M)^+$, found 1989.20.

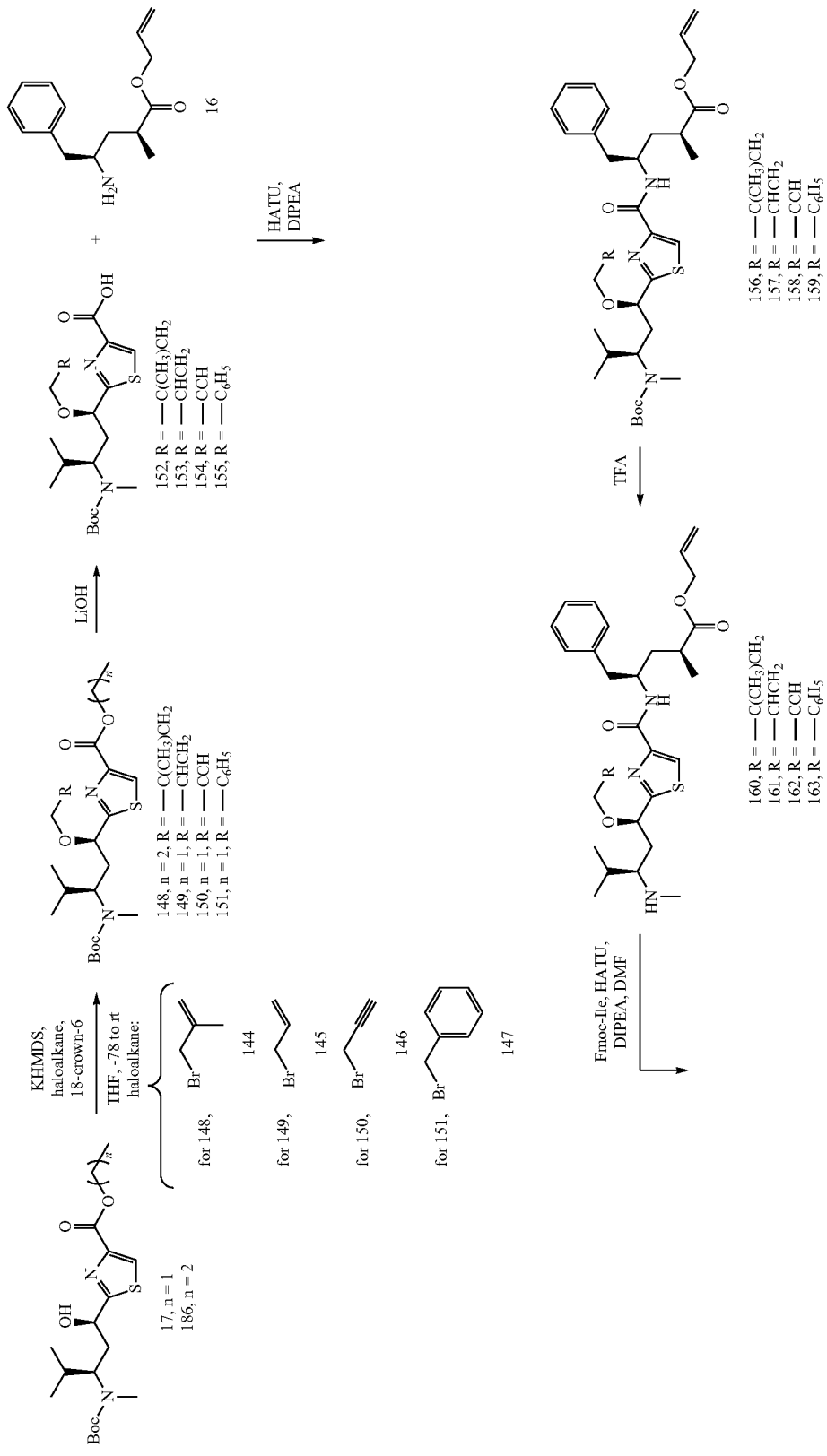

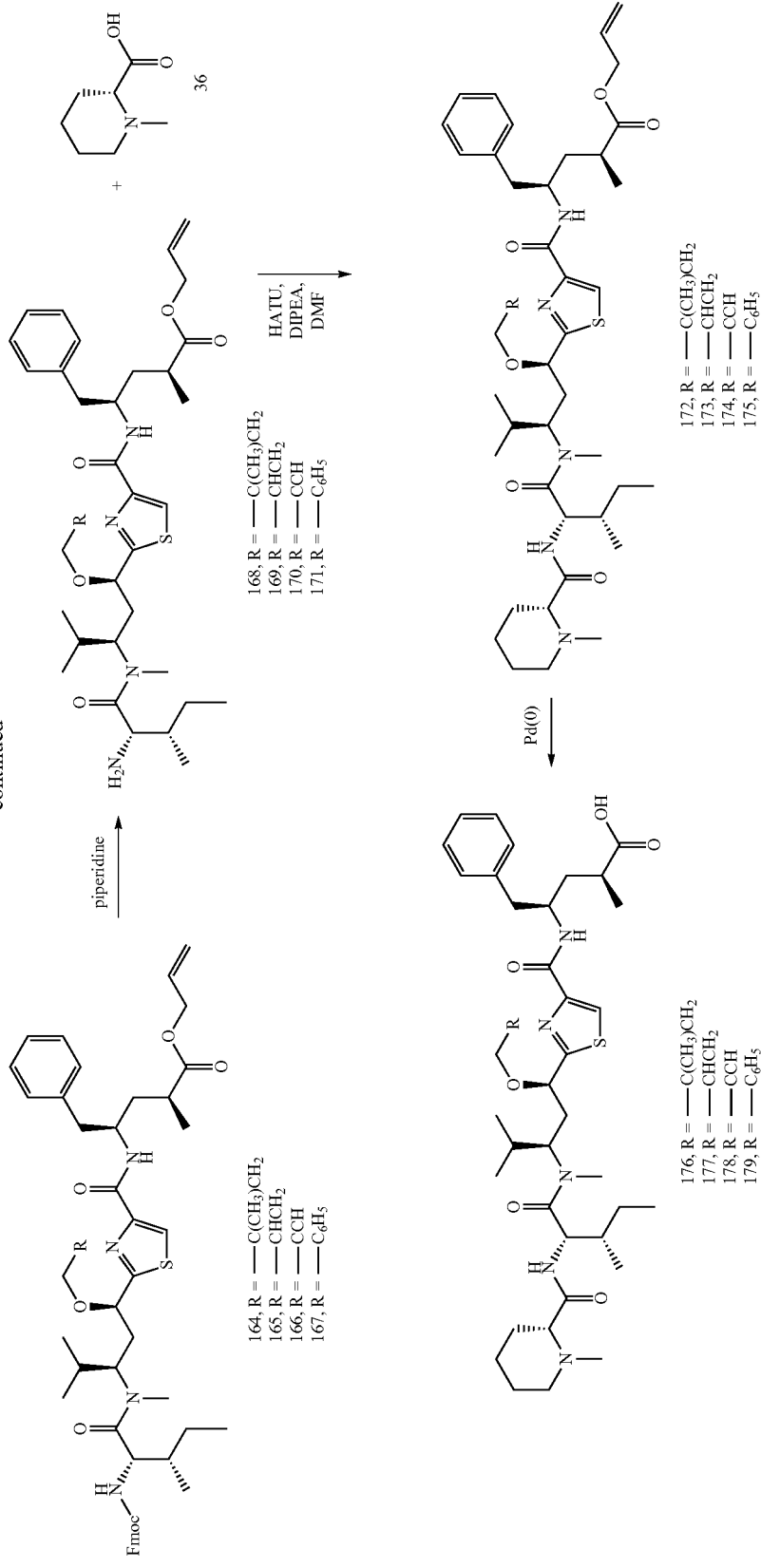

General Procedure for the Etherification of Tubuvaline.

A flame-dried flask was charged with the Boc-protected known tubuvaline (*J. Org. Chem.,* 2008, 73, 4362-4369) intermediate 17 (or 186) in anhydrous tetrahydrofuran (50 mM), to which was added 18-crown-6 (2.0 equivalents) and cooled to −78 C. Potassium hexamethyldisilazide (1.5 equivalents) as a 1 M solution in tetrahydrofuran was added dropwise and the reaction was then stirred for 1 hour at −78 C under nitrogen. Unsaturated bromoalkane (2 equivalents) was then added and the reaction slowly warmed to room temperature and followed by UPLC/MS. Once the starting material was consumed, the reaction was cooled on ice and quenched with saturated ammonium chloride and diluted in dichloromethane (10 volumes). The organic layer was washed with 0.1 M HCl and the resulting aqueous phase extracted twice with dichloromethane. The combined organics were then dried over sodium sulfate, filtered, and concentrated to dryness. Purification of the crude O-alkylated products was achieved by flash chromatography over silica gel or preparative HPLC.

Ethyl 2-((1R,3R)-3-((tert-butoxycarbonyl)(methyl) amino)-4-methyl-1-((2-methylallyl)oxy)pentyl)thiazole-4-carboxylate (148)

Propyl ester protected tubuvaline intermediate 186 (299 mg, 750 μmol) was O-alkylated as described above with 3-bromo-2-methylprop-1-ene (151 μl, 1.5 mmol) to provide 243 mg (71%) of the title compound after silica gel purification eluting methanol and dichloromethane mixtures. UPLC-MS (system 2): $t_r$=1.77 min, m/z (ES+) calculated 455.26 (M+H)$^+$, found 455.32.

Ethyl 2-((1R,3R)-1-(allyloxy)-3-((tert-butoxycarbonyl)(methyl)amino)-4-methylpentyl)thiazole-4-carboxylate (149)

Tubuvaline intermediate 17 (84 mg, 218 mol) was O-allylated as described above with allyl bromide (40 μl, 436 μmol) to provide 77 mg (83%) of the title compound after silica gel purification eluting methanol and dichloromethane mixtures. UPLC-MS (system 2): $t_r$=1.69 min, m/z (ES+) calculated 427.23 (M+H)$^+$, found 427.30.

Ethyl 2-((1R,3R)-3-((tert-butoxycarbonyl)(methyl) amino)-4-methyl-1-(prop-2-yn-1-yloxy)pentyl)thiazole-4-carboxylate (150)

Tubuvaline intermediate 17 (101 mg, 262 μmol) was O-propargylated as described above with propargyl bromide (56 μl, 524 μmol) to provide 76 mg (68%) of the title compound after purification. UPLC-MS (system 2): $t_r$=1.63 min, m/z (ES+) calculated 425.21 (M+H)$^+$, found 425.28.

Ethyl 2-((1R,3R)-1-(benzyloxy)-3-((tert-butoxycarbonyl)(methyl)amino)-4-methylpentyl)thiazole-4-carboxylate (151)

Tubuvaline intermediate 17 (90 mg, 230 μmol) was O-benzylated as described above with benzyl bromide (55 μl, 460 μmol) to provide 21 mg (19%) of the title compound after purification. UPLC-MS (system 1): $t_r$=1.95 min, m/z (ES+) calculated 477.24 (M+H)$^+$, found 477.22.

General Procedure for the Saponification of O-Alkylated Tubuvaline Esters.

Saponification reactions were carried out at 20 mM reaction concentration using a 1:1:1 mixture of tetrahydrofuran: methanol:water solvent mixture. O-alkylated tubuvaline intermediates 148-151 were dissolved in 1 volume each tetrahydrofuran and methanol. The mixture was then cooled in an ice bath at 0 C. Lithium hydroxide monohydrate (2-3 equivalents) was dissolved in 1 volume of distilled water and added dropwise to the reaction flask, with stirring at 0 C. The reaction was then allowed to warm up to room temperature and monitored by UPLC/MS. Once the starting material had converted to free acid, the reaction was quenched with glacial acetic acid (2-3 equivalents) and concentrated by rotary evaporation. The crude carboxylic acids were then purified by preparative HPLC.

2-((1R,3R)-3-((tert-butoxycarbonyl)(methyl)amino)-4-methyl-1-((2-methylallyl)oxy)pentyl)thiazole-4-carboxylic Acid (152)

Tubuvaline ether intermediate 148 (143 mg, 315 μmol) was saponified as described above with lithium hydroxide monohydrate (27 mg, 630 μmol) to provide 114 mg (88%) of the title compound. UPLC-MS (system 1): $t_r$=1.57 min, m/z (ES+) calculated 413.21, found 413.28.

2-((1R,3R)-1-(allyloxy)-3-((tert-butoxycarbonyl)(methyl)amino)-4-methylpentyl)thiazole-4-carboxylic Acid (153)

Tubuvaline allyl ether intermediate 149 (77 mg, 181 μmol) was saponified as described above with lithium hydroxide monohydrate (15 mg, 360 μmol) to provide 51 mg (71%) of the title compound. UPLC-MS (system 2): $t_r$=1.51 min, m/z (ES+) calculated 399.20 (M+H)$^+$, found 399.26.

2-((1R,3R)-3-((tert-butoxycarbonyl)(methyl)amino)-4-methyl-1-(prop-2-yn-1-yloxy)pentyl)thiazole-4-carboxylic Acid (154)

Tubuvaline propargyl ether intermediate 150 (76 mg, 180 μmol) was saponified as described above with lithium hydroxide monohydrate (15 mg, 360 μmol) to provide 50 mg (69%) of the title compound. UPLC-MS (system 2): $t_r$=1.47 min, m/z (ES+) calculated 397.18 (M+H)$^+$, found 397.25.

2-((1R,3R)-1-(benzyloxy)-3-((tert-butoxycarbonyl)(methyl)amino)-4-methylpentyl)thiazole-4-carboxylic Acid (155)

Tubuvaline benzyl ether intermediate 151 (21 mg, 44 μmol) was saponified as described above with lithium hydroxide monohydrate (5.5 mg, 132 μmol) to provide the title compound. UPLC-MS (system 1): $t_r$=1.72 min, m/z (ES+) calculated 449.21 (M+H)$^+$, found 449.18.

General Procedure for the Amide Coupling of O-Alkylated Tubuvaline Free Acids and Tubuphenylalanine Allyl Ester:

O-alkylated tubuvaline free acids 152-155 were preactivated by dissolution in anhydrous dimethylformamide (25-50 mM) and addition of HATU (2.4 equivalents) and DIPEA (5 equivalents); the mixture was then stirred under nitrogen at room temperature for 10 minutes. The activated acid was then added to the known (*Org. Lett.,* 2007, 9, 1605-1607) tubuphenylalanine allyl ester 16 and the reaction was then stirred at an ambient temperature under nitrogen, with progress monitored by UPLC/MS. Upon reaction completion, glacial acetic acid (14 equivalents) was then added and the product was purified by preparative HPLC.

(2S,4R)-allyl 4-(2-((1R,3R)-3-((tert-butoxycarbonyl) (methyl)amino)-4-methyl-1-((2-methylallyl)oxy) pentyl)thiazole-4-carboxamido)-2-methyl-5-phenyl-pentanoate (156)

Tubuvaline ether intermediate 152 (114 mg, 277 µmol) was coupled to tubuphenylalanine (Tup) allyl ester 16 (137 mg, 554 µmol) to provide 159 mg (90%) of the title compound. UPLC-MS (system 1): $t_r$=1.97 min, m/z (ES+) calculated 642.36 (M+H)$^+$, found 642.44.

(2S,4R)-allyl 4-(2-((1R,3R)-1-(allyloxy)-3-((tert-butoxycarbonyl)(methyl)amino)-4-methylpentyl) thiazole-4-carboxamido)-2-methyl-5-phenylpentano-ate (157)

Tubuvaline allyl ether intermediate 153 (44 mg, 100 µmol) was coupled to tubuphenylalanine (Tup) allyl ester 16 (37 mg, 150 µmol) to provide 60 mg (95%) of the title compound. UPLC-MS (system 1): $t_r$=2.06 min, m/z (ES+) calculated 628.34 (M+H)$^+$, found 628.26.

(2S,4R)-allyl 4-(2-((1R,3R)-3-((tert-butoxycarbonyl) (methyl)amino)-4-methyl-1-(prop-2-yn-1-yloxy) pentyl)thiazole-4-carboxamido)-2-methyl-5-phenyl-pentanoate (158)

Tubuvaline propargyl ether intermediate 154 (42 mg, 106 µmol) was coupled to tubuphenylalanine (Tup) allyl ester 16 (52 mg, 212 µmol) to provide 48 mg (73%) of the title compound. UPLC-MS (system 2): $t_r$=1.73 min, m/z (ES+) calculated 626.33 (M+H)$^+$, found 626.41.

(2S,4R)-allyl 4-(2-((1R,3R)-1-(benzyloxy)-3-((tert-butoxycarbonyl)(methyl)amino)-4-methylpentyl) thiazole-4-carboxamido)-2-methyl-5-phenylpentano-ate (159)

Tubuvaline benzyl ether intermediate 155 (50 mg, 110 µmol) was coupled to tubuphenylalanine (Tup) allyl ester 16 (60 mg, 165 µmol) to provide 43 mg (58%) of the title compound. UPLC-MS (system 2): $t_r$=1.93 min, m/z (ES+) calculated 678.36 (M+H)$^+$, found 678.45.

General Procedure for the Boc Deprotection of Tuv (OAlk)-Tup Intermediates.

O-alkylated tubuvaline-tubuphenylalanine intermediates 156-159 were deprotected to reveal the secondary amine functional group under acidic conditions with 10% TFA in dichloromethane (25 mM). Specifically, the starting material was dissolved in anhydrous dichloromethane (9 volumes) and stirred under nitrogen at 0 C. Trifluoroacetic acid (1 volume) was then added dropwise to the stirred solution. The reaction was warmed slowly to room temperature and monitored by UPLC/MS. Upon completion, the reaction was concentrated by rotary evaporation and pumped down on a vacuum line overnight. The free amines 160-163 were carried forward without further purification.

(2S,4R)-allyl 2-methyl-4-(2-((1R,3R)-4-methyl-1-((2-methylallyl)oxy)-3-(methylamino)pentyl)thiaz-ole-4-carboxamido)-5-phenylpentanoate (160)

Boc-protected Tuv-Tup intermediate 156 (159 mg, 248 µmol) was deprotected as described above to provide 127 mg (95%) of the title compound. UPLC-MS (system 1): $t_r$=1.18 min, m/z (ES+) calculated 542.31 (M+H)$^+$, found 542.38.

(2S,4R)-allyl 4-(2-((1R,3R)-1-(allyloxy)-4-methyl-3-(methylamino)pentyl)thiazole-4-carboxamido)-2-methyl-5-phenylpentanoate (161)

Boc-protected Tuv(O-allyl)-Tup intermediate 157 (60 mg, 96 µmol) was deprotected as described above to provide 52 mg (quant.) of the title compound. UPLC-MS (system 1): $t_r$=1.16 min, m/z (ES+) calculated 528.29 (M+H)+, found 528.05.

(2S,4R)-allyl 2-methyl-4-(2-((1R,3R)-4-methyl-3-(methylamino)-1-(prop-2-yn-1-yloxy)pentyl)thiaz-ole-4-carboxamido)-5-phenylpentanoate (162)

Boc-protected Tuv(O-propargyl)-Tup intermediate 158 (39 mg, 62 µmol) was deprotected as described above to provide 45 mg (quant.) of the title compound. UPLC-MS (system 2): $t_r$=1.08 min, m/z (ES+) calculated 526.28 (M+H)$^+$, found 526.35.

(2S,4R)-allyl 4-(2-((1R,3R)-1-(benzyloxy)-4-methyl-3-(methylamino)pentyl)thiazole-4-carbox-amido)-2-methyl-5-phenylpentanoate (163)

Boc-protected Tuv(O-benzyl)-Tup intermediate 159 (38 mg, 56 µmol) was deprotected as described above to provide the title compound in quantitative yield. UPLC-MS (system 2): $t_r$=1.20 min, m/z (ES+) calculated 578.31 (M+H)$^+$, found 578.38.

General Procedure for the Amide Coupling of O-Alkylated Tubuvaline-Tubuphenylalanine Dipeptides with Fmoc-Protected L-Isoleucine.

Commercially available Fmoc-L-Isoleucine (1.3-2 equivalents) was dissolved in anhydrous dimethylformamide (50-200 mM) and pre-activated with HATU (1.5-2 equivalents) and DIPEA (2 equivalents); the mixture was stirred for 10 minutes at room temperature under nitrogen. The activated acid was then added to the Tuv(O-ether)-Tup dipeptides 160-163; the reaction was stirred at room temperature under nitrogen and monitored by UPLC/MS. Once the reaction had stopped progressing or had reached completion, glacial acetic acid (13 equivalents) was added and the reaction was purified by prep HPLC.

(2S,4R)-allyl 4-(2-((5S,8R,10R)-5-((S)-sec-butyl)-1-(9H-fluoren-9-yl)-8-isopropyl-7,13-dimethyl-3,6-dioxo-2,11-dioxa-4,7-diazatetradec-13-en-10-yl) thiazole-4-carboxamido)-2-methyl-5-phenylpentanoate (164)

Tuv-Tup intermediate 160 (127 mg, 235 µmol) was coupled to Fmoc-L-Ile as described above to provide 90 mg (44%) of the title compound. UPLC-MS (system 1): $t_r$=2.14 min, m/z (ES+) calculated 877.46 (M+H)$^+$, found 877.56.

(2S,4R)-allyl 4-(2-((5S,8R,10R)-5-((S)-sec-butyl)-1-(9H-fluoren-9-yl)-8-isopropyl-7-methyl-3,6-dioxo-2, 11-dioxa-4,7-diazatetradec-13-en-10-yl)thiazole-4-carboxamido)-2-methyl-5-phenylpentanoate (165)

Tuv(O-allyl)-Tup intermediate 161 (52 mg, 100 µmol) was coupled to Fmoc-L-Ile as described above to provide 38 mg (44%) of the title compound. UPLC-MS (system 2): $t_r$=1.94 min, m/z (ES+) calculated 863.44 (M+H)$^+$, found 863.54.

(2S,4R)-allyl 4-(2-((5S,8R,10R)-5-((S)-sec-butyl)-1-(9H-fluoren-9-yl)-8-isopropyl-7-methyl-3,6-dioxo-2,11-dioxa-4,7-diazatetradec-13-yn-10-yl)thiazole-4-carboxamido)-2-methyl-5-phenylpentanoate (166)

Tuv(O-propargyl)-Tup intermediate 162 (62 µmol) was coupled to Fmoc-L-Ile as described above to provide 33 mg (62%) of the title compound. UPLC-MS (system 2): $t_r$=1.83 min, m/z (ES+) calculated 861.43 (M+H)$^+$, found 861.53.

(2S,4R)-allyl 4-(2-((5S,8R,10R)-5-((S)-sec-butyl)-1-(9H-fluoren-9-yl)-8-isopropyl-7-methyl-3,6-dioxo-12-phenyl-2,11-dioxa-4,7-diazadodecan-10-yl)thiazole-4-carboxamido)-2-methyl-5-phenylpentanoate (167)

Tuv(O-benzyl)-Tup intermediate 163 (56 µmol) was coupled to Fmoc-L-Ile as described above to provide 23 mg (45%) of the title compound. UPLC-MS (system 2): $t_r$=2.04 min, m/z (ES+) calculated 913.46 (M+H)$^+$, found 913.56.

General Procedure for the Fmoc-Deprotection of Isoleucine-O-Alkylated Tubuvaline-Tubuphenylalanine Tripeptides:

Fmoc-Ile-Tuv(O-ether)-Tup allyl ester (164-167) was treated with 20% piperidine in dimethylformamide (20 mM), with stirring under nitrogen at room temperature. Once complete deprotection had been achieved, as monitored by UPLC/MS, the reaction mixture was concentrated by rotary evaporation. The crude product was then purified by preparative HPLC to provide free amine tripeptides 168-171.

(2S,4R)-allyl 4-(2-((1R,3R)-3-((2S,3S)-2-amino-N,3-dimethylpentanamido)-4-methyl-1-((2-methylallyl)oxy)pentyl)thiazole-4-carboxamido)-2-methyl-5-phenylpentanoate (168)

Fmoc-Ile-Tuv-Tup intermediate 164 (90 mg, 103 µmol) was deprotected as described above to provide 29 mg (43%) of the title compound. UPLC-MS (system 1): $t_r$=1.29 min, m/z (ES+) calculated 655.39 (M+H)$^+$, found 655.48.

(2S,4R)-allyl 4-(2-((1R,3R)-1-(allyloxy)-3-((2S,3S)-2-amino-N,3-dimethylpentanamido)-4-methylpentyl)thiazole-4-carboxamido)-2-methyl-5-phenylpentanoate (169)

Fmoc-Ile-Tuv(O-allyl)-Tup intermediate 165 (38 mg, 44 µmol) was deprotected as described above to provide 25 mg (89%) of the title compound. UPLC-MS (system 2): $t_r$=1.20 min, m/z (ES+) calculated 641.38 (M+H)$^+$, found 641.46.

(2S,4R)-allyl 4-(2-((1R,3R)-3-((2S,3S)-2-amino-N,3-dimethylpentanamido)-4-methyl-1-(prop-2-yn-1-yloxy)pentyl)thiazole-4-carboxamido)-2-methyl-5-phenylpentanoate (170)

Fmoc-Ile-Tuv(O-propargyl)-Tup intermediate 166 (33 mg, 38 µmol) was deprotected as described above to provide 25 mg (quant.) of the title compound. UPLC-MS (system 2): $t_r$=1.15 min, m/z (ES+) calculated 639.36 (M+H)$^+$, found 639.44.

(2S,4R)-allyl 4-(2-((1R,3R)-3-((2S,3S)-2-amino-N,3-dimethylpentanamido)-1-(benzyloxy)-4-methylpentyl)thiazole-4-carboxamido)-2-methyl-5-phenylpentanoate (171)

Fmoc-Ile-Tuv(O-benzyl)-Tup intermediate 167 (23 mg, 25 µmol) was deprotected as described above to provide the title compound in quantitative yield. UPLC-MS (system 2): $t_r$=1.30 min, m/z (ES+) calculated 691.39 (M+H)$^+$, found 691.48.

General Procedure for the Amide Coupling of Isoleucine-Tubuvaline(Ether)-Tubuphenylalanine Tripeptides with (R)—N-Methyl-Pipecolic Acid:

Commercially available (R)—N-methyl-pipecolic acid (D-Mep) 36 (1.5-2 equivalents) was dissolved in anhydrous dimethylformamide (25-50 mM) and pre-activated with HATU (2 equivalents) and DIPEA (4 equivalents); the mixture was stirred for 10 minutes at room temperature under nitrogen. The activated acid was then added to the Ile-Tuv(O-ether)-Tup tripeptides 168-171; the reaction was stirred at room temperature under nitrogen and monitored by UPLC/MS. Upon reaction completion, glacial acetic acid (14 equivalents) was then added and the product was purified by preparative HPLC.

(2S,4R)-allyl 4-(2-((1R,3R)-3-((2S,3S)—N,3-dimethyl-2-((R)-1-methylpiperidine-2-carboxamido)pentanamido)-4-methyl-1-((2-methylallyl)oxy)pentyl)thiazole-4-carboxamido)-2-methyl-5-phenylpentanoate (172)

Ile-Tuv-Tup intermediate 168 (55 mg, 84 µmol) was coupled to D-Mep 36 as described above to provide 40 mg (62%) of the title compound. UPLC-MS (system 1): $t_r$=1.27 min, m/z (ES+) calculated 780.48 (M+H)$^+$, found 780.58.

(2S,4R)-allyl 4-(2-((1R,3R)-1-(allyloxy)-3-((2S,3S)—N,3-dimethyl-2-((R)-1-methylpiperidine-2-carboxamido)pentanamido)-4-methylpentyl)thiazole-4-carboxamido)-2-methyl-5-phenylpentanoate (173)

Ile-Tuv(O-allyl)-Tup intermediate 169 (5 mg, 7.8 µmol) was coupled to D-Mep 36 as described above to provide 6 mg (quant.) of the title compound. UPLC-MS (system 2): $t_r$=1.28 min, m/z (ES+) calculated 766.46 (M+H)$^+$, found 766.54.

(2S,4R)-allyl 4-(2-((1R,3R)-3-((2S,3S)—N,3-dimethyl-2-((R)-1-methylpiperidine-2-carboxamido)pentanamido)-4-methyl-1-(prop-2-yn-1-yloxy)pentyl)thiazole-4-carboxamido)-2-methyl-5-phenylpentanoate (174)

Ile-Tuv(O-propargyl)-Tup intermediate 170 (18 mg, 28 µmol) was coupled to D-Mep 36 as described above to provide 20 mg (93%) of the title compound. UPLC-MS (system 2): $t_r$=1.23 min, m/z (ES+) calculated 764.44 (M+H)$^+$, found 764.53.

(2S,4R)-allyl 4-(2-((1R,3R)-1-(benzyloxy)-3-((2S,3S)—N,3-dimethyl-2-((R)-1-methylpiperidine-2-carboxamido)pentanamido)-4-methylpentyl)thiazole-4-carboxamido)-2-methyl-5-phenylpentanoate (175)

Ile-Tuv(O-benzyl)-Tup intermediate 171 (5 mg, 7 µmol) was coupled to D-Mep 36 as described above to provide 4.4 mg (75%) of the title compound. UPLC-MS (system 1): $t_r$=1.42 min, m/z (ES+) calculated 816.48 (M+H)$^+$, found 816.64.

General Procedure for the Allyl Ester Removal from D-Methylpipecolic Acid-Isoleucine-Tubuvaline(Ether)-Tubuphenylalanine Tubulysin Intermediates:

Allyl ester-protected tubulysin ether intermediate (172-175) was dissolved in anhydrous dichloromethane (20 mM)

treated with palladium tetrakis(triphenylphosphine) (0.1 equiv.), triphenylphosphine (0.2 equivalents), and anhydrous pyrrolidine (8 equivalents), and the reaction was stirred at an ambient temperature under nitrogen. Once UPLC/MS revealed conversion to the product free acid, the reaction was quenched with glacial acetic acid (22 equivalents), diluted with acetonitrile and dimethylformamide, and then concentrated by rotary evaporation. The crude tubulysin ether was then purified by preparative HPLC.

(2S,4R)-4-(2-((1R,3R)-3-((2S,3S)—N,3-dimethyl-2-((R)-1-methylpiperidine-2-carboxamido)pentanamido)-4-methyl-1-((2-methylallyl)oxy)pentyl)thiazole-4-carboxamido)-2-methyl-5-phenylpentanoic Acid (176)

Allyl ester-protected tubulysin methylallyl ether intermediate 172 (19 mg, 24 μmol) was deprotected as described above to provide 14 mg (93%) of tubulysin ether 176. UPLC-MS (system 2): $t_r$=1.16 min, m/z (ES+) calculated 740.44 (M+H)$^+$, found 740.54.

(2S,4R)-4-(2-((1R,3R)-1-(allyloxy)-3-((2S,3S)—N,3-dimethyl-2-((R)-1-methylpiperidine-2-carboxamido)pentanamido)-4-methylpentyl)thiazole-4-carboxamido)-2-methyl-5-phenylpentanoic Acid (177)

Allyl ester-protected tubulysin allyl ether intermediate 173 (7 mg, 9 μmol) was deprotected as described above to provide 6 mg (92%) of tubulysin allyl ether 177. UPLC-MS (system 1): $t_r$=1.20 min, m/z (ES+) calculated 726.43 (M+H)$^+$, found 726.33.

(2S,4R)-4-(2-((1R,3R)-3-((2S,3S)—N,3-dimethyl-2-((R)-1-methylpiperidine-2-carboxamido)pentanamido)-4-methyl-1-(prop-2-yn-1-yloxy)pentyl)thiazole-4-carboxamido)-2-methyl-5-phenylpentanoic Acid (178)

Allyl ester-protected tubulysin propargyl ether intermediate 174 (5.2 mg, 6.8 μmol) was deprotected as described above to provide 2.7 mg (55%) of tubulysin propargyl ether 178. UPLC-MS (system 2): $t_r$=1.09 min, m/z (ES+) calculated 724.41 (M+H)$^+$, found 724.50.

(2S,4R)-4-(2-((1R,3R)-1-(benzyloxy)-3-((2S,3S)—N,3-dimethyl-2-((R)-1-methylpiperidine-2-carboxamido)pentanamido)-4-methylpentyl)thiazole-4-carboxamido)-2-methyl-5-phenylpentanoic Acid (179)

Allyl ester-protected tubulysin benzyl ether intermediate 175 (5 mg, 6 μmol) was deprotected as described above to provide 4.5 mg (96%) of tubulysin benzyl ether 179. UPLC-MS (system 1): $t_r$=1.26 min, m/z (ES+) calculated 776.44 (M+H)$^+$, found 776.58.

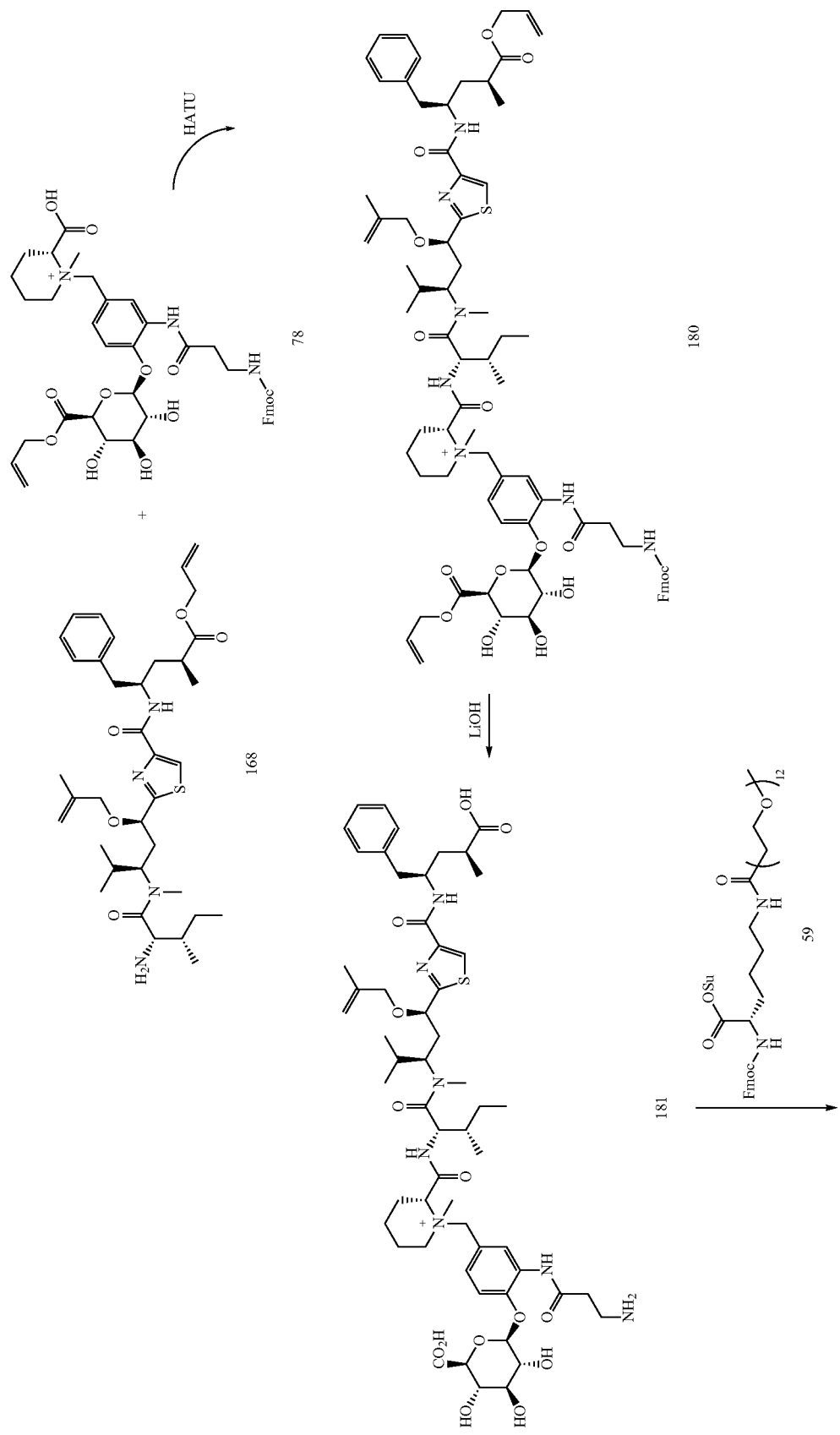

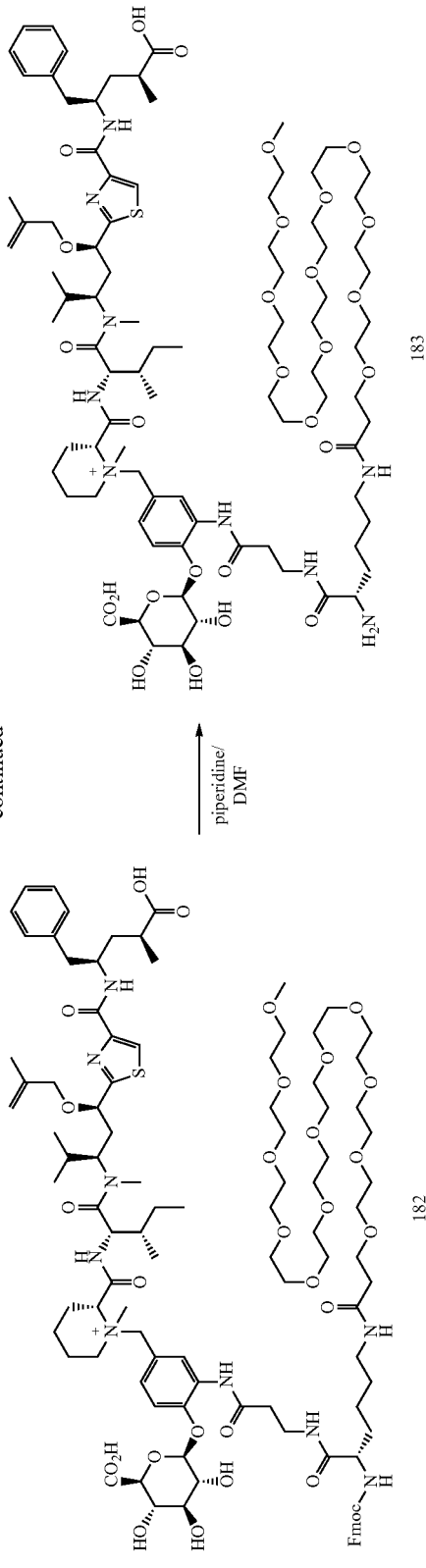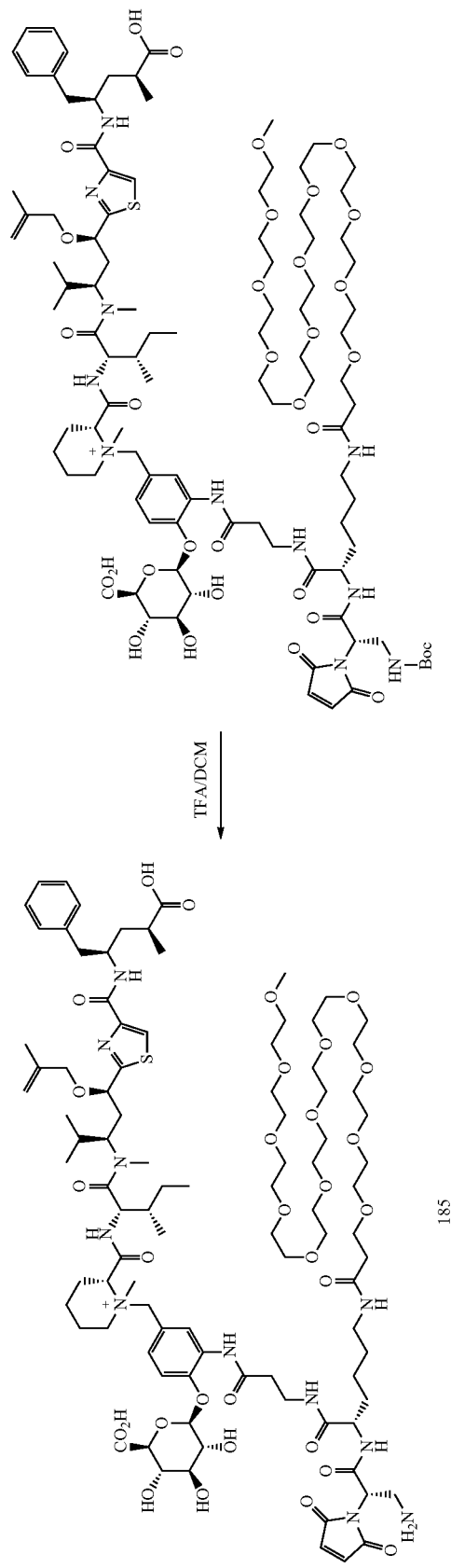

(2R)-1-(3-(3-(((((9H-fluoren-9-yl)methoxy)carbonyl) amino)propanamido)-4-(((2S,3R,4S,5S,6S)-6-((allyloxy)carbonyl)-3,4,5-trihydroxytetrahydro-2H-pyran-2-yl)oxy)benzyl)-2-(((2S,3S)-1-(((1R,3R)-1-(4-(((2R,4S)-5-(allyloxy)-4-methyl-5-oxo-1-phenylpentan-2-yl)carbamoyl)thiazol-2-yl)-4-methyl-1-((2-methylallyl)oxy)pentan-3-yl)(methyl) amino)-3-methyl-1-oxopentan-2-yl)carbamoyl)-1-methylpiperidin-1-ium (180)

To a flask charged with H-Ile-Tuv(O-methylpropene)-Tup-OAllyl (168, 24 mg, 31 μmol) was added Fmoc-Gluc(Allyl)Q-Mep-OH (78, 28 mg, 31 μmol) and HATU (18 mg, 45 μmol) as solids followed by THF (1.2 mL). N,N-Diisopropylethylamine (19 μL, 109 μmol) was added and the reaction was stirred at room temperature for 1 hour. The reaction was then taken up in DMSO and purified by preparative LC to provide 180 (21 mg, 49%). Analytical UPLC-MS (system 2): $t_r$=1.46 min, m/z (ES+) calculated 1410.69 (M)$^+$, found 1410.84.

(2R)-1-(3-(3-aminopropanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-4-methyl-1-((2-methylallyl)oxy)pentan-3-yl)(methyl)amino)-3-methyl-1-oxopentan-2-yl)carbamoyl)-1-methylpiperidin-1-ium (181)

Fmoc-GlucQ-Tub(O-methylpropene)-OAllyl 180 (12 mg, 8 μmol) was deprotected as above (see: General procedure for global deprotection of Fmoc-GlucQ-Tub(OR)-OAllyl) to provide 181 (8.6 mg, 97%). Analytical UPLC-MS (system 1): $t_r$=1.02 min, m/z (ES+) calculated 1108.56 (M)$^+$, found 1108.69.

(2R)-1-(3-((S)-44-(((((9H-fluoren-9-yl)methoxy)carbonyl)amino)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-4-methyl-1-((2-methylallyl)oxy)pentan-3-yl)(methyl) amino)-3-methyl-1-oxopentan-2-yl)carbamoyl)-1-methylpiperidin-1-ium (182)

H-GlucQ-Tub(O-methylpropene) 181 (12.5 mg, 11 μmol) was coupled to Fmoc-Lys(PEG12)-OSu 59 (14 mg, 13.5 μmol) as above (see: General procedure for coupling of H-GlucQ-Tub(OR) to Fmoc-Lys(PEG12)-OSu) to provide 182 (13 mg, 56%). Analytical UPLC-MS (system 2): $t_r$=1.32 min, m/z (ES+) calculated 2029.05 (M)$^+$, found 2029.24.

(2R)-1-(3-((S)-44-amino-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl)thiazol-2-yl)-4-methyl-1-((2-methylallyl)oxy)pentan-3-yl)(methyl)amino)-3-methyl-1-oxopentan-2-yl)carbamoyl)-1-methylpiperidin-1-ium (183)

Fmoc-Lys(PEG 12)-GlucQ-Tub(O-methylpropene) 182 (13 mg, 6 μmol) was deprotected as above (see: General procedure deprotection of Fmoc-Lys(PEG12)-GlucQ-Tub(OR)) to provide 183 (11 mg, quant.). Analytical UPLC-MS (system 2): $t_r$=1.04 min, m/z (ES+) calculated 1806.98 (M)$^+$, found 1807.16.

(2R)-1-(3-((S)-44-((S)-3-((tert-butoxycarbonyl) amino)-2-(2,5-dioxo-2,5-dihydro-1H-pyrrol-1-yl) propanamido)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl) thiazol-2-yl)-4-methyl-1-((2-methylallyl)oxy)pentan-3-yl)(methyl)amino)-3-methyl-1-oxopentan-2-yl) carbamoyl)-1-methylpiperidin-1-ium (184)

H-Lys(PEG12)-GlucQ-Tub(O-methylpropene) 183 (11.5 mg, 6.4 μmol) was coupled to mDPR-OPFP 44 (4.3 mg, 9.5 μmol) as above (see: General procedure for coupling H-Lys(PEG12)-GlucQ-Tub(OR) to mDPR-OPFP) to provide 184 (8.3 mg, 63%). Analytical UPLC-MS (system 2): $t_r$=1.24 min, m/z (ES+) calculated 2073.07 (M)$^+$, found 2073.25.

(2R)-1-(3-((S)-44-((S)-3-amino-2-(2,5-dioxo-2,5-dihydro-1H-pyrrol-1-yl)propanamido)-38,45-dioxo-2,5,8,11,14,17,20,23,26,29,32,35-dodecaoxa-39,46-diazanonatetracontanamido)-4-(((2S,3R,4S,5S,6S)-6-carboxy-3,4,5-trihydroxytetrahydro-2H-pyran-2-yl)oxy)benzyl)-2-(((2S,3S)-1-(((1R,3R)-1-(4-(((2R,4S)-4-carboxy-1-phenylpentan-2-yl)carbamoyl) thiazol-2-yl)-4-methyl-1-((2-methylallyl)oxy)pentan-3-yl)(methyl)amino)-3-methyl-1-oxopentan-2-yl) carbamoyl)-1-methylpiperidin-1-ium (185)

mDPR(Boc)-Lys(PEG12)-GlucQ-Tub(O-methylpropene) 184 (8.3 mg, 4 μmol) was deprotected as above (see: General procedure for deprotection of mDPR(Boc)-Lys(PEG12)-GlucQ-Tub(OR)) to provide 185 (7.4 mg, 94%). Analytical UPLC-MS (system 2): $t_r$=1.05 min, m/z (ES+) calculated 1973.02 (M)$^+$, found 1973.21.

Solid Phase Synthesis of TubOEt Analogues Replacing Tubulysin Ile or D-Mep Residues:

Scheme 18

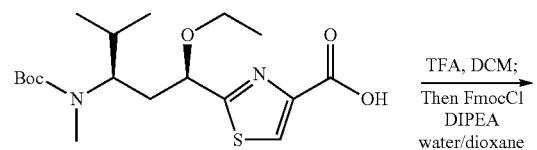

22

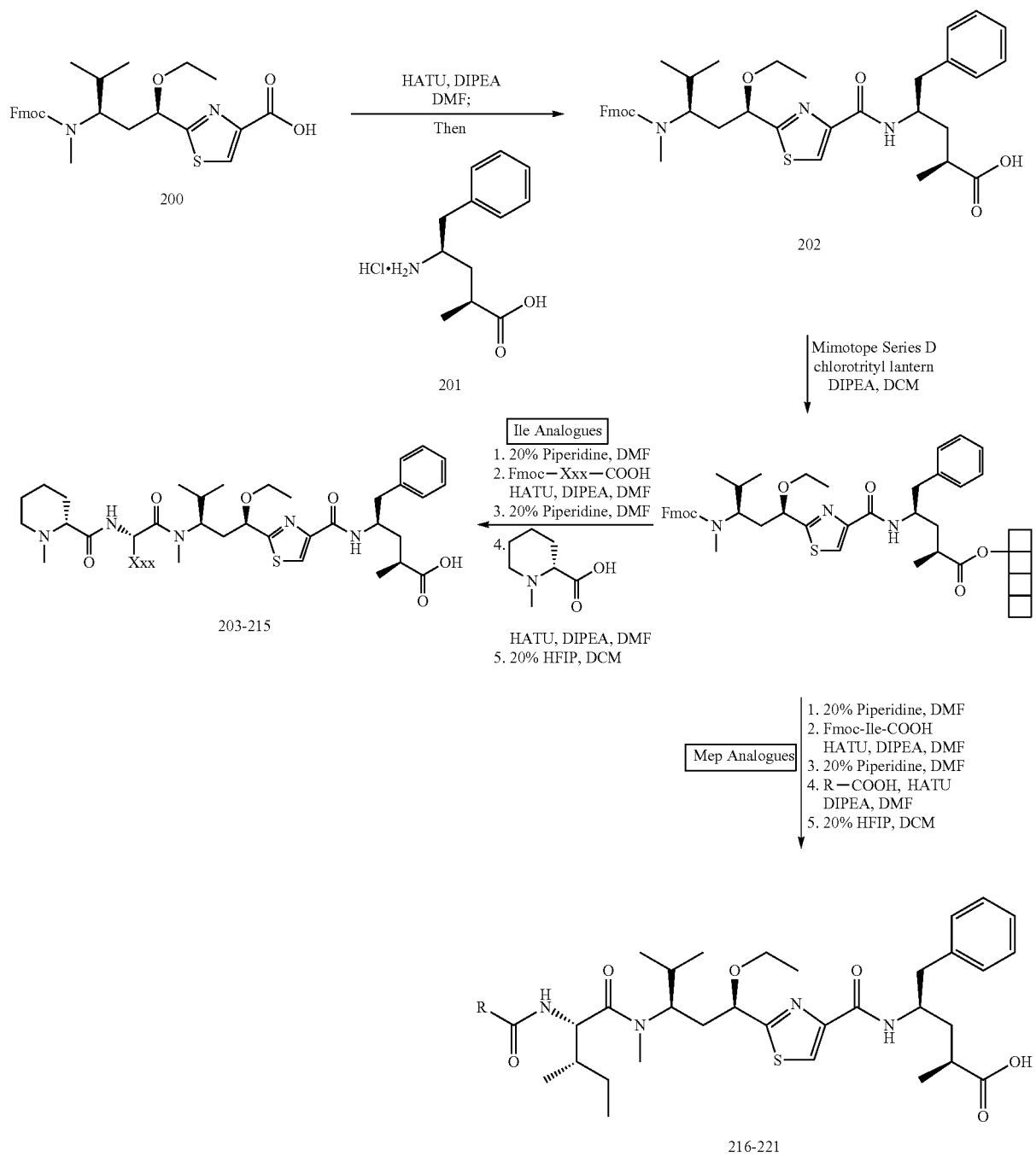

2-((1R,3R)-3-((((9H-fluoren-9-yl)methoxy)carbonyl)(methyl)amino)-1-ethoxy-4-methylpentyl)thiazole-4-carboxylic Acid (200)

A vial was charged with Boc-MeN-TuvOEt-COOH (22, 153 mg, 0.40 mmol) and dissolved in anhydrous DCM (4 mL). The solution was cooled to 0° C., then TFA (0.40 mL, 5.22 mmol) was added dropwise. Following the TFA addition the reaction was allowed to slowly warm to room temperature. After 4 h complete removal of the Boc protecting group was observed. The reaction was diluted with 5 mL of toluene and concentrated to dryness. The intermediate amine was used without further purification. Analytical UPLC-MS (system 1): $t_r$=0.86 min, m/z (ES+) calculated 287.1 (M+H)$^+$, found 287.2. The intermediate amine-trifluoroacetic acid salt was dissolved in 1,4-dioxane (2.0 mL), then water (2.0 mL) and DIPEA (0.41 mL, 2.4 mmol) were added. A solution of FmocCl (122 mg, 0.47 mmol) in 1,4-dioxane was then added dropwise. After 8 h the reaction was diluted with 10% DMSO in MeCN and purified by preparative HPLC to provide FmocMeN-TuvOEt-COOH (200, 88 mg, 44%). Analytical UPLC-MS (system 1): $t_r$=2.35 min, m/z (ES+) calculated 509.2 (M+H)$^+$, found 509.2; calculated 531.2 (M+Na)$^+$, found 531.1

(2S,4R)-4-(2-((1R,3R)-3-((((9H-fluoren-9-yl)methoxy)carbonyl)(methyl)-amino)-1-ethoxy-4-methylpentyl)thiazole-4-carboxamido)-2-methyl-5-phenylpentanoic Acid (202)

FmocMeN-TuvOEt-COOH (200, 80 mg, 0.16 mmol) was dissolved in anhydrous DMF (0.8 mL) and then a solution HATU (60 mg, 0.16 mmol) in anhydrous DMF (0.8 mL) was added, followed by DIPEA (0.21 mL, 1.2 mmol). After 5 min the hydrochloride salt of (2S,4R)-4-amino-2-methyl-5-phenylpentanoic Acid (201, HCl·Tup-COOH, 96 mg, 0.39 mmol) was added in one portion. The reaction was stirred for 5 h at room temperature, then diluted with 10% DMSO in MeCN and purified by preparative HPLC to provide Fmoc-MeN-TuvOEt-Tup-COOH (202, 95 mg, 87%). Analytical UPLC-MS (system 1): $t_r$=2.40 min, m/z (ES+) calculated 698.3(M+H)$^+$, found 698.3.

General Procedure for Chlorotrityl Lantern Loading:

Six SynPhase™ polyacrylamide series-D lanterns functionalized with a trityl alcohol linker and a nominal loading of 8 µmol (Mimotopes, Victoria, Australia) were placed in a dry vial and converted to the trityl chloride linker by treatment with 3 mL of a 10% AcCl in anhydrous DCM solution. After 3 h of gentle swirling at room temperature the solution was removed and the lanterns were washed 3 times with 5 mL of anhydrous DCM. Next, a solution of 202 (57 mg, 81.7 µmol) and DIPEA (57 µL, 327 µmol) in 3 mL of anhydrous DCM was added to the lanterns. After 5 h of gentle swirling at room temperature the solution was removed from the lanterns and the lanterns were washed 3 times with 5 mL of DMF, 3 times with 5 mL of DCM, then dried overnight under a stream of argon to obtain lanterns loaded with FmocMeN-TuvOEt-Tup.

General Procedure for the Preparation of Ile Replacement Analogues of TubOEt (203-215):

Step 1: Fmoc Removal. A lantern loaded with FmocMeN-TuvOEt-Tup as prepared above was treated with 1 mL of 20% piperidine in DMF for 30 min. The solution was removed and the lantern was then washed 3 times with 1.5 mL of DMF. Step 2: Amino Acid Coupling. In a separate vial 0.5 mL of a 240 mM solution of the appropriate Fmoc-protected amino acid (FmocHN-Xxx-COOH) in DMF and 0.5 mL of a 200 mM solution of HATU in DMF were combined and DIPEA (45 µL, 0.24 mmol) was added. After 2 min the activated amino acid solution was added to the lantern and gently stirred for 2 h. The lantern was treated a second time with the activated Fmoc amino acid solution for 2 h. The solution was then removed and the lantern was washed 3 times with 1.5 mL DMF. Step 3: Fmoc Removal. The lantern loaded with FmocHNXxx-TuvOEt-Tup was treated with 1 mL of 20% piperidine in DMF for 30 min. The solution was removed, and then the lantern was washed 3 times with 1.5 mL of DMF. Step 4: Mep Coupling. In a separate vial 0.5 mL of a 240 mM solution of (R)-1-methylpiperidine-2-carboxylic acid (Mep) in DMF and 0.5 mL of a 200 mM solution of HATU in DMF were combined, and DIPEA (45 µL, 0.24 mmol) was added. After 2 min the activated Mep solution was added to the lantern and gently stirred for 1.5 h. The solution was removed and the lantern was then washed 3 times with 1.5 mL DMF and 3 times with 1.5 mL of DCM. Step 5: Cleavage from the Lantern. Each lantern was treated for 90 min with a 20% HFIP solution in DCM. The solution was removed and the lantern was washed with an additional 0.5 mL of 20% HFIP in DCM. The combined solutions were filtered through a 45 micron syringe filter and concentrated to dryness to provide analogues 203-215 (shown immediately below). The analogues were obtained in >85% purity based on UPLC-MS analysis and the diode array chromatogram.

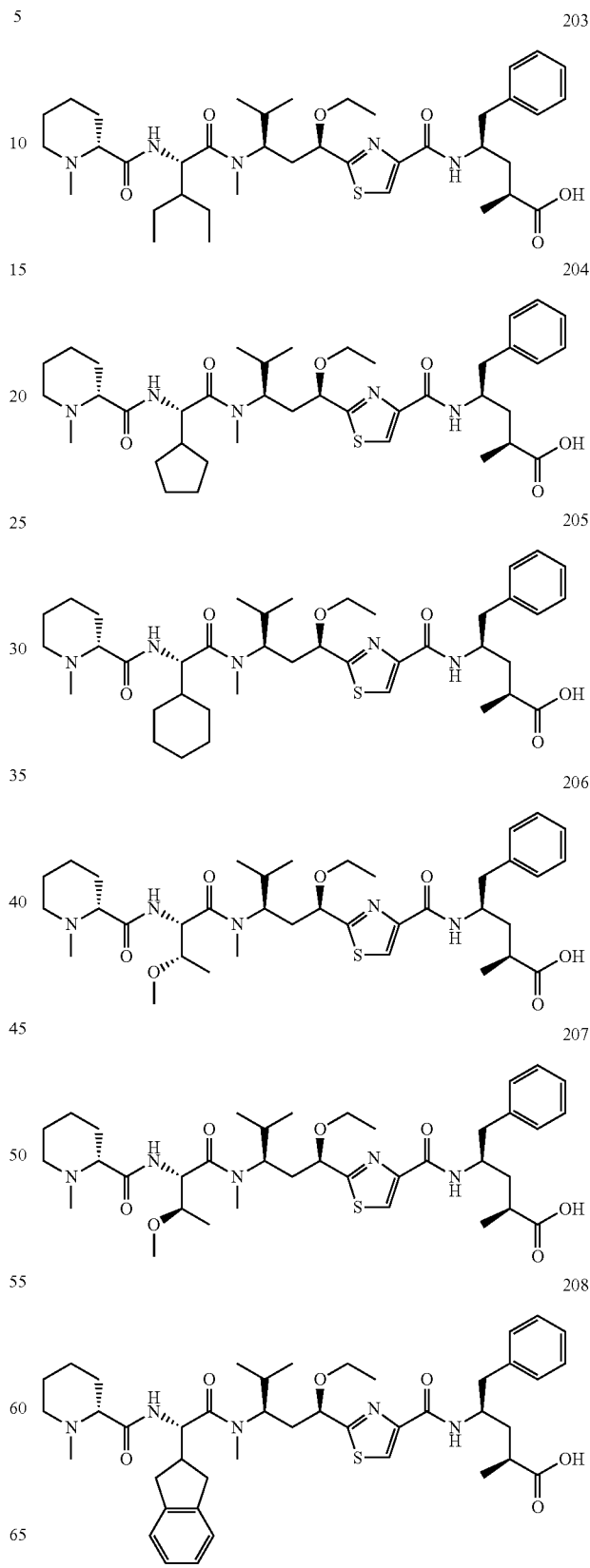

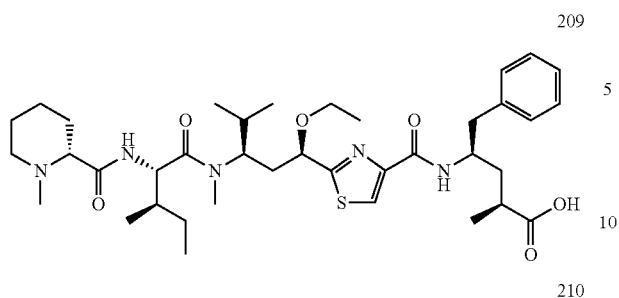

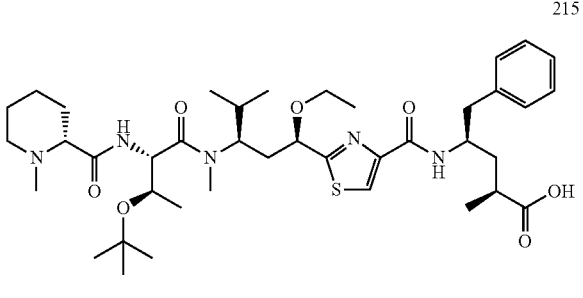 [SMILES: CCO[C@H](C[C@H](C(C)C)N(C)C(=O)[C@@H](NC(=O)[C@H]1CCCCN1C)[C@@H](C)OC(C)(C)C)c1nc(C(=O)N[C@@H](Cc2ccccc2)C[C@H](C)C(=O)O)cs1]

(2S,4R)-4-(2-((1R,3R)-1-ethoxy-3-((S)-3-ethyl-N-methyl-2-((R)-1-methylpiperidine-2-carboxamido)pentanamido)-4-methylpentyl)thiazole-4-carboxamido)-2-methyl-5-phenylpentanoic Acid (203)

The TubOEt analogue at the Ile position was prepared according to the general method described above, employing (S)-2-((((9H-fluoren-9-yl)methoxy)carbonyl)amino)-3-ethylpentanoic acid in Step 2, to provide 203 (1.17 mg). Analytical UPLC-MS (system N): $t_r$=1.77 min, m/z (ES+) calculated 728.4 (M+H)$^+$, found 728.4.

(2S,4R)-4-(2-((1R,3R)-3-((S)-2-cyclopentyl-N-methyl-2-((R)-1-methylpiperidine-2-carboxamido)acetamido)-1-ethoxy-4-methylpentyl)thiazole-4-carboxamido)-2-methyl-5-phenylpentanoic Acid (204)

The TubOEt analogue at the Ile position was prepared according to the general method described above, employing (S)-2-((((9H-fluoren-9-yl)methoxy)carbonyl)amino)-2-cyclopentylacetic acid in Step 2, to provide 204 (1.71 mg). Analytical UPLC-MS (system 1): $t_r$=1.72 min, m/z (ES+) calculated 726.4 (M+H)$^+$, found 726.4.

(2S,4R)-4-(2-((1R,3R)-3-((S)-2-cyclohexyl-N-methyl-2-((R)-1-methylpiperidine-2-carboxamido)acetamido)-1-ethoxy-4-methylpentyl)thiazole-4-carboxamido)-2-methyl-5-phenylpentanoic Acid (205)

The TubOEt analogue at the Ile position was prepared according to the general method described above, employing (S)-2-((((9H-fluoren-9-yl)methoxy)carbonyl)amino)-2-cyclohexylacetic acid in Step 2, to provide 205 (1.59 mg). Analytical UPLC-MS (system 1): $t_r$=1.77 min, m/z (ES+) calculated 740.4 (M+H)$^+$, found 740.4.

(2S,4R)-4-(2-((1R,3R)-1-ethoxy-3-((2S,3S)-3-methoxy-N-methyl-2-((R)-1-methylpiperidine-2-carboxamido)butanamido)-4-methylpentyl)thiazole-4-carboxamido)-2-methyl-5-phenylpentanoic Acid (206)

The TubOEt analogue at the Ile position was prepared according to the general method described above, employing N-(((9H-fluoren-9-yl)methoxy)carbonyl)-O-methyl-L-allothreonine in Step 2, to provide 206 (1.50 mg). Analytical UPLC-MS (system 1): $t_r$=1.58 min, m/z (ES+) calculated 716.4 (M+H)$^+$, found 716.4.

(2S,4R)-4-(2-((1R,3R)-1-ethoxy-3-((2S,3R)-3-methoxy-N-methyl-2-((R)-1-methylpiperidine-2-carboxamido)butanamido)-4-methylpentyl)thiazole-4-carboxamido)-2-methyl-5-phenylpentanoic Acid (207)

The TubOEt analogue at the Ile position was prepared according to the general method described above, employing N-(((9H-fluoren-9-yl)methoxy)carbonyl)-O-methyl-L-threonine in Step 2, to provide 207 (1.44 mg). Analytical UPLC-MS (system 1): $t_r$=1.59 min, m/z (ES+) calculated 716.4 (M+H)+, found 716.4.

(2S,4R)-4-(2-((1R,3R)-3-((S)-2-(2,3-dihydro-1H-inden-2-yl)-N-methyl-2-((R)-1-methylpiperidine-2-carboxamido)acetamido)-1-ethoxy-4-methylpentyl)thiazole-4-carboxamido)-2-methyl-5-phenylpentanoic Acid (208)

The TubOEt analogue at the Ile position was prepared according to the general method described above, employing (S)-2-((((9H-fluoren-9-yl)methoxy)carbonyl)amino)-2-(2,3-dihydro-1H-inden-2-yl)acetic acid in Step 2, to provide 208 (1.15 mg). Analytical UPLC-MS (system 1): $t_r$=1.84 min, m/z (ES+) calculated 774.4 (M+H)$^+$, found 774.4.

(2S,4R)-4-(2-((1R,3R)-3-((2S,3R)—N,3-dimethyl-2-((R)-1-methylpiperidine-2-carboxamido)pentanamido)-1-ethoxy-4-methylpentyl)thiazole-4-carboxamido)-2-methyl-5-phenylpentanoic Acid (209)

The TubOEt analogue at the Ile position was prepared according to the general method described above, employing (((9H-fluoren-9-yl)methoxy)carbonyl)-L-alloisoleucine in Step 2, to provide 209 (1.33 mg). Analytical UPLC-MS (system 1): $t_r$=1.78 min, m/z (ES+) calculated 714.4 (M+H)$^+$, found 714.4.

(2S,4R)-4-(2-((1R,3R)-1-ethoxy-4-methyl-3-((S)—N-methyl-2-((R)-1-methylpiperidine-2-carboxamido)-2-(tetrahydro-2H-pyran-4-yl)acetamido)pentyl)thiazole-4-carboxamido)-2-methyl-5-phenylpentanoic Acid (210)

The TubOEt analogue at the Ile position was prepared according to the general method described above, employing (S)-2-((((9H-fluoren-9-yl)methoxy)carbonyl)amino)-2-(tetrahydro-2H-pyran-4-yl)acetic acid in Step 2, to provide 210 (1.07 mg). Analytical UPLC-MS (system 1): $t_r$=1.20 min, m/z (ES+) calculated 742.4 (M+H)$^+$, found 742.4.

(2S,4R)-4-(2-((1R,3R)-1-ethoxy-3-(2-(3-fluorobicyclo[1.1.1]pentan-1-yl)-N-methyl-2-((R)-1-methylpiperidine-2-carboxamido)acetamido)-4-methylpentyl)thiazole-4-carboxamido)-2-methyl-5-phenylpentanoic Acid (211)

The TubOEt analogue at the Ile position was prepared according to the general method described above, employing racemic 2-((((9H-fluoren-9-yl)methoxy)carbonyl)amino)-2-(3-fluorobicyclo[1.1.1]pentan-1-yl)acetic acid in Step 2, to provide 211 (2.69 mg) as a mixture of epimers. Analytical UPLC-MS (system 1): Epimer 1: $t_r$=1.67 min, m/z (ES+) calculated 742.4 (M+H)$^+$, found 742.3; Epimer 2: $t_r$=1.83 min, m/z (ES+) calculated 742.4 (M+H)$^+$, found 742.3.

(2S,4R)-4-(2-((1R,3R)-3-((S)-3-cyclopropyl-N-methyl-2-((R)-1-methylpiperidine-2-carboxamido)propanamido)-1-ethoxy-4-methylpentyl)thiazole-4-carboxamido)-2-methyl-5-phenylpentanoic Acid (212)

The TubOEt analogue at the Ile position was prepared according to the general method described above, employing (S)-2-((((9H-fluoren-9-yl)methoxy)carbonyl)amino)-3-cyclopropylpropanoic acid in Step 2, to provide 212 (3.21 mg). Analytical UPLC-MS (system 1): $t_r$=1.66 min, m/z (ES+) calculated 712.4 (M+H)$^+$, found 712.3.

(2S,4R)-4-(2-((1R,3R)-3-((S)-3-cyclohexyl-N-methyl-2-((R)-1-methylpiperidine-2-carboxamido)propanamido)-1-ethoxy-4-methylpentyl)thiazole-4-carboxamido)-2-methyl-5-phenylpentanoic Acid (213)

The TubOEt analogue at the Ile position was prepared according to the general method described above, employing (S)-2-((((9H-fluoren-9-yl)methoxy)carbonyl)amino)-3-cyclohexylpropanoic acid in Step 2, to provide 213 (1.72 mg). Analytical UPLC-MS (system 1): $t_r$=1.87 min, m/z (ES+) calculated 754.5 (M+H)$^+$, found 754.4.

(2S,4R)-4-(2-((1R,3R)-3-((2S,3S)-3-(tert-butoxy)-N-methyl-2-((R)-1-methylpiperidine-2-carboxamido)butanamido)-1-ethoxy-4-methylpentyl)thiazole-4-carboxamido)-2-methyl-5-phenylpentanoic Acid (214)

The TubOEt analogue at the Ile position was prepared according to the general method described above, employing N-(((9H-fluoren-9-yl)methoxy)carbonyl)-O-(tert-butyl)-L-allothreonine in Step 2, to provide 214 (2.31 mg). Analytical UPLC-MS (system 1): $t_r$=1.77 min, m/z (ES+) calculated 758.5 (M+H)$^+$, found 758.4.

(2S,4R)-4-(2-((1R,3R)-3-((2S,3R)-3-(tert-butoxy)-N-methyl-2-((R)-1-methylpiperidine-2-carboxamido)butanamido)-1-ethoxy-4-methylpentyl)thiazole-4-carboxamido)-2-methyl-5-phenylpentanoic Acid (215)

The TubOEt analogue at the Ile position was prepared according to the general method described above, employing N-(((9H-fluoren-9-yl)methoxy)carbonyl)-O-(tert-butyl)-L-threonine in Step 2, to provide 215 (2.35 mg). Analytical UPLC-MS (system 1): $t_r$=1.76 min, m/z (ES+) calculated 758.5 (M+H)$^+$, found 758.4.

General Procedure for the Preparation of D-Mep Replacement Analogues of TubOEt:

Step 1: Fmoc Removal. A lantern loaded with Fmoc-MeN-TuvOEt-Tup as described above was treated with 1 mL of 20% piperidine in DMF for 30 min. The solution was removed and the lantern was then washed 3 times with 1.5 mL of DMF. Step 2: Amino Acid Coupling. In a separate vial 0.5 mL of a 240 mM solution of FmocHN-Ile-COOH in DMF and 0.5 mL of a 200 mM solution of HATU in DMF were combined and DIPEA (45 µL, 0.24 mmol) was added. After 2 min the activated Fmoc-Ile solution was added to the lantern and gently stirred for 2 h. The lantern was treated a second time with the activated Fmoc-Ile amino acid solution for 2 h. The solution was then removed and the lantern was washed 3 times with 1.5 mL DMF. Step 3: Fmoc Removal. The lantern loaded with FmocHN-Ile-TuvOEt-Tup was treated with 1 mL of 20% piperidine in DMF for 30 min. The solution was removed and the lantern was washed 3 times with 1.5 mL of DMF. Step 4: Mep analogue Coupling. In a separate vial 0.5 mL of a 240 mM solution of the appropriate Mep analogue in DMF and 0.5 mL of a 200 mM solution of HATU in DMF were combined, and DIPEA (45 µL, 0.24 mmol) was added. After 2 min, the activated Mep analogue solution was added to the lantern and gently stirred for 2 h. The lantern was treated a second time with the activated Mep analogue solution for 2 h. The solution was removed and the lantern was washed 3 times with 1.5 mL DMF and then washed 3 times with 1.5 mL of DCM. Step 5: Cleavage from the Lantern. Each lantern was treated for 90 min with a 20% HFIP solution in DCM. The solution was removed and the lantern was washed with an additional 0.5 mL of 20% HFIP in DCM. The combined solutions were filtered through a 45 micron syringe filter and concentrated to dryness to provide analogues 216-221 (shown immediately below). The analogues were obtained in >85% purity based on UPLC-MS analysis and the diode array chromatogram.

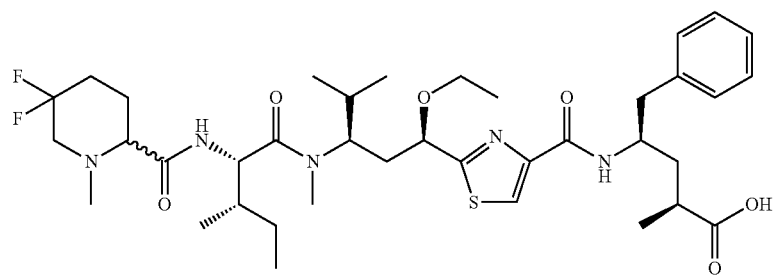

216

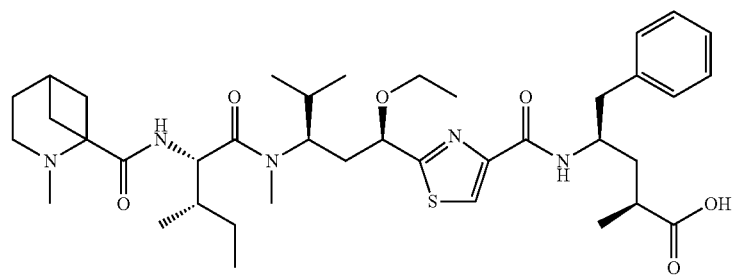

217

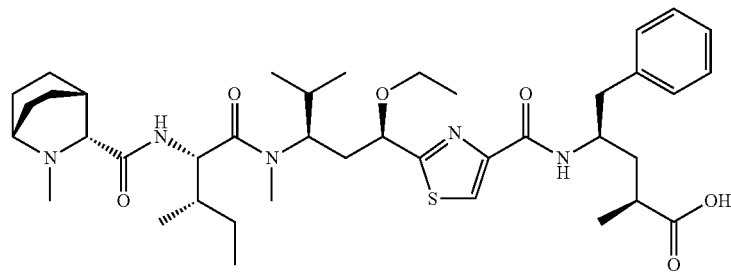

218

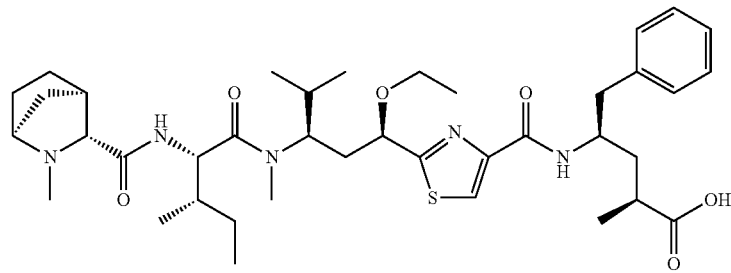

219

220

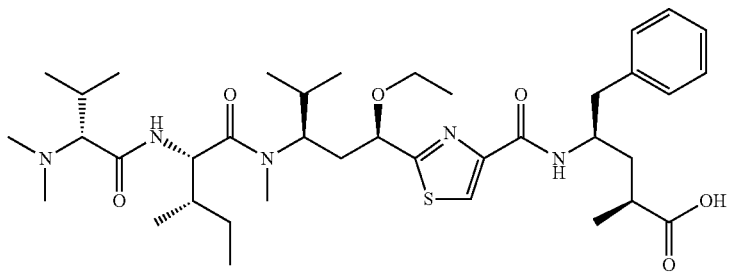

221

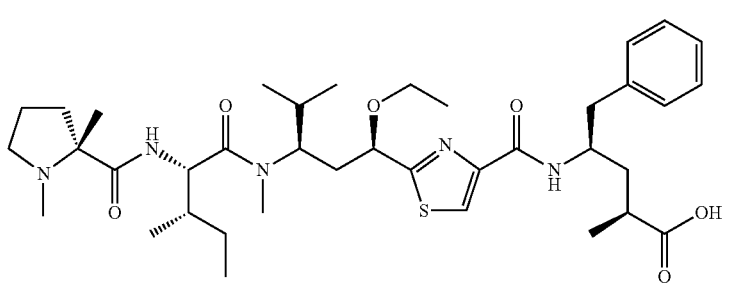

General Procedure for the N-Methylation of D-Mep Analogues (224-227).

Commercially available pipecolic acid analogues (cf. 222, 0.30 mmol) were dissolved in a mixture of 0.4 mL of methanol and a solution of 37% formaldehyde in water (0.23 mL, 3.0 mmol). Pd/C (10 wt. %, 10 mg) was added, the flask was equipped with a hydrogen-filled balloon, and the reactions were stirred overnight. The Pd was removed by filtering through a plug of Celite and concentrated by rotary evaporation. The residue obtained was concentrated from 2.0 mL of methanol 5 additional times to obtain the desired N-methylated pipecolic acid analogues 224-227.

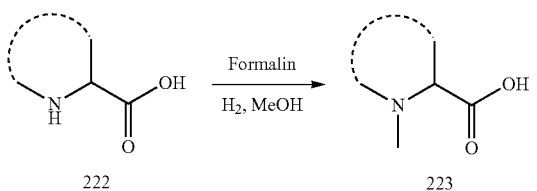

222    223

224

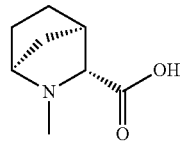

225

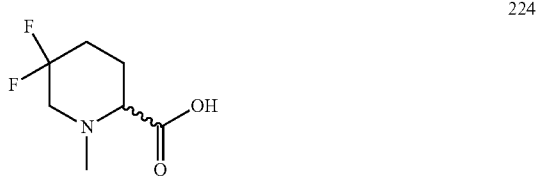

226

227

5,5-difluoro-1-methylpiperidine-2-carboxylic Acid (224)

5,5-difluoropiperidine-2-carboxylic acid (50 mg, 0.30 mmol) was methylated using the procedure described above to provide 5,5-difluoro-1-methylpiperidine-2-carboxylic acid (224, 47 mg, 87%). Analytical UPLC-MS (system 1): $t_r$=0.32 min, m/z (ES+) calculated 180.1 (M+H)$^+$, found 180.0.

2-methyl-2-azabicyclo[3.1.1]heptane-1-carboxylic Acid (225)

2-azabicyclo[3.1.1]heptane-1-carboxylic acid hydrochloride (53 mg, 0.30 mmol) was methylated using the procedure described above to provide 2-methyl-2-azabicyclo[3.1.1]heptane-1-carboxylic acid (225, 60 mg, quantitative yield). Analytical UPLC-MS (system 1): $t_r$=0.39 min, m/z (ES+) calculated 156.1 (M+H)$^+$, found 156.1.

(1S,3R,4S)-2-methyl-2-azabicyclo[2.2.2]octane-3-carboxylic Acid (226)

(1S,3R,4S)-2-azabicyclo[2.2.2]octane-3-carboxylic acid (47 mg, 0.30 mmol) was methylated using the procedure described above to provide (1S,3R,4S)-2-methyl-2-azabicyclo[2.2.2]octane-3-carboxylic acid (226, 53 mg, quantitative yield). Analytical UPLC-MS (system 1): $t_r$=0.40 min, m/z (ES+) calculated 170.1 (M+H)$^+$, found 170.0.

(1S,3R,4R)-2-methyl-2-azabicyclo[2.2.1]heptane-3-carboxylic Acid (227)

(1S,3R,4R)-2-(tert-butoxycarbonyl)-2-azabicyclo[2.2.1]heptane-3-carboxylic Acid (73 mg, 0.30 mmol) was dissolved in 1.0 mL of DCM, then 0.30 mL of TFA was added and the reaction was stirred for 1.5 h to remove the Boc protecting group. The reaction was diluted with 3 mL of toluene and concentrated to dryness to afford (1S,3R,4R)-2-azabicyclo[2.2.1]heptane-3-carboxylic acid. Analytical UPLC-MS (system 1): $t_r$=0.85 min, m/z (ES+) calculated 142.1 (M+H)$^+$, found 142.1. The intermediate (1S,3R,4R)-2-azabicyclo[2.2.1]heptane-3-carboxylic acid was then methylated using the procedure described above to provide the trifluoroacetic acid salt of (1S,3R,4R)-2-methyl-2-azabicyclo[2.2.1]heptane-3-carboxylic acid (227, 66 mg, 83%). Analytical UPLC-MS (system 1): $t_r$=0.89 min, m/z (ES+) calculated 156.1 (M+H)$^+$, found 156.1

(2S,4R)-4-(2-((1R,3R)-3-((2S,3S)-2-(5,5-difluoro-1-methylpiperidine-2-carboxamido)-N,3-dimethylpentanamido)-1-ethoxy-4-methylpentyl)thiazole-4-carboxamido)-2-methyl-5-phenylpentanoic Acid (216)

The TubOEt analogue at the Mep position was prepared according to the general procedure described above, employing racemic 5,5-difluoro-1-methylpiperidine-2-carboxylic acid (224, prepared above) in Step 4, to provide 216 (3.05 mg) as a mixture of epimers. Analytical UPLC-MS (system 1): Epimer 1: $t_r$=2.06 min, m/z (ES+) calculated 750.4 (M+H)$^+$, found 750.3; Epimer 2: $t_r$=2.10 min, m/z (ES+) calculated 750.4 (M+H)$^+$, found 750.4.

(2S,4R)-4-(2-((1R,3R)-3-((2S,3S)—N,3-dimethyl-2-(2-methyl-2-azabicyclo[3.1.1]heptane-1-carboxamido)pentanamido)-1-ethoxy-4-methylpentyl)thiazole-4-carboxamido)-2-methyl-5-phenylpentanoic Acid (217)

The TubOEt analogue at the Mep position was prepared according to the general procedure described above, employing 2-methyl-2-azabicyclo[3.1.1]heptane-1-carboxylic acid (225, prepared above) in Step 4, to provide 217 (4.44 mg). Analytical UPLC-MS (system 1): $t_r$=1.69 min, m/z (ES+) calculated 726.4 (M+H)$^+$, found 726.3.

(2S,4R)-4-(2-((1R,3R)-3-((2S,3S)—N,3-dimethyl-2-((1 S,3R,4S)-2-methyl-2-azabicyclo[2.2.2]octane-3-carboxamido)pentanamido)-1-ethoxy-4-methylpentyl)thiazole-4-carboxamido)-2-methyl-5-phenylpentanoic Acid (218)

The TubOEt analogue at the Mep position was prepared according to the general procedure described above, employing (1S,3R,4S)-2-methyl-2-azabicyclo[2.2.2]octane-3-carboxylic (226, prepared above) acid in Step 4, to provide 218 (3.35 mg). Analytical UPLC-MS (system 1): $t_r$=1.74 min, m/z (ES+) calculated 740.4 (M+H)$^+$, found 740.6.

(2S,4R)-4-(2-((1R,3R)-3-((2S,3S)—N,3-dimethyl-2-((1 S,3R,4R)-2-methyl-2-azabicyclo[2.2.1]heptane-3-carboxamido)pentanamido)-1-ethoxy-4-methylpentyl)-thiazole-4-carboxamido)-2-methyl-5-phenylpentanoic Acid (219)

The TubOEt analogue at the Mep position was prepared according to the general procedure described above, employing (1S,3R,4R)-2-methyl-2-azabicyclo[2.2.1]heptane-3-carboxylic acid (227, prepared above) in Step 4, to provide 219 (2.82 mg). Analytical UPLC-MS (system 1): $t_r$=1.70 min, m/z (ES+) calculated 726.4 (M+H)$^+$, found 726.4.

(2S,4R)-4-(2-((3R,6S,9R,11R)-6-((S)-sec-butyl)-3,9-diisopropyl-2,8-dimethyl-4,7-dioxo-12-oxa-2,5,8-triazatetradecan-11-yl)thiazole-4-carboxamido)-2-methyl-5-phenylpentanoic Acid (220)

The TubOEt analogue at the Mep position was prepared according to the general procedure described above, employing N,N-dimethyl-D-valine in Step 4, to provide 220 (3.51 mg). Analytical UPLC-MS (system 1): $t_r$=1.72 min, m/z (ES+) calculated 716.4 (M+H)$^+$, found 716.3.

(2S,4R)-4-(2-((1R,3R)-3-((2S,3S)-2-((R)-1,2-dimethylpyrrolidine-2-carboxamido)-N,3-dimethylpentanamido)-1-ethoxy-4-methylpentyl)thiazole-4-carboxamido)-2-methyl-5-phenylpentanoic Acid (221)

The TubOEt analogue at the Mep position was prepared according to the general procedure described above, employing (R)-1,2-dimethylpyrrolidine-2-carboxylic acid in Step 4, to provide 221 (2.90 mg). Analytical UPLC-MS (system 1): $t_r$=1.67 min, m/z (ES+) calculated 714.4 (M+H)$^+$, found 714.4.

In Vitro Assays.

Cells cultured in log-phase growth were seeded for 24 h in 96-well plates containing 150 µL RPMI 1640 supplemented with 20% FBS. Serial dilutions of antibody-drug conjugates in cell culture media were prepared at 4× working concentrations; 50 µL of each dilution was added to the 96-well plates. Following addition of ADC, cells were incubated with test articles for 4 d at 37° C. After 96 h, growth inhibition was assessed by CellTiter-Glo® (Promega, Madison, Wis.) and luminescence was measured on a plate reader. The IC$_{50}$ value, determined in triplicate, is defined here as the concentration that results in a 50% reduction in cell growth relative to untreated controls.

In Vivo Xenograft Models.

All experiments were conducted in concordance with the Animal Care and Use Committee in a facility fully accredited by the Association for Assessment and Accreditation of Laboratory Animal Care. Efficacy experiments were conducted in L540cy Hodgkin's lymphoma, Karpas:KarpasBVR anaplastic large cell lymphoma, MDR+DELBVR anaplastic large cell lymphoma, and MDR+786-0 renal cell carcinoma xenograft models. Tumor cells were implanted sub-cutaneous in immune-compromised SCID mice. Tumor cells, as a cell suspension, were implanted sub-cutaneous in immune-compromised SCID mice. Upon tumor engraftment, mice were randomized to study groups when the average tumor volume reached about 100 mm$^3$. The ADC or controls were dosed once via intraperitoneal injection. Tumor volume as a function of time was determined using the formula (L×W$^2$)/2. Animals were euthanized when tumor volumes reached 1000 mm$^3$. Mice showing durable regressions were terminated around day 100 post implant.

ADC Pharmacokinetic (PK) Experiments.

Pharmacokinetic (PK) experiments were performed using radiolabeled antibody or ADC. PK test articles were radiolabeled using the following procedure. To a solution of antibody or ADC in PBS supplemented with an additional 50 mM potassium phosphate (pH 8.0) and 50 mM sodium chloride was added 55 µCi N10 succinimidyl propionate, [propionate-2,3-3H]-(Moravek Biochemicals, Cat. No.: MT 919, 80 Ci/mmol, 1 mCi/mL, 9:1 hexane:ethyl acetate solution) per mg of antibody or ADC. The resulting mixture was vortexed and left at room temperature for 2 hours. The mixture was centrifuged at 4,000×g for 5 minutes and the lower aqueous layer was removed and split into Amicon Ultra-15 Centrifugal Filter Units (Millipore, Cat. No.: UFC903024, 30 kDa MWCO). Unconjugated radioactivity was removed by 4 rounds of dilution and centrifugation at 4,000×g. The resulting products were filtered through sterile 0.22 m Ultrafree-MC Centrifugal Filter Units (Millipore, Cat. No.: UFC30GV0S) and the final antibody or ADC concentration was measured spectrophotometrically. The specific activity (µCi/mg) of each product was determined by liquid scintillation counting.

The pharmacokinetic properties of the unconjugated antibody or ADC were examined in several rodent models. In each experiment, 1-3 mg of radiolabeled antibody or ADC per kg of animal weight were injected via the tail vein. Each test article was dosed once in replicate animals. Blood was drawn into K2EDTA tubes via the saphenous vein or by cardiac puncture for terminal bleeds at various time points. Plasma was isolated by centrifugation for 10 minutes at 10,000×g. A 10-20 µL of sample of plasma from each time point was added to 4 mL Ecoscint-A liquid scintillation cocktail (National Diagnostics) and the total radioactivity was measured by liquid scintillation 5 counting. The resulting disintegrations per minute values were converted to µCi and the specific activity of the radiolabeled test articles was used to calculate the concentration of antibody or ADC remaining in the plasma at each time point.

In Vitro Assays—Tubulysin Free Drugs.

Cells were treated for 96 hours with tubulysin ether analogs (40-42) or tubulysin M (7), then assessed for viability as described in the methods.

TABLE 1

| compd | drug | Karpas299, ALCL | L540cy, HL | L428, MDR+ HL | HL60, AML | HL60/ RV, MDR+ AML |
|---|---|---|---|---|---|---|
| 7 | TubM | 0.17 | 0.14 | 0.11 | 0.3 | 2.2 |
| 40 | TubOMe | 0.19 | 0.12 | 0.5 | 0.13 | 29 |
| 41 | TubOEt | 0.05 | 0.05 | 0.14 | 0.05 | 5 |
| 42 | TubOPr | 0.15 | 0.13 | 0.4 | 0.17 | 14 |

The $IC_{50}$ values (nM) of Table 1 shows that all four test articles were highly potent on each of the cell lines. The tubulysin ethyl ether (41) trended more potent than the methyl (40) and propyl (42) analogs. The ethyl ether and tubulysin M maintained the highest level of potency in the context of MDR+L428 and HL60/RV cell lines.

The tubulysin ester analogs (133-137) and unsaturated ether analogs (176-179) were tested in vitro for potency relative to tubulysin M (7), following a 96 hour exposure. As shown by IC50 values (nM) of Table 2, Tubulysin esters 133-136 performed comparably to tubulysin M, with similar potencies across of the cell lines. The most hindered, bulky tubulysin analog (137) displayed reduced potency relative to tubulysin M, with potency losses ranging from 5- to 47-fold relative to tubulysin M.

Tubulysin unsaturated ethers 176 and 177 displayed comparable potency compared to the parent tubulysin 7. In contrast, the tubulysin propargyl (178) and benzyl (179) ethers were attenuated in potency relative to tubulysin 7.

A series of analogues of the ethyl ether tubulysin compound TubOEt (41) were synthesized on solid phase lanterns that maintain the ethyl ether substitution, while either varying the residue at the Ile position (203-215) or the Mep position (216-221). Following cleavage from the solid phase, the analogues were obtained in >85% purity and tested without further purification. The compounds were tested in vitro for potency relative to a sample of TubOEt synthesized in parallel on a lantern (41-lantern), following a 96 hour exposure, with $IC_{50}$ values expressed in nM (Table 3). While in many cases an attenuation in activity was observed relative to 41-lantern, some well-tolerated substitutions were found. At the Ile position the cyclic $R^5$ substituents cyclopentyl (204) and cyclohexyl (205) afford potent compounds; however, the tetrahydropyranyl analogue (210) was inactive against all cell lines tested. Furthermore, when Ile is replaced with allo-Ile (209) a loss of 25- to 40-fold in potency is observed. While this stereochemical preference is not observed when Ile is replaced with O-methyl threonine (207) or O-methyl allothreonine (206), bulkier substituents led to a greater differentiation. Specifically, replacement with O-t-butyl threonine (215) provides an analogue significantly more potent than the corresponding O-t-butyl allothreonine compound 216. Replacement of the Mep residue was generally less-well tolerated. The most potent compounds obtained in this series (217 and 221) possess substitution at the 4- and 2-position of the piperidine or pyrrollidine-2-carboxylic acid core, respectively. Substitution at the 5-position (216) or 6-position (218 and 219) led to a decrease in the observed cytotoxicity, particularly in the HL60/RV cell line.

TABLE 2

| compd | drug | Karpas299, ALCL | L540cy, HL | L428, MDR+ HL | HL60, AML | HL60/RV, MDR+ AML |
|---|---|---|---|---|---|---|
| 7 | TubM | 0.04 | 0.08 | 0.04 | 0.15 | 1 |
| 133 | Tub-propionate | 0.02 | 0.06 | 0.04 | 0.1 | 1 |
| 135 | Tub-isobutyrate | 0.02 | 0.1 | 0.12 | 0.1 | 6 |
| 134 | Tub-butyrate | 0.011 | 0.04 | 0.05 | 0.08 | 3 |
| 136 | Tub-isovalerate | 0.02 | 0.06 | 0.11 | 0.04 | 6 |
| 137 | Tub-3,3-di-Methylbutyrate | 0.18 | 0.7 | 0.93 | 0.7 | 47 |
| 176 | Tub-methyl-(propen-2-yl) | 0.12 | 0.06 | 0.12 | 0.07 | 6 |
| 177 | Tub allyl ether | 0.02 | 0.12 | 0.15 | 0.1 | 9 |
| 178 | Tub propargyl ether | 0.05 | 0.17 | 0.41 | 0.2 | 27 |
| 179 | Tub benzyl ether | 0.08 | 0.4 | 0.57 | 0.4 | 24 |

TABLE 3

| compound | Residue Replaced | HepG2, HCC | L540cy, HL | Ramos, NHL | U266 MM | HL60, AML | HL60/RV, MDR+ AML |
|---|---|---|---|---|---|---|---|
| 41-lantern | NA | 2 | 0.3 | 0.3 | 0.3 | 4 | 94 |
| 203 | Ile | 8 | 1 | 0.4 | 0.5 | 8 | 604 |
| 204 | Ile | 2 | 0.4 | 0.2 | 0.1 | 1 | 40 |
| 205 | Ile | 7 | 1 | 0.5 | 0.5 | 2 | 177 |
| 206 | Ile | 41 | 6 | 2 | 3 | 16 | >1000 |
| 207 | Ile | 46 | 6 | 2 | 2 | 9 | >1000 |
| 208 | Ile | 250 | 58 | 44 | 40 | 221 | >1000 |
| 209 | Ile | 50 | 12 | 7 | 8 | 15 | >1000 |
| 210 | Ile | >1000 | >1000 | >1000 | >1000 | >1000 | >1000 |
| 211 | Ile | 14 | 2 | 1 | 2 | 5 | 224 |
| 212 | Ile | 19 | 2 | 1 | 1 | 8 | 810 |
| 213 | Ile | 70 | 20 | 10 | 9 | 42 | >1000 |
| 214 | Ile | 91 | 30 | 20 | 22 | 190 | >1000 |
| 215 | Ile | 1 | 0.2 | 0.2 | 0.1 | 1 | 33 |
| 216 | Mep | 58 | 12 | 10 | 9 | 61 | >1000 |
| 217 | Mep | 2 | 1 | 0.4 | 0.4 | 4 | 244 |
| 218 | Mep | 9 | 5 | 6 | 7 | 24 | >1000 |
| 219 | Mep | 19 | 6 | 8 | 8 | 25 | >1000 |
| 220 | Mep | 41 | 13 | 10 | 10 | 299 | >1000 |
| 221 | Mep | 4 | 1 | 1 | 2 | 12 | 522 |

In Vitro Assays—Tubulysin ADCs.

ADCs were prepared by full reduction of interchain disulfides to reveal 8-conjugatable cysteines/antibody that were alkylated through Michael addition with the maleimide-containing Drug Linker compounds. Anti-CD30 conjugates bearing quaternized tubulysin ethers with and without a PEG12 side-chain were compared to their tubulysin M analogs. Cells were treated with cAC10 (anti-CD30) Conjugates loaded at 8 drug/Ab for 96 h and then assessed for viability. The $IC_{50}$ values (ng/mL) are shown in Table 4.

Several hydrophilic linker constructs incorporating quaternized tubulysin M were prepared and evaluated in vitro; the results are shown in Table 5. The data ($IC_{50}$ values in ng/mL) indicate that Conjugates prepared from Drug Linker compounds having quaternized tubulysin M linked via a hydrophilic ValGlu dipeptide with (95) or without (91) a PEG12 side chain, or linked via a hydrophilic glucuronide (82) provide ADCs that are equipotent to the ValAla comparator (15). All conjugates displayed a high degree of

TABLE 4

| cAC10 ADCs DAR 8 drug-linker | description | Karpas299, ALCL | L540cy, HL | L428, MDR+ HL | DEL, ALCL | DEL/BVR, MDR+ ALCL |
|---|---|---|---|---|---|---|
| 82 | glucQ-TubM | 0.6 | 4 | 0.5 | 2 | 3 |
| 56 | glucQ-TubOMe | 3 | 10 | >1000 | 2 | 20 |
| 57 | glucQ-TubOEt | 1 | 5 | 4 | 2 | 5 |
| 58 | glucQ-TubOPr | 2 | 6 | 117 | 2 | 10 |
| 99 | PEG12-glucQ-TubM | 0.3 | 2 | 0.5 | 1 | 2 |
| 66 | PEG12-glucQ-TubOEt | 1 | 5 | 6 | 2 | 6 |
| 67 | PEG12-glucQ-TubOPr | 4 | 10 | >1000 | 2 | 12 |

The conjugate bearing the tubulysin ethyl ether linker 57 was consistently more potent than the methyl (56) or propyl (58) analogs. With the exception of L428, the tubulysin ethyl ether linker 57 performed similarly to the tubulysin M analog 82. The presence of a PEG12 side chain in the linker had minimal impact on conjugate potency. All ADCs were inactive (no effect at 1000 ng/mL) on a CD30-negative Ramos NHL cell line, indicating a high degree of immunological specificity.

immunological specificity, with $IC_{50}s>1000$ ng/mL on antigen-negative Hep3B hepatocellular carcinoma cells.

In Vivo Xenograft Models—Comparison of Dipeptide and Glucuronide Linked Tubulysin.

Quaternary amine-linked tubulysin M conjugated with the ValAla dipeptide linker (15) and glucuronide (82) were compared in a CD30+L540cy Hodgkin lymphoma xenograft model alongside the glucuronide-linked tubulysin ethyl ether (57). The glucuronide drug-linker has been shown to

TABLE 5

| cAC10 ADCs 8 drugs/mAb drug-linker | MDPR-Linker-TubM | L540cy, HL | L428, MDR+ HL | DEL, ALCL | DEL/BVR, MDR+ ALCL | Hep3B CD30− HCC |
|---|---|---|---|---|---|---|
| 15 | ValAlaPABQ | 2 | 1 | 0.3 | 4 | >1000 |
| 82 | glucQ | 1 | 0.4 | 0.3 | 4 | >1000 |
| 91 | ValGluPABQ | 1 | 0.3 | 0.1 | 2 | >1000 |
| 95 | PEG12-ValGluPABQ | 0.8 | 0.2 | 0.1 | 2 | >1000 | offer improved physicochemical and pharmacokinetic conjugate properties relative to dipeptide linkers for ADC payloads (*Bioconjugate Chem.*, 2006, 17, 831-840; *Nature Biotech*, 2014, 32, 1059-1062). Conjugates were loaded at 4-drugs/mAb to minimize the effects of ADC PK. The results are shown in FIG. 1. Tumor-bearing mice were administered a single dose i.p. of test article once the average tumor volume reached 100 mm$^3$ on day 7. Significantly greater conjugate activity was observed when Tubulysin M (7) was conjugated in quaternized form as the glucuronide in cAC10-82. Mice treated with a single dose of 0.6 mg/Kg cAC10-82 achieved 5/5 durable, complete regressions. In contrast, the cohort treated with one 0.6 mg/Kg dose of the ValAla dipeptide conjugate, cAC10-15, had one cure, with the remaining mice experiencing a transient tumor growth delay. A higher dose of 2 mg/Kg of the dipeptide conjugate was also inferior to the glucuronide, with only 2/5 mice cured at day 78. Thus, the glucuronide based conjugate bearing tubulysin 7 was greater than 3-fold more potent than the corresponding val-ala dipeptide control. Likewise, the glucuronide-linked tubulysin ethyl ether (41) in the form of conjugate cAC10-57 was also highly active. A single dose of 0.6 mg/Kg of cAC10-57 induced 5/5 durable, complete regressions.

In Vivo Xenograft Models—Effect of PEGylation with DAR 8 Conjugates.

Figure 2:
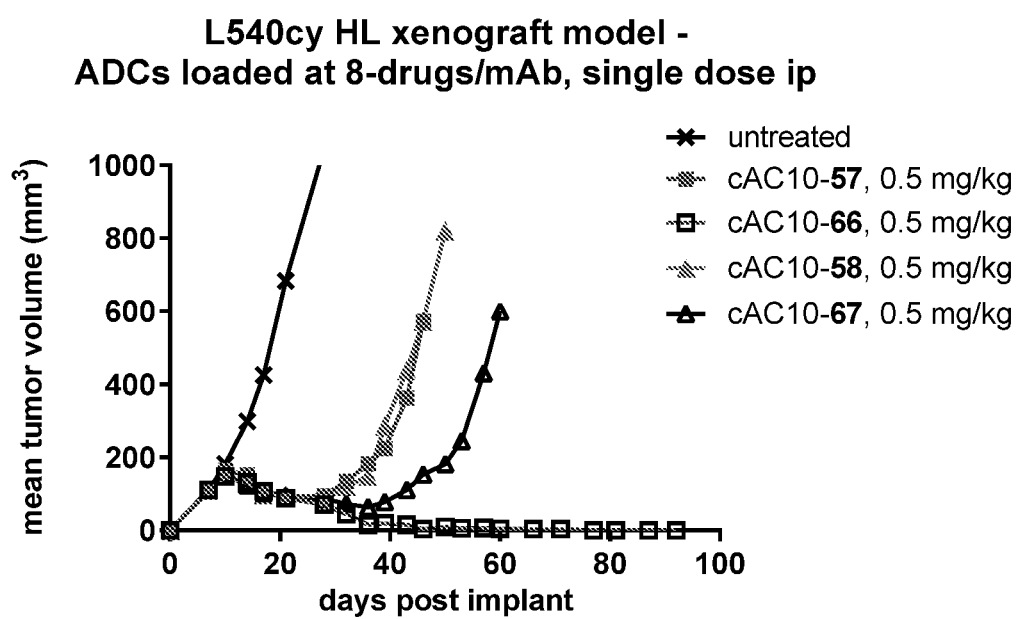
FIG. 2. Mean tumor volume ($mm^3$) versus time (days) post-implant subsequent to treatment with DAR 8 glucuronide quaternary amine-linked tubulysin antibody-drug conjugates containing quaternized tubulysin ethyl ether Drug Units with (cAC10-66) or without (cAC10-57) PEGylation of their Linker Units, and quaternized tubulysin propyl ether Drug Units with (cAC10-67) and without (cAC10-58) PEGylation of their Linker Units.
Figure 3:
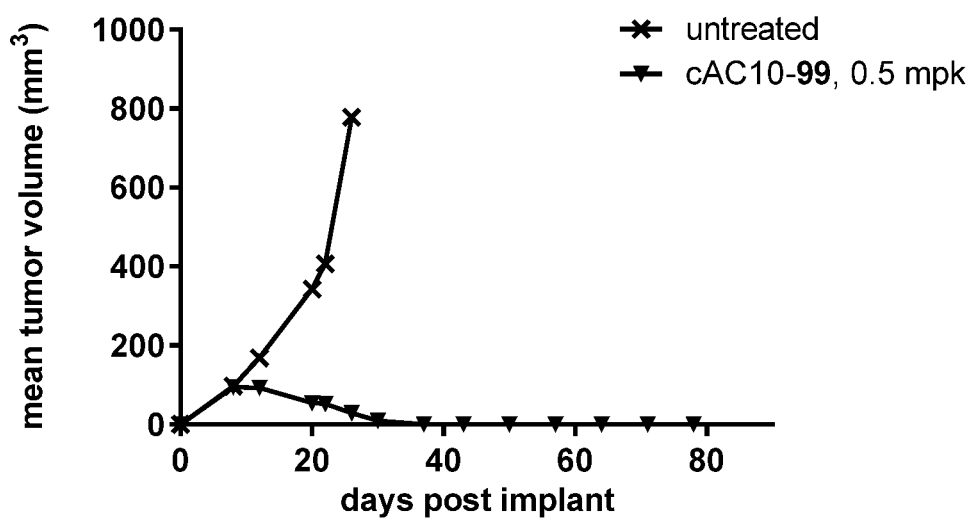
FIG. 3. Mean tumor volume (mm³) versus time (days) post-implant subsequent to treatment of CD30⁺ L540cy Hodgkin lymphoma xenograft with a DAR 8 glucuronide quaternary amine-linked Tubulysin M antibody-drug conjugate (cAC10-99) with PEGylation of its Linker Unit.

Recently, we reported that addition of PEG side-chain to the glucuronide-monomethylauristatin E drug-linker provided improved ADC pharmacological properties with ADCs loaded at 8-drugs/mAb (*Nature Biotech*, 2014, 32, 1059-1062). A PEG12 side-chain was incorporated into quaternary amine-linked tubulysin ethyl ether and propyl ether drug linker moieties providing Conjugates cAC10-66 and c-AC10-67, respectively. Anti-CD30 cAC10 conjugates loaded at 8-drugs/mAb were prepared and evaluated relative to the non-PEGylated ethyl (cAC10-57) and propyl (cAC10-58) ether analogs in the L540cy xenograft model. The results are shown in FIG. 2. For ethyl and propyl ether glucuronide constructs, inclusion of PEG12 resulted in enhanced antitumor activity. In the case of the ethyl ether, non-PEGylated Conjugate, cAC10-57 induced a tumor growth delay in mice treated with a single dose of 0.5 mg/Kg; whereas the PEGylated variant cAC10-66 provided cures in 5/5 mice at the same antibody dose. For the propyl ether, non-PEGylated Conjugate, cAC10-58 induced a tumor growth delay with outgrowth around day 40 in mice treated with a single dose of 0.5 mg/Kg; whereas the PEGylated variant cAC10-67 further delayed outgrowth to around day 60.

The PEGylated version of the glucuronide-tubulysin M, denoted as linker 99, was also tested in the CD30+L540cy xenograft as a DAR 8 cAC10 conjugate. As above, tumor-bearing mice were administered a single 0.5 mg/Kg dose i.p. of test article once the average tumor volume reached 100 mm$^3$ on day 8. Like the PEGylated ethyl ether construct (cAC10-66) and the PEGylated Tubulysin M conjugate cAC10-99 induced 5/5 cures in mice treated at 0.5 mg/Kg.

Figure 8:
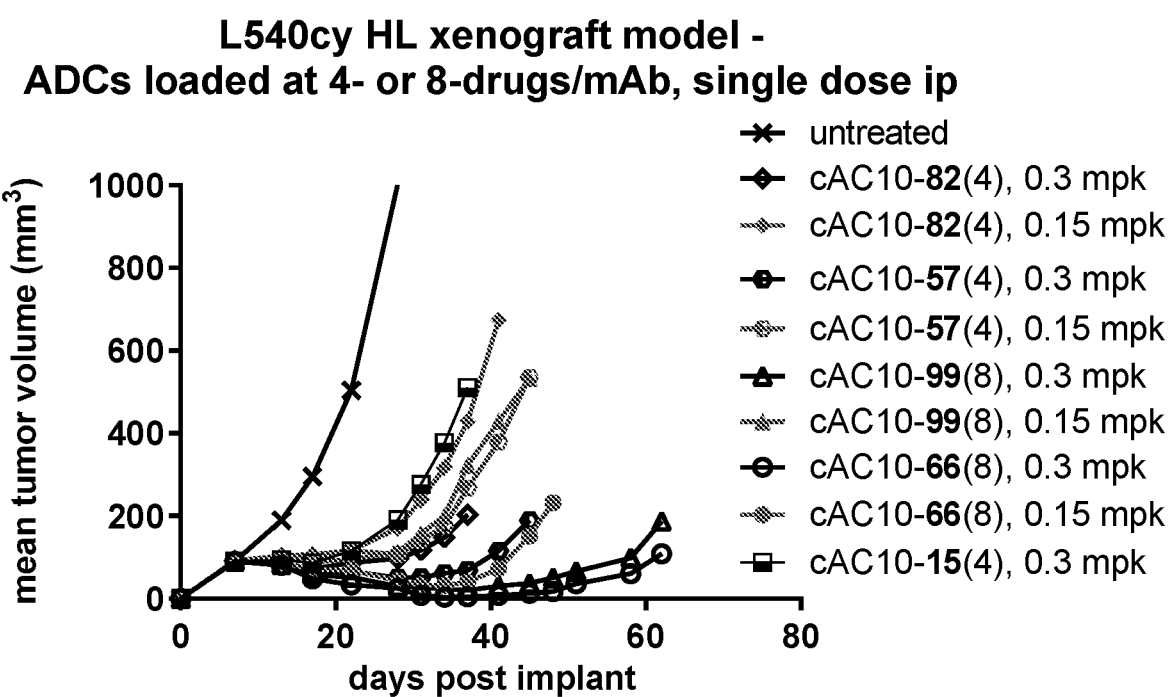
FIG. 8. Mean tumor volume (mm³) versus time (days) post-implant subsequent to treatment of CD30⁺ L540cy Hodgkin lymphoma xenograft dosed i.p. with 0.15 mg/Kg or 0.3 mg/Kg glucuronide quaternary amine-linked Tubulysin M antibody-drug conjugate with (cAC10-99) or without (cAC10-82) PEGylation of the linker having DAR of 8 and 4, respectively, or treatment with glucuronide quaternary amine-linked tubulysin ethyl ether antibody drug conjugate with (cAC10-66) or without (cAC10-57) Linker Unit PEGylation having DAR of 8 and 4, respectively, in comparison to treatment by i.p. dosing at 0.3 mg/Kg with DAR 4 quaternary amine-linked Tubulysin M antibody-drug conjugate linked via protease-cleavable val-ala dipeptide (cAC10-15) without Linker Unit PEGylation.

A subset of antibody-drug conjugates were evaluated at lower doses in the L540cy xenograft model. Anti-CD30 conjugates bearing PEGylated drug linker moieties containing quaternized tubulysin M (cAC10-99) or quaternized tubulysin ethyl ether (cAC10-66) were conjugated at 8-drugs/mAb. Similarly, anti-CD30 conjugates bearing non-PEGylated glucuronide drug linker moieties containing quaternized tubulysin M (cAC10-82) or quaternized tubulysin ethyl ether (cAC10-57), or the val-ala dipeptide version containing quaternized tubulysin M (cAC10-15) at 4-drugs/mAb were prepared. Mice bearing tumors were administered a single dose of each Conjugate at 0.15 or 0.3 mg/kg once the tumor reached approximately 100 mm$^3$. The results are shown in FIG. 8. At the lower dose of 0.15 mg/kg, all of the Conjugates displayed a tumor growth delay, with the longest delay observed for mice treated with conjugate (cAC10-66) bearing PEGylated glucuronide drug linker moieties having quaternized tubulysin ethyl ether quaternized Drug Units. At the 0.3 mg/kg dose, durable, complete regressions were observed in 2/6 mice treated with ADC bearing non-PEGylated glucuronide drug linker moieties having quaternized tubulysin ethyl ether (cAC10-57) Drug Units and 3/6 mice treated with conjugates bearing both PEGylated glucuronide drug linker moieties having quaternized tubulysin M (cAC10-99) or quaternized tubulysin ethyl ether (cAC10-66) Drug Units.

In Vivo Xenograft Models—Demonstration of Bystander Effects.

Figure 4:
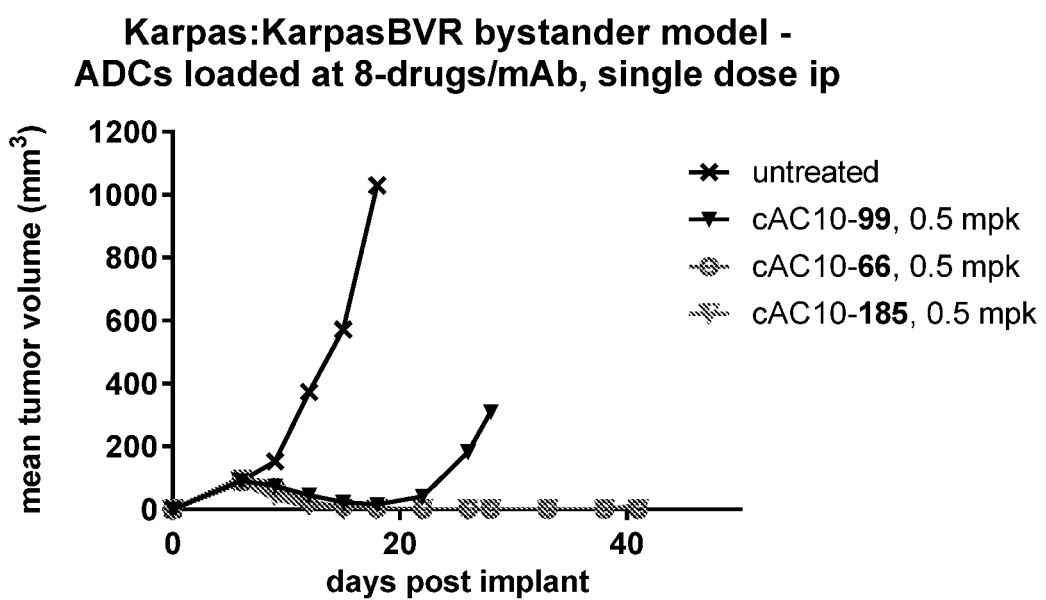
FIG. 4. Mean tumor volume (mm³) versus time (days) post-implant subsequent to treatment of a xenograft comprised of a mixed population of CD30⁺ Karpas and CD30-negative KarpasBVR tumor cells to assess bystander activity, wherein mice being the xenograft tumor were treated with a 0.5 mg/Kg single dose of glucuronide quaternary amine-linked tubulysins antibody-drug conjugates in which the quaternized Drug Unit is that of Tubulysin M (cAC10-99), tubulysin ethyl ether (cAC10-66), or tubulysin methyl-(propen-2-yl) ether (cAC10-185).

The PEGylated constructs were tested in a Karpas:KarpasBVR xenograft model of bystander activity. An equal number of CD30$^+$ Karpas299 and CD30$^-$ KarpasBVR cells were injected subcutaneously to establish a tumor mass with a heterogeneous population of antigen positive and negative cells. Conjugates bearing warheads incapable of freely diffusing across plasma membranes display minimal activity. Anti-CD30 cAC10 conjugates loaded at 8-drugs/mAb with PEGylated glucuronide drug linker moieties bearing quaternized tubulysin M (cAC-10-99), quaternized tubulysin ethyl ether (cAC10-66), and quaternized tubulysin methyl-(propen-2yl) ether (cAC10-185) were evaluated. Tumor-bearing mice were administered a single 0.5 mg/Kg dose i.p. of test article once the average tumor volume reached 100 mm$^3$ on day 6. The results are shown in FIG. 4. All of the mice treated with conjugates containing the quaternized tubulysin ether (cAC10-66 and cAC10-185) Drug Units achieved complete tumor regressions through study day 41. The quaternized tubulysin M conjugate (cAC10-99) displayed more variable activity, with 2/5 mice achieving a complete regression at day 41 and the remaining 3/5 mice experiencing a transient tumor regression.

In Vivo Xenograft Models—Demonstration of Activity in MDR+ Models.

Figure 9:
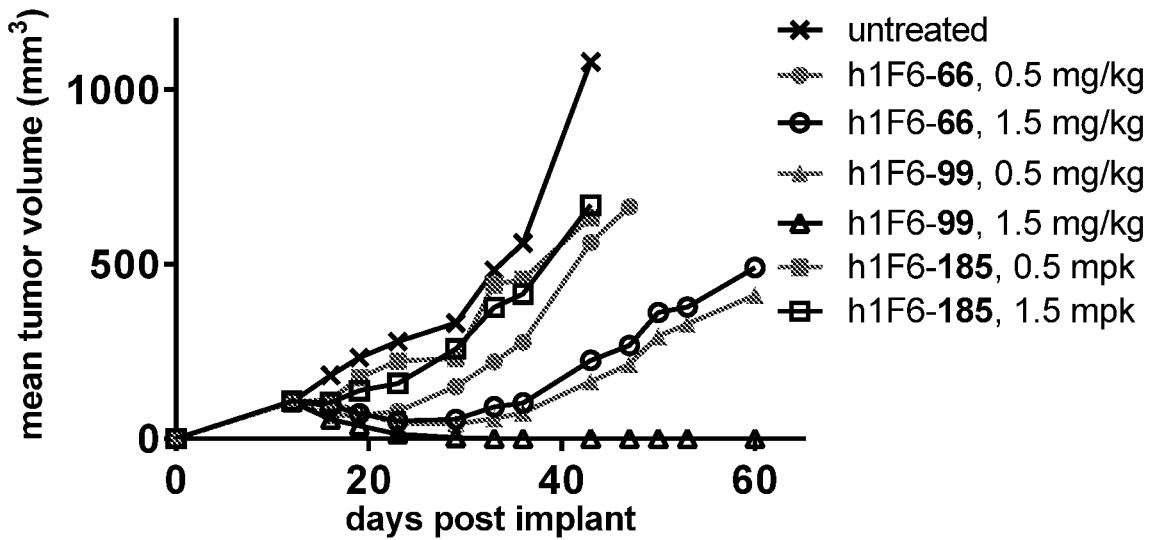
FIG. 9. Mean tumor volume (mm³) versus time (days) post-implant subsequent to treatment of drug resistant CD70⁺786-0 Renal Cell Carcinoma xenograft (MDR+) dosed i.p. with 0.5 mg/Kg or 1.5 mg/Kg PEGylated glucuronide quaternary amine-linked tubulysin ethyl ether antibody drug conjugate (hIF6-66) or PEGylated glucuronide quaternary amine-linked tubulysin methyl-(propen-2-yl) ether (hF16-185) both having DAR of 8 in comparison to treatment with PEGylated glucuronide quaternary amine-linked tubulysin M antibody-drug conjugate (hIF6-99) having DAR of 8.

Conjugates bearing the PEGylated constructs were tested in an MDR+786-0 renal cell carcinoma and DELBVR anaplastic large cell lymphoma xenograft models. Anti-CD70 conjugates (mAb=hIF6) were loaded at 8-drugs/mAb with PEGylated glucuronide drug linker moieties containing quaternized tubulysin M (cAC10-99), quaternized tubulysin ethyl ether (cAC10-66), or quaternized tubulysin methyl-propene ether (cAC10-185) Drug Units. Mice bearing CD70$^+$786-0 renal cell carcinoma tumors were administered a single dose of test articles at 0.5 or 1 mg/kg once the tumor reached approximately 100 mm$^3$. The results are shown in FIG. 9. Tumor growth delay was observed in mice treated with ADC conjugated to quaternized tubulysin M (cAC10-99) at 0.5 mg/kg or with ADCs conjugated to quaternized tubulysin ethyl ether (cAC10-66) at 1.5 mg/kg. A higher dose of 1.5 mg/kg of the quaternized tubulysin M conjugate (cAC10-99) induced 5/5 durable, complete regressions.

Figure 10:
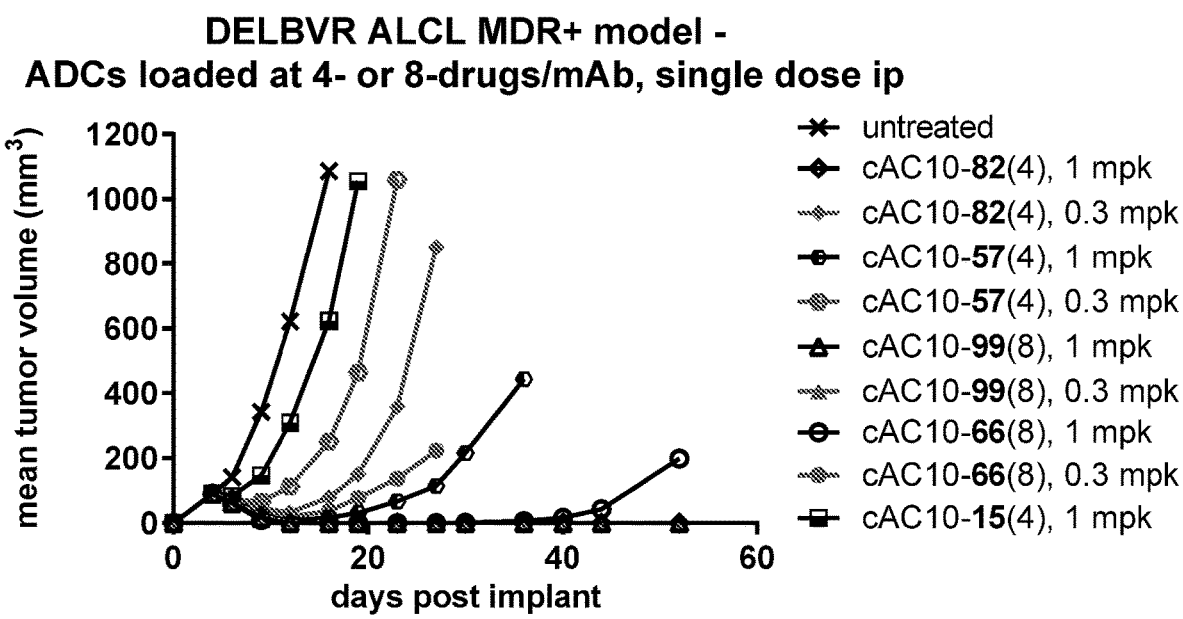
FIG. 10. Mean tumor volume (mm³) versus time (days) post-implant subsequent to treatment of CD30⁺ cAC10-mc-val-cit-MMAE drug-resistant Anaplastic Large Cell Lymphoma xenograft (DELBVR ALCL) with DAR 4 non-PEGylated glucuronide quaternary amine-linked tubulysin ethyl ether antibody drug conjugate (cAC10-57) or non-PEGylated glucuronide quaternary amine-linked tubulysin M in comparison to their corresponding DAR 8 PEGylated Conjugates (cAC10-66 and cAC10-99) dosed i.p at 0.3 mg/Kg or 1 mg/Kg and to DAR 4 quaternary amine-linked Tubulysin M antibody-drug conjugate linked via protease-cleavable Val-Ala dipeptide without Linker Unit PEGylation (cAC10-15) dosed i.p. at 1 mg/Kg.

ADCs having a subset of the linkers were also tested in the MDR+, CD30-expressing DELBVR anaplastic large cell lymphoma xenograft model. Anti-CD30 conjugates (mAb=cAC10) bearing PEGylated linkers drug linker moieties containing quaternized tubulysin M (cAC10-99) and quaternized tubulysin ethyl ether (cAC10-66) were conjugated at 8-drugs/mAb. Similarly, anti-CD30 conjugates bearing non-PEGylated glucuronide drug-linker moieties containing quaternized tubulysin M (cAC10-82) and quaternized tubulysin ethyl ether (cAC10-57), and the val-ala dipeptide version of quaternized tubulysin M (cAC10-15) were conjugated at 4-drugs/mAb. Mice bearing tumors were administered a single dose of test articles at 0.3 or 1 mg/kg once the tumor reached approximately 100 mm$^3$. The results are shown in FIG. 10. At the 0.3 mg/kg dose, Conjugates having PEGylated glucuronide drug linker moieties containing quaternized tubulysin ethyl ether (cAC10-66) provided 2/5 durable, complete regressions and having PEGylated glucuronide drug linker moieties containing quaternized tubulysin M (cAC10-99) provided 5/5 durable, complete regressions. At the higher dose of 1 mg/kg, durable, complete regressions were observed with the non-PEGylated glucuronide tubulysin ethyl ether (1/5, cAC10-57) and tubulysin M (5/5 mice cured, cAC10-82) Conjugates. In the PEGylated series, a dose of 1 mg/kg provided 4/5 and 5/5 durable, complete regressions for the glucuronide tubulysin ethyl ether (cAC10-66) and tubulysin M (cAC10-99) Conjugates, respectively.

Rat Pharmacokinetic Assessment.

Figure 5:
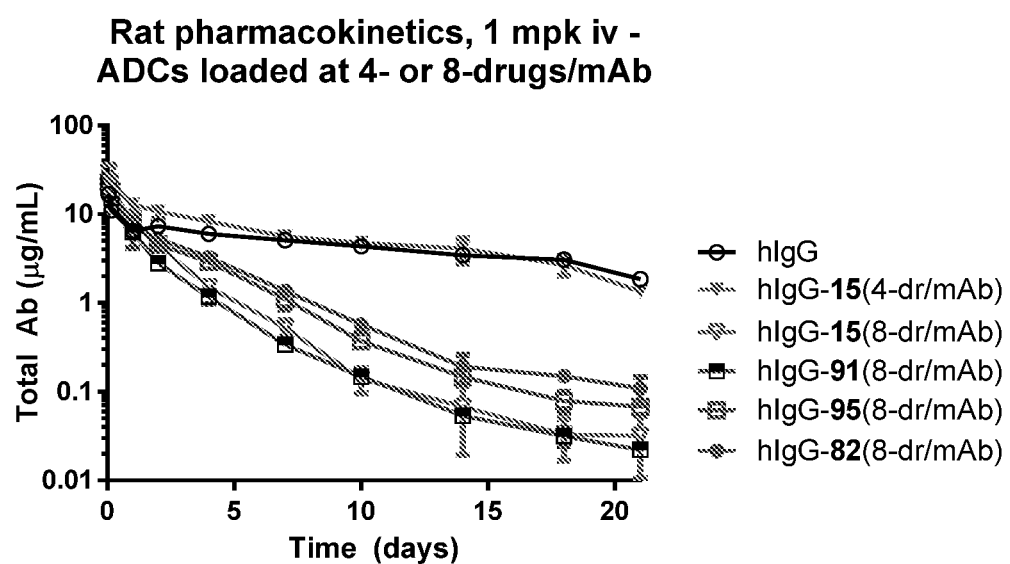
FIG. 5. Pharmacokinetic profiles, shown as amount of total antibody (g/mL) vs. time (days), of antibody-drug conjugates dosed i.v. in rats at 1 mg/Kg having DAR 4 or 8 of quaternized Tubulysin M conjugated to humanized IgG through a protease-cleavable val-ala (hIgG-15) or val-glu (hIgG-91) dipeptide quaternary amine linker without or with (hIgG-95) Linker Unit PEGylation in comparison to a β-glucuronidase-cleavable glucuronide antibody-drug conjugate of quaternized Tubulysin M (hIgG-82) having DAR of 4 without Linker Unit PEGylation.
Figure 6:
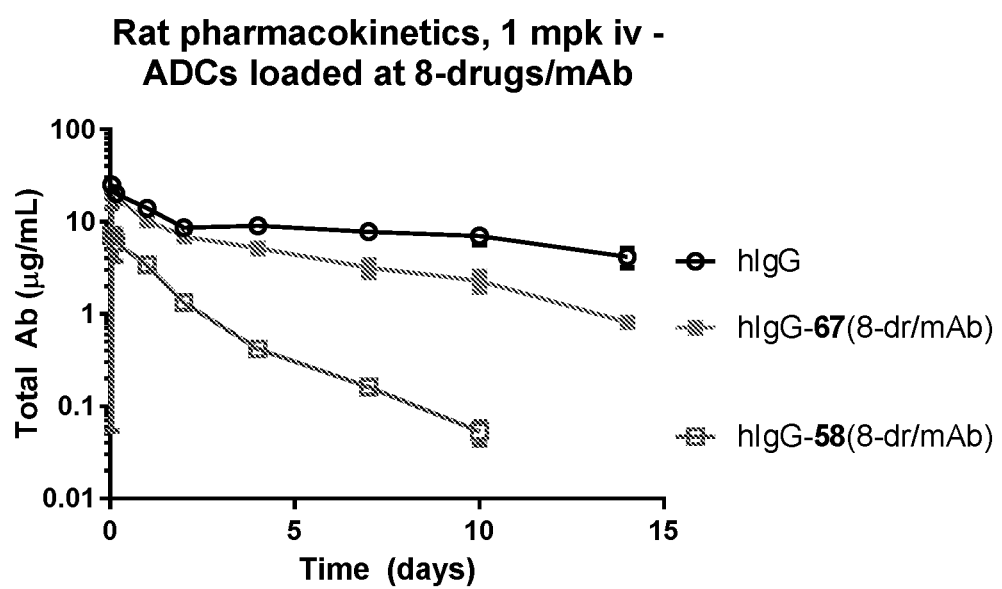
FIG. 6. Pharmacokinetic profiles, shown as amount of total antibody (µg/mL) vs. time (days), of antibody-drug conjugates dosed i.v. in rats at 1 mg/Kg with DAR 8 loading on humanized IgG antibody with glucuronide quaternary amine-linked tubulysin propyl ether with (hIgG-67) and without (hIgG-58) Linker Unit PEGylation.
Figure 7:
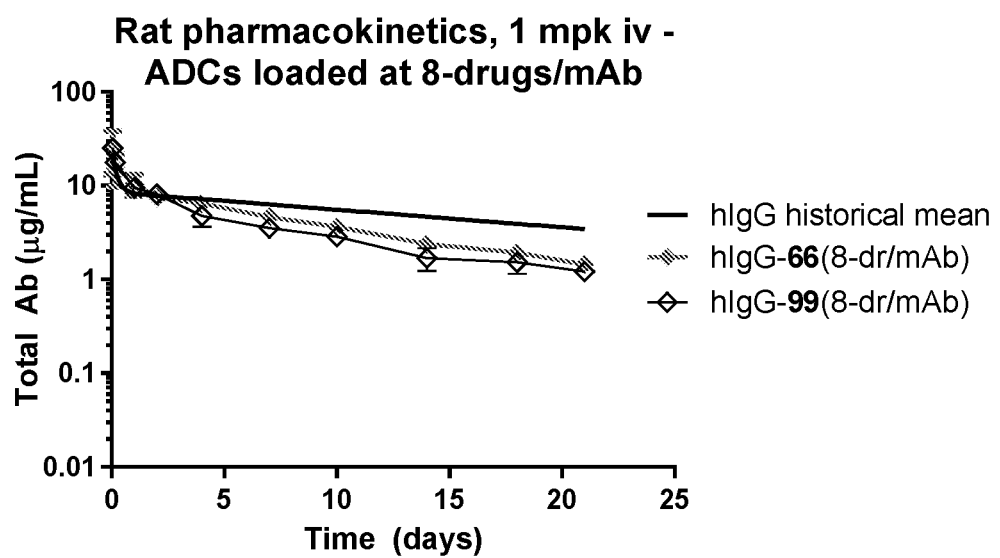
FIG. 7. Pharmacokinetic profiles, shown as amount of total antibody (µg/mL) vs. time (days), of antibody-drug conjugates dosed i.v. in rats at 1 mg/Kg with DAR 8 substitution on humanized IgG antibody with glucuronide quaternary amine-linked Tubulysin M (hIgG-99) and tubulysin ethyl ether (hIgG-66) both with Linker Unit PEGylated.

FIGS. 5-7 contain the clearance profiles for various tubulysin quaternary amine linker constructs. In all experiments, rats were administered a single i.v. dose at 1 mg/Kg at time zero with radiolabeled ADCs. Plasma samples were collected at various time points and analyzed as described to quantify total antibody as a function of time. FIG. 5 contains the exposure profiles for humanized IgG conjugates prepared from the Drug Linker compound MDPR-val-ala-PABQ-TubM (15) and the hydrophilic Drug Linker compounds MDPR-GlucQ-TubM (82) MDPR-val-glu-TubM (91), and MDPR-val-glu(PEG12)-TubM (9). Humanized IgG bearing four copies of the val-Ala dipeptide-linked quaternized TubM (hIgG 15) had a clearance profile identical to unmodified antibody; however, at a DAR of 8 the ADC was cleared from circulation much more rapidly. Substitution of the alanine residue of hIgG-15 with the glutamate residue providing IgG-91 did not result in an appreciable increase in exposure. Addition of a PEG12 side chain to the val-glu linker of hIgG-91, resulting in hIgG-95, did provide an increase in ADC exposure. Likewise, replacement of the val-ala dipeptide of IgG-15 with a Glucuronide Unit providing hIgG-82 did result in an increase in conjugate exposure with DAR 8 conjugates.

FIG. 6 contains the PK exposures for DAR 8 humanized IgG conjugates bearing the glucuronide quaternary amine-linked tubulysin propyl ether drug linker moieties in the absence (hIgG-58) and presence (hIgG-67) of a PEG12 side chain. The conjugate bearing 8 copies of quaternized drug linker moieties from the Drug linker compound MDPR-glucQ-TubOPr (58) was cleared from circulation much more rapidly than the unmodified antibody. The addition of a PEG12 side chain providing hIgG-67 significantly improved exposure, more closely approximating naked antibody PK properties.

The PK exposure of DAR 8 humanized IgG conjugates containing PEGylated glucuronide drug linkers moieties having quaternized tubulysin M (hIgG-99) and quaternized tubulysin ethyl ether (hIgG-66) Drug Units are shown in FIG. 7. Both conjugates displayed prolonged exposures closely approximating a line representing the historical mean exposure for the parental antibody.

What is claimed is:
1. A Ligand Drug Conjugate compound of Formula 1A:

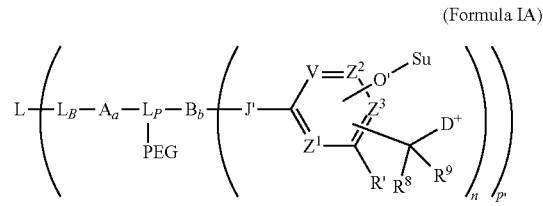

(Formula IA)

wherein
L is an antibody Ligand Unit;
$L_B$ is a Ligand Covalent Binding Unit;
$L_P$ is a Parallel Connector Unit;
PEG is a Polyethylene Glycol Unit;
subscript a is 0 or 1;
subscript b is 0 or 1;
A is a first optional Stretcher Unit so that subscript a is 0 when A is absent or A is present so that subscript a is 1 and optionally comprises two, three or four independently selected subunits ($A_1$, $A_2$, $A_3$, $A_4$);
B is a Branching Unit or a second optional Stretcher Unit ($A_O$) so that subscript b is 0 when B is absent or B is present so that subscript b is 1 and optionally comprises two, three or four subunits independently of A;
subscript n is 1, 2, 3 or 4, provided that subscript b is 1 and B is a Branching Unit when subscript n is 2, 3 or 4 and provided that B is $A_O$ or is absent when subscript n is 1;
Su is a carbohydrate moiety;
—O'— represents an oxygen atom of an O-glycosidic bond cleavable by a glycosidase;
-J'- represents a heteroatom, optionally substituted when nitrogen, from a functional group of B, when B is present, or $L_B$, when B is absent;
wherein two of V, $Z^1$, $Z^2$ and $Z^3$ are each =C($R^{24}$)—, wherein one $R^{24}$ is C($R^8$)($R^9$)-D$^+$ so that the indicated C($R^8$)($R^9$)-D$^+$ moiety is bonded to one of V, $Z^1$, $Z^2$, $Z^3$ and the other $R^{24}$ is —O'-Su so that the indicated —O'-Su moiety is bonded to another one of V, $Z^1$, $Z^2$, $Z^3$,
provided the —O'Su and —C($R^8$)($R^9$)-D$^+$ moieties are ortho or para to each other; and
wherein the remainder of V, $Z^1$, $Z^2$ and $Z^3$ are each =C($R^{24}$)—, wherein each $R^{24}$ is independently selected from the group consisting of hydrogen, optionally substituted alkyl, and halogen, —NO$_2$, —CN and other electron withdrawing groups;
one of $R^8$ and $R^9$ is hydrogen and the other is hydrogen, alkyl, alkenyl or alkynyl, optionally substituted, or aryl or heteroaryl, optionally substituted;
R' is hydrogen or is halogen, —NO$_2$, —CN or other electron withdrawing group;
D$^+$ is a quaternized tubulysin Drug Unit having the structure of:

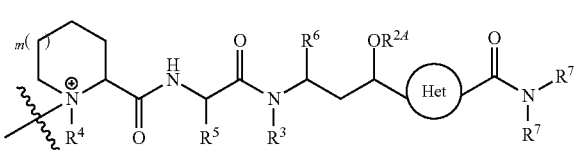

wherein the circle represents a 5-membered nitrogen-containing heteroarylene and wherein the indicated required substituents to that heteroarylene are in a 1,3-relationship with each other with optional substitution at the remaining positions;

subscript m is 1;

$R^{2A}$ is hydrogen or optionally substituted alkyl, or $R^{2A}$ along with the oxygen atom to which it is attached defines an O-linked substituent;

$R^3$ is hydrogen or optionally substituted alkyl;

$R^4$, $R^5$ and $R^6$ are independently optionally substituted alkyl;

one $R^7$ is an optionally substituted alkyl, an optionally substituted arylalkyl, or an optionally substituted heteroarylalkyl, and the other $R^7$ is hydrogen or an optionally substituted alkyl; and subscript p' is an integer ranging from 1 to 24; and wherein the wavy line indicates covalent bonding of $D^+$ to the remainder of the Ligand Drug Conjugate compound structure and wherein each optionally substituted alkyl is independently selected, and wherein cleavage of said O-glycosidase bond results in release of a tubulysin compound (D) from the Ligand Drug Conjugate compound, wherein the tubulysin compound so released is a tubulin disrupting agent.

2. The Ligand Drug Conjugate compound of claim 1, represented by the structure of one of Formula 2A-2F:

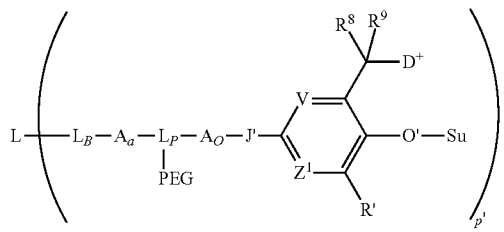
(Formula 2A)

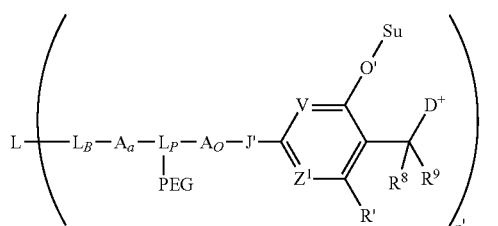
(Formula 2B)

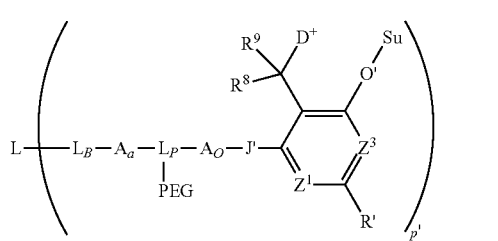
(Formula 2C)

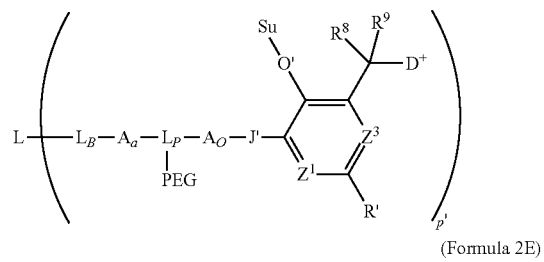
(Formula 2D)

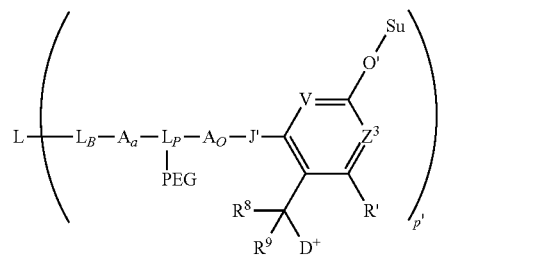
(Formula 2E)

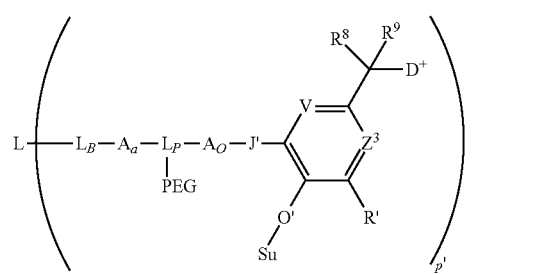
(Formula 2F)

wherein the antibody Ligand Unit is capable of selectively binding to an accessible cell-surface antigen of an abnormal cell, wherein the antigen is capable of cellular internalization of the bound Ligand Drug Conjugate compound and is preferentially present on the abnormal cell in comparison to normal cells.

3. The Ligand Drug Conjugate compound of claim 2, represented by the structure of Formula 4:

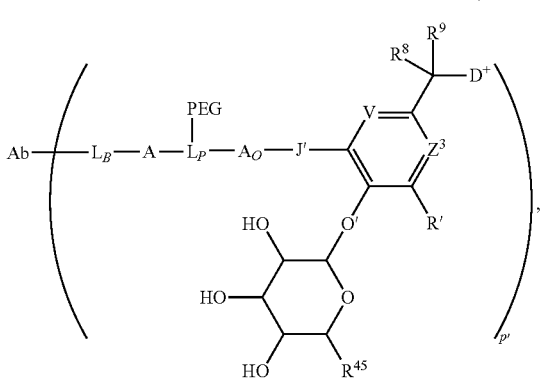
(Formula 4)

wherein
Ab is the antibody Ligand Unit;
J' is —N($R^{33}$)—, wherein $R^{33}$ is hydrogen or methyl;
V and $Z^3$ independently are =CH—;
R' is hydrogen or an electron withdrawing group;

$R^8$ is hydrogen;
$R^9$ is hydrogen, optionally substituted $C_1$-$C_6$ alkyl or optionally substituted phenyl;
$R^{45}$ is —$CO_2H$; and
subscript p' is an integer ranging from 1-8, 2-8, 2-6, 2-5 or 2-4.

4. The Ligand Drug Conjugate compound of claim 3, represented by the structure of Formula 6:

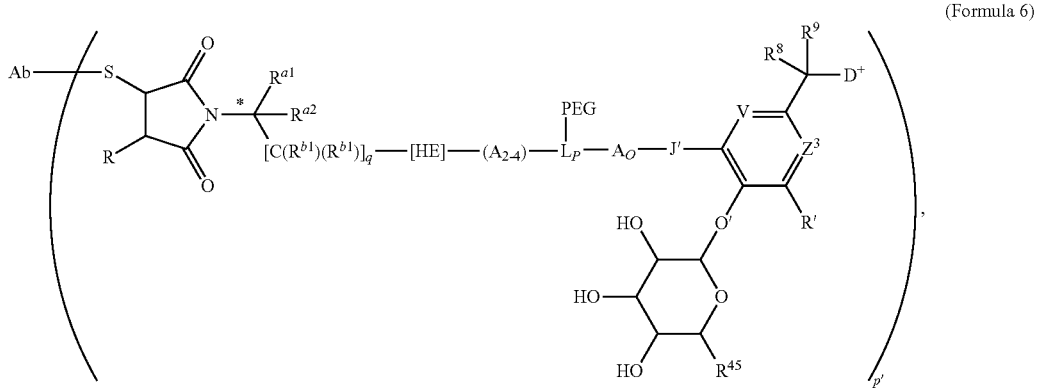

(Formula 6)

wherein
S is a sulfur atom of the antibody Ligand Unit (Ab);
the asterisk (*) designates chirality or absence thereof at the indicated carbon atom, wherein that carbon atom is in the same absolute configuration as the alpha carbon atom of an L-amino acid when the indicated carbon atom is chiral;
$A_{2-4}$ are independently selected optional subunits of A, wherein —$[C(R^{b1})(R^{b1})]_q$—[HE] is $A_1$ when one or more such subunits are present;
R is hydrogen;
R' is hydrogen or an electron withdrawing group;
$R^{a1}$ is hydrogen or $R^{a1}$ is BU and the succinimide ring is in hydrolyzed form, wherein BU is a Basic Unit having the structure of —$CH_2$—$N(R^{22})(R^{23})$, or an acid addition salt thereof, wherein $R^{22}$ and $R^{23}$ independently are hydrogen, methyl or ethyl or both together with the nitrogen atom to which they are attached define a 5- or 6-membered heterocycloalkyl;
$R^{a2}$ is hydrogen;
subscript q is an integer ranging from 0 to 5 when HE is present or from 1 to 5 when HE is absent;
each $R^{b1}$ independently is hydrogen or optionally substituted $C_1$-$C_6$ alkyl;
HE is absent or is —C(=O)—;
$R^{45}$ is —$CO_2H$;
J' is —NH—;
$R^8$ is hydrogen;
$R^9$ is hydrogen or methyl;
subscript p' is an integer a number ranging from 1 to 8 or 2 to 8; and
wherein the remaining variable groups are as defined for Formula 1A.

5. The Ligand Drug Conjugate compound of claim 1, represented by the structure of Formula 9A or Formula 9B:

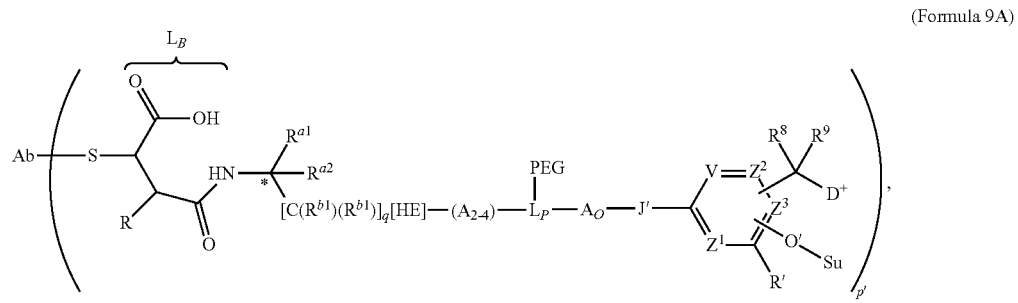

(Formula 9A)

-continued

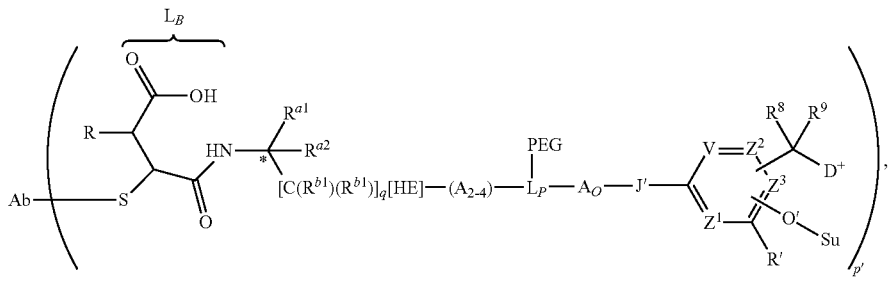
(Formula 9B)

wherein

S is a sulfur atom of the antibody Ligand Unit (Ab);

the asterisk (*) designates chirality or absence thereof at the indicated carbon atom, wherein that carbon atom is in the same absolute configuration as the alpha carbon of an L-amino acid when the indicated atom is chiral;

$A_{2-4}$ are independently selected optional subunits of A, wherein —$[C(R^{b1})(R^{b1})]_q$—[HE] is $A_1$ when one or more such subunits are present;

R is hydrogen;

R' is hydrogen or an electron withdrawing group;

$R^{a1}$ is BU wherein BU is a Basic Unit having the structure of —$CH_2$—$N(R^{22})(R^{23})$, or an acid addition salt thereof, wherein $R^{22}$ and $R^{23}$ independently are hydrogen or methyl or both together with the nitrogen atom to which they are attached define a basic nitrogen-containing 5- or 6-membered heterocycloalkyl;

$R^{a2}$ is hydrogen;

subscript q is an integer ranging from 0 to 5 when HE is present or from 1 to 5 when HE is absent;

each $R^{b1}$ independently is hydrogen or optionally substituted $C_1$-$C_6$ alkyl;

HE is absent or is —C(=O)—;

J' is —O— or —NH—;

one of $R^8$ and $R^9$ is hydrogen and the other is —H or optionally substituted alkyl; and subscript p' is an integer ranging from 1 to 24; and wherein the remaining variable groups are as defined for Formula 1A.

6. The Ligand Drug Conjugate compound of claim 5, represented by the structure of Formula 10A or Formula 10B:

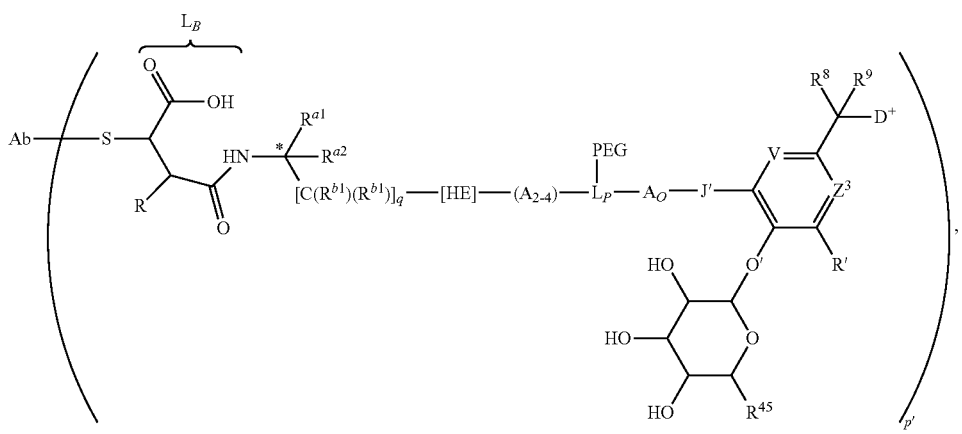
(Formula 10A)

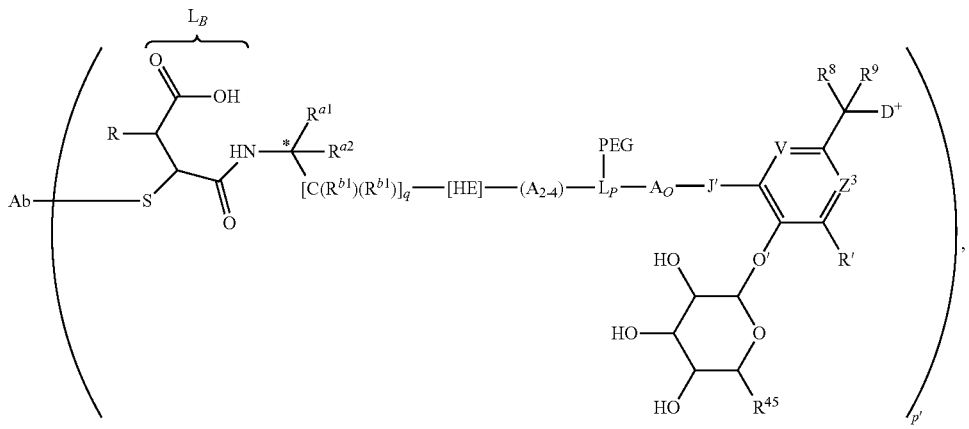

wherein
R is hydrogen;
R' is hydrogen, —NO$_2$, —Cl or —F;
HE is —C(=O)—;
R$^{45}$ is —CO$_2$H;
J' is —NH—;
V and Z$^3$ are each =CH—;
R$^8$ is hydrogen;
R$^9$ is hydrogen or methyl;
p' is an integer ranging from 1 to 12; and
wherein the remaining variable groups are as defined for Formula 1A.

7. The Ligand Drug Conjugate compound of claim 1, wherein A and A$_O$, independently have the structure of Formula 7 or Formula 8:

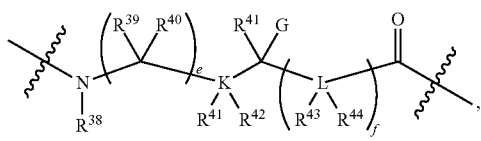

(Formula 7)

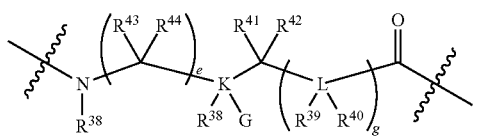

(Formula 8)

wherein the wavy lines indicate covalent attachment within the compound structure, wherein K and L independently are C, N, O or S, provided that when K or L is O or S, R$^{41}$ and R$^{42}$ to K or R$^{43}$ and R$^{44}$ to L are absent, and when K or L are N, one of R$^{41}$, R$^{42}$ to K or one of R$^{42}$, R$^{43}$ to L are absent, and provided that no two adjacent L are independently selected as N, O, or S;
wherein subscripts e and f are independently selected integers that range from 0 to 12, and subscript g is an integer ranging from 1 to 12;
wherein G is hydrogen, optionally substituted C$_1$-C$_6$ alkyl, —OH, —OR$^{PR}$, —CO$_2$H, CO$_2$R$^{PR}$, wherein R$^{PR}$ is a suitable protecting, —N(R$^{PR}$)(R$^{PR}$), wherein R$^{PR}$ are independently a protecting group or R$^{PR}$ together form a suitable protecting group, or —N(R$^{45}$)(R$^{46}$), wherein one of R$^{45}$, R$^{46}$ is hydrogen or R$^{PR}$, wherein R$^{PR}$ is a suitable protecting group, and the other is hydrogen or optionally substituted C$_1$-C$_6$ alkyl;

wherein R$^{38}$ is hydrogen or optionally substituted C$_1$-C$_6$ alkyl; R$^{39}$-R$^{44}$ independently are hydrogen, optionally substituted C$_1$-C$_6$ alkyl, optionally substituted aryl, or optionally substituted heteroaryl, or both R$^{39}$, R$^{40}$ together with the carbon to which they are attached comprise a C$_3$-C$_6$ cycloalkyl, or R$^{41}$, R$^{42}$ together with K to which they are attached when K is C, or R$^{43}$, R$^{44}$ together with L to which they are attached when L is a carbon atom comprise a C$_3$-C$_6$ cycloalkyl, or R$^{40}$ and R$^{41}$, or R$^{40}$ and R$^{43}$, or R$^{41}$ and R$^{43}$ to together with the carbon atom or heteroatom to which they are attached and the atoms intervening between those carbon atoms and/or heteroatoms comprise a 5- or 6-membered cycloalkyl or heterocycloalkyl, provided that when K is O or S, R$^{41}$ and R$^{42}$ are absent, when K is N, one of R$^{41}$, R$^{42}$ is absent, when L is O or S, R$^{43}$ and R$^{44}$ are absent, and when L is N, one of R$^{43}$, R$^{44}$ is absent, or wherein A$_O$ has a structure corresponding to an alpha-amino, beta-amino or another amine-containing acid and wherein the quaternized tubulysin Drug Unit (-D$^+$) has the structure of:

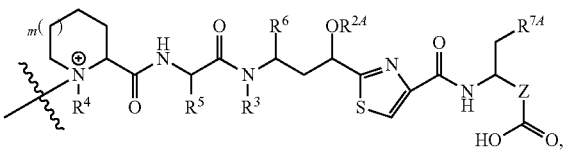

wherein
Z is an optionally substituted alkylene or an optionally substituted alkenylene; and
R$^{7A}$ is optionally substituted aryl or optionally substituted heteroaryl.

8. The Ligand Drug Conjugate compound of claim 1, wherein the quaternized tubulysin Drug Unit (-D$^+$) has the structure of:

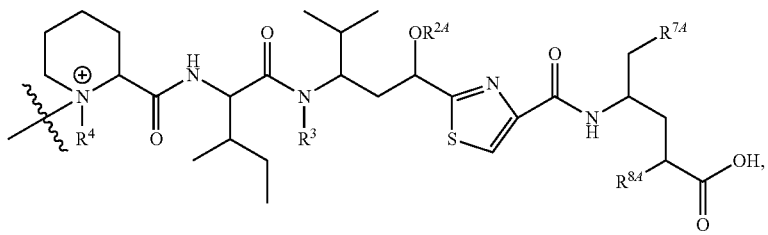

wherein $R^{7A}$ is optionally substituted phenyl and $R^{8A}$ is hydrogen or methyl.

9. The Ligand Drug Conjugate compound of claim 8 wherein the quaternized tubulysin Drug Unit (-D⁺) has the structure of:

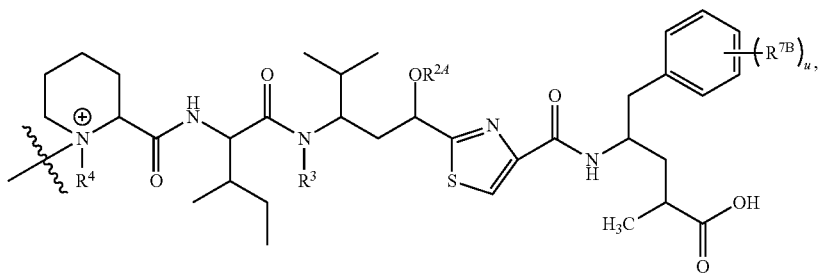

wherein $R^4$ is methyl;
subscript u is 0, 1 or 2;
$R^3$ is H, methyl, ethyl, propyl, —CH₂—OC(O)R³ᴬ, —CH₂CH(R³ᴮ)C(O)R³ᴬ or —CH(R³ᴮ)C(O)NHR³ᴬ, wherein $R^{3A}$ is $C_1$-$C_6$ alkyl and $R^{3B}$ is H or $C_1$-$C_6$ alkyl, independently selected from $R^{3A}$;
$R^{2A}$ along with the oxygen atom to which it is attached is an O-linked substituent selected from the group consisting of —OCH₂OCH₂R²ᴮ, —OCH₂R²ᴮ, —OC(O)R²ᴮ, —CH₂OC(O)R²ᴮ, —OC(O)N(R²ᴮ)(R²ᶜ), and —OCH₂C(O)N(R²ᴮ)(R²ᶜ), wherein $R^{2B}$ and $R^{2C}$ are independently selected from the group consisting of H, $C_1$-$C_6$ alkyl and $C_2$-$C_6$ alkenyl; and
each $R^{7B}$, when present, independently is —OH or —OCH₃.

10. The Ligand Drug Conjugate compound of claim 9, wherein the quaternized tubulysin Drug Unit (-D⁺) has the structure of:

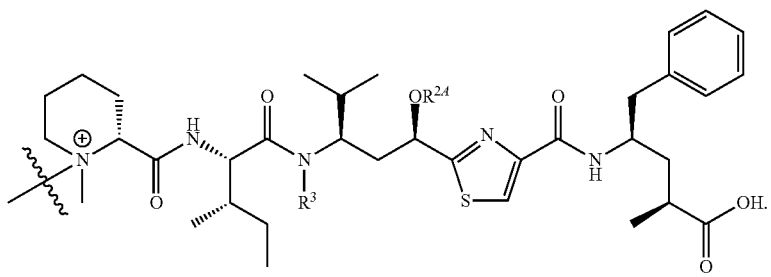

11. The Ligand Drug Conjugate compound of claim 10, wherein $R^{2A}$ is —CH$_2$CH$_3$ or CH$_2$—CH═CH$_2$.

12. The Ligand Drug Conjugate compound of claim 9, wherein
$R^{2A}$ is —CH$_2$CH$_3$, —CH$_2$—CH═CH$_2$ or —CH$_2$C(CH$_3$)═CH$_2$, $R^{2B}$ is —CH$_3$, $R^3$ is —CH$_3$ and subscript u is 0, or $R^{2A}$ is —CH$_2$CH$_3$ or —CH$_2$—CH═CH$_2$, or —CH$_2$C(CH$_3$)═CH$_2$, $R^{2B}$ is —CH$_3$, $R^3$ is —CH$_3$ and subscript u is 1, wherein $R^{7B}$ is —OH.

13. The Ligand Drug Conjugate compound of claim 9, wherein the quaternized tubulysin Drug Unit (-D$^+$) has the structure of:

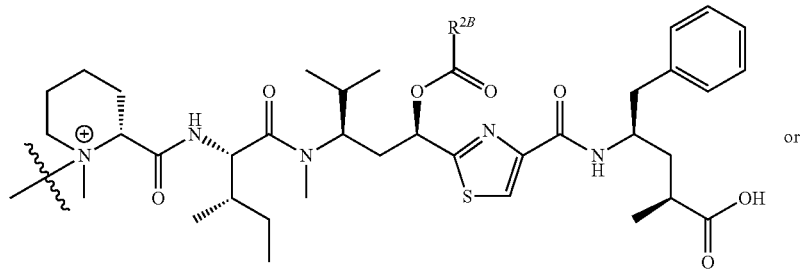 or

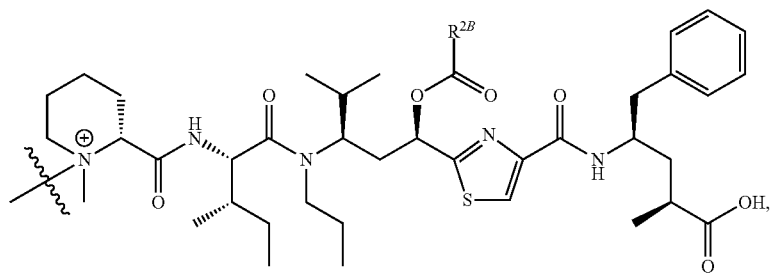

wherein $R^{2B}$ is —CH$_3$, —CH$_2$CH$_3$, —CH$_2$CH$_2$CH$_3$, —CH(CH$_3$)$_2$, —CH$_2$CH(CH$_3$)$_2$, or —CH$_2$C(CH$_3$)$_3$, or wherein the quaternized tubulysin Drug Unit (-D$^+$) has the structure of:

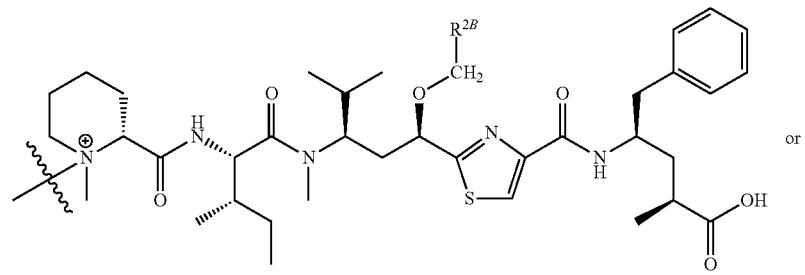 or

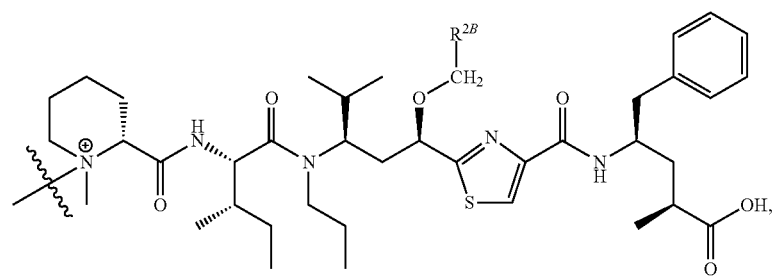

wherein

R$^{2B}$ is hydrogen, methyl or —OCH$_3$, or
—OCH$_2$R$^{2B}$ is —OCH$_2$CH=CH$_2$ or —OCH$_2$C(CH$_3$)=CH$_2$.

14. The Ligand Drug Conjugate compound of claim 9, wherein the quaternized tubulysin Drug Unit -D$^+$ is that of tubulysin M, which has the structure of:

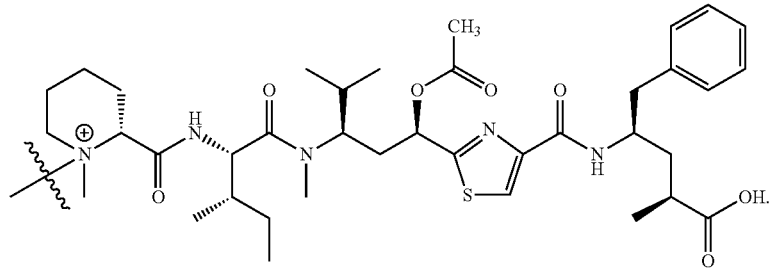

15. The Ligand Drug Conjugate compound of claim 1, wherein L$_P$ is an aminoalkanedioic acid, diaminoalkanoic acid, sulfur-substituted aminoalkanoic acid or hydroxyl substituted aminoalkanoic acid residue having the structure of Formula A or Formula B:

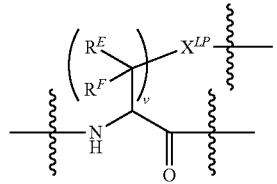
(Formula A)

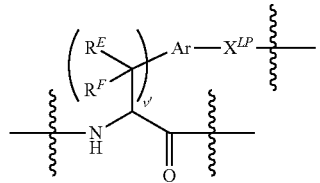
(Formula B)

wherein subscript v is an integer ranging from 1 to 4;
subscript v' is an integer ranging from 0 to 4;
X$^{LP}$ is selected from the group consisting of —O—, —NR$^{LP}$—, —S—, —S(=O)—, —S(=O)$_2$—, —C(=O)—, —C(=O)N(R$^{LP}$)—, —N(R$^{LP}$)C(=O)N(R$^{LP}$)—, and —N(R$^{LP}$)C(=NR$^{LP}$)N(R$^{LP}$)— wherein each R$^{LP}$ is independently selected from the group consisting of hydrogen and optionally substituted alkyl or two of R$^{LP}$ together along with their intervening atoms define an optionally substituted heterocycloalkyl and any remaining R$^{LP}$ are as previously defined;

Ar is an arylene or heteroarylene, optionally substituted;
each R$^E$ and R$^F$ is independently selected from the group consisting of —H, optionally substituted alkyl, optionally substituted aryl and optionally substituted heteroaryl, or R$^E$ and R$^F$ together with the same carbon to which they are attached, or R$^E$ and R$^F$ from adjacent carbons together with these carbons, define an optionally substituted cycloalkyl with any remaining R$^E$ and R$^F$ substituents are as previously defined; and wherein the wavy lines indicate covalent attachments of the Formula A or Formula B structure within the compound structure.

16. The Ligand Drug Conjugate compound of claim 1 wherein -L$_P$(PEG)- has the structure of Formula A1 or A2:

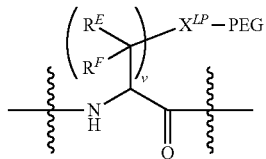
(Formula A1)

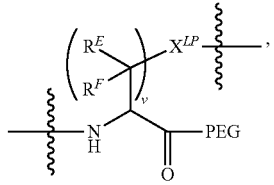
(Formula A2)

wherein

X$^{LP}$ is selected from the group consisting of —O—, —NH, —S— and —C(=O)—;

R$^E$ and R$^F$ are independently selected from the group consisting of —H, and —C$_1$-C$_4$ alkyl; and wherein the wavy lines indicate covalent attachments of Formula A1 or Formula A2 within the compound structure.

17. The Ligand Drug Conjugate compound of claim 1, represented by the structure of:

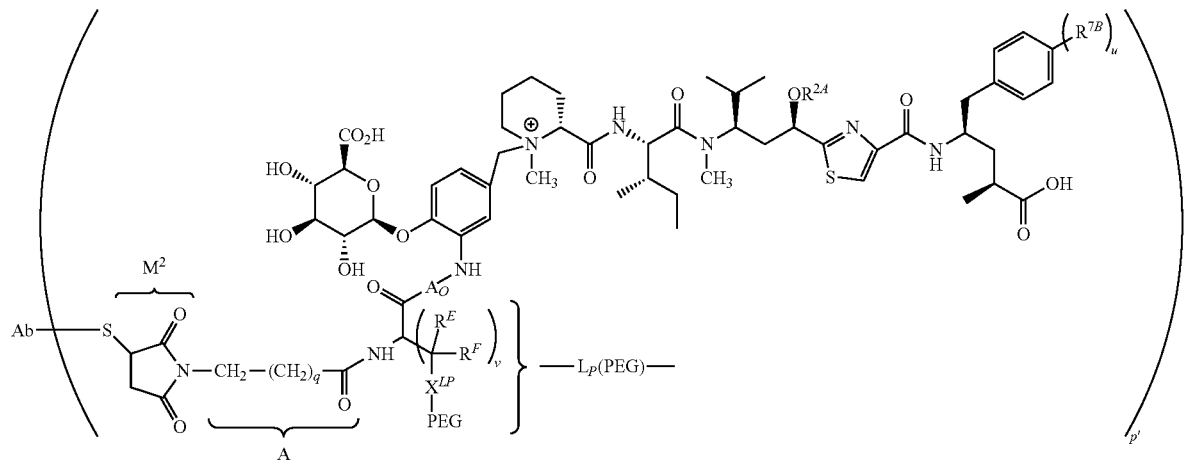

wherein
Ab is the antibody Ligand Unit;
S is a sulfur atom of the antibody Ligand Unit;
$R^{2A}$ is saturated $C_1$-$C_4$ alkyl, unsaturated $C_2$-$C_4$ alkyl, —C(=O)$R^{2B}$, wherein $R^{2B}$ is $C_1$-$C_4$ alkyl;
$A_O$ is absent or is an amine-containing acid residue;
Subscript p' is an integer ranging from 1 to 8;
subscript q is an integer ranging from 1 to 4;
subscript u is 0 or 1;
subscript v is an integer ranging from 1 to 4;
$R^{7B}$, when present, is —OH;
$X^{LP}$ is selected from the group consisting of —O—, —NH, —S— and —C(=O)—; and
$R^E$ and $R^F$ are independently selected from the group consisting of —H, and $C_1$-$C_4$ alkyl.

18. The Ligand Drug Conjugate compound of claim 1, represented by the structure of:

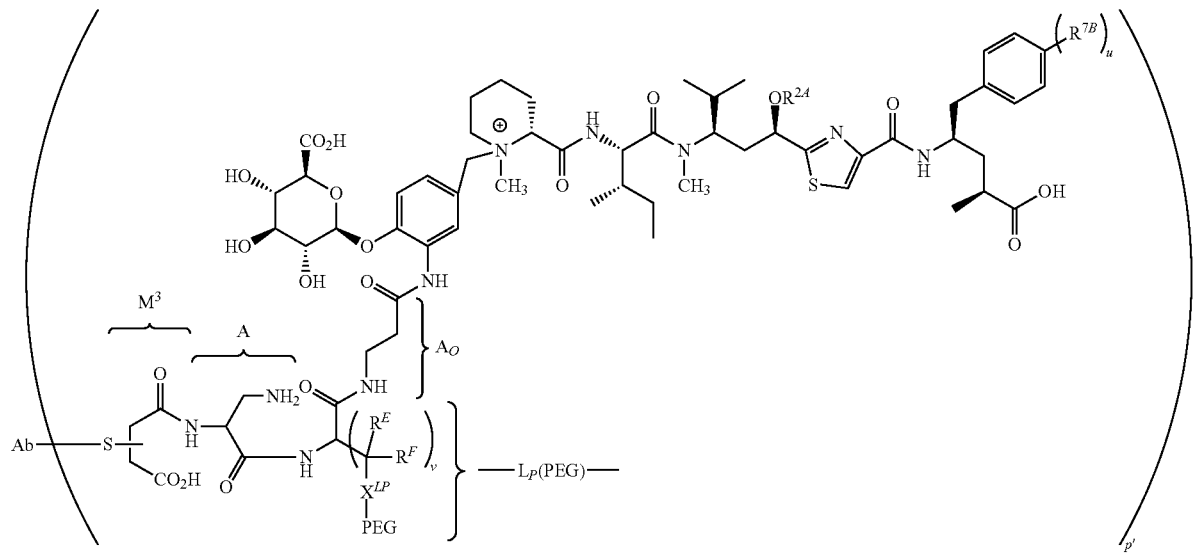

wherein
Ab is the antibody Ligand Unit;
S is a sulfur atom of the antibody Ligand Unit;
wherein the Ab-S— moiety is bonded to the carbon α or β to the indicated $M^3$ carboxylic acid;
$R^{2A}$ is saturated $C_1$-$C_4$ alkyl, unsaturated $C_2$-$C_4$ alkyl, or —C(=O)$R^{2B}$, wherein $R^{2B}$ is $C_1$-$C_4$ alkyl;
subscript p' is an integer ranging from 1 to 8;
subscript q is an integer ranging from 1 to 4;
subscript u is 0 or 1;
subscript v is an integer ranging from 1 to 4;
$R^{7B}$, when present, is —OH;
$X^{LP}$ is selected from the group consisting of —O—, —NH, —S— and —C(=O)—; and
$R^E$ and $R^F$ are independently selected from the group consisting of —H, and $C_1$-$C_4$ alkyl.

19. The Ligand Drug Conjugate compound of claim 17, wherein $R^{2A}$ is saturated $C_1$-$C_4$ alkyl or unsaturated $C_3$-$C_4$ alkyl, wherein saturated $C_1$-$C_4$ alkyl is —$CH_3$, —$CH_2CH_3$, —CH$_2$CH$_2$CH$_3$ and unsaturated C$_3$-C$_4$ alkyl is —CH$_2$CH=CH$_2$ or —CH(CH$_3$)CH=CH$_2$.

20. The Ligand Drug Conjugate compound of claim 18, wherein R$^{2A}$ is —C(O)CH$_3$, —CH$_2$CH$_3$ or —CH$_2$CH=CH$_2$.

21. The Ligand Drug Conjugate compound of claim 1, wherein PEG has the structure selected from the group consisting of:

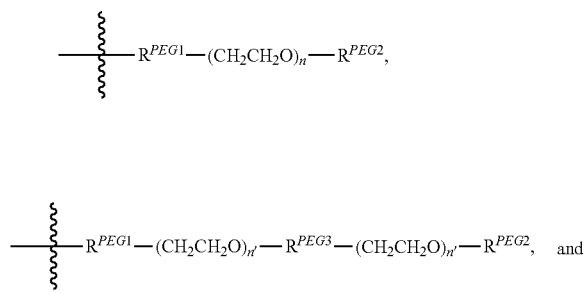

wherein the wavy line indicates site of attachment to X$^{LP}$ of the Parallel Connector Unit (L$_P$), R$^{PEG1}$ is an optional PEG Attachment Unit, R$^{PEG2}$ is a PEG Capping Unit;

R$^{PEG3}$ is an PEG Coupling Unit;

subscript n ranges from 2 to 72;

each subscript n' is independently selected from 1 to 72; and subscript e ranges from 2 to 5.

22. The Ligand Drug Conjugate compound of claim 18 wherein —X$^{LP}$—PEG has the structure of:

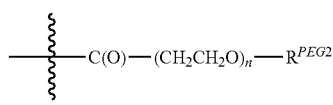

wherein subscript n is 12 and R$^{PEG2}$ is hydrogen or —CH$_3$.

23. The Ligand Drug Conjugate compound of claim 1, represented by the structure of:

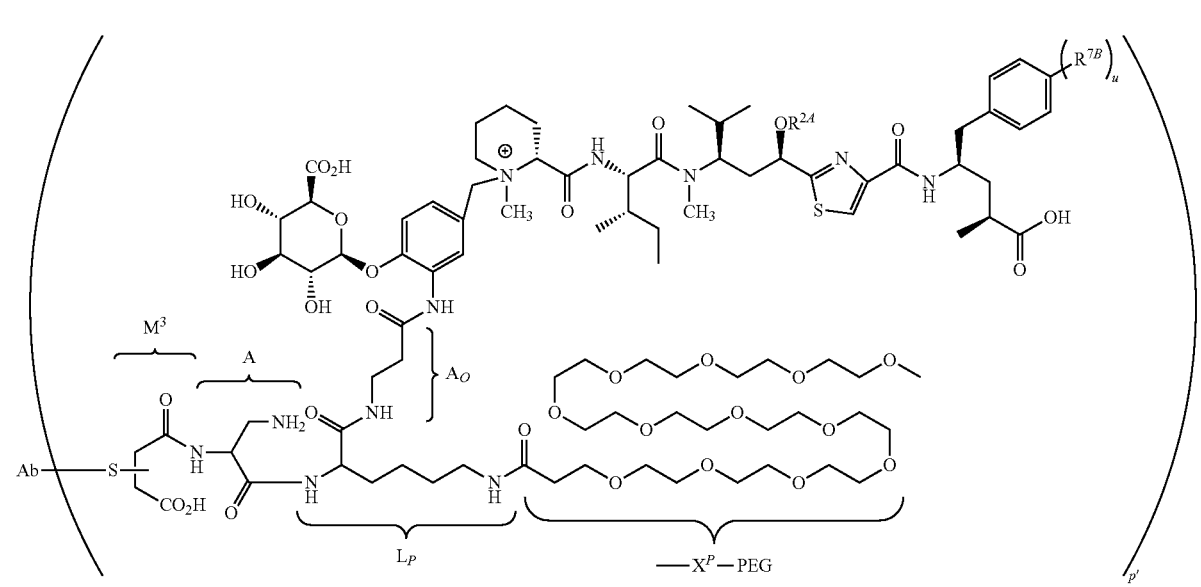

-continued

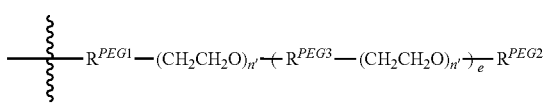

wherein

Ab is the antibody Ligand Unit;

S is a sulfur atom of the antibody Ligand Unit;

the Ab-S— moiety is bonded to the carbon α or β to the indicated M$^3$ carboxylic acid;

subscript p' is an integer ranging from 1 to 8;

subscript u is 0 or 1;

R$^{7B}$, when present, is —OH; and $R^{2A}$ along with the oxygen atom to which it is attached is —OC(O)CH$_3$, —CH$_2$CH$_3$ or —CH$_2$CH=CH$_2$.

24. The Ligand Drug Conjugate compound of claim 23, represented by the structure of:

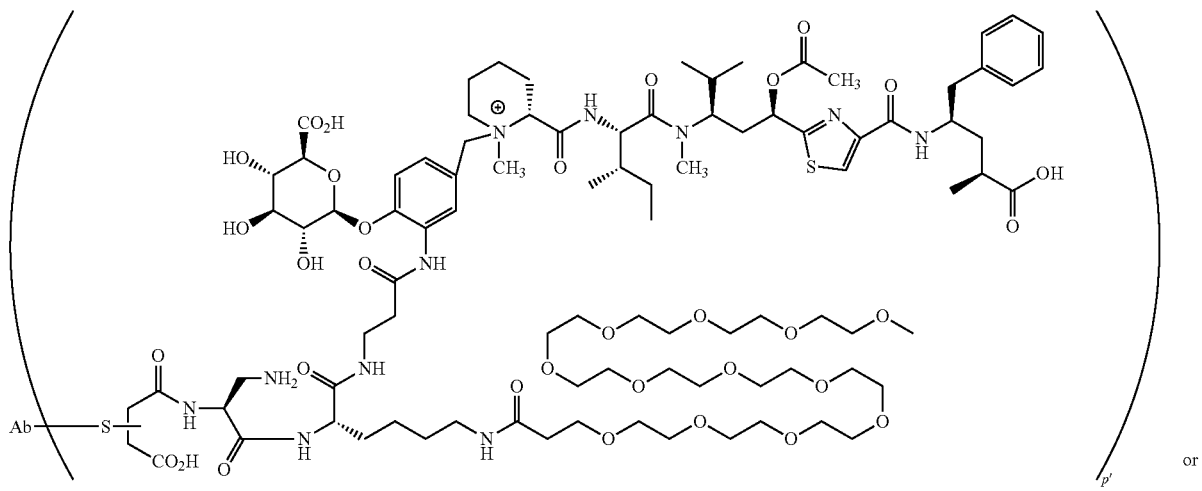

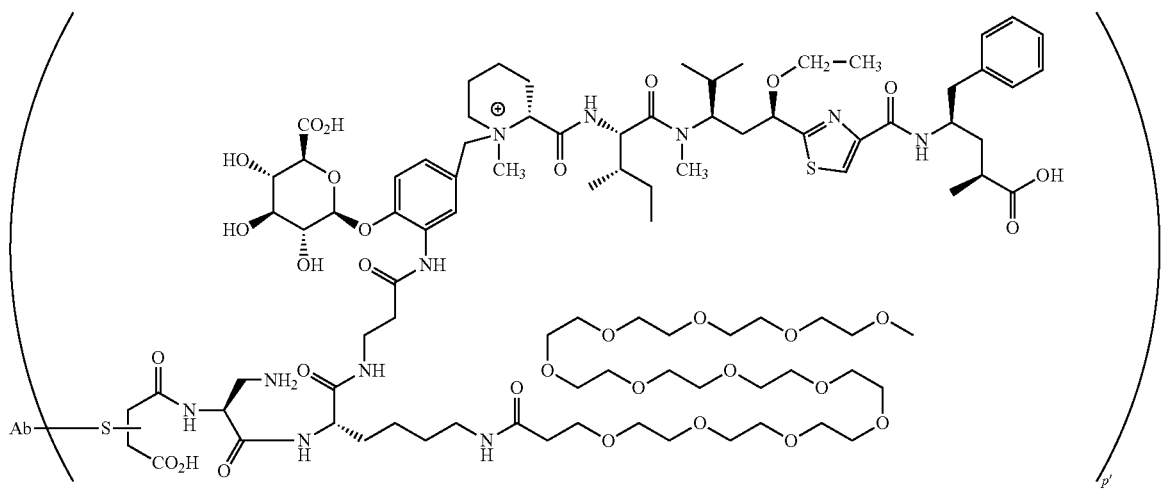

25. A formulation comprising a Ligand Drug Conjugate composition and one or more excipients, wherein
the Ligand Drug Conjugate composition comprises a plurality of Ligand Drug Conjugate compounds of claim 1; and
p' is, independently for each Ligand Drug Conjugate compound of the Ligand Drug Conjugate composition, an integer ranging from 1 to 24.

26. The formulation of claim 25, wherein the formulation is a pharmaceutically acceptable formulation or a precursor thereof, wherein the Ligand Drug Conjugate composition is present in the pharmaceutically acceptable formulation or precursor thereof in an effective amount for treatment of a hyperproliferative condition; and
wherein the pharmaceutically acceptable formulation is a liquid suitable for intravenous injection to a subject, and the pharmaceutically acceptable formulation precursor is a solid suitable for reconstitution as a solution for intravenous injection to a subject.

27. The Ligand Drug Conjugate compound of claim 23, wherein $R^{2A}$ is -CH$_2$CH$_3$.

28. The Ligand Drug Conjugate compound of claim 12, wherein $R^{2A}$ is -CH$_2$CH$_3$.

* * * * *